US006265202B1

(12) United States Patent
Sherman et al.

(10) Patent No.: US 6,265,202 B1
(45) Date of Patent: Jul. 24, 2001

(54) DNA ENCODING METHYMYCIN AND PIKROMYCIN

(75) Inventors: David H. Sherman, St. Louis Park; Hung-Wen Liu, Roseville; Yongquan Xue; Lishan Zhao, both of St. Paul, all of MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/105,537

(22) Filed: Jun. 26, 1998

(51) Int. Cl.[7] .............................. C12N 1/20; C07H 21/04
(52) U.S. Cl. ................................ 435/252.31; 435/252.3; 435/252.33; 435/320.1; 435/183; 536/23.2; 536/23.7; 536/23.1
(58) Field of Search .................................. 435/183, 320.1, 435/252.3, 252.31, 252.33, 189, 190, 193, 200; 536/23.2, 23.7, 23.1

(56) References Cited

U.S. PATENT DOCUMENTS

| | | | |
|---|---|---|---|
| 4,874,748 | 10/1989 | Katz et al. | 514/29 |
| 4,935,340 | 6/1990 | Baltz et al. | 435/6 |
| 4,952,502 | 8/1990 | Epp et al. | 435/76 |
| 5,057,425 | 10/1991 | Stanzak | 435/252.3 |
| 5,063,155 | 11/1991 | Cox et al. | 435/76 |
| 5,068,189 | 11/1991 | Epp et al. | 435/183 |
| 5,098,837 | 3/1992 | Beckmann et al. | 435/172.3 |
| 5,116,968 | 5/1992 | Lawrence et al. | 536/71 |
| 5,141,926 | 8/1992 | Weber et al. | 514/29 |
| 5,149,638 | 9/1992 | Beckmann et al. | 435/76 |
| 5,149,639 | 9/1992 | Katz et al. | 435/76 |
| 5,168,052 | 12/1992 | Cox et al. | 435/72 |
| 5,229,279 | 7/1993 | Peoples et al. | 435/135 |
| 5,245,023 | 9/1993 | Peoples et al. | 536/23.2 |
| 5,250,430 | 10/1993 | Peoples et al. | 435/232 |
| 5,480,794 | 1/1996 | Peoples et al. | 435/232 |
| 5,512,669 | 4/1996 | Peoples et al. | 536/23.2 |
| 5,514,544 | 5/1996 | Rao et al. | 435/6 |
| 5,534,432 | 7/1996 | Peoples et al. | 435/240.4 |
| 5,545,553 | 8/1996 | Gotschlich | 435/252.33 |
| 5,610,041 | 3/1997 | Somerville et al. | 435/135 |
| 5,661,026 | 8/1997 | Peoples et al. | 435/252.3 |
| 5,663,063 | 9/1997 | Peoples et al. | 435/135 |
| 5,672,491 | 9/1997 | Khosla et al. | 435/148 |

(List continued on next page.)

FOREIGN PATENT DOCUMENTS

| | | |
|---|---|---|
| 0 238 323 | 9/1987 | (EP) . |
| 0 361 905 | 4/1990 | (EP) . |
| 0 468 217 | 1/1992 | (EP) . |
| 0 791 655 | 8/1997 | (EP) . |
| 0 791 656 | 8/1997 | (EP) . |
| 61-205484 | 9/1986 | (JP) . |
| 62-029595 | 2/1987 | (JP) . |
| 62-61765 | 9/1994 | (JP) . |
| 87/03907 | 7/1987 | (WO) . |
| 92/16629 | 10/1992 | (WO) . |
| 93/13663 | 7/1993 | (WO) . |
| 95/08548 | 3/1995 | (WO) . |

(List continued on next page.)

OTHER PUBLICATIONS

Kao, C.M., et al., "Manipulation of Macrolide Ring Size by Directed Mutagenesis of a Modular Polyketide Synthase", *J. Am. Chem. Soc.*, 117, 9105–9106 (1995).

Kealey, J.T., et al., "Production of a Polyketide Natural Product in Nonpolyketide–Producing Prokaryotic and Eukaryotic Hosts", *Proc. Natl. Acad. Sci. USA*, 95, 505–509 (Jan. 1988).

Katz, L., "Manipulation of Modular Polyketide Synthases", *Chem. Rev.*, 97, 2557–2575 (1997).

Khosla, C., "Harnessing the Biosynthetic Potential of Modular Polyketide Synthases", *Chem. Rev.*, 97, 2577–2590 (1997).

Staunton, J., et al., "Biosynthesis of Erythromycin and Rapamycin", *Chem. Rev.*, 97, 2611–2629 (1997).

Andersen, J.F., et al., "Characterization of *Saccharopolyspora erythraea* Cytochrome P–450 Genes and Enzymes, Including 6–Deoxyerythronolide B Hydroxylase", *Journal of Bacteriology*, 174, 725–735 (Feb. 1992).

Gaisser, S., et al., "Analysis of Seven Genes from the eryAI–eryK Region of the Erythromycin Biosynthetic Gene Cluster in *Saccharopolyspora erythraea*", *Mol. Gen. Genet.*, 256, 239–251 (1997).

Hernandez, C., et al., "Characterization of a *Streptomyces antibioticus* Gene Cluster Encoding a Glycosyltransferase Involved in Oleandomycin Inactivation", *Gene*, 134, 139–140 (1993).

Hopwood, D.A., et al., "Molecular Genetics of Polyketides and Its Comparison to Fatty Acid Biosynthesis", *Annu. Rev. Genet.*, 24, 37–66 (1990).

Jacobsen, J.R., et al., "Precursor–Directed Biosynthesis of Erythromycin Analogs by an Engineered Polyketide Synthease", *Science*, 277, 367–369 (Jul. 18, 1997).

(List continued on next page.)

Primary Examiner—Nashaat T. Nashed
(74) Attorney, Agent, or Firm—Schwegman, Lundberg, Woessner & Kluth, P.A.

(57) ABSTRACT

A novel pathway for the synthesis of polyhydroxyalkanoates is provided. A method of synthesizing a recombinant polyhydroxyalkanoate monomer synthase is also provided. These recombinant polyhydroxyalkanoate synthases are derived from multifunctional fatty acid synthases or polyketide synthases and generate hydroxyacyl acids capable of polymerization by a polyhydroxyalkanoate synthase. Also provided is a biosynthetic gene cluster for methymycin and pikomycin as well as a biosynthetic gene cluster for desosamine.

8 Claims, 158 Drawing Sheets

U.S. PATENT DOCUMENTS

| | | | |
|---|---|---|---|
| 5,672,497 | 9/1997 | Cox et al. | 435/320.1 |
| 5,702,717 | 12/1997 | Cha et al. | 424/425 |
| 5,712,146 | 1/1998 | Khosla et al. | 435/252.35 |
| 5,716,849 | 2/1998 | Ligon et al. | 435/419 |
| 5,744,350 | 4/1998 | Vinci et al. | 435/254.11 |
| 5,798,235 | 8/1998 | Peoples et al. | 435/135 |
| 5,824,513 | 10/1998 | Katz et al. | 435/76 |
| 5,830,750 | 11/1998 | Khosla et al. | 435/252.35 |
| 5,843,718 | 12/1998 | Khosla et al. | 435/69.1 |
| 5,962,290 | 10/1999 | Khosla et al. | 435/183 |
| 6,022,731 | 2/2000 | Khosla et al. | 435/252.35 |
| 6,033,883 | 3/2000 | Barr et al. | 435/148 |
| 6,077,696 | 6/2000 | Khosla et al. | 435/135 |
| 6,090,601 | 7/2000 | Gustafsson et al. | 435/183 |
| 6,117,659 * | 9/2000 | Ashley et al. | 435/155 |

FOREIGN PATENT DOCUMENTS

| | | |
|---|---|---|
| 96/40968 | 12/1996 | (WO) . |
| 97/02358 | 1/1997 | (WO) . |
| 97/22711 | 6/1997 | (WO) . |
| 97/23630 | 7/1997 | (WO) . |
| 98/00557 | 1/1998 | (WO) . |
| 98/01546 | 1/1998 | (WO) . |
| 98/01571 | 1/1998 | (WO) . |
| 98/04713 | 2/1998 | (WO) . |
| 98/07868 | 2/1998 | (WO) . |
| 98/09978 | 3/1998 | (WO) . |
| 98/11230 | 3/1998 | (WO) . |
| 98/27203 | 6/1998 | (WO) . |
| 98/36078 | 8/1998 | (WO) . |
| 98/51695 | 11/1998 | (WO) . |
| 99/61599 | 12/1999 | (WO) . |

OTHER PUBLICATIONS

Liu, L., et al., "Biosynthesis of 2–Nor–6–deoxyerythronolide B by Rationally Designed Domain Substitution", *J. Am. Chem. Soc.*, 119, 10553–10554 (1997).

Marahiel, M.A., et al., "Modular Peptide Synthetases Involved in Nonribosomal Peptide Synthesis", *Chemical Reviews*, 97, 2651–2673 (1997).

McDaniel, R., et al., "Engineered Intermodular and Intramodular Polyketide Synthase Fusions", *Chemistry and Biology*, 4, 667–674 (1997).

McDaniel, R., et al., "Rational Design of Aromatic Polyketide Natural Products by Recombinant Assembly of Enzymatic Subunits", *Nature*, 375, 549–554 (Jun. 15, 1995).

Schneider, A., et al., "Genetic Evidence for a Role of Thioesterase Domains, Integratd in or Associated with Peptide Synthetases, in Non–Ribosomal Peptide Biosynthesis in *Bacillus subtilis*", *Arch. Microbiol.*, 169, 404–410 (1998).

Schwecke, T., et al., "The Biosynthetic Gene Cluster for the Polyketide Immunosuppressant Rapamycin", *Proc. Natl. Acad. Sci. USA*, 92, 7839–7843 (Aug. 1995).

Service, R.F., "Hijacking a Cell's Chemical Paths to Make New Antibiotics", *Science*, 277, 319 (Jul. 18, 1997).

Stassi, D., et al., "Identification of a *Saccharopolyspora erythraea* Gene Required for the Final Hydroxylation Step in Erythromycin Biosynthesis", *Journal of Bacteriology*, 175, 182–189 (Jan. 1993).

Tsoi, C.J., et al., "Combinatorial Biosynthesis of 'Unnatural' Natural Products: The Polyketide Example", *Chemistry and Biology*, 2, 355–362 (Jun. 1995).

Verdine, G.L., et al., "The Combinatorial Chemistry of Nature", *Nature*, 384, Supp., 11–13 (Nov. 7, 1996).

Vilches, C., et al., "Role of Glycosylation and Deglycosylation in Biosynthesis of and Resistance to Oleandomycin in the Producer Organism, *Streptomyces antibioticus*", *Journal of Bacteriology*, 174, 161–165 (Jan. 1992).

Betlach, M.C., et al., "Characterization of the macrolide P–450 hydroxylase from *Streptomyces venezuelae* which converts narbomycin to picromycin", *Bichemistry*, 37 (42), pp. 14937–14942, (Oct. 1998).

Cane, D.E., et al., "Methymycin biosynthesis. Isolation of P450 Monooxygenase activity in a cell–free system from *Streptomyces venezuelae*", *Journal of the American Chemical Society*, 120 (11), pp. 2682–2683, (1998).

Ruan, X., et al., "Acyltransferase domain substitutions in erythromycin polyketide synthase yield novel erythromycin derivatives", *Journal of Bacteriology*, 179 (20), pp. 6416–6425, (Oct. 1997).

Salah–Bey, K., et al., "Targeted gene inactivation for the elucidation of deoxysugar biosynthesis in the erythromycin producer *Saccharopolyspora erythraea*", *Molecular and General Genetics*, 257 (5), pp. 542–553, (Mar. 1998).

Summers, R.G., et al., "Sequencing and mutagenesis of genes from the erythromycin biosynthetic gene cluster of *Saccharopolyspora erythraea* that are involved in 1–mycarose and d–desosamine production", *Microbiology*, 143, pp. 3251–3262, (Oct. 1997).

Xue, Y., et al., "A gene cluster for macrolide antibiotic biosynthesis in *Streptomyces venezuelae*: architecture of metabolic diversity", *Proceedings of the Natlional Academy of Sciences of the USA*, 95 (21), pp. 12111–12116, (Oct. 1998).

Zhao, L., et al., "Biosynthesis of desosamine: molecular evidence suggestion B–glucosylation as a self–resistance mechanism in Methymycin/neomethymycin producing strain, *Streptomyces venezuelae*", *Journal of the American Chemical Society*, 120 (36), pp. 9374–9375, (Sep. 1998).

Ylihonko K., et al., "A Gene Cluster Involved in Nogalamycin biosynthesis from streptomyces nogalater: sequence analysis and complementation of early–block mutations in the anthracyclin pathway", *Molecular and General Genetics*, 251, pp. 113–120, (1996).

Adler, T., "Plants: The New Plastics Makers", *Science News of the Week*, 146(26–27), 420 (1994).

Anderson, A.J., et al., "Occurrence, Metabolism, Metabolic Role, and Industrial Uses of Bacterial Polyhydroxyalkanoates", *Microbiological Review*, 54 (4), 450–472 (1990).

Bevitt, D.J., et al., "6–Deoxyerythronolide–B synthase 2 from *Saccharopolyspora erythraea*; cloning of the structural gene, sequence analysis and inferred domain structure of the multifunctional enzyme", *European Journal of Biochemistry*, 204, 39–49 (1992).

Brandl, H., et al., "Plastics from Bacteria and for Bacteria: Poly(β–hydroxy–alkanoates) as Natural, Biocompatible, and Biodegradable Polyesters", *Advances in Biochemical Engineering Biotechnology*, 41, 77–93 (1990).

Byrom, D., "Polymer synthesis by micro–organisms: technology and economics", *Tibtech*, 5, 246–250 (1987).

Cortes, J., et al., "Repositioning of a Domain in a Modular Polyketide Synthase to Promote Specific Chain Cleavage", *Science*, 268, 1487–1489 (1995).

Cundliff, E., "Glycosylation of Macrolide Antibiotics in Extracts of *Streptomyces lividans*", *Antimicrobial Agents and Chemotherapy*, 36(2), 348–352 (1992).

Donadio, S., et al., "An erythromycin analog produced by reprogramming of polyketide synthesis", *Proceedings of the National Academy of Sciences, 90,* 7119–7123 (1993).

Donadio, S., et al., "Modular Organization of Genes Required for Complex Polyketide Biosynthesis", *Science, 252,* 675–679 (1991).

Donadio, S., et al., "Organization of the enzymatic domains in the multifunctional polyketide synthase involved in erythromycin formation in *saccharopolyspora erythraea*", *Gene, 111(1),* 51–60 (1992).

Fernandez–Moreno, M.A., et al., "Streptothricin Biosyntheses Is Catalyzed by Enzymes Related to Nonribosomal Peptide Bond Formation", *Journal of Bacteriology, 179(22),* 6929–6936 (1997).

Fu, H., et al., "Antibiotic activity of polyketide products derived from combinatorial biosynthesis: Implications for directed evolution", *Molecular Diversity, 1(2),* 121–124 (1995).

Gaisser, S., et al., "Analysis of eryBI, eryBIII and eryBVII from the erthromycin biosynthetic gene cluster in *Saccharopolyspora erthraea*", *Molecular & General Genetics, 258,* 78–88 (1998).

Gaisser, S., et al., "Cloning of an Avilamycin Biosynthetic Gene Cluster from *Streptomyces viridochromogenes* Tu57", *Journal of Bacteriology, 179(20),* 6271–6278 (1997).

Han, L., et al., "Cloning and Characterization of Polyketide Synthase Genes for Jadomycin B Biosynthesis in *Streptomyces venezuelae* ISP5230", *Microbiology, 140,* 3379–3389 (1984).

Hopwood, et al., "Genetic Manipulation of Streptomyces: A Laboratory Manual", 77–78, 292–293, 214–224 (1985).

Hopwood, D.A., "Antibiotics: Opportunities for Genetic Manipulation", *Philosophical Transactions of the Royal Society of London, 324,* 549–562 (1989).

Joshi, A.K., et al., "Construction of a cDNA encoding the multifunctional animal fatty acid synthase and expression in Spodoptera frugiperda cells using buculoviral vectors", *Biochem. J., 296,* 143–149 (1993).

Joshi, A.K., et al., "Construction, Expression and Characterization of a Mutated Animal Fatty Acid Synthase Deficient in the Dehydrase Function", *The Journal of Biological Chemistry, 268(30),* 22508–22513 (1993).

Kao, C.M., et al., "Engineered Biosynthesis of a Complete Macrolactone in a Heterologous Host", *Science, 265,* 509–512 (1994).

Lomovskaya, N., et al., "Gene disruption and replacement in the rapamycin–producing *Stretomyces hygroscopicus* strain ATCC 29253", *Microbiology, 143,* 875–883 (1997).

Peoples, O.P., et al., "Poly–β–hydroxybutyrate Biosynthesis in Alcaligenes eutrophus H16 characterization of the genes encoding β–Ketothiolase and acetoacetyl–CoA", *The Journal of Biological Chemistry, 264(26),* 15293–15297 (1989).

Poirier, Y., et al., "Polyhydroxybutyrate, a Biodegradable Thermplastic, Produced in Transgenic Plants", *Science, 256,* 520–523 (1992).

Poirier, Y., et al., "Production of Polyhydroxyalkanoates, a Family of Biodegradable Plastics and Elastomers, in Bacteria Plants", *Bio/Technology, 13,* 142–150 (1995).

Quiros, L.M., et al., "Two glycosylatransferases and a glycosidase are involved in oleandomycin modification during its biosynthesis by *Streptomyces antibioticus*", *Molecular Microbiology, 28,* 1177–1185 (1998).

Witt, D., et al., "Unification of the Genera Streptoverticillum and Streptomyces, and Amendation of Streptomyces Waksman and Henrici 1943, 339", *System. Appl. Microbiol., 13,* 361–371 (1990).

Yang, K., et al., "Accumulation of the angucycline antibiotic rabelomycin after disruption of an oxygenase gene in the jadomycin B biosynthetic gene cluster of *Stretomyces venezuelae*", *Microbiology, 142(1),* 123–132 (1996).

* cited by examiner

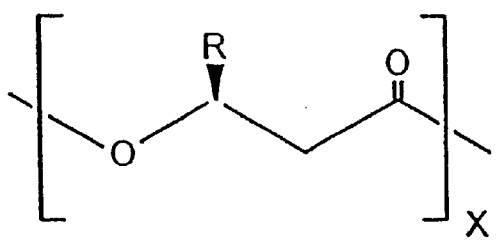

| R-group | Monomer | Abbreviation |
|---|---|---|
| methyl | 3-hydroxybutyrate | (3HB) |
| ethyl | 3-hydroxyvalerate | (3HV) |
| propyl | 3-hydroxycaproate | (3HC) |
| butyl | 3-hydroxyheptanoate | (3HH) |
| pentyl | 3-hydroxyoctanoate | (3HO) |
| hexyl | 3-hydroxynonanoate | (3HN) |
| heptyl | 3-hydroxydecanoate | (3HD) |
| octyl | 3-hydroxyundecanoate | (3HUD) |
| nonyl | 3-hydroxydodecanoate | (3HDD) |

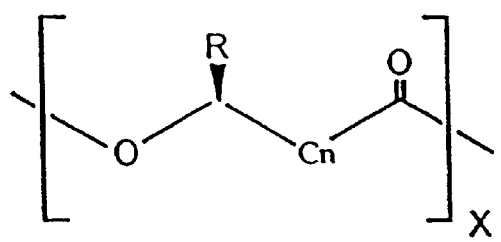

n = 1  3-hydroxyacyl monomer
n = 2  4-hydroxyacyl monomer
n = 3  5-hydroxyacyl monomer

FIG. 2

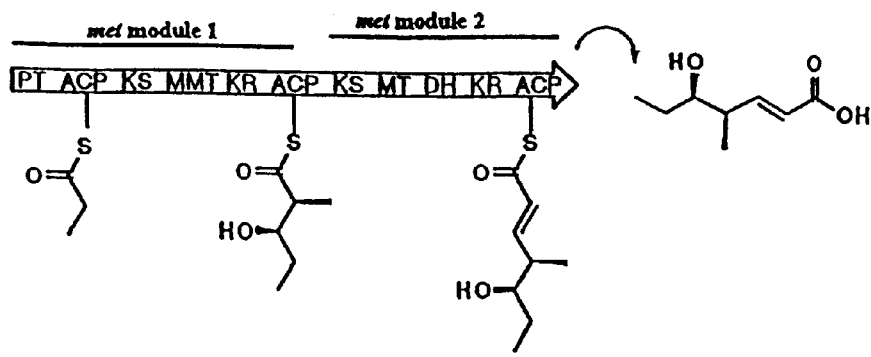
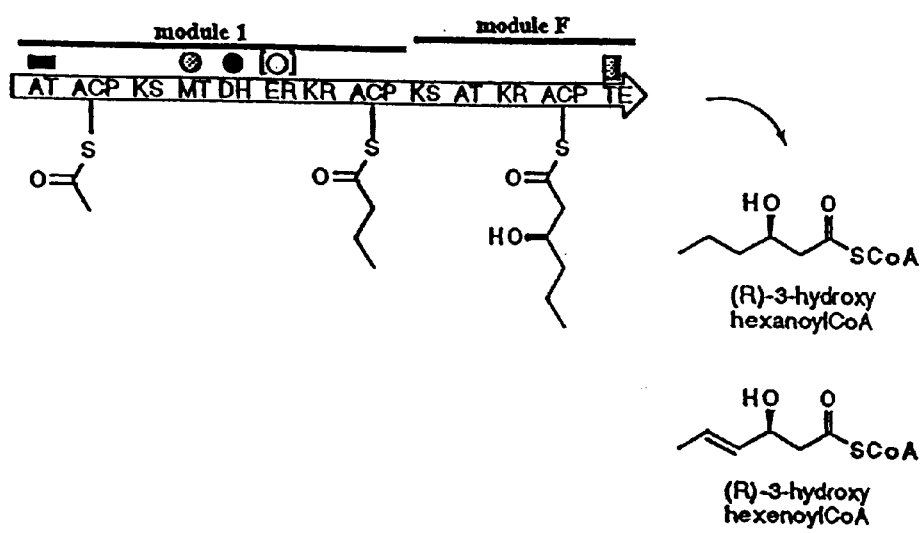
1. introduce TE domain and establish release of acyl CoA ester
2. change MMT to MT domain in module 1
3. introduce DH/ER (or DH only) domain into module 1
4. inactivate DH domain in module 2
5. replace PT starter domain with AT in module 1
FIG. 6

| N-terminal sequence determined for PHA synthase |
|---|

```
       1          10            20    25
a    MATGKGAAASTQEGKSQPFKVTPGP— b          AAASTQEGKSQPFKVTPGP— c             STQEGKSQPFKVTPGP—
```

FIG. 8

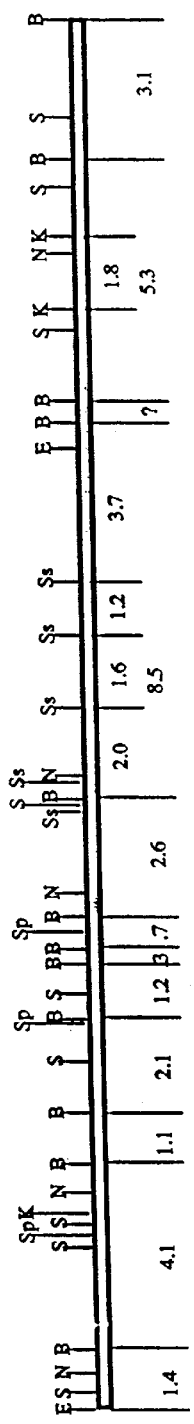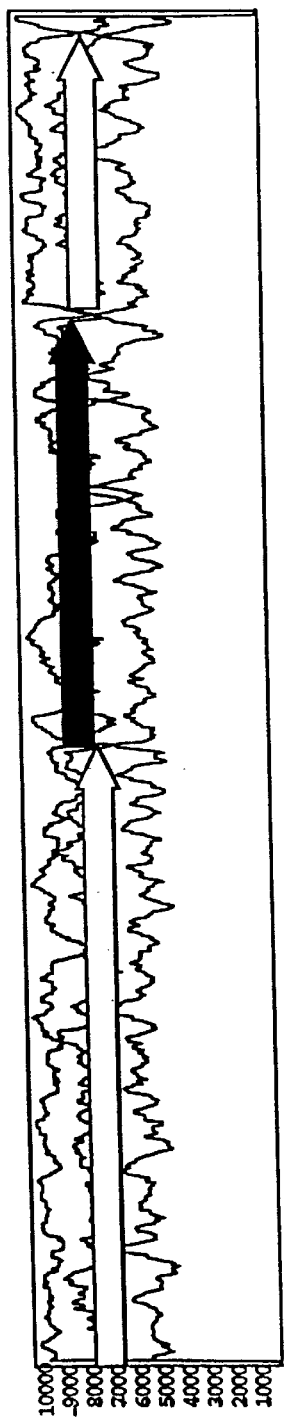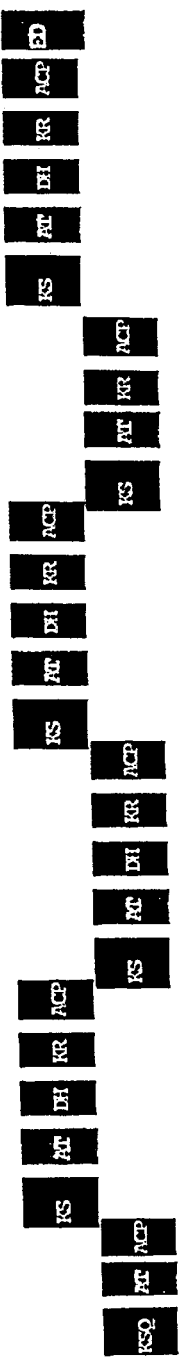
FIG. 19

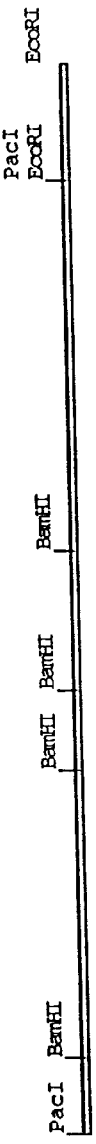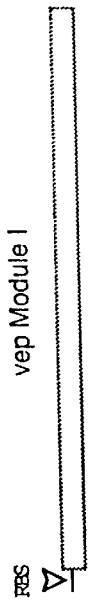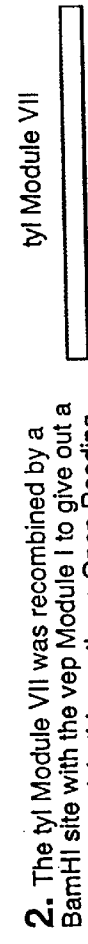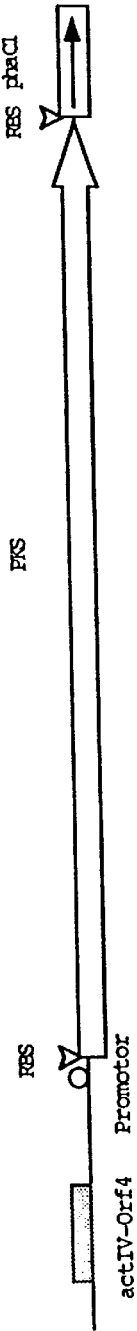
FIG. 22

```
  1 TTAATTAAGGAGGACCATC ATG AAC GAG GCC ATC GCC GTC GTC GGC ATG TCC TGC CGC CTG CCG  64
  1                     M   N   E   A   I   A   V   V   G   M   S   C   R   L   P    15

65 AAG GCC TCG AAC CCG GCC GCC TTC TGG GAG CTG CTG CGG AAC GGG GAG AGC GCC GTC ACC 124
 16 K   A   S   N   P   A   A   F   W   E   L   L   R   N   G   E   S   A   V   T    35

125 GAC GTG CCC TCC GGC CGG TGG ACG TCG GTG CTC GGG GGA GCG GAC GCC GAG GAG CCG GCG 184
 36 D   V   P   S   G   R   W   T   S   V   L   G   G   A   D   A   E   E   P   A    55

185 GAG TCC GGT GTC CGC CGG GGC GGC TTC CTC GAC TCC CTC GAC CTC TTC GAC GCG GCC TTC 244
 56 E   S   G   V   R   R   G   G   F   L   D   S   L   D   L   F   D   A   A   F    75

245 TTC GGA ATC TCG CCC CGT GAG GCC GCC GCC ATG GAC CCG CAG CAG CGA CTG GTC CTC GAA 304
 76 F   G   I   S   P   R   E   A   A   A   M   D   P   Q   Q   R   L   V   L   E    95

305 CTC GCC TGG GAG GCG CTG GAG GAC GCC GGA ATC GTC CCC GGC ACC CTC GCC GGA AGC CGC 364
 96 L   A   W   E   A   L   E   D   A   G   I   V   P   G   T   L   A   G   S   R   115

365 ACC GCC GTC TTC GTC GGC ACC CTG CGG GAC GAC TAC ACG AGC CTC CTC TAC CAG CAC GGC 424
116 T   A   V   F   V   G   T   L   R   D   D   Y   T   S   L   L   Y   Q   H   G   135

425 GAG CAG GCC ATC ACC CAG CAC ACC ATG GCG GGC GTG AAC CGG GGC GTC ATC GCC AAC CGC 484
136 E   Q   A   I   T   Q   H   T   M   A   G   V   N   R   G   V   I   A   N   R   155

485 GTC TCG TAC CAC CTC GGC CTG CAG GGC CCG AGC CTC ACC GTC GAC GCC GCG CAG TCG TCC 544
156 V   S   Y   H   L   G   L   Q   G   P   S   L   T   V   D   A   A   Q   S   S   175

545 TCG CTC GTC GCC GTG CAC CTG GCC TGC GAG TCC CTG CGC GCC GGG GAG TCC ACG ACG GCG 604
176 S   L   V   A   V   H   L   A   C   E   S   L   R   A   G   E   S   T   T   A   195

605 CTC GTC GCC GGC GTG AAC CTC AAC ATC CTC GCG GAG AGC GCC GTG ACG GAG GAG CGC TTC 664
196 L   V   A   G   V   N   L   N   I   L   A   E   S   A   V   T   E   E   R   F   215

665 GGT GGA CTC TCC CCG GAC GGC ACC GCC TAC ACC TTC GAC GCG CGG GCC AAC GGA TTC GTC 724
216 G   G   L   S   P   D   G   T   A   Y   T   F   D   A   R   A   N   G   F   V   235

725 CGG GGC GAG GGC GGC GGA GTC GTC GTA CTC AAG CCG CTC TCC CGC GCC CTC GCC GAC GGC 784
236 R   G   E   G   G   G   V   V   V   L   K   P   L   S   R   A   L   A   D   G   255

785 GAC CGT GTC CAC GGC GTC ATC CGC GCC AGC GCC GTC AAC AAC GAC GGA GCC ACC CCG GGT 844
256 D   R   V   H   G   V   I   R   A   S   A   V   N   N   D   G   A   T   P   G   275

845 CTC ACC GTG CCC AGC AGG GCC GCC CAG GAG AAG GTG CTG CGC GAG GCG TAC CGG AAG GCG 904
276 L   T   V   P   S   R   A   A   Q   E   K   V   L   R   E   A   Y   R   K   A   295

905 GCC CTG GAC CCG TCC GCC GTC CAG TAC GTC GAA CTC CAC GGC ACC GGA ACC CCC GTC GGC 964
296 A   L   D   P   S   A   V   Q   Y   V   E   L   H   G   T   G   T   P   V   G   315

965 GAC CCC ATC GAG GCC GCC GCG CTC GGC GCC GTC CTC GGC TCG GCG CGC CCC GCG GAC GAA 1024
316 D   P   I   E   A   A   A   L   G   A   V   L   G   S   A   R   P   A   D   E   335

1025 CCC CTG CTC GTC GGC TCG GCC AAG ACG AAC GTC GGG CAC CTC GAA GGC GCC GCC GGC ATC 1084
336  P   L   L   V   G   S   A   K   T   N   V   G   H   L   E   G   A   A   G   I   355

1085 GTC GGC CTC ATC AAG ACG CTC CTC GCG CTC GGC CGG CGG ATC CCG GCG AGC CTC AAC 1144
356  V   G   L   I   K   T   L   L   A   L   G   R   R   I   P   A   S   L   N   375

1145 TTC CGT ACG CCC CAC CCG GAC ATC CCG CTC GAC ACC CTC GGC CTC GAC GTG CCC GAC GGC 1204
376  F   R   T   P   H   P   D   I   P   L   D   T   L   G   L   D   V   P   D   G   395

1205 CTG CGG GAG TGG CCG CAC CCG GAC CGC GAA CTC CTC GCC GGC GTC AGC TCG TTC GGC ATG 1264
396  L   R   E   W   P   H   P   D   R   E   L   L   A   G   V   S   S   F   G   M   415

1265 GGC GGC ACC AAC GCC CAC GTC GTC CTC AGC GAA GGC CCC GCC CAG GGC GGC GAG CAG CCC 1324
416  G   G   T   N   A   H   V   V   L   S   E   G   P   A   Q   G   G   E   Q   P   435

1325 GGC ATC GAT GAG GAG ACC CCC GTC GAC AGC GGG GCC GCA CTG CCC TTC GTC GTC ACC GGC 1384
436  G   I   D   E   E   T   P   V   D   S   G   A   A   L   P   F   V   V   T   G   455

1385 CGC GGC GGC GAG GCC CTG CGC GCC CAG GCC CGG CGC CTG CAC GAG GCC GTC GAA GCG GAC 1444
456  R   G   G   E   A   L   R   A   Q   A   R   R   L   H   E   A   V   E   A   D   475
```

FIG. 23A

```
1445 CCG GAG CTC GCG CCC GCC GCA CTC GCC CGG TCG CTG GTC ACC ACC CGT ACG GTC TTC ACG 1504
476  P   E   L   A   P   A   A   L   A   R   S   L   V   T   T   R   T   V   F   T   495

1505 CAC CGG TCG GTC GTC CTC GCC CCG GAC CGC GCC CGC CTC CTC GAC GGC CTC GGC GCC CTC 1564
496  H   R   S   V   V   L   A   P   D   R   A   R   L   L   D   G   L   G   A   L   515

1565 GCC GCC GGG ACG CCC GCG CCC GGC GTG GTC ACC GGC ACC CCC GCC CCC GGG CGC CTC GCC 1624
516  A   A   G   T   P   A   P   G   V   V   T   G   T   P   A   P   G   R   L   A   535

1625 GTC CTG TTC AGC GGC CAG GGT GCC CAA CGT ACG GGC ATG GGC ATG GAG TTG TAC GCC GCC 1684
536  V   L   F   S   G   Q   G   A   Q   R   T   G   M   G   M   E   L   Y   A   A   555

1685 CAC CCC GCC TTC GCG ACG GCC TTC GAC GCC GTC GCC GCC GAA CTG GAC CCC CTC CTC GAC 1744
556  H   P   A   F   A   T   A   F   D   A   V   A   A   E   L   D   P   L   L   D   575

1745 CGG CCC CTC GCC GAA CTC GTC GCG GCG GGC GAC ACC CTC GAC CGC ACC GTC CAC ACA CAG 1804
576  R   P   L   A   E   L   V   A   A   G   D   T   L   D   R   T   V   H   T   Q   595

1805 CCC GCG CTC TTC GCC GTG GAG GTC GCC CTC CAC CGC CTC GTC GAG TCC TGG GGC GTC ACG 1864
596  P   A   L   F   A   V   E   V   A   L   H   R   L   V   E   S   W   G   V   T   615

1865 CCC GAC CTG CTC GCC GGC CAC TCC GTC GGC GAG ATC AGC GCC GCC CAC GTC GCC GGG GTC 1924
616  P   D   L   L   A   G   H   S   V   G   E   I   S   A   A   H   V   A   G   V   635

1925 CTG TCG CTG CGC GAC GCC GCC CGC CTC GTC GCG GCG CGC GGC CGC CTC ATG CAG GCG CTC 1984
636  L   S   L   R   D   A   A   R   L   V   A   A   R   G   R   L   M   Q   A   L   655

1985 CCC GAG GGC GGC GCG ATG GTC GCG GTC GAG GCG AGC GAG GAG GAA GTG CTT CCG CAC CTC 2044
656  P   E   G   G   A   M   V   A   V   E   A   S   E   E   V   L   P   H   L   675

2045 GCG GGA CGC GAG CGG GAG CTC TCC CTC GCG GCC GTG AAC GGC CCC CGC GCG GTC GTC CTC 2104
676  A   G   R   E   R   E   L   S   L   A   A   V   N   G   P   R   A   V   V   L   695

2105 GCG GGC GCC GAG CGC GCC GTC CTC GAC GTC GCC GAG CTG CTG CGC GAA CAG GGC CGC CGG 2164
696  A   G   A   E   R   A   V   L   D   V   A   E   L   L   R   E   Q   G   R   R   715

2165 ACG AAG CGG CTC AGC GTC TCG CAC GCC TTC CAC TCG CCG CTC ATG GAG CCG ATG CTC GAC 2224
716  T   K   R   L   S   V   S   H   A   F   H   S   P   L   M   E   P   M   L   D   735

2225 GAC TTC CGC CGG GTC GTC GAA GAG CTG GAC TTC CAG GAG CCC CGC GTC GAC GTC GTG TCC 2284
736  D   F   R   R   V   V   E   E   L   D   F   Q   E   P   R   V   D   V   V   S   755

2285 ACG GTG ACG GGC CTG CCT GTC ACA GCG GGC CAA TGG ACC GAT CCC GAG TAC TGG GTG GAC 2344
756  T   V   T   G   L   P   V   T   A   G   Q   W   T   D   P   E   Y   W   V   D   775

2345 CAG GTC CGC AGG CCC GTA CGC TTC CTC GAC GCC GTA CGC ACC CTG GAG GAA TCG GGC GCC 2404
776  Q   V   R   R   P   V   R   F   L   D   A   V   R   T   L   E   E   S   G   A   795

2405 GAC ACC TTC CTG GAG CTC GGT CCC GAC GGG GTC TGC TCC GCG ATG GCG GCG GAC TCC GTA 2464
796  D   T   F   L   E   L   G   P   D   G   V   C   S   A   M   A   A   D   S   V   815

2465 CGC GAC CAG GAG GCC GCC ACG GCG GTC TCC GCC CTG CGC AAG GGC CGC CCG GAG CCC CAG 2524
816  R   D   Q   E   A   A   T   A   V   S   A   L   R   K   G   R   P   E   P   Q   835

2525 TCG CTC CTC GCC GCA CTC ACC ACC GTC TTC GTC CGG GGC CAC GAC GTC GAC TGG ACC GCC 2584
836  S   L   L   A   A   L   T   T   V   F   V   R   G   H   D   V   D   W   T   A   855

2585 GCG CAC GGG AGC ACC GGC ACG GTC AGG GTG CCC CTG CCG ACC TAC GCC TTC CAG CGC GAA 2644
856  A   H   G   S   T   G   T   V   R   V   P   L   P   T   Y   A   F   Q   R   E   875

2645 CGC CAC TGG TTC GAC GGC GCC GCG CGA ACG GCG GCC CCG CTC ACG GCG GGC CGA TCG GGC 2704
876  R   H   W   F   D   G   A   A   R   T   A   A   P   L   T   A   G   R   S   G   895

2705 ACC GGT GCG GGC ACC GGC CCG GCC GCG GGT GTG ACG TCG GGC GAG GGC GAG GGC GAG GGC 2764
896  T   G   A   G   T   G   P   A   A   G   V   T   S   G   E   G   E   G   E   G   915

2765 GAG GGC GCG GGT GCG GGT GGC GGT GAT CGG CCG GCT CGC CAC GAG ACG ACC GAG CGC GTG 2824
916  E   G   A   G   A   G   G   G   D   R   P   A   R   H   E   T   T   E   R   V   935

2825 CGC GCA CAC GTC GCC GCC GTC CTC GAG TAC GAC GAC CCG ACC CGC GTC GAA CTC GGC CTC 2884
936  R   A   H   V   A   A   V   L   E   Y   D   D   P   T   R   V   E   L   G   L   955

2885 ACC TTC AAG GAG CTG GGC TTC GAC TCC CTC ATG TCC GTC GAG CTG CGG AAC GCG CTC GTC 2944
956  T   F   K   E   L   G   F   D   S   L   M   S   V   E   L   R   N   A   L   V   975

2945 GAC GAC ACG GGA CTG CGC CTG CCC AGC GGA CTG CTC TTC GAC CAC CCG ACG CCG CGC GCC 3004
976  D   D   T   G   L   R   L   P   S   G   L   L   F   D   H   P   T   P   R   A   995
```

FIG. 23B

```
3005 CTC GCC GCC CAC CTG GGC GAC CTG CTC ACC GGC GGC AGC GGC GAG ACC GGA TCG GCC GAC 3064
 996 L   A   A   H   L   G   D   L   L   T   G   G   S   G   E   T   G   S   A   D  1015

3065 GGG ATA CCG CCC GCG ACC CCG GCG GAC ACC ACC GCC GAG CCC ATC GCG ATC ATC GGC ATG 3124
1016 G   I   P   P   A   T   P   A   D   T   T   A   E   P   I   A   I   I   G   M  1035

3125 GCC TGC CGC TAC CCC GGC GGC GTC ACC TCC CCC GAG GAC CTG TGG CGG CTC GTC GCC GAG 3184
1036 A   C   R   Y   P   G   G   V   T   S   P   E   D   L   W   R   L   V   A   E  1055

3185 GGG CGC GAC GCC GTC TCG GGG CTG CCC ACC GAC CGC GGC TGG GAC GAG GAC CTC TTC GAC 3244
1056 G   R   D   A   V   S   G   L   P   T   D   R   G   W   D   E   D   L   F   D  1075

3245 GCC GAC CCC GAC CGC AGC GGC AAG AGC TCG GTC CGC GAG GGC GGA TTC CTG CAC GAC GCC 3304
1076 A   D   P   D   R   S   G   K   S   S   V   R   E   G   G   F   L   H   D   A  1095

3305 GCC CTG TTC GAC GCC GGC TTC TTC GGG ATA TCG CCC CGC GAG GCC CTC GGC ATG GAC CCG 3364
1096 A   L   F   D   A   G   F   F   G   I   S   P   R   E   A   L   G   M   D   P  1115

3365 CAG CAG CGG CTG CTC CTG GAG ACG GCA TGG GAG GCC GTG GAG CGC GCA GGG CTC GAC CCC 3424
1116 Q   Q   R   L   L   L   E   T   A   W   E   A   V   E   R   A   G   L   D   P  1135

3425 GAA GGC CTC AAG GGC AGC CGG ACG GCC GTC TTC GTC GGC GCC ACC GCC CTG GAC TAC GGC 3484
1136 E   G   L   K   G   S   R   T   A   V   F   V   G   A   T   A   L   D   Y   G  1155

3485 CCG CGC ATG CAC GAC GGC GCC GAG GGC GTC GAG GGC CAC CTC CTG ACC GGG ACC ACG CCC 3544
1156 P   R   M   H   D   G   A   E   G   V   E   G   H   L   L   T   G   T   T   P  1175

3545 AGC GTG ATG TCG GGC CGC ATC GCC TAC CAG CTC GGC CTC ACC GGT CCT GCG GTC ACC GTC 3604
1176 S   V   M   S   G   R   I   A   Y   Q   L   G   L   T   G   P   A   V   T   V  1195

3605 GAC ACG GCC TGC TCG TCC TCG CTC GTC GCG CTG CAC CTG GCC GTC CGT TCG CTG CGG CAG 3664
1196 D   T   A   C   S   S   S   L   V   A   L   H   L   A   V   R   S   L   R   Q  1215

3665 GGC GAG TCG AGC CTC GCG CTC GCC GGC GGA GCG ACC GTC ATG TCG ACA CCG GGC ATG TTC 3724
1216 G   E   S   S   L   A   L   A   G   G   A   T   V   M   S   T   P   G   M   F  1235

3725 GTC GAG TTC TCG CGG CAG CGC GGC CTC GCC GCC GAC GGC CGC TCC AAG GCC TTC TCC GAC 3784
1236 V   E   F   S   R   Q   R   G   L   A   A   D   G   R   S   K   A   F   S   D  1255

3785 TCC GCC GAC GGC ACC TCC TGG GCC GAG GGC GTC GGC CTC CTC GTC GTC GAG CGG CTC TCG 3844
1256 S   A   D   G   T   S   W   A   E   G   V   G   L   L   V   V   E   R   L   S  1275

3845 GAC GCC GAG CGC AAC GGC CAC CCC GTG CTC GCC GTG ATC CGG GGC AGC GCG GTC AAC CAG 3904
1276 D   A   E   R   N   G   H   P   V   L   A   V   I   R   G   S   A   V   N   Q  1295

3905 GAC GGC GCC TCC AAC GGG CTC ACC GCC CCC AAC GGC CCG TCC CAG CAG CGC GTC ATC CGA 3964
1296 D   G   A   S   N   G   L   T   A   P   N   G   P   S   Q   Q   R   V   I   R  1315

3965 CAG GCC CTG GCC GAC GCC GGG CTC ACC CCG GCC GAC GTC GAC GCC GTC GAG GCG CAC GGT 4024
1316 Q   A   L   A   D   A   G   L   T   P   A   D   V   D   A   V   E   A   H   G  1335

4025 ACG GGT ACC CGG CTC GGC GAC CCC ATC GAG GCC GAG GCG ATC CTC GGC ACC TAC GGC CGG 4084
1336 T   G   T   R   L   G   D   P   I   E   A   E   A   I   L   G   T   Y   G   R  1355

4085 GAC CGG GGC GAG GGC GCT CCG CTC CAG CTC GGC TCG CTG AAG TCG AAC ATC GGC CAC GCG 4144
1356 D   R   G   E   G   A   P   L   Q   L   G   S   L   K   S   N   I   G   H   A  1375

4145 CAG GCC GCC GCG GGC GTG GGC GGG CTC ATC AAG ATG GTC CTC GCG ATG CGC CAC GGC GTC 4204
1376 Q   A   A   A   G   V   G   G   L   I   K   M   V   L   A   M   R   H   G   V  1395

4205 CTG CCC AGG ACG CTC CAC GTG GAC CGG CCC ACC ACC CGC GTC GAC TGG GAG GCC GGC GGC 4264
1396 L   P   R   T   L   H   V   D   R   P   T   T   R   V   D   W   E   A   G   G  1415

4265 GTC GAG CTC CTC ACC GAG GAG CGG GAG TGG CCG GAG ACG GGC CGC CCG CGC CGC GCG GCG 4324
1416 V   E   L   L   T   E   E   R   E   W   P   E   T   G   R   P   R   R   A   A  1435

4325 ATC TCC TCC TTC GGC ATC AGC GGC ACC AAC GCC CAC ATC GTG GTC GAA CAG GCC CCG GAA 4384
1436 I   S   S   F   G   I   S   G   T   N   A   H   I   V   V   E   Q   A   P   E  1455

4385 GCC GGG GAG GCG GCG GTC ACC ACC ACC GCC CCG GAA GCA GGG GAA GCC GGG GAA GCG GCG 4444
1456 A   G   E   A   A   V   T   T   T   A   P   E   A   G   E   A   G   E   A   A  1475

4445 GAC ACC ACC GCC ACC ACG ACG CCG GCC GCG GTC GGC GTC CCC GAA CCC GTA CGC GCC CCC 4504
1476 D   T   T   A   T   T   P   A   A   V   G   V   P   E   P   V   R   A   P  1495

4505 GTC GTG GTC TCC GCG CGG GAC GCC GCC GCC CTG CGC GCC CAG GCC GTT CGG CTG CGG ACC 4564
1496 V   V   V   S   A   R   D   A   A   A   L   R   A   Q   A   V   R   L   R   T  1515
```

FIG. 23C

```
4565 TTC CTC GAC GGC CGA CCG GAC GTC ACC GTC GCC GAC CTC GGA CGC TCG CTG GCC GCC CGT 4624
1516 F   L   D   G   R   P   D   V   T   V   A   D   L   G   R   S   L   A   A   R   1535

4625 ACC GCC TTC GAG CAC AAG GCC GCC CTC ACC ACC GCC ACC AGG GAC GAG CTG CTC GCC GGG 4684
1536 T   A   F   E   H   K   A   A   L   T   T   A   T   R   D   E   L   L   A   G   1555

4685 CTC GAC GCC CTC GGC CGC GGG GAG CAA GCC ACG GGC CTG GTC ACC GGC GAA CCG GCC AGG 4744
1556 L   D   A   L   G   R   G   E   Q   A   T   G   L   V   T   G   E   P   A   R   1575

4745 GCC GGA CGC ACG GCC TTC CTG TTC ACC GGC CAG GGA GCG CAG CGC GTC GCC ATG GGC GAG 4804
1576 A   G   R   T   A   F   L   F   T   G   Q   G   A   Q   R   V   A   M   G   E   1595

4805 GAA CTG CGC GCC GCG CAC CCC GTG TTC GCC GCC GCC CTC GAC ACC GTG TAC GCG GCC CTC 4864
1596 E   L   R   A   A   H   P   V   F   A   A   A   L   D   T   V   Y   A   A   L   1615

4865 GAC CGT CAC CTC GAC CGG CCG CTG CGG GAG ATC GTC GCC GCC GGG GAG GAG CTG GAC CTC 4924
1616 D   R   H   L   D   R   P   L   R   E   I   V   A   A   G   E   E   L   D   L   1635

4925 ACC GCG TAC ACC CAG CCC GCC CTC TTC GCC TTC GAG GTG GCG CTG TTC CGC CTC CTC GAA 4984
1636 T   A   Y   T   Q   P   A   L   F   A   F   E   V   A   L   F   R   L   L   E   1655

4985 CAC CAC GGC CTC GTC CCC GAC CTG CTC ACC GGC CAC TCC GTC GGC GAG ATC GCC GCC GCG 5044
1656 H   H   G   L   V   P   D   L   L   T   G   H   S   V   G   E   I   A   A   A   1675

5045 CAC GTC GCC GGT GTC CTC TCC CTC GAC GAC GCC GCA CGT CTC GTC ACC GCC CGC GGC CGG 5104
1676 H   V   A   G   V   L   S   L   D   D   A   A   R   L   V   T   A   R   G   R   1695

5105 CTC ATG CAG TCG GCC CGC GAG GGC GGC GCG ATG ATC GCC GTG CAG GCG GGC GAG GCC GAG 5164
1696 L   M   Q   S   A   R   E   G   G   A   M   I   A   V   Q   A   G   E   A   E   1715

5165 GTC GTC GAG TCC CTG AAG GGC TAC GAG GGC AGG GTC GCC GTC GCC GCC GTC AAC GGA CCC 5224
1716 V   V   E   S   L   K   G   Y   E   G   R   V   A   V   A   A   V   N   G   P   1735

5225 ACC GCC GTG GTC GTC TCC GGC GAC GCG GAC GCC GCC GAG GAG ATC CGC GCC GTA TGG GCG 5284
1736 T   A   V   V   V   S   G   D   A   D   A   A   E   E   I   R   A   V   W   A   1755

5285 GGA CGC GGC CGG CGC ACC CGC AGG CTG CGC GTC AGC CAC GCC TTC CAC TCC CCG CAC ATG 5344
1756 G   R   G   R   R   T   R   R   L   R   V   S   H   A   F   H   S   P   H   M   1775

5345 GAC GAC GTC CTC GAC GAG TTC CTC CGG GTC GCC GAG GGC CTG ACC TTC GAG GAG CCG CGG 5404
1776 D   D   V   L   D   E   F   L   R   V   A   E   G   L   T   F   E   E   P   R   1795

5405 ATC CCC GTC GTC TCC ACG GTC ACC GGC GCG CTC GTC ACG TCC GGC GAG CTC ACC TCG CCC 5464
1796 I   P   V   V   S   T   V   T   G   A   L   V   T   S   G   E   L   T   S   P   1815

5465 GCG TAC TGG GTC GAC CAG ATC CGG CGG CCC GTG CGC TTC CTG GAC GCC GTC CGC ACC CTG 5524
1816 A   Y   W   V   D   Q   I   R   R   P   V   R   F   L   D   A   V   R   T   L   1835

5525 GCC GCC CAG GAC GCG ACC GTC CTC GTC GAG ATC GGC CCC GAC GCC GTC CTC ACG GCA CTC 5584
1836 A   A   Q   D   A   T   V   L   V   E   I   G   P   D   A   V   L   T   A   L   1855

5585 GCC GAG GAG GCT CTC GCG CCC GGC ACG GAC GCC CCG GAC GCC CGG GAC GTC ACG GTC GTC 5644
1856 A   E   E   A   L   A   P   G   T   D   A   P   D   A   R   D   V   T   V   V   1875

5645 CCG CTG CTG CGC GCG GGG CGC CCC GAG CCC GAG ACC CTC GCC GCC GGT CTC GCG ACC GCC 5704
1876 P   L   L   R   A   G   R   P   E   P   E   T   L   A   A   G   L   A   T   A   1895

5705 CAT GTC CAC GGC GCA CCC TTG GAC CGG GCG TGG TTC TTC CCG GAC GGG CGC CGC ACG GAC 5764
1896 H   V   H   G   A   P   L   D   R   A   S   F   F   P   D   G   R   R   T   D   1915

5765 CTG CCC ACG TAC GCC TTC CGG CGC GAG CAC TAC TGG CTG ACG CCC GAG GCC CGT ACG GAC 5824
1916 L   P   T   Y   A   F   R   R   E   H   Y   W   L   T   P   E   A   R   T   D   1935

5825 GCC CGC GCA CTC GGC TTC GAC CCG GCG CGG CAC CCG CTG CTG ACG ACC ACG GTC GAG GTC 5884
1936 A   R   A   L   G   F   D   P   A   R   H   P   L   L   T   T   T   V   E   V   1955

5885 GCC GGC GGC GAC GGC GTC CTG CTG ACC GGC CGT CTC TCC CTG ACC GAC CAG CCC TGG CTG 5944
1956 A   G   G   D   G   V   L   L   T   G   R   L   S   L   T   D   Q   P   W   L   1975

5945 GCC GAC CAC ATG GTC AAC GGC GCC GTC CTG TTG CCG GCC ACC GCC TTC CTG GAG CTC GCC 6004
1976 A   D   H   M   V   N   G   A   V   L   L   P   A   T   A   F   L   E   L   A   1995

6005 CTC GCG GCG GGC GAC CAC GTC GGG GCG GTC CGG GTG GAG GAA CTC ACC CTC GAA GCG CCG 6064
1996 L   A   A   G   D   H   V   G   A   V   R   V   E   E   L   T   L   E   A   P   2015

6065 CTC GTC CTG CCC GAG CGG GGC GCC GTC CGC ATC CAG GTC GGC GTG AGC GGC GAC GGC GAG 6124
2016 L   V   L   P   E   R   G   A   V   R   I   Q   V   G   V   S   G   D   G   E   2035
```

FIG. 23D

```
6125 TCG CCG GCC GGG CGC ACC TTC GGT GTG TAC AGC ACC CCC GAC TCC GGC GAC ACC GGT GAC 6184
2036  S   P   A   G   R   T   F   G   V   Y   S   T   P   D   S   G   D   T   G   D  2055

6185 GAC GCG CCC CGG GAG TGG ACC CGC CAT GTC TCC GGC GTA CTC GGC GAA GGG GAC CCG GCC 6244
2056  D   A   P   R   E   W   T   R   H   V   S   G   V   L   G   E   G   D   P   A  2075

6245 ACG GAG TCG GAC CAC CCC GGC ACC GAC GGG GAC GGT TCA GCG GCC TGG CCG CCT GCG GCG 6304
2076  T   E   S   D   H   P   G   T   D   G   D   G   S   A   A   W   P   P   A   A  2095

6305 GCG ACC GCC ACA CCC CTC GAC GGC GTC TAC GAC CGG CTC GCG GAG CTC GGC TAC GGA TAC 6364
2096  A   T   A   T   P   L   D   G   V   Y   D   R   L   A   E   L   G   Y   G   Y  2115

6365 GGT CCG GCC TTC CAG GGC CTG ACG GGC CTG TGG CGC GAC GGC GCC GAC ACG CTC GCC GAG 6424
2116  G   P   A   F   Q   G   L   T   G   L   W   R   D   G   A   D   T   L   A   E  2135

6425 ATC CGG CTG CCC GCG GCG CAG CAC GAG AGC GCG GGG CTC TTC GGC GTA CAC CCG GCG CTG 6484
2136  I   R   L   P   A   A   Q   H   E   S   A   G   L   F   G   V   H   P   A   L  2155

6485 CTC GAC GCG GCG CTC CAC CCG ATC GTC CTG GAG GGC AAC TCA GCT GCC GGT GCC TGT GAC 6544
2156  L   D   A   A   L   H   P   I   V   L   E   G   N   S   A   A   G   A   C   D  2175

6545 GCC GAT ACC GAC GCG ACC GAC CGG ATC CGG CTG CCG TTC GCG TGG GCG GGG GTG ACC CTC 6604
2176  A   D   T   D   A   T   D   R   I   R   L   P   F   A   W   A   G   V   T   L  2195

6605 CAC GCC GAA GGG GCC ACC GCG CTC CGC GTA CGG ATC ACA CCC ACC GGC CCG GAC ACG GTC 6664
2196  H   A   E   G   A   T   A   L   R   V   R   I   T   P   T   G   P   D   T   V  2215

6665 ACG CTC CGC CTC ACC GAC ACC ACC GGT GCG CCC GTG GCC ACC GTG GAG TCC CTG ACC CTG 6724
2216  T   L   R   L   T   D   T   T   G   A   P   V   A   T   V   E   S   L   T   L  2235

6725 CGC GCG GTG GCG AAG GAC CGG CTG GGC ACC ACC GCC GGG CGC GTC GAC GAC GCC CTG TTC 6784
2236  R   A   V   A   K   D   R   L   G   T   T   A   G   R   V   D   D   A   L   F  2255

6785 ACG GTC GTG TGG ACG GAG ACC GGC ACA CCG GAA CCC GCA GGG CGC GGA GCC GTG GAG GTC 6844
2256  T   V   V   W   T   E   T   G   T   P   E   P   A   G   R   G   A   V   E   V  2275

6845 GAG GAA CTC GTC GAC CTC GCC GGC CTC GGC GAC CTC GTG GAG CTC GGC GCC GCG GAC GTC 6904
2276  E   E   L   V   D   L   A   G   L   G   D   L   V   E   L   G   A   A   D   V  2295

6905 GTC CTC CGG GCC GAC CGC TGG ACG CTC GAC GGG GAC CCG TCC GCC GCC GCG CGC ACA GCC 6964
2296  V   L   R   A   D   R   W   T   L   D   G   D   P   S   A   A   A   R   T   A  2315

6965 GTC CGG CGC ACC CTC GCC ATC GTC CAG GAG TTC CTG TCC GAG CCG CGC TTC GAC GGC TCG 7024
2316  V   R   R   T   L   A   I   V   Q   E   F   L   S   E   P   R   F   D   G   S  2335

7025 CGA CTG GTG TGC GTC ACC AGG GGC GCG GTC GCC GCA CTC CCC GGC GAG GAC GTC ACC TCC 7084
2336  R   L   V   C   V   T   R   G   A   V   A   A   L   P   G   E   D   V   T   S  2355

7085 CTC GCC ACC GGC CCC CTC TGG GGC CTC GTC CGC TCC GCC CAG TCC GAG AAC CCG GGA CGC 7144
2356  L   A   T   G   P   L   W   G   L   V   R   S   A   Q   S   E   N   P   G   R  2375

7145 CTG TTC CTC CTG GAC CTG GGT GAA GGC GAA GGC GAG CGC GAC GGA GCC GAG GAG CTG ATC 7204
2376  L   F   L   L   D   L   G   E   G   E   G   E   R   D   G   A   E   E   L   I  2395

7205 CGC GCG GCC ACG GCC GGG GAC GAG CCG CAG CTC GCG GCA CGG GAC GGC CGA CTG CTC GCG 7264
2396  R   A   A   T   A   G   D   E   P   Q   L   A   A   R   D   G   R   L   L   A  2415

7265 CCG AGG CTG GCC CGT ACC GCC GCC CTT TCG AGT GAG GAC ACC GCC GGC GCC GAC CGT 7324
2416  P   R   L   A   R   T   A   A   L   S   S   E   D   T   A   G   A   D   R  2435

7325 TTC GGC CCC GAC GGC ACC GTC CTC GTC ACC GGG GGC ACC GGA GGC CTC GGA GCG CTC CTC 7384
2436  F   G   P   D   G   T   V   L   V   T   G   G   T   G   G   L   G   A   L   L  2455

7385 GCC CGC CAC CTC GTG GAG CGT CAC GGG GTG CGC CGG CTG CTG CTG GTG AGC CGC CGC GGG 7444
2456  A   R   H   L   V   E   R   H   G   V   R   R   L   L   L   V   S   R   R   G  2475

7445 GCC GAC GCC CCC GGC GCG GCC GAC CTG GGC GAG GAC CTC GCG GGC CTC GGC GCG GAG GTG 7504
2476  A   D   A   P   G   A   A   D   L   G   E   D   L   A   G   L   G   A   E   V  2495

7505 GCG TTC GCC GCC GCC GAC GCC GCC GAC CGC GAG AGC CTG GCG CGG GCG ATC GCC ACC GTG 7564
2496  A   F   A   A   A   D   A   A   D   R   E   S   L   A   R   A   I   A   T   V  2515

7565 CCC GCC GAG CAT CCG CTG ACG GCC GTC GTG CAC ACG GCG GGA GTC GTC GAC GAC GCG ACG 7624
2516  P   A   E   H   P   L   T   A   V   V   H   T   A   G   V   V   D   D   A   T  2535

7625 GTG GAG GCG CTC ACA CCG GAA CGG CTG GAC GCG GTA CTG CGC CCG AAG GTC GAC GCC GCG 7684
2536  V   E   A   L   T   P   E   R   L   D   A   V   L   R   P   K   V   D   A   A  2555
```

```
7685 TGG AAC CTG CAC GAG CTC ACC AAG GAC CTG CGG CTC GAC GCC TTC GTC CTC TTC TCC TCC 7744
2556  W   N   L   H   E   L   T   K   D   L   R   L   D   A   F   V   L   F   S   S  2575

7745 GTC TCC GGC ATC GTC GGC ACC GCC GGC CAG GCC AAC TAC GCG GCG GCC AAC ACG GGC CTC 7804
2576  V   S   G   I   V   G   T   A   G   Q   A   N   Y   A   A   A   N   T   G   L  2595

7805 GAC GCC CTC GCC GCC CAC CGC GCC GCC ACG GGC CTG GCC GCC ACG TCG CTG GCC TGG GGC 7864
2596  D   A   L   A   A   H   R   A   A   T   G   L   A   A   T   S   L   A   W   G  2615

7865 CTC TGG GAC GGC ACG CAC GGC ATG GGC GGC ACG CTC GGC GCC GCC GAC CTC GCC CGC TGG 7924
2616  L   W   D   G   T   H   G   M   G   G   T   L   G   A   A   D   L   A   R   W  2635

7925 AGC CGG GCC GGA ATC ACC CCG CTC ACC CCG CTG CAG GGC CTC GCG CTC TTC GAC GCC GCG 7984
2636  S   R   A   G   I   T   P   L   T   P   L   Q   G   L   A   L   F   D   A   A  2655

7985 GTC GCC AGG GAC GAC GCC CTC CTC GTA CCC GCC GGG CTC CGT CCC ACC GCC CAC CGG GGC 8044
2656  V   A   R   D   D   A   L   L   V   P   A   G   L   R   P   T   A   H   R   G  2675

8045 ACG GAC GGA CAG CCT CCT GCG CTG TGG CGC GGC CTC GTC CGG GCG CGC CCG CGC CGT GCC 8104
2676  T   D   G   Q   P   P   A   L   W   R   G   L   V   R   A   R   P   R   R   A  2695

8105 GCG CGG ACG GCC GCC GAG GCG GCG GAC ACG ACC GGC GGC TGG CTG AGC GGG CTC GCC GCA 8164
2696  A   R   T   A   A   E   A   A   D   T   T   G   G   W   L   S   G   L   A   A  2715

8165 CAG TCC CCC GAG GAG CGG CGC AGC ACA GCC GTC ACG CTC GTG ACG GGT GTC GTC GCG GAC 8224
2716  Q   S   P   E   E   R   R   S   T   A   V   T   L   V   T   G   V   V   A   D  2735

8225 GTC CTC GGG CAC GCC GAC TCC GCC GCG GTC GGG GCG GAG CGG TCC TTC AAG GAC CTC GGC 8284
2736  V   L   G   H   A   D   S   A   A   V   G   A   E   R   S   F   K   D   L   G  2755

8285 TTC GAC TCC CTG GCC GGG GTG GAG CTC CGC AAC CGG CTG AAC GCC GCC ACC GGC CTG CGG 8344
2756  F   D   S   L   A   G   V   E   L   R   N   R   L   N   A   A   T   G   L   R  2775

8345 CTC CCC GCG ACC ACG GTC TTC GAC CAT CCC TCG CCG GCC GCG CTC GCG TCC CAT CTC CTC 8404
2776  L   P   A   T   T   V   F   D   H   P   S   P   A   A   L   A   S   H   L   L  2795

8405 GCC CAG GTG CCC GGG TTG AAG GAG GGG ACG GCG GCG ACC GCG ACC GTC GTG GCC GAG CGG 8464
2796  A   Q   V   P   G   L   K   E   G   T   A   A   T   A   T   V   V   A   E   R  2815

8465 GGC GCT TCC TTC GGT GAC CGT GCG ACC GAC GAC GAT CCG ATC GCG ATC GTG GGC ATG GCA 8524
2816  G   A   S   F   G   D   R   A   T   D   D   D   P   I   A   I   V   G   M   A  2835

8525 TGC CGC TAT CCG GGT GGT GTG TCG TCG CCG GAG GAC CTG TGG CGG CTG GTG GCC GAG GGG 8584
2836  C   R   Y   P   G   G   V   S   S   P   E   D   L   W   R   L   V   A   E   G  2855

8585 ACG GAC GCG ATC AGC GAG TTC CCC GTC AAC CGC GGC TGG GAC CTG GAG AGC CTC TAC GAC 8644
2856  T   D   A   I   S   E   F   P   V   N   R   G   W   D   L   E   S   L   Y   D  2875

8645 CCG GAT CCC GAG TCG AAG GGC ACC ACG TAC TGC CGG GAG GGC GGG TTC CTG GAA GGC GCC 8704
2876  P   D   P   E   S   K   G   T   T   Y   C   R   E   G   G   F   L   E   G   A  2895

8705 GGT GAC TTC GAC GCC GCC TTC TTC GGC ATC TCG CCG CGC GAG GCC CTG GTG ATG GAC CCG 8764
2896  G   D   F   D   A   A   F   F   G   I   S   P   R   E   A   L   V   M   D   P  2915

8765 CAG CAG CGG CTG CTG CTG GAG GTG TCC TGG GAG GCG CTG GAA CGC GCG GGC ATC GAC CCG 8824
2916  Q   Q   R   L   L   L   E   V   S   W   E   A   L   E   R   A   G   I   D   P  2935

8825 TCC TCG CTG CGC GGC AGC CGC GGT GGT GTC TAC GTG GGC GCC GCG CAC GGC TCG TAC GCC 8884
2936  S   S   L   R   G   S   R   G   G   V   Y   V   G   A   A   H   G   S   Y   A  2955

8885 TCC GAT CCC CGG CTG GTG CCC GAG GGC TCG GAG GGC TAT CTG CTG ACC GGC AGC GCC GAC 8944
2956  S   D   P   R   L   V   P   E   G   S   E   G   Y   L   L   T   G   S   A   D  2975

8945 GCG GTG ATG TCC GGC CGC ATC TCC TAC GCG CTC GGT CTC GAA GGA CCG TCC ATG ACG GTG 9004
2976  A   V   M   S   G   R   I   S   Y   A   L   G   L   E   G   P   S   M   T   V  2995

9005 GAG ACG GCC TGC TCC TCC TCG CTG GTG GCG CTG CAT CTG GCG GTA CGG GCG CTG CGG CAC 9064
2996  E   T   A   C   S   S   S   L   V   A   L   H   L   A   V   R   A   L   R   H  3015

9065 GGC GAG TGC GGG CTC GCG CTG GCG GGC GGG GTG GCG GTG ATG GCC GAT CCG GCG GCG TTC 9124
3016  G   E   C   G   L   A   L   A   G   G   V   A   V   M   A   D   P   A   A   F  3035

9125 GTG GAG TTC TCC CGG CAG AAG GGG CTG GCC GCC GAC GGC CGC TGC AAG GCG TTC TCG GCC 9184
3036  V   E   F   S   R   Q   K   G   L   A   A   D   G   R   C   K   A   F   S   A  3055

9185 GCC GCC GAC GGC ACC GGC TGG GCC GAG GGC GTC GGC GTG CTC GTC CTG GAG CGG CTG TCG 9244
3056  A   A   D   G   T   G   W   A   E   G   V   G   V   L   V   L   E   R   L   S  3075
```

FIG. 23F

```
9245 GAC GCG CGC CGC GCG GGG CAC ACG GTC CTC GGC CTG GTC ACC GGC ACC GCG GTC AAC CAG 9304
3076 D   A   R   R   A   G   H   T   V   L   G   L   V   T   G   T   A   V   N   Q   3095

9305 GAC GGT GCC TCC AAC GGG CTG ACC GCG CCC AAC GGC CCA GCC CAG CAA CGC GTC ATC GCC 9364
3096 D   G   A   S   N   G   L   T   A   P   N   G   P   A   Q   Q   R   V   I   A   3115

9365 GAG GCG CTC GCC GAC GCC GGG CTG TCC CCG GAG GAC GTG GAC GCG GTC GAG GCG CAC GGC 9424
3116 E   A   L   A   D   A   G   L   S   P   E   D   V   D   A   V   E   A   H   G   3135

9425 ACC GGC ACC CGG CTC GGC GAC CCC ATC GAG GCC GGG GCG CTG CTC GCC GCC TCC GGA CGG 9484
3136 T   G   T   R   L   G   D   P   I   E   A   G   A   L   L   A   A   S   G   R   3155

9485 AAC CGT TCC GGC GAC CAC CCG CTG TGG CTC GGC TCG CTG AAG TCC AAC ATC GGG CAT GCC 9544
3156 N   R   S   G   D   H   P   L   W   L   G   S   L   K   S   N   I   G   H   A   3175

9545 CAG GCC GCC GCC GGT GTC GGC GGC GTC ATC AAG ATG CTC CAG GCG CTG CGG CAC GGC TTG 9604
3176 Q   A   A   A   G   V   G   G   V   I   K   M   L   Q   A   L   R   H   G   L   3195

9605 CTG CCC CGC ACC CTC CAC GCC GAC GAG CCG ACC CCG CAT GCC GAC TGG AGC TCC GGC CGG 9664
3196 L   P   R   T   L   H   A   D   E   P   T   P   H   A   D   W   S   S   G   R   3215

9665 GTA CGG CTG CTC ACC TCC GAG GTG CCG TGG CAG CGG ACC GGC CGG CCC CGG CGG ACC GGG 9724
3216 V   R   L   L   T   S   E   V   P   W   Q   R   T   G   R   P   R   R   T   G   3235

9725 GTG TCC GCC TTC GGC GTC GGC GGC ACC AAT GCC CAT GTC GTC CTC GAA GAG GCA CCC GCC 9784
3236 V   S   A   F   G   V   G   G   T   N   A   H   V   V   L   E   E   A   P   A   3255

9785 CCG CCC GCG CCG GAA CCG GCC GGG GAG GCC CCC GGC GGC TCC CGC GCC GCA GAA GGG GCG 9844
3256 P   P   A   P   E   P   A   G   E   A   P   G   G   S   R   A   A   E   G   A   3275

9845 GAA GGG CCC CTG GCC TGG GTG GTC TCC GGA CGC GAC GAG CCG GCC CTG CGG TCC CAG GCC 9904
3276 E   G   P   L   A   W   V   V   S   G   R   D   E   P   A   L   R   S   Q   A   3295

9905 CGG CGG CTC CGC GAC CAC CTC TCC CGC ACC CCC GGG GCC CGC CCG CGT GAC ATC GCC TTC 9964
3296 R   R   L   R   D   H   L   S   R   T   P   G   A   R   P   R   D   I   A   F   3315

9965 TCC CTC GCC GCC ACG CGC GCA GCC TTT GAC CAC CGC GCC GTG CTG ATC GGC TCG GAC GGG 10024
3316 S   L   A   A   T   R   A   A   F   D   H   R   A   V   L   I   G   S   D   G   3335

10025 GCC GAA CTC GCC GCC GCC CTG GAC GCG TTG GCC GAA GGA CGC GAC GGT CCG GCG GTG GTG 10084
3336  A   E   L   A   A   A   L   D   A   L   A   E   G   R   D   G   P   A   V   V   3355

10085 CGC GGA GTC CGC GAC CGG GAC GGC AGG ATG GCC TTC CTC TTC ACC GGG CAG GGC AGC CAG 10144
3356  R   G   V   R   D   R   D   G   R   M   A   F   L   F   T   G   Q   G   S   Q   3375

10145 CGC GCC GGG ATG GCC CAC GAC CTG CAT GCC GCC CAT ACC TTC TTC GCG TCC GCC CTC GAC 10204
3376  R   A   G   M   A   H   D   L   H   A   A   H   T   F   F   A   S   A   L   D   3395

10205 GAG GTG ACG GAC CGT CTC GAC CCG CTG CTC GGC CGG CCG CTC GGC GCG CTG CTG GAC GCC 10264
3396  E   V   T   D   R   L   D   P   L   L   G   R   P   L   G   A   L   L   D   A   3415

10265 CGA CCC GGC TCG CCC GAA GCG GCA CTC CTG GAC CGG ACC GAG TAC ACC CAG CCG GCG CTC 10324
3416  R   P   G   S   P   E   A   A   L   L   D   R   T   E   Y   T   Q   P   A   L   3435

10325 TTC GCC GTC GAG GTG GCG CTC CAC CGG CTG CTG GAG CAC TGG GGG ATG CGC CCC GAC CTG 10384
3436  F   A   V   E   V   A   L   H   R   L   L   E   H   W   G   M   R   P   D   L   3455

10385 CTG CTG GGG CAC TCG GTG GGC GAA CTG GCG GCC GCC CAC GTC GCG GGT GTG CTC GAT CTC 10444
3456  L   L   G   H   S   V   G   E   L   A   A   A   H   V   A   G   V   L   D   L   3475

10445 CAC GAC GCC TGC GCG CTG GTG GCC GCC CGC GGC AGG CTG ATG CAG CGC CTG CCG CCC GGC 10504
3476  D   D   A   C   A   L   V   A   A   R   G   R   L   M   Q   R   L   P   P   G   3495

10505 GGC GCG ATG GTC TCC GTG CGG GCC GGC GAG GAC GAG GTC CGC GCA CTG CTG GCC GGC CGC 10564
3496  G   A   M   V   S   V   R   A   G   E   D   E   V   R   A   L   L   A   G   R   3515

10565 GAG GAC GCC GTC TGC GTC GCC GCG GTG AAC GGC CCC CGG TCG GTG GTG ATC TCC GGC GCG 10624
3516  E   D   A   V   C   V   A   A   V   N   G   P   R   S   V   V   I   S   G   A   3535

10625 GAG GAA GCG GTG GCC GAG GCG GCG GCG CAG CTC GCC GGA CGA GGC CGC CGC ACC AGG CGG 10684
3536  E   E   A   V   A   E   A   A   A   Q   L   A   G   R   G   R   R   T   R   R   3555

10685 CTC CGC GTC GCG CAC GCC TTC CAC TCA CCC CTG ATG GAC GGC ATG CTC GCC GGA TTC CGG 10744
3556  L   R   V   A   H   A   F   H   S   P   L   M   D   G   M   L   A   G   F   R   3575

10745 GAG GTC GCC GCC GGC CTG CGC TAC CGG GAA CCG GAG CTG ACG GTC GTC TCC ACG GTC ACG 10804
3576  E   V   A   A   G   L   R   Y   R   E   P   E   L   T   V   V   S   T   V   T   3595
```

FIG. 23G

```
10805 GGG CGG CCC GCC CGC CCC GGT GAA CTC ACC GGC CCC GAC TAC TGG GTG GCC CAG GTC CGT 10864
3596  G   R   P   A   R   P   G   E   L   T   G   P   D   Y   W   V   A   Q   V   R   3615

10865 GAG CCC GTG CGC TTC GCG GAC GCG GTC CGC ACG GCA CAC CGC CTC GGA GCC CGC ACC TTC 10924
3616  E   P   V   R   F   A   D   A   V   R   T   A   H   R   L   G   A   R   T   F   3635

10925 CTG GAG ACC GGC CCG GAC GGC GTG CTG TGC GGC ATG GCA GAG GAG TGC CTG GAG GAC GAC 10984
3636  L   E   T   G   P   D   G   V   L   C   G   M   A   E   E   C   L   E   D   D   3655

10985 ACC GTG GCC CTG CTG CCG GCG ATC CAC AAG CCC GGC ACC GCG CCG CAC GGT CCG GCG GCT 11044
3656  T   V   A   L   L   P   A   I   H   K   P   G   T   A   P   H   G   P   A   A   3675

11045 CCC GGC GCG CTG CGG GCG GCC GCC GCC GCG TAC GGC CGG GGC GCC CGG GTG GAC TGG GCC 11104
3676  P   G   A   L   R   A   A   A   A   A   Y   G   R   G   A   R   V   D   W   A   3695

11105 GGG ATG CAC GCC GAC GGC CCC GAG GGG CCG GCC CGC CGC GTC GAA CTG CCC GTC CAC GCC 11164
3696  G   M   H   A   D   G   P   E   G   P   A   R   R   V   E   L   P   V   H   A   3715

11165 TTC CGG CAC CGC CGC TAC TGG CTC GCC CCG GGC CGC GCG GCG GAC ACC GAC GAC TGG ATG 11224
3716  F   R   H   R   R   Y   W   L   A   P   G   R   A   A   D   T   D   D   W   M   3735

11225 TAC CGG ATC GGC TGG GAC CGG CTG CCG GCT GTG ACC GGC GGG GCC CGG ACC GCC GGC CGC 11284
3736  Y   R   I   G   W   D   R   L   P   A   V   T   G   G   A   R   T   A   G   R   3755

11285 TGG CTG GTG ATC CAC CCC GAC AGC CCG CGC TGC CGG GAG CTG TCC GGC CAC GCC GAA CGC 11344
3756  W   L   V   I   H   P   D   S   P   R   C   R   E   L   S   G   H   A   E   R   3775

11345 GCG CTG CGC GCC GCG GGC GCG AGC CCC GTA CCG CTG CCC GTG GAC GCT CCG GCC GCC GAC 11404
3776  A   L   R   A   A   G   A   S   P   V   P   L   P   V   D   A   P   A   A   D   3795

11405 CGG GCG TCC TTC GCG GCA CTG CTG CGC TCC GCC ACC GGA CCT GAC ACA CGA GGT GAC ACA 11464
3796  R   A   S   F   A   A   L   L   R   S   A   T   G   P   D   T   R   G   D   T   3815

11465 GCC GCG CCC GTG GCC GGT GTG CTG TCG CTG CTG TCC GAG GAG GAT CGG CCC CAT CGC CAG 11524
3816  A   A   P   V   A   G   V   L   S   L   L   S   E   E   D   R   P   H   R   Q   3835

11525 CAC GCC CCG GTA CCC GCC GGG GTC CTG GCG ACG CTG TCC CTG ATG CAG GCT ATG GAG GAG 11584
3836  H   A   P   V   P   A   G   V   L   A   T   L   S   L   M   Q   A   M   E   E   3855

11585 GAG GCG GTG GAG GCT CGC GTG TGG TGC GTC TCC CGC GCC GCG GTC GCC GCC GCC GAC CGG 11644
3856  E   A   V   E   A   R   V   W   C   V   S   R   A   A   V   A   A   A   D   R   3875

11645 GAA CGG CCC GTC GGC GCG GGC GCC GCC CTG TGG GGG CTG GGG CGG GTG GCC GCC CTG GAA 11704
3876  E   R   P   V   G   A   G   A   A   L   W   G   L   G   R   V   A   A   L   E   3895

11705 CGC CCC ACC CGG TGG GGC GGT CTC GTG GAC CTG CCC GCC TCG CCC GGT GCG GCG CAC TGG 11764
3896  R   P   T   R   W   G   G   L   V   D   L   P   A   S   P   G   A   A   H   W   3915

11765 GCG GCC GCC GTG GAA CGG CTC GCC GGT CCC GAG GAC CAG ATC GCC GTG CGC GCG TCC GGC 11824
3916  A   A   A   V   E   R   L   A   G   P   E   D   Q   I   A   V   R   A   S   G   3935

11825 AGT TGG GGC CGG CGC CTC ACC AGG CTG CCG CGC GAC GGC GGC GGC CGG ACG GCC GCA CCC 11884
3936  S   W   G   R   R   L   T   R   L   P   R   D   G   G   R   T   A   A   P   3955

11885 GCG TAC CGG CCG CGC GGC ACG GTG CTC GTC ACC GGT GGC ACC GGC GCG CTC GGC GGG CAT 11944
3956  A   Y   R   P   R   G   T   V   L   V   T   G   G   T   G   A   L   G   G   H   3975

11945 CTC GCC CGC TGG CTC GCC GCG GCG GGC GCC GAA CAC CTG GCG CTC ACC AGC CGC CGG GGC 12004
3976  L   A   R   W   L   A   A   A   G   A   E   H   L   A   L   T   S   R   R   G   3995

12005 CCG GAC GCG CCC GGC GCC GCC GGA CTC GAG GCC GAA CTC CTC CTC CTG GCC GCC AAG GTG 12064
3996  P   D   A   P   G   A   A   G   L   E   A   E   L   L   L   L   G   A   K   V   4015

12065 ACG TTC GCC GCC TGC GAC ACC GCC GAC CGC GAC GGC CTC GCC CGG GTC CTG CGG GCG ATA 12124
4016  T   F   A   A   C   D   T   A   D   R   D   G   L   A   R   V   L   R   A   I   4035

12125 CCG GAG GAC ACC CCG CTC ACC GCG GTG TTC CAC GCC GCG GGC GTA CCG CAG GTC ACG CCG 12184
4036  P   E   D   T   P   L   T   A   V   F   H   A   A   G   V   P   Q   V   T   P   4055

12185 CTG TCC CGT ACC TCG CCC GAG CAC TTC GCC GAC GTG TAC GCG GGC AAG GCG GCG GGC GCC 12244
4056  L   S   R   T   S   P   E   H   F   A   D   V   Y   A   G   K   A   A   G   A   4075

12245 GCG CAC CTG GAC GAA CTG ACC CGC GAA CTC GGC GCC GGA CTC GAC GCG TTC GTC CTC TAC 12304
4076  A   H   L   D   E   L   T   R   E   L   G   A   G   L   D   A   F   V   L   Y   4095

12305 TCC TCC GGC GCC GGC GTC TGG GGC AGC GCC GGC CAG GGT GCC TAC GCC GCC GCC AAC GCC 12364
4096  S   S   G   A   G   V   W   G   S   A   G   Q   G   A   Y   A   A   A   N   A   4115
```

FIG. 23H

```
12365 GCC CTG GAC GCG CTC GCC CGG CGC CGT GCG GCG GAC GGA CTC CCC GCC ACC TCC ATC GCC 12424
 4116 A   L   D   A   L   A   R   R   R   A   A   D   G   L   P   A   T   S   I   A   4135

12425 TGG GGC GTG TGG GGC GGC GGC GGT ATG GGG GCC GAC GAG GCG GGC GCG GAG TAT CTG GGC 12484
 4136 W   G   V   W   G   G   G   G   M   G   A   D   E   A   G   A   E   Y   L   G   4155

12485 CGG CGC GGT ATG CGC CCC ATG GCA CCG GTC TCC GCG CTC CGG GCG ATG GCC ACC GCC ATC 12544
 4156 R   R   G   M   R   P   M   A   P   V   S   A   L   R   A   M   A   T   A   I   4175

12545 GCC TCC GGG GAA CCC TGC CCC ACC GTC ACC CAC ACC GAC TGG GAG CGC TTC GGC GAG GGC 12604
 4176 A   S   G   E   P   C   P   T   V   T   H   T   D   W   E   R   F   G   E   G   4195

12605 TTC ACC GCC TTC CGG CCC AGC CCT CTG ATC GCG GGC CTC GGC ACG CCG GGC GGC GGC CGG 12664
 4196 F   T   A   F   R   P   S   P   L   I   A   G   L   G   T   P   G   G   G   R   4215

12665 GCG GCG GAG ACC CCC GAG GAG GGG AAC GCC ACC GCT GCG GCG GAC CTC ACC GCC CTG CCG 12724
 4216 A   A   E   T   P   E   E   G   N   A   T   A   A   A   D   L   T   A   L   P   4235

12725 CCC GCC GAA CTC CGC ACC GCG CTG CGC GAG CTG GTG CGA GCC CGG ACC GCC GCG GCG CTC 12784
 4236 P   A   E   L   R   T   A   L   R   E   L   V   R   A   R   T   A   A   A   L   4255

12785 GGC CTC GAC GAC CCG GCC GAG GTC GCC GAG GGC GAA CGG TTC CCC GCC ATG GGC TTC GAC 12844
 4256 G   L   D   D   P   A   E   V   A   E   G   E   R   F   P   A   M   G   F   D   4275

12845 TCC CTG GCC ACC GTA CGG CTG CGC CGC GGA CTC GCC TCG GCC ACG GGC CTC GAC CTG CCC 12904
 4276 S   L   A   T   V   R   L   R   R   G   L   A   S   A   T   G   L   D   L   P   4295

12905 CCC GAT CTG CTC TTC GAC CGG GAC ACC CCG GCC GCG CTC GCC GCC CAC CTG GCC GAA CTG 12964
 4296 P   D   L   F   D   R   D   T   P   A   A   L   A   A   H   L   A   E   L   4315

12965 CTC GCC ACC GCA CGG GAC CAC GGA CCC GGC GGC CCC GGG ACC GGT GCC GCG CCG GCC GAT 13024
 4316 L   A   T   A   R   D   H   G   P   G   G   P   G   T   G   A   A   P   A   D   4335

13025 GCC GGA AGC GGC CTG CCG GCC CTC TAC CGG GAG GCC GTC CGC ACC GGC CGG GCC GCG GAA 13084
 4336 A   G   S   G   L   P   A   L   Y   R   E   A   V   R   T   G   R   A   A   E   4355

13085 ATG GCC GAA CTG CTC GCC GCC GCT TCC CGG TTC CGC CCC GCC TTC GGG ACG GCG GAC CGG 13144
 4356 M   A   E   L   L   A   A   A   S   R   F   R   P   A   F   G   T   A   D   R   4375

13145 CAG CCG GTG GCC CTC GTG CCG CTG GCC GAC GGC GCG GAG GAC ACC GGG CTC CCG CTG CTC 13204
 4376 Q   P   V   A   L   V   P   L   A   D   G   A   E   D   T   G   L   P   L   L   4395

13205 GTG GGC TGC GCC GGG ACG GCG GTG GCC TCC GGC CCG GTG GAG TTC ACC GCC TTC GCC GGA 13264
 4396 V   G   C   A   G   T   A   V   A   S   G   P   V   E   F   T   A   F   A   G   4415

13265 GCG CTG GCG GAC CTC CCG GCG GCG GCC CGG ATG GCC GCG CTG CCG CAG CCC GGC TTT CTG 13324
 4416 A   L   A   D   L   P   A   A   A   R   M   A   A   L   P   Q   P   G   F   L   4435

13325 CCG GGA GAA CGA GTC CCG GCC ACC CCG GAG GCA TTG TTC GAG GCC CAG GCG GAA GCG CTG 13384
 4436 P   G   E   R   V   P   A   T   P   E   A   L   F   E   A   Q   A   E   A   L   4455

13385 CTG CGC TAC GCG GCC GGC CGG CCC TTC GTG CTG CTG GGG CAC TCC GCC GGC GCC AAC ATG 13444
 4456 L   R   Y   A   A   G   R   P   F   V   L   L   G   H   S   A   G   A   N   M   4475

13445 GCC CAC GCC CTG ACC CGT CAT CTG GAG GCG AAC GGT GGC GGC CCC GCA GGG CTG GTG CTC 13504
 4476 A   H   A   L   T   R   H   L   E   A   N   G   G   P   A   G   L   V   L   4495

13505 ATG GAC ATC TAC ACC CCC GCC GAC CCC GGC GCG ATG GGC GTC TGG CGG AAC GAC ATG TTC 13564
 4496 M   D   I   Y   T   P   A   D   P   G   A   M   G   V   W   R   N   D   M   F   4515

13565 CAG TGG GTC TGG CGG CGC TCG GAC ATC CCC CCG GAC GAC CAC CGC CTC ACG GCC ATG GGC 13624
 4516 Q   W   V   W   R   R   S   D   I   P   P   D   D   H   R   L   T   A   M   G   4535

13625 GCC TAC CAC CGG CTG CTT CTC GAC TGG TCG CCC ACC CCG GTC CGC GCC CCC GTA CTG CAT 13684
 4536 A   Y   H   R   L   L   L   D   W   S   P   T   P   V   R   A   P   V   L   H   4555

13685 CTG CGC GCC GCG GAA CCC ATG GGC GAC TGG CCA CCC GGG GAC ACC GGC TGG CAG TCC CAC 13744
 4556 L   R   A   A   E   P   M   G   D   W   P   P   G   D   T   G   W   Q   S   H   4575

13745 TGG GAC GGC GCG CAC ACC ACC GCC GGC ATC CCC GGA AAC CAC TTC ACG ATG ATG ACC GAA 13804
 4576 W   D   G   A   H   T   T   A   G   I   P   G   N   H   F   T   M   M   T   E   4595

13805 CAC GCC TCC GCC GCC GCC CGG CTC GTG CAC GGC TGG CTC GCG GAA CGG ACC CCG TCC GGG 13864
 4596 H   A   S   A   A   A   R   L   V   H   G   W   L   A   E   R   T   P   S   G   4615

13865 CAG GGC GGG TCA CCG TCC CGC GCG GCG GGG AGA GAG GAG AGG CCG TGA ACACGGCAGCCGGCCC 13928
 4616 Q   G   G   S   P   S   R   A   A   G   R   E   E   R   P   *                    4631
```

FIG. 231

```
13929 GACCGGCACCGCCGCCGGCGGCACCACCGCCCCGGCGGCGGCACACGACCTGTCCCGCGCCGGACGCAGGCTCCAACTCA 14008

14009 CCCGGGCCGCACAGTGGTTCGCCGGCAACCAGGGAGACCCCTACGGG ATG ATC CTG CGC GCC GGC ACC GCC 14079
      1                                                  M   I   L   R   A   G   T   A   8

14080 GAC CCG GCA CCG TAC GAG GAA GAG ATC CCC GGG TAC CGA GCT CGA ATT CTT AAT TAA GGAG 14140
    9 D   P   A   P   Y   E   E   E   I   P   G   Y   R   A   R   I   L   N   *       27

14141 GTCGTAG ATG AGT AAC AAG AAC AAC GAT GAG CTG CAG CGG CAG GCC TCG GAA AAC ACC CTG 14201
      1       M   S   N   K   N   N   D   E   L   Q   R   Q   A   S   E   N   T   L   18

14202 GGG CTG AAC CCG GTC ATC GGT ATC CGC CGC AAA GAC CTG TTG AGC TCG GCA CGC ACC GTG 14261
   19 G   L   N   P   V   I   G   I   R   R   K   D   L   L   S   S   A   R   T   V   38

14262 CTG CGC CAG GCC GTG CGC CAA CCG CTG CAC AGC GCC AAG CAT GTG GCC CAC TTT GGC CTG 14321
   39 L   R   Q   A   V   R   Q   P   L   H   S   A   K   H   V   A   H   F   G   L   58

14322 GAG CTG AAG AAC GTG CTG CTG GGC AAG TCC AGC CTT GCC CCG GAA AGC GAC GAC CGT CGC 14381
   59 E   L   K   N   V   L   L   G   K   S   S   L   A   P   E   S   D   D   R   R   78

14382 TTC AAT GAC CCG GCA TGG AGC AAC AAC CCA CTT TAC CGC CGC TAC CTG CAA ACC TAT CTG 14441
   79 F   N   D   P   A   W   S   N   N   P   L   Y   R   R   Y   L   Q   T   Y   L   98

14442 GCC TGG CGC AAG GAG CTG CAG GAC TGG ATC GGC AAC AGC GAC CTG TCG CCC CAG GAC ATC 14501
   99 A   W   R   K   E   L   Q   D   W   I   G   N   S   D   L   S   P   Q   D   I   118

14502 AGC CGC GGC CAG TTC GTC ATC AAC CTG ATG ACC GAA GCC ATG GCT CCG ACC AAC ACC CTG 14561
  119 S   R   G   Q   F   V   I   N   L   M   T   E   A   M   A   P   T   N   T   L   138

14562 TCC AAC CCG GCA GCA GTC AAA CGC TTC TTC GAA ACC GGC GGC AAG AGC CTG CTC GAT GGC 14621
  139 S   N   P   A   A   V   K   R   F   F   E   T   G   G   K   S   L   L   D   G   158

14622 CTG TCC AAC CTG GCC AAG GAC CTG GTC AAC AAC GGT GGC ATG CCC AGC CAG GTG AAC ATG 14681
  159 L   S   N   L   A   K   D   L   V   N   N   G   G   M   P   S   Q   V   N   M   178

14682 GAC GCC TTC GAG GTG GGC AAG AAC CTG GGC ACC AGT GAA GGC GCC GTG GTG TAC CGC AAC 14741
  179 D   A   F   E   V   G   K   N   L   G   T   S   E   G   A   V   V   Y   R   N   198

14742 GAT GTG CTG GAG CTG ATC CAG TAC AAG CCC ATC ACC GAG CAG GTG CAT GCC CGC CCG CTG 14801
  199 D   V   L   E   L   I   Q   Y   K   P   I   T   E   Q   V   H   A   R   P   L   218

14802 CTG GTG GTG CCG CCG CAG ATC AAC AAG TTC TAC GTA TTC GAC CTG AGC CCG GAA AAG AGC 14861
  219 L   V   V   P   P   Q   I   N   K   F   Y   V   F   D   L   S   P   E   K   S   238

14862 CTG GCA CGC TAC TGC CTG CGC TCG CAG CAG CAG ACC TTC ATC ATC AGC TGG CGC AAC CCG 14921
  239 L   A   R   Y   C   L   R   S   Q   Q   Q   T   F   I   I   S   W   R   N   P   258

14922 ACC AAA GCC CAG CGC GAA TGG GGC CTG TCC ACC TAC ATC GAC GCG CTC AAG GAG GCG GTC 14981
  259 T   K   A   Q   R   E   W   G   L   S   T   Y   I   D   A   L   K   E   A   V   278

14982 GAC GCG GTG CTG GCG ATT ACC GGC AGC AAG GAC CTG AAC ATG CTC GGT GCC TGC TCC GGC 15041
  279 D   A   V   L   A   I   T   G   S   K   D   L   N   M   L   G   A   C   S   G   298

15042 GGC ATC ACC TGC ACG GCA TTG GTC GGC CAC TAT GCC GCC CTC GGC GAA AAC AAG GTC AAT 15101
  299 G   I   T   C   T   A   L   V   G   H   Y   A   A   L   G   E   N   K   V   N   318

15102 GCC CTG ACC CTG CTG GTC AGC GTG CTG GAC ACC ACC ATG GAC AAC CAG GTC GCC CTG TTC 15161
  319 A   L   T   L   L   V   S   V   L   D   T   T   M   D   N   Q   V   A   L   F   338

15162 GTC GAC GAG CAG ACT TTG GAG GCC GCC AAG CGC CAC TCC TAC CAG GCC GGT GTG CTC GAA 15221
  339 V   D   E   Q   T   L   E   A   A   K   R   H   S   Y   Q   A   G   V   L   E   358

15222 GGC AGC GAG ATG GCC AAG GTG TTC GCC TGG ATG CGC CCC AAC GAC CTG ATC TGG AAC TAC 15281
  359 G   S   E   M   A   K   V   F   A   W   M   R   P   N   D   L   I   W   N   Y   378

15282 TGG GTC AAC AAC TAC CTG CTC GGC AAC GAG CCG CCG GTG TTC GAC ATC CTG TTC TGG AAC 15341
  379 W   V   N   N   Y   L   L   G   N   E   P   P   V   F   D   I   L   F   W   N   398

15342 AAC GAC ACC ACG CGC CTG CCG GCC GCC TTC CAC GGC GAC CTG ATC GAA ATG TTC AAG AGC 15401
  399 N   D   T   T   R   L   P   A   A   F   H   G   D   L   I   E   M   F   K   S   418

15402 AAC CCG CTG ACC CGC CCG GAC GCC CTG GAG GTT TGC GGC ACT CCG ATC GAC CTG AAA CAG 15461
  419 N   P   L   T   R   P   D   A   L   E   V   C   G   T   P   I   D   L   K   Q   438

15462 GTC AAA TGC GAC ATC TAC AGC CTT GCC GGC ACC AAC GAC CAC ATC ACC CCG TGG CAG TCA 15521
  439 V   K   C   D   I   Y   S   L   A   G   T   N   D   H   I   T   P   W   Q   S   458
```

FIG. 23J

```
15522 TGC TAC CGC TCG GCG CAC CTG TTC GGC GGC AAG ATC GAG TTC GTG CTG TCC AAC AGC GGC 15581
  459 C   Y   R   S   A   H   L   F   G   G   K   I   E   F   V   L   S   N   S   G   478

15582 CAC ATC CAG AGC ATC CTC AAC CCG CCA GGC AAC CCC AAG GCG CGC TTC ATG ACC GGT GCC 15641
  479 H   I   Q   S   I   L   N   P   P   G   N   P   K   A   R   F   M   T   G   A   498

15642 GAT CGC CCG GGT GAC CCG GTG GCC TGG CAG GAA AAC GCC ACC AAG CAT GCC GAC TCC TGG 15701
  499 D   R   P   G   D   P   V   A   W   Q   E   N   A   T   K   H   A   D   S   W   518

15702 TGG CTG CAC TGG CAA AGC TGG CTG GGC GAG CGT GCC GGC GAG CTG GAA AAG GCG CCG ACC 15761
  519 W   L   H   W   Q   S   W   L   G   E   R   A   G   E   L   E   K   A   P   T   538

15762 CGC CTG GGC AAC CGT GCC TAT GCC GCT GGC GAG GCA TCC CCG GGC ACC TAC GTT CAC GAG 15821
  539 R   L   G   N   R   A   Y   A   A   G   E   A   S   P   G   T   Y   V   H   E   558

15822 CGT TGA GCTGCAGCGCCGTGGCCACCTGCGGGACGCCACGGTGTTGAATTC                            15872
  559 R   *                                                                          560
```

FIG. 23K

Scheme 2

Scheme 1 pikPKS Sequence

```
          10         20         30         40         50         60         70         80         90        100
  1234567890 1234567890 1234567890 1234567890 1234567890 1234567890 1234567890 1234567890 1234567890 1234567890

BamHI
▶
  GGATCCGACC GTGGGTGTGA ATCTCCGGGT GCTCGCCTCG TCCTGCCCCG TTACCTGTCC GCCTCCCGCT CCAGACCAGC GGGAGGCGGA CAGGGGCATG    100

SphI
  ▶
  CCCGCCGGGC GGCTAACGGC CCGTGCGGCG TCCGTACGAC GAGCCTTGCG CGCCCTGGCG GCCCTTGTC TGCCGACCT GTGCGCGGGG TGCGCAGGGT     200

BstXI
                                                                                                ▶
  TCGCCGCCGC GGGTGGGGCC GTATCTGCGG CTCCCGGGCA CGGCGGCCCT GCTCGTCTCC GAGTCATAGT CCCTGCCGCC GGCGCCACCG CCCTGCCCCG    300

SphI
  ▶
  GCATGCGCGG GCCGGCGCGC CCCGGCGCGT AACTCGGCTG GGAGGCCTGG AAAAGGGCGA TCCATTGGGT GAGCGTGAGG TCCTTCGGCA GTCCGCCGTC    400

EcoRI
  ApoI
  ▶
  CGGAATTCCG TGGCGGTCGG CGAGGGAACG GTAGGTCCGC TTGGGGATGT GGCGCCCGGAG GATCTCCGCG AGGCCCCGTC CGGGGCCGGT GAAGACGGCT    500
```

Figure 31 - 1 pikPKS Sequence

```
          10         20         30         40         50         60         70         80         90        100
1234567890 1234567890 1234567890 1234567890 1234567890 1234567890 1234567890 1234567890 1234567890 1234567890

TCGGCGAAGT TCTGGAAGGC GCGGCTCGCG CTCTCGGGCA GCAGGGGCTG GGGGCGTCGC CTGATCGTCA GGACGCCGCC GTCGACGCGG GGCATCGGAC    600

GGAACGACGA GGGCGCGGACG CGGTCGTGGA CCGCGAACTC GTACCAGGGG GCCCAGGAGG TCGTGAGGAG CGATCCGCCG CTGCGACCCGG CGCGTTTGCG    700

EcoRV      BsmI
                                          ▼          ▼
GGCGACCTCC CACTGCACTA TCAGGGCCGC CGACTGCCAG TTCGTCGATT CCAGGAGACT CCGGAGAATC TGGGTCGTGA TGCCGAAGGG AACGTTTCCG    800

ApoI
                                                                                      BstBI
                                                                                       ▼ ▼
ACGACGGTGT CGATATGCGG AAGTCGAGGA AATCACCCTG GAATACGGTG ACCCTCTCCC CTTCGAATTT CCGCCGCACA TGCCGCGGCCC              900

AGTGCGGGTC CATCTCCACG ACCGTCACGG TGTCGAAGGA GGGCACCAAC TCCTCGGTTA TCGCGCCCTT TCCGGGGCCG ATTTCGAGAA CGTTCCTACC   1000
```

Figure 31 - 2 pikPKS Sequence

```
         10         20         30         40         50         60         70         80         90        100
1234567890 1234567890 1234567890 1234567890 1234567890 1234567890 1234567890 1234567890 1234567890 1234567890
GTCCCCCTCG ACATGCGTGA CGAGATTGCG CACGGCTCTG TCGTCCTGAA GGAAGTTCTG GCCTAATTCG CGGCGAAGGG TGTCGCGGTC CGCTCGCCTC   1100

GGTATGGAGT CGCGGCATTGC CATgaacgat ccCCtccCctg gatgccgtgg tcaatggact tggcacggac catacctcac ggtccgtcgg acgaccggag   1200
  XmnI
  ▶
aagaagttca cgcacgggcg ttccggagta cgggagttgt gaacggccgc gacgaagtcg gtcgcggctc ggcggggcggt gacgagcgag gtccggagga   1300
acgcgacgaa gcagccgaac cccaagtgag gtgcgacgga gtgacattgg gggcatacgg agggttgtcg tacggagcgc actcaacgag gctccaggag   1400
ggaggggttg aacccgccgc cgactggcct tcgccggccg cgcggccgga gtatgtcatg tcggggggtga aatcaagcca ttccccccggg atcggctgtt   1500
```

Figure 31 - 3 plkPKS Sequence

```
         10         20         30         40         50         60         70         80         90        100
1234567890 1234567890 1234567890 1234567890 1234567890 1234567890 1234567890 1234567890 1234567890 1234567890 acccatccct ttacctggcg tggatttccc aacccttggt atagagcggg agacgacgcg acaccatgga gaccacgcac accacgagcg ccacccccg    1600 gccatcccga caaggggggt ccggctcgcc tcccgacacc catggcctgg ggtacacgcc aggtataggg ggaacgtagg ggggggtgcc             1700 ctgggggttgg gtgaaagcgc ggcttccgga gacggagccg gATGTCTTCA GCCGGAATTA CCAGGACCGG TGCGAGAACA CCGGTGACAG GGCGTGGGGC   1800
                                            M  S  S   A  G  I  T   R  T  G   A  R  T   P  V  T  G   R  G  A GGCAGCGTGG GACACGGGGG AAGTGCGGGT CCGACGGGGG TTGCCCCCTG CCGGCCCCGA TCATGCGGAG CACTCCTTCT CTCGTGCTCC TACCGGTGAT   1900
 A  A  W   D  T  G  E   V  R  V   R  R  G   L  P  P  A   G  P  D   H  A  E   H  S  F  S   R  A  P   T  G  D EcoRI
                                            ApoI
                                             ▼
GTGCGGCGCC AATTGATTCG TGGAGAGATG TCGACAGTGT CCAAGAGTGA GTCCGAGGAA TTCGTGTCCG TGTCGAACGA CGCCGGTTCC GCGCACGGCA   2000
 V  R  A  E   L  I  R   G  E  M   S  T  V  S   K  S  E   S  E  E   F  V  S   V  S  N  D   A  G  S   A  H  G  T
       ▲
      XmnI
```

Figure 31 - 4 pikPKS Sequence

```
          10         20         30         40         50         60         70         80         90        100
1234567890 1234567890 1234567890 1234567890 1234567890 1234567890 1234567890 1234567890 1234567890 1234567890

CAGCGGAACC CGTCGCCGTC GTCGGCATCT CCTGCCGGGT GCCCGGCGCC CGGGACCCGA GAGAGTTCTG GGAACTCCTG GCGGCAGGCG GCCAGGCCGT  2100
 A  E  P   V  A  V    V  G  I  S  C  R  V     P  G  A   R  D  P  R  E  F  W   E  L  L    A  A  G  G  Q  A  V

CACCGACGTC CCCGCGGACC GCTGGAACGC CGGCGACTTC TACGACCCGG ACCGCTCCGC CCCCGGCCGC TCGAACAGCC GGTGGGGCGG GTTCATCGAG  2200
 T  D  V   P  A  D  R  W  N  A   G  D  F    Y  D  P  D  R  S  A   P  G  R   S  N  S  R  W  G  G    F  I  E

GACGTCGACC GGTTCGACGC CGCCTTCTTC GGCATCTCGC CCCGCGAGGC CGCGGAGATG GACCCGCAGC AGCGGCTCGC CCTGGAGCTG GGCTGGGAGG  2300
 D  V  D  R  F  D  A   A  F  F   G  I  S  P  R  E  A   A  E  M   D  P  Q  Q  R  L  A    L  E  L   G  W  E  A

CCCTGGAGCG CGCCGGGATC GACCCGTCCT CGCTCACCGG CACCCGCACC GGCGTCTTCG CCGGCGCCAT CTGGGACGAC TACGCCACCC TGAAGCACCG  2400
 A  L  E  R  A  G  I   D  P  S  S  L  T  G   T  R  T   G  V  F  A  G  A  I  W  D  D    Y  A  T  L  K  H  R

CCAGGGGCGGC GCCGCGGATCA CCCCGCACAC CGTCACCGGC CTCCACCGCG GCATCATCGC GAACCGACTC TCGTACACGC TCGGGCTCCG CGGCCCCAGC  2500
 Q  G  G   A  A  I  T   P  H  T   V  T  G   L  H  R  G  I  I  A   N  R  L    S  Y  T  L  G  L  R   G  P  S
```

Figure 31 - 5 pikPKS Sequence

```
         10         20         30         40         50         60         70         80         90        100
1234567890 1234567890 1234567890 1234567890 1234567890 1234567890 1234567890 1234567890 1234567890 1234567890

ATGGTCGTCG ACTCCGGCCA GTCCTCGTCG CTCGTCGCCG TCCACCTCGC GTGCGAGAGC CTGCGGGCG GCGAGTCCGA GCTCGCCCTC GCCGGGGGCG  2600
 M  V  V  D  S  G  Q  S  S  S  L  V  A  V  H  L  A  C  E  S  L  R  R  G  E  S  E  L  A  L  A  G  G  V

TCTCGCTCAA CCTGGTGCCG GACAGCATCA TCGGGGCGAG CAAGTTCGGC GGCCTCTCCC CCGACGGCCG CGCCTACACC TTCGACGCGC GCGCCAACGG  2700
 S  L  N  L  V  P  D  S  I  I  G  A  S  K  F  G  G  L  S  P  D  G  R  A  Y  T  F  D  A  R  A  N  G

SnaBI
CTACGTACGC GGGGAGGGCG GCGGTTTCGT CGTCCTGAAG CGCCTCTCCC GGGCCGTCGC CGACGGCGAC CCGGTGCTCG CCGTGATCCG GGGCAGCGCC  2800
 Y  V  R  G  E  G  G  G  F  V  V  L  K  R  L  S  R  A  V  A  D  G  D  P  V  L  A  V  I  R  G  S  A

GTCAACAACG GCGGGGCCGC CCAGGGCATG ACGACCCCCG ACGGCGAGGC GCAGGAGGCC GTGCTCCGGG AGGCCCACGA GCGGGCCGGG ACCGCCCCGG  2900
 V  N  N  G  A  A  A  Q  G  M  T  T  P  D  A  Q  A  Q  E  A  V  L  R  E  A  H  E  R  A  G  T  A  P  A

CCGACGTGCG GTACGTCGAG CTGCACGGCA CCGGCACCCC CGTGGGCGAC CCGATCGAGG CCGCTGCGCT CGGCGCCGCC CTCGGCACCG GCCGCCCGGC  3000
 D  V  R  Y  V  E  L  H  G  T  G  T  P  V  G  D  P  I  E  A  A  A  L  G  A  A  L  G  T  G  R  P  A
```

Figure 31 - 6 pikPKS Sequence

```
         10         20         30         40         50         60         70         80         90        100
1234567890 1234567890 1234567890 1234567890 1234567890 1234567890 1234567890 1234567890 1234567890 1234567890

CGGACAGCCG CTCCTGGTCG GCTCGGTCAA GACGAACATC GGCCACCTGG AGGGCGCGGC CGGCATCGCC GGCCTCATCA AGGCCGTCCT GGCGGTCCGC  3100
 G  Q  P    L  L  V  G   S  V  K   T  N  I   G  H  L  E   G  A  A   G  I  A   G  L  I  K   A  V  L   A  V  R

GGTCGCGCGC TGCCCGCCAG CCTGAACTAC GAGACCCCGA ACCCGGCGAT CCCGTTCGAG GAACTGAACC TCCGGGTGAA CACGGAGTAC CTGCCCGTGGG  3200
 G  R  A  L   P  A  S   L  N  Y    E  T  P  N   P  A  I   P  F  E    E  L  N  L   R  V  N   T  E  Y   L  P  W  E

AGCCGGAGCA CGACGGGCAG CGGATGGTCG TCGGCGTGTC CTCGTTCGGC ATGGGCGGCA CGAACGCGCA TGTCGTGCTC GAAGAGGCCC CCGGGGGTTG  3300
 P  E  H   D  G  Q   R  M  V  V    G  V  S   S  F  G   M  G  G  T   N  A  H   V  V  L   E  E  A  P   G  G  C

TCGAGGTGCT TCGGTCGTGG AGTCGACGGT CGGCGGGTCG GCGGGGGTCG GCGGTGTGGT GCCGTGGGTG GTGTCGGCGA AGTCCGCTGC CGCGCTGGAC  3400
 R  G  A   S  V  V  E   S  T  V    G  G  S   A  V  G  G   G  V  V   P  W  V   V  S  A  K   S  A  A    A  L  D

GCCCAGGATCG AGCGGCTTGC CGCGGTTCGCC TCGCGGGATC GTACGGATGG TGTCGACGCG GGCGCTGTCG ATGCGGGGTGC TGTCGATGCG GGTGCTGTCG  3500
 A  Q  I  E   R  L  A    A  F  A    S  R  D  R   T  D  G    V  D  A   G  A  V  D   A  G  A    V  D  A   G  A  V  A
```

Figure 31 - 7 pikPKS Sequence

```
          10         20         30         40         50         60         70         80         90        100
 1234567890 1234567890 1234567890 1234567890 1234567890 1234567890 1234567890 1234567890 1234567890 1234567890
                                                                                      Eco47III      Bsu36I
                                                                                         ▶            ▶
CTCGGGTACT GGCCGGCGGG CGTGCTCAGT TCGAGCACCG GGCCGTCGTC GTCGGCAGCG GGCCGGACGA TCTGGGGGCA GGCTGGGCCG CGCCTGAGGG 3600
 R  V  L    A  G  G    R  A  Q  F  E  H  R   A  V  V   V  G  S  G  G  P  D  D  L  A  A  A  L  A  A  P  E  G

TCTGGTCCGG GGCGTGGCTT CCGGTGTCGG GCGAGTGGCG TTCGTGTTCC CCGGGCAGGG CACGCAGTGG GCCGGCATGG GTGCCGAACT GCTGGACTCT 3700
 L  V  R   G  V  A  S  G  V  G   R  V  A   F  V  F  P  G  Q  G   T  Q  W   A  G  M  G  A  E  L    L  D  S
                                         BsmI
                                          ▶
TCCGGGGTGT TCGCGGCGGC CATGGCCGAA TGCGAGGCCG CACTCTCCCC GTACGTCGAC TGGTCGCTGG AGGCCGTCGT ACGGCAGGCC CCCGGTGCGC 3800
 S  A  V  F  A  A  A   M  A  E   C  E  A  A  L  S  P   Y  V  D   W  S  L  E  A  V  V   R  Q  A    P  G  A  P

CCACGCTGGA GCGGGTCGAT GTCGTGCAGC CTGTGACGTT CGCCGTCATG GTCTCGCTGG CTCGCGTGTG GCAGCACCAC GGGGTGACGC CCCAGGCGGT 3900
 T  L  E   R  V  D   V  V  Q  P   V  T  F   A  V  M   V  S  L  A  R  V  W   Q  H  H   G  V  T  P  Q  A  V

CGTCGGCCAC TCGCAGGGCG AGATCGCCGC GGCGTACGTC GCCGGTGCCC TGAGCCTGGA CGACGCCGCT CGTGTCGTGA CCCTGCGCAG CAAGTCCATC 4000
 V  G  H   S  Q  G   E  I  A  A   A  Y  V   A  G  A  L  S  L  D  D  A  A    R  V  V  T  L  R  S   K  S  I
```

Figure 31 - 8 pikPKS Sequence

```
          10         20         30         40         50         60         70         80         90        100
 1234567890 1234567890 1234567890 1234567890 1234567890 1234567890 1234567890 1234567890 1234567890 1234567890

GGGAGGCGGC GGCGAACCCG GCCGGTGCGG AGCCGGCTCC GGTGGCGGGCG GCCGGTGCCG TCGACGAGCC GGTGGCGATC GTCGGCATGG CCTGCCGCCT   5100
 E  A  A   A  N  P    A  G  A  E    P  A  P    V  A  A     A  G  A  V    D  E  P    V  A  I     V  G  M  A    C  R  L

GCCCGGTGGG GTCGCCCTCGC CGGAGGACCT GTGGCGGCTG GTGGCCGGCG GCGGGGACGC GATCTCGGAG TTCCCGCAGG ACCGCGGCTG GGACGTGGAG   5200
 P  G  G    V  A  S  P    E  D  L    W  R  L    V  A  G  G    G  D  A    I  S  E    F  P  Q  D    R  G  W    D  V  E
                BamHI
GGGCTGTACC ACCCGGATCC GGAGCACCCC GGCACGTCGT ACGTCCGCCA GGGCGGTTTC ATCGAGAACG TCGCCGGCTT CGACGGGGCC TTCTTCGGGA   5300
 G  L  Y  H    P  D  D    P  E  H  P    G  T  S  Y    V  R  Q    G  G  F    I  E  N  V    A  G  F    D  A  A    F  F  G  I

TCTCGCCGCG CGAGGCCCTC GCCATGGACC CGCAGCAGCG GCTCCTCCTC GAAACCTCCT GGGAGGCCGT CGAGGACGCC GGGATCGACC CGACCTCCCT   5400
 S  P  R    E  A  L    A  M  D  P    Q  Q  R    L  L  L    E  T  S  W    E  A  V    E  D  A    G  I  D  P    T  S  L

GCGGGGGACGG CAGGTCGGCG TCTTCACTGG GGCGATGACC CACGAGTACG GCCGAGCCT GCGGGACGGC GGGAAGGCC TCGACGGCTA CCTGCTGACC   5500
 R  G  R    Q  V  G  V    F  T  G    A  M  T    H  E  Y  G    P  S  L    R  D  G    G  E  G  L    D  G  Y    L  L  T
```

Figure 31 - 11 plkPKS Sequence

```
            10         20         30         40         50         60         70         80         90        100
   1234567890 1234567890 1234567890 1234567890 1234567890 1234567890 1234567890 1234567890 1234567890 1234567890

GGCAACACGG CCAGCGTGAT GTCGGGCCGC GTCTCGTACA CACTCGGCCT TGAGGGCCCC GCCCTGACGG TGGACACGGC CTGCTCGTCG TCGCTGGTCG   5600
 G  N  T  A  S  V  M   S  G  R    V  S  Y  T  L  G  L   E  G  P   A  L  T  V  D  T  A   C  S  S    S  L  V  A

CCCTGCACCT CGCCGTGCAG GCCCTGCGCA AGGGCGAGGT CGACATGGCG CTCGCCGGCG GCGTGGCCGT GATGCCCACG CCCGGGATGT TCGTCGAGTT   5700
 L  H  L   A  V  Q    A  L  R  K  G  E  V    D  M  A   L  A  G  G  V  A  V   M  P  T   P  G  M  F  V  E  F
                                                                XmnI
CAGCCGGCAG CGCGGGCTGG CCGGGGACGG CCGGTCGAAG GCGTTCGCCG CGGTCGGCGA CGGTCGGCGA CGGACCAGC TGGTCCGAGG GCGTCGGCGT   5800
 S  R  Q   R  G  L  A  G  D  G   R  S  K    A  F  A  A  S  A  D   G  T  S   W  S  E  G  V  G  V   L  L  V

GAGCGCCTGT CGGACGCCCG CCGCAACGGA CACCAGTCC TCGCGGTCGT CCGGCGCAGC GCCTTGAACC AGGACGGGCG CGAGCAACGGC CTCACGGCTC   5900
 E  R  L  S  D  A  R   R  N  G    H  Q  V  L  A  V  V  R  G  S   A  L  N  Q  D  G  A    S  N  G   L  T  A  P

CGAACGGGCC CTCGCAGCAG CGCGTCATCC GGCGCGCGCT GGCCGACGAC CCTCCGACGT CGGCTGACGA CCTCCCGACG GCACGGGCAC             6000
 N  G  P   S  Q  Q    R  V  I  R  R  A  L    A  D  A   R  L  T  T  S  D  V   D  V  V   E  A  H  G  T  G  T
```

Figure 31 - 12 pikPKS Sequence

```
           10         20         30         40         50         60         70         80         90        100
  1234567890 1234567890 1234567890 1234567890 1234567890 1234567890 1234567890 1234567890 1234567890 1234567890

ATCGTACGGA TGACGCCGAC GCCGGTGCTG TCGACGCGGG CGCTGTCGCT CACGTACTGG CTGACGGGCG TGCTCAGTTC GAGCACCGGG CCGTCGCGCT   6600
 R  T  D    D  A  D    A  G  A  V    D  A  G    A  V  A    H  V  L  A    D  G  R    A  Q  F    E  H  R  A    V  A  L

XmnI
                                                                            ▼
CGGCGCCGGG GCGGACGACC TCGTACAGGC GCTGGCCGAT CCGGACGGGC TGATACGCGG AACGGCTTCC GGTGTCGGGC GAGTGGCGTT CGTGTTCCCC   6700
 G  A  G    A  D  D  L    V  Q  A    L  A  D    P  D  G  L    I  R  G    T  A  S    G  V  G  R    V  A  F    V  F  P

GGTCAGGGCA CGCAGTGGGC TGGCATGGGT GCCGAACTGC TGGACTCTTC CGCGGTGTTC GCGGGCGGCC ATGGCCGAGTG CGTGACGTTCG CTGTCCCCGT   6800
 G  Q  G  T    Q  W  A    G  M  G    A  E  L  L    D  S  S    A  V  F    A  A  A  M    A  E  C    E  A  A    L  S  P  Y

ACGTCGACTG GTCGCTGGAG GCCGTCGTAC GGCAGGCCCC CGGTGCCGCC ACGCTGGAGC GGGTCGATGT CGTGCAGCCT GTGACGTTCG CCGTCATGGT   6900
 V  D  W    S  L  E    A  V  V  R    Q  A  P    G  A  P    T  L  E  R    V  D  V    V  Q  P    V  T  F  A    V  M  V

CTCGCTCTGGCT CGGCGTGTGGC AGCACCACGG TGTGACGCCC CAGGCGGGTCG TCGGCCACTC GCAGGGCGAG ATCGCCGCCG CGTACGTCGC CGGAGCCCTG   7000
 S  L  A    R  V  W  Q    H  H  G    V  T  P    Q  A  V  V    G  H  S    Q  G  E  I    A  A  A    Y  V  A    G  A  L
```

Figure 31 - 14 pikPKS Sequence

```
          10         20         30         40         50         60         70         80         90        100
1234567890 1234567890 1234567890 1234567890 1234567890 1234567890 1234567890 1234567890 1234567890 1234567890
                                                                                    SphI
                                                                                    ▼
CCCCTGGACG ACGGCGCCCG CGTCGTCACC CTGCGCAGCA AGTCCATCGC CGCCCACCTC GCCGGCAAGG GCGGCATGCT GTCCCTCGCG CTGAACGAGG   7100
 P  L  D  D   A  A  R    V  V  T    L  R  S  K    S  I  A    A  H  L    A  G  K  G    G  M  L    S  L  A    L  N  E  D

ACGCCGTCCT GGAGCGACTG AGTGACTTCG ACGGGCTGTC CGTCGCCGCC GTCAACGGGC CCACCGCCAC TGTCGTGTCG GGTGACCCCG TACAGATCGA   7200
 A  V  L    E  R  L    S  D  F  D    G  L  S    V  A  A    A  V  N  G  P    T  A  T    V  V  S    G  D  P  V    Q  I  E
                                                                   MluI
                                                                   ▼
AGAGCTTGCT CAGGGGTGCA AGGGCGGACGG ATTCCGCGCG CGGATCATTC CCGTCGACTA CGGCGTCCCAC AGCCGGCAGG TCGAGATCAT CGAGAGCGAG   7300
 E  L  A    Q  A  C  K    A  D  G    F  R  A    R  I  I  P    V  D  Y    A  S  H    S  R  Q  V    E  I  I    E  S  E

CTCGCCCCAGG TCCTCGCCGG TCTTCAGCCCG CAGGCCCCCGC GCGTGCCGTT CTTCTCGACG CTCGAAGGCA CCTGGATCAC CGAGCCCGTC CTCGACGGCA   7400
 L  A  Q  V    L  A  G    L  S  P    Q  A  P  R    V  P  F    F  S  T    L  E  G  T    W  I  T    E  P  V    L  D  G  T
   KpnI
   Acc65I
   ▼
CCTACTGGTA CCGCAACCTC CGTCACCGCG TCGGCTTCGC CCCCGCCATC GAGACCCTGG CCGTCGACGA GGGCTTCACG CACTTCGTCG AGGTCAGCGC   7500
 Y  W  Y    R  N  L    R  H  R  V    G  F  A    P  A  I    E  T  L  A    V  D  E    G  F  T    H  F  V  E    V  S  A
```

Figure 31 - 15 pikPKS Sequence

```
          10         20         30         40         50         60         70         80         90        100
1234567890 1234567890 1234567890 1234567890 1234567890 1234567890 1234567890 1234567890 1234567890 1234567890

CCACCCCGTC CTCACCATGA CCCTCCCCGA GACCGTCACC GGCCTCGGCA CCCTCCGTCG CGAACAGGGA GGCCAAGAGC GTCTGGTCAC CTCGCTCGCC 7600
 H  P  V    L  T  M  T    L  P  E    T  V  T    G  L  G  T    L  R  R    E  Q  G    G  Q  E  R    L  V  T    S  L  A

Eco47III
                                                                                                           ▶
GAGGGCGTGGG TCAACGGGCT TCCCGTGGCA TGGACTTCGC CGCCCCCGTC TGCCCACCTA CGCCTTCCAG GCCGAGCGCT 7700
 E  A  W  V    N  G  L    P  V  A    W  T  S  L    L  P  A    T  A  S    R  P  G  L    P  T  Y    A  F  Q    A  E  R  Y

XhoI              MscI
           PaeR7I            BalI
           ▶                 ▶
ACTGGCTCGA GAACACTCCC GCCGCCCTGG CCACCGGCGA CGACTGGCGC TACCGGATCG ACTGGAAGCG CCTCCCGGCC GCCGAGGGGT CCGAGCGCAC 7800
 W  L  E    N  T  P    A  A  L  A    T  G  D    D  W  R    Y  R  I  D    W  K  R    L  P  A    A  E  G  S    E  R  T

CGGGCCTGTCC GGCCGCTGGC TCGCCGTCAC GCCGGAGGAC CACTCCGCGC AGGCCCGCGC CGTGCTCACC GCGGCCGTG GGCCGGGGC GAAGGTGGAG 7900
 G  L  S    G  R  W  L    A  V  T    P  E  D    H  S  A  Q    A  A  A    V  L  T    A  L  V  D    A  G  A    K  V  E

GTGCTGACGG CCGGGGCGGA CGACGACCGT GAGGCCCTCG CCGCCCGGCT CACCGGCACTG ACGACCGGTG ACGGCTTCAC CGGCGTGGTC TGCTCCTCG 8000
 V  L  T    A  G  A  D    D  D  R    E  A  L  A    A  R  L    T  A  L    T  T  G  D    G  F  T    G  V  V    S  L  L  D
```

Figure 31 - 16 pikPKS Sequence

```
          10         20         30         40         50         60         70         80         90        100
1234567890 1234567890 1234567890 1234567890 1234567890 1234567890 1234567890 1234567890 1234567890 1234567890

ACGGACTCGT ACCGCAGGTC GCCTGGGTCC AGGCGCTCGG CGACGCCGGA ATCAAGGCGC CCCTGTGGTC CGTCACCCAG GGCGCGGTCT CCGTCGGACG  8100
 G  L  V   P  Q  V   A  W  V  Q   A  L  G    D  A  G    I  K  A  P   L  W  S   V  T  Q   G  A  V  S   V  G  R

TCTCGACACC CCCGCCGACC CCGACCGGGC CATGCTCTGG GGCCTCGGCC GCGTCGTCGC CCTTGAGCAC CCCGAACGCT GGGCCGGCCT CGTCGACCTC  8200
 L  D  T   P  A  D  P   D  R  A   M  L  W   G  L  G  R   V  V  A   L  E  H   P  E  R  W   A  G  L   V  D  L

CCCGCCCAGC CCGATGCCGC CGCCCTCGCC CACCTCGTCA CCGCACTCTC CGGCGCCACC GGCGAGGACC AGATCGCCAT CCGCACCACC GGACTCCACG  8300
 P  A  Q  P   D  A  A   A  L  A   H  L  V  T   A  L  S   G  A  T   G  E  D  Q   I  A  I   R  T  T   G  L  H  A
                                                                                BsaBI
                                                                                ▼

CCCGCGCCT CGCCCGGCA CCCCTCCACG GACGTCGGCC CACCCGCGAC TGGCAGCCCC ACGGCACCGT CCTCATCACC GGCGGCACCG GAGCCCTCGG  8400
 R  R  L   A  R  A   P  L  H  G   R  R  P   T  R  D   W  Q  P  H   G  T  V   L  I  T   G  G  T  G   A  L  G

CAGCCACGCC GCACGCTGGA TGGCCCACCA CGGAGCCGAA CACCTCCTCC TCGTCAGCCG CAGCGGGCGA GAGCCCACCG GAGCCACCCA ACTCACCGCC  8500
 S  H  A   A  R  W  M   A  H  H   G  A  E   H  L  L  L   V  S  R   S  G  E   Q  A  P  G   A  T  Q   L  T  A
```

Figure 31 - 17 pikPKS Sequence

```
          10         20         30         40         50         60         70         80         90        100
 1234567890 1234567890 1234567890 1234567890 1234567890 1234567890 1234567890 1234567890 1234567890 1234567890

GAACTCACCG CATCGGGCGC CCGGTCACC CCGGTCACC ATCGCCGCCT GCGACGTCGC CGACCCCAC GCCATGCGCA CCCTCCTCGA CGCCATCCCC GCCGAGACGC  8600
 E  L  T  A  S  G  A  R  V  T  I  A  A  C  D  V  A  D  P  H  A  M  R  T  L  L  D  A  I  P  A  E  T  P

CCCTCACCGC CGTCGTCCAC ACCGCCGGCG CGCTCGACGA CGGCATCGTG GACACGCTGA CCGCCGAGCA GGTCCGGCGG GCCCACCGTG CGAAGGCCGT  8700
 L  T  A  V  V  H  T  A  G  A  L  D  D  G  I  V  D  T  L  T  A  E  Q  V  R  R  A  H  R  A  K  A  V
                                                                       MluI
CGGCGCCCTG GTGCTCGACG AGCTGACCCG GGACCTCGAC CTCGACGCGT TCGTGCTCTT CTCGTCCGTG TCGAGCACTC TGGGCATCCC CGGTCAGGGC  8800
 G  A  S  V  L  D  E  L  T  R  D  L  D  L  D  A  F  V  L  F  S  S  V  S  S  T  L  G  I  P  G  Q  G

AACTACGCCC CGCACAACGC CTACCTCGAC GCCCTCGCGG CTCGCCGCCG CGGCCACCGG CGGTCCGCCG TCTCGGTGGC CTGGGGACCG TGGGACGGTG  8900
 N  Y  A  P  H  N  A  Y  L  D  A  L  A  A  R  R  R  A  T  G  R  S  A  V  S  V  A  W  G  P  W  D  G  G

GCGGCATGGC CGCCGGTGAC GGCGTGGCCG AGCGGCTGCG CAACCACGGC GTGCCCGGCA TGGACCCGGA ACTCGCCCTG GCCGACTGG AGTCCGGCT  9000
 G  M  A  A  G  D  G  V  A  E  R  L  R  N  H  G  V  P  G  M  D  P  E  L  A  L  A  A  L  E  S  A  L
```

Figure 31 - 18 pikPKS Sequence

```
         10         20         30         40         50         60         70         80         90        100
1234567890 1234567890 1234567890 1234567890 1234567890 1234567890 1234567890 1234567890 1234567890 1234567890

CGGCCGGGAC GAGACCGCGA TCACCGTCGC GGACATCGAC TGGGACCGCT TCTACCTCGC GTACTCCTCC GGTCGCCCGC AGCCCCTCGT CGAGGAGCTG     9100
 G  R  D   E  T  A  I   T  V  A   D  I  D   W  D  R  F   Y  L  A   Y  S  S   G  R  P  Q   P  L  V    E  E  L

BstXI
                                                                               ▼
CCCGAGGTGC GGGCGCATCAT CGACGCACGG GACAGCGCCA CGTCCGGACA GGGCGGGAGC TCCGCCCAGG GCGCCAACCC CCTGGCCGAG CGGCTGGCCG     9200
 P  E  V  R   R  I  I   D  A  R   D  S  A  T   S  G  Q   G  G  S   A  Q  G   A  N  P   L  A  E   R  L  A  A

CCGGCGCTCC CGGCGAGCGT ACGGAGATCC TCCTCGGTCT CGTACGGGCG CAGGCCGCCG CCGTGCTCCG GATGCGTTCG CCGGAGGACG TCGCCGCCGA     9300
 A  A  P   G  E  R   T  E  I  L   L  G  L   V  R  A   Q  A  A  A   V  L  R   M  R  S   P  E  D  V   A  A  D

CCGGCGCCTTC AAGGACATCG GCTTCGACTC GCTCGCCGGT GTCGAGCTGC GCAACAGGCT GACCCGGGCG ACCGGGCTCC AGCTGCCCGC GACGCTCGTC     9400
 R  A  F   K  D  I  G   F  D  S   L  A  G   V  E  L  R   N  R  L   T  R  A   T  G  L  Q   L  P  A   T  L  V

TTCGACCACC CGACGCCGCT GGCCCTCGTG TCGCTGCTCC GCAGCGAGTT CCTCGGTGAC GAGGAGACGG CGGACGCCCG GCGGTCCGCG GCGCTGCCCG     9500
 F  D  H  P   T  P  L   A  L  V   S  L  L  R   S  E  F   L  G  D   E  E  T  A   D  A  R   R  S  A   A  L  P  A
```

Figure 31 - 19 pikPKS Sequence

```
          10         20         30         40         50         60         70         80         90        100
1234567890 1234567890 1234567890 1234567890 1234567890 1234567890 1234567890 1234567890 1234567890 1234567890

CATCGAGGCC CAGGGCCTCC AGGCCACGTA CGGCAAGGAG CGGCCCGCGG AACGGCGCT CGCCATCGGC TCCGTGAAGT CCAACATCGG ACACACCCAG  10600
 I  E  A   Q  G  L  Q   A  T  Y   G  K  E    R  P  A  E   R  P  L  A  I  G    S  V  K  S   N  I  G    H  T  Q

GCCGCGGCCG GTGCGGGCGG CATCATCAAG ATGGTCCTCG CGATGCGCCA CGGCACCCTG CCGAAGACCC TCCACGCCGA CGAGCCGAGC CCGCACGTCG  10700
 A  A  A   G  V  A  A   G  I  I  K   M  V  L  A   M  R  H    G  T  L   P  K  T  L    H  A  D   E  P  S    P  H  V  D

ACTGGGGCGAA CAGCGGCCTG GCCCTCGTCA CCGAGCCGAT CGACTGGCCG GCCGGCACCG GTCCGCGCCG CGCCGCCGTC TCCTCCTTCG GCATCAGCGG  10800
 W  A  N   S  G  L    A  L  V  T   E  P  I   D  W  P    A  G  T  G    P  R  R   A  A  V    S  S  F  G    I  S  G
                                                                                            Bsu36I
                                                                                            ▼
GACGAACGCG CACGTCGTGC TGGAGCAGGC GCCGGATGCT GCTGGTGAGG TGCTTGGGGC CGATGAGGTG CCTGAGGTGT CTGAGACGGT AGCGATGGCT  10900
 T  N  A   H  V  V  L   E  Q  A   P  D  A    A  G  E  V   L  G  A   D  E  V    P  E  V  S   E  T  V   A  M  A

GGGACGGCTG GGACCTCCGA GGTCGCTGAG GGCTCTGAGG CCTCCGAGGC CCCGGCAGCC CCCCGGGAGC GTGAGGCGTC CCTCCCCGGG CACCTGCCCT  11000
 G  T  A   G  T  S  E   V  A  E   G  S  E  A   S  E  A   P  A  A  A   P  G  S   R  E  A  S    L  P  G    H  L  P  W
```

Figure 31 - 22 pikPKS Sequence

```
          10         20         30         40         50         60         70         80         90        100
  1234567890 1234567890 1234567890 1234567890 1234567890 1234567890 1234567890 1234567890 1234567890 1234567890
                                                                    MluI
                                                                    ▶
GGGTGCTGTC CGCCAAGGAC GAGCAGTCGC TGCGCGGCCA TCGGGGACGC TGGCGCCGCC CTGCACGCGT GGCTGTCCGA GCCCGCCGCC GACCTGTCGG ACGCGGACGG  11100
 V  L  S    P  A  K  D   E  Q  S   L  R  G  Q   A  A  A   L  H  A  W   L  S  E   P  A  A   D  L  S  D   A  D  G

ACCGGCCCGC CTGCGGGACG TCGGGGTACAC GCTCGCCACG AGCCGTACCG CCTTCGCGCA CCGGCCGCC GTGACCGCCG CCGACCGGGA CGGGTTCCTG  11200
 P  A  R    L  R  D  V   G  Y  T   L  A  T  S   R  T  A   F  A  H   R  A  A   V  T  A  A   D  R  D   G  F  L
           MscI
           BalI
           ▶
GACGGGCTGG CCAGCGCTGGC CCAGGGCGGC ACCTCGGCCC AGGTCCACCT GGACACCGCC CGGGACGGCA CCACCGCGTT CCTCTTCACC GGCCAGGGCA  11300
 D  G  L  A   Q  G  G   T  S  A  H   V  H  L   D  T  A   R  D  G  T   A  F   L  F  T   G  Q  G  S
                                                                    BglII
                                                                    ▶
GTCAGCGCCC CGGCGCCGGC CGTGAGCTGT ACGACCGGCA CCCCGTCTTC GCCGGGGCGC TCGACGAGAT CTGGCGCCAC CTCGACGGTC ACCTCGAACT  11400
 Q  R  P   G  A  G   R  E  L  Y   D  R  H   P  V  F   A  R  A  L   D  E  I   C  A  H   L  D  G  H   L  E  L

GCCCCTGCTC GACGTGATGT TCGCGGGCCGA GGGCAGCGCG GAGGCCGCGC TGCTCGACGA GACGCGGTAC ACGCAGTGCG CGCTGTTCGC CCTGGAGGTC  11500
 P  L  L   D  V  M  F   A  A  E   G  S  A   E  A  A  L   L  D  E   T  R  Y   T  Q  C  A   L  F  A   L  E  V
```

Figure 31 - 23 pikPKS Sequence

```
          10         20         30         40         50         60         70         80         90        100
1234567890 1234567890 1234567890 1234567890 1234567890 1234567890 1234567890 1234567890 1234567890 1234567890
                                         ▼SphI
GCGCTCTTCC GGCTCGTCGA GAGCTGGGGC ATGCGGCCGG CCGCACTGCT CGGTCACTCG GTCGGCGAGA TCGCCGCCGC GCACGTCGCC GGTGTGTTCT  11600
 A  L  F  R  L  V  E  S  W  G  M  R  P  A  A  L  L  G  H  S  V  G  E  I  A  A  A  H  V  A  G  V  F  S

CGCTCGCCGA CGCCGCCCGC CTGGTCGCCG CGGCGGCCGC GCTCATGCAG GAGCTGCCCG CCGGTGGCGC GATGCTCGCC GTCCAGGCCG CGGAGGACGA  11700
 L  A  D  A  A  R  L  V  A  A  R  G  R  L  M  Q  E  L  P  A  G  G  A  M  L  A  V  Q  A  A  E  D  E

GATCCGGCGTG TGGCTGGAGA CGGAGGAGCG GTACGCGGGA CGTCTGGACG TCGCCGCCGT CAACGGCCCC GAGGCCGCCG TCCTGTCCGG CGACGCGGAC  11800
 I  R  V  W  L  E  T  E  E  R  Y  A  G  R  L  D  V  A  A  V  N  G  P  E  A  A  V  L  S  G  D  A  D

▼SphI
GCGGCGCGGG AGGCGGAGGC GTACTGGTCC GGGCTCGGCC GCAGGACCCG CGGCTGCGCG GTCAGCCACG CCTTCCACTC CGCGCACATG GACGGCATGC  11900
 A  A  R  E  A  E  A  Y  W  S  G  L  G  R  R  T  R  A  L  R  V  S  H  A  F  H  S  A  H  M  D  G  M  L

TCGACGGGTT CCGGCGCGTC CTGGAGACGG TGGAGTTCCG GCGCCCCTCC CTGACCGTGG TCTCGAACGT CACCGGCCTG GCCGCCGGCC CGGACGACCT  12000
 D  G  F  R  A  V  L  E  T  V  E  F  R  R  P  S  L  T  V  V  S  N  V  T  G  L  A  A  G  P  D  D  L
```

Figure 31 - 24 pikPKS Sequence

```
          10         20         30         40         50         60         70         80         90        100
1234567890 1234567890 1234567890 1234567890 1234567890 1234567890 1234567890 1234567890 1234567890 1234567890
                   ScaI
                   ▼
GTGCGACCCC GAGTACTGGG TCCGGCACGT CCGGGCACC GTCCGCTTCC TCGACGGCGT CCGTGTCCTG CGGGACCTCG GCGTGCGGAC CTGCCTGGAG  12100
 C D P      E Y W V     R H V R     G T  P G T     V R F L D G V R V L R D L G V R T C L E

CTGGGCCCCG ACGGGGTCCT CACCGCCATG GCGGCCGACG GCCTCGCGGA CACCCCCGCG GATTCCGCTG CCGGCTCCCC CGTCGGCTCT CCCGCCGGCT  12200
 L G P D     G V L       T A M     A A D G     L A D     T P A    D S A A     G S P     V G S      P A G S

CTCCCGCGGA CTCCGCCGCC GGGGCGCTCC GGCCCCGTCC GGCCCCGCGG CCGCCGCGCC GCTGCTCGTG GCGCTGCTGC GCCGCAAGCG GTCGGAGACC GAGACCGTCG CGGACGCCCT  12300
 P A D      S A A         G A L R     P R P     R P       L L V     A L L R    R K R       S E T     E T V A D A L

CGGCAGGGCG CACGCCCACG GCACCGGGACC CGACTGGCAC GCCTGGTTCG CCGGCTCCGG GGCGCACCGC GTGGACCTGC CCACGTACTC CTTCCGGCGC  12400
 G R A       H A H G     T G P     D W H     A W F A       G S G     A H R     V D L P     T Y S     F R R

GACCGCTACT GGCTGGACGC CCCGGCGGCC GACACCGCGG TGGACACCGC CGGCCTCGGT CTCGGCACCG CCGACCACCC GCTGCTCGGC GCCGTGGTCA  12500
 D R Y W     L D A      P A A      D T A V    D T A       G L G     L G T A     D H P      L L G     A V V S
```

Figure 31 - 25 pikPKS Sequence

```
          10         20         30         40         50         60         70         80         90        100
1234567890 1234567890 1234567890 1234567890 1234567890 1234567890 1234567890 1234567890 1234567890 1234567890

GCCTTCCGGA CCGGGACGGC CTGCTGCTCA CCGGCCGCCT CTCCCTGCGC ACCCACCCGT GGCTCGCGGA CCACGCCGTC CTGGGGAGCG TCCTGCTCCC   12600
 L  P  D   R  D  G    L  L  L  T   G  R  L   S  L  R    T  H  P  W  L  A  D   H  A  V   L  G  S  V  L  L  P

CGGCGCCGCG ATGGTCGAAC TCGCCGCGCA CGCTGCGGAG TCCGCCGGTC TGCCGTGACGT GCGGGAGCTG ACCCTCCTTG AACCGCTGGT ACTGCCCGAG   12700
 G  A  A   M  V  E  L  A  A  H    A  A  E    S  A  G  L  R  D  V   R  E  L    T  L  L  E   P  L  V   L  P  E

CACGGTGGGC TCGAGCTGCG CGTGACGGTC GGGGGCGCCG CCGGAGAGCC CGGTGGCGAG TCGGCCGGGG ACGGGCGCACG GCCCGTCTCC CTCCACTCGC   12800
 H  G  G  V  E  L  R   V  T  V    G  A  P  A   G  E  P   G  G  E   S  A  G  D   G  A  R   P  V  S    L  H  S  R
                                  KpnI                                          MscI
                                  Acc65I                                        BalI
                                  ▶                                             ▶

GGCTGCCGGA CGGGCCCGCC GGTACCGCT  GGTCCTGCCA CGGCCGGCCA CTGCTGGCCA CCGACCGGT   CGAGCTTCCC GTCGCGCCCG ACCGTGCGGC   12900
 L  A  D   A  P  A    G  T  A  W   S  C  H   A  T  G    L  L  A  T   D  R  P   E  L  P   V  A  P  D   R  A  A

CATGTGGCCG CCGCAGGGCG CCGAGGAGGT GCCGCTCGAC GGTCTCTACG AGCGGCTCGA CGGGAACGGC CTCGCCTTCG GTCCGCTGTT CCAGGGGCTG   13000
 M  W  P   P  Q  G  A   E  E  V   P  L  D    G  L  Y  E   R  L  D   G  N  G    L  A  F  G   P  L  F  Q  G  L
```

Figure 31 - 26 pikPKS Sequence

```
         10         20         30         40         50         60         70         80         90        100
1234567890 1234567890 1234567890 1234567890 1234567890 1234567890 1234567890 1234567890 1234567890 1234567890
                                                                                                    PmlI
                                                                                                     ▼
CCGAGACCGG CACCGCCGCA CCGGCGCTCG CCCCGGAGGG CACGGTCCTG CTGACCGGCG GCACCGGGCG CCTGGGCGGA CTGGTCGCCC GGCACGTGGT  14100
 E  T  G   T  A  A    P  A  L  A  P  E  G    T  V  L    L  T  G   G  T  G   R  L  G  G   L  V  A  R  H  V  V

ApaLI
                                                                      ▼
GGGCGAGTGG GGCGTACGAC GCCTGCTGCT GGTGAGCCGG CGGGGCACGG ACGCCCCGGG CGCCGACGAG CTCGTGCACG AGCTGGAGGC CCTGGGAGCC  14200
 G  E  W   G  V  R  R  L  L  L   V  S  R   R  G  T  D  A  P  G    A  D  E   L  V  H  E   L  E  A   L  G  A

GACGTCTCGG TGGCCGCGTG CGACGTCGCC GACCGCGAAG CCCTCACCGC CGTACTCGAC GCCATCCCCG CCGAACACCC GCTCACCGCG GTCGTCCACA  14300
 D  V  S  V  A  A  C   D  V  A   D  R  E  A  L  T  A   V  L  D   A  I  P   A  E  H  P    L  T  A   V  V  H  T

CGGCAGGCGT CCTCTCCGAC GGCACCCTCC CGTCCATGAC GACGGAGGAC GTGGAACACG TACTGCGGCC CAAGGTCGAC GCCGCGTTCC TCCTCGACGA  14400
 A  G  V   L  S  D   G  T  L  P   S  M  T   T  T  E  D  V  E  H  V  L  R  P  K  V  D   A  A  F  L   L  D  E

ACTCACCTCG ACGCCCGCAT ACGACCTGGC AGCGTTCGTC ATGTTCTCCT CCGCCGCCGC CGTCTTCGGT GGCGCGGGGC AGGGGGCCTA CGCCGCCGCC  14500
 L  T  S   T  P  A  Y  D  L  A   A  F  V   M  F  S  S  A  A  A   A  V  F  G  G  A  G   Q  G  A  Y   A  A  A
```

Figure 31 - 29 plkPKS Sequence

```
         10         20         30         40         50         60         70         80         90        100
1234567890 1234567890 1234567890 1234567890 1234567890 1234567890 1234567890 1234567890 1234567890 1234567890
ScaI
▶
ACTCGGCCAC GCCCGCGGTC ACCGGATCGA CGCCGAACGG GGCTTCCTCG ACCTGGGCTT CGACTCCCTG ACCGCCGTCG AACTCCGCAA CCGGCTCAAC   15100
 L  G  H   A  R  G   H  R  I  D   A  E  R   G  F  L  D   L  G  F   D  S  L   T  A  V  E   L  R  N   R  L  N

TCCGCCGGTG GCCTCGCCCT CCCGGCGACC CTGGTCTTCG ACCACCCAAG CCCGGCGGCA CTCGCCTCCC ACCTGGACGC CGAGCTGCCG CGGCGGCGCT   15200
 S  A  G  G   L  A  L   P  A  T   L  V  F  D   H  P  S   P  A  A   L  A  S  H   L  D  A   E  L  P   R  G  A  S

CGGACCAGGA CGGAGCCGGG AACCGGAACG GGAACGAGAA CGGGACGACG GCGTCCCGGA GCACCGCCGA GACGGACGCG CTGCTGGCAC AACTGACCCG   15300
 D  Q  D   G  A  G   N  R  N  G   N  E  N   G  T  T   A  S  R  S   T  A  E   T  D  A   L  L  A  Q   L  T  R

CCTGGAAGGC GCCTTGGTGC TGACGGGGCT CTCGGACGCC CCCGGGAGCG AAGAAGTCCT GGAGCACCTG CGGTCCCTGC GCTCGATGGT CACGGGCGAG   15400
 L  E  G   A  L  V  L   T  G  L   S  D  A   P  G  S  E   E  V  L   E  H  L   R  S  L  R   S  M  V   T  G  E

ACCGGGACCG GGACCGCGTC CGGAGCCCCG GACGGCGCCG GGTCCGGCGC CGAGGACCGG CCCTGGGCGG CCGGGGACGG AGCCGGGGGC GGGAGTGAGG   15500
 T  G  T  G   T  A  S   G  A  P   D  G  A  G   S  G  A   E  D  R   P  W  A  A   A  G  D  G   A  G  G   G  S  E  D
```

Figure 31 - 31 pikPKS Sequence

```
          10         20         30         40         50         60         70         80         90        100
 1234567890 1234567890 1234567890 1234567890 1234567890 1234567890 1234567890 1234567890 1234567890 1234567890

BspHI
                              ▼
ACGGGCGGGG AGTGCCGGAC TTCATGAACG CCTCGGCCGA GGAACTCTTC GGCCTCCTCG ACCAGGACCC CAGCACGGAC TGATCCCTGC CGCACGGTCG  15600
 G  A  G   E  V  P  D   F  M  N  A   S  A  E   E  L  F   G  L  L   D  Q  D  P   S  T  D

XmnI
                                           ▼
CCTCCCGCCC CGGACCCCGT CCCGGGCACC TCGACTCGAA TCACTTCATG CGCGCCTCGG GCGCCTCCAG GAACTC AAGG GGA AGCGTG TCCACGGTGA  15700
                                                                                              V  S  T  V  N

ACGAAGAGAA GTACCTCGAC TACCTGCGTC GTGCCACGGC GGACCTCCAC GAGGCCCGTG GCCGCCTCCG CGAGCTGGAG GCGAAGGCGG GCGAGCCGGT  15800
  E  E  K   Y  L  D   Y  L  R  R   A  T  A   D  L  H   E  A  R  G   R  L  R   E  L  E   A  K  A  G   E  P  V

GGGCGATCGT GGCATGGCCT GCCGCCTGCC CGGCGGCGTC GCCTCGCCCG AGGACCTGTG GCGGCTGGTG GCCGGCGGCG AGGACGCCGAT CTCGGAGTTC  15900
 A  I  V   G  M  A  C   R  L  P   G  G  V   A  S  P  E   D  L  W   R  L  V   A  G  G  E   D  A  I   S  E  F

CCCCAGGACC GCGGCTGGGA CGTGGAGGGC CTGTACGACC CGAACCCGGA GGCCACGGGC AAGAGTTACG CCCGCGAGGC CGGATTCCTG TACGAGGCGG  16000
  P  Q  D   R  G  W  D   V  E  G   L  Y  D   P  N  P  E   A  T  G   K  S  Y   A  R  E  A   G  F  L   Y  E  A  G
```

Figure 31 - 32 pikPKS Sequence

```
         10         20         30         40         50         60         70         80         90        100
1234567890 1234567890 1234567890 1234567890 1234567890 1234567890 1234567890 1234567890 1234567890 1234567890
                                                              AscI
                                                              ▼
CGCTCTCCCG CTATGTCGAC TGGTCGCTGG AGGCCGTCGT CCGGCAGGCG CCGGGCGCGC CCACGCTGGA GCGGGTCGAC GTCGTCCAGC CCGTGACCTT  17600
 L  S  R    Y  V  D    W  S  L  E   A  V  V    R  Q  A    P  G  A  P   T  L  E    R  V  D    V  V  Q  P   V  T  F

CGCTGTCATG GTTTCGCTGG CGAAGGTCTG GCAGCACCAC GGCGTGACGC CGCAGGCCGT CGTCGGCCAC TCGCAGGGCG AGATCGCCGC CGCGTACGTC  17700
 A  V  M    V  S  L  A   K  V  W    Q  H  H    G  V  T  P   Q  A  V    V  G  H    S  Q  G  E   I  A  A    A  Y  V

GCCGGTGCCC TCACCCTCGA CGACGCCGCC CGCGTCGTCA CCCTGCGCAG CAAGTCCATC GCCGCCCACC TCGCCGGCAA GGGCGGCATG ATCTCCCTCG  17800
 A  G  A  L   T  L  D    D  A  A    R  V  V  T   L  R  S    K  S  I    A  A  H  L   A  G  K    G  G  M    I  S  L  A

CCCTCAGCGA GGAAGCCACC CGGCAGCGCA TCGAGAACCT CCACGGACTG TCGATCGCCG CCGTCAACGG CCCCACCGCC ACCGTGGTTT CGGGCGACCC  17900
 L  S  E    E  A  T    R  Q  R  I   E  N  L    H  G  L    S  I  A  A   A  V  N  G   P  T  A    T  V  V  S   G  D  P

CACCCAGATC CAAGAGCTCG CTCAGGGCGT GAGGCCGGAC GGGGTCCGCG CACGGATCAT CCCCGTCGAC TACGCCTCCC ACAGCGCCCA CGTCGAGACC  18000
 T  Q  I    Q  E  L  A   Q  G  V    E  A  D    G  V  R  A   R  I  I    P  V  D    Y  A  S  H   S  A  H    V  E  T
```

Figure 31 - 36 pikPKS Sequence

```
         10         20         30         40         50         60         70         80         90        100
1234567890 1234567890 1234567890 1234567890 1234567890 1234567890 1234567890 1234567890 1234567890 1234567890

EspI
                                      Bpu1102I                       Bsu36I
                                      ▼                              ▼
ATCGAGAGCG AACTCGCCGA GGTCCTCGCC GGGCTCAGCC CGCGGACACC TGAGGTGCCG TTCTTCTCGA CACTCGAAGG CGCCTGGATC ACCGAGCCGG  18100
 I  E  S  E  L  A  E  V  L  A  G  L  S  P  R  T  P  E  V  P  F  F  S  T  L  E  G  A  W  I  T  E  P  V

KpnI
        Acc65I
        ▼
TGCTCGACGG CACCTACTGG TACCGCAACC TCCGCCACCG CGTCGGCTTC GCCCCCGCCG TCGAGACCCT CGCCACCGAC GAAGGCTTCA CCCACTTCAT  18200
 L  D  G  T  Y  W  Y  R  N  L  R  H  R  V  G  F  A  P  A  V  E  T  L  A  T  D  E  G  F  T  H  F  I

CGAGGTCAGC GCCCACCCCG TCCTCACCAT GACCCTCCCC GAGACCGTCA CCGGCCTCGG CACCCTCCGC CGGGAACAGG GAGGCCAGGA GCGTCTGGTC  18300
 E  V  S  A  H  P  V  L  T  M  T  L  P  E  T  V  T  G  L  G  T  L  R  R  E  Q  G  G  Q  E  R  L  V

ACCTCACTCG CCGAAGCCTG GACCAACGGC CTCACCATCG ACTGGGCGCC CGTCCTCCCC ACCGCAACCG GCCACCACCC CGAGCTCCCC ACCTACGCCT  18400
 T  S  L  A  E  A  W  T  N  G  L  T  I  D  W  A  P  V  L  P  T  A  T  G  H  H  P  E  L  P  T  Y  A  F

TCCAGGCGCC TCACTACTGG CTCCACGACT CCCCCGCCGT CCAGGGCTCC GTGCAGGACT CCTGGCGCTA CCGCATCGAC TGGAAGCGCC TCGCGGTCGC  18500
 Q  R  R  H  Y  W  L  H  D  S  P  A  V  Q  G  S  V  Q  D  S  W  R  Y  R  I  D  W  K  R  L  A  V  A
```

Figure 31 - 37 pikPKS Sequence

```
          10         20         30         40         50         60         70         80         90        100
1234567890 1234567890 1234567890 1234567890 1234567890 1234567890 1234567890 1234567890 1234567890 1234567890
MluI
▶
CGACGGCGTCC GAGCGCGCCG GGCTGTCCGG GCGCTGGCTC GTCGTCGTCC CCGAGGACCG TTCCGCCGAG GCCGCCCCGG TGCTCGCCGC GCTGTCCGGC  18600
 D  A  S   E  R  A  G   L  S  G   R  W  L    V  V  V  P  E  D  R   S  A  E    A  A  P  V  L  A  A   L  S  G

GCCGGGCGCCG ACCCCGTACA GCTGGACGTG TCCCCGCTGG GCGACCGGCA GCGGCTCGCC GCGAGGCCCT GGCCGGGCGCC GGTGGAGCCG  18700
 A  G  A  D  P  V  Q    L  D  V    S  P  L  G   D  R  Q   R  L  A    A  T  L  G  E  A  L   A  A  A   G  G  A  V

TCGACGGCGT CCTCTCGCTG CTCGCGTGGG ACGAGAGCGC GCACCCCGGC CCTTCACCCG GGGCACCGGC GCCACCCTCA CCCTGGTGCA  18800
 D  G  V   L  S  L    L  A  W  D   E  S  A   H  P  G     H  P  A  P  F  T  R   G  T  G    A  T  L  T   L  V  Q

GGCGCTGGAG GACGCCGGCG TGGCCGCCCC GCTGTGGTGC GTGACCCACG GCGCGGTGTC CGTCGGCCCG GCCGACCACG TCACCTCCCCC CGCCCAGGCC  18900
 A  L  E    D  A  G  V   A  A  P   L  W  C    V  T  H  G   A  V  S    V  G  R   A  D  H  V  T  S  P   A  Q  A

ATGGTGTGGG GCATGGGCCG GGTCGCCGCC CTGGAGCACC CCGAGCGGTG GGGCGGCCTG ATCGACCTGC CCTCGGACGC CGACCGGGCG GCCCTGGACC  19000
 M  V  W  G   M  G  R   V  A  A    L  E  H  P   E  R  W   G  G  L   I  D  L  P   S  D  A   D  R  A    A  L  D  R
```

Figure 31 - 38 plkPKS Sequence

```
          10         20         30         40         50         60         70         80         90        100
 1234567890 1234567890 1234567890 1234567890 1234567890 1234567890 1234567890 1234567890 1234567890 1234567890

GCATGACCAC GGTCCTCGCC GGGCGGTACGG GTGAGGACCA GGTCGCGGTA CGGCGCCTCC GGCTGCTCGC CCGCCGCCTC GTCCGCGCCT CCCTCCCGGC  19100
 M  T  T   V  L  A    G  G  T  G   E  D  Q    V  A  V    R  A  S  G   L  L  A   R  R  L   V  R  A  S   L  P  A

GCACGGCACG GCTTCGCCGT GGTGGCAGGC CGACGGCACG GTGCTCGTCA CCGGTGCCGA GGAGCCTGCC GCCGCCGAGG CCGCACGCCG GCTGGCCCGC  19200
 H  G  T   A  S  P  W   Q  A    D  G  T    V  L  V  T   G  A  E    E  P  A    A  A  E  A   A  R  R   L  A  R
                                                                                      ▼ NotI

GACGGGGCCG GACACCCTCC CCTCCACACC ACCCCCTCCG GCAGCGAAGG CGCCGAAGGC ACCTCCGGTG CCGCCGAGGA CTCCGGCCTC GCCGGGCTCG  19300
 D  G  A  G   H  L  L   L  H  T   T  P  S  G   S  E  G   A  E  G   T  S  G   A  E  D    S  G  L   A  G  L  V

TCGCCGAACT CGCGGACCTG GGCCGACGGG GCCGACGCCG CTCACGGACG CGGAGGCGGC CGCCCGGCTG CTCGCCGGCG TCTCCGACGC  19400
 A  E  L   A  D  L    G  A  T    A  V  V  T   C  D    L  T  D  A   E  A  A    A  R  L   L  A  G  V   S  D  A
                                                                                    ▼ NotI

TCGGCCGAACT CGGCGACCTG GGCCGACGGG GCCGACGCCG CTCACGGACG CGGAGGCGGC CGCCCGGCTG CTCGCCGGCG TCTCCGACGC  19400

GCACCCGGTC AGGGCCGTCC TCCACCTGCC GCCCACCGTC GACTCCGAGC CGCTCGCCGC GACCGACGCG GACGGCGCTCG CCGTGTCGT GACCGCGAAG  19500
 H  P  L   S  A  V  L   H  L  P    P  T  V    D  S  E  P   L  A  A   T  D  A   D  A  L  A   R  V  V   T  A  K
    ▼ EspI
    ▼ Bpu1102I
```

Figure 31 - 39 pikPKS Sequence

```
         10         20         30         40         50         60         70         80         90        100
1234567890 1234567890 1234567890 1234567890 1234567890 1234567890 1234567890 1234567890 1234567890 1234567890

GCCACCGCCG CGCTCCACCT GGACCGCCTC CTGCGGGAGG CCGCGGCTGC CGGAGGCCGT CGCCCCGTCC TGGTCCTCTT CTCCTCGGTC GCCGCGATCT  19600
 A  T  A  A  L  H  L  D  R  L  L  R  E  A  A  A  A  G  G  R  P  P  V  L  F  S  S  V  A  A  I  W

GGGGGGGGC CGGTCAGGGC GCGTACGCCG CCGGTACGGC CTTCCTCGAC GCCCTCGCCG GTCAGCACCG GGCCGACGGC CCCACCGTGA CCTCGGTGGC  19700
 G  G  A  G  Q  Q  G  A  Y  A  A  G  T  A  F  L  D  A  L  A  G  Q  H  R  A  D  G  P  T  V  T  S  V  A

CTGGAGCCCC TGGGAGGGCA GCCGCGTCAC CGAGGGTGCG ACCGGGGAGC GGCTGCGCCG CCTCGGCCTG CGTCGACTGG TCGAGCTTCG CCCCCGGCTT CACCACGGCC CGGCCGGGCA  19800
 W  S  P  W  E  G  S  R  V  T  E  G  A  T  G  E  R  L  R  R  L  G  L  R  P  L  A  P  A  T  A  L  T

GCCCTGGACA CCGCGCTCGG CCACGGCGAC ACCGCCGTCA CGATCGCCGA CGTCGACTGG TCGAGCTTCG CCCCCGGCTT CACCACGGCC CGGCCGGGCA  19900
 A  L  D  T  A  L  G  H  G  D  T  A  V  T  I  A  D  V  D  W  S  S  F  A  P  G  F  T  T  A  R  P  G  T
          AscI
         ▼
CCCTCCTCGC CGATCTGCCC GAGGGCGCGC GCGCGGCTCGA CGAGCAGCAG TCGACGACGG CCGCCGACGA CACCGTCCTG AGCCGGGAGC TCGGTGCGCT  20000
 L  L  A  D  L  P  E  A  R  R  A  L  D  E  Q  Q  S  T  T  A  D  D  T  V  L  S  R  E  L  G  A  L
```

Figure 31 - 40 pikPKS Sequence

```
         10         20         30         40         50         60         70         80         90        100
1234567890 1234567890 1234567890 1234567890 1234567890 1234567890 1234567890 1234567890 1234567890 1234567890

CACCGGCGCC GAACAGCAGC GCCGTATGCA GGAGTTGGTC CGCGAGCACC TCGCCGTGGT CCTCAACCAC CCCTCCCCCG AGGCCGTCGA CACGGGGCGG  20100
 T  G  A   E  Q  Q  R   R  M  Q   E  L  V   R  E  H  L   A  V  V   L  N  H   P  S  P  E   A  V  D   T  G  R
                                                                                   BstXI
                                                                                     ▼
GCCTTCCGTG ACCTCGGATT CGACTCGCTG ACGGCGGTCG AGCTCCGCAA CCGCCTCAAG AACGCCACCG GCCTGGCCCT CTGGTCTTCG  20200
 A  F  R  D   L  G  F   D  S  L   T  A  V  E   L  R  N   R  L  K   N  A  T  G   L  A  L   P  A  T   L  V  F  D

ACTACCCGAC CCCCCCGGACG CTGGCGGAGT TCCTCCTCGC GGAGATCCTG GGCGAGCAGG CCGGTGCCGG CGAGCAGCTT CCGGTGGACG GCGGGGTCGA  20300
 Y  P  T   P  R  T   L  A  E  F   L  L  A   E  I  L   G  E  Q  A   G  A  G   E  Q  L   P  V  D  G   G  V  D
                                                                                         MluI
                                                                                          ▼
CGACGAGCCC GTCGCGATCG TCGGCATGGC CCGGCTGCCG GGCGGGGTG TCGCCCTCGCC GGAGGACCTG TGGCCGGCGG CGAGGACGCG  20400
 D  E  P   V  A  I  V   G  M  A   C  R  L   P  G  G  V   A  S  P   E  D  L   W  R  L  V   A  G  G   E  D  A

ATCTCCGGCT TCCCGCAGGA CCGGCGCTGG GACGTGGAGG GGCTGTACGA CCCGGACCCC GACGGCGTCC GGCGGAGCGTA CTGCCGTGCC GGTGGCTTCC  20500
 I  S  G  F   P  Q  D   R  G  W   D  V  E  G   L  Y  D   P  D  P   D  A  S  G   R  T  Y   C  R  A   G  G  F  L
```

Figure 31 - 41 pikPKS Sequence

```
          10         20         30         40         50         60         70         80         90        100
 1234567890 1234567890 1234567890 1234567890 1234567890 1234567890 1234567890 1234567890 1234567890 1234567890
                                       SphI
                                       ▼
GGCTTCGGCC CGGCGGAGGG CGTCGGCATG CTCCTCGTCG AGCGCCTGTC GGACGCCCGC CGCAACGGAC ACCGTGTGCT GGCGGTCGTG CGCGGCAGCG   21100
 G  F  G  P  A  E  G   V  G  M   L  L  V  E   R  L  S    D  A  R   R  N  G  H   R  V  L   A  V  V    R  G  S  A

CGGTCAACCA GGACGGCGCG AGCAACGGCC TGACCGCCCC GAACGGGCCC TCGCAGCAGC GCGTCATCCG GGCGCGCTC GCGGACGCCC GACTGACGAC   21200
 V  N  Q    D  G  A   S  N  G  L   T  A  P   N  G  P   S  Q  Q  R   V  I  R   R  A  L   A  D  A  R   L  T  T

CGCCGACGTG GACGTCGTCG AGGCCCACGG CACGGGACAC CGACTCGGCG ACCCGATCGA GGCACAGGCC CTCATCGCCA CCTACGGCCA GGGGCGCGAC   21300
 A  D  V    D  V  V  E   A  H  G   T  G  T   R  L  G  D   P  I  E   A  Q  A   L  I  A  T   Y  G  Q   G  G  R  D

ACCGAACAGC CGCTGCGCCT GGGGTCGTTG AAGTCCAACA TCGGACACAC CCAGGCCGCC GCCGGTGTCT CCGGCATCAT CAAGATGGTC CAGGCGATGC   21400
 T  E  Q  P   L  R  L   G  S  L   K  S  N  I   G  H  T   Q  A  A   A  G  V  S   G  I  I   K  M  V   Q  A  M  R

GCCACGGCGT CCTGCCGAAG ACGCTCCACG TGGACCGGCC GTCGGACCAG ATCGACTGGT CGGCGGGCAC GGTCGAGCTG CTCACCGAGG CCATGGACTG   21500
 H  G  V    L  P  K   T  L  H  V   D  R  P   S  D  Q   I  D  W  S   A  G  T   V  E  L   L  T  E  A   M  D  W
              PmlI
              ▼
```

Figure 31 - 43 plkPKS Sequence

```
         10         20         30         40         50         60         70         80         90        100
1234567890 1234567890 1234567890 1234567890 1234567890 1234567890 1234567890 1234567890 1234567890 1234567890

GGACTCCGAC GGCTGCCTGC TCACGGGGAG CCTCTCCCTC CGTACGCACC CCTGGCTGGC GGACCACGCG GTGGCCGGCA CCGTGCTGCT GCCGGGAACG 23100
 D  S  D   G  C  L    T  G  S    L  S  L    R  T  H  P   W  L  A    D  H  A    V  A  G    T  V  L  L   P  G  T

GCGTTCGTGG AGCTGGCGTT CCGAGCCGGG GACCAGGTCG GTTGCGATCT GGTCGAGGAG CTCACCCTCG ACGGCGCGCT CGTGCTGCCC CGTCGTGGCG 23200
 A  F  V   E  L  A  F   R  A  G   D  Q  V  G   C  D  L    V  E  E    L  T  L  D   A  P  L    V  L  P    R  R  G  A

CGGTCCGTGT GCAGCTGTCC GTCGGCGCGA GCGACGAGTC CGGGGCGTCGT ACCTTCGGGC TCTACGCGCA CCCGGAGGAC GCGCCGGGCG AGGCGGAGTG 23300
 V  R  V   Q  L  S    V  G  A  S    D  E  S    G  R  R   T  F  G  L   Y  A  H    P  E  D    A  P  G  E   A  E  W

GACGCGGCAC GCCACCGGTG TGCTGGCCGC CCGTGCCGAC CGCACCGCCC CCGTGCGGAC CCGGAGGCC TGGCCGCCGC CGGGCGCCGA GCCGGTGGAC 23400
 T  R  H   A  T  G  V   L  A  A    R  A  D    R  T  A  P   V  A  D    P  E  A   W  P  P  P   G  A  E    P  V  D
       Eco47III
          ▼
GTGGACGGTC TGTACGAGCG CTTCGCGGCG AACGGCTACG GCTACGGCCC CCTCTTCCAG GGCGTCCGTG GGGTCTGGCG GCGTGGCGAC GAGGTGTTCG 23500
 V  D  G   L  Y  E  R   F  A  A   N  G  Y  G   Y  G  P    L  F  Q    G  V  R  G   V  W  R    R  G  D    E  V  F  A
```

Figure 31 - 47 pikPKS Sequence

```
         10         20         30         40         50         60         70         80         90        100
1234567890 1234567890 1234567890 1234567890 1234567890 1234567890 1234567890 1234567890 1234567890 1234567890

CCGACGTGGC CCTGCCGGCC GAGGTCGCCG GTGCCGAGGG CGCGGGGTTC GGCCTTCACC CGGCGGCTGCT CGACGCCGCC GTGCAGGGCGG CCGGTGCGGG  23600
 D  V  A   L  P  A    E  V  A  G   A  E  G    A  R  F   G  L  H  P   A  L  L   D  A  A    V  Q  A  A   G  A  G

CCGGGGCGTT CGGGCGCGGGC ACGCGGCTGC CGTTCGCCTG GAGCGGGATC TCCTGTACGC GGTCGGGCGCC ACCGCCCTCC GCGTGCGGCT GGCCCCCGCC  23700
 R  G  V   R  R  G  H   A  A  A   V  R  L     E  R  D  L  L  Y  A   V  G  A    T  A  L  R   V  R  L    A  P  A

GGCCCGGACA CGGTGTCCGT GAGCGCCGCC GACTCCCTCG GGCAGCCGGT GTTCGCCGCG GACTCCCTCA CGGTGCTGCC CGTCGACCCC GCGCAGCTGG  23800
 G  P  D  T   V  S  V    S  A  A   D  S  S  G    Q  P  V    F  A  A   A  D  S  L  T    V  L  P    V  D  P    A  Q  L  A

CGGCCTTCAG CGACCCGACT CTGGACGCGC TGCACCTGCT GGAGTGGACC GCCCTGGGAC GTGCCGGCGCA GGCCCTGCCC GGCGGGGTCG TGCTGGGCGG  23900
 A  F  S   D  P  T   L  D  A  L   H  L  L    E  W  T    A  W  D  G    A  A  Q    A  L  P    G  A  V  V    L  G  G

CGACGCCGAC GGTCTCGCCG CGGCGCTGCG CGCCGGTGGC ACCGAGGTCC TGTCCTTCCC GGACCTTACG GACCTGGTGG AGGCCGTCGA CCGGGGCGAG  24000
 D  A  D   G  L  A  A    A  L  R    A  G  G    T  E  V  L   S  F  P    D  L  T    D  L  V  E    A  V  D    R  G  E
```

Figure 31 - 48 pikPKS Sequence

```
          10         20         30         40         50         60         70         80         90        100
1234567890 1234567890 1234567890 1234567890 1234567890 1234567890 1234567890 1234567890 1234567890 1234567890

ACCCCGGCCC CGGCGACCGT CCTGGTGGCC TGCCCCGCCG CCGGCCCCGA TGGGCCGGAG CATGTCCGCG AGGCCCTGCA CGGGTCGCTC GCGCTGATGC  24100
 T  P  A  P  A  T  V  L  V  A  C  P  A  A  G  P  D  G  P  E  H  V  R  E  A  L  H  G  S  L  A  L  M  Q

AGGCCTGGCT GGCCGACGAG CGGTTCACCG ATGGGCGCCT GGTGCTCGTG ACCCGCGACG CGGTCGCCGC CCGTTCGCCG GACGGCCTGC GGTCCACGGG  24200
 Q  A  W  L  A  D  E  R  F  T  D  G  R  L  V  L  V  T  R  D  A  V  A  A  R  S  G  D  G  L  R  S  T  G

ACAGGCCGCC GTCTGGGGCC TCGGCCGGTC CGCGCAGACG GAGAGCCCGG GCCGGTTCGT CCTGCTCGAC CTCGCCGGGG AAGCCCGGAC GGCCGGGGAC  24300
 T  G  Q  A  A  V  W  G  L  G  R  S  A  Q  T  E  S  P  G  R  F  V  L  L  D  L  A  G  E  A  R  T  A  G  D

GCCACCGCCG GGGACGGCCT GACGACCGGG GACGCCACCG TCGGCGGCAC CTCTGGAGAC GCCGCCCTCG GCAGCGCCCT CGGCACCGCC CTCGGCTCGG  24400
 D  A  T  A  G  D  G  L  T  T  G  D  A  T  V  G  G  T  S  G  D  A  A  L  G  S  A  L  A  T  A  L  G  S  G

GCGAGCCGCA GCTCGCCCTC CGGGACGGGG CGCTCCTCGT ACCCCGCCTG GCGCGGGCCG CCGCGCCCGC GGCCCTCGCC CGGCCGACGG  24500
 G  E  P  Q  L  A  L  R  D  G  A  L  L  V  P  R  L  A  R  A  A  A  P  A  A  A  D  G  L  A  A  A  D  G
```

Figure 31 - 49 pikPKS Sequence

```
         10          20          30          40          50          60          70          80          90         100
1234567890  1234567890  1234567890  1234567890  1234567890  1234567890  1234567890  1234567890  1234567890  1234567890

CCTCGCCGCT CTGCCGCTGC CCGGCCGCTCC GGCCCTCTGG CGTCTGGAGC CCGGTACGGA CGGCAGCCTG GAGAGCCTCA CGGGGGCGCC CGGCGACGCC  24600
 L  A  A    L  P  L  P    A  A  P    A  L  W    R  L  E  P    G  T  D    G  S  L    E  S  L  T    A  A  P    G  D  A

GAGACCCTCG CCCCGGAGCC GCTCGGGCCG GGACAGGTCC GCATCGCGAT CCGGGCCACC GTCTCTCAACT TCCGCGACGT CCTGATCGCC CTCGGCATGT  24700
 E  T  L  A    P  E  P    L  G  P    G  Q  V  R    I  A  I    R  A  T    G  L  N  F    R  D  V    L  I  A    L  G  M  Y

ACCCCGATCC GGCGCTGATG GGCACCGAGG GAGCCGGGCGT GGTCACCGGG ACCGGCCCCG GCGTCACGCA CCTCGCCCCC GGCGACCGGG TCATGGGCCT  24800
 P  D  P    A  L  M    G  T  E  G    A  G  V    V  T  A    T  G  P  G    V  T  H    L  A  P    G  D  R  V    M  G  L

GCTCTCCGGC GCGTACGCCC CGGTCGTCGT GGCCGGACGCG CGGACCGTCG CGGCGGATGCC CGAGGGGTGG ACGTTCGCCC AGGGCGCCTC CGTGCCGGTG  24900
 L  S  G    A  Y  A  P    V  V  V    A  D  A    R  T  V  A    R  M  P    E  G  W    T  F  A  Q    G  A  S    V  P  V

GTGTTCCTGA CGGCCGTCTA CGCCCTGCGC GACCTGGCGG ACGTCAAGCC CGGCGAGCGC CTCCTGGTCC ACTCCGCCGC GGCATGGCCG GGTGGCGTG  25000
 V  F  L  T    A  V  Y    A  L  R    D  L  A  D    V  K  P    G  E  R    L  L  V  H    S  A  A    G  G  V    G  M  A  A
```

Figure 31 - 50 pikPKS Sequence

```
          10         20         30         40         50         60         70         80         90        100
 1234567890 1234567890 1234567890 1234567890 1234567890 1234567890 1234567890 1234567890 1234567890 1234567890

CCGTGCAGCT CGCCCGGCAC TGGGGCGTGG AGGTCCACGG CACGGGAAGT GGGACGCCCT GGCGGCGCTC GGCCTGGACG ACGCGCACAT 25100
 V  Q  L   A  R  H    W  G  V  E    V  H  G    T  A  S    H  G  K  W    D  A  L    R  A  L    G  L  D  D    A  H  I

CGCCTCCTCC CGACCCTGG  ACTTCGAGTC CGCGTTCCGT GCCGCTTCCG GCGGGGGCGG CATGGACGTC GTACTGAACT CGCTCGCCCG CGAGTTCGTC 25200
 A  S  S    R  T  L  D    F  E  S    A  F  R    A  A  S  G    G  A  G    M  D  V    V  L  N  S    L  A  R    E  F  V

GACGGCCTCG TGGCCCTGCT CGGGGCCGGG GGCCCGGTTCG TGGAGATGGG GAAGACCGAC GTCCGGGACG CGGAGCGGGT CGCCGCCGAC CACCCCGGTG 25300
 D  A  S  L    R  L  L    G  P  G    G  R  F  V    E  M  G    K  T  D    V  R  D  A    E  R  V    A  A  D    H  P  G  V

TCGGCTACCG CGCCTTCGAC CTGGGGCGAGG CCGGGCCGGA GCGGATCGGC GAGATGCTCG CCGAGGTCAT CGCCCTCTTC GAGGACGGGG TGCTCCGGCA 25400
 G  Y  R    A  F  D    L  G  E  A    G  P  E    R  I  G    E  M  L  A    E  V  I    A  L  F    E  D  G  V    L  R  H

CCTGCCCGTC ACGACCTGGG ACGTGCGCCG GCCTTCCGGC ACGTCAGCCA GGCCCGCCAC ACGGGCAAGG TCGTCCTCAC GATGCCGTCG 25500
 L  P  V    T  T  W  D    V  R  R    A  R  D    A  F  R  H    V  S  Q    A  R  H    T  G  K  V    V  L  T    M  P  S
```

Figure 31 - 51 pikPKS Sequence

```
          10         20         30         40         50         60         70         80         90        100
1234567890 1234567890 1234567890 1234567890 1234567890 1234567890 1234567890 1234567890 1234567890 1234567890
                                                                                   PmlI
                                                                                    ▼
GGCCTCGACC CGGAGGGTAC GGTCCTGCTG ACCGGCGGCA CCGGTGCGCT GGGGGGCATC GTGGCCCGGC ACGTGGTGGG CGAGTGGGGC GTACGACGCC  25600
 G  L  D  P  E  G  T  V  L  L  T  G  G  T  G  A  L  G  G  I  V  A  R  H  V  V  G  E  W  G  V  R  R  L
                                    ApaLI
                                     ▼
TGCTGCTCGT GAGCCGGCGG GGCACGGACG CCCCGGGCGC CGGCGAGCTC GTGCACGAGC TGGAGGCCCT GGGAGCCGAC GTCTCGGTGG CCGCGTGCGA  25700
 L  L  V  S  R  R  G  T  D  A  P  G  A  G  E  L  V  H  E  L  E  A  L  G  A  D  V  S  V  A  C  D

CGTCGCCGAC CGGGAAGCCC TCACCGCCGT ACTCGACTCG ATCCCCGCCG AACACCCGCT CACCGCGGTC GTCCACACGG CAGGCGTCCT CTCCGACGGC  25800
 V  A  D  R  E  A  L  T  A  V  L  D  S  I  P  A  E  H  P  L  T  A  V  V  H  T  A  G  V  L  S  D  G

ACCCTCCCCT CGATGACAGC GGAGGATGTG GAACACGTAC TGCGTCCCAA GGTCGACGCC GGTTCCTCCC TCGACGAACT CACCTCGACG CCCGGCTACG  25900
 T  L  P  S  M  T  A  E  D  V  E  H  V  L  R  P  K  V  D  A  A  F  L  L  D  E  L  T  S  T  P  G  Y  D

ACCTGGCCAG GTTCGTCATG TTCTCCTCCG CCGCCGCCGT CTTCGGTGGC GCGGGGCAGG GGCCTACGC CGCCGCCAAC GCCACCCTCG ACGCCCTCGC  26000
 L  A  A  F  V  M  F  S  S  A  A  A  V  F  G  G  A  G  Q  G  A  Y  A  A  A  N  A  T  L  D  A  L  A
```

Figure 31 - 52 plkPKS Sequence

```
          10         20         30         40         50         60         70         80         90        100
1234567890 1234567890 1234567890 1234567890 1234567890 1234567890 1234567890 1234567890 1234567890 1234567890

CGCTCACCGC CGTCGAACTC CGCAACCGTC TCAACGCCGC GACCGGGCTG CGGCTGCCGG CCACGCTGGT CTTCGACCAC CCCACCCCGG GGGAGCTCGC  26600
 L  T  A   V  E  L    R  N  R  L  N  A  A   T  G  L    R  L  P  A  T  L  V   F  D  H    P  T  P  G   E  L  A

CGGGCACCTG CTCGACGAAC TCGCCACGGC CGCGGGCGGG TCCTGGGCGG AAGGCACCGG GTCCGGAGAC ACGGCCTCGG CGACCGATCG GCAGACCACG  26700
G  H  L    L  D  E  L  A  T  A   A  G  G    S  W  A  E  G  T  G   S  G  D    T  A  S  A  T  D  R    Q  T  T

GCGGGCCCTCG CCGAACTCGA CCGGCTGGAA GGCGTGCTCG CCTCCCTCGC GCCCGCCGCC GGCGGCCGTC CGGAGCTCGC CGCCCGGCTC AGGGGCGCTGG  26800
 A  A  L  A  E  L  D   R  L  E    G  V  L  A  S  L  A   P  A  A    G  G  R  P  E  L  A   A  R  L    R  A  L  A
                                                        BstXI
                                                        ▼
CCGGGGGCCCT GGGGACGAC GGCGACGACG CCACCGACCT GGACGAGGCG TCCGACGACG ACCTCTTCTC CTTCATCGAC AAGGAGCTGG GCGACTCCGA  26900
 A  A  L    G  D  D    D  D  A    T  D  L    D  E  A   S  D  D  D  L  F  S   F  I  D    K  E  L  G   D  S  D

CTTCTGACCT GCCCGACACC ACCGGCACCA CCGGGCACCAC CAGCCCCCCT CACACACGGA ACACGGAACG GACAGGCGAG AACGGGAGCC ATGGCGAACA  27000
 F                                                                                                    M  A  N  N
```

Figure 31 - 54 pikPKS Sequence

```
         10         20         30         40         50         60         70         80         90        100
1234567890 1234567890 1234567890 1234567890 1234567890 1234567890 1234567890 1234567890 1234567890 1234567890

CGTGGACGTC GTCGAGGCGC ACGGCACGGG CACGCGGCTC GGCGACCCGA TCGAGGCGCA GGCCCTCATC GCCACCTACG GCCAGGAGAA GAGCAGCGAA  28100
 V  D  V   V  E  A  H   G  T  G   T  R  L   G  D  P  I   E  A  Q   A  L  I   A  T  Y  G   Q  E  K   S  S  E

CAGCCGCTGA GGCTGGGCGC GTTGAAGTCG AACATCGGGC ACACGCAGGC CGCGGCCCGT GTCGCAGGTG TCATCAAGAT GGTCCAGGCG ATGCGCCACG  28200
 Q  P  L  R  L  G  A   L  K  S   N  I  G  H   T  Q  A   A  A  G   V  A  G  V   I  K  M   V  Q  A   M  R  H  G

GACTGCTGCC GAAGACGCTG CACGTCGACG AGCCCTCGGA CCAGATCGAC TGGTCGGCGG GCACGGTGGA ACTCCTCACC GAGGCCGTCG ACTGGCCCGA  28300
 L  L  P   K  T  L   H  V  D  E   P  S  D   Q  I  D  W   S  A  G   T  V  E   L  L  T   E  A  V  D   W  P  E

GAAGCAGGAC GGCGGGCTGC GCCGCGCGGC TGTCTCCTCC TTCGGCATCA GCCCCTCGGA AGGCCCCGGC GTCCTGGAGG AGGCCCCGGC GGTCGAGGAC  28400
 K  Q  D   G  G  L  R   R  A  A   V  S  S   F  G  I  S   P  S  E   A  P  A   V  L  E  E   A  P  A   V  E  D

TCCCCCGGCCG TCGAGCCGCC GGCCGGTGGC GGTGTGGTGC CGGTCGTGCC GGCCGGTGGT GCCGGTGGCG CCGGTGGCGG CCAGATCGGG CAGCTCGCCG  28500
 S  P  A  V   E  P  P   A  G  G   G  V  V  P   V  V  P   A  G  G   V  G  G  V   G  G  G   Q  I  G   Q  L  A  A
```

Figure 31 - 57 pikPKS Sequence

```
         10         20         30         40         50         60         70         80         90        100
1234567890 1234567890 1234567890 1234567890 1234567890 1234567890 1234567890 1234567890 1234567890 1234567890

CCTCACCATG ACCCTCCCCG AGACCGTCAC CGGCCTCGGC ACCCTCCGCC GCGAACAGGG AGGCCAGGAG CGTCTGGTCA CCTCACTCGC CGAAGCCTGG  29600
 L  T  M   T  L  P  E   T  V  T   G  L  G    T  L  R  R  E  Q  G  G  Q  E   R  L  V  T   S  L  A   E  A  W

Eco47III
GCCAACGGCC TCACCATCGA CTGGGCGCCC ATCCTCCCCA CCGCAACCGG CCACCACCCC GAGCTCCCCA CCTACGCCTT CCAGACCGAG CGCTTCTGGC  29700
 A  N  G  L  T  I  D   W  A  P    I  L  P  T  A  T  G   H  H  P   E  L  P  T  Y  A  F   Q  T  E   R  F  W  L
      PstI
      ▶
     SfcI
      ▶
TGCAGAGCTC CGGCCCACC AGCGCCGCCG ACGACTGGCG TTACCGCGTC GAGTGGAAGC CGCTGACGGC CTCCGGCCAG GCGGACCTGT CCGGGCGGTG  29800
 Q  S  S   A  P  T    S  A  A  D   D  W  R   Y  R  V   E  W  K  P   L  T  A   S  G  Q   A  D  L  S   G  R  W

GATCGTCGCC GTCGGGAGCC AGCCAGAAGC CGAGCTGCTG GGCGCGCTGA AGGCCGCGGG AGCGGAGGTC GACGTACTGG GAGGCAGGAC GGACGACGAC  29900
 I  V  A   V  G  S  E  P  E  A    E  L  L    G  A  L  K   A  A  G   A  E  V   D  V  L  E   A  G  A   D  D  D

CGTGAGGCCC TCGCCGCCCG GCTCACCGCA CTGACGACCG GCGACGGCTT CACCGGCGTG GTCTCGCTCC TCGACGACCT CGTGCCACAG GTCGCCTGGG  30000
 R  E  A  L  A  A  R   L  T  A    L  T  T  G   D  G  F   T  G  V   V  S  L  L   D  D  L   V  P  Q   V  A  W  V
```

Figure 31 - 60 pikPKS Sequence

```
          10         20         30         40         50         60         70         80         90        100
 1234567890 1234567890 1234567890 1234567890 1234567890 1234567890 1234567890 1234567890 1234567890 1234567890

CGATGTCGAC TGGGAGCGGT TCGGCCCCGC GTTCACGGTG TCCCGTCCCA GCCTTCTGCT CGACGGCGTC CCGGAGGCCC GGCAGGCGCT CGCCGCACCC  31100
 D  V  D   W  E  R  F  A  P  A   F  T  V    S  R  P  S   L  L  L   D  G  V    P  E  A  R  Q  A  L   A  A  P

GTCGGTGCCC CGGCTCCCGG CGACGCCGCC GTGGGCCGA CCGGCAGTC GTCGGCGCTG GCCGCGATCA CCGCGCTCCC CGAGCCCGAG CGCCGGCCGG  31200
 V  G  A  P  A  P  G   D  A  A   V  A  P  T  G  Q  S   S  A  L   A  A  I  T   A  L  P   E  P  E   R  R  P  A

CGCTCCTCAC CCTCGTCCGT ACCCACGCGG CGGCCGTACT CGGCCATTCC TCCCCCGACC GGGTGGCCCC CGGCCGTGCC TTCACCGAGC TCGGCTTCGA  31300
 L  L  T   L  V  R    T  H  A  A   A  V  L   G  H  S   S  P  D  R   V  A  P   G  R  A    F  T  E  L   G  F  D

CTCGCTGACG GCCGTGCAGC TCCGCAACCA GCTCTCCACG GTGGTCGGCA ACAGGCTCCC CGCCACCACG GTCTTCGACC ACCCGACGCC CGCCGCACTC  31400
 S  L  T   A  V  Q  L   R  N  Q    L  S  T   V  V  G  N   R  L  P   A  T  T   V  F  D  H   P  T  P   A  A  L

GCCGCGCACC TCCACGAGGC GTACCTCGCA CCGGCCGAGC CGGCCCCGAC GGACTGGGAG GGGCGGGTGC GCCGGGCCCT GGCCGAACTG CCCCTCGACC  31500
 A  A  H  L  H  E  A   Y  L  A    P  A  E  P   A  P  T   D  W  E    G  R  V  R  R  A  L   A  E  L   P  L  D  R
```

Figure 31 - 63 pikPKS Sequence

```
          10         20         30         40         50         60         70         80         90        100
1234567890 1234567890 1234567890 1234567890 1234567890 1234567890 1234567890 1234567890 1234567890 1234567890

GGCTGCGGGA CGCGGGGGTC CTCGACACCG TCCTGCGCCT CACCGGCATC GAGCCCGAGC CGGGTTCCGG CGGTTCGGAC GGCGGGCGCG CCGACCCTGG   31600
 L  R  D   A  G  V   L  D  T  V   L  R  L   T  G  I    E  P  E  P   G  S  G    G  S  D   G  G  A   A  D  P  G

TGGGGAGCCG GAGGCGTCGA TCGACGACCT GGACGCCGAG GCCCTGATCC GGATGGCTCT CGGCCCCCGT AACACCTGAC ACCCACCCA CGAGGGAAG A  31700
 A  E  P   E  A  S  I  D  D  L   D  A  E    A  L  I  R   M  A  L   G  P  R    N  T

CGGCGCCGAC CCCGCGCATC CCGCGCCACA CCCGCCCCCA CACGCCCACA ACCCCCATCC CGAGGGAAG A CCACACCCA GATGACGAGT TCCAACGAAC  31800
                                                                                          M  T  S   N  E  Q

AGTTGGTGGA CGCTCTGCGC GCCTCTCTCA AGGAGAACGA AGAACTCCGG AAAGAGAGCC GTCGCCGGGC CGACCGTCGG CAGGAGCCCA TGGCCGATCGT 31900
 L  V  D   A  L  R    A  S  L  K   E  N  E   E  L  R    K  E  S  R   R  R  A   D  R  R   Q  E  P   M  A  I  V

Acc65I  KpnI

CGGCATGAGC TGCCGGTTCG CGGGCGGAAT CCGGTCCCCC GAGGACCTCT GGGACGCCGT CGCCGCGGGC AAGGACCTGG TCTCCGAGGT ACCGGAGGAG  32000
 G  M  S    C  R  F   A  G  G  I   R  S  P   E  D  L  W   D  A  V   A  A  G   K  D  L    V  S  E  V   P  E  E
```

Figure 31 - 64 pikPKS Sequence

```
          10         20         30         40         50         60         70         80         90        100
1234567890 1234567890 1234567890 1234567890 1234567890 1234567890 1234567890 1234567890 1234567890 1234567890

CGGGGCTGGG ACATCGACTC CCTCTACGAC CCGGTGCCCG GGGCAAGGG CACGACGTAC GTCCGCAACG CCGCGTTCCT CGACGACGCC GCCGGATTCG  32100
 R  G  W  D  I  D  S   L  Y  D   P  V  P  G   R  K  G   T  T  Y   V  R  N   A  A  F  L   D  D  A   A  G  F  D

ACGGGGCCTT CTTCGGGATC TCGCCGCGCG AGGCCCTCGC CATGGACCCG CAGCAGCGGC AGCTCCTCGA AGCCTCCTGG GAGGTCTTCG AGCGGGCCGG  32200
 A  A  F   F  G  I   S  P  R  E   A  L  A   M  D  P   Q  Q  R  Q   L  L  E   A  S  W   E  V  F   F  E  R  A  G

CATCGACCCC GCGTCGGTCC GCGGCACCGA CGTCGGCGTG TACGTGGGCT GTGGCTACCA GGACTACGCG CCGGACATCC GGGTCGCCCC CGAAGGCACC  32300
 I  D  P   A  S  V  R   G  T  D   V  G  V   Y  V  G  C   G  Y  Q   D  Y  A   P  D  I  R   V  A  P   E  G  T

GGCGGGTTACG TCGTCACCGG CAACTCCTCC GCCGTGGCCT CCGGGCGCAT CGCGTACTCC CTCGGCCTGG AGGGACCCGC CGTGACCGTG GACACGGCGT  32400
 G  G  Y  V   V  T  G   N  S  S   A  V  A  S   G  R  I   A  Y  S   L  G  L  E   G  P  A   V  T  V   D  T  A  C

GCTCCTCTTC GCTCGTCGCC CTGCACCTCG CCCTGAAGGG CCTGCGGAAC GGCGACTGCT CGACGGCACT CGTGGGCGGC GTGGCCGTCC TCGCGACGCC  32500
 S  S  S   L  V  A  L   H  L  A   L  K  G   L  R  N   G  D  C  S   T  A  L   V  G  G   V  A  V  L   A  T  P
```

Figure 31 - 65 pIkPKS Sequence

```
          10         20         30         40         50         60         70         80         90        100
1234567890 1234567890 1234567890 1234567890 1234567890 1234567890 1234567890 1234567890 1234567890 1234567890

GGGCGCGGTTC ATCGAGTTCA GCAGCCAGCA GGCCATGGCC GCCGACGGCC GGACCAAGGG CTTCGCCTCG GCGGGGGACG GCCTCGCCTG GGGCGAGGGC  32600
 G  A  F  I  E  F  S  Q  Q  A  M  A  A  D  G  R  T  K  G  F  A  S  A  A  D  G  L  A  W  G  E  G

GTCGCGCGTAC TCCTCCTCGA ACGGCTCTCC GACGCGCGGC GCAAGGGCCA CCGGGTCCTG GCCGTCGTGC GCCGTCGTGC CATCAACCAG GACGGGCGCGA  32700
 V  A  V  L  L  L  E  R  L  S  D  A  R  R  K  G  H  R  V  L  A  V  V  R  G  S  A  I  N  Q  D  G  A  S

GCAACGGCCT CACGGGCTCCG CAGGGGCCCT CCCAGCAGCA CCTGATCCGC CAGGCCCTGG CCGACGCGCG GCTCACGGTCG AGCGACGTGG ACGTCGTGGA  32800
 N  G  L  T  G  S  Q  G  P  S  Q  Q  H  L  I  R  Q  A  L  A  D  A  R  L  T  S  S  D  V  D  V  V  E
                                                                                        AscI
                                                                                         ▼
GGGCCACGGC ACGGGGACCC GTCTCGGCGA CCCGATCGAG GCGCAGGCGC TGCTCGCCAC GTACGGGCAG GGGGCGCGCC CGGGGGCAGCC GCTGCCGGCTG  32900
 G  H  G  T  G  T  R  L  G  D  P  I  E  A  Q  A  L  L  A  T  Y  G  Q  G  R  A  P  G  Q  P  L  R  L

GGGACGCTGA AGTCGAACAT CGGGCACACG CAGGCCGCTT CGGGTGTCGC CGGTGTCATC AAGATGGTGC AGGGCGCTGCG CCACGGGGTG CTGCCGAAGA  33000
 G  T  L  K  S  N  I  G  H  T  Q  A  A  S  G  V  A  G  V  I  K  M  V  Q  G  A  L  R  H  G  V  L  P  K  T
```

Figure 31 - 66 plkPKS Sequence

```
          10         20         30         40         50         60         70         80         90        100
1234567890 1234567890 1234567890 1234567890 1234567890 1234567890 1234567890 1234567890 1234567890 1234567890
```

PmlI
▶
CCCTGCACGT GGACGAGCCG ACGGACCAGG TCGACTGGTC GGCCGGTTCG GTCGAGCTGC TCACCGAGGC CGTGGACTGG CCGGAGCGGC CGGGCCGGCT 33100
 L  H  V   D  E  P    T  D  Q  V  D  W  S   A  G  S    V  E  L  L  T  E  A    V  D  W   P  E  R  P   G  R  L

CCGCCGGGCG GGCGTCTCCG CGTTCGGCGT GGGCGGGACG AACGCGCACG TCGTCCTGGA GGAGGCCCCG GCGGTCGAGG AGTCCCCTGC CGTCGAGCCG 33200
 R  R  A   G  V  S  A  F  G  V   G  G  T    N  A  H  V  V  L  E    E  A  P   A  V  E  E  S  P  A    V  E  P

CCGGGCCGGTG GCGGGCGTGGT GCCCGTGGCCG GTGTCCGGCGA AGACCTCGGC CGCACTGGAC GCCCAGATCG GGCAGCTCGC CGCATACGCG GAAGACCGCA 33300
 P  A  G  G  G  V  V   P  W  P    V  S  A  K  T  S  A    A  L  D    A  Q  I  G  Q  L  A   A  Y  A   E  D  R  T

CCGGACGTGGA TCCGGCGGTG GCCGCCCGGG CCCTGGTCGA CAGCCGTACG GCGATGGAGC ACCGGGCGGT CGGGGTCGGC GACAGCCGGG AGGCACTGCG 33400
 D  V  D    P  A  V    A  A  R  A  L  V  D    S  R  T   A  M  E  H  R  A  V   A  V  G    D  S  R  E  A  L  R

GGACGCCCTG CGGATGCCGG AAGGACTGGT ACGGGGCACG GTCACCGATC CGGGCCGGGT GGCGTTCGTC TTCCCCGGCC AGGGCACGCA GTGGGCCGGC 33500
 D  A  L   R  M  P  E  G  L  V   R  G  T    V  T  D  P  G  R  V   A  F  V    F  P  G  Q  G  T  Q    W  A  G

Figure 31 - 67 plkPKS Sequence

```
         10         20         30         40         50         60         70         80         90        100
1234567890 1234567890 1234567890 1234567890 1234567890 1234567890 1234567890 1234567890 1234567890 1234567890

CCGCGGGTCC CGGCGAGGCG CCCGCGCACA CCGCTTCCGG GCGCGAGGCC GTCGCCGAGA CGGGGCTCGC GTGGGGCCCG GGTGCCGAGG ACCTCGACGA  34600
 A  G  P    G  E  A    P  A  H  T   A  S  G   R  E  A   V  A  E  T   G  L  A   W  G  P   G  A  E   D  L  D  E

GGAGGGCCGG CGCAGCGCCG TACTCGCGAT GGTGATGCGG CAGGGCGGCCT CCGTGCTCCG GTGCCGACTCG CCCGAAGAGG TCCCCGTCGA CCGCCCGCTG  34700
 E  G  R   R  S  A  V   L  A  M   V  M  R    Q  A  A  S   V  L  R    C  D  S   P  E  E  V   P  V  D   R  P  L

CGGGAGATCG GCTTCGACTC GCTGACCGCC GTCGACTTCC GCAACCGCGT CAACCGGCTG ACCGGTCTCC AGCTGCCGCC CACCGTCGTG TTCCAGCACC  34800
 R  E  I  G   F  D  S   L  T  A   V  D  F  R   N  R  V   N  R  L   T  G  L  Q   L  P  P   T  V  V   F  Q  H  P
          *                                                                                              ACP 6

CGACGCCCGT CGGCGCTCGCC GAGGCGCATCA GCGACGAGCT GGCCGAGCGG AACTGGGCCG TCGCCGAGCC GTCGGATCAC GAGCAGGCGG AGGAGGAGAA  34900
 T  P  V   A  L  A   E  R  I  S   D  E  L    A  E  R   N  W  A  V   A  E  P   S  D  H   E  Q  A  E   E  E  K
                            ↑                                                                         TE domain GGCCGCCGCT CCGGCGGGGG CCCGCTCCGG GGCCGACACC GGCCGCGGCG CCGGGGATGTT CCGGCGCCCTG TTCCGGCAGG CCGTGGAGGA CGACCGGTAC  35000
 A  A  A   P  A  G  A   R  S  G   A  D  T   G  A  G  A   G  M  F   R  A  L   F  R  Q  A   V  E  D   D  R  Y
```

Figure 31 - 70 pikPKS Sequence

```
          10         20         30         40         50         60         70         80         90        100
 1234567890 1234567890 1234567890 1234567890 1234567890 1234567890 1234567890 1234567890 1234567890 1234567890

CCAGGACCGG CGTGCCGAGC CGTGTCTGGA GAGGGTCGAG GAGCTCGCCG AGCATGTGGT CGCGGCCACC GAACCCTGGT GGCAGGAGGG CCGGCTGGCC  36100
 Q  D  R   R  A  E  P   C  L  E   S  V  E    E  L  A  E   H  V  V   A  A  T   E  P  W   W  Q  E  G   R  L  A

TTCTTCGGGC ACAGCCTCGG CGCCTCCGTC GCCTTCGAGA CGGCCCGCAT CCTGGAACAG CGGCACGGGG TACGGCCCGA GGGCCTGTAC GTCTCCGGTC  36200
 F  F  G    H  S  L  G   A  S  V   A  F  E  T   A  R  I   L  E  Q    R  H  G  V   R  P  E    G  L  Y    V  S  G   R
        ▲
       AscI                                                                                EspI
                                                                                           Bpu1102I
GGGCGGCCCC GTCGCTGGCG CCGGACCGGC TCGTCCACCA GCTGGACGAC CGGGCGTTCC TGGCCGAGAT CCGGCGGCTC AGCGGCACCG ACGAGCGGTT  36300
 G  R  P    R  S  W  R   R  T  G   S  S  T  S   W  T  T   G  R  R   L  A  E  I    R  R  L    S  G  T  D   E  R  F

CCTCCAGGAC GACGAGCTGC TGCGGCCCGC CTGCGCCCGG CTGCCCGCGC TGCGCAGCGA CTACAAGGC GGCGGAGACG TACCTGCACC GGCCGTCCGC CAAGCTCACC  36400
 L  Q  D   D  E  L  L   R  L  V    L  P  A    L  R  S  D   Y  K  A   A  E  T   Y  L  H  R   P  S  A   K  L  T

TGCCCGGTGA TGGCCCTGGC CGGCGACCGT GACCCGAAGG CGCCGCTGAA CGAGGTGGCC GAGTGGCGTC GGCACACCAG CGGGCCGTTC TGCCTCCGGG  36500
 C  P  V  M   A  L  A   G  D  R   D  P  K  A   P  L  N   E  V  A    E  W  R  R   H  T  S    G  P  F    C  L  R  A
```

Figure 31 - 73 sugar.finalgene b-1 Sequence

```
         10        20        30        40        50        60        70        80        90
1234567890123456789012345678901234567890123456789012345678901234567890123456789012345678901234567890
BamHI
▶
GGATCCGGCGCTTCCACCCGCGCCGAACAGCGCGGTGCGGCTGGTCTGCTGCCGCACGCCCGGCTCCGCCAGCTACTTCTTCCGCT            90
CCTAGGCCGCGAAGGTGGGCGCGGCTTGTCGCGCCACCGACGCCGACCAGACGACGGCGTGCGGGCCGAGGCGGTCGATGAAGAAGGCGA
  I  R  R  F  H  P  A  P  N  S  A  V  R  L  V  C  L  P  H  A  G  G  S  A  S  Y  F  F  R  F

TCTTCGAGGAGCTGCACCCCTCCGTCGAGGCCCTGTCGGTGCAGTATCCGGGCCGCCAGGACCGGCGTGCCGAGCCGTGTCTGGAGAGCG     180
AGAGCCTCCTCGACGTGGGGAGGCAGCTCCGGGACAGCAGCGTCATAGGCCCGGCGGTCCTGGCCGCACGGCTCGGCACAGACCTCTCGC
  S  E  E  L  H  P  S  V  E  A  L  S  V  Q  Y  P  G  R  Q  D  R  R  A  E  P  C  L  E  S  V
                                              NspHI
                                              ▶
TCGAGGAGCTCGCCGAGCATGTGGTCGCGGCCACCGAACCCTGGTGGCAGGAGGGCCGGCTGGCCTTCTTCGGGCACAGCCTCGGCGCCT     270
AGCTCCTCGAGCGGCTCGTACACCAGCGCCGGTGGCTTGGGACCACCGTCCTCCCGGCCGACCGGAAGAAGCCCGTGTCGGAGCCGCGGA
  E  E  L  A  E  H  V  V  A  A  T  E  P  W  W  Q  E  G  R  L  A  F  F  G  H  S  L  G  A  S

AscI
                                                      ▶
CCGTCGCCGCCTTCGAGACGGCCCGCATCCTGGAACAGCGGCACGGGGTACGGCCCGAGGGCCTGTACGTCTCCGGTCGGGCGCCCCGTCGC    360
GGCAGCGGCGGAAGCTCTGCCGGGCGTAGGACCTTGTCGCCGTGCCCCATGCCGGGCTCCCGGACATGCAGGCCAGCCCGCGGGGCAGCG
  V  A  F  E  T  A  R  I  L  E  Q  R  H  G  V  R  P  E  G  L  Y  V  S  G  R  R  A  P  S  L
```

FIG. 32 – 1 sugar.finalgene b-1 Sequence

```
          10        20        30        40        50        60        70        80        90
1234567890123456789012345678901234567890123456789012345678901234567890123456789012345678901234567890
                              PvuII                                       EspI
                              PflMI                                       Bpu1102I
    RsrII                      ▼                                            ▼
TGGGCGCCGGACCGGCTCGTCTCCACCAGCTGGACGACGACCGGGCCGGGCGGCGCTCAGCGGCACCGGACGAGCGGTTCCTCC    450
ACCGGGCCTGGCCGAGCCAGTGGTCGACCTGCTGGCCGAGGACCGGCTCTAGGCCGCCCGAGTCGCCGTGGCCTGCTCGCCAAGGAGG
 A  P  D  R  L  V  H  Q  L  D  D  D  R  A  F  L  A  E  I  R  R  L  S  G  T  D  E  R  F  L  Q

FspI
                                            ▼
AGGACGACGAGCTGCTGCGCTGTGTCGCCCGCGCTGCGCAGCGACTACAAGGCGGCGGAGACGTACCTGCACCGGCCGTCCGCCAAGC    540
TCCTGCTGCTCGACGACGCGACACAGCGGGCGCGACGCGTCGCTGATGTTCCGCCGCCTCTGCATGGACGTGGCCGGCCAGGCGGTTCG
 D  D  E  L  L  R  L  V  L  P  A  L  R  S  D  Y  K  A  A  E  T  Y  L  H  R  P  S  A  K  L

TCACCTGCCCGGTGATGGCCCTGGCCGGGACCGGGACCCGGCTGGACTTGCTCCGCGGCTCACCGGCTCCACCGCCGTGGTCGCCCG    630
AGTGGACGGGCCACTACCGGGACCGGCCCTGGCCCTGGGCCGACCTGAACGAGGCGCCGAGTGGCCGAGTGGCGCACCAGCGGGC
 T  C  P  V  M  A  L  A  G  D  R  D  P  K  A  P  L  N  E  V  A  E  W  R  R  H  T  S  G  P

BglII
                                      ▼
CGTTCTGCCTCCGGCGTACTCCGGCGGCCACTTCTACCTCAACGACCAGTGGCACGAGATCTGCAACGACATCTCCGACCACCTGCTCG    720
GCAAGACGGAGGCCGCGATGAGGCCGCCGGTGAAGATGGAGTTGCTGGTCACCGTGCTCTAGACGTTGCTGTAGAGGCTGGTGGACGAGC
 F  C  L  R  A  Y  S  G  G  H  F  Y  L  N  D  Q  W  H  E  I  C  N  D  I  S  D  H  L  L  V
```

FIG. 32 – 2 sugar.finalgene b-1 Sequence

```
          10        20        30        40        50        60        70        80        90
 1234567890123456789012345678901234567890123456789012345678901234567890123456789012345678901234567890
   AscI                                                         EarI                    BstEII
   ▶                                                            ▶                       ▶
 TCACCCGGCGGCGGCCCGATGCCCGCGTCGTGCAGCCCCCGACCAGCCTTATCGAAGGAGCGGCGAAGAGATGGCAGAA CCCACGGTGAC       810
 AGTGGGCGCCGCCGCGGCTACGGGCGCGCAGTCGGGGGCTGGTCGGAATAGCTTCCTCGCCGCTTCTCTACCGTCTTGGGTGCCACTG
  T  R  G  A  P  D  A  R  V  V  Q  P  P  T  S  L  I  E  G  A  A  K  R  W  Q  N  P  R  V  T
                                ApaI                                              PflMI
                                ▶                                                 ▶
 CGACGACCTGACGGGGGGCCCTCACGCAGCAGCCCCCGCTGGGCCGTCCGCGGTGGCCGACCTGAACTCGCACCACCTCCTGGA           900
 GCTGCTGGACTGCCCCCCGGGAGTGCGTCGTCGGGGGCGACCCGGCAGGCGCCACCGGCTGGACTTGAGCGTGGTGGAGGACCT
  D  D  L  T  G  A  L  T  Q  P  P  L  G  R  T  V  R  A  V  A  D  R  E  L  G  T  H  L  L  E
                       BamHI
                       ▶
 GACCCCGCGGTACGCCACTGATCCACGCCGGAACGGCGACCCGTGCTGCGGCCAGGCGGACGACCCGTATCCCGCGTA        990
 CTGGGGCGCCATGCGGTGACTAGGTGACGGCCTTGCCGCTGGGCACGACGCCGGTCCGCCTGCTGGGCATAGGGCGCAT
  T  R  G  I  H  W  I  H  A  A  N  G  D  P  Y  A  T  V  L  R  G  Q  A  D  D  P  Y  P  A  Y
                                                                 BstEII
                                                                 PvuII
                                                                 ▶
 CGAGCGGGTGCGTGCCCGGGCGGCGCTCTCCTTCAGCCGACGGCAGCTGGGTCACGCGCGATCACGCCCTGGCGGCGAGCATCCTCTG       1080
 GCTCGCCCACGCACGGGCCCGCCGCGAGAGGAAGTCGGCTGCCGTCGACCCAGTGCGCGCTAGTGCGGGACCGCCGCTCGTAGGAGAC
  E  R  V  R  A  R  G  A  L  S  F  S  P  T  G  S  W  V  T  A  D  H  A  L  A  A  S  I  L  C
```

FIG. 32-3 sugar.finalgene b-1 Sequence

```
          10        20        30        40        50        60        70        80        90
 123456789012345678901234567890123456789012345678901234567890123456789012345678901234567890
 CTCGACGGACTTCGGGGTCTCCGGCGCCGACGGCGTCCCGGTGCCGCAGCAGTCCTCTCGTACGGGGAGTCCTGCTGTCCGCTGAGCGCGA    1170
 GAGCTGCCTGAAGCCCCAGAGGCCGCGGCTGCCGCAGGGCCACGGCGTCGTCAGGAGAGCATGCCCCTCCAGCAGGCGACCTCGCGCT
  S  T  D  F  G  V  S  G  A  D  G  V  P  Q  Q  V  L  S  Y  G  E  G  C  P  L  E  R  E
            ▼AlwNI                                              ▼BamHI
 GCAGGTGCTGCCGGCGGCCGGTGACGTGCCGGAGGGCCAGCGTGCCGTGGTCGAGGGGATCCACCGGGAGACGCTGGAGGGTCTCGC    1260
 CGTCCACGACGGCCGCCGGCCACTGCACGGCCTCCCGGTCGCACGGCACCAGCTCCCCTAGGTGGCCCTCTGCGACCTCCCAGAGCG
  Q  V  L  P  A  A  G  D  V  P  E  G  G  Q  R  A  V  V  E  G  I  H  R  E  T  L  E  G  L  A

GCCGGACCCGTCGGCTGTGTACGCCTTGAGCTGCCGCGCGGTTTCGTCCGCCCCGCGCCGTGCTGGGTGT    1350
 CGGCCTGGGCAGCCGCAGACATGCGGAACTCGACGAGCTGAAGCGCCGGGCGCGGCGCGGCACGACCCACA
  P  D  P  S  A  S  Y  A  F  E  L  L  G  G  F  V  R  P  A  V  T  A  A  A  A  V  L  G  V
    ▼RsrII                                                              ▼AlwNI
 TCCCGCGGACCGGCGGCGCGGGACTTCGCGGATCTGCTGGAGCGGCTCCGGCCGCTGTCCGACAGCCTGCTGGCCCCCGAGTCCCTGCGGAC    1440
 AGGGCGCCTGGCCGCCGCGCCCTGAAGCGCCTAGACGACCTCGCCGAGGCCGGCGACAGGCTGTCGGACGACCGGGGCTCAGGGACGCCTG
  P  A  D  R  R  A  D  F  A  D  L  L  E  R  L  R  P  L  S  D  S  L  L  A  P  Q  S  L  R  T
```

FIG. 32 – 4 sugar.finalgene b-1 Sequence

```
          10        20        30        40        50        60        70        80        90
 1234567890123456789012345678901234567890123456789012345678901234567890123456789012345678901234567890
                                                      TfiI                            ApaI
                                                        ▼                               ▼
GGTACGGGCGGGACGGCGGCGCGCTGGCCGAGCTCACGGCTGCCGATTCGGACGACTCCCCGGGGGCCCTGCTGTCGGCGCTCGG    1530
CCATGCCCGCCCTGCCGCCGCGCGACCGGCTCGAGTGCCGACGGCTAAGCCTGCTGAGGGGCCCCCGGGACGACAGCCGCGAGCC
 V  R  A  A  D  G  A  L  A  E  L  T  A  L  L  A  D  S  D  D  S  P  G  A  L  L  S  A  L  G
BstEII
  ▼
GGTCACCGCAGCCGTCCAGCTCACCGGGAACGCGGTGCTCGCGCTGCTCGCGCATCCCGAGCAGTGGCGGGAGCTGTGCGACCGGCCCGG    1620
CCAGTGGCGTCGGCAGTCGAGTGGCCCTTGCGCCACGAGCGCGTAGGGCTCGTCACCGCCCTCGACACGCTGGCCGGGCC
 V  T  A  A  V  Q  L  T  G  N  A  V  L  A  L  L  A  H  P  E  Q  W  R  E  L  C  D  R  P  G
                      NotI
                        ▼
GCTCGCGGCGGCCGCCGGGTGAGGAGACCCTCCGCTACGACCCCCCGGTGCAGCTCGACGCGCCGGTGTCGCGGGAGACGGAGCTGGC    1710
CGAGCGCCGCCGGCGGCCCACTCCTCTGGGAGGCGATGCTGGGGGCCACGTCGAGCTGCGCGGCCACAGCGCCCTCTGCCTCGACCG
 L  A  A  A  V  E  E  T  L  R  Y  D  P  P  V  Q  L  D  A  R  V  V  R  G  E  T  E  L  A
                       NspHI                                    BbsI                Eco47III
                         ▼                                        ▼                     ▼
GGGCCCGGCGGCTGCCGGCGCCGGCGCATGTCGTCCTGACGTCGTCGCTGACCGGCGGGAGAGTCTTCACGGACCCGGAGCGCTT    1800
CCCGGGCCGCCGACGGCCGCGGCCGCGTACAGCAGGACTGCAGCAGCGACTGGCCGCCCTCTCAGAAGTGCCTGGGCCTCGCGAA
 G  R  R  L  P  A  G  A  H  V  V  V  L  T  A  A  T  G  R  D  P  P  E  V  F  T  D  P  E  R  F
```

FIG. 32-5 sugar.finalgene b-1 Sequence

```
          10         20         30         40         50         60         70         80         90
 1234567890123456789012345678901234567890123456789012345678901234567890123456789012345678901234567890
                                                          RsrII
                                                          ▼
 CGACCCTCGCGGCGCCCGACGCGCCGCCGCACCTCGCGCTGCACCCCGCGCTCGTACGGCCGGTCCCTGGTCCGGCTTCAGGC        1890
 GCTGGAGCGCCGCGGGGCTGCGCGGCGGCGTGGAGCGCGACGTGGGGCGCGAGCATGCCGGCCAGGACCAGGCCGAAGTCCG
  D  L  A  R  P  D  A  A  A  H  L  A  L  H  P  A  G  P  Y  G  P  V  A  S  L  V  R  L  Q  A

GGAGGTCGCGCTGAGGACCCTGGCCGGGCGGTTTCCCCGGCTGCGGCAGGCGGGGACGTGTCCGCGCCGCGGCCTGTCGGCCG        1980
 CCTCCAGCGCGACTCCTGGGACCGGCCCGCCAAAGGGGCCGACGCCGTCCGCCCCCTGCACAGGCGCGGCGCCGGACAGCCGGC
  E  V  A  L  R  T  L  A  G  R  F  P  G  L  R  Q  A  G  D  V  L  R  P  R  R  A  P  V  G  R

EspI                       AlwNI                ApaI    RsrII
       Bpu1102I                   ▼                    ▼       ▼
       ▼
 CGGGCCGCTGAGCGTCCCGGTCAGCAGTCCTGAGACACCGGGCCCCCGGTCCGCCGGGACGGCTCGGAC                      2070
 GCCCGGCGACTCGCAGGGCCAGTCGTCAGGACTCTGTGGCCCGGGGGCCAGGCGGCCCTGCCGAGCCTG
  G  P  L  S  V  P  V  S  S  S

CACGGGGACGGCTCAGACCGTCCCGTGTCCCGTCCGGCTCCCCGTCCGCCCATCCCGCCCTCCACCGGCAAG GAAGGA CACGACGC  2160
 GTGCCCCTGCCGAGTCTGGCAGGCACAGGGCAGGCCGAGGGCAGGCGGGTAGGGCGGGAGGTGGCCGTTCCTTCCTGTGCTGCG
```

FIG. 32 – 6 sugar.finalgene b-1 Sequence

```
          10        20        30        40        50        60        70        80        90
 123456789012345678901234567890123456789012345678901234567890123456789012345678901234567890
 CATGCGCGTCCTGCTGACCTCGTTCGCACATCACACGCACTACGGCCTGGTGCCCCTGGCCTGGGCGCTGCTCGCCGCGGGCACGA    2250
 GTACGCGCAGGACGACTGGAGCAAGCGTGTAGTGCGTGATGATGCCGGACCACGGGACCGACGAGCGGCGGCCCGTGCT
  M  R  V  L  L  T  S  F  A  H  H  T  H  Y  Y  G  L  V  P  L  A  W  A  L  L  A  A  G  H  E

DraIII
▶
 GGTGCGGGTCGCGCCAGCCAGCCCGCGCTCACGGACACCATCACCGGTCTCCGGGTGCCGGTCGGCACCGACCACCTCATCCA       2340
 CCACGCCCAGCGCGGTCGGGCGTCGGGCGCGAGTGCCTGTGGTAGTGGCCCAGGCCCAGCAGCCGTGGCTGGTGGAGTAGT
  V  R  V  A  S  Q  P  A  L  T  D  T  I  T  G  S  G  L  A  A  V  P  V  G  T  D  H  L  I  H

PvuI
                                          ▶
 CGAGTACCGGGTGCGGATGGCGGGCGAGCCCGAACCATCCGGCGATCGCCTTCGACGAGGCCCGTCCCGAGCCGCTGGA           2430
 GCTCATGGCCCACGCCCTACCGCCCGCTCGGCGCCTTGGTAGGCCGCTAGCGGAAGCTGCTCCGGGCAGGGCTCGGCGACCTGACCCT
  E  Y  R  V  R  M  A  G  E  P  P  R  P  N  H  P  A  I  A  F  D  E  A  R  P  E  P  L  D  W  D

CCACGCCCCTCGGCATCGAGGCGATCCTCGCCCCCGTACTTCCATCTGCTCGCCAACAACGACTCGATGGTCGACGACCTCGTCGACTTCGC   2520
 GGTGCGGGGAGCCGTAGCTCCGCTAGGAGCGGGGGCATGAAGGTAGACGAGCGGTTGTTGCTGAGCTACCAGCTGCTGGAGCAGCTGAAGCG
  H  A  L  G  I  E  A  I  L  A  P  Y  F  H  L  L  A  N  N  D  S  M  V  D  D  L  V  D  F  A
```

FIG. 32-7 sugar.finalgene b-1 Sequence

```
         10        20        30        40        50        60        70        80        90
1234567890123456789012345678901234567890123456789012345678901234567890123456789012345678901234567890
```

```
                                                                       AgeI
                                                                    BstEII
                                                                    ▼  ▼
CCGGTCCTGGCAGCCGGACCTGGTGCTGTGGGAGCCGACGACCTACGCGGGGCCCGTGCCGCCCAGTCACCGGTGCCGCGCACGCCCG   2610
GGCCAGGACCGTCGGCCTGGACCACGACACCCCTCGGCTGCTGGATGCGCCCCCGGGGCAGCGGGTCAGTGGCCACGGCGCGTGCGGGC
R  S  W  Q  P  D  L  V  L  W  E  P  T  T  Y  A  G  A  V  A  A  Q  V  T  G  A  A  H  A  R

ApaI
      ▼
GGTCCTGTGGGGCCCGACGTGATGGGCAGCGCCCGCAAGTTCGTCGCGCTGCGGGACCGGCAGCCCCCGGAGCACCGCGAGGACCCC   2700
CCAGGACACCCCGGGCTGCACTACCCGTCGCGGGCGTTCAAGCAGCGCGACGCCCTGGCCGTCGGGGGCCTCGTGGCGCTCCTGGG
V  L  W  G  P  D  V  M  G  S  A  R  R  K  F  V  A  L  R  D  R  Q  P  P  E  H  R  E  D  P

BstBI
                          AgeI    EarI                                                PvuI
                          ▼        ▼  ▼                                               ▼
CACCGCGGAGTGGCTGACGTGGACCCTCGACCGGTACGGCGCCTCCTTCGAAGAGGAGCTGCTCACCGGCCAGTTCACGATCGACCCGAC   2790
GTGGCGCCTCACCGACTGCACCTGGGAGCTGGCCATGCCGCGGAGGAAGCTTCTCCTCGACGAGTTGGCCGGTCAAGTGCTAGCTGGGCTG
T  A  E  W  L  T  W  T  L  D  R  Y  G  A  S  F  E  E  E  L  L  T  G  Q  F  T  I  D  P  T

CCCGCCGAGCCTGCGCCTGCGACACGGGCCTGCCGACCGTCGGGATGCGTTATGTTCCGTACAACGGCACGTCGGTCGTGCCGGACTGGCT   2880
GGGCGGCTCGGACGCGGAGCTGTGCCCGGACGCTGGCAGCCCTACGCAATACAAGGCATGTTGCCGTGCAGCACGGCCTGACCGA
P  P  P  S  L  R  L  D  T  G  L  P  T  V  G  M  R  Y  V  P  Y  N  G  T  S  V  V  P  D  W  L
```

FIG. 32–8 sugar.finalgene b-1 Sequence

```
          10         20         30         40         50         60         70         80         90
 1234567890123456789012345678901234567890123456789012345678901234567890123456789012345678901234567890
 GAGTGAGCCGCCCGCGCGGCCCCGGGTCTGCCTGACCCTCGGCGTCTCCGGCGTGAGGTCCTCGAGGCGGTCTCGCGGGACGCGGGGTCTCGCAGGGCGA    2970
 CTCACTCGGCGGGCGCGCCGGGCCCAGACGGACTGGGAGCCGCACTCCAGGAGCGCGCAGAGCGCCGCACAGAGCTCCAGCTCCAGCAGAGCGTCCCGCT
  S  E  P  P  A  R  P  P  R  V  C  L  T  L  G  V  S  A  R  E  V  L  G  G  D  D  G  V  S  Q  G  D

CATCCTGAGGCGCTCGCCGACATCGAGCTCGTCGCCACGCTCGACGCGAGTCAGCGCGCCGAGATCCGCAACTACCCGAAGCA                   3060
 GTAGGACCTCCGCGAGCGGCTGTAGCTCGAGCAGCGGTGCGAGCTGCGCTCAGTCGCGGGCTTCTAGGCGTTGATGGGCTTCGT
  I  L  E  A  L  A  D  L  D  I  E  L  V  A  T  L  D  A  S  Q  R  A  E  I  R  N  Y  P  K  H

CACCCGGTTCACGGACTTCGTGCCGATGCACGCGCTCCTGCCGAGCTGCTCGGCGATCATCCACGGCGGGGCCACTACGCGAC                   3150
 GTGGGCCAAGTGCCTGAAGCACGGCTACGTGCGCGAGGACGGCTCGACGAGCCGCTAGTAGGTGCCGCCCCCGGTGATGCGCTG
  T  R  F  T  D  F  V  P  M  H  A  L  L  P  S  C  S  A  I  I  H  H  G  G  A  G  T  Y  A  T
           BclI
           ▼
 CGCCGTGATCAACGCGGTGCCGCAGGTCATGCTCGCCGAGCTGTGGGACGCGCCGGTCAAGGCGCGGGCCGTCGCCGAGCAGGGGCGGG             3240
 GCGGCACTAGTTGCGCCACGGCGTCCAGTACGAGCGGCTCGACACCCTGCGCGGCCAGTTCCGCGCCCGGCAGCGGCTCGTCCCCGCCC
  A  V  I  N  A  V  P  Q  V  M  L  A  E  L  W  D  A  P  V  K  A  R  A  V  A  E  Q  G  A  G
```

FIG. 32–9 sugar.finalgene b-1 Sequence

```
         10        20        30        40        50        60        70        80        90
123456789012345678901234567890123456789012345678901234567890123456789012345678901234567890
GTTCTTCCTGCCGCCGGAGCTCACGCCGGCCGCGGGGACGCCGTGCGGCCAGGCCGTGCGCGACGCCTCGACATCCTCGACGACCCCTCGGTCGCCACCGCGC    3330
CAAGAAGGACGCGGGCGGCCGCGGCGCGGCGCTCCGGCACGTGCGGCCAGGCGTGCAGGCGTGGCTGGGGAGCTGTCGGGGAGCTGCCAGCGGTGGCGGCG
 F F L P P A E L T P Q A V R D A V V R I L D D P S V A T A A

GCACCGGCTGCGCGAGGAGACCTTCGGCGACCCCACCCCGGCCGGGATCGTCCCCGAGCTGGAGCGGCTCGCCGCGCAGCACCGCCGCCC              3420
CGTGGCCGACGCGCTCCTCTGGAAGCCGCTGGGGTGGGGCCGGCCCTAGCAGGGGCTCGACTTCGCCGAGCGGCGCGTCGTGGCGGCGGG
 H R L R E E T F G D P T P A G I V P E L E R L A A Q H R R P

GCCGGGCCGACGCCCCGGCACTGAGCCGCACCCCTGCGCCCAGGCCTCACCCTGTATCTGCGCCGGGAGCGCCCCGGCCCACCCTCCGA                3510
CGGCCCGGCTGCGGGGCCGTGACTCGGCGTGGGGACGCGGGTCCGGAGTGGGGACATAGACGCGGCCCTCGCGGGGCCGGGTGGGAGGCT
 P A D A R H                                              StuI

AatII       EarI
                ▼           ▼
AAGACCGAAAGC AGGAG CACCGTGTACGAAGTCGACACCGCCGACGTCTACGACCTCTTCTACCTGGTCGCGGAAGGACTACGCCGCC              3600
TTCTGGCTTTCGTCCTCGTGGCACATGCTTCAGCTGTGCGGCTGCAGAAGATGCTGGAGAAGATGGACCCAGCGCCTTCCTGATGCGGCCGG
      V Y E V D H A D V Y D L F Y L G R G K D Y A A
```

FIG. 32 – 10 sugar.finalgene b-1 Sequence

```
         10        20        30        40        50        60        70        80        90
1234567890123456789012345678901234567890123456789012345678901234567890123456789012345678901234567890
                                            StuI
                                            ▶
GAGGCCTCCGACATCGCCGACCTGGTGCGCTCCCGTACCCCCGAGGCCTCCTCGCTCCTGGACGTGGCCTGCGGTACGGGCACGCATCTG        3690
CTCCGGAGGCTGTAGCGGCTGGACCACGCGAGGGCATGGGGGCTCCGGAGGAGGAGACCTGCACCGGACGCCATGCCCGTGCGTAGAC
 E  A  S  D  I  A  D  L  V  R  S  R  T  P  E  A  S  S  L  L  D  V  A  C  G  T  G  T  H  L
            StyI                                        NspHI
            ▶                                           ▶
GAGCACTTCACCAAGGAGTTCGGCGACACCGCCGGCCTGGAGCTGTCCGAGGACATGCTCACCCACGCCCGCAAGCGGCTGCCCGACGCC        3780
CTCGTGAAGTGGTTCCTCAAGCCGCTGTGGCGGCCGGACTCGACAGGCTCCTGTACGAGTGGGTGCGGGCGTTCGCCGACGGGCTGCGG
 E  H  F  T  K  E  F  G  D  T  A  G  L  E  L  S  E  D  M  L  T  H  A  R  K  R  L  P  D  A
                                 NspHI                                      NspHI
                                 ▶                                          ▶
ACGCTCCACCAGGGCGACATGCGGGACTTCCGGCTTCGGGGAAGTTCTCCGCCGTGGTCAGCATGTTCAGCTCCGTGGTACCTGAAG        3870
TGCGAGGTGGTCCCGCTGTACGCCCTGAAGGCCGAGCCCTTCAAGAGGCGGCACCAGTCGTACAAGTCGAGGCAGCCGATGGACTTC
 T  L  H  Q  G  D  M  R  D  F  R  L  G  R  K  F  S  A  V  V  S  M  F  S  S  V  G  Y  L  K
 BbsI
 ▶
ACGACCGAGGAACTCGGCGCCGCCGTCGCCTCGTTCGCGGAGCACCTGGAGCCGGGCGTCGTCGTTGAGCCGTGGTGTTCCCG        3960
TGCTGGCTCCTTGAGCCGCGGCGGCAGCGGAGCAAGCGCCTCGTGGACCTCGGCCCGCAGCAGCTCGGCACCACCAAGGGC
 T  T  E  E  L  G  A  A  V  A  S  F  A  E  H  L  E  P  G  G  V  V  V  E  P  W  W  F  P
```

FIG. 32-11 sugar.finalgene b-1 Sequence

```
          10         20         30         40         50         60         70         80         90
 1234567890123456789012345678901234567890123456789012345678901234567890123456789012345678901234567890
                                         AatII                                            DraIII
                                          ▶                                                 ▶
 GAGACCTTCGCCGACGGCTGGGTCAGCGCCGACGTCGTCCGCCGTGACGGGCGCACCGTGGCCCGTGTCTCGCACTCGGTGCGGGAGGGG           4050
 CTCTGGAAGCGGCTGCCGACCCAGTCGCGGCTGCAGCAGGGCGGCACTGCCCGCGTGGCACCGGGCACAGAGCGTGAGCCACGCCCTCCC
  E  T  F  A  D  G  W  V  S  A  D  V  V  R  R  D  G  R  T  V  A  R  V  S  H  S  V  R  E  G

AatII
                                                                ▶
 AACGCGACGCGCATGGAGGTCCACTTCACCGTGGCCGACCCCGGGCAAGGGCGTGCGGCACTTCTCCGACGTCCATCTCATCACCCTGTTC           4140
 TTGCGCTGCGCGTACCTCCAGGTGAAGTGGCACCGGCTGGGGCCCGTTCCCGCACGCCGTGAAGAGGCTGCAGGTAGTAGTGGGACAAG
  N  A  T  R  M  E  V  H  F  T  V  A  D  P  G  K  G  V  R  H  F  S  D  V  H  L  I  T  L  F

SfiI            EarI
                                                                                 ▶                ▶
 CACCAGGCCGAGTACGAGGCCGTTCACGGCCGCCGGGCTGCGCGTGAGTACCTGGAGGGCGGCCCGTGGCCCTCTTCGTC                     4230
 GTGGTCCGGCTCATGCTCCGGCAAGTGCCGGCGGCCCGACGCGCACTCATGGACCTCCCGCCGGGCACCGGGAGAAGCAG
  H  Q  A  E  Y  E  A  V  H  G  R  R  A  A  G  L  R  A  V  E  Y  L  E  G  G  P  S  G  R  G  L  F

AatII ApaLI
                                          ▶   ▶
 GGCGTCCCCGCCTGAGCACCGCCCAAGACCCCCGGGGCGGGACGTCCCGGTGCACCAGCGTCCCCAAGAGAGAAACGAACCGTGACAGGT           4320
 CCGCAGGGGCGGACTCGTGGCGGGTTCTGGGGGCCCCGCCCTGCAGGGCCACGTGGTCGCAGGGGTTCGTTCTCTCTTTGCTTGGCACTGTCCA
  G  V  P  A                                                                 V  T  G
```

FIG. 32 – 12 sugar.finalgene b-1 Sequence

```
         10        20        30        40        50        60        70        80        90
123456789012345678901234567890123456789012345678901234567890123456789012345678901234567890

NotI
AAGACCCGAATACCGGTGTCCGCGCCGGCCGACCACGCGGCCCCAGGGCCTTCACCCTGGCCGTCGTGGGCACCCTGCTGGCGGCACCACC   4410
TTCTGGGCTTATGGCCACAGGCGCACAGGCGGCCGGCCGGGTCCCGGAAGTGGGACCAGCCGCAGCAGCCGTGGGACGACCGCCGTGGTGG
 K  T  R  I  P  R  V  R  R  G  R  T  T  P  R  A  F  T  L  A  V  V  G  T  L  L  A  G  T  T
      NotI
GTGGCGGCCGCGCTCCCGGCGCCGCGGGGCCCGCGAGGGCGGCCAATGTTCAGTACACGAGCCGGGGCGGAGCTCGTCGCCCAGATGACGCTCGAC   4500
CACCGCCGGCGCGAGGGCCGCGGCGCCCCGGGCGCTCCCGCCGGTTACAAGTCATGTGCTCGGCCCCGCCTCGAGCAGCGGGTCTACTGCGAGCTG
 V  A  A  A  P  G  A  A  D  T  A  N  V  Q  Y  T  S  R  A  A  E  L  V  A  Q  M  T  L  D

GAGAAGATCAGCTTCGTCCACTGGGCGCTGGACCCCGACAGAACGTCGGCTACCTTCCCGGCTGCCGCTCTCGGGCATCCCGGAG   4590
CTCTTCTAGTCGAAGCAGGTGACCCGCGACCTGGGGCTGGGGCCGGTCTTGCAGCCGATGGAAGGGCCGACGGCGAGACCCGTAGGGCCTC
 E  K  I  S  F  V  H  W  A  L  D  P  D  R  Q  N  V  G  Y  L  P  G  V  P  R  L  G  I  P  E

MscI
                                                          BalI
CTGGCGTGCCGCCGACGGCCCGAACGGCATCCGCCTGGTGGGCAGACCGGCCACCGGCCGCCACCGGCGTCGCCGCCGTGCCCTGCCAGCACCTTC   4680
GACGCACGGCGGCTGCCGGGCTTGCCGGTAGGCGGACCACCCGTCTGGCCGGTGGCCGGCGGTGGCCGCAGCGGCGGCACGGGACGGTCGTGGAAG
 L  R  A  A  D  G  P  N  G  I  R  L  V  G  Q  T  A  T  A  L  P  A  P  V  A  L  A  S  T  F
```

FIG. 32–13 sugar.finalgene b-1 Sequence

```
          10         20         30         40         50         60         70         80         90
1234567890123456789012345678901234567890123456789012345678901234567890123456789012345678901234567890
                                                              StyI                    PflMI           ApaI
          StyI                                                ▼                       ▼               ▼
          NcoI
          ▼
GACGACACACCATGGCCGACAGTACGGCAAGTCATGGGCCGCGACGGTCGCGCCGACGTGCCGCGCTCAACCAGGACATGTCCTGGCCCGATGATGAAC       4770
CTGCTGTGTGGTACCCGGCTGTCGTGCCGTTCCAGTACCCGGCCGCCGCGCCGCCGACGAGTTGGTCCTGTACCAGGACCCGGGCTACTACTTG
 D  D  T  M  A  D  S  Y  G  K  V  M  G  R  D  G  R  A  L  N  Q  D  M  V  L  G  P  M  M  N

AACATCCGGGTGCCGCACGGCGGCCGCAACTACGAGACCTTCAGCGAGGACCCCCTGGTCTCCTCGCGCACCGCGGTGCCCAGATCAAG               4860
TTGTAGGCCCACGGCGTGCCGCCGGCGTTGATGCTCTGGAAGTCGCTCCTGGGGACCAGAGGAGCGCGTGGCGCCAGCGGTCTAGTTC
 N  I  R  V  P  H  G  G  R  N  Y  E  T  F  S  E  D  P  L  V  S  S  R  T  A  V  A  Q  I  K

GGCATCCAGGGTGCGGGTCTGATGACCACGGCCCAAGCACTTCGCGGCCAAGCACCGGAGAACAACCGCTTCTCCGTGAACGCCAATGTC             4950
CCGTAGGTCCCACGCCCAGACTACTGGTGCCGGGTTCGTGAAGCGCCGGTTCGTGGTGGCCTCTTGTTGGCGAAGAGGCACTTGCGGTTACAG
 G  I  Q  G  A  G  L  M  T  T  A  K  H  F  A  A  N  N  Q  E  N  N  R  F  S  V  N  A  N  V

StyI                          SfiI
                                                        ▼                             ▼
GACGAGCAGAGACGCTCCGGCGAGATCGAGTTCCCCGGCGTTCGAGGCGTCCTCAAGGCGCTCCCGGCGCCGCGGCCCTTCATGTGCCTACAACGGC       5040
CTGCTCGTCTCTGCGAGGCCGCTCTAGCTCAAGGGCCGCAAGCTCCGACGAGAGTTCCGGCGCCGGCCGAGGAAGTACACACGGATGTTGCCG
 D  E  Q  T  L  R  E  I  E  F  P  A  F  E  A  S  S  K  A  G  A  A  S  F  M  C  A  Y  N  G
```

FIG. 32 – 14 sugar.finalgene b-1 Sequence

```
          10         20         30         40         50         60         70         80         90
 1234567890123456789012345678901234567890123456789012345678901234567890123456789012345678901234567890
                                                              FspI     DraIII
                                                               ▼         ▼
CTCAACGGGAAGCCGTCTGCGCAACGACGAGCTCCTCAACAACGTGCTGCGCACGCAGTGGGGCTTCCAGGGCTGGGTGATGTCCGAC          5130
 L  N  G  K  P  S  C  G  N  D  E  L  L  N  N  V  L  R  T  Q  W  G  F  Q  G  W  V  M  S  D

StyI         EcoNI PflMI                                                  AatII
         ▼             ▼    ▼                                                      ▼
GAGTTGCCCTTCCGGCAGGACGACCGCCGTTGCTGCTGCACGACGTGTTGCAGACGCGTGCTGCTGCACCCGAAGTCCGACCACTACAGGCTG
                                    BbsI
                                     ▼
TGGCTCGCCACCCCGGGGACACCGACGCGCCATCACCAAGGGCCTCGACCAGGAGATGGGCGTCGAGCTCCCCGGCGACGTCCCGAAGGGCGAG          5220
 W  L  A  T  P  G  T  D  A  I  T  K  G  L  D  Q  E  M  G  V  E  L  P  G  D  V  P  K  G  E

ACCGAGCGGTGGGCGGCCGTTGCCGGTAGTGGTTCCCGGACTGGTCCTACCCCCAGTCCAGTCTCGAGGGCCGCTCGAGGGCTTCCCGCTC

CCCTCGCCGCCGGCCAAGTTCTTCGGCGAGGCGCTGAAGACGGCCGTCCTGAACGGCACGGTTCCGGAGGCCGCCGTGACGCGGTCGGCG           5310
 P  S  P  P  A  K  F  F  G  E  A  L  K  T  A  V  L  N  G  T  V  P  E  A  A  V  T  R  S  A

GGGAGCGGCGGCCGTTCAAGAAGCCGCTCCGGACTTCTGCCGGAGACTTGCCTGCCAGGGCTCCAGGGGCTGCCGGCCACTGCGCCAGCCGC

GAGCGGATCGTCGGCCAGATGGAGAAGTTCGGTCTGCTCCTCGCCACTCCGGCGCCCCGAGCGCGACAAGGCGGGTGCCCAGGCG           5400
 E  R  I  V  G  Q  M  E  K  F  G  L  L  L  A  T  P  A  P  R  P  E  R  D  K  A  G  A  Q  A

CTCGCCTAGCAGCCGGTTCACCTCTTCAAGCACCAGAGCGAGGAGCGCGGCGCCGGGCTCGAGGCGCTCGTTCCGCCACGGGTCCGC
```

FIG. 32 – 15 sugar.finalgene b-1 Sequence

```
          10         20         30         40         50         60         70         80         90
 1234567890123456789012345678901234567890123456789012345678901234567890123456789012345678901234567890
                                                                     AlwNI
                                               FspI                   ▼
GTGTCCCGCAAGGTCGCCGAGAACGGCGCGGTGCTCCTGCGCAACGAGGGCCAGGCCCTGCCGCTCGCCGGTGACGCCGGCAAGAGCATC        5490
CACAGGGCGTTCCAGGCGCTCTTGCCGCGCCACGAGGACGCGGTTGCTCCCGGTCCGGGACGCGGCCACTGCGGCCGCGTTCTCGTAG
 V  S  R  K  V  A  E  N  G  A  V  L  L  R  N  E  G  Q  A  L  P  L  A  G  D  A  G  K  S  I
            BstEII
         StyI▼
GCGGTCATCGGCCCGACGGCCCGTCGACCTCACCGGCAGGTCACCGGCCTGGGCAGCGCCCAAGTCGTCCCGGACTCGGCGGCCACTCGAC        5580
CGCCAGTAGCCGGGCTGCCGGGCAGCTGGAGTGGCCGTCCAGTGGCCGGACCCGTCGCGGGTTCAGCAGGCCTGAGCCGCCGGTGAGCTG
 A  V  I  G  P  T  A  V  D  P  K  V  T  G  L  G  S  A  H  V  V  P  D  S  A  A  A  P  L  D
ACCATCAAGGCCCGCGGGGCTGGGGTGCGACGGTGACGTACGAGAGACGGGTGAGGAGACCTTCGGGACGCAGATCCCGGCGGGAACCTC        5670
TGGTAGTTCCGGGCGCCCCGACCCCACGCTGCCACTGCATGCTCTGCCCACTCCTCTGGAAGCCCTGCGTCTAGGGCCGCCCCTTGGAG
 T  I  K  A  R  A  G  A  G  A  T  V  T  Y  E  T  G  E  E  T  F  G  T  Q  I  P  A  G  N  L
         XhoI
         PaeR7I
         ▼
AGCCCCGGCGTTCAACCAGGGCCACCAGTTCCTCGAGCCGGGCAAGGCGGGCGCTGTACGACGGCACGCTGACCGTGCCCGCCGACGGCGAG        5760
TCGGGGCCGCAAGTTGGTCCCGGTGGTCAAGGAGCTCGGCCCGTTCCGCCCGCGACATGCTGCCGTGCGACTGGCACGGGCGGCTGCCGCTC
 S  P  A  F  N  Q  G  H  Q  L  E  P  G  K  A  G  A  L  Y  D  G  T  L  T  V  P  A  D  G  E
```

FIG. 32—16 sugar.finalgene b-1 Sequence

```
           10        20        30        40        50        60        70        80        90
  123456789012345678901234567890123456789012345678901234567890123456789012345678901234567890
         RsrII   AgeI
         ▼       ▼
  TACCGCATCGCGGTCCGTGCCACCGGTGGTTACGCCACGGTGCCAGTCTCGGCAGCCACCATCGAGCCGGTCAGGTCTACGGCAAGGTG   5850
  ATGGCGTAGCGCCAGGCACGGTGGCCACCAATGCGGTGCCACGGTCGAGAGCCGTCGGTGTGTAGCTCGGCCAGTCCAGATGCCGTTCAC
   Y  R  I  A  V  R  A  T  G  G  Y  A  T  V  Q  L  G  S  H  T  I  E  A  G  Q  V  Y  G  K  V
                                StyI                              NruI
                                ▼                                 ▼
  AGCAGCCCGCTCCTCAAGCTGACCAAGGGCACGCACAAGCTCACGATCTCGGGCTTCGCGATGAGTGCCACCCCGCTCTCCCTGGAGCTG   5940
  TCGTCGGGCGAGGAGTTCGACTGGTTCCCGTGCGTGTTCGAGTGCTAGAGCCCGAAGCGCTACTCACGGTGGGGCGAGAGGGACCTCGAC
   S  S  P  L  L  K  L  T  K  G  T  H  K  L  T  I  S  G  F  A  M  S  A  T  P  L  S  L  E  L
                         NruI
                         PvuI                                                      BbsI
                         ▼                                                         ▼
  GGCTGGGGTGACGCGCCGGCGGCCGCGGACGATCGCGGAGCTCGGCGAGTCGGCGAAGGCCCGTGGCGGTCGTCTTCGCCTAC   6030
  CCGACCCCACTGCGCGGCCGCCGGCGCCTGCTAGCGCCTCGAGCCGCTCAGCCGCTTCCGGGCCATGCCGGCCAGCAGAAGCGGATG
   G  W  V  T  P  A  A  A  D  A  T  I  A  K  A  V  E  S  A  R  K  A  R  T  A  V  V  F  A  Y

GACGACGGCACCGAGGGCGTCGACCGTCCGAACCTGTCGCTGCCGGGTACGCAGGACAAGCTGATCTCGGCTGTGCGCGGACGCCAACCCG   6120
  CTGCTGCCGGTGGCTCCCGCAGCTGGCAGCTTGGACAGCGACGGCCCATGCGTCCTGTTCGACTAGAGCCGACACGCGCCTGCGGTTGGGC
   D  D  G  T  E  G  V  D  R  P  N  L  S  L  P  G  T  Q  D  K  L  I  S  A  V  A  D  A  N  P
```

FIG. 32 – 17 sugar.finalgene b-1 Sequence

```
         10        20        30        40        50        60        70        80        90
1234567890123456789012345678901234567890123456789012345678901234567890123456789012345678901234567890
                                                                     Acc65I
                                                                     NspHI
                                                               AflII   KpnI
                                                                 ▼   ▼▼
                    AgeI
                     ▼
  PvuI
   ▼
AACACGATCGTGTCCTCAACACCGGTTCGTCGGTCTGATGCCGTGCTGTCCAAGACCCGCGCGGTCCTGGACATGTGTACCCGGGC    6210
TTGTGCTAGCACCAGGAGTTGTGGCCAAGCAGCACTACGGCACAGAGTTCTGGGCGCCGCCAGGACCTGTACACCATGGGCCCG
 N  T  I  V  V  L  N  T  G  S  S  V  L  M  P  W  L  S  K  T  R  A  V  L  D  M  W  Y  P  G

AatII
                              ▼
CAGGGGGGGCGCCGAGGCCGCCACCGCGCCGGCTCTCTACGGTGACGTCAACCCGAGCGGCAAGCTCACGCAGAGCTTCCCGCCGAGAAC    6300
GTCCCCCCGCGGCTCCGGCGGTGGCGCGGCCGAGAGATGCCACTGCAGTTGGGCTCGCCGTTCGAGTGCGTCTCGAAGGGCGGCTCTTG
 Q  A  G  A  E  A  T  A  A  L  L  Y  G  D  V  N  P  S  G  K  L  T  Q  S  F  P  P  A  A  E  N

KpnI
                                                                       Acc65I
                                                                          ▼
CAGCACGCGGTCGCCGGCGACCCGACCAGCTACCCGGACAACCAGCAGACGTACCGCGAGGGCATCCACGTCGGGTACCGCTGG    6390
GTCGTGCGCCAGCGGCCGCTGGGCTGGTCGATGGGCCTGTTGGTCGTCTGCATGGCGCTCCCGTAGGTGCAGCCCATGGCGACC
 Q  H  A  V  A  G  D  P  T  S  Y  P  G  V  D  N  Q  Q  T  Y  R  E  G  I  H  V  G  Y  R  W

TTCGACAAGGAGAACGTCAAGCCGCTGTTCCCGTTCCCGGCACGCCTGTTCAGCAGCAGCGCCCGACCGTCGTGCGT    6480
AAGCTGTTCCTCTTGCAGTTCGGCGACAAGGGCAAGGGCCAAGTGGCAAGCAAGTCGTCGTCGCGGGCTGGCAGCACGCA
 F  D  K  E  N  V  K  P  L  F  P  F  G  H  G  L  S  Y  T  S  F  T  Q  S  A  P  T  V  V  R
```

FIG. 32 – 18 sugar.finalgene b-1 Sequence

```
          10         20         30         40         50         60         70         80         90
 1234567890123456789012345678901234567890123456789012345678901234567890123456789012345678901234567890
                                                                           ▼PvuI
 CGACCCGCTCGGCCTCGGCCCATTCGCGACACGGGCGTCGATCACCCGCAGCGCCTGCGGGGCGCTCCAGGTGCGGGCCGATCGGGCAGGCTGAGGACCT   6930
 GCTGGGCGAGCCGGGTAAGCGCTGCCGCAGTGGGCGTCGCCCGAGGTCGGGAGCGCCCGGAGGTCCACGCCCGGCTAGCCCGTCCGACTCCTGA
  D  V  R  E  A  W  E  R  V  A  D  I  V  R  L  A  Q  P  R  E  L  H  P  G  I  P  L  S  L  V
                                                                                     KpnI
                                                                                ApaLI▼Acc65I
                                                                                  ▼  ▼
 GCCGCGCGAAGCTCTCGCGGGAGCCTTCCGGCGGCGAGCCCGTAGGCGGTGCCTCGCCCGCGTAGGCGGCGAGAGGTGCACGGGTACCGGGTAGT     7020
 CGGCGCGCTTCGAGAGCGCCCTCGGAAGGCCGCCGCTCGGCATCCGCCACGGAGCGGGCGCATCCGCCGCTCTCCACGTGCCCATGGCCCATCA
  Q  R  A  F  S  E  A  R  P  L  S  G  E  P  P  A  E  G  A  Y  A  P  S  L  H  V  P  V  P  Y
                                                         EarI
                                                        ▼FspI
                                                         ▼
 GCGTGAGGGTGTCGATGCCGCGGCGTCGCAGCTCGTGCCGCAGCTCGGTGCGCTCGGTGCAGCCGCACGCGTGCCACTTCTCCACGGTCTGGCCCA      7110
 CGCACTCCCACAGCTACGGCGCCGCAGCGTCGAGCACGGCGTCGAGCCACGCGAGCCACGCGAGGCCACGTCGGCGTGCGCACGGTGAAGAGGTGCCAGA
  H  L  T  D  I  G  R  A  D  L  H  S  R  L  E  D  R  R  E  T  R  V  T  F  L  H  W  V  P
         FspI
         ▼
  CGGTGTCGGGGCGGTCACCGGCCAGGCCGATGCCGGGCAGTCCGGCGCCGAGCCCGGAGGTACTCCGGCCCAGCGCCGACCTGCGGCCGT          7200
  GCCACAGCCCCGCCAGTGGCCGGTCCGGCTACGGCCCGTCAGGCCGCGGCTCGGGCCTCCATGAGGCCGGGTCGCGGCTGGACGCCGGCA
   D  T  D  P  A  T  V  P  L  G  I  G  P  L  G  A  L  G  S  L  Y  E  A  A  L  A  S  R  R  G
       ▼BstEII
```

FIG. 32 – 20 sugar.finalgene b-1 Sequence

```
          10        20        30        40        50        60        70        80        90
1234567890123456789012345678901234567890123456789012345678901234567890123456789012345678901234567890
                                           ApaLI
                                            ▼
GCCCGCGAGGACGAGCGGCGATGCCCCGGCAGTGGTCGTCGGCACCCACTCGCGGACGTTCGCGCCGTCGCCGTACAGCGGGAGCGT      8370
CGGGCGCTCCTGCTCGCGCCGCTACGGGGCCGTCACCAGCAGCCGTGGGTGAGCGCCTGCAAGCGGCGGCAGCGGCATGTCGCCCTCGCA

G  A  L  V  L  A  I  G  R  C  H  D  D  T  H  V  W  E  R  V  N  A  G  D  G  Y  L  P  L  T

EarI
               ▼
CCCGCCGTCGAGGAGTTCGTCACGAAGAGGGGGATGAGCTTCTCGGGGTGCTGTGGTGTACGGCCCGTAGTTGTTGCAGCAGCGGGTGATCCG    8460
GGGCGGCAGCTCCTCAAGCAGTGCTTCTCCCCCTACTCGAAGAGCCGACACGACCATGCCGGGCATCAACAACGTCGTCGCCCACTAGGC

G  G  D  L  N  T  V  F  L  P  I  L  K  E  P  H  Q  Y  P  G  Y  N  N  C  C  R  T  I  R

StyI
                                                   ▼
TACGTCGAGGCCGTACGTCCGGTGGTAGGCGCGGCAACGAGGTCGAGCCCGGCCTTGACGCCGCGTAGGCGAGTTGGCTCCAGCGG         8550
ATGCAGCTCCGGCATGCAGGCCACCATCCGCGCCGTTGCTCCAGCTCGGGCCGGAACCTGCGGCGCATCCCGCTCAACCCGAGGTCGCC

V  D  L  G  Y  T  R  H  Y  A  R  A  V  L  D  S  G  A  K  S  A  A  Y  P  S  N  P  E  L  P

PvuI                                          ApaLI
               ▼                                             ▼
GCTGCTCTCGGTCCAGGAGCCGGAGTCGATCGACCCGTACACCTCGTCGGTGGAGACGTGCACGACCCGGCCGACGCCGGCGTCGACGGC    8640
CGACGAGAGCCAGGTCCTCGGCCTCAGCTAGCTGGGCATGTGGAGCAGCCACCTCTGCACGTGCTGGGCCGGCTGCGGCCGCAGCTGCCG

S  S  E  T  W  S  G  S  D  I  S  G  Y  V  E  D  T  S  V  H  V  V  R  G  V  G  A  D  V  A
```

FIG. 32 – 24 sugar.finalgene b-1 Sequence

```
         10        20        30        40        50        60        70        80        90
123456789012345678901234567890123456789012345678901234567890123456789012345678901234567890

PmlI
                                                                       BsaAI
                  ▼                                                    ▼
                AlwNI
GCACTGGAGCAGCTCTGCGTGCCCTGCACGTTGGTCTCGGTGAACACGGACGCGCCCGCGATGGAGCGGTCCGCCAGTGGCTCTCGGCCGC     8730
CGTGACCTCGTCGAGACGCACGGGACGTGCAACCAGAGCCACTTGTGCCTGCGCGGGCGCTACCTCGCCAGGCGGTCACCGAGAGCCGGCG

C  Q  L  L  T  Q  T  G  Q  V  N  T  E  T  F  V  S  A  G  A  I  S  R  D  V  H  S  E  A  A

GAAGTGGACGATGGCGTCCACGCCGCGGCGGTCCAGTTCCCGGGCGAGGAGGCCGGCGGCGTCGCGTGACGAAGCCAGTCGCGGGTC     8820
CTTCACCTGCTACCGCAGGTGCGGCGCCGCCAGGTCAAGGGCCCGCTCCTCCGGCCGCCGCAGCGCACCTGCTTCGGTCAGCGCCCAG

F  H  V  I  A  D  V  G  R  L  E  R  A  L  L  G  A  D  R  I  D  G  H  V  F  R  L  R  P  D

CGGCGTCCACCGGGGCGAGGTTGGCGCGCGGTGCCCGCGTAGTGAGGCTGTCCAGGACGATCACCTCATCGGCGGCACGTCGGGTACGC     8910
GCCGCAGGTGGCCCCGCTCCAACCGCGCGCCACGGGCGCATCACTCCGACAGGTCCTGCTAGTGGAGTAGCCGCCGTGCAGCGCCATGCG

BstEII       BbsI
                                               ▼            ▼
 A  D  V  P  A  L  N  A  R  N  G  A  Y  T  L  S  D  L  V  I  V  E  D  A  P  V  D  P  Y  A

▼
       DraIII
CCCGGGCGAGGAGCTGCCGCACGAAGTGCGAGCCCGACGATGAAGCCCGACACCTCCGGTCACCAGAGCCGCACTGCCGTCTTCCTTTCGGTCGC     9000
GGGCCCGCTCCTCGACGGCGTGCTTCACGCTCGGGCTGCTACTTCGGGCTGTGGAGGCCAGTGGTCTTCGGCGTGACGGCAGAAGGAAAGCCAGCG

G  A  L  L  Q  R  V  F  H  S  G  I  F  G  A  G  G  T  V  L  L  R  V
```

FIG. 32 – 25 sugar.finalgene b-1 Sequence

```
          10        20        30        40        50        60        70        80        90
123456789012345678901234567890123456789012345678901234567890123456789012345678901234567890
```
▶ SfcI
```
                                                                                    MluI
                                                                                    AflIII
                                                                                    ▶         9090
GCTGTAGGTCGGTGGGTCGTGGGGTCGCACTGTCGGTGGCGTCGGGTGTGGGTCGCACTGTCGGTGGCGTGTCGGTCGTGGGAAC
CGACATCCAGGCGCCACACCCAGCGTGACAGCGTGACAGCGTGACAGCGTGACACCCAGCGTGACAGCGTGACACCCAGCGTGACAGCCAGCACCCTTG
```
```
                              BsaBI                     StuI
                              ▶                         ▶                                     9180
GCGTCGGCCGCGAGGTGCCCTCACGGGGCTCCCTGCGGCGTCGGATCTCCATCAGATAGCTGCCGTACTCGGTGTGCGGAGAGGCCTTCT
CGCAGCCGGCGCTCCACGGAGTGCCCCGAGGGACGCCGCAGGCCTAGAGGTAGTCTATCGACGGCATGAGCCACGCCCTCTCCGAAGA
 .  P  A  G  E  R  G  A  I  E  M  L  Y  S  G  Y  E  T  R  S  L  G  E
```
```
                                                                                              9270
CCCAGGCCGTGACAGGCCTCGGCGTCGATGAAGCCCATGCGGAAGGCGATCTCTTCAAGGCCCGCGATCCAGAGCGCCCTGCCGCTCCTCC
GGGTCCGGCACTGTCCGGAGCCGCAGCTACTTCGGGTACGCCTTCCGCTAGAGAAGTTCCGGGCGCTAGGTCTCGCGGGACGGCGAGGAGG
  G  L  G  H  C  A  E  A  D  I  F  G  M  R  F  A  I  E  E  L  G  A  I  W  V  G  Q  R  E  E
```
▶ StuI
▶ PflMI
▶ AlwNI
```
                                                                                              9360
AGGACCTGGACGTACTGGGCGCCCGCAGGAGCGAGTCGTGGGTGCCGGTGTCCAGCCAGGCCAAGCCGGCGGAAGCCGGCGGCCGCAGTTCG
TCCTGGACCTGCATGACCCGCGGGCGTCCTCGCTCAGCACCCACGGCCACAGGTCGGTCCGGTTCGGCCGCCTTCGGCCGCCGGGTCAACTGCTCAAGC
  L  V  Q  V  Y  Q  A  A  R  L  L  S  D  H  T  G  T  D  L  W  A  F  G  R  G  L  N  V  L  E
```

FIG. 32 – 26 sugar.finalgene b-1 Sequence

```
          10        20        30        40        50        60        70        80        90
 1234567890123456789012345678901234567890123456789012345678901234567890123456789012345678901234567890
                                         AatII
                                         ▼
 GCCCGGCCCGCTCCAGGTAGACGCGGTTGACGTCGGTGATCTCCAGCTCGCCGCGCGGCGGAGGGCCGGATGTTCTTGGCGATGTCGACG          9450
 CGGGCCGGGCGAGGTCCATCTGCGCCAACTGCAGCCACTAGAGGTCGAGCGGCGCGCCGCCTCCCGGCCTACAAGAACCGCTACAGCTGC
  A  R  G  R  E  L  Y  V  R  N  V  D  T  I  E  L  E  G  R  P  S  P  R  I  N  K  A  I  D  V
      AatII
      ▼
 ACGTCGTTGTCGTAGAGGTAGAGGCCGGTGAGCGCCGAGTTGGACGGCCTTGACGGGCTTCTCGACGAGGTCGGTCAGCCGGCCCGTC          9540
 TGCAGCAACAGCATCTCCATCTCCGGCCACTCGCGGCTCAACCTGCCGGAACTGCCCGAAGAGCTGCTCCAGCCAGTCGGCCGGGCAG
  V  D  N  D  Y  L  Y  L  G  T  V  A  L  N  S  R  P  K  V  P  K  E  V  L  D  T  L  R  G  T
                              ApaI                            EarI
                              ▼                               ▼
 GCGTCCACCTCGGCGACGCCGTACCGGCTCGGGGTCCTTGACCGGGTAGCCGAAGAGCACGCAGCCTCGAGGCGCGATGCTGTCCCGC          9630
 CGCAGGTGGAGCCGCTGCGGCATGGCCGATGGCCGAGCCCCAGGAACTGGCCCATCGGCTTCTCGTGCGTCGGAGCTCCGCGCTACGACAGGGCG
  A  D  V  E  A  V  G  Y  R  E  P  D  K  V  P  Y  G  F  L  V  C  G  D  L  R  A  I  S  D  R

AGGAGCGTGTAGAGGCCCGGGGCCCGTGGAAGAGATGTTGTCGCCCAGGATCAGGGGCCAGGTGTCGTCGCCGATGTGCTCGGCTTCGACGAGA          9720
 TCCTCGCACATCTCCGGGCCCGGGCACCTTCTACAACAGCGGGTCCTAGTCCCGGTCCACAGCAGCGGCTACAGCGAGCTGCTCT
  L  L  T  Y  L  G  P  G  H  F  I  N  D  G  L  I  L  A  C  T  D  D  G  I  H  E  A  G  V  L
```

FIG. 32–27 sugar.finalgene b-1 Sequence

```
          10        20        30        40        50        60        70        80        90
1234567890123456789012345678901234567890123456789012345678901234567890123456789012345678901234567890
                                                                                              EarI
    TfiI                                                                                      ▼
    ▼
AGTGCGTCCGCGATTCCTGCGCGGGCTCTTTCTGGACCGCGCATAGTCGAGTTCTATTCCCAGGTGCCTGCCGTTTCCGAGAAGCGACTGGAAG   9810
TCACGCAGGCGCCTAAGGACGCCCGAGAAGACTTGGCGTATCAGCTCAAGATAAGGGTCCACGACGGCAAGGCTCTTCGCTGACCTTC
 L  A  D  A  I  G  A  P  E  K  Q  V  A  Y  D  L  E  I  G  L  H  R  G  N  G  L  L  S  Q  F

TfiI
                       BsaBI    NruI
                       ▼▼       ▼
AGTTCGATGTGCTGGGGGTGGAGATGATTGAAATCTCGCGAATACCGCGAGCATGAGAACCGACAGCGGATAGTAGATCATCGGTTTG          9900
TCAAGCTACACGACCCCCCAGCTCTACTAAACTTAGAGCGCTTATGGCGCTCGTGTACTCTTGGCTGTCGCCTATCATCTAGTAGCCAAAC
 L  E  I  H  Q  P  T  S  I  Q  I  E  R  I  G  G  L  M  L  V  S  L  P  Y  Y  I  M  P  K

TfiI    BstBI
       ▼       ▼
TTGTAGACCGGAAGAATCTGCTTCGAAATGACCGAGGTCGCCGGATGCAGCCGAGTTCCGCTCCCGCCGGCCAGGACTATTCCCTTCATT       9990
AACATCTGGCCTTCTTAGACGAAGCTTTACTGGCTCCAGCGGCCTACGTCGGCTCAAGGCGGAGGGCGGCCGGTCCTGATAAGGAAGTAA
 N  Y  V  P  L  I  Q  K  S  I  V  S  T  A  P  H  L  R  T  G  S  G  G  A  L  V  I  G  K  M

MaeI                                                MaeI
     BfaI                                                BfaI       FspI
     ▼                                                   ▼          ▼
CTCGGAAACTAGCAGCAGGGCGCCGGTGATAACGGTCGGCGTGGCGTTAGGGGCGCTAGGGGCGCTGCGCAGGGGAGTGTCACCACC            10080
GAGCCTTTGATCGTCGTCCCCGCGGCCACTATTGCCAGCCGCACCGCACCCGCGATCCCCGCGACGCGTCCCCTCACAGTGGTGG
```

FIG. 32 – 28 sugar.finalgene b-1 Sequence

```
          10        20        30        40        50        60        70        80        90
 1234567890123456789012345678901234567890123456789012345678901234567890123456789012345678901234567890
                                                      Bsu36I
 BstXI                         ApaI                   ApaI
 ▼                             ▼                      ▼
 CCTTTGGGGGTGGGAAAACACCGAGGGCCGGGACGGCCCGGCCCCTCAGGTGGGGGATCGTGGGGGGATCGGG                            10170
 GGAAACCCCCACCCTTTTGTGGCTCCCGGCCTGCCGGGCCCGGGAGTCCACCCCCCTAGCACCCCCTAGCCC
                                                                        PvuII
                                                                        ▼
 GCGGGTGCGGGTCAGCGGCAGGAAGCCGGGGGCCTCCTCCCAGCCGTCCGGCGTCGCAGCCGTGTTCAGGCGGCGCTGGTTCAGGGGCGGTGACGACC   10260
 CGCCCACGCCCAGTCGCCGTCCTTCGGCCCCCGGAGGAGGGTCGGCAGGCCGCAGAGGTCGGCAGCGTCGGCACGAAGTCCGCCGCCACTGCTGG
   R  L  F  G  R  A  E  E  W  G  D  A  A  D  R  E  L  Q  N  L  R  A  T  V  V
                   ScaI                                                         EcoNI
                   ▼                                                            ▼
 TGATCGAAGCCGTCCATGAAGTACTCGTCGCCGTCGACGAGCAGCAGCTGCCGGGCCACCTCGCCGCGCTCGACGAAGTCCCTGACGACCTCGGTGAGG   10350
 ACTAGCTTCGGCAGGTACTTCATGAGCAGCGGCAGCTGCTCGTCGTCGACGGCCCGGTGGAGCGGCGCGAGACTGCTTCAGGGACTGCTGGAGCCACTCC
  Q  D  F  G  D  M  F  Y  E  D  G  D  V  A  A  V  E  G  G  R  E  V  F  D  R  V  V  E  T  L
                                                 AflIII
                                                 ▼
 GAGGTGTCGGGGTCACGCGGCCCGCGATGTAGCGGGTCGGGCCGTCCAGGTCGGGAAGCCGGCCTCGCGGTACAGGTACACGTCGCCG             10440
 CTCCACAGCCCCAGTGCGCCGGGCGCTACATCGCCCAGCCCGGCAGGTCCAGTCCAGCCCTTCGGCCGGAGCGCCATGTCCATGTGCAGCGGC
   S  T  D  P  T  V  R  G  A  I  Y  R  T  A  G  D  L  D  P  F  G  A  E  R  Y  L  Y  V  D  G
```

FIG. 32-29 sugar.finalgene b-1 Sequence

```
         10        20        30        40        50        60        70        80        90
1234567890123456789012345678901234567890123456789012345678901234567890123456789012345678901234567890

AGGAGATCGACCTGCACCGGCGACCTGCGGGTGCGCGGTGGGCCGCATGGTGGCCAGCAGTTCGGCTGCGGCCCCGGTG        10530
TCCTCTAGCTGGACGTGGCGCTGGACGCGCCACCGCCCGAACTAGGCGTCGTCAAGCCGCAGCCGGGGCCAC
 L  L  D  V  Q  V  A  V  Q  P  H  A  T  P  R  M  T  A  P  K  I  R  L  L  E  A  D  A  G  T
                                                                          ▼
                                                                         FspI

CGCAGGCTGTTCAGGGCGTAGCCGTAGTCGATGTGGAGTCCGGCGTGCGCTCGCGGACCCGCTCCTCGAAGGCGTTGAGGGCCTCCTGG        10620
GCGTCCGACAAGTCCCGCATCGGCTACAGCTACACCTCAGCCGCACGCGAGCGCCTGGGCGAGGAGCTTCCGCAACTCCCGGAGGACC
 R  L  S  N  L  A  Y  G  Y  D  I  H  L  G  P  T  R  E  R  V  R  E  E  F  A  N  L  A  E  Q
                  ▼                                                 ▼
                 SfcI                                              NruI

AGCTCGGCCCCGCTCCTCCTGCGGCAGCTTGCCGTCACGGGCCGTGTAGTCCTCACGGCCGAATGTTGACGAAGTCGATCGTCCCCTGC        10710
TCGAGCCGGGGCGAGGAGGACGCCGTCGAACGGCAGTGCCCGGCACATCAGGAGCGTTACAACTGCTTCAGCTAGCAGGACGGGACG
 L  E  A  R  E  E  Q  P  L  K  G  D  D  R  G  S  Y  D  E  R  I  N  V  F  D  I  T  R  G  Q
                                                                        ▼
                                                                       PvuI

CCGGCGTCGTTGAGGTCGGCGATGAAGTCGACCAGGTCGAGCAGGCGGAGCACGGCCCGGAGCACGATGTAGGCGAAGCCGAGGTTG        10800
GGCCGCAGCAACTCCAGCCGCTACTTCAGCTGGTCCAGCTCGTCCGCCTCGTGCCGGGCCCTCGTGCTACATCCGCTTCGGCTCCAAC
 G  A  D  N  L  D  A  I  F  D  V  L  D  L  L  R  S  A  R  G  P  L  V  I  Y  A  F  G  L  N
```

FIG. 32 – 30 sugar.finalgene b-1 Sequence

```
         10        20        30        40        50        60        70        80        90
1234567890123456789012345678901234567890123456789012345678901234567890123456789012345678901234567890
                              AlwNI
                              PvuII
                              ▼
ATCGGGACTCGCGGCTCGGCCGCGCGAGCTGCTGAAGCGGCGGAGGTTCTGCGGACGCGGGGAAGGCGGCCTTCTTGCCGGTGGTCTGC    10890
TAGCCCTGAGCGCCGAGCCGGCGCGCTCGACGACTTCGCCGCCTCCAAGACGCCTGCGCCCCTTCGCCGAAGAACGGCCACCAGACG
 I  P  S  E  R  E  A  R  L  Q  Q  F  R  R  L  N  E  R  V  R  R  F  A  A  K  K  G  T  T  Q

SfiI
                                                    ▼
TCGTACTCCTCGTCGTTGAGGCCGTAGAGCGAGGTGCGGATGGCGTGCAGGCCCCAGAGGCGTGCGCTCCAGGGTGCGCTCGGTG         10980
AGCATGAGGAGCAGCAACTCCGGCATCTCGCTCCACGCCTACCGCACGTCCGGGGTCTCCGCCGCCAGGCCCCACGAGGTCCCACGCGAGCCAC
 E  Y  E  E  D  N  L  G  Y  L  S  T  R  I  A  H  L  G  W  L  G  P  P  Q  R  E  L  T  R  E  T

XmnI
    ▼
AGCGCGGAAGGAGTTCGTGTAGACGGTGTGGGCCCAGGCCGGCGGCTGGTTCGGTTCGGTTGTGAGCGGC         11070
TCGCGCCTTCCTCAAGCACATCTGCCACCCGGGTCCGGCCGCCGACCGGCCGCCAACCACTCGCCG
 L  A  F  S  N  T  Y  V  T  P  R  L  G  H  D  T  A  H  A  A  L  S  G  L  G  P  N  T  L  P

TCCAGGCCGCCGAGAAGTACATCGCCGAGGGTTGCCCGGGGTATCTCGTCGATGACCGAACATGGCGTTGCCGGCGTCGAGG        11160
AGGTCCGGCGGCTCTTCATGTAGCGGCTCCCAACGGCGCCCATAGAGACAGCTACTGCCTTGTACCGCAACGGCCGAGCTCC
 E  L  G  G  S  F  Y  M  A  S  P  N  G  A  P  I  E  D  I  V  S  R  F  M  A  N  G  A  D  L
```

FIG. 32 – 31 sugar.finalgene b-1 Sequence

```
          10        20        30        40        50        60        70        80        90
1234567890123456789012345678901234567890123456789012345678901234567890123456789012345678901234567890
                                                            NspHI
                                                            ▼
GCGGACGGGTCGTAGCGGCGCCGTCACACGGACGCAGAAGTGGCAGCGGAACATGCAGGTCGGGCCGGGGTAGAGGCCGACGCTGTAC    11250
CGCCTGCCCAGCATCGCCCGCGGCCAGTCGTGCCTGCGTCTTCACCGTCGCCTTGTACGTCCAGCCCGGCCCCATCTCCGGCTGCGACATG
 A  S  P  D  Y  R  A  G  T  V  R  V  C  F  H  C  R  F  M  C  T  P  G  P  Y  L  G  V  S  Y
            BbsI                  BbsI
            ▼                     ▼
GGGAAGACGGGCTTCCTGGCGAGCGCCGCTCGAAGACGCCGGGCCGTCGTTGTTCGAGCGGGAGCAGGGTGTTCTTCCAGTACGCCCCGGGG    11340
CCCTTCTGCCCGAAGGACCGCTCGCGGCTTCTGCGGCCCGGCAGCTTCTGCCCTCGTCCACAAGAAGGTCATGCGGGGCCCC
 P  F  V  P  K  R  A  L  A  A  D  F  V  G  R  Q  E  L  P  L  L  T  N  K  W  Y  A  G  A  P
                                                                            PflMI
                                                                            ▼
CCGGTCTCGACCGCGCGGTGCGGAGCTCCGGAGACCTGCCCGAACAGGGCGAGGAGGCGTCCCGGTCGACGCCCAGGTCGTGG    11430
GGCCAGAGCTGGCGCGCCACGCCTCGAGGCCTCTGGACGGGGCTTGTCCCGCTCCTCCGCAGGGCCTTCCGCAGGGTCCAGCACC
 G  T  E  V  A  T  R  L  E  P  V  Q  G  F  L  A  L  L  R  R  F  A  D  R  D  V  G  L  D  H

CGGGGCCTCCTCCAGCGGGGTGAAGGGGCTGTTGCCGTAGCGCCACGGCGAGCGAGGTGGCCAGCCGCCGGTGCGTTCCGGCCTCGTCGGGC    11520
GCCCGGAGGAGGTCGCCCCACTTCCCCGACAACGGCATCGCGGTGCCGCTCGGCGCTCCACCGGTCGGCGGCCACGCAAGGCCGGAGCAGCCG
 R  A  E  E  L  P  T  F  P  P  S  N  G  Y  R  V  A  L  R  V  L  H  R  A  T  T  G  A  E  D  P
```

FIG. 32 – 32 sugar.finalgene b-1 Sequence

```
         10         20         30         40         50         60         70         80         90
1234567890123456789012345678901234567890123456789012345678901234567890123456789012345678901234567890

GGCACGAGGCCGCCGGCGGCGGAGGGTCTGGCCGAGGGCCGCCCCAGATCGGCTCCGAGCGGTGCGCGCAGCGTTCGGCCGG                    11610
CCGTGCTCCGGCGGCCGCCGCCCCTCCCAGACCGGCTCCCGACTGCCGGGGGTCTAGCGAGGGCTCGAGCCGCGTCGCAAGCCGGCCC
  P   V   L   G   G   A   A   L   T   Q   G   V   A   H   V   A   A   G   L   D   A   G   P   H   A   C   R   E   A   P

GCGGTGGCGGGAAAGGGCGGGGGCGGTCATCGGAGCGTCCAATCGTGTGGGCGTGATGTCTGGGGGCGAGCGGGCCCGTGT              11700
CGCCACCGCCCTTTCCCGCCCCCGCCAGTAGCCCTCGCAGGTTAGCACCCGCACTACAGACCCCGCGCTCGCCGCCCCGGCACA
  A   T   A   S   L   A   P   A   T   M   .   R   S   R   G   I   T   P   T   S   T   Q   P   P   A   A   L   P   A   P   A   T
                                          NotI
                                            ▼
CGGGGTGGCGGCGGGTCAGTTCGGCGGCCCGGCGGTCGCGCAGAGACGCAGCAGGTCGGCGACCCGGCGGATGTCGTCGCCGATGGCGG              11790
GCCCCACCGCCGCGCGCAGTCAAGCCGCCGGGCCGCCAGCGCGTCTCTGCGTCGTCCAGCCGCTGGGCCGCCTACAGCAGCGGCTACCGCC
  D   R   H   R   A   T   L   E   R   G   R   T   A   C   L   R   L   L   D   A   V   R   R   I   D   D   D   G   I   A
                                                                                                    PflMI
                                                                                                      ▼
TGCCGGTCGCCAGGGACAGCACGCGCGCGGCGCGCGAGGCGTTCGGTGTGCGGCAGCGGCGCTGCCCGCGGCTGCGGCGTACGGCTCCAGCTCGT    11880
ACGGCCAGCGGTCCCTGTCGTGCGCGCGCCGCGCGCTCCGCAAGCCACACGCCGTCGCCGCGACGGGCGCCATGCCGAGGTCGAGCA
  T   G   T   P   P   L   S   L   V   R   A   A   L   R   E   T   H   P   L   P   A   H   P   Q   G   R   Y   P   E   L   E
```

FIG. 32 – 33 sugar.finalgene b-1 Sequence

```
         10         20         30         40         50         60         70         80         90
1234567890123456789012345678901234567890123456789012345678901234567890123456789012345678901234567890
                                        ApaLI
GGCAGCCCGGCGAGAAGTAGGCGCGGGTGTGCACGCCTTCGGCCTTCAGGACCTTCAGGACCTCCATGACGAGGTCGCGGTGATGCCGGTGGTGCCT    11970
CCGTCGGGCCGCTCTTCATCCGCGCCCACACGTGCGGAAGCCGGAAGTCCTGGAGTACTGCTCCAGGCGTCACCTACGGCCACCACCGGA
 H  C  G  P  S  F  Y  A  R  T  H  V  G  E  A  K  L  V  E  M  V  L  D  R  H  I  G  T  T  A
                BsaAI
                                                                              MluI
                                                                              AflIII
CGTCGGATCTCGACGATCACGTACTGGTGGTTGTTGAGGCCGTGGCCGTCGTGTGGCCGTCGTGGCCGTGGCCGTGGCGACGAGGACGCCGGGAGGTCCGAGTGCT    12060
GCAGCTAGAGCTGCTAGTGCATGACCACCAACAACTCCGGCACCGGCAGCAGCACCGGCAGCACCGGCACCGCTGCTCCTGCGGCCCTCCAGGCTCCACGA
 E  D  I  E  V  I  V  Y  Q  H  N  N  L  G  H  R  D  H  D  A  V  L  V  G  P  L  D  A  L  H
                                                         StyI
                                                         NcoI
CGCGGTAGGCGGCGGTGTGGTTGCGCCGGTTCCGGTCGATGACCTCGGGAAAACGCGTCGGAGGAGGTGAGGCCCATGGCGGCGGCGGCCTCGC    12150
GCGCCATCCGCCGCCACCAACGCGGCCAAGGCCAAGCTACTGGAGCCCTTTGCGCAGCTCCCTCCACTCCGGGTACCGCCGCCGCCGGAGCG
 E  R  Y  A  A  H  N  R  R  N  R  D  I  V  E  P  F  A  D  L  S  T  L  G  M  A  A  A  A  E
                                        BamHI
TCATCTTGGCGTTGGTCCCGGCGGCGGGGCGGCGCGGCGGCCCCGGACGGCGGCGCCCGTCGTGCCGCCCGGGGACCGGCAGGTCGAAGCCGAAGTTGTGAGGGCGCGGATCCGGGCGGCGAGGTCGG    12240
AGTAGAACCGCAACCAGGGCCGCCCCGCCGCGCCGCGGGGCCTGCCGCCGCGGGCAGCACGGCGGGCCCCTGGCCGTCCAGCGGCGCCCCTGGCCGTCCAGCTTCGGCTTCAACACTTCCCGCGCTCCCTAGCCGCCTAGCCGCTCCAGCC
 S  M  K  A  N  T  G  G  A  P  S  G  G  P  L  D  F  G  F  N  H  L  A  R  I  R  A  A  L  D
```

FIG. 32 – 34 sugar.finalgene b-1 Sequence

```
          10        20        30        40        50        60        70        80        90
 1234567890123456789012345678901234567890123456789012345678901234567890123456789012345678901234567890
                                                              StyI                BbsI
                                                                ▼                   ▼
 CGTCGTCGTGGTGACGACGGCCGCGCCGGGGCGCCCTCGAAGGCGTTGACGGCCTTGGTGGCTGAAGCTGAAGACCTCGGCGTCGCGAGGCTGCCGG    12330
 GCAGCAGCCACTGCTGCCGGCGCGGCCCCGCGGGAGCTTCCGCAACTGCCGGAACCACCGACTTCGACTTCTGACGCCAGCGCTCCGACGGCC
  A  D  D  T  V  V  A  G  G  E  F  A  N  V  A  K  T  A  H  F  S  F  V  E  A  D  G  L  S  G
                                                                                         PvuII
                                                                                           ▼
 CGGGCCGGCCGTCGACGGCGCAGCCGCTGGCGCGCGCTCCCGACGTCGGCGCGTGAAGTACAGCCCGCAGGCCGTGCTCGTCGGCGACCTTCCGCAGCTGGT    12420
 GCCCGGCCGGCAGCTGCCGCGTCGGCGACCGCGCGAGGGCTGCAGCCGCGCACTTCATGTCGGGCGTCCGGCACGAGCAGCGCAGCCTGGAAGGCGTCGACCA
  A  P  R  G  D  V  A  C  G  L  A  H  A  A  D  F  Y  L  R  L  G  H  E  D  A  V  K  R  L  Q

CGGCGGCGCAGGGCGGCCCCAGAGGTGGACGCGCCGAGGTGCGGGTGTGACCGGCGGCGCCACCTGGTCCGGGTCGAGGT    12510
 GCCGCCGCGTCCCGCCGGGGTCTCCACTGCGCGGCTGCGCGGCTCCACGCCCACACTGGCGCCGCGGTGGACCAGGCCCAGCTCCA
  D  A  A  C  P  R  G  W  L  H  V  G  V  V  A  S  T  R  P  T  V  A  A  A  V  Q  D  P  D  L
                                              BbsI
                                                ▼
 TGCCGGTGTCCGGTCGATGTCGGCGAAGACCGGGCTGAGGCCGATCCAGCGCAGTGCGTCGGGGTGGCGGCGAACGTCATCGACGGCA    12600
 ACGGCCACAGGCCAGCTACAGCCGCTTCTGGCCCGACTCCGGCTAGGTCGCGTCACGCAGCCCCACCGCCGCTTGCAGTAGCTGCCGT
  N  G  T  D  P  D  I  D  A  F  V  P  T  L  G  I  W  R  L  A  H  P  T  A  A  F  T  M  S  P
```

FIG. 32 – 35 sugar.finalgene b-1 Sequence

```
          10         20         30         40         50         60         70         80         90
 1234567890123456789012345678901234567890123456789012345678901234567890123456789012345678901234567890
                                                                           MscI          SphI
                                                                           BalI          NspHI
 BclI                                                                       ▼             ▼
 TGATCACTTCGCCGGTGAGGCCGGCGGCGTGCGCGGCCGCGTGCGGAGGAGCTGAGCCCGGCCGCGTTGCAGTGGCCACGGCATGCCGACCCCGG    12690
 ACTAGTGAAGCGGCCACTCCGGCCGCCGCACGCGCCGGCGCACGCCTCCTCGACTCGGGCCGGCGCAACGTCACCGGTGCCGTACGGCCTGGGCC
  M  I  V  E  G  T  L  G  A  A  H  A  L  L  Q  L  G  A  T  A  N  C  T  A  V  A  H  R  V  G

AlwNI              ApaI
                                                            ▼                 ▼
 CGAGCCCGGCGACGCGCTCCTCGAACTCGCGGACGAGCGGCCGCCGTTGGACAGCCACTGGCTGTGAGGCCCGGTCGAGCCGCTCGT          12780
 GCTCGGGCCGCTGCGCGAGGAGCTTGAGCGCCTGCTCGCCGGCGGCAACCTGTCGGTGACCGACAGTCCCGGGCCAGTCGGCGAGCA
  A  L  G  A  V  R  E  E  F  F  E  R  V  L  P  G  G  N  S  L  W  Q  S  D  L  A  R  D  L  R  E

BsmI
                                                                     ▼
 ACAGCCTGGCGCGGTCGATGCGGTTGGGCCGCCCCACGAGGAGCGGCTGTCGAAAGCGGGCGCCGAAGAATGCGAGGTCGGATA              12870
 TGTCGGACCGCGCCAGCTACGCCAACCCGGCGGGGTGCTCCTCGCCGACAGCTTTCGCCCGCGGCTTCTTACGCTCCAGCCTAT
  Y  L  R  A  R  D  I  R  N  P  R  G  V  L  L  P  Q  D  F  A  A  P  G  G  F  F  A  L  D  S

TfiI
                                    XmnI                        TfiI
                                     ▼                           ▼
 AGGGCGCTTTTCACGGATGTTCCCTCCGGGCCACCGTCACGAAATGATTCGCCGATCCGGAATCCCGAACGAGTCGCCGCTCCACCG          12960
 TCCCGCGAAAAGTGCCTACAAGGCCCGGTGGCAGTGCTTTACTAAGCGGCTAGGCCCTTAGGGCTTGCTCCAGCGGCGGAGGTGGC
  L  A  S  K  V
```

FIG. 32 – 36 sugar.finalgene b-1 Sequence

```
          10        20        30        40        50        60        70        80        90
 1234567890123456789012345678901234567890123456789012345678901234567890123456789012345678901234567890
TGACGTACGACGAGATGGTCGATTGTGGTCGTGATTTCGGGGGACTCTAATCCGCGGAACGGAGACCGACACAAGAGACACGCTATGCGC
ACTGCATGCTGCTCTACCAGTCTAACACCAGCTAAAGCCCCCCTGAGATTAGGCGCGGCCCTTGCCCTGCTGTTCTCGTGCGATACGCG     13050
                                                            BamHI    TfiI
                                                             ▼        ▼
TCTCGATGTGCTTCGGATCACATCGGCCCTCCGGGGTATTCCATCGGCGGCCCGAAATGTGATGATCCTTGACAGGATCCGGGAATCAGCCG
AGAGCTACACGAAGCCTAGTGTAGGCCGGGAGGCCCCCATAAGGTAGCCGCGGGCCTTACACTACTAGGAACTGTCCTAGGCCCTTAGTCGGC  13140
                       BsaAI
                       AflIII                     EarI
                        ▼                          ▼
AGCCGCGGAGGCGCCGGAGGGGCGCGCTCCGCGGAAGAGTACGTGAGAAGTCCCGTTCCTCTTCCCGTTCCGTTCCGCTTCCGGCCCGG
TCGGCGGCCCTCCCGCGGCCTCCCCGCGCGAGGCGCCTTCTCATGCACACTCTTCAGGGCAAGAGAAGGCAAGGCGAAGGCCGGGCC       13230
     EarI
      ▼                                          EcoNI
                                                 ApaI
                                                  ▼
TCTGGAGTTCTCCGTGCGCCGTACCCAGCAGGGAACGACCGCTTCTCCCCGTACTCGACCTCGGGGCCCTGGGCAGGATTTCGCGGC
AGACCTCAAGAGGCAGCGCGGATGGGTGCGTCCCTTGCTGCTGGAAGAGAGGGGACCCCGTCCTAAAGCGCCG                     13320
  V  E  F  S  V  R  R  T  Q  Q  G  T  T  A  S  P  P  V  L  D  D  L  G  A  L  G  Q  D  F  A  A
```

FIG. 32-37 sugar.finalgene b-1 Sequence

```
          10         20         30         40         50         60         70         80         90
1234567890123456789012345678901234567890123456789012345678901234567890123456789012345678901234567890
```

BsaBI
▶
```
                                                                   FspI
                                                                   DraIII
                                                                   ▶
CGATCCGTATCCGACGTACGCGAGACTGCTGGTGCCGAGGGTCCGGCTGCCGGGTGCGCCACCGGGTGCGAGGGGACGAGGTGTGGCTGGTCGT   13410
GCTAGGCATAGGCTGCATGCGCTCTGACGCTGCATGCGCACCGGCTCCCAGGCCGACGGCCCACGCGTGGGGCCCCTGCTCCACACGACCAGCA
 D   P   Y   P   T   Y   A   R   L   R   A   E   G   P   A   H   R   V   R   T   P   E   G   D   E   V   W   L   V   V

CGGCTACGACCGGGGCGGCGCCGGCCCCGCCAGGAGCGGCTAGGGGCCAAGTCGTTCTGACCGGTTCAGCAAGACTGGCGCAACTCCAGACTCCCCTGACCGAAGCC   13500
GCCGATGCTGGCCCCGCGGCCGGGGCGGTCCTCGCCGATCCCCGGTTCAGCAAGACTGGCGCAACTCCAGACTCCCCTGACCGAAGCCGAAGCC
 G

NspHI                                     PflMI
                         ▶                                          PvuII
                                                                    ▶
GCGCTCAACCACAACATGCTGAGTTCCGAACCCGCCGGGCACACCCGGCTGCCGTGAGTTCACCATGCGCCGGTG   13590
CGCGAGTTGGTTGTTGTACGACTCAAGGCTTGGGCGGCCGTGTGGGCCGACACTCAAGTGGTACGGCGGCCAC

CGAGTTGCTGCCGCCCCGGGTCC   13613
GCTCAACGACGGCGGGGCCCAGG
```

FIG. 32 - 38

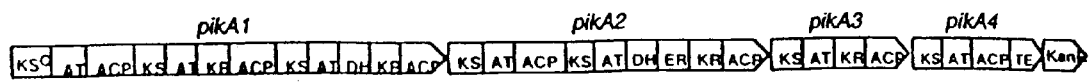
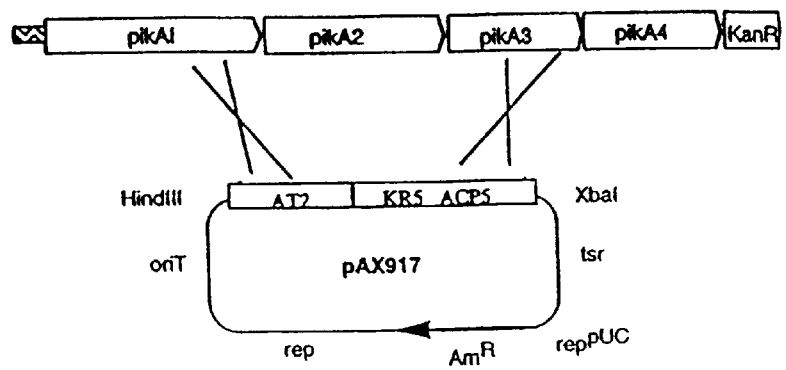
FIG. 33

| Amino Acid | Codon |
| --- | --- |
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

FIG. 38

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

FIG. 39

SEQUENCE LISTING

```
<160> NUMBER OF SEQ ID NOS: 43

<210> SEQ ID NO: 1
<211> LENGTH: 15872
<212> TYPE: DNA
<213> ORGANISM: Streptomyces venezuelae

<400> SEQUENCE: 1
ttaattaagg aggaccatca tgaacgaggc catcgccgtc gtcggcatgt cctgccgcct      60
gccgaaggcc tcgaacccgg ccgccttctg ggagctgctg cggaacgggg agagcgccgt     120
caccgacgtg ccctccggcc ggtggacgtc ggtgctcggg ggagcggacg ccgaggagcc     180
ggcggagtcc ggtgtccgcc ggggcggctt cctcgactcc ctcgacctct tcgacgcggc     240
cttcttcgga atctcgcccc gtgaggccgc cgccatggac ccgcagcagc gactggtcct     300
cgaactcgcc tgggaggcgc tggaggacgc cggaatcgtc cccggcaccc tcgccggaag     360
ccgcaccgcc gtcttcgtcg gcaccctgcg ggacgactac acgagcctcc tctaccagca     420
cggcgagcag gccatcaccc agcacaccat ggcgggcgtg aaccggggcg tcatcgccaa     480
ccgcgtctcg taccacctcg gcctgcaggg cccgagcctc accgtcgacg ccgcgcagtc     540
gtcctcgctc gtcgccgtgc acctggcctg cgagtccctg cgcgccgggg agtccacgac     600
ggcgctcgtc gccggcgtga acctcaacat cctcgcggag agcgccgtga cggaggagcg     660
cttcggtgga ctctccccgg acggcaccgc ctacaccttc gacgcgcggg ccaacggatt     720
cgtccggggc gagggcggcg gagtcgtcgt actcaagccg ctctcccgcg ccctcgccga     780
cggcgaccgt gtccacggcg tcatccgcgc cagcgccgtc aacaacgacg gagccacccc     840
gggtctcacc gtgcccagca gggccgccca ggagaaggtg ctgcgcgagg cgtaccggaa     900
ggcggccctg gacccgtccg ccgtccagta cgtcgaactc cacggcaccg gaaccccgt     960 cggcgacccc atcgaggccg ccgcgctcgg cgccgtcctc ggctcggcgc gccccgcgga    1020 cgaaccctg ctcgtcggct cggccaagac gaacgtcggg cacctcgaag gcgccgccgg    1080
catcgtcggc ctcatcaaga cgctcctcgc gctcggccgg cgccggatcc cggcgagcct    1140
caacttccgt acgccccacc cggacatccc cgtcgacacc ctcgggctcg acgtgcccga    1200
cggcctgcgg gagtggccgc acccggaccg cgaactcctc gccggcgtca gtcgttcgg    1260 catgggcggc accaacgccc acgtcgtcct cagcgaaggc cccgcccagg gcggcgagca    1320
gcccggcatc gatgaggaga cccccgtcga cagcggggcc gcactgccct tcgtcgtcac    1380
cggccgcggc ggcgaggccc tgcgcgccca ggcccggcgc ctgcacgagg ccgtcgaagc    1440
```

-continued

```
ggacccggag ctcgcgcccg ccgcactcgc ccggtcgctg gtcaccaccc gtacggtctt    1500
cacgcaccgg tcggtcgtcc tcgccccgga ccgcgcccgc ctcctcgacg gcctcggcgc    1560
cctcgccgcc gggacgcccg cgcccggcgt ggtcaccggc accccgccc ccgggcgcct    1620 cgccgtcctg ttcagcggcc agggtgccca acgtacgggc atgggcatgg agttgtacgc    1680
cgcccacccc gccttcgcga cggccttcga cgccgtcgcc gccgaactgg acccctcct    1740 cgaccggccc ctcgccgaac tcgtcgcggc gggcgacacc ctcgaccgca ccgtccacac    1800
acagcccgcg ctcttcgccg tggaggtcgc cctccaccgc ctcgtcgagt cctggggcgt    1860
cacgcccgac ctgctcgccg gccactccgt cggcgagatc agcgccgccc acgtcgccgg    1920
ggtcctgtcg ctgcgcgacg ccgcccgcct cgtcgcggcg cgcggccgcc tcatgcaggc    1980
gctccccgag ggcggcgcga tggtcgcggt cgaggcgagc gaggaggaag tgcttccgca    2040
cctcgcggga cgcgagcggg agctctccct cgcggccgtg aacggccccc gcgcggtcgt    2100
cctcgcgggc gccgagcgcg ccgtcctcga cgtcgccgag ctgctgcgcg aacagggccg    2160
ccggacgaag cggctcagcg tctcgcacgc cttccactcg ccgctcatgg agccgatgct    2220
cgacgacttc cgccgggtcg tcgaagagct ggacttccag gagccccgcg tcgacgtcgt    2280
gtccacggtg acgggcctgc ctgtcacagc gggccaatgg accgatcccg agtactgggt    2340
ggaccaggtc cgcaggcccg tacgcttcct cgacgccgta cgcaccctgg aggaatcggg    2400
cgccgacacc ttcctggagc tcggtcccga cggggtctgc tccgcgatgg cggcggactc    2460
cgtacgcgac caggaggccg ccacggcggt tccgccctg cgcaagggcc gcccggagcc    2520
ccagtcgctg ctcgccgac tcaccaccgt cttcgtccgg ggccacgacg tcgactggac    2580
cgccgcgcac gggagcaccg gcacggtcag ggtgcccctg ccgacctacg ccttccagcg    2640
cgaacgccac tggttcgacg gcgccgcgcg aacggcggcg ccgctcacgg cgggccgatc    2700
gggcaccggt gcgggcaccg gcccggccgc gggtgtgacg tcgggcgagg gcgagggcga    2760
gggcgagggc gcgggtgcgg gtggcggtga tcggccggct cgccacgaga cgaccgagcg    2820
cgtgcgcgca cacgtcgccg ccgtcctcga gtacgacgac ccgacccgcg tcgaactcgg    2880
cctcaccttc aaggagctgg gcttcgactc cctcatgtcc gtcgagctgc ggaacgcgct    2940
cgtcgacgac acgggactgc gcctgcccag cggactgctc ttcgaccacc cgacgccgcg    3000
cgccctcgcc gcccacctgg gcgacctgct caccggcggc agcggcgaga ccggatcggc    3060
cgacgggata ccgcccgcga ccccggcgga caccaccgcc gagcccatcg cgatcatcgg    3120
catggcctgc cgctaccccg gcggcgtcac ctcccccgag gacctgtggc ggctcgtcgc    3180
cgaggggcgc gacgccgtct cggggctgcc caccgaccgc ggctgggacg aggacctctt    3240
cgacgccgac cccgaccgca gcggcaagag ctcggtccgc gagggcggat tcctgcacga    3300
cgccgccctg ttcgacgccg gcttcttcgg gatatcgccc cgcgaggccc tcggcatgga    3360
cccgcagcag cggctgctcc tggagacggc atgggaggcc gtggagcgcg cagggctcga    3420
ccccgaaggc ctcaagggca gccggacggc cgtcttcgtc ggcgccaccg ccctggacta    3480
cggcccgcgc atgcacgacg gcgccgaggg cgtcgagggc cacctcctga ccgggaccac    3540
gcccagcgtg atgtcgggcc gcatcgccta ccagtcggc ctcaccggtc ctgcggtcac    3600
cgtcgacacg gcctgctcgt cctcgctcgt cgcgctgcac ctggccgtcc gttcgctgcg    3660
gcagggcgag tcgagcctcg cgctcgccgg cggagcgacc gtcatgtcga caccgggcat    3720
gttcgtcgag ttctcgcggc agcgcggcct cgccgccgac ggccgctcca aggccttctc    3780
cgactccgcc gacggcacct cctgggccga gggcgtcggc ctcctcgtcg tcgagcggct    3840
```

```
ctcggacgcc gagcgcaacg gccacccgt  gctcgccgtg atccggggca gcgcggtcaa    3900
ccaggacggc gcctccaacg ggctcaccgc ccccaacggc ccgtcccagc agcgcgtcat    3960
ccgacaggcc ctggccgacg ccgggctcac cccggccgac gtcgacgccg tcgaggcgca    4020
cggtacgggt acccggctcg cgacccccat cgaggccgag cgatcctcg  gcacctacgg    4080
ccgggaccgg ggcgagggcg ctccgctcca gctcggctcg ctgaagtcga acatcggcca    4140
cgcgcaggcc gccgcgggcg tgggcgggct catcaagatg gtcctcgcga tgcgccacgg    4200
cgtcctgccc aggacgctcc acgtggaccg gcccaccacc cgcgtcgact gggaggccgg    4260
cggcgtcgag ctcctcaccg aggagcggga gtggccggag acgggccgcc cgcgccgcgc    4320
ggcgatctcc tccttcggca tcagcggcac caacgcccac atcgtggtcg aacaggcccc    4380
ggaagccggg gaggcggcgg tcaccaccac cgccccggaa gcaggggaag ccggggaagc    4440
ggcggacacc accgccacca cgacgccggc cgcggtcggc gtcccgaac  ccgtacgcgc    4500
ccccgtcgtg gtctccgcgc gggacgccgc cgccctgcgc gcccaggccg ttcggctgcg    4560
gaccttcctc gacggccgac cggacgtcac cgtcgccgac ctcggacgct cgctggccgc    4620
ccgtaccgcc ttcgagcaca aggccgccct caccaccgcc accagggacg agctgctcgc    4680
cgggctcgac gccctcggcc gcggggagca agccacgggc ctggtcaccg gcgaaccggc    4740
cagggccgga cgcacggcct tcctgttcac cggccaggga gcgcagcgcg tcgccatggg    4800
cgaggaactg cgccgccgcg accccgtgtt cgccgccgcc ctcgacaccg tgtacgcggc    4860
cctcgaccgt cacctcgacc ggccgctgcg ggagatcgtc gccgccgggg aggagctgga    4920
cctcaccgcg tacacccagc ccgccctctt cgccttcgag gtggcgctgt tccgcctcct    4980
cgaacaccac ggcctcgtcc ccgacctgct caccggccac tccgtcggcg agatcgccgc    5040
cgcgcacgtc gccggtgtcc tctccctcga cgacgccgca cgtctcgtca ccgcccgcgg    5100
ccggctcatg cagtcggccc gcgagggcgg cgcgatgatc gccgtgcagg cgggcgaggc    5160
cgaggtcgtc gagtccctga agggctacga gggcagggtc gccgtcgccg ccgtcaacgg    5220
acccaccgcc gtggtcgtct ccggcgacgc ggacgccgcc gaggagatcc gcgccgtatg    5280
ggcgggacgc ggccggcgca cccgcaggct gcgcgtcagc cacgccttcc actccccgca    5340
catggacgac gtcctcgacg agttcctccg ggtcgccgag ggcctgacct tcgaggagcc    5400
gcggatcccc gtcgtctcca cggtcaccgg cgcgctcgtc acgtccggcg agctcacctc    5460
gcccgcgtac tgggtcgacc agatccggcg gcccgtgcgc ttcctggacg ccgtccgcac    5520
cctggccgcc caggacgcga ccgtcctcgt cgagatcggc cccgacgccg tcctcacggc    5580
actcgccgag gaggctctcg cgcccggcac ggacgccccg gacgcccggg acgtcacggt    5640
cgtcccgctg ctgcgcgcgg ggcgccccga gcccgagacc ctcgccgccg gtctcgcgac    5700
cgcccatgtc cacggcgcac ccttggaccg ggcgtcgttc ttcccggacg ggcgccgcac    5760
ggacctgccc acgtacgcct tccggcgcga gcactactgg ctgacgcccg aggcccgtac    5820
ggacgcccgc gcactcggct tcgacccggc gcggcacccg ctgctgacga ccacggtcga    5880
ggtcgccggc ggcgacggcg tcctgctgac cggccgtctc tccctgaccg accagccctg    5940
gctggccgac cacatggtca acggcgccgt cctgttgccg gccaccgcct tcctggagct    6000
cgccctcgcg gcgggcgacc acgtcggggc ggtccgggtg gaggaactca ccctcgaagc    6060
gccgctcgtc ctgcccgagc ggggcgccgt ccgcatccag gtcggcgtga gcggcgacgt    6120
cgagtcgccg gccgggcgca ccttcggtgt gtacagcacc cccgactccg gcgacaccgg    6180
```

-continued

```
tgacgacgcg ccccgggagt ggacccgcca tgtctccggc gtactcggcg aaggggaccc    6240
ggccacggag tcggaccacc ccggcaccga cggggacggt tcagcggcct ggccgcctgc    6300
ggcggcgacc gccacacccc tcgacggcgt ctacgaccgg ctcgcggagc tcggctacgg    6360
atacggtccg gccttccagg gcctgacggg gctgtggcgc gacggcgccg acacgctcgc    6420
cgagatccgc ctgcccgcgg cgcagcacga gagcgcgggg ctcttcggcg tacacccggc    6480
gctgctcgac gcggcgctcc acccgatcgt cctggagggc aactcagctg ccggtgcctg    6540
tgacgccgat accgacgcga ccgaccggat ccggctgccg ttcgcgtggg cggggtgac    6600 cctccacgcc gaaggggcca ccgcgctccg cgtacggatc acacccaccg gcccggacac    6660
ggtcacgctc cgcctcaccg acaccaccgg tgcgcccgtg ccaccgtgg agtccctgac    6720 cctgcgcgcg gtggcgaagg accggctggg caccaccgcc gggcgcgtcg acgacgccct    6780
gttcacggtc gtgtggacgg agaccggcac accggaaccc gcaggcgcg gagccgtgga    6840 ggtcgaggaa ctcgtcgacc tcgccggcct cggcgacctc gtggagctcg gcgccgcgga    6900
cgtcgtcctc cgggccgacc gctggacgct cgacggggac ccgtccgccg ccgcgcgcac    6960
agccgtccgg cgcaccctcg ccatcgtcca ggagttcctg tccgagccgc gcttcgacgg    7020
ctcgcgactg gtgtgcgtca ccaggggcgc ggtcgccgca ctccccggcg aggacgtcac    7080
ctccctcgcc accggccccc tctggggcct cgtccgctcc gcccagtccg agaacccggg    7140
acgcctgttc ctcctggacc tgggtgaagg cgaaggcgag cgcgacggag ccgaggagct    7200
gatccgcgcg ccacggccg gggacgagcc gcagctcgcg gcacgggacg gccgactgct    7260
cgcgccgagg ctggcccgta ccgccgccct ttcgagtgag gacaccgccg gcggcgccga    7320
ccgtttcggc cccgacggca ccgtcctcgt caccgggggc accggaggcc tcggagcgct    7380
cctcgcccgc cacctcgtgg agcgtcacgg ggtgcgccgg ctgctgctgg tgagccgccg    7440
cggggccgac gccccggcg cggccgacct gggcgaggac ctcgcgggcc tcggcgcgga    7500
ggtggcgttc ccgccgccg acgccgccga ccgcgagagc ctggcgcggg cgatcgccac    7560
cgtgcccgcc gagcatccgc tgacggccgt cgtgcacacg gcgggagtcg tcgacgacgc    7620
gacggtggag gcgctcacac cggaacggct ggacgcggta ctgcgcccga aggtcgacgc    7680
cgcgtggaac ctgcacgagc tcaccaagga cctgcggctc gacgccttcg tcctcttctc    7740
ctccgtctcc ggcatcgtcg gcaccgccgg ccaggccaac tacgcggcgg ccaacacggg    7800
cctcgacgcc ctcgccgccc accgcgccgc cacgggcctg gccgccacgt cgctggcctg    7860
gggcctctgg gacggcacgc acggcatggg cggcacgctc ggcgccgccg acctcgcccg    7920
ctggagccgg gccggaatca ccccgctcac cccgctgcag ggcctcgcgc tcttcgacgc    7980
cgcggtcgcc agggacgacg ccctcctcgt acccgccggg ctccgtccca ccgcccaccg    8040
gggcacggac ggacagcctc ctgcgctgtg gcgcggcctc gtccgggcgc gcccgcgccg    8100
tgccgcgcgg acggccgccg aggcggcgga cacgaccggc ggctggctga gcgggctcgc    8160
cgcacagtcc cccgaggagc ggcgcagcac agccgtcacg ctcgtgacgg gtgtcgtcgc    8220
ggacgtcctc gggcacgccg actccgccgc ggtcggggcg gagcggtcct tcaaggacct    8280
cggcttcgac tcctggccg gggtggagct ccgcaaccgg ctgaacgccg ccaccggcct    8340
gcggctcccc gcgaccacgg tcttcgacca tccctcgccg gccgcgctcg cgtcccatct    8400
cctcgcccag gtgcccgggt tgaaggaggg gacggcggcg accgcgaccg tcgtggccga    8460
gcggggcgct tccttcggtg accgtgcgac cgacgacgat ccgatcgcga tcgtgggcat    8520
ggcatgccgc tatccggggtg gtgtgtcgtc gccggaggac ctgtggcggc tggtggccga    8580
```

-continued

```
ggggacggac gcgatcagcg agttccccgt caaccgcggc tgggacctgg agagcctcta    8640
cgacccggat cccgagtcga agggcaccac gtactgccgg gagggcgggt tcctggaagg    8700
cgccggtgac ttcgacgccg ccttcttcgg catctcgccg cgcgaggccc tggtgatgga    8760
cccgcagcag cggctgctgc tggaggtgtc ctgggaggcg ctggaacgcg cgggcatcga    8820
cccgtcctcg ctgcgcggca gccgcggtgg tgtctacgtg ggcgccgcgc acggctcgta    8880
cgcctccgat ccccgctggt gcccgaggg ctcggagggc tatctgctga ccggcagcgc    8940
cgacgcggtg atgtccggcc gcatctccta cgcgctcggt ctcgaaggac cgtccatgac    9000
ggtggagacg gcctgctcct cctcgctggt ggcgctgcat ctggcggtac gggcgctgcg    9060
gcacggcgag tgcgggctcg cgctggcggg cggggtgggc gtgatggccg atccggcggc    9120
gttcgtggag ttctccccgg agaagggggct ggccgccgac ggccgctgca aggcgttctc    9180
ggccgccgcc gacggcaccg gctgggccga gggcgtcggc gtgctcgtcc tggagcggct    9240
gtcggacgcg cgccgcgcgg ggcacacggt cctcggcctg gtcaccggca ccgcggtcaa    9300
ccaggacggt gcctccaacg ggctgaccgc gcccaacggc ccagcccagc aacgcgtcat    9360
cgccgaggcg ctcgccgacg ccgggctgtc cccggaggac gtggacgcgg tcgaggcgca    9420
cggcaccggc accggctcg gcgaccccat cgaggccggg gcgctgctcg ccgcctccgg    9480
acggaaccgt tccggcgacc accccgctgtg gctcggctcg ctgaagtcca acatcgggca    9540
tgcccaggcc gccgccggtg tcggcggcgt catcaagatg ctccaggcgc tgcggcacgg    9600
cttgctgccc cgcacccctcc acgccgacga gccgaccccg catgccgact ggagctccgg    9660
ccgggtacgg ctgctcacct ccgaggtgcc gtggcagcgg accggccggc cccggcggac    9720
cggggtgtcc gccttcggcg tcggcggcac caatgcccat gtcgtcctcg aagaggcacc    9780
cgccccgccc gcgccggaac cggccgggga ggccccccggc ggctcccgcg ccgcagaagg    9840
ggcggaaggg ccccctggcct gggtggtctc cggacgcgac gagccggccc tgcggtccca    9900
ggcccggcgg ctccgcgacc acctctcccg cacccccggg gcccgcccgc gtgacatcgc    9960 cttctcccctc gccgccacgc gcgcagcctt tgaccaccgc gccgtgctga tcggctcgga    10020
cggggccgaa ctcgccgccg ccctggacgc gttggccgaa ggacgcgacg gtccggcggt    10080
ggtgcgcgga gtccgcgacc gggacggcag gatggccttc ctcttcaccg gcagggcag    10140 ccagcgcgcc gggatggccc acgacctgca tgccgcccat accttcttcg cgtccgccct    10200
cgacgaggtg acgaccgtc tcgacccgct gctcggccgg ccgtcggcg cgctgctgga    10260 cgcccgaccc ggctcgcccg aagcggcact cctggaccgg accgagtaca cccagccggc    10320
gctcttcgcc gtcgaggtgg cgctccaccg gctgctggag cactggggga tgcgcccga    10380 cctgctgctg gggcactcgg tgggcgaact ggcggccgcc cacgtcgcgg tgtgctcga    10440 tctcgacgac gcctgcgcgc tggtggccgc ccgcggcagg ctgatgcagc gcctgccgcc    10500
cggcggcgcg atggtctccg tgcgggccgg cgaggacgag gtccgcgcac tgctggccgg    10560
ccgcgaggac gccgtctgcg tcgccgcggt gaacggcccc cggtcggtgg tgatctccgg    10620
cgcggaggaa gcggtggccg aggcggcggc gcagctcgcc ggacgaggcc gccgcaccag    10680
gcggctccgc gtcgcgcacg ccttccactc acccctgatg gacggcatgc tcgccggatt    10740
ccgggaggtc gccgccggcc tgcgctaccg ggaaccggag ctgacggtcg tctccacggt    10800
cacggggcgg cccgccgcc ccgtgaact caccggcccc gactactggg tggcccaggt    10860
ccgtgagccc gtgcgcttcg cggacgcggt ccgcacggca caccgcctcg gagcccgcac    10920
```

```
cttcctggag accggcccgg acggcgtgct gtgcggcatg gcagaggagt gcctggagga      10980
cgacaccgtg gccctgctgc cggcgatcca caagcccggc accgcgccgc acggtccggc      11040
ggctcccggc gcgctgcggg cggccgccgc cgcgtacggc cggggcgccc gggtggactg      11100
ggccgggatg cacgccgacg gccccgaggg gccggcccgc cgcgtcgaac tgcccgtcca      11160
cgccttccgg caccgccgct actggctcgc cccgggccgc gcggcggaca ccgacgactg      11220
gatgtaccgg atcggctggg accggctgcc ggctgtgacc ggcggggccc ggaccgccgg      11280
ccgctggctg tgatccacc ccgacagccc gcgctgccgg gagctgtccg gccacgccga       11340
acgcgcgctg cgcgccgcgg gcgcgagccc cgtaccgctg cccgtggacg ctccggccgc      11400
cgaccgggcg tccttcgcgg cactgctgcg ctccgccacc ggacctgaca cacgaggtga      11460
cacagccgcg cccgtggccg gtgtgctgtc gctgctgtcc gaggaggatc ggccccatcg      11520
ccagcacgcc ccggtacccg ccggggtcct ggcgacgctg tccctgatgc aggctatgga      11580
ggaggaggcg gtggaggctc gcgtgtggtg cgtctcccgc gccgcggtcg ccgccgccga      11640
ccgggaacgg cccgtcggcg cgggcgccgc cctgtggggg ctggggcggg tggccgccct      11700
ggaacgcccc accggtggg gcggtctcgt ggacctgccc gcctcgcccg gtgcggcgca       11760
ctgggcggcc gccgtggaac ggctcgccgg tcccgaggac cagatcgccg tgcgcgcgtc      11820
cggcagttgg ggccggcgcc tcaccaggct gccgcgcgac ggcggcggcc ggacggccgc      11880 accgcgtac cggccgcgcg gcacggtgct cgtcaccggt ggcaccggcg cgctcggcgg       11940
gcatctcgcc cgctggctcg ccgcggcggg cgccgaacac ctggcgctca ccagccgccg      12000
gggcccggac gcgccggcg ccgccggact cgaggccgaa ctcctcctcc tgggcgccaa       12060
ggtgacgttc gccgcctgcg acaccgccga ccgcgacggc ctcgcccggg tcctgcgggc      12120
gataccggag gacaccccgc tcaccgcggt gttccacgcc gcgggcgtac cgcaggtcac      12180
gccgctgtcc cgtacctcgc ccgagcactt cgccgacgtg tacgcgggca aggcggcggg      12240
cgccgcgcac ctggacgaac tgacccgcga actcggcgcc ggactcgacg cgttcgtcct      12300
ctactcctcc ggcgccggcg tctggggcag cgccggccag ggtgcctacg ccgccgccaa      12360
cgccgccctg gacgcgctcg cccggcgccg tgcggcggac ggactccccg ccacctccat      12420
cgcctggggc gtgtgggggcg cggcggtat ggggggccgac gaggcggggcg cggagtatct     12480 gggccggcgc ggtatgcgcc ccatggcacc ggtctccgcg ctccgggcga tggccaccgc      12540
catcgcctcc ggggaaccct gccccaccgt cacccacacc gactgggagc gcttcggcga      12600
gggcttcacc gccttccggc ccagccctct gatcgcgggg ctcggcacgc cggcggcgg      12660 ccgggcggc gagacccccg aggaggggaa cgccaccgct gcggcggacc tcaccgcgcct      12720 gccgcccgcc gaactccgca ccgcgctgcg cgagctggtg cgagcccgga ccgccgcggc      12780
gctcggcctc gacgacccgg ccgaggtcgc gagggcgaa cggttccccg ccatgggctt       12840
cgactccctg gccaccgtac ggctgcgccg cggactcgcc tcgccacgg gcctcgacct      12900 gccccccgat ctgctcttcg accgggacac cccggccgcg ctcgccgccc acctggccga      12960
actgctcgcc accgcacggg accacggacc cggcggcccc gggaccggtg ccgcgccggc      13020
cgatgccgga agcggcctgc cggccctcta ccgggaggcc gtccgcaccg ccgggccgc       13080 ggaaatggcc gaactgctcg ccgccgcttc ccggttccgc cccgccttcg ggacggcgga      13140
ccggcagccg gtggccctcg tgccgctggc cgacggcgcg gaggacaccg gctcccgct      13200 gctcgtgggc tgcgccggga cggcgtggc ctccggcccg gtggagttca ccgccttcgc      13260
cggagcgctg gcggacctcc cggcggcggc cccgatggcc gcgctgccgc agcccggctt      13320
```

```
tctgccggga gaacgagtcc cggccacccc ggaggcattg ttcgaggccc aggcggaagc    13380
gctgctgcgc tacgcggccg gccggcccct cgtgctgctg gggcactccg ccggcgccaa    13440
catggcccac gccctgaccc gtcatctgga ggcgaacggt ggcggcccg cagggctggt     13500 gctcatggac atctacaccc ccgccgaccc cggcgcgatg ggcgtctggc ggaacgacat    13560
gttccagtgg gtctggcggc gctcggacat ccccccggac gaccaccgcc tcacggccat    13620
gggcgcctac caccggctgc ttctcgactg gtcgcccacc ccgtccgcg ccccgtact     13680 gcatctgcgc gccgcggaac ccatgggcga ctggccaccc ggggacaccg gctggcagtc    13740
ccactgggac ggcgcgcaca ccaccgccgg catccccgga aaccacttca cgatgatgac    13800
cgaacacgcc tccgccgccg cccggctcgt gcacggctgg ctcgcggaac ggaccccgtc    13860
cgggcagggc gggtcaccgt cccgcgcggc ggggagagag gagaggccgt gaacacggca    13920
gccgccccga ccggcaccgc cgccggcggc accaccgccc cggcggcggc acacgacctg    13980
tcccgcgccg gacgcaggct ccaactcacc cgggccgcac agtggttcgc cggcaaccag    14040
ggagacccct acgggatgat cctgcgcgcc ggcaccgccg accggcacc gtacgaggaa     14100 gagatccccg ggtaccgagc tcgaattctt aattaaggag gtcgtagatg agtaacaaga    14160
acaacgatga gctgcagcgg caggcctcgg aaaacaccct ggggctgaac ccggtcatcg    14220
gtatccgccg caaagacctg ttgagctcgg cacgcaccgt gctgcgccag gccgtgcgcc    14280
aaccgctgca cagcgccaag catgtggccc actttggcct ggagctgaag aacgtgctgc    14340
tgggcaagtc cagccttgcc ccggaaagcg acgaccgtcg cttcaatgac ccggcatgga    14400
gcaacaaccc actttaccgc cgctacctgc aaacctatct ggcctggcgc aaggagctgc    14460
aggactggat cggcaacagc gacctgtcgc cccaggacat cagccgcggc cagttcgtca    14520
tcaacctgat gaccgaagcc atggctccga ccaacacccct gtccaacccg gcagcagtca    14580
aacgcttctt cgaaaccggc ggcaagagcc tgctcgatgg cctgtccaac ctggccaagg    14640
acctggtcaa caacggtggc atgcccagcc aggtgaacat ggacgccttc gaggtgggca    14700
agaacctggg caccagtgaa ggcgccgtgg tgtaccgcaa cgatgtgctg gagctgatcc    14760
agtacaagcc catcaccgag caggtgcatg cccgcccgct gctggtggtg ccgccgcaga    14820
tcaacaagtt ctacgtattc gacctgagcc cggaaaagag cctggcacgc tactgcctgc    14880
gctcgcagca gcagaccttc atcatcagct ggcgcaaccc gaccaaagcc cagcgcgaat    14940
ggggcctgtc cacctacatc gacgcgctca aggaggcggt cgacgcggtg ctggcgatta    15000
ccggcagcaa ggacctgaac atgctcggtg cctgctccgg cggcatcacc tgcacggcat    15060
tggtcggcca ctatgccgcc ctcggcgaaa acaaggtcaa tgccctgacc ctgctggtca    15120
gcgtgctgga caccaccatg gacaaccagg tcgccctgtt cgtcgacgag cagactttgg    15180
aggccgccaa gcgccactcc taccaggccg gtgtgctcga aggcagcgag atggccaagg    15240
tgttcgcctg gatgcgcccc aacgacctga tctggaacta ctgggtcaac aactacctgc    15300
tcggcaacga gccgccggtg ttcgacatcc tgttctggaa caacgacacc acgcgcctgc    15360
cggccgcctt ccacggcgac ctgatcgaaa tgttcaagag caacccgctg acccgcccgg    15420
acgccctgga ggtttgcggc actccgatcg acctgaaaca ggtcaaatgc gacatctaca    15480
gccttgccgg caccaacgac cacatcaccc cgtggcagtc atgctaccgc tcggcgcacc    15540
tgttcggcgc caagatcgag ttcgtgctgt ccaacagcgg ccacatccag agcatcctca    15600
acccgccagg caaccccaag gcgcgcttca tgaccggtgc cgatcgcccg ggtgaccgg     15660
```

-continued

```
tggcctggca ggaaaacgcc accaagcatg ccgactcctg gtggctgcac tggcaaagct    15720
ggctgggcga gcgtgccggc gagctggaaa aggcgccgac ccgcctgggc aaccgtgcct    15780
atgccgctgg cgaggcatcc ccgggcacct acgttcacga gcgttgagct gcagcgccgt    15840
ggccacctgc gggacgccac ggtgttgaat tc                                  15872
```

<210> SEQ ID NO: 2
<211> LENGTH: 5215
<212> TYPE: PRT
<213> ORGANISM: Streptomyces venezuelae

<400> SEQUENCE: 2

```
Met Asn Glu Ala Ile Ala Val Val Gly Met Ser Cys Arg Leu Pro Lys
  1               5                  10                  15

Ala Ser Asn Pro Ala Ala Phe Trp Glu Leu Leu Arg Asn Gly Glu Ser
                 20                  25                  30

Ala Val Thr Asp Val Pro Ser Gly Arg Trp Thr Ser Val Leu Gly Gly
             35                  40                  45

Ala Asp Ala Glu Glu Pro Ala Glu Ser Gly Val Arg Arg Gly Gly Phe
         50                  55                  60

Leu Asp Ser Leu Asp Leu Phe Asp Ala Ala Phe Phe Gly Ile Ser Pro
 65                  70                  75                  80

Arg Glu Ala Ala Ala Met Asp Pro Gln Gln Arg Leu Val Leu Glu Leu
                 85                  90                  95

Ala Trp Glu Ala Leu Glu Asp Ala Gly Ile Val Pro Gly Thr Leu Ala
            100                 105                 110

Gly Ser Arg Thr Ala Val Phe Val Gly Thr Leu Arg Asp Asp Tyr Thr
        115                 120                 125

Ser Leu Leu Tyr Gln His Gly Glu Gln Ala Ile Thr Gln His Thr Met
    130                 135                 140

Ala Gly Val Asn Arg Gly Val Ile Ala Asn Arg Val Ser Tyr His Leu
145                 150                 155                 160

Gly Leu Gln Gly Pro Ser Leu Thr Val Asp Ala Ala Gln Ser Ser Ser
                165                 170                 175

Leu Val Ala Val His Leu Ala Cys Glu Ser Leu Arg Ala Gly Glu Ser
            180                 185                 190

Thr Thr Ala Leu Val Ala Gly Val Asn Leu Asn Ile Leu Ala Glu Ser
        195                 200                 205

Ala Val Thr Glu Glu Arg Phe Gly Gly Leu Ser Pro Asp Gly Thr Ala
    210                 215                 220

Tyr Thr Phe Asp Ala Arg Ala Asn Gly Phe Val Arg Gly Glu Gly Gly
225                 230                 235                 240

Gly Val Val Leu Lys Pro Leu Ser Arg Ala Leu Ala Asp Gly Asp
                245                 250                 255

Arg Val His Gly Val Ile Arg Ala Ser Ala Val Asn Asn Asp Gly Ala
            260                 265                 270

Thr Pro Gly Leu Thr Val Pro Ser Arg Ala Ala Gln Glu Lys Val Leu
        275                 280                 285

Arg Glu Ala Tyr Arg Lys Ala Ala Leu Asp Pro Ser Ala Val Gln Tyr
    290                 295                 300

Val Glu Leu His Gly Thr Gly Thr Pro Val Gly Asp Pro Ile Glu Ala
305                 310                 315                 320

Ala Ala Leu Gly Ala Val Leu Gly Ser Ala Arg Pro Ala Asp Glu Pro
                325                 330                 335
```

-continued

```
Leu Leu Val Gly Ser Ala Lys Thr Asn Val Gly His Leu Glu Gly Ala
                340                 345                 350
Ala Gly Ile Val Gly Leu Ile Lys Thr Leu Ala Leu Gly Arg Arg
            355                 360                 365
Arg Ile Pro Ala Ser Leu Asn Phe Arg Thr Pro His Pro Asp Ile Pro
        370                 375                 380
Leu Asp Thr Leu Gly Leu Asp Val Pro Asp Gly Leu Arg Glu Trp Pro
385                 390                 395                 400
His Pro Asp Arg Glu Leu Leu Ala Gly Val Ser Ser Phe Gly Met Gly
                405                 410                 415
Gly Thr Asn Ala His Val Val Leu Ser Glu Gly Pro Ala Gln Gly Gly
                420                 425                 430
Glu Gln Pro Gly Ile Asp Glu Thr Pro Val Asp Ser Gly Ala Ala
            435                 440                 445
Leu Pro Phe Val Val Thr Gly Arg Gly Glu Ala Leu Arg Ala Gln
        450                 455                 460
Ala Arg Arg Leu His Glu Ala Val Glu Ala Asp Pro Glu Leu Ala Pro
465                 470                 475                 480
Ala Ala Leu Ala Arg Ser Leu Val Thr Thr Arg Thr Val Phe Thr His
                485                 490                 495
Arg Ser Val Val Leu Ala Pro Asp Arg Ala Arg Leu Leu Asp Gly Leu
                500                 505                 510
Gly Ala Leu Ala Ala Gly Thr Pro Ala Pro Gly Val Val Thr Gly Thr
            515                 520                 525
Pro Ala Pro Gly Arg Leu Ala Val Leu Phe Ser Gly Gln Gly Ala Gln
        530                 535                 540
Arg Thr Gly Met Gly Met Glu Leu Tyr Ala Ala His Pro Ala Phe Ala
545                 550                 555                 560
Thr Ala Phe Asp Ala Val Ala Ala Glu Leu Asp Pro Leu Leu Asp Arg
                565                 570                 575
Pro Leu Ala Glu Leu Val Ala Ala Gly Asp Thr Leu Asp Arg Thr Val
            580                 585                 590
His Thr Gln Pro Ala Leu Phe Ala Val Glu Val Ala Leu His Arg Leu
        595                 600                 605
Val Glu Ser Trp Gly Val Thr Pro Asp Leu Leu Ala Gly His Ser Val
    610                 615                 620
Gly Glu Ile Ser Ala Ala His Val Ala Gly Val Leu Ser Leu Arg Asp
625                 630                 635                 640
Ala Ala Arg Leu Val Ala Ala Arg Gly Arg Leu Met Gln Ala Leu Pro
                645                 650                 655
Glu Gly Gly Ala Met Val Ala Val Glu Ala Ser Glu Glu Val Leu
                660                 665                 670
Pro His Leu Ala Gly Arg Glu Arg Glu Leu Ser Leu Ala Ala Val Asn
        675                 680                 685
Gly Pro Arg Ala Val Val Leu Ala Gly Ala Glu Arg Ala Val Leu Asp
    690                 695                 700
Val Ala Glu Leu Leu Arg Glu Gln Gly Arg Arg Thr Lys Arg Leu Ser
705                 710                 715                 720
Val Ser His Ala Phe His Ser Pro Leu Met Glu Pro Met Leu Asp Asp
                725                 730                 735
Phe Arg Arg Val Val Glu Glu Leu Asp Phe Gln Glu Pro Arg Val Asp
                740                 745                 750
```

-continued

```
Val Val Ser Thr Val Thr Gly Leu Pro Val Thr Ala Gly Gln Trp Thr
        755                 760                 765

Asp Pro Glu Tyr Trp Val Asp Gln Val Arg Arg Pro Val Arg Phe Leu
        770                 775                 780

Asp Ala Val Arg Thr Leu Glu Glu Ser Gly Ala Asp Thr Phe Leu Glu
785                 790                 795                 800

Leu Gly Pro Asp Gly Val Cys Ser Ala Met Ala Ala Asp Ser Val Arg
                805                 810                 815

Asp Gln Glu Ala Ala Thr Ala Val Ser Ala Leu Arg Lys Gly Arg Pro
                820                 825                 830

Glu Pro Gln Ser Leu Leu Ala Ala Leu Thr Thr Val Phe Val Arg Gly
                835                 840                 845

His Asp Val Asp Trp Thr Ala Ala His Gly Ser Thr Gly Thr Val Arg
                850                 855                 860

Val Pro Leu Pro Thr Tyr Ala Phe Gln Arg Glu Arg His Trp Phe Asp
865                 870                 875                 880

Gly Ala Ala Arg Thr Ala Ala Pro Leu Thr Ala Gly Arg Ser Gly Thr
                885                 890                 895

Gly Ala Gly Thr Gly Pro Ala Ala Gly Val Thr Ser Gly Glu Gly Glu
                900                 905                 910

Gly Glu Gly Glu Gly Ala Gly Ala Gly Gly Asp Arg Pro Ala Arg
                915                 920                 925

His Glu Thr Thr Glu Arg Val Arg Ala His Val Ala Ala Val Leu Glu
                930                 935                 940

Tyr Asp Asp Pro Thr Arg Val Glu Leu Gly Leu Thr Phe Lys Glu Leu
945                 950                 955                 960

Gly Phe Asp Ser Leu Met Ser Val Glu Leu Arg Asn Ala Leu Val Asp
                965                 970                 975

Asp Thr Gly Leu Arg Leu Pro Ser Gly Leu Leu Phe Asp His Pro Thr
                980                 985                 990

Pro Arg Ala Leu Ala Ala His Leu Gly Asp Leu Leu Thr Gly Gly Ser
                995                 1000                1005

Gly Glu Thr Gly Ser Ala Asp Gly Ile Pro Pro Ala Thr Pro Ala Asp
        1010                1015                1020

Thr Thr Ala Glu Pro Ile Ala Ile Ile Gly Met Ala Cys Arg Tyr Pro
1025                1030                1035                1040

Gly Gly Val Thr Ser Pro Glu Asp Leu Trp Arg Leu Val Ala Glu Gly
                1045                1050                1055

Arg Asp Ala Val Ser Gly Leu Pro Thr Asp Arg Gly Trp Asp Glu Asp
                1060                1065                1070

Leu Phe Asp Ala Asp Pro Asp Arg Ser Gly Lys Ser Ser Val Arg Glu
                1075                1080                1085

Gly Gly Phe Leu His Asp Ala Ala Leu Phe Asp Ala Gly Phe Phe Gly
                1090                1095                1100

Ile Ser Pro Arg Glu Ala Leu Gly Met Asp Pro Gln Gln Arg Leu Leu
1105                1110                1115                1120

Leu Glu Thr Ala Trp Glu Ala Val Glu Arg Ala Gly Leu Asp Pro Glu
                1125                1130                1135

Gly Leu Lys Gly Ser Arg Thr Ala Val Phe Val Gly Ala Thr Ala Leu
                1140                1145                1150

Asp Tyr Gly Pro Arg Met His Asp Gly Ala Glu Gly Val Glu Gly His
                1155                1160                1165
```

-continued

```
Leu Leu Thr Gly Thr Thr Pro Ser Val Met Ser Gly Arg Ile Ala Tyr
    1170            1175                1180
Gln Leu Gly Leu Thr Gly Pro Ala Val Thr Val Asp Thr Ala Cys Ser
    1185            1190                1195                1200
Ser Ser Leu Val Ala Leu His Leu Ala Val Arg Ser Leu Arg Gln Gly
                1205                1210                1215
Glu Ser Ser Leu Ala Leu Ala Gly Gly Ala Thr Val Met Ser Thr Pro
            1220                1225                1230
Gly Met Phe Val Glu Phe Ser Arg Gln Arg Gly Leu Ala Ala Asp Gly
            1235                1240                1245
Arg Ser Lys Ala Phe Ser Asp Ser Ala Asp Gly Thr Ser Trp Ala Glu
            1250                1255                1260
Gly Val Gly Leu Leu Val Val Glu Arg Leu Ser Asp Ala Glu Arg Asn
1265                1270                1275                1280
Gly His Pro Val Leu Ala Val Ile Arg Gly Ser Ala Val Asn Gln Asp
                1285                1290                1295
Gly Ala Ser Asn Gly Leu Thr Ala Pro Asn Gly Pro Ser Gln Gln Arg
                1300                1305                1310
Val Ile Arg Gln Ala Leu Ala Asp Ala Gly Leu Thr Pro Ala Asp Val
            1315                1320                1325
Asp Ala Val Glu Ala His Gly Thr Gly Thr Arg Leu Gly Asp Pro Ile
            1330                1335                1340
Glu Ala Glu Ala Ile Leu Gly Thr Tyr Gly Arg Asp Arg Gly Glu Gly
1345                1350                1355                1360
Ala Pro Leu Gln Leu Gly Ser Leu Lys Ser Asn Ile Gly His Ala Gln
                1365                1370                1375
Ala Ala Ala Gly Val Gly Gly Leu Ile Lys Met Val Leu Ala Met Arg
            1380                1385                1390
His Gly Val Leu Pro Arg Thr Leu His Val Asp Arg Pro Thr Thr Arg
            1395                1400                1405
Val Asp Trp Glu Ala Gly Gly Val Glu Leu Leu Thr Glu Glu Arg Glu
    1410                1415                1420
Trp Pro Glu Thr Gly Arg Pro Arg Arg Ala Ala Ile Ser Ser Phe Gly
1425                1430                1435                1440
Ile Ser Gly Thr Asn Ala His Ile Val Val Glu Gln Ala Pro Glu Ala
                1445                1450                1455
Gly Glu Ala Ala Val Thr Thr Thr Ala Pro Glu Ala Gly Glu Ala Gly
                1460                1465                1470
Glu Ala Ala Asp Thr Thr Ala Thr Thr Thr Pro Ala Ala Val Gly Val
            1475                1480                1485
Pro Glu Pro Val Arg Ala Pro Val Val Ser Ala Arg Asp Ala Ala
    1490                1495                1500
Ala Leu Arg Ala Gln Ala Val Arg Leu Arg Thr Phe Leu Asp Gly Arg
1505                1510                1515                1520
Pro Asp Val Thr Val Ala Asp Leu Gly Arg Ser Leu Ala Ala Arg Thr
                1525                1530                1535
Ala Phe Glu His Lys Ala Ala Leu Thr Thr Ala Thr Arg Asp Glu Leu
                1540                1545                1550
Leu Ala Gly Leu Asp Ala Leu Gly Arg Gly Glu Gln Ala Thr Gly Leu
            1555                1560                1565
Val Thr Gly Glu Pro Ala Arg Ala Gly Arg Thr Ala Phe Leu Phe Thr
    1570                1575                1580
```

```
Gly Gln Gly Ala Gln Arg Val Ala Met Gly Glu Glu Leu Arg Ala Ala
1585                1590                1595                1600

His Pro Val Phe Ala Ala Ala Leu Asp Thr Val Tyr Ala Ala Leu Asp
            1605                1610                1615

Arg His Leu Asp Arg Pro Leu Arg Glu Ile Val Ala Ala Gly Glu Glu
        1620                1625                1630

Leu Asp Leu Thr Ala Tyr Thr Gln Pro Ala Leu Phe Ala Phe Glu Val
            1635                1640                1645

Ala Leu Phe Arg Leu Leu Glu His His Gly Leu Val Pro Asp Leu Leu
        1650                1655                1660

Thr Gly His Ser Val Gly Glu Ile Ala Ala His Val Ala Gly Val
1665                1670                1675                1680

Leu Ser Leu Asp Asp Ala Ala Arg Leu Val Thr Ala Arg Gly Arg Leu
            1685                1690                1695

Met Gln Ser Ala Arg Glu Gly Gly Ala Met Ile Ala Val Gln Ala Gly
        1700                1705                1710

Glu Ala Glu Val Val Glu Ser Leu Lys Gly Tyr Glu Gly Arg Val Ala
            1715                1720                1725

Val Ala Ala Val Asn Gly Pro Thr Ala Val Val Ser Gly Asp Ala
1730                1735                1740

Asp Ala Ala Glu Glu Ile Arg Ala Val Trp Ala Gly Arg Gly Arg Arg
1745                1750                1755                1760

Thr Arg Arg Leu Arg Val Ser His Ala Phe His Ser Pro His Met Asp
            1765                1770                1775

Asp Val Leu Asp Glu Phe Leu Arg Val Ala Glu Gly Leu Thr Phe Glu
            1780                1785                1790

Glu Pro Arg Ile Pro Val Val Ser Thr Val Thr Gly Ala Leu Val Thr
        1795                1800                1805

Ser Gly Glu Leu Thr Ser Pro Ala Tyr Trp Val Asp Gln Ile Arg Arg
        1810                1815                1820

Pro Val Arg Phe Leu Asp Ala Val Arg Thr Leu Ala Ala Gln Asp Ala
1825                1830                1835                1840

Thr Val Leu Val Glu Ile Gly Pro Asp Ala Val Leu Thr Ala Leu Ala
                1845                1850                1855

Glu Glu Ala Leu Ala Pro Gly Thr Asp Ala Pro Asp Ala Arg Asp Val
            1860                1865                1870

Thr Val Val Pro Leu Leu Arg Ala Gly Arg Pro Glu Pro Glu Thr Leu
        1875                1880                1885

Ala Ala Gly Leu Ala Thr Ala His Val His Gly Ala Pro Leu Asp Arg
        1890                1895                1900

Ala Ser Phe Phe Pro Asp Gly Arg Arg Thr Asp Leu Pro Thr Tyr Ala
1905                1910                1915                1920

Phe Arg Arg Glu His Tyr Trp Leu Thr Pro Glu Ala Arg Thr Asp Ala
                1925                1930                1935

Arg Ala Leu Gly Phe Asp Pro Ala Arg His Pro Leu Leu Thr Thr Thr
            1940                1945                1950

Val Glu Val Ala Gly Gly Asp Gly Val Leu Leu Thr Gly Arg Leu Ser
        1955                1960                1965

Leu Thr Asp Gln Pro Trp Leu Ala Asp His Met Val Asn Gly Ala Val
    1970                1975                1980

Leu Leu Pro Ala Thr Ala Phe Leu Glu Leu Ala Leu Ala Ala Gly Asp
1985                1990                1995                2000
```

-continued

```
His Val Gly Ala Val Arg Val Glu Glu Leu Thr Leu Glu Ala Pro Leu
            2005                2010                2015
Val Leu Pro Glu Arg Gly Ala Val Arg Ile Gln Val Gly Val Ser Gly
        2020                2025                2030
Asp Gly Glu Ser Pro Ala Gly Arg Thr Phe Gly Val Tyr Ser Thr Pro
        2035                2040                2045
Asp Ser Gly Asp Thr Gly Asp Asp Ala Pro Arg Glu Trp Thr Arg His
        2050                2055                2060
Val Ser Gly Val Leu Gly Glu Gly Asp Pro Ala Thr Glu Ser Asp His
2065                2070                2075                2080
Pro Gly Thr Asp Gly Asp Gly Ser Ala Ala Trp Pro Ala Ala Ala
            2085                2090                2095
Thr Ala Thr Pro Leu Asp Gly Val Tyr Asp Arg Leu Ala Glu Leu Gly
            2100                2105                2110
Tyr Gly Tyr Gly Pro Ala Phe Gln Gly Leu Thr Gly Leu Trp Arg Asp
            2115                2120                2125
Gly Ala Asp Thr Leu Ala Glu Ile Arg Leu Pro Ala Ala Gln His Glu
            2130                2135                2140
Ser Ala Gly Leu Phe Gly Val His Pro Ala Leu Leu Asp Ala Ala Leu
2145                2150                2155                2160
His Pro Ile Val Leu Glu Gly Asn Ser Ala Ala Gly Ala Cys Asp Ala
            2165                2170                2175
Asp Thr Asp Ala Thr Asp Arg Ile Arg Leu Pro Phe Ala Trp Ala Gly
            2180                2185                2190
Val Thr Leu His Ala Glu Gly Ala Thr Ala Leu Arg Val Arg Ile Thr
            2195                2200                2205
Pro Thr Gly Pro Asp Thr Val Thr Leu Arg Leu Thr Asp Thr Thr Gly
        2210                2215                2220
Ala Pro Val Ala Thr Val Glu Ser Leu Thr Leu Arg Ala Val Ala Lys
2225                2230                2235                2240
Asp Arg Leu Gly Thr Thr Ala Gly Arg Val Asp Asp Ala Leu Phe Thr
            2245                2250                2255
Val Val Trp Thr Glu Thr Gly Thr Pro Glu Pro Ala Gly Arg Gly Ala
            2260                2265                2270
Val Glu Val Glu Glu Leu Val Asp Leu Ala Gly Leu Gly Asp Leu Val
        2275                2280                2285
Glu Leu Gly Ala Ala Asp Val Val Leu Arg Ala Asp Arg Trp Thr Leu
    2290                2295                2300
Asp Gly Asp Pro Ser Ala Ala Arg Thr Ala Val Arg Arg Thr Leu
2305                2310                2315                2320
Ala Ile Val Gln Glu Phe Leu Ser Glu Pro Arg Phe Asp Gly Ser Arg
            2325                2330                2335
Leu Val Cys Val Thr Arg Gly Ala Val Ala Ala Leu Pro Gly Glu Asp
            2340                2345                2350
Val Thr Ser Leu Ala Thr Gly Pro Leu Trp Gly Leu Val Arg Ser Ala
            2355                2360                2365
Gln Ser Glu Asn Pro Gly Arg Leu Phe Leu Leu Asp Leu Gly Glu Gly
        2370                2375                2380
Glu Gly Glu Arg Asp Gly Ala Glu Glu Leu Ile Arg Ala Ala Thr Ala
2385                2390                2395                2400
Gly Asp Glu Pro Gln Leu Ala Ala Arg Asp Gly Arg Leu Leu Ala Pro
            2405                2410                2415
```

```
Arg Leu Ala Arg Thr Ala Ala Leu Ser Ser Glu Asp Thr Ala Gly Gly
            2420                2425                2430

Ala Asp Arg Phe Gly Pro Asp Gly Thr Val Leu Val Thr Gly Gly Thr
            2435                2440                2445

Gly Gly Leu Gly Ala Leu Leu Ala Arg His Leu Val Glu Arg His Gly
            2450                2455                2460

Val Arg Arg Leu Leu Leu Val Ser Arg Arg Gly Ala Asp Ala Pro Gly
2465                2470                2475                2480

Ala Ala Asp Leu Gly Glu Asp Leu Ala Gly Leu Gly Ala Glu Val Ala
            2485                2490                2495

Phe Ala Ala Ala Asp Ala Ala Asp Arg Glu Ser Leu Ala Arg Ala Ile
            2500                2505                2510

Ala Thr Val Pro Ala Glu His Pro Leu Thr Ala Val Val His Thr Ala
            2515                2520                2525

Gly Val Val Asp Asp Ala Thr Val Glu Ala Leu Thr Pro Glu Arg Leu
            2530                2535                2540

Asp Ala Val Leu Arg Pro Lys Val Asp Ala Ala Trp Asn Leu His Glu
2545                2550                2555                2560

Leu Thr Lys Asp Leu Arg Leu Asp Ala Phe Val Leu Phe Ser Ser Val
            2565                2570                2575

Ser Gly Ile Val Gly Thr Ala Gly Gln Ala Asn Tyr Ala Ala Ala Asn
            2580                2585                2590

Thr Gly Leu Asp Ala Leu Ala Ala His Arg Ala Ala Thr Gly Leu Ala
            2595                2600                2605

Ala Thr Ser Leu Ala Trp Gly Leu Trp Asp Gly Thr His Gly Met Gly
            2610                2615                2620

Gly Thr Leu Gly Ala Ala Asp Leu Ala Arg Trp Ser Arg Ala Gly Ile
2625                2630                2635                2640

Thr Pro Leu Thr Pro Leu Gln Gly Leu Ala Leu Phe Asp Ala Ala Val
            2645                2650                2655

Ala Arg Asp Asp Ala Leu Leu Val Pro Ala Gly Leu Arg Pro Thr Ala
            2660                2665                2670

His Arg Gly Thr Asp Gly Gln Pro Pro Ala Leu Trp Arg Gly Leu Val
            2675                2680                2685

Arg Ala Arg Pro Arg Arg Ala Ala Arg Thr Ala Ala Glu Ala Ala Asp
            2690                2695                2700

Thr Thr Gly Gly Trp Leu Ser Gly Leu Ala Ala Gln Ser Pro Glu Glu
2705                2710                2715                2720

Arg Arg Ser Thr Ala Val Thr Leu Val Thr Gly Val Val Ala Asp Val
            2725                2730                2735

Leu Gly His Ala Asp Ser Ala Ala Val Gly Ala Glu Arg Ser Phe Lys
            2740                2745                2750

Asp Leu Gly Phe Asp Ser Leu Ala Gly Val Glu Leu Arg Asn Arg Leu
            2755                2760                2765

Asn Ala Ala Thr Gly Leu Arg Leu Pro Ala Thr Thr Val Phe Asp His
            2770                2775                2780

Pro Ser Pro Ala Ala Leu Ala Ser His Leu Leu Ala Gln Val Pro Gly
2785                2790                2795                2800

Leu Lys Glu Gly Thr Ala Ala Thr Ala Thr Val Val Ala Glu Arg Gly
            2805                2810                2815

Ala Ser Phe Gly Asp Arg Ala Thr Asp Asp Pro Ile Ala Ile Val
            2820                2825                2830
```

-continued

```
Gly Met Ala Cys Arg Tyr Pro Gly Val Ser Ser Pro Glu Asp Leu
        2835                2840                2845

Trp Arg Leu Val Ala Glu Gly Thr Asp Ala Ile Ser Glu Phe Pro Val
2850                2855                2860

Asn Arg Gly Trp Asp Leu Glu Ser Leu Tyr Asp Pro Asp Pro Glu Ser
2865                2870                2875                2880

Lys Gly Thr Thr Tyr Cys Arg Glu Gly Phe Leu Glu Gly Ala Gly
        2885                2890                2895

Asp Phe Asp Ala Ala Phe Phe Gly Ile Ser Pro Arg Glu Ala Leu Val
                2900                2905                2910

Met Asp Pro Gln Gln Arg Leu Leu Leu Glu Val Ser Trp Glu Ala Leu
        2915                2920                2925

Glu Arg Ala Gly Ile Asp Pro Ser Ser Leu Arg Gly Ser Arg Gly Gly
    2930                2935                2940

Val Tyr Val Gly Ala Ala His Gly Ser Tyr Ala Ser Asp Pro Arg Leu
2945                2950                2955                2960

Val Pro Glu Gly Ser Glu Gly Tyr Leu Leu Thr Gly Ser Ala Asp Ala
                2965                2970                2975

Val Met Ser Gly Arg Ile Ser Tyr Ala Leu Gly Leu Glu Gly Pro Ser
        2980                2985                2990

Met Thr Val Glu Thr Ala Cys Ser Ser Leu Val Ala Leu His Leu
        2995                3000                3005

Ala Val Arg Ala Leu Arg His Gly Glu Cys Gly Leu Ala Leu Ala Gly
        3010                3015                3020

Gly Val Ala Val Met Ala Asp Pro Ala Ala Phe Val Glu Phe Ser Arg
3025                3030                3035                3040

Gln Lys Gly Leu Ala Ala Asp Gly Arg Cys Lys Ala Phe Ser Ala Ala
        3045                3050                3055

Ala Asp Gly Thr Gly Trp Ala Glu Gly Val Gly Val Leu Val Leu Glu
        3060                3065                3070

Arg Leu Ser Asp Ala Arg Arg Ala Gly His Thr Val Leu Gly Leu Val
        3075                3080                3085

Thr Gly Thr Ala Val Asn Gln Asp Gly Ala Ser Asn Gly Leu Thr Ala
        3090                3095                3100

Pro Asn Gly Pro Ala Gln Gln Arg Val Ile Ala Glu Ala Leu Ala Asp
3105                3110                3115                3120

Ala Gly Leu Ser Pro Glu Asp Val Asp Ala Val Glu Ala His Gly Thr
                3125                3130                3135

Gly Thr Arg Leu Gly Asp Pro Ile Glu Ala Gly Ala Leu Leu Ala Ala
        3140                3145                3150

Ser Gly Arg Asn Arg Ser Gly Asp His Pro Leu Trp Leu Gly Ser Leu
        3155                3160                3165

Lys Ser Asn Ile Gly His Ala Gln Ala Ala Ala Gly Val Gly Gly Val
        3170                3175                3180

Ile Lys Met Leu Gln Ala Leu Arg His Gly Leu Leu Pro Arg Thr Leu
3185                3190                3195                3200

His Ala Asp Glu Pro Thr Pro His Ala Asp Trp Ser Ser Gly Arg Val
                3205                3210                3215

Arg Leu Leu Thr Ser Glu Val Pro Trp Gln Arg Thr Gly Arg Pro
        3220                3225                3230

Arg Thr Gly Val Ser Ala Phe Gly Val Gly Gly Thr Asn Ala His Val
        3235                3240                3245
```

-continued

Val Leu Glu Glu Ala Pro Ala Pro Pro Ala Pro Glu Pro Ala Gly Glu
    3250            3255            3260

Ala Pro Gly Gly Ser Arg Ala Ala Glu Gly Ala Glu Gly Pro Leu Ala
3265            3270            3275            3280

Trp Val Val Ser Gly Arg Asp Glu Pro Ala Leu Arg Ser Gln Ala Arg
            3285            3290            3295

Arg Leu Arg Asp His Leu Ser Arg Thr Pro Gly Ala Arg Pro Arg Asp
            3300            3305            3310

Ile Ala Phe Ser Leu Ala Ala Thr Arg Ala Ala Phe Asp His Arg Ala
            3315            3320            3325

Val Leu Ile Gly Ser Asp Gly Ala Glu Leu Ala Ala Leu Asp Ala
            3330            3335            3340

Leu Ala Glu Gly Arg Asp Gly Pro Ala Val Val Arg Gly Val Arg Asp
3345            3350            3355            3360

Arg Asp Gly Arg Met Ala Phe Leu Phe Thr Gly Gln Gly Ser Gln Arg
            3365            3370            3375

Ala Gly Met Ala His Asp Leu His Ala Ala His Thr Phe Phe Ala Ser
            3380            3385            3390

Ala Leu Asp Glu Val Thr Asp Arg Leu Asp Pro Leu Leu Gly Arg Pro
            3395            3400            3405

Leu Gly Ala Leu Leu Asp Ala Arg Pro Gly Ser Pro Glu Ala Ala Leu
    3410            3415            3420

Leu Asp Arg Thr Glu Tyr Thr Gln Pro Ala Leu Phe Ala Val Glu Val
3425            3430            3435            3440

Ala Leu His Arg Leu Leu Glu His Trp Gly Met Arg Pro Asp Leu Leu
            3445            3450            3455

Leu Gly His Ser Val Gly Glu Leu Ala Ala Ala His Val Ala Gly Val
            3460            3465            3470

Leu Asp Leu Asp Asp Ala Cys Ala Leu Val Ala Ala Arg Gly Arg Leu
            3475            3480            3485

Met Gln Arg Leu Pro Pro Gly Gly Ala Met Val Ser Val Arg Ala Gly
            3490            3495            3500

Glu Asp Glu Val Arg Ala Leu Leu Ala Gly Arg Glu Asp Ala Val Cys
3505            3510            3515            3520

Val Ala Ala Val Asn Gly Pro Arg Ser Val Val Ile Ser Gly Ala Glu
            3525            3530            3535

Glu Ala Val Ala Glu Ala Ala Gln Leu Ala Gly Arg Gly Arg Arg
            3540            3545            3550

Thr Arg Arg Leu Arg Val Ala His Ala Phe His Ser Pro Leu Met Asp
    3555            3560            3565

Gly Met Leu Ala Gly Phe Arg Glu Val Ala Ala Gly Leu Arg Tyr Arg
    3570            3575            3580

Glu Pro Glu Leu Thr Val Val Ser Thr Val Thr Gly Arg Pro Ala Arg
3585            3590            3595            3600

Pro Gly Glu Leu Thr Gly Pro Asp Tyr Trp Val Ala Gln Val Arg Glu
            3605            3610            3615

Pro Val Arg Phe Ala Asp Ala Val Arg Thr Ala His Arg Leu Gly Ala
            3620            3625            3630

Arg Thr Phe Leu Glu Thr Gly Pro Asp Gly Val Leu Cys Gly Met Ala
            3635            3640            3645

Glu Glu Cys Leu Glu Asp Asp Thr Val Ala Leu Leu Pro Ala Ile His
            3650            3655            3660

-continued

```
Lys Pro Gly Thr Ala Pro His Gly Pro Ala Ala Pro Gly Ala Leu Arg
3665                3670                3675                3680

Ala Ala Ala Ala Ala Tyr Gly Arg Gly Ala Arg Val Asp Trp Ala Gly
                3685                3690                3695

Met His Ala Asp Gly Pro Glu Gly Pro Ala Arg Arg Val Glu Leu Pro
            3700                3705                3710

Val His Ala Phe Arg His Arg Arg Tyr Trp Leu Ala Pro Gly Arg Ala
        3715                3720                3725

Ala Asp Thr Asp Asp Trp Met Tyr Arg Ile Gly Trp Asp Arg Leu Pro
    3730                3735                3740

Ala Val Thr Gly Gly Ala Arg Thr Ala Gly Arg Trp Leu Val Ile His
3745                3750                3755                3760

Pro Asp Ser Pro Arg Cys Arg Glu Leu Ser Gly His Ala Glu Arg Ala
                3765                3770                3775

Leu Arg Ala Ala Gly Ala Ser Pro Val Pro Leu Pro Val Asp Ala Pro
            3780                3785                3790

Ala Ala Asp Arg Ala Ser Phe Ala Ala Leu Leu Arg Ser Ala Thr Gly
        3795                3800                3805

Pro Asp Thr Arg Gly Asp Thr Ala Ala Pro Val Ala Gly Val Leu Ser
    3810                3815                3820

Leu Leu Ser Glu Glu Asp Arg Pro His Arg Gln His Ala Pro Val Pro
3825                3830                3835                3840

Ala Gly Val Leu Ala Thr Leu Ser Leu Met Gln Ala Met Glu Glu Glu
                3845                3850                3855

Ala Val Glu Ala Arg Val Trp Cys Val Ser Arg Ala Ala Val Ala Ala
            3860                3865                3870

Ala Asp Arg Glu Arg Pro Val Gly Ala Gly Ala Ala Leu Trp Gly Leu
        3875                3880                3885

Gly Arg Val Ala Ala Leu Glu Arg Pro Thr Arg Trp Gly Gly Leu Val
    3890                3895                3900

Asp Leu Pro Ala Ser Pro Gly Ala Ala His Trp Ala Ala Ala Val Glu
3905                3910                3915                3920

Arg Leu Ala Gly Pro Glu Asp Gln Ile Ala Val Arg Ala Ser Gly Ser
                3925                3930                3935

Trp Gly Arg Arg Leu Thr Arg Leu Pro Arg Asp Gly Gly Arg Thr
            3940                3945                3950

Ala Ala Pro Ala Tyr Arg Pro Arg Gly Thr Val Leu Val Thr Gly Gly
        3955                3960                3965

Thr Gly Ala Leu Gly Gly His Leu Ala Arg Trp Leu Ala Ala Ala Gly
    3970                3975                3980

Ala Glu His Leu Ala Leu Thr Ser Arg Arg Gly Pro Asp Ala Pro Gly
3985                3990                3995                4000

Ala Ala Gly Leu Glu Ala Glu Leu Leu Leu Gly Ala Lys Val Thr
                4005                4010                4015

Phe Ala Ala Cys Asp Thr Ala Asp Arg Asp Gly Leu Ala Arg Val Leu
            4020                4025                4030

Arg Ala Ile Pro Glu Asp Thr Pro Leu Thr Ala Val Phe His Ala Ala
        4035                4040                4045

Gly Val Pro Gln Val Thr Pro Leu Ser Arg Thr Ser Pro Glu His Phe
    4050                4055                4060

Ala Asp Val Tyr Ala Gly Lys Ala Ala Gly Ala Ala His Leu Asp Glu
4065                4070                4075                4080
```

-continued

```
Leu Thr Arg Glu Leu Gly Ala Gly Leu Asp Ala Phe Val Leu Tyr Ser
            4085                4090                4095
Ser Gly Ala Gly Val Trp Gly Ser Ala Gly Gln Gly Ala Tyr Ala Ala
        4100                4105                4110
Ala Asn Ala Ala Leu Asp Ala Leu Ala Arg Arg Ala Ala Asp Gly
        4115                4120            4125
Leu Pro Ala Thr Ser Ile Ala Trp Gly Val Trp Gly Gly Gly Met
    4130                4135                4140
Gly Ala Asp Glu Ala Gly Ala Glu Tyr Leu Gly Arg Arg Gly Met Arg
4145                4150                4155                4160
Pro Met Ala Pro Val Ser Ala Leu Arg Ala Met Ala Thr Ala Ile Ala
                4165                4170                4175
Ser Gly Glu Pro Cys Pro Thr Val Thr His Thr Asp Trp Glu Arg Phe
            4180                4185                4190
Gly Glu Gly Phe Thr Ala Phe Arg Pro Ser Pro Leu Ile Ala Gly Leu
        4195                4200                4205
Gly Thr Pro Gly Gly Gly Arg Ala Ala Glu Thr Pro Glu Glu Gly Asn
    4210                4215                4220
Ala Thr Ala Ala Ala Asp Leu Thr Ala Leu Pro Pro Ala Glu Leu Arg
4225                4230                4235                4240
Thr Ala Leu Arg Glu Leu Val Arg Ala Arg Thr Ala Ala Ala Leu Gly
                4245                4250                4255
Leu Asp Asp Pro Ala Glu Val Ala Glu Gly Glu Arg Phe Pro Ala Met
            4260                4265                4270
Gly Phe Asp Ser Leu Ala Thr Val Arg Leu Arg Arg Gly Leu Ala Ser
        4275                4280                4285
Ala Thr Gly Leu Asp Leu Pro Pro Asp Leu Leu Phe Asp Arg Asp Thr
    4290                4295                4300
Pro Ala Ala Leu Ala Ala His Leu Ala Glu Leu Leu Ala Thr Ala Arg
4305                4310                4315                4320
Asp His Gly Pro Gly Gly Pro Gly Thr Gly Ala Ala Pro Ala Asp Ala
                4325                4330                4335
Gly Ser Gly Leu Pro Ala Leu Tyr Arg Glu Ala Val Arg Thr Gly Arg
            4340                4345                4350
Ala Ala Glu Met Ala Glu Leu Leu Ala Ala Ala Ser Arg Phe Arg Pro
        4355                4360                4365
Ala Phe Gly Thr Ala Asp Arg Gln Pro Val Ala Leu Val Pro Leu Ala
    4370                4375                4380
Asp Gly Ala Glu Asp Thr Gly Leu Pro Leu Leu Val Gly Cys Ala Gly
4385                4390                4395                4400
Thr Ala Val Ala Ser Gly Pro Val Glu Phe Thr Ala Phe Ala Gly Ala
                4405                4410                4415
Leu Ala Asp Leu Pro Ala Ala Pro Met Ala Ala Leu Pro Gln Pro
            4420                4425                4430
Gly Phe Leu Pro Gly Glu Arg Val Pro Ala Thr Pro Glu Ala Leu Phe
        4435                4440                4445
Glu Ala Gln Ala Glu Ala Leu Leu Arg Tyr Ala Ala Gly Arg Pro Phe
    4450                4455                4460
Val Leu Leu Gly His Ser Ala Gly Ala Asn Met Ala His Ala Leu Thr
4465                4470                4475                4480
Arg His Leu Glu Ala Asn Gly Gly Gly Pro Ala Gly Leu Val Leu Met
                4485                4490                4495
```

-continued

```
Asp Ile Tyr Thr Pro Ala Asp Pro Gly Ala Met Gly Val Trp Arg Asn
            4500                4505                4510

Asp Met Phe Gln Trp Val Trp Arg Arg Ser Asp Ile Pro Pro Asp Asp
        4515                4520                4525

His Arg Leu Thr Ala Met Gly Ala Tyr His Arg Leu Leu Leu Asp Trp
        4530                4535                4540

Ser Pro Thr Pro Val Arg Ala Pro Val Leu His Leu Arg Ala Ala Glu
4545                4550                4555                4560

Pro Met Gly Asp Trp Pro Pro Gly Asp Thr Gly Trp Gln Ser His Trp
                4565                4570                4575

Asp Gly Ala His Thr Thr Ala Gly Ile Pro Gly Asn His Phe Thr Met
            4580                4585                4590

Met Thr Glu His Ala Ser Ala Ala Ala Arg Leu Val His Gly Trp Leu
        4595                4600                4605

Ala Glu Arg Thr Pro Ser Gly Gln Gly Gly Ser Pro Ser Arg Ala Ala
        4610                4615                4620

Gly Arg Glu Glu Arg Pro Met Ile Leu Arg Ala Gly Thr Ala Asp Pro
4625                4630                4635                4640

Ala Pro Tyr Glu Glu Glu Ile Pro Gly Tyr Arg Ala Arg Ile Leu Asn
                4645                4650                4655

Met Ser Asn Lys Asn Asn Asp Glu Leu Gln Arg Gln Ala Ser Glu Asn
            4660                4665                4670

Thr Leu Gly Leu Asn Pro Val Ile Gly Ile Arg Arg Lys Asp Leu Leu
        4675                4680                4685

Ser Ser Ala Arg Thr Val Leu Arg Gln Ala Val Arg Gln Pro Leu His
    4690                4695                4700

Ser Ala Lys His Val Ala His Phe Gly Leu Glu Leu Lys Asn Val Leu
4705                4710                4715                4720

Leu Gly Lys Ser Ser Leu Ala Pro Glu Ser Asp Asp Arg Arg Phe Asn
                4725                4730                4735

Asp Pro Ala Trp Ser Asn Asn Pro Leu Tyr Arg Arg Tyr Leu Gln Thr
            4740                4745                4750

Tyr Leu Ala Trp Arg Lys Glu Leu Gln Asp Trp Ile Gly Asn Ser Asp
        4755                4760                4765

Leu Ser Pro Gln Asp Ile Ser Arg Gly Gln Phe Val Ile Asn Leu Met
    4770                4775                4780

Thr Glu Ala Met Ala Pro Thr Asn Thr Leu Ser Asn Pro Ala Ala Val
4785                4790                4795                4800

Lys Arg Phe Phe Glu Thr Gly Gly Lys Ser Leu Leu Asp Gly Leu Ser
                4805                4810                4815

Asn Leu Ala Lys Asp Leu Val Asn Asn Gly Gly Met Pro Ser Gln Val
            4820                4825                4830

Asn Met Asp Ala Phe Glu Val Gly Lys Asn Leu Gly Thr Ser Glu Gly
        4835                4840                4845

Ala Val Val Tyr Arg Asn Asp Val Leu Glu Leu Ile Gln Tyr Lys Pro
    4850                4855                4860

Ile Thr Glu Gln Val His Ala Arg Pro Leu Leu Val Val Pro Pro Gln
4865                4870                4875                4880

Ile Asn Lys Phe Tyr Val Phe Asp Leu Ser Pro Glu Lys Ser Leu Ala
                4885                4890                4895

Arg Tyr Cys Leu Arg Ser Gln Gln Gln Thr Phe Ile Ile Ser Trp Arg
            4900                4905                4910
```

```
Asn Pro Thr Lys Ala Gln Arg Glu Trp Gly Leu Ser Thr Tyr Ile Asp
        4915                4920                4925

Ala Leu Lys Glu Ala Val Asp Ala Val Leu Ala Ile Thr Gly Ser Lys
        4930                4935                4940

Asp Leu Asn Met Leu Gly Ala Cys Ser Gly Ile Thr Cys Thr Ala
4945                4950                4955                4960

Leu Val Gly His Tyr Ala Ala Leu Gly Glu Asn Lys Val Asn Ala Leu
            4965                4970                4975

Thr Leu Leu Val Ser Val Leu Asp Thr Thr Met Asp Asn Gln Val Ala
            4980                4985                4990

Leu Phe Val Asp Glu Gln Thr Leu Glu Ala Ala Lys Arg His Ser Tyr
        4995                5000                5005

Gln Ala Gly Val Leu Glu Gly Ser Glu Met Ala Lys Val Phe Ala Trp
        5010                5015                5020

Met Arg Pro Asn Asp Leu Ile Trp Asn Tyr Trp Val Asn Asn Tyr Leu
5025                5030                5035                5040

Leu Gly Asn Glu Pro Pro Val Phe Asp Ile Leu Phe Trp Asn Asn Asp
        5045                5050                5055

Thr Thr Arg Leu Pro Ala Ala Phe His Gly Asp Leu Ile Glu Met Phe
        5060                5065                5070

Lys Ser Asn Pro Leu Thr Arg Pro Asp Ala Leu Glu Val Cys Gly Thr
        5075                5080                5085

Pro Ile Asp Leu Lys Gln Val Lys Cys Asp Ile Tyr Ser Leu Ala Gly
        5090                5095                5100

Thr Asn Asp His Ile Thr Pro Trp Gln Ser Cys Tyr Arg Ser Ala His
5105                5110                5115                5120

Leu Phe Gly Gly Lys Ile Glu Phe Val Leu Ser Asn Ser Gly His Ile
            5125                5130                5135

Gln Ser Ile Leu Asn Pro Pro Gly Asn Pro Lys Ala Arg Phe Met Thr
        5140                5145                5150

Gly Ala Asp Arg Pro Gly Asp Pro Val Ala Trp Gln Glu Asn Ala Thr
        5155                5160                5165

Lys His Ala Asp Ser Trp Trp Leu His Trp Gln Ser Trp Leu Gly Glu
        5170                5175                5180

Arg Ala Gly Glu Leu Glu Lys Ala Pro Thr Arg Leu Gly Asn Arg Ala
5185                5190                5195                5200

Tyr Ala Ala Gly Glu Ala Ser Pro Gly Thr Tyr Val His Glu Arg
            5205                5210                5215

<210> SEQ ID NO: 3
<211> LENGTH: 13613
<212> TYPE: DNA
<213> ORGANISM: Streptomyces venezuelae

<400> SEQUENCE: 3
ggatccggcg cttccacccc gcgccgaaca gcgcggtgcg gctggtctgc ctgccgcacg      60
ccggcggctc cgccagctac ttcttccgct tctcggagga gctgcacccc tccgtcgagg     120
ccctgtcggt gcagtatccg ggccgccagg accggcgtgc cgagccgtgt ctggagagcg     180
tcgaggagct cgccgagcat gtggtcgcgg ccaccgaacc ctggtggcag gagggccggc     240
tggccttctt cgggcacagc ctcggcgcct ccgtcgcctt cgagacggcc cgcatcctgg     300
aacagcggca cggggtacgg cccgagggcc tgtacgtctc cggtcggcgc gccccgtcgc     360
tggcgccgga ccggctcgtc caccagctgg acgaccgggc gttcctggcc gagatccggc     420
```

-continued

```
ggctcagcgg caccgacgag cggttcctcc aggacgacga gctgctgcgg ctggtgctgc    480
ccgcgctgcg cagcgactac aaggcggcgg agacgtacct gcaccggccg tccgccaagc    540
tcacctgccc ggtgatggcc ctggccgcg accgtgaccg gaaggcgccg ctgaacgagg     600
tggccgagtg cgctcggcac accagcgggc cgttctgcct ccgggcgtac tccgcggcc     660 acttctacct caacgaccag tggcacgaga tctgcaacga catctccgac cacctgctcg    720
tcacccgcgg cgcgcccgat gcccgcgtcg tgcagccccc gaccagcctt atcgaaggag    780
cggcgaagag atggcagaac ccacggtgac cgacgacctg acggggcccc tcacgcagcc    840
cccgctgggc cgcaccgtcc gcgcggtggc cgaccgtgaa ctcggcaccc acctcctgga    900 gacccgcgg atccactgga tccacgccgc gaacggcgac ccgtacgcca ccgtgctgcg     960
cggccaggcg gacgacccgt atcccgcgta cgagcgggtg cgtgcccgcg gcgcgctctc   1020
cttcagcccg acgggcagct gggtcaccgc cgatcacgcc ctggcggcga gcatcctctg   1080
ctcgacggac ttcggggtct ccggcgccga cggcgtcccg gtgccgcagc aggtcctctc   1140
gtacggggag ggctgtccgc tggagcgcga gcaggtgctg ccggcggccg gtgacgtgcc   1200
ggagggcggg cagcgtgccg tggtcgaggg gatccaccgg agagacgctgg agggtctcgc   1260 gccggacccg tcggcgtcgt acgccttcga gctgctgggc ggtttcgtcc gcccggcggt   1320
gacggccgct gccgccgccg tgctgggtgt tcccgcggac cggcgcgcgg acttcgcgga   1380
tctgctggag cggctccggc cgctgtccga cagcctgctg ccccgcagt ccctgcggac    1440 ggtacgggcg gcggacggcg cgctggccga gctcacggcg ctgctcgccg attcggacga   1500 ctccccccggg gccctgctgt cggcgctcgg ggtcaccgca gccgtccagc tcaccgggaa   1560
cgcggtgctc gcgctcctcg cgcatcccga gcagtggcgg gagctgtgcg accggcccgg   1620
gctcgcggcg gccgcggtgg aggagaccct ccgctacgac ccgccggtgc agctcgacgc   1680
ccgggtggtc cgcggggaga cggagctggc gggccggcgg ctgccggccg ggcgcatgt    1740 cgtcgtcctg accgccgcga ccggccggga cccggaggtc ttcacggacc cggagcgctt   1800
cgacctcgcg cgccccgacg ccgccgcgca cctcgcgctg caccccgccg gtccgtacgg   1860
cccggtggcg tccctggtcc ggcttcaggc ggaggtcgcg ctgcggaccc tggccgggcg   1920
tttcccgggg ctgcggcagg cgggggacgt gctccgcccc cgccgcgcgc ctgtcggccg   1980
cgggccgctg agcgtcccgg tcagcagctc ctgagacacc ggggcccgg tccgcccggc    2040 cccccttcgg acgaccgga cggctcggac cacggggacg gctcagaccg tcccgtgtgt   2100
ccccgtccgg ctcccgtccg ccccatcccg cccctccacc ggcaaggaag gacacgacgc   2160
catgcgcgtc ctgctgacct cgttcgcaca tcacacgcac tactacggcc tggtgcccct   2220
ggcctgggcg ctgctcgccc ccgggcacga ggtgcgggtc gccagccagc ccgcgctcac   2280
ggacaccatc accgggtccg ggctcgccgc ggtgccggtc ggcaccgacc acctcatcca   2340
cgagtaccgg gtgcggatgg cgggcgagcc gcgcccgaac catccggcga tcgccttcga   2400
cgaggcccgt cccgagccgc tggactggga ccacgccctc ggcatcgagg cgatcctcgc   2460
cccgtacttc catctgctcg ccaacaacga ctcgatggtc gacgacctcg tcgacttcgc   2520
ccggtcctga cagccggacc tggtgctgtg ggagccgacg acctacgcgg gcgccgtcgc   2580
cgcccaggtc accggtgccg cgcacgcccg ggtcctgtgg gggccgacg tgatgggcag    2640 cgcccgccgc aagttcgtcg cgctgcggga ccggcagccg cccgagcacc gcgaggaccc   2700
caccgcggag tggctgacgt ggacgctcga ccggtacggc gcctccttcg aagaggagct   2760
```

```
gctcaccggc cagttcacga tcgacccgac cccgccgagc ctgcgcctcg acacgggcct    2820
gccgaccgtc gggatgcgtt atgttccgta caacggcacg tcggtcgtgc cggactggct    2880
gagtgagccg cccgcgcggc cccgggtctg cctgaccctc ggcgtctccg cgcgtgaggt    2940
cctcggcggc gacggcgtct cgcagggcga catcctggag gcgctcgccg acctcgacat    3000
cgagctcgtc gccacgctcg acgcgagtca gcgcgccgag atccgcaact acccgaagca    3060
cacccggttc acggacttcg tgccgatgca cgcgctcctg ccgagctgct cggcgatcat    3120
ccaccacggg ggcgcgggca cctacgcgac cgccgtgatc aacgcggtgc cgcaggtcat    3180
gctcgccgag ctgtgggacg cgccggtcaa ggcgcgggcc gtcgccgagc aggggcgggg    3240
gttcttcctg ccgccggccg agctcacgcc gcaggccgtg cgggacgccg tcgtccgcat    3300
cctcgacgac ccctcggtcg ccaccgccgc gcaccggctg cgcgaggaga ccttcggcga    3360
ccccaccccg gccgggatcg tccccgagct ggagcggctc gccgcgcagc accgccgccc    3420
gccggccgac gcccggcact gagccgcacc cctcgcccca ggcctcaccc ctgtatctgc    3480
gccggggac gcccccggcc caccctccga aagaccgaaa gcaggagcac cgtgtacgaa    3540
gtcgaccacg ccgacgtcta cgacctcttc tacctgggtc gcggcaagga ctacgccgcc    3600
gaggcctccg acatcgccga cctggtgcgc tcccgtaccc ccgaggcctc ctcgctcctg    3660
gacgtggcct gcggtacggg cacgcatctg gagcacttca ccaaggagtt cggcgacacc    3720
gccggcctgg agctgtccga ggacatgctc acccacgccc gcaagcggct gcccgacgcc    3780
acgctccacc agggcgacat gcgggacttc cggctcggcc ggaagttctc cgccgtggtc    3840
agcatgttca gctccgtcgg ctacctgaag acgaccgagg aactcggcgc ggccgtcgcc    3900
tcgttcgcgg agcacctgga gcccggtggc gtcgtcgtcg tcgagccgtg gtggttcccg    3960
gagaccttcg ccgacggctg ggtcagcgcc gacgtcgtcc gccgtgacgg gcgcaccgtg    4020
gcccgtgtct cgcactcggt gcgggagggg aacgcgacgc gcatggaggt ccacttcacc    4080
gtggccgacc cgggcaaggg cgtgcggcac ttctccgacg tccatctcat caccctgttc    4140
caccaggccg agtacgaggc gcgttcacg gccgccgggc tgcgcgtcga gtacctggag    4200
ggcggcccgt cgggccgtgg cctcttcgtc ggcgtccccg cctgagcacc gcccaagacc    4260
cccgggggcg ggacgtcccg ggtgcaccaa gcaaagagag agaaacgaac cgtgacaggt    4320
aagacccgaa taccgcgtgt ccgccgcggc cgcaccacgc ccagggcctt caccctggcc    4380
gtcgtcggca ccctgctggc gggcaccacc gtggcggccg ccgctcccgg cgccgcgac    4440
acggccaatg ttcagtacac gagccgggcg gcggagctcg tcgcccagat gacgctcgac    4500
gagaagatca gcttcgtcca ctgggcgctg accccgaccc ggcagaacgt cggctacctt    4560
cccggcgtgc cgcgtctggg catcccggag ctgcgtgccg ccgacggccc gaacggcatc    4620
cgcctggtgg ggcagaccgc caccgcgctg ccgcgccgg tcgccctggc cagcaccttc    4680
gacgacacca tggccgacag ctacggcaag gtcatgggcc gcgacggtcg cgcgctcaac    4740
caggacatgg tcctgggccc gatgatgaac aacatccggg tgccgcacgg cggccggaac    4800
tacgagacct tcagcgagga cccctggtc tcctcgcgca ccgcggtcgc ccagatcaag    4860
ggcatccagg gtgcgggtct gatgaccacg gccaagcact cgcgggccaa caaccaggag    4920
aacaaccgct tctccgtgaa cgccaatgtc gacgagcaga cgctccgcga gatcgagttc    4980
ccggcgttcg aggcgtcctc caaggccggc gcggcctcct tcatgtgtgc ctacaacggc    5040
ctcaacggga agcgtcctg cggcaacgac gagctcctca caacgtgct gcgcacgcag    5100
tggggcttcc agggctgggt gatgtccgac tggctcgcca ccccgggcac cgacgccatc    5160
```

```
accaagggcc tcgaccagga gatgggcgtc gagctcgccg gcgacgtccc gaagggcgag    5220
ccctcgccgc cggccaagtt cttcggcgag gcgctgaaga cggccgtcct gaacggcacg    5280
gtccccgagg cggccgtgac gcggtcggcg gagcggatcg tcggccagat ggagaagttc    5340
ggtctgctcc tcgccactcc ggcgccgcgg cccgagcgcg acaaggcggg tgcccaggcg    5400
gtgtcccgca aggtcgccga gaacggcgcg gtgctcctgc gcaacgaggg ccaggccctg    5460
ccgctcgccg gtgacgccgg caagagcatc gcggtcatcg gcccgacggc cgtcgacccc    5520
aaggtcaccg gcctgggcag cgcccacgtc gtcccggact cggcggcggc gccactcgac    5580
accatcaagg cccgcgcggg tgcgggtgcg acggtgacgt acgagacggg tgaggagacc    5640
ttcgggacgc agatcccggc ggggaacctc agcccggcgt tcaaccaggg ccaccagctc    5700
gagccgggca aggcgggggc gctgtacgac ggcacgctga ccgtgcccgc cgacggcgag    5760
taccgcatcg cggtccgtgc caccggtggt tacgccacgg tgcagctcgg cagccacacc    5820
atcgaggccg gtcaggtcta cggcaaggtg agcagcccgc tcctcaagct gaccaagggc    5880
acgcacaagc tcacgatctc gggcttcgcg atgagtgcca ccccgctctc cctggagctg    5940
ggctgggtga cgccggcggc ggccgacgcg acgatcgcga aggccgtgga gtcggcgcgg    6000
aaggcccgta cggcggtcgt cttcgcctac gacgacggca ccgagggcgt cgaccgtccg    6060
aacctgtcgc tgccgggtac gcaggacaag ctgatctcgg ctgtcgcgga cgccaacccg    6120
aacacgatcg tggtcctcaa caccggttcg tcggtgctga tgccgtggct gtccaagacc    6180
cgcgcggtcc tggacatgtg gtacccgggc caggcgggcg ccgaggccac cgccgcgctg    6240
ctctacggtg acgtcaaccc gagcggcaag ctcacgcaga gcttcccggc cgccgagaac    6300
cagcacgcgg tcgccggcga cccgacaagc tacccgggcg tcgacaacca gcagacgtac    6360
cgcgagggca tccacgtcgg gtaccgctgg ttcgacaagg agaacgtcaa gccgctgttc    6420
ccgttcgggc acggcctgtc gtacacctcg ttcacgcaga gcgccccgac cgtcgtgcgt    6480
acgtccacgg gtggtctgaa ggtcacggtc acggtccgca acagcgggaa gcgcgccggc    6540
caggaggtcg tccaggcgta cctcggtgcc agcccgaacg tgacggctcc gcaggcgaag    6600
aagaagctcg tgggctacac gaaggtctcg ctcgccgcgg gcgaggcgaa gacggtgacg    6660
gtgaacgtcg accgccgtca gctgcagacc ggttcgtcct ccgccgacct gcggggcagc    6720
gccacggtca acgtctggtg acgtgacgcc gtgaaagcgg cggtgcccgc cacccgggag    6780
ggtggcgggc accgcttttt cggcctgctg ggtctaccgg accacctgac taggcctggt    6840
cgacccgctc ggcccattcg cgcacggcgt cgatcacccg cagcgcctgc gggcgctcca    6900
ggtgcgggcc gatcggcagg ctgaggacct gccgcgcgaa gctctcggcc gcgggagcg    6960
agccttccgg cggtgcctcg cccgcgtagg cgggcgagag gtgcacgggt accgggtagt    7020
gcgtgagggt gtcgatgccg cgggcgtcga ggtggctgcg cagctcgtcg cggcgctcgg    7080
tgcgcacggt gaagaggtgc cagaccgggt cggtgtcggg cgcggtcacc ggcaggccga    7140
tgccgggcag tccggcgagc ccggagaggt actccgcggc cagcgccgac ctgcggccgt    7200
tccagctgtc caggtgggcg agccggatcc gcagcacggc ggcctgcatc tcgtccaggc    7260
gggagttggt gccttcgtc tcgtggctgt acttctgccg cgagccgtag ttgcggagca    7320
tccggagccg ttcggcgagc tcggggtcgc cggtgacgac ggcgccgccg tcgccgaagc    7380
agccgaggtt cttgcccggg tagaagctga acgcggccac cgacgacccg cgccgatcc    7440
gccggccccg gtagcgggcg ccgtgggcct gcgcggcgtc ctcgacgatg tgcaggccgt    7500
```

-continued

```
gccggtccgc gagctcgcgg agggcgtcca tgtcggcggg gtgcccgtag aggtggacgg    7560
ggaggagcgc ccgggtgcgg ggggtgatcg ccttctcgac gagcagcggg tccagggtgg    7620
ggtggtcctc gtgcggctcg acgggcacgg gggtcgcgcc ggtggcggac accgcgagcc    7680
agctggcgat gtacgtgtgc gaggggacga tcacctcgtc cccgggtccg atgccgaggc    7740
cgcggagggc gagctggagg gcgtccatcc cgctgttcac gccgacggcg tggtccgtct    7800
cgcagtacgc ggcgaactcc gcctcgaatc cttcgagttc gggtccgagg aggtagcgcc    7860
ccgagtcgag gacgcgggcg atcgcggcgt cggtctccgc gcggagctcc tcgtaggcgg    7920
ccttgaggtc gaggaagggg acgcgggggg tctcggcgcg gctgctcacg cggacacctc    7980
cacggcggtg gcgggcagct gcgggcggt cgccttgagc ggctcccacc agccgcggtt    8040
ctcccggtac cagcggacgg tccgcgcgag gccgtccgcg aaggagacct gcgggcggta    8100
gccgagctcg cgctcgatct cgccgccgtc gagggagtag cgcaggtcgt ggcccttgcg    8160
gtcggcgacc ttccggaccg aggaccagtc ggcgccgagc gagtccagga ggatgccggt    8220
gagttcgcgg ttggtcagct ccaggccgcc gccgatgtgg tagatctcgc cggcccggcc    8280
gcccgcgagg acgagcgcga tgccccggca gtggtcgtcg gtgtgcaccc actcgcggac    8340
gttcgcgccg tcgccgtaca gcgggagcgt cccgccgtcg aggaggttcg tcacgaagag    8400
ggggatgagc ttctcggggt gctggtacgg cccgtagttg ttgcagcagc gggtgatccg    8460
tacgtcgagg ccgtacgtcc ggtggtaggc gcgggcaacg aggtcggagc cggccttgga    8520
cgccgcgtag ggcgagttgg gctccagcgg gctgctctcg gtccaggagc cggagtcgat    8580
cgacccgtac acctcgtcgg tggagacgtg cacgacccgg ccgacgccgg cgtcgacggc    8640
gcactggagc agcgtctgcg tgccctgcac gttggtctcg gtgaacacgg acgcgcccgc    8700
gatggagcgg tccacgtggc tctcggccgc gaagtggacg atggcgtcca cgccgcgcag    8760
ttcccgggcg aggaggccgg cgtcgcggat gtcgccgtgg acgaagcgca gtcgcgggtc    8820
cgcgtccacc ggggcgaggt tggcgcggtt gcccgcgtag gtgaggctgt ccaggacgat    8880
cacctcatcg gcgggcacgt cggggtacgc cccggcgagg agctgccgca cgaagtgcga    8940
gccgatgaag cccgcacctc cggtcaccag aagccgcact gccgtcttcc tttcggtcgc    9000
gctgtaggtc gcggtgtggg tcgcactgtc ggtggcggtg cgggtcgcgg tgtgggtcgc    9060
actgtcggtg gcgctgtcgg tcgtgggaac gcgtcggccg cgaggtgccc tcacggggct    9120
ccctcgcggc cggcgatctc catcagatag ctgccgtact cggtgcggga gaggccttct    9180
cccaggccgt gacaggcctc ggcgtcgatg aagcccatgc ggaaggcgat ctcctcaagg    9240
cccgcgatcc agacgccctg ccgctcctcc aggacctgga cgtactgggc ggcccgcagg    9300
agcgagtcgt gggtgccggt gtccagccag gcgaagccgc ggcccaggtt gacgagttcg    9360
gcccggcccc gctccaggta gacgcggttg acgtcggtga tctccagctc gccgcgcggc    9420
gagggccgga tgttcttggc gatgtcgacg acgtcgttgt cgtagaggta gaggccggtg    9480
acggcgaggt tggagcgcgg cttgacgggc ttctcgacga ggtcggtcag ccggcccgtc    9540
gcgtccacct cggcgacgcc gtaccgctcg gggtccttga ccgggtagcc gaagagcacg    9600
cagccgtcga ggcgcgcgat gctgtcccgc aggagcgtgt agaggccggg cccgtggaag    9660
atgttgtcgc ccaggatcag ggcgcaggtg tcgtcgccga tgtgctcggc tccgacgaga    9720 agtcgtccg cgattcctgc gggctctttc tggaccgcat agtcgagttc tattcccagg    9780
tgcctgccgt ttccgagaag cgactggaag agttcgatgt gctgggggt cgagatgatt    9840 tgaatctcgc gaataccgcc gagcatgaga accgacagcg gatagtagat catcggtttg    9900
```

```
ttgtagaccg gaagaatctg cttcgaaatg accgaggtcg ccggatgcag ccgagttccg    9960
ctcccgccgg ccaggactat tcccttcatt ctcggaaact agcagcaggg cgccggtgat   10020
aacggtcggc gtggcgagtt aggggggcgc tagggctgc gcaggggag tgtcaccacc     10080
cctttggggg gtgggaaaac accgagggcc cggccggacg gccgggccct caggtggggg   10140
gatcgtgggg gggggatcgg ggggatcggg gcggtgcgg gtcagcgcag gaagccgcgg    10200
gcctcctccc agccgtccgc ggcgtcgcgc tccagctggt tcaggcgggc ggtgacgacc   10260
tgatcgaagc cgtccatgaa gtactcgtcg ccgtcgacgg ccgccacctc gccgccgcgc   10320
tcgacgaagt ccctgacgac ctcggtgagg gaggtgtcgg gggtcacgcg gcccgcgatg   10380
tagcgggtcg cgccgtccag gtcggggaag ccggcctcgc ggtacaggta cacgtcgccg   10440
aggagatcga cctgcaccgc gacctgcggg tgcgcggtgg gccgcatggt ggcgggcttg   10500
atccgcagca gttcggcgtc ggccccggtg cgcaggctgt tcaggcgta gccgtagtcg    10560
atgtggagtc cgggggtgcg ctcgcggacc cgctcctcga aggcgttgag ggcctcctgg   10620
agctcggccc gctcctcctg cggcagcttg ccgtcgtcac ggccgctgta gtcctcgcga   10680
atgttgacga agtcgatcgt cctgccctgc ccggcgtcgt tgaggtcggc gatgaagtcg   10740
accaggtcga gcaggcggga ggcacggccc gggagcacga tgtaggcgaa gccgaggttg   10800
atcggcgact cgcgctcggc gcgcagctgc tggaagcggc gcaggttctc gcggacgcgg   10860
cggaaggcgg ccttcttgcc ggtggtctgc tcgtactcct cgtcgttgag gccgtagagc   10920
gaggtgcgga tggcgtgcag gccccagagg ccgggctggc gctccagggt gcgctcggtg   10980
agcgcgaagg agttcgtgta gacgtgggc gcaggccgt ggtcggtggc gtgcgcggcc     11040
aggctcccga ggccggggtt ggtgagcggc tccaggccgc cggagaagta catcgccgag   11100
gggttgcccg cgggtatctc gtcgatgacc gaccggaaca tggcgttgcc ggcgtcgagg   11160
gcggacgggt cgtagcgggc gccggtcaca cggacgcaga agtggcagcg gaacatgcag   11220
gtcgggccgg ggtagaggcc gacgctgtac gggaagacgg gcttcctggc gagcgccgcg   11280
tcgaagacgc cgcgctgttc gagcgggagc agggtgttct tccagtacgc cccggcgggg   11340
ccggtctcga ccgcggtgcg gagctccggg acctgcccga acagggcgag gaggcgccgg   11400
aaggcgtccc ggtcgacgcc caggtcgtgg cgggcctcct ccagcggggt gaaggggctg   11460
ttgccgtagc gcacggcgag ccggacgagg tggcgggcgg tcgttccggc ctcgtcgggc   11520
ggcacgaggc cgccggcggc gagggtctgg ccgacggcgt ggaccgccgc ccccagatcg   11580
gctccgggt gcgcgcagcg ttcggccggg gcggtggcgg aaaggcggg ggcggtcatc     11640
gggagcgtcc aatcgtgggc gtggatgtct gggggccgc gagcggggcg ggggccgtgt    11700
cgcggtggcg cgcggtcagt tcgcggccgc gggtcgcgca gagacgcagc aggtcggcga   11760
cccggcggat gtcgtcgtcg ccgatggcgg tgccggtcgg cagggacagc acgcgcgcg    11820
cgaggcgttc ggtgtgcggc agcggggcgt gcggctgccc gcggtacggc tccagctcgt   11880
ggcagcccgc cgagaagtag gcgcggggt gcacgccttc ggccttcagg acctccatga    11940
cgaggtcgcg gtggatgccg gtggtggcct cgtcgatctc gacgatcacg tactggtggt   12000
tgttgaggcc gtgcggtcg tggtcggcga cgaggacgcc ggggaggtcc gcgaggtgct    12060
cgcggtaggc ggcgtggttg cgccggttcc ggtcgatgac ctcgggaaac gcgtcgaggg   12120
aggtgaggcc catggcggcg gcggcctcgc tcatctttgc gttggtcccg ccggcggggc   12180
tgccgccggg caggtcgaag ccgaagttgt ggagggcgcg gatccgggcg gcgaggtcgg   12240
```

-continued

```
cgtcgtcggt gacgacggcg ccgccctcga aggcgttgac ggccttggtg gcgtggaagc   12300
tgaagacctc ggcgtcgccg aggctgccgg cgggccggcc gtcgaccgcg cagccgaggg   12360
cgtgcgcggc gtcgaagtac agccgcaggc cgtgctcgtc ggcgaccttc cgcagctggt   12420
cggcggcgca ggggcggccc cagaggtgga cgccgacgac ggccgaggtg cggggtgtga   12480
ccgcggcggc cacctggtcc gggtcgaggt tgccggtgtc cgggtcgatg tcggcgaaga   12540
ccggggtgag gccgatccag cgcagtgcgt gcggggtggc ggcgaacgtc atcgacggca   12600
tgatcacttc gccggtgagg ccggcggcgt gcgcgaggag ctggagcccg gccgtggcgt   12660
tgcaggtggc cacggcatgc cggaccccgg cgagcccggc gacgcgctcc tcgaactcgc   12720
ggacgagcgg gccgccgttg acagccact ggctgtcgag ggcccggtcg agccgctcgt   12780
acagcctggc gcggtcgatg cggttgggcc gccccacgag gagcggctgg tcgaaagcgg   12840
cggggccgcc gaagaatgcg aggtcggata aggcgctttt cacggatgtt ccctccgggc   12900
caccgtcacg aaatgattcg ccgatccggg aatcccgaac gaggtcgccg cgctccaccg   12960
tgacgtacga cgagatggtc gattgtggtg gtcgatttcg gggggactct aatccgcgcg   13020
gaacgggacc gacaagagca cgctatgcgc tctcgatgtg cttcggatca catccgcctc   13080
cggggtattc catcggcggc ccgaatgtga tgatccttga caggatccgg gaatcagccg   13140
agccgccggg agggccgggg cgcgctccgc ggaagagtac gtgtgagaag tcccgttcct   13200
cttcccgttt ccgttccgct tccggcccgg tctggagttc tccgtgcgcc gtacccagca   13260
gggaacgacc gcttctcccc cggtactcga cctcggggcc ctggggcagg atttcgcggc   13320
cgatccgtat ccgacgtacg cgagactgcg tgccgagggt ccggcccacc gggtgcgcac   13380
ccccgagggg gacgaggtgt ggctggtcgt cggctacgac cgggcgcggg cggtcctcgc   13440
cgatccccgg ttcagcaaga ctggcgcaac tccacgactc ccctgaccga agccgaagcc   13500
gcgctcaacc acaacatgct gagttccgaa cccgccgcgg cacacccggc tgcgccagct   13560
ggtggcccgt gagttcacca tgcgccggtg cgagttgctg ccgccccggg tcc          13613
```

<210> SEQ ID NO: 4
<211> LENGTH: 3782
<212> TYPE: PRT
<213> ORGANISM: Streptomyces venezuelae

<400> SEQUENCE: 4

```
Met Thr Asp Asp Leu Thr Gly Ala Leu Thr Gln Pro Pro Leu Gly Arg
 1               5                  10                  15

Thr Val Arg Ala Val Ala Asp Arg Glu Leu Gly Thr His Leu Leu Glu
            20                  25                  30

Thr Arg Gly Ile His Trp Ile His Ala Ala Asn Gly Asp Pro Tyr Ala
        35                  40                  45

Thr Val Leu Arg Gly Gln Ala Asp Asp Pro Tyr Pro Ala Tyr Glu Arg
    50                  55                  60

Val Arg Ala Arg Gly Ala Leu Ser Phe Ser Pro Thr Gly Ser Trp Val
65                  70                  75                  80

Thr Ala Asp His Ala Leu Ala Ala Ser Ile Leu Cys Ser Thr Asp Phe
                85                  90                  95

Gly Val Ser Gly Ala Asp Gly Val Pro Val Pro Gln Gln Val Leu Ser
            100                 105                 110

Tyr Gly Glu Gly Cys Pro Leu Glu Arg Glu Gln Val Leu Pro Ala Ala
        115                 120                 125
```

-continued

```
Gly Asp Val Pro Glu Gly Gln Arg Ala Val Val Glu Gly Ile His
    130                 135                 140

Arg Glu Thr Leu Glu Gly Leu Ala Pro Asp Pro Ser Ala Ser Tyr Ala
145                 150                 155                 160

Phe Glu Leu Leu Gly Gly Phe Val Arg Pro Ala Val Thr Ala Ala Ala
                165                 170                 175

Ala Ala Val Leu Gly Val Pro Ala Asp Arg Arg Ala Asp Phe Ala Asp
            180                 185                 190

Leu Leu Glu Arg Leu Arg Pro Leu Ser Asp Ser Leu Leu Ala Pro Gln
        195                 200                 205

Ser Leu Arg Thr Val Arg Ala Ala Asp Gly Ala Leu Ala Glu Leu Thr
    210                 215                 220

Ala Leu Leu Ala Asp Ser Asp Asp Ser Pro Gly Ala Leu Leu Ser Ala
225                 230                 235                 240

Leu Gly Val Thr Ala Ala Val Gln Leu Thr Gly Asn Ala Val Leu Ala
                245                 250                 255

Leu Leu Ala His Pro Glu Gln Trp Arg Glu Leu Cys Asp Arg Pro Gly
            260                 265                 270

Leu Ala Ala Ala Val Glu Glu Thr Leu Arg Tyr Asp Pro Pro Val
        275                 280                 285

Gln Leu Asp Ala Arg Val Val Arg Gly Glu Thr Glu Leu Ala Gly Arg
    290                 295                 300

Arg Leu Pro Ala Gly Ala His Val Val Leu Thr Ala Ala Thr Gly
305                 310                 315                 320

Arg Asp Pro Glu Val Phe Thr Asp Pro Glu Arg Phe Asp Leu Ala Arg
                325                 330                 335

Pro Asp Ala Ala Ala His Leu Ala Leu His Pro Ala Gly Pro Tyr Gly
            340                 345                 350

Pro Val Ala Ser Leu Val Arg Leu Gln Ala Glu Val Ala Leu Arg Thr
        355                 360                 365

Leu Ala Gly Arg Phe Pro Gly Leu Arg Gln Ala Gly Asp Val Leu Arg
    370                 375                 380

Pro Arg Arg Ala Pro Val Gly Arg Gly Pro Leu Ser Val Pro Val Ser
385                 390                 395                 400

Ser Ser Met Arg Val Leu Leu Thr Ser Phe Ala His His Thr His Tyr
                405                 410                 415

Tyr Gly Leu Val Pro Leu Ala Trp Ala Leu Leu Ala Ala Gly His Glu
            420                 425                 430

Val Arg Val Ala Ser Gln Pro Ala Leu Thr Asp Thr Ile Thr Gly Ser
        435                 440                 445

Gly Leu Ala Ala Val Pro Val Gly Thr Asp His Leu Ile His Glu Tyr
    450                 455                 460

Arg Val Arg Met Ala Gly Glu Pro Arg Pro Asn His Pro Ala Ile Ala
465                 470                 475                 480

Phe Asp Glu Ala Arg Pro Glu Pro Leu Asp Trp Asp His Ala Leu Gly
                485                 490                 495

Ile Glu Ala Ile Leu Ala Pro Tyr Phe His Leu Leu Ala Asn Asn Asp
            500                 505                 510

Ser Met Val Asp Asp Leu Val Asp Phe Ala Arg Ser Trp Gln Pro Asp
        515                 520                 525

Leu Val Leu Trp Glu Pro Thr Thr Tyr Ala Gly Ala Val Ala Ala Gln
    530                 535                 540
```

-continued

```
Val Thr Gly Ala Ala His Ala Arg Val Leu Trp Gly Pro Asp Val Met
545                 550                 555                 560

Gly Ser Ala Arg Arg Lys Phe Val Ala Leu Arg Asp Arg Gln Pro Pro
                565                 570                 575

Glu His Arg Glu Asp Pro Thr Ala Glu Trp Leu Thr Trp Thr Leu Asp
                580                 585                 590

Arg Tyr Gly Ala Ser Phe Glu Glu Leu Leu Thr Gly Gln Phe Thr
                595                 600                 605

Ile Asp Pro Thr Pro Pro Ser Leu Arg Leu Asp Thr Gly Leu Pro Thr
            610                 615                 620

Val Gly Met Arg Tyr Val Pro Tyr Asn Gly Thr Ser Val Val Pro Asp
625                 630                 635                 640

Trp Leu Ser Glu Pro Pro Ala Arg Pro Arg Val Cys Leu Thr Leu Gly
                645                 650                 655

Val Ser Ala Arg Glu Val Leu Gly Gly Asp Gly Val Ser Gln Gly Asp
                660                 665                 670

Ile Leu Glu Ala Leu Ala Asp Leu Asp Ile Glu Leu Val Ala Thr Leu
            675                 680                 685

Asp Ala Ser Gln Arg Ala Glu Ile Arg Asn Tyr Pro Lys His Thr Arg
690                 695                 700

Phe Thr Asp Phe Val Pro Met His Ala Leu Leu Pro Ser Cys Ser Ala
705                 710                 715                 720

Ile Ile His His Gly Gly Ala Gly Thr Tyr Ala Thr Ala Val Ile Asn
                725                 730                 735

Ala Val Pro Gln Val Met Leu Ala Glu Leu Trp Asp Ala Pro Val Lys
                740                 745                 750

Ala Arg Ala Val Ala Glu Gln Gly Ala Gly Phe Phe Leu Pro Pro Ala
            755                 760                 765

Glu Leu Thr Pro Gln Ala Val Arg Asp Ala Val Val Arg Ile Leu Asp
770                 775                 780

Asp Pro Ser Val Ala Thr Ala Ala His Arg Leu Arg Glu Glu Thr Phe
785                 790                 795                 800

Gly Asp Pro Thr Pro Ala Gly Ile Val Pro Glu Leu Glu Arg Leu Ala
                805                 810                 815

Ala Gln His Arg Arg Pro Pro Asp Ala Arg His Met Tyr Glu Val
            820                 825                 830

Asp His Ala Asp Val Tyr Asp Leu Phe Tyr Leu Gly Arg Gly Lys Asp
                835                 840                 845

Tyr Ala Ala Glu Ala Ser Asp Ile Ala Asp Leu Val Arg Ser Arg Thr
850                 855                 860

Pro Glu Ala Ser Ser Leu Leu Asp Val Ala Cys Gly Thr Gly Thr His
865                 870                 875                 880

Leu Glu His Phe Thr Lys Glu Phe Gly Asp Thr Ala Gly Leu Glu Leu
                885                 890                 895

Ser Glu Asp Met Leu Thr His Ala Arg Lys Arg Leu Pro Asp Ala Thr
                900                 905                 910

Leu His Gln Gly Asp Met Arg Asp Phe Arg Leu Gly Arg Lys Phe Ser
            915                 920                 925

Ala Val Val Ser Met Phe Ser Ser Val Gly Tyr Leu Lys Thr Thr Glu
            930                 935                 940

Glu Leu Gly Ala Ala Val Ala Ser Phe Ala Glu His Leu Glu Pro Gly
945                 950                 955                 960
```

-continued

```
Gly Val Val Val Val Glu Pro Trp Trp Phe Pro Glu Thr Phe Ala Asp
                965                 970                 975
Gly Trp Val Ser Ala Asp Val Val Arg Arg Asp Gly Arg Thr Val Ala
                980                 985                 990
Arg Val Ser His Ser Val Arg Glu Gly Asn Ala Thr Arg Met Glu Val
                995                1000                1005
His Phe Thr Val Ala Asp Pro Gly Lys Gly Val Arg His Phe Ser Asp
               1010                1015                1020
Val His Leu Ile Thr Leu Phe His Gln Ala Glu Tyr Glu Ala Ala Phe
1025                1030                1035                1040
Thr Ala Ala Gly Leu Arg Val Glu Tyr Leu Glu Gly Gly Pro Ser Gly
                1045                1050                1055
Arg Gly Leu Phe Val Gly Val Pro Ala Met Thr Gly Lys Thr Arg Ile
                1060                1065                1070
Pro Arg Val Arg Arg Gly Arg Thr Thr Pro Arg Ala Phe Thr Leu Ala
                1075                1080                1085
Val Val Gly Thr Leu Leu Ala Gly Thr Thr Val Ala Ala Ala Pro
                1090                1095                1100
Gly Ala Ala Asp Thr Ala Asn Val Gln Tyr Thr Ser Arg Ala Ala Glu
1105                1110                1115                1120
Leu Val Ala Gln Met Thr Leu Asp Glu Lys Ile Ser Phe Val His Trp
                1125                1130                1135
Ala Leu Asp Pro Asp Arg Gln Asn Val Gly Tyr Leu Pro Gly Val Pro
                1140                1145                1150
Arg Leu Gly Ile Pro Glu Leu Arg Ala Ala Asp Gly Pro Asn Gly Ile
                1155                1160                1165
Arg Leu Val Gly Gln Thr Ala Thr Ala Leu Pro Ala Pro Val Ala Leu
                1170                1175                1180
Ala Ser Thr Phe Asp Asp Thr Met Ala Asp Ser Tyr Gly Lys Val Met
1185                1190                1195                1200
Gly Arg Asp Gly Arg Ala Leu Asn Gln Asp Met Val Leu Gly Pro Met
                1205                1210                1215
Met Asn Asn Ile Arg Val Pro His Gly Gly Arg Asn Tyr Glu Thr Phe
                1220                1225                1230
Ser Glu Asp Pro Leu Val Ser Ser Arg Thr Ala Val Ala Gln Ile Lys
                1235                1240                1245
Gly Ile Gln Gly Ala Gly Leu Met Thr Thr Ala Lys His Phe Ala Ala
                1250                1255                1260
Asn Asn Gln Glu Asn Asn Arg Phe Ser Val Asn Ala Asn Val Asp Glu
1265                1270                1275                1280
Gln Thr Leu Arg Glu Ile Glu Phe Pro Ala Phe Glu Ala Ser Ser Lys
                1285                1290                1295
Ala Gly Ala Ala Ser Phe Met Cys Ala Tyr Asn Gly Leu Asn Gly Lys
                1300                1305                1310
Pro Ser Cys Gly Asn Asp Glu Leu Leu Asn Asn Val Leu Arg Thr Gln
                1315                1320                1325
Trp Gly Phe Gln Gly Trp Val Met Ser Asp Trp Leu Ala Thr Pro Gly
                1330                1335                1340
Thr Asp Ala Ile Thr Lys Gly Leu Asp Gln Glu Met Gly Val Glu Leu
1345                1350                1355                1360
Pro Gly Asp Val Pro Lys Gly Glu Pro Ser Pro Ala Lys Phe Phe
                1365                1370                1375
```

-continued

```
Gly Glu Ala Leu Lys Thr Ala Val Leu Asn Gly Thr Val Pro Glu Ala
            1380                1385                1390

Ala Val Thr Arg Ser Ala Glu Arg Ile Val Gly Gln Met Glu Lys Phe
        1395                1400                1405

Gly Leu Leu Leu Ala Thr Pro Ala Arg Pro Glu Arg Asp Lys Ala
        1410                1415                1420

Gly Ala Gln Ala Val Ser Arg Lys Val Ala Glu Asn Gly Ala Val Leu
1425                1430                1435                1440

Leu Arg Asn Glu Gly Gln Ala Leu Pro Leu Ala Gly Asp Ala Gly Lys
                1445                1450                1455

Ser Ile Ala Val Ile Gly Pro Thr Ala Val Asp Pro Lys Val Thr Gly
                1460                1465                1470

Leu Gly Ser Ala His Val Val Pro Asp Ser Ala Ala Ala Pro Leu Asp
            1475                1480                1485

Thr Ile Lys Ala Arg Ala Gly Ala Gly Ala Thr Val Thr Tyr Glu Thr
        1490                1495                1500

Gly Glu Glu Thr Phe Gly Thr Gln Ile Pro Ala Gly Asn Leu Ser Pro
1505                1510                1515                1520

Ala Phe Asn Gln Gly His Gln Leu Glu Pro Gly Lys Ala Gly Ala Leu
                1525                1530                1535

Tyr Asp Gly Thr Leu Thr Val Pro Ala Asp Gly Glu Tyr Arg Ile Ala
            1540                1545                1550

Val Arg Ala Thr Gly Gly Tyr Ala Thr Val Gln Leu Gly Ser His Thr
        1555                1560                1565

Ile Glu Ala Gly Gln Val Tyr Gly Lys Val Ser Ser Pro Leu Leu Lys
        1570                1575                1580

Leu Thr Lys Gly Thr His Lys Leu Thr Ile Ser Gly Phe Ala Met Ser
1585                1590                1595                1600

Ala Thr Pro Leu Ser Leu Glu Leu Gly Trp Val Thr Pro Ala Ala Ala
                1605                1610                1615

Asp Ala Thr Ile Ala Lys Ala Val Glu Ser Ala Arg Lys Ala Arg Thr
            1620                1625                1630

Ala Val Val Phe Ala Tyr Asp Asp Gly Thr Glu Gly Val Asp Arg Pro
        1635                1640                1645

Asn Leu Ser Leu Pro Gly Thr Gln Asp Lys Leu Ile Ser Ala Val Ala
1650                1655                1660

Asp Ala Asn Pro Asn Thr Ile Val Val Leu Asn Thr Gly Ser Ser Val
1665                1670                1675                1680

Leu Met Pro Trp Leu Ser Lys Thr Arg Ala Val Leu Asp Met Trp Tyr
                1685                1690                1695

Pro Gly Gln Ala Gly Ala Glu Ala Thr Ala Ala Leu Leu Tyr Gly Asp
            1700                1705                1710

Val Asn Pro Ser Gly Lys Leu Thr Gln Ser Phe Pro Ala Ala Glu Asn
        1715                1720                1725

Gln His Ala Val Ala Gly Asp Pro Thr Ser Tyr Pro Gly Val Asp Asn
        1730                1735                1740

Gln Gln Thr Tyr Arg Glu Gly Ile His Val Gly Tyr Arg Trp Phe Asp
1745                1750                1755                1760

Lys Glu Asn Val Lys Pro Leu Phe Pro Phe Gly His Gly Leu Ser Tyr
                1765                1770                1775

Thr Ser Phe Thr Gln Ser Ala Pro Thr Val Val Arg Thr Ser Thr Gly
            1780                1785                1790
```

-continued

```
Gly Leu Lys Val Thr Val Thr Val Arg Asn Ser Gly Lys Arg Ala Gly
            1795                1800                1805
Gln Glu Val Val Gln Ala Tyr Leu Gly Ala Ser Pro Asn Val Thr Ala
    1810                1815                1820
Pro Gln Ala Lys Lys Lys Leu Val Gly Tyr Thr Lys Val Ser Leu Ala
1825                1830                1835                1840
Ala Gly Glu Ala Lys Thr Val Thr Val Asn Val Asp Arg Arg Gln Leu
                1845                1850                1855
Gln Thr Gly Ser Ser Ser Ala Asp Leu Arg Gly Ser Ala Thr Val Asn
            1860                1865                1870
Val Trp Met Ser Ser Arg Ala Glu Thr Pro Arg Val Pro Phe Leu Asp
            1875                1880                1885
Leu Lys Ala Ala Tyr Glu Glu Leu Arg Ala Glu Thr Asp Ala Ala Ile
            1890                1895                1900
Ala Arg Val Leu Asp Ser Gly Arg Tyr Leu Leu Gly Pro Glu Leu Glu
1905                1910                1915                1920
Gly Phe Glu Ala Glu Phe Ala Ala Tyr Cys Glu Thr Asp His Ala Val
            1925                1930                1935
Gly Val Asn Ser Gly Met Asp Ala Leu Gln Leu Ala Leu Arg Gly Leu
            1940                1945                1950
Gly Ile Gly Pro Gly Asp Glu Val Ile Val Pro Ser His Thr Tyr Ile
            1955                1960                1965
Ala Ser Trp Leu Ala Val Ser Ala Thr Gly Ala Thr Pro Val Pro Val
            1970                1975                1980
Glu Pro His Glu Asp His Pro Thr Leu Asp Pro Leu Leu Val Glu Lys
1985                1990                1995                2000
Ala Ile Thr Pro Arg Thr Arg Ala Leu Leu Pro Val His Leu Tyr Gly
            2005                2010                2015
His Pro Ala Asp Met Asp Ala Leu Arg Glu Leu Ala Asp Arg His Gly
            2020                2025                2030
Leu His Ile Val Glu Asp Ala Ala Gln Ala His Gly Ala Arg Tyr Arg
            2035                2040                2045
Gly Arg Arg Ile Gly Ala Gly Ser Ser Val Ala Ala Phe Ser Phe Tyr
            2050                2055                2060
Pro Gly Lys Asn Leu Gly Cys Phe Gly Asp Gly Gly Ala Val Val Thr
2065                2070                2075                2080
Gly Asp Pro Glu Leu Ala Glu Arg Leu Arg Met Leu Arg Asn Tyr Gly
                2085                2090                2095
Ser Arg Gln Lys Tyr Ser His Glu Thr Lys Gly Thr Asn Ser Arg Leu
            2100                2105                2110
Asp Glu Met Gln Ala Ala Val Leu Arg Ile Arg Leu Ala His Leu Asp
            2115                2120                2125
Ser Trp Asn Gly Arg Arg Ser Ala Leu Ala Ala Glu Tyr Leu Ser Gly
            2130                2135                2140
Leu Ala Gly Leu Pro Gly Ile Gly Leu Pro Val Thr Ala Pro Asp Thr
2145                2150                2155                2160
Asp Pro Val Trp His Leu Phe Thr Val Arg Thr Glu Arg Arg Asp Glu
                2165                2170                2175
Leu Arg Ser His Leu Asp Ala Arg Gly Ile Asp Thr Leu Thr His Tyr
            2180                2185                2190
Pro Val Pro Val His Leu Ser Pro Ala Tyr Ala Gly Glu Ala Pro Pro
            2195                2200                2205
```

-continued

Glu Gly Ser Leu Pro Arg Ala Glu Ser Phe Ala Arg Gln Val Leu Ser
2210                2215                2220

Leu Pro Ile Gly Pro His Leu Glu Arg Pro Gln Ala Leu Arg Val Ile
2225                2230                2235                2240

Asp Ala Val Arg Glu Trp Ala Glu Arg Val Asp Gln Ala Met Arg Leu
            2245                2250                2255

Leu Val Thr Gly Gly Ala Gly Phe Ile Gly Ser His Phe Val Arg Gln
            2260                2265                2270

Leu Leu Ala Gly Ala Tyr Pro Asp Val Pro Ala Asp Glu Val Ile Val
                2275                2280                2285

Leu Asp Ser Leu Thr Tyr Ala Gly Asn Arg Ala Asn Leu Ala Pro Val
            2290                2295                2300

Asp Ala Asp Pro Arg Leu Arg Phe Val His Gly Asp Ile Arg Asp Ala
2305                2310                2315                2320

Gly Leu Leu Ala Arg Glu Leu Arg Gly Val Asp Ala Ile Val His Phe
                2325                2330                2335

Ala Ala Glu Ser His Val Asp Arg Ser Ile Ala Gly Ala Ser Val Phe
                2340                2345                2350

Thr Glu Thr Asn Val Gln Gly Thr Gln Thr Leu Leu Gln Cys Ala Val
            2355                2360                2365

Asp Ala Gly Val Gly Arg Val Val His Val Ser Thr Asp Glu Val Tyr
            2370                2375                2380

Gly Ser Ile Asp Ser Gly Ser Trp Thr Glu Ser Ser Pro Leu Glu Pro
2385                2390                2395                2400

Asn Ser Pro Tyr Ala Ala Ser Lys Ala Gly Ser Asp Leu Val Ala Arg
                2405                2410                2415

Ala Tyr His Arg Thr Tyr Gly Leu Asp Val Arg Ile Thr Arg Cys Cys
            2420                2425                2430

Asn Asn Tyr Gly Pro Tyr Gln His Pro Glu Lys Leu Ile Pro Leu Phe
            2435                2440                2445

Val Thr Asn Leu Leu Asp Gly Gly Thr Leu Pro Leu Tyr Gly Asp Gly
            2450                2455                2460

Ala Asn Val Arg Glu Trp Val His Thr Asp Asp His Cys Arg Gly Ile
2465                2470                2475                2480

Ala Leu Val Leu Ala Gly Gly Arg Ala Gly Glu Ile Tyr His Ile Gly
                2485                2490                2495

Gly Gly Leu Glu Leu Thr Asn Arg Glu Leu Thr Gly Ile Leu Leu Asp
            2500                2505                2510

Ser Leu Gly Ala Asp Trp Ser Ser Val Arg Lys Val Ala Asp Arg Lys
            2515                2520                2525

Gly His Asp Leu Arg Tyr Ser Leu Asp Gly Gly Glu Ile Glu Arg Glu
    2530                2535                2540

Leu Gly Tyr Arg Pro Gln Val Ser Phe Ala Asp Gly Leu Ala Arg Thr
2545                2550                2555                2560

Val Arg Trp Tyr Arg Glu Asn Arg Gly Trp Trp Glu Pro Leu Lys Ala
            2565                2570                2575

Thr Ala Pro Gln Leu Pro Ala Thr Ala Val Glu Val Ser Ala Met Lys
            2580                2585                2590

Gly Ile Val Leu Ala Gly Gly Ser Gly Thr Arg Leu His Pro Ala Thr
            2595                2600                2605

Ser Val Ile Ser Lys Gln Ile Leu Pro Val Tyr Asn Lys Pro Met Ile
    2610                2615                2620

-continued

```
Tyr Tyr Pro Leu Ser Val Leu Met Leu Gly Gly Ile Arg Glu Ile Gln
2625                2630                2635                2640

Ile Ile Ser Thr Pro Gln His Ile Glu Leu Phe Gln Ser Leu Leu Gly
                2645                2650                2655

Asn Gly Arg His Leu Gly Ile Glu Leu Asp Tyr Ala Val Gln Lys Glu
            2660                2665                2670

Pro Ala Gly Ile Ala Asp Ala Leu Leu Val Gly Ala Glu His Ile Gly
        2675                2680                2685

Asp Asp Thr Cys Ala Leu Ile Leu Gly Asp Asn Ile Phe His Gly Pro
    2690                2695                2700

Gly Leu Tyr Thr Leu Leu Arg Asp Ser Ile Ala Arg Leu Asp Gly Cys
2705                2710                2715                2720

Val Leu Phe Gly Tyr Pro Val Lys Asp Pro Glu Arg Tyr Gly Val Ala
                2725                2730                2735

Glu Val Asp Ala Thr Gly Arg Leu Thr Asp Leu Val Glu Lys Pro Val
            2740                2745                2750

Lys Pro Arg Ser Asn Leu Ala Val Thr Gly Leu Tyr Leu Tyr Asp Asn
        2755                2760                2765

Asp Val Val Asp Ile Ala Lys Asn Ile Arg Pro Ser Pro Arg Gly Glu
    2770                2775                2780

Leu Glu Ile Thr Asp Val Asn Arg Val Tyr Leu Glu Arg Gly Arg Ala
2785                2790                2795                2800

Glu Leu Val Asn Leu Gly Arg Gly Phe Ala Trp Leu Asp Thr Gly Thr
                2805                2810                2815

His Asp Ser Leu Leu Arg Ala Ala Gln Tyr Val Gln Val Leu Glu Glu
            2820                2825                2830

Arg Gln Gly Val Trp Ile Ala Gly Leu Glu Glu Ile Ala Phe Arg Met
        2835                2840                2845

Gly Phe Ile Asp Ala Glu Ala Cys His Gly Leu Gly Glu Gly Leu Ser
    2850                2855                2860

Arg Thr Glu Tyr Gly Ser Tyr Leu Met Glu Ile Ala Gly Arg Glu Gly
2865                2870                2875                2880

Ala Pro Met Thr Ala Pro Ala Leu Ser Ala Thr Ala Pro Ala Glu Arg
                2885                2890                2895

Cys Ala His Pro Gly Ala Asp Leu Gly Ala Ala Val His Ala Val Gly
            2900                2905                2910

Gln Thr Leu Ala Ala Gly Gly Leu Val Pro Pro Asp Glu Ala Gly Thr
        2915                2920                2925

Thr Ala Arg His Leu Val Arg Leu Ala Val Arg Tyr Gly Asn Ser Pro
    2930                2935                2940

Phe Thr Pro Leu Glu Glu Ala Arg His Asp Leu Gly Val Asp Arg Asp
2945                2950                2955                2960

Ala Phe Arg Arg Leu Leu Ala Leu Phe Gly Gln Val Pro Glu Leu Arg
                2965                2970                2975

Thr Ala Val Glu Thr Gly Pro Ala Gly Ala Tyr Trp Lys Asn Thr Leu
            2980                2985                2990

Leu Pro Leu Glu Gln Arg Gly Val Phe Asp Ala Ala Leu Ala Arg Lys
        2995                3000                3005

Pro Val Phe Pro Tyr Ser Val Gly Leu Tyr Pro Gly Pro Thr Cys Met
    3010                3015                3020

Phe Arg Cys His Phe Cys Val Arg Val Thr Gly Ala Arg Tyr Asp Pro
3025                3030                3035                3040
```

-continued

```
Ser Ala Leu Asp Ala Gly Asn Ala Met Phe Arg Ser Val Ile Asp Glu
            3045                3050                3055

Ile Pro Ala Gly Asn Pro Ser Ala Met Tyr Phe Ser Gly Gly Leu Glu
        3060                3065                3070

Pro Leu Thr Asn Pro Gly Leu Gly Ser Leu Ala Ala His Ala Thr Asp
        3075                3080                3085

His Gly Leu Arg Pro Thr Val Tyr Thr Asn Ser Phe Ala Leu Thr Glu
        3090                3095                3100

Arg Thr Leu Glu Arg Gln Pro Gly Leu Trp Gly Leu His Ala Ile Arg
3105                3110                3115                3120

Thr Ser Leu Tyr Gly Leu Asn Asp Glu Glu Tyr Glu Gln Thr Thr Gly
            3125                3130                3135

Lys Lys Ala Ala Phe Arg Arg Val Arg Glu Asn Leu Arg Arg Phe Gln
            3140                3145                3150

Gln Leu Arg Ala Glu Arg Glu Ser Pro Ile Asn Leu Gly Phe Ala Tyr
            3155                3160                3165

Ile Val Leu Pro Gly Arg Ala Ser Arg Leu Leu Asp Leu Val Asp Phe
        3170                3175                3180

Ile Ala Asp Leu Asn Asp Ala Gly Gln Gly Arg Thr Ile Asp Phe Val
3185                3190                3195                3200

Asn Ile Arg Glu Asp Tyr Ser Gly Arg Asp Asp Gly Lys Leu Pro Gln
            3205                3210                3215

Glu Glu Arg Ala Glu Leu Gln Glu Ala Leu Asn Ala Phe Glu Glu Arg
            3220                3225                3230

Val Arg Glu Arg Thr Pro Gly Leu His Ile Asp Tyr Gly Tyr Ala Leu
            3235                3240                3245

Asn Ser Leu Arg Thr Gly Ala Asp Ala Glu Leu Leu Arg Ile Lys Pro
        3250                3255                3260

Ala Thr Met Arg Pro Thr Ala His Pro Gln Val Ala Val Gln Val Asp
3265                3270                3275                3280

Leu Leu Gly Asp Val Tyr Leu Tyr Arg Glu Ala Gly Phe Pro Asp Leu
            3285                3290                3295

Asp Gly Ala Thr Arg Tyr Ile Ala Gly Arg Val Thr Pro Asp Thr Ser
            3300                3305                3310

Leu Thr Glu Val Val Arg Asp Phe Val Glu Arg Gly Gly Glu Val Ala
            3315                3320                3325

Ala Val Asp Gly Asp Glu Tyr Phe Met Asp Gly Phe Asp Gln Val Val
            3330                3335                3340

Thr Ala Arg Leu Asn Gln Leu Gly Arg Asp Ala Ala Asp Gly Trp Glu
3345                3350                3355                3360

Glu Ala Arg Gly Phe Leu Arg Met Lys Ser Ala Leu Ser Asp Leu Ala
            3365                3370                3375

Phe Phe Gly Gly Pro Ala Ala Phe Asp Gln Pro Leu Leu Val Gly Arg
            3380                3385                3390

Pro Asn Arg Ile Asp Arg Ala Arg Leu Tyr Glu Arg Leu Asp Arg Ala
            3395                3400                3405

Leu Asp Ser Gln Trp Leu Ser Asn Gly Gly Pro Leu Val Arg Glu Phe
        3410                3415                3420

Glu Glu Arg Val Ala Gly Leu Ala Gly Val Arg His Ala Val Ala Thr
3425                3430                3435                3440

Cys Asn Ala Thr Ala Gly Leu Gln Leu Leu Ala His Ala Ala Gly Leu
            3445                3450                3455
```

```
Thr Gly Glu Val Ile Met Pro Ser Met Thr Phe Ala Ala Thr Pro His
            3460                3465                3470

Ala Leu Arg Trp Ile Gly Leu Thr Pro Val Phe Ala Asp Ile Asp Pro
            3475                3480                3485

Asp Thr Gly Asn Leu Asp Pro Asp Gln Val Ala Ala Val Thr Pro
        3490                3495                3500

Arg Thr Ser Ala Val Val Gly Val His Leu Trp Gly Arg Pro Cys Ala
3505                3510                3515                3520

Ala Asp Gln Leu Arg Lys Val Ala Asp Glu His Gly Leu Arg Leu Tyr
            3525                3530                3535

Phe Asp Ala Ala His Ala Leu Gly Cys Ala Val Asp Gly Arg Pro Ala
            3540                3545                3550

Gly Ser Leu Gly Asp Ala Glu Val Phe Ser Phe His Ala Thr Lys Ala
            3555                3560                3565

Val Asn Ala Phe Glu Gly Gly Ala Val Val Thr Asp Asp Ala Asp Leu
        3570                3575                3580

Ala Ala Arg Ile Arg Ala Leu His Asn Phe Gly Phe Asp Leu Pro Gly
3585                3590                3595                3600

Gly Ser Pro Ala Gly Gly Thr Asn Ala Lys Met Ser Glu Ala Ala Ala
            3605                3610                3615

Ala Met Gly Leu Thr Ser Leu Asp Ala Phe Pro Glu Val Ile Asp Arg
            3620                3625                3630

Asn Arg Arg Asn His Ala Ala Tyr Arg Glu His Leu Ala Asp Leu Pro
            3635                3640                3645

Gly Val Leu Val Ala Asp His Asp Arg His Gly Leu Asn Asn His Gln
            3650                3655                3660

Tyr Val Ile Val Glu Ile Asp Glu Ala Thr Thr Gly Ile His Arg Asp
3665                3670                3675                3680

Leu Val Met Glu Val Leu Lys Ala Glu Gly Val His Thr Arg Ala Tyr
            3685                3690                3695

Phe Ser Pro Gly Cys His Glu Leu Glu Pro Tyr Arg Gly Gln Pro His
            3700                3705                3710

Ala Pro Leu Pro His Thr Glu Arg Leu Ala Ala Arg Val Leu Ser Leu
            3715                3720                3725

Pro Thr Gly Thr Ala Ile Gly Asp Asp Ile Arg Arg Val Ala Asp
        3730                3735                3740

Leu Leu Arg Leu Cys Ala Thr Gly Arg Glu Leu Thr Ala Arg His
3745                3750                3755                3760

Arg Asp Thr Ala Pro Ala Pro Leu Ala Ala Pro Gln Thr Ser Thr Pro
            3765                3770                3775

Thr Ile Gly Arg Ser Arg
            3780

<210> SEQ ID NO: 5
<211> LENGTH: 36778
<212> TYPE: DNA
<213> ORGANISM: Streptomyces venezuelae

<400> SEQUENCE: 5
ggatccgacc gtgggtgtga atctccgggt gctcgcctcg tcctgccccg ttacctgtcc    60
gcctcccgct ccagaccagc gggaggcgga caggggcatg cccgccgggc ggctaacggc   120
ccgtgcggcg tccgtacgac gagcctcgcg cgccctggcg gccttggtc tgccggacct    180 gtgcgcgggg tgcgcagggt tcgccgccgc gcgtggggcc gtatctgcgg ctcccgggca   240
```

-continued

```
cggcggccct gctcgtctcc gagtcatagt ccctgccgcc ggcgccaccg ccctggcccg    300
gcatgcgcgt gccgggcgcc cccggcgcgt aactcggctg ggaggcctgg aaaagggcga    360
tccattgggt gagcgtgagg tccttcggca gtccgccgtc cggaattccg tggcggtcgg    420
cgagggaacg gtaggtccgc ttggggatgt ggcgccggag gatctccgcg aggcccgtc    480
cggggccggt gaagacggct tcggcgaagt tctggaaggc gcggctcgcg ctctcgggca    540
gcaggggctg gggcgtcgc ctgatcgtca ggacgccgcc gtcgacgcgg ggcatcggac    600
ggaacgacga ggcgcggacg cggtcgtgga ccgcgaactc gtaccagggg gcccaggagg    660
tcgtgaggag cgatccgccg ctgcgaccgg cgcgtttgcg ggcgacctcc cactgcacta    720
tcagggccgc cgactgccag ttcgtcgatt ccaggagact ccggagaatc tgggtcgtga    780
tgccgaaggg aacgtttccg acgacggtgt cgatatcgcg cggaatgcgg aagtcgagga    840
aatcaccctg gaatacggtg accctctccc cttcgaattt ccgccgcaca tgcgcggccc    900
agtgcgggtc catctccacg accgtcacgg tgtcgaagga gcgcaccaac tcctcggtta    960
tcgcgccctt tccggggccg atttcgagaa cgttcctacc gtcccctcg acatgcgtga    1020
cgagattgcg cacggctctg tcgtcctgaa ggaagttctg gcctaattcg cggcgaaggg    1080
tgtcgcggtc cgctcgcctc ggtatggagt gcgcattgc catgaacgat cccctccctg    1140
gatgccgtgg tcaatggact tggcacggac catacctcac ggtccgtcgg acgaccggag    1200
aagaagttca cgcacgggcg ttccggagta cgggagttgt gaacgccgc gacgaagtcg    1260
gtcgcggctc ggcgggcggt gacgagcgag gtccggagga acgcgacgaa gcagccgaac    1320
cccaagtgag gtgcgacgga gtgacattgg gggcatacgg agggttgtcg tacggagcgc    1380
actcaacgag gctccaggag ggaggggttg aacccgccgc cgactggcct tcgccgcccg    1440
cgcggccgga gtatgtcatg tcgggggtga aatcaagcca ttcccccggg atcggctgtt    1500
acccatccct ttacctggcg tggatttccc aaccttggt atagagcggg agacgacgcg    1560
acaccatgga gaccacgcac accacgagcg ccaccccccg gccatcccga caagggggt    1620
ccggctcgcc tcccgacacc catggcctgg ggtacacgcg aggtataggg ggaacgtagg    1680
gggagcatag gggggtgcc ctggggttgg gtgaaagcgc ggcttccgga gacggagccg    1740
gatgtcttca gccggaatta ccaggaccgg tgcgagaaca ccggtgacag ggcgtggggc    1800
ggcagcgtgg gacacggggg aagtgcgggt ccgacggggg ttgccccctg ccggccccga    1860
tcatgcggag cactccttct ctcgtgctcc taccggtgat gtgcgcgccg aattgattcg    1920
tggagagatg tcgacagtgt ccaagagtga gtccgaggaa ttcgtgtccg tgtcgaacga    1980
cgccggttcc gcgcacggca cagcggaacc cgtcgccgtc gtcggcatct cctgccgggt    2040
gcccggcgcc cgggacccga gagttctg ggaactcctg gcggcaggcg gccaggccgt    2100
caccgacgtc cccgcggacc gctggaacgc cggcgacttc tacgacccgg accgctccgc    2160
ccccggccgc tcgaacagcc ggtggggcgg gttcatcgag gacgtcgacc ggttcgacgc    2220
cgccttcttc ggcatctcgc cccgcgaggc gcggagatg gacccgcagc agcggctcgc    2280
cctggagctg ggctgggagg ccctggagcg cgccgggatc gacccgtcct cgctcaccgg    2340
cacccgcacc ggcgtcttcg ccggcgccat ctggacgacg tacgccaccc tgaagcaccg    2400
ccagggcggc gccgcgatca ccccgcacac cgtcaccggc ctccaccgcg gcatcatcgc    2460
gaaccgactc tcgtacacgc tcgggctccg cggcccccagc atggtcgtcg actccggcca    2520
gtcctcgtcg ctcgtcgccg tccacctcgc gtgcgagagc ctgcggcgcg gcgagtccga    2580
```

```
gctcgccctc gccggcggcg tctcgctcaa cctggtgccg acagcatca tcggggcgag    2640 caagttcggc ggcctctccc ccgacggccg cgcctacacc ttcgacgcgc gcgccaacgg    2700
ctacgtacgc ggcgagggcg gcggtttcgt cgtcctgaag cgcctctccc gggccgtcgc    2760
cgacggcgac ccggtgctcg ccgtgatccg gggcagcgcc gtcaacaacg cggcgccgc     2820 ccagggcatg acgaccccg acgcgcaggc gcaggaggcc gtgctccgcg aggcccacga    2880
gcgggccggg accgcgccgg ccgacgtgcg gtacgtcgag ctgcacggca ccggcacccc    2940
cgtgggcgac ccgatcgagg ccgctgcgct cggcgccgcc ctcggcaccg ccgcccggc     3000 cggacagccg ctcctggtcg gctcggtcaa gacgaacatc ggccacctgg agggcgcggc    3060
cggcatcgcc ggcctcatca aggccgtcct ggcggtccgc ggtcgcgcgc tgcccgccag    3120
cctgaactac gagaccccga acccggcgat cccgttcgag gaactgaacc tccgggtgaa    3180
cacggagtac ctgccgtggg agccggagca cgacgggcag cggatggtcg tcggcgtgtc    3240
ctcgttcggc atgggcggca cgaacgcgca tgtcgtgctc gaagaggccc ccgggggttg    3300
tcgaggtgct tcggtcgtgg agtcgacggt cggcgggtcg gcggtcggcg gcggtgtggt    3360
gccgtgggtg gtgtcggcga agtccgctgc cgcgctggac gcgcagatcg agcggcttgc    3420
cgcgttcgcc tcgcgggatc gtacggatgg tgtcgacgcg ggcgctgtcg atgcgggtgc    3480
tgtcgatgcg ggtgctgtcg ctcgcgtact ggccggcggg cgtgctcagt tcgagcaccg    3540
ggccgtcgtc gtcggcagcg ggccggacga tctggcggca gcgctggccg cgcctgaggg    3600
tctggtccgg ggcgtggctt ccggtgtcgg gcgagtggcc ttcgtgttcc ccgggcaggg    3660
cacgcagtgg gccggcatgg gtgccgaact gctggactct ccgcggtgt tcgcggcggc     3720 catggccgaa tgcgaggccg cactctcccc gtacgtcgac tggtcgctgg aggccgtcgt    3780
acggcaggcc cccggtgcgc ccacgctgga gcgggtcgat gtcgtgcagc ctgtgacgtt    3840
cgccgtcatg gtctcgctgg ctcgcgtgtg gcagcaccac ggggtgacgc cccaggcggt    3900
cgtcggccac tcgcagggcg agatcgccgc cgcgtacgtc gccggtgccc tgagcctgga    3960
cgacgccgct cgtgtcgtga ccctgcgcag caagtccatc gccgcccacc tcgccggcaa    4020
gggcggcatg ctgtccctcg cgctgagcga ggacgccgtc ctggagcgac tggccgggtt    4080
cgacgggctg tccgtcgccg ctgtgaacgg gcccaccgcc accgtggtct ccggtgaccc    4140
cgtacagatc gaagagcttg ctcgggcgtg tgaggccgat ggggtccgtg cgcgggtcat    4200
tcccgtcgac tacgcgtccc acagccggca ggtcagatc atcgagagcg agctcgccga    4260
ggtcctcgcc gggctcagcc cgcaggctcc cgcgcgtgccg ttcttctcga cactcgaagg    4320
cgcctggatc accgagcccg tgctcgacgg cggctactgg taccgcaacc tgcgccatcg    4380
tgtgggcttc gccccggccg tcgagaccct ggccaccgac gagggcttca cccacttcgt    4440
cgaggtcagc gcccacccg tcctcaccat ggccctcccc gggaccgtca ccggtctggc     4500
gaccctgcgt cgcgacaacg gcggtcagga ccgcctagtc gcctccctcg ccgaagcatg    4560
ggccaacgga ctcgcggtcg actggagccc gctcctcccc tccgcaccg gccaccactc     4620 cgacctcccc acctacgcgt tccagaccga cgcactggg ctgggcgaga tcgaggcgct     4680
cgccccggcg ggcgagccgg cggtgcagcc cgccgtcctc cgcacggagg cggccgagcc    4740
ggcggagctc gaccgggacg agcagctgcg cgtgatcctg acaaggtcc gggcgcagac     4800 ggcccaggtg ctggggtacg cgacaggcg gcagatcgag gtcgaccgga ccttccgtga    4860
ggccggttgc acctccctga ccggcgtgga cctgcgcaac cggatcaacg ccgccttcgg    4920
cgtacggatg gcgccgtcca tgatcttcga cttcccccacc cccgaggctc tcgcggagca    4980
```

```
gctgctcctc gtcgtgcacg gggaggcggc ggcgaacccg gccggtgcgg agccggctcc    5040
ggtggcggcg gccggtgccg tcgacgagcc ggtggcgatc gtcggcatgg cctgccgcct    5100
gcccggtggg gtcgcctcgc cggaggacct gtggcggctg gtggccggcg gcggggacgc    5160
gatctcggag ttcccgcagg accgcggctg ggacgtggag gggctgtacc acccggatcc    5220
ggagcacccc ggcacgtcgt acgtccgcca ggcggtttc atcgagaacg tcgccggctt     5280
cgacgcggcc ttcttcggga tctcgccgcg cgaggccctc gccatggacc cgcagcagcg    5340
gctcctcctc gaaacctcct gggaggccgt cgaggacgcc gggatcgacc cgacctcccg    5400
gcggggacgg caggtcggcg tcttcactgg ggcgatgacc cacgagtacg gccgagcct     5460 gcgggacggc ggggaaggcc tcgacggcta cctgctgacc ggcaacacgg ccagcgtgat    5520
gtcgggccgc gtctcgtaca cactcggcct tgagggcccc gccctgacgg tggacacggc    5580
ctgctcgtcg tcgctggtcg ccctgcacct cgccgtgcag gccctgcgca agggcgaggt    5640
cgacatggcg ctcgccggcg gcgtggccgt gatgcccacg cccgggatgt tcgtcgagtt    5700
cagccggcag cgcgggctgg ccggggacgg ccggtcgaag gcgttcgccg cgtcggcgga    5760
cggcaccagc tggtccgagg gcgtcggcgt cctcctcgtc gagcgcctgt cggacgcccg    5820
ccgcaacgga caccaggtcc tcgcggtcgt ccgcggcagc gccttgaacc aggacggcgc    5880
gagcaacggc ctcacggctc cgaacgggcc ctcgcagcag cgcgtcatcc ggcgcgcgct    5940
ggcggacgcc cggctgacga cctccgacgt ggacgtcgtc gaggcacacg gcacgggcac    6000
gcgactcggc gacccgatcg aggcgcaggc cctgatcgcc acctacggcc agggccgtga    6060
cgacgaacag ccgctgcgcc tcgggtcgtt gaagtccaac atcgggcaca cccaggccgc    6120
ggccggcgtc tccggtgtca tcaagatggt ccaggcgatg cgccacggac tgctgccgaa    6180
gacgctgcac gtcgacgagc cctcggacca gatcgactgg tcggctggcg ccgtggaact    6240
cctcaccgag gccgtcgact ggccggagaa gcaggacggc gggctgcgcc gggccgccgt    6300
ctcctccttc gggatcagcg gcaccaatgc gcatgtggtg ctcgaagagg ccccggtggt    6360
tgtcgagggt gcttcggtcg tcgagccgtc ggttggcggg tcggcggtcg gcggcggtgt    6420
gacgccttgg gtggtgtcgg cgaagtccgc tgccgcgctc gacgcgcaga tcgagcggct    6480
tgccgcattc gcctcgcggg atcgtacgga tgacgccgac gccggtgctg tcgacgcggg    6540
cgctgtcgct cacgtactgg ctgacgggcg tgctcagttc gagcaccggg ccgtcgcgct    6600
cggcgccggg gcggacgacc tcgtacaggc gctggccgat ccggacgggc tgatacgcgg    6660
aacggcttcc ggtgtcgggc gagtggcgtt cgtgttcccc ggtcagggca cgcagtgggc    6720
tggcatgggt gccgaactgc tggactcttc cgcggtgttc gcggcggcca tggccgagtg    6780
tgaggccgcg ctgtccccgt acgtcgactg gtcgctggag gccgtcgtac ggcaggcccc    6840
cggtgcgccc acgctggagc gggtcgatgt cgtgcagcct gtgacgttcg ccgtcatggt    6900
ctcgctggct cgcgtgtggc agcaccacgg tgtgacgccc caggcggtcg tcggccactc    6960
gcagggcgag atcgccgccg cgtacgtcgc cggagccctg ccctggacg acgccgcccg     7020 cgtcgtcacc ctgcgcagca agtccatcgc cgcccacctc gccggcaagg gcggcatgct    7080
gtccctcgcg ctgaacgagg acgccgtcct ggagcgactg agtgacttcg acgggctgtc    7140
cgtcgccgcc gtcaacgggc ccaccgccac tgtcgtgtcg ggtgacccg tacagatcga     7200 agagcttgct caggcgtgca aggcggacg attccgcgcg cggatcattc ccgtcgacta     7260
cgcgtcccac agccggcagg tcgagatcat cgagagcgag ctcgcccagg tcctcgccgg    7320
```

-continued

```
tctcagcccg caggccccgc gcgtgccgtt cttctcgacg ctcgaaggca cctggatcac    7380
cgagcccgtc ctcgacggca cctactggta ccgcaacctc cgtcaccgcg tcggcttcgc    7440
ccccgccatc gagaccctgg ccgtcgacga gggcttcacg cacttcgtcg aggtcagcgc    7500
ccaccccgtc ctcaccatga ccctccccga ccgtcaccg gcctcggca cctccgtcg      7560
cgaacaggga ggccaagagc gtctggtcac ctcgctcgcc gaggcgtggg tcaacgggct    7620
tcccgtggca tggacttcgc tcctgcccgc cacggcctcc cgcccggtc tgcccaccta    7680
cgccttccag gccgagcgct actggctcga gaacactccc gccgccctgg ccaccggcga    7740
cgactggcgc taccgcatcg actggaagcg cctcccggcc gccagggggt ccgagcgcac    7800
cggcctgtcc ggccgctggc tcgccgtcac gccggaggac cactccgcgc aggccgccgc    7860
cgtgctcacc gcgctggtcg acgccggggc gaaggtcgag gtgctgacgg ccggggcgga    7920
cgacgaccgt gaggccctcg ccgcccggct caccgcactg acgaccggtg acggcttcac    7980
cggcgtggtc tcgctcctcg acggactcgt accgcaggtc gcctgggtcc aggcgctcgg    8040
cgacgccgga atcaaggcgc ccctgtggtc cgtcacccag ggcgcggtct ccgtcggacg    8100
tctcgacacc cccgccgacc ccgaccgggc catgctctgg ggcctcggcc gcgtcgtcgc    8160
ccttgagcac cccgaacgct gggccggcct cgtcgacctc cccgcccagc ccgatgccgc    8220
cgccctcgcc cacctcgtca ccgcactctc cggcgccacc ggcgaggacc agatcgccat    8280
ccgcaccacc ggactccacg cccgccgcct cgcccgcgca ccctccacg gacgtcggcc    8340
caccccgcgac tggcagcccc acggcaccgt cctcatcacc ggcggcaccg gagccctcgg    8400
cagccacgcc gcacgctgga tgcccacca cggagccgaa cacctcctcc tcgtcagccg    8460
cagcggcgaa caagccccg gagccaccca actcaccgcc gaactcaccg catcgggcgc    8520
ccgcgtcacc atcgccgcct gcgacgtcgc cgaccccac gccatgcgca ccctcctcga    8580
cgccatcccc gccgagacgc ccctcaccgc cgtcgtccac accgcggcg cgctcgacga    8640
cggcatcgtg gacacgctga ccgccgagca ggtccggcgg gcccaccgtg cgaaggccgt    8700
cggcgcctcg gtgctcgacg agctgacccg ggacctcgac ctcgacgcgt tcgtgctctt    8760
ctcgtccgtg tcgagcactc tgggcatccc cggtcagggc aactacgccc cgcacaacgc    8820
ctacctcgac gccctcgcgg ctcgccgccg gccaccggc cggtccgccg tctcggtggc    8880
ctggggaccg tgggacggtg cggcatggc cgccggtgac ggcgtggccg agcggctgcg    8940
caaccacggc gtgcccggca tggacccgga actcgccctg ccgcactgg agtccgcgct    9000
cggccgggac gagaccgcga tcaccgtcgc ggacatcgac tgggaccgct ctacctcgc    9060
gtactcctcc ggtcgcccgc agcccctcgt cgaggagctg cccgaggtgc ggcgcatcat    9120
cgacgcacgg gacagcgcca cgtccggaca gggcgggagc tccgcccagg cgccaacccc    9180
cctggccgag cggctggccg ccgcggctcc cggcgagcgt acggagatcc tcctcggtct    9240
cgtacgggcg caggccgccg ccgtgctccg gatgcgttcg ccggaggacg tcgccgccga    9300
ccgcgccttc aaggacatcg gcttcgactc gctcgccggt gtcgagctgc gcaacaggct    9360
gacccgggcg accgggctcc agctgcccgc gacgctcgtc ttcgaccacc gacgccgct    9420
ggccctcgtg tcgctgctcc gcagcgagtt cctcggtgac gaggagacgg cggacgcccg    9480
gcggtccgcg gcgctgcccg cgactgtcgg tgccggtgcc ggcgccggcg ccggcaccga    9540
tgccgacgac gatccgatcg cgatcgtcgc gatgagctgc cgctacccg gtgacatccg    9600
cagcccggag gacctgtggc ggatgctgtc cgagggcggc gagggcatca cgccgttccc    9660
caccgaccgc ggctgggacc tcgacggcct gtacgacgcc gacccggacg cgctcggcag    9720
```

```
ggcgtacgtc cgcgagggcg ggttcctgca cgacgcggcc gagttcgacg cggagttctt    9780
cggcgtctcg ccgcgcgagg cgctggccat ggacccgcag cagcggatgc tcctgacgac    9840
gtcctgggag gccttcgagc gggccggcat cgagccggca tcgctgcgcg gcagcagcac    9900
cggtgtcttc atcggcctct cctaccagga ctacgcggcc cgcgtcccga acgcccgcg    9960 tggcgtggag ggttacctgc tgaccggcag cacgccgagc gtcgcgtcgg gccgtatcgc   10020
gtacaccttc ggtctcgaag ggcccgcgac gaccgtcgac accgcctgct cgtcgtcgct   10080
gaccgccctg cacctggcgg tgcgggcgct gcgcagcggc gagtgcacga tggcgctcgc   10140
cggtggcgtg gcgatgatgg cgaccccgca catgttcgtg gagttcagcc gtcagcgggc   10200
gctcgccccg gacggccgca gcaaggcctt ctcggcggac gccgacgggt tcggcgccgc   10260
ggagggcgtc ggcctgctgc tcgtggagcg gctctcggac gcgcggcgca acggtcaccc   10320
ggtgctcgcc gtggtccgcg gtaccgccgt caaccaggac ggcgccagca acgggctgac   10380
cgcgcccaac ggaccctcgc agcagcgggt gatccggcag gcgctcgccg acgcccggct   10440
ggcacccggc gacatcgacg ccgtcgagac gcacggcacg gaacctcgc tgggcgaccc   10500 catcgaggcc cagggcctcc aggccacgta cggcaaggag cggcccgcgg aacggccgct   10560
cgccatcggc tccgtgaagt ccaacatcgg acacacccag gccgcggccg gtgcggcggg   10620
catcatcaag atggtcctcg cgatgcgcca cggcaccctg ccgaagaccc tccacgccga   10680
cgagccgagc ccgcacgtcg actgggcgaa cagcggcctg gccctcgtca ccgagccgat   10740
cgactggccg gccggcaccg gtccgcgccg cgccgccgtc tcctccttcg gcatcagcgg   10800
gacgaacgcg cacgtcgtgc tggagcaggc gccggatgct gctggtgagg tgcttggggc   10860
cgatgaggtg cctgaggtgt ctgagacggt agcgatggct gggacggctg ggacctccga   10920
ggtcgctgag ggctctgagg cctccgaggc ccccgcggcc cccggcagcc gtgaggcgtc   10980
cctccccggg cacctgccct gggtgctgtc cgccaaggac gagcagtcgc tgcgcggcca   11040
ggccgccgcc ctgcacgcgt ggctgtccga gcccgccgcc gacctgtcgg acgcggacgg   11100
accggcccgc ctgcgggacg tcgggtacac gctcgccacg agccgtaccg ccttcgcgca   11160
ccgcgccgcc gtgaccgccg ccgacccggga cgggttcctg gacgggctgg ccacgctggc   11220
ccagggcggc acctcggccc acgtccacct ggacaccgcc cgggacggca ccaccgcgtt   11280
cctcttcacc ggccagggca gtcagcgccc cggcgccggc cgtgagctgt acgaccggca   11340
ccccgtcttc gcccgggcgc tcgacgagat ctgcgcccac ctcgacggtc acctcgaact   11400
gcccctgctc gacgtgatgt tcgcggccga gggcagcgcg gaggccgcgc tgctcgacga   11460
gacgcggtac acgcagtgcg cgctgttcgc cctggaggtc gcgctcttcc ggctcgtcga   11520
gagctggggc atgcggccgg ccgcactgct cggtcactcg gtcggcgaga tcgccgccgc   11580
gcacgtcgcc ggtgtgttct cgctcgccga cgccgcccgc ctggtcgccg cgcgcggccg   11640
gctcatgcag gagctgcccg ccggtggcgc gatgctcgcc gtccaggccg cggaggacga   11700
gatccgcgtg tggctggaga cggaggagcg gtacgcggga cgtctggacg tcgccgccgt   11760
caacggcccc gaggccgccg tcctgtccgg cgacgcggac gcggcgcggg aggcggaggc   11820
gtactggtcc gggctcggcc gcaggacccg cgcgctgcgg gtcagccacg ccttccactc   11880
cgcgcacatg gacggcatgc tcgacgggtt ccgcgccgtc ctggagacgg tggagttccg   11940
gcgcccctcg ctgaccgtgg tctcgaacgt caccggcctg gccgccggcc ggacgacct    12000 gtgcgacccc gagtactggg tccggcacgt ccgcggcacc gtccgcttcc tcgacggcgt   12060
```

```
ccgtgtcctg cgcgacctcg gcgtgcggac ctgcctggag ctgggcccg acggggtcct    12120 caccgccatg gcggccgacg gcctcgcgga caccccgcg gattccgctg ccggctcccc    12180
cgtcggctct cccgccggct ctcccgccga ctccgccgcc ggcgcgctcc ggccccggcc    12240
gctgctcgtg gcgctgctgc gccgcaagcg gtcggagacc gagaccgtcg cggacgccct    12300
cggcagggcg cacgcccacg gcaccggacc cgactggcac gcctggttcg ccggctccgg    12360
ggcgcaccgc gtggacctgc ccacgtactc cttccggcgc gaccgctact ggctggacgc    12420
cccggcggcc gacaccgcgg tggacaccgc cggcctcggt ctcggcaccg ccgaccaccc    12480
gctgctcggc gccgtggtca gccttccgga ccgggacgg ctgctgctca ccggccgcct    12540
ctccctgcgc acccacccgt ggctcgcgga ccacgccgtc ctggggagcg tcctgctccc    12600
cggcgccgcg atggtcgaac tcgccgcgca cgctgcggag tccgccggtc tgcgtgacgt    12660
gcgggagctg accctccttg aaccgctggt actgcccgag cacggtggcg tcgagctgcg    12720
cgtgacggtc ggggcgccgg ccggagagcc cggtggcgag tcggccgggg acggcgcacg    12780
gcccgtctcc ctccactcgc ggctcgccga cgcgcccgcc ggtaccgcct ggtcctgcca    12840
cgcgaccggt ctgctggcca ccgaccggcc cgagcttccc gtcgcgcccg accgtgcggc    12900
catgtggccg ccgcagggcg ccgaggaggt gccgctcgac ggtctctacg agcggctcga    12960
cgggaacggc ctcgccttcg gtccgctgtt ccagggctg aacgcggtgt ggcggtacga    13020
gggtgaggtc ttcgccgaca tcgcgctccc cgccaccacg aatgcgaccg cgcccgcgac    13080
cgcgaacggc ggcgggagtg cggcggcggc ccctacgg atccaccccg ccctgctcga    13140
cgcttcgctg cacgccatcg cggtcggcgg tctcgtcgac gagcccgagc tcgtccgcgt    13200
ccccttccac tggagcggtg tcaccgtgca cgcggccggt gccgcggcgg cccgggtccg    13260
tctcgcctcc gcggggacgg acgccgtctc gctgtccctg acggacggcg agggacgccc    13320
gctggtctcc gtgaacggc tcacgctgcg cccggtcacc gccgatcagg cggcggcgag    13380
ccgcgtcggc gggctgatgc accgggtggc ctggcgtccg tacgccctcg cctcgtccgg    13440
cgaacaggac ccgcacgcca cttcgtacgg gccgaccgcc gtcctcggca aggacgagct    13500
gaaggtcgcc gccgccctgg agtccgcggg cgtcgaagtc gggctctacc cgacctggc    13560 cgcgctgtcc caggacgtgg cggccggcgc cccggcgccc gtaccgtcc ttgccgct    13620 gcccgcgggt cccgccgacg gcggcgcgga gggtgtacgg ggcacggtgg cccggacgct    13680
ggagctgctc caggcctggc tggccgacga gcacctcgcg ggcacccgcc tgctcctggt    13740
cacccgcggt gcggtgcggg accccgaggg gtccggcgcc gacgatggcg gcgaggacct    13800
gtcgcacgcg gccgcctggg gtctcgtacg gaccgcgcag accgagaacc ccggccgctt    13860
cggccttctc gacctggccg acgacgcctc gtcgtaccgg accctgccgt cggtgctctc    13920
cgacgcgggc ctgcgcgacg aaccgcagct cgccctgcac gacggcacca tcaggctggc    13980
ccgcctggcc tcgtccggc ccgagaccgg caccgccgca ccggcgctcg ccccggaggg    14040
cacggtcctg ctgaccggcg gcaccggcgg cctgggcgga ctggtcgccc ggcacgtggt    14100
gggcgagtgg ggcgtacgac gcctgctgct ggtgagccgc cggggcacgg acgccccggg    14160
cgccgacgag ctcgtgcacg agctggaggc cctgggagcc gacgtctcgg tggccgcgtg    14220
cgacgtcgcc gaccgcgaag ccctcaccgc cgtactcgac gccatccccg ccgaacaccc    14280
gctcaccgcg gtcgtccaca cggcaggcgt cctctccgac ggcaccctcc cgtccatgac    14340 gacgaggac gtgaacacg tactgcgcc caaggtcgac gccgcgttcc tcctcgacga    14400
actcacctcg acgcccgcat acgacctggc agcgttcgtc atgttctcct ccgccgccgc    14460
```

```
cgtcttcggt ggcgcggggc agggcgccta cgccgccgcc aacgccaccc tcgacgccct    14520
cgcctggcgc cgccgggcag ccggactccc cgccctctcc ctcggctggg gcctctgggc    14580
cgagaccagc ggcatgaccg gcgagctcgg ccaggcggac ctgcgccgga tgagccgcgc    14640
gggcatcggc gggatcagcg acgccgaggg catcgcgctc ctcgacgccg ccctccgcga    14700
cgaccgccac ccggtcctgc tgcccctgcg gctcgacgcc gccgggctgc gggacgcggc    14760
cgggaacgac ccggccggaa tcccggcgct cttccgggac gtcgtcggcg ccaggaccgt    14820
ccgggcccgg ccgtccgcgg cctccgcctc gacgacagcc gggacggccg gcacgccggg    14880
gacggcggac ggcgcggcgg aaacggcggc ggtcacgctc ccgaccgggc cgccaccgt     14940 ggacgggccc gcacggcagc gcctgctgct cgagttcgtc gtcggcgagg tcgccgaagt    15000
actcggccac gcccgcggtc accggatcga cgccgaacgg ggcttcctcg acctcggctt    15060
cgactccctg accgccgtcg aactccgcaa ccggctcaac tccgccggtg gcctcgccct    15120
cccggcgacc ctggtcttcg accacccaag cccggcggca ctcgcctccc acctggacgc    15180
cgagctgccg cgcggcgcct cggaccagga cggagccggg aaccggaacg gaacgagaa     15240 cgggacgacg gcgtcccgga gcaccgccga gacggacgcg ctgctggcac aactgacccg    15300
cctggaaggc gccttggtgc tgacgggcct ctcggacgcc cccgggagcg aagaagtcct    15360
ggagcacctg cggtccctgc gctcgatggt cacgggcgag accggaccg ggaccgcgtc      15420 cggagccccg gacggcgccg ggtccggcgc cgaggaccgg ccctgggcgg ccggggacgg    15480 agccggggc gggagtgagg acggcgcggg agtgccggac ttcatgaacg cctcggccga     15540
ggaactcttc ggcctcctcg accaggaccc cagcacggac tgatccctgc cgcacggtcg    15600
cctcccgccc cggaccccgt cccgggcacc tcgactcgaa tcacttcatg cgcgcctcgg    15660
gcgcctccag gaactcaagg ggacagcgtg tccacggtga acgaagagaa gtacctcgac    15720
tacctgcgtc gtgccacggc ggacctccac gaggcccgtg gccgcctccg cgagctggag    15780
gcgaaggcgg gcgagccggt ggcgatcgtc ggcatggcct gccgcctgcc cggcggcgtc    15840
gcctcgcccg aggacctgtg gcggctggtg gccggcggcg aggacgcgat ctcggagttc    15900
ccccaggacc gcggctggga cgtggagggc ctgtacgacc cgaacccgga ggccacgggc    15960
aagagttacg cccgcgaggc cggattcctg tacgaggcgg gcgagttcga cgccgacttc    16020
ttcgggatct cgccgcgcga ggccctcgcc atggacccgc agcagcgtct cctcctggag    16080
gcctcctggg aggcgttcga gcacgccggg atcccggcgg ccaccgcgcg cggcacctcg    16140
gtcggcgtct tcaccggcgt gatgtaccac gactacgcca cccgtctcac cgatgtcccg    16200
gagggcatcg agggctacct gggcaccggc aactccggca gtgtcgcctc gggccgcgtc    16260
gcgtacacgc ttggcctgga ggggccggcc gtcacggtcg acaccgcctg ctcgtcctcg    16320
ctggtcgccc tgcacctcgc cgtgcaggcc ctgcgcaagg gcgaggtcga catggcgctc    16380
gccggcggcg tgacggtcat gtcgacgccc agcaccttcg tcgagttcag ccgtcagcgc    16440
gggctggcgc cggacggccg gtcgaagtcc ttctcgtcga cggccgacgg caccagctgg    16500
tccgagggcg tcggcgtcct cctcgtcgag cgcctgtccg acgcgcgtcg caagggccat    16560
cggatcctcg ccgtggtccg gggcaccgcc gtcaaccagg acggcccag cagcggcctc     16620 acggctccga acggccgtc gcagcagcgc gtcatccgac gtgccctggc ggacgcccgg    16680
ctcacgacct ccgacgtgga cgtcgtcgag gcccacggca cggtacgcg actcggcgac     16740 ccgatcgagg cgcaggccgt catcgccacg tacgggcagg gccgtgacgg cgaacagccg    16800
```

```
ctgcgcctcg ggtcgttgaa gtccaacatc ggacacaccc aggccgccgc cggtgtctcc   16860
ggcgtgatca agatggtcca ggcgatgcgc cacggcgtcc tgccgaagac gctccacgtg   16920
gagaagccga cggaccaggt ggactggtcc gcgggcgcgg tcgagctgct caccgaggcc   16980
atggactggc cggacaaggg cgacggcgga ctgcgcaggg ccgcggtctc ctccttcggc   17040
gtcagcggga cgaacgcgca cgtcgtgctc gaagaggccc cggcggccga ggagacccct   17100
gcctccgagg cgaccccggc cgtcgagccg tcggtcggcg ccggcctggt gccgtggctg   17160
gtgtcggcga agactccggc cgcgctggac gcccagatcg gacgcctcgc cgcgttcgcc   17220
tcgcagggcc gtacggacgc cgccgatccg ggcgcggtcg ctcgcgtact ggccggcggg   17280
cgcgccgagt tcgagcaccg ggccgtcgtg ctcggcaccg gacaggacga tttcgcgcag   17340
gcgctgaccg ctccggaagg actgatacgc ggcacgccct cggacgtggg ccgggtggcg   17400
ttcgtgttcc ccggtcaggg cacgcagtgg gccgggatgg gcgccgaact cctcgacgtg   17460
tcgaaggagt tcgcggcggc catggccgag tgcgagagcg cgctctcccg ctatgtcgac   17520
tggtcgctgg aggccgtcgt ccggcaggcg ccgggcgcgc ccacgctgga gcgggtcgac   17580
gtcgtccagc ccgtgacctt cgctgtcatg gtttcgctgg cgaaggtctg gcagcaccac   17640
ggcgtgacgc cgcaggccgt cgtcggccac tcgcagggcg agatcgccgc cgcgtacgtc   17700
gccggtgccc tcaccctcga cgacgccgcc cgcgtcgtca ccctgcgcag caagtccatc   17760 gccgccacc tcgccggcaa gggcggcatg atctccctcg ccctcagcga ggaagccacc   17820
cggcagcgca tcgagaacct ccacggactg tcgatcgccg ccgtcaacgg ccccaccgcc   17880
accgtggttt cgggcgaccc cacccagatc caagagctcg ctcaggcgtg tgaggccgac   17940
ggggtccgcg cacggatcat ccccgtcgac tacgcctccc acagcgccca cgtcgagacc   18000
atcgagagcg aactcgccga ggtcctcgcc gggctcagcc cgcggacacc tgaggtgccg   18060
ttcttctcga cactcgaagg cgcctggatc accgagccgg tgctcgacgg cacctactgg   18120
taccgcaacc tccgccaccg cgtcggcttc gccccgccg tcgagaccct cgccaccgac   18180
gaaggcttca cccacttcat cgaggtcagc gcccaccccg tcctcaccat gacccctccc   18240
gagaccgtca ccggcctcgg caccctccgc cgcgaacagg gaggccagga cgtctggtc   18300 acctcactcg ccgaagcctg gaccaacggc ctcaccatcg actgggcgcc cgtcctcccc   18360
accgcaaccg gccaccaccc cgagctcccc acctacgcct tccagcgccg tcactactgg   18420
ctccacgact ccccgccgt ccagggctcc gtgcaggact cctggcgcta ccgcatcgac   18480
tggaagcgcc tcgcggtcgc cgacgcgtcc gagcgcgccg ggctgtccgg cgctggctc   18540 gtcgtcgtcc ccgaggaccg ttccgccgag gccgccccgg tgctcgccgc gctgtccggc   18600
gccggcgccg accccgtaca gctggacgtg tccccgctgg gcgaccggca gcggctcgcc   18660
gcgacgctgg gcgaggccct ggcggcggcc ggtggagccg tcgacggcgt cctctcgctg   18720
ctcgcgtggg acgagagcgc gcaccccggc caccccgccc ccttcacccg gggcaccggc   18780
gccaccctca ccctggtgca ggcgctggag gacgccggcg tcgccgcccc gctgtggtgc   18840
gtgacccacg gcgcggtgtc cgtcggccgg gccgaccacg tcacctcccc cgcccaggcc   18900
atggtgtggg gcatgggccg ggtcgccgcc ctggagcacc ccgagcggtg gggcggcctg   18960
atcgacctgc cctcggacgc cgaccgggcg gccctggacc gcatgaccac ggtcctcgcc   19020
ggcggtacgg gtgaggacca ggtcgcggta cgcgcctccg ggctgctcgc ccgccgcctc   19080
gtccgcgcct ccctcccggc gcacggcacg gcttcgccgt ggtggcaggc cgacggcacg   19140
gtgctcgtca ccggtgccga ggagcctgcg gccgccgagg ccgcacgccg gctggcccgc   19200
```

```
gacggcgccg gacacctcct cctccacacc accccctccg gcagcgaagg cgccgaaggc   19260
acctccggtg ccgccgagga ctccggcctc gccgggctcg tcgccgaact cgcggacctg   19320
ggcgcgacgg ccaccgtcgt gacctgcgac ctcacggacg cggaggcggc cgcccggctg   19380
ctcgccggcg tctccgacgc gcacccgctc agcgccgtcc tccacctgcc gcccaccgtc   19440
gactccgagc cgctcgccgc gaccgacgcg gacgcgctcc ccgtgtcgt gaccgcgaag   19500
gccaccgccg cgctccacct ggaccgcctc ctgcgggagg ccgcggctgc cggaggccgt   19560
ccgcccgtcc tggtcctctt ctcctcggtc gccgcgatct ggggcggcgc cggtcagggc   19620
gcgtacgccg ccggtacggc cttcctcgac gccctcgccg gtcagcaccg gccgacggc    19680
cccaccgtga cctcggtggc ctggagcccc tgggagggca gccgcgtcac cgagggtgcg   19740
accggggagc ggctgcgccg cctcggcctg cgcccctcg ccccgcgac ggcgctcacc     19800
gccctggaca ccgcgctcgg ccacggcgac accgccgtca cgatcgccga cgtcgactgg   19860
tcgagcttcg cccccggctt caccacggcc cggccgggca cctcctcgc cgatctgccc    19920
gaggcgcgcc gcgcgctcga cgagcagcag tcgacgacgg ccgccgacga caccgtcctg   19980
agccgcgagc tcggtgcgct caccggcgcc gaacagcagc gccgtatgca ggagttggtc   20040
cgcgagcacc tcgccgtggt cctcaaccac ccctcccccg aggccgtcga cacggggcgg   20100
gccttccgtg acctcggatt cgactcgctg acggcggtcg agctccgcaa ccgcctcaag   20160
aacgccaccg gcctggccct cccggccact ctggtcttcg actacccgac ccccggacg    20220
ctggcggagt tcctcctcgc ggagatcctg ggcgagcagg ccggtgccgg cgagcagctt   20280
ccggtggacg gcggggtcga cgacgagccc gtcgcgatcg tcggcatggc cgtgccgcctg  20340
ccgggcggtg tcgcctcgcc ggaggacctg tggcggctgg tggccggcgg cgaggacgcg   20400
atctccggct tcccgcagga ccgcggctgg gacgtggagg ggctgtacga cccggacccg   20460
gacgcgtccg ggcggacgta ctgccgtgcc ggtggcttcc tcgacgaggc gggcgagttc   20520
gacgccgact tcttcgggat ctcgccgcgc gaggccctcg ccatggaccc gcagcagcgg   20580
ctcctcctgg agacctcctg ggaggccgtc gaggacgccg ggatcgaccc gacctcccttt  20640
caggggcagc aggtcggcgt gttcgcgggc accaacggcc cccactacga gccgctgctc   20700
cgcaacaccg ccgaggatct tgagggttac gtcgggacgg gcaacgccgc cagcatcatg   20760
tcgggccgtg tctcgtacac cctcggcctg gagggcccgg ccgtcacggt cgacaccgcc   20820
tgctcctcct cgctggtcgc cctgcacctc gccgtgcagg ccctgcgcaa gggcgaatgc   20880
ggactggcgc tcgcgggcgg tgtgacggtc atgtcgacgc ccacgacgtt cgtggagttc   20940
agccggcagc gcgggctcgc ggaggacggc cggtcgaagg cgttcgccgc gtcggcggac   21000
ggcttcggcc cggcggaggg cgtcggcatg ctcctcgtcg agcgcctgtc ggacgcccgc   21060
cgcaacggac accgtgtgct ggcggtcgtg cgcggcagcc cggtcaacca ggacggcgcg   21120
agcaacggcc tgaccgcccc gaacgggccc tcgcagcagc gcgtcatccg gcgcgcgctc   21180
gcggacgccc gactgacgac cgccgacgtg gacgtcgtcg aggcccacgg cacgggcacg   21240
cgactcggcg acccgatcga ggcacaggcc ctcatcgcca cctacggcca ggggcgcgac   21300
accgaacagc cgctgcgcct gggtcgttaa aagtccaaca tcggacacac ccaggccgcc   21360
gccggtgtct ccggcatcat caagatggtc caggcgatgc ccacggcgt cctgccgaag    21420
acgtccacg tggaccggcc gtcggaccag atcgactggt cggcgggcac ggtcgagctg    21480
ctcaccgagg ccatggactg gccgaggaag caggagggcg ggctgcgccg cgcggccgtc   21540
```

-continued

```
tcctccttcg gcatcagcgg cacgaacgcg cacatcgtgc tcgaagaagc ccgtcgac      21600
gaggacgccc cggcggacga gccgtcggtc ggcggtgtgg tgccgtggct cgtgtccgcg    21660
aagactccgg ccgcgctgga cgcccagatc ggacgcctcg ccgcgttcgc ctcgcagggc    21720
cgtacggacg ccgccgatcc gggcgcggtc gctcgcgtac tggccggcgg gcgtgcgcag    21780
ttcgagcacc gggccgtcgc gctcggcacc ggacaggacg acctggcggc cgcactggcc    21840
gcgcctgagg gtctggtccg gggtgtggcc tccggtgtgg gtcgagtggc gttcgtgttc    21900
ccgggacagg gcacgcagtg ggccgggatg ggtgccgaac tcctcgacgt gtcgaaggag    21960
ttcgcggcgg ccatggccga gtgcgaggcc gcgctcgctc cgtacgtgga ctggtcgctg    22020
gaggccgtcg tccgacaggc ccccggcgcg cccacgctgg agcgggtcga tgtcgtccag    22080
cccgtgacgt tcgccgtcat ggtctcgctg gcgaaggtct ggcagcacca cggggtgacc    22140
ccgcaagccg tcgtcggcca ctcgcagggc gagatcgccg ccgcgtacgt cgccggtgcc    22200
ctgagcctgg acgacgccgc tcgtgtcgtg accctgcgca gcaagtccat cggcgcccac    22260
ctcgcgggcc agggcggcat gctgtccctc gcgctgagcg aggcggccgt tgtggagcga    22320
ctggccgggt tcgacgggct gtccgtcgcc gccgtcaacg ggcctaccgc caccgtggtt    22380
tcgggcgacc cgacccagat ccaagagctc gctcaggcgt gtgaggccga cggggtccgc    22440
gcacggatca tccccgtcga ctacgcctcc cacagcgccc acgtcgagac catcgagagc    22500
gaactcgccg acgtcctggc gggggttgtcc cccagacac cccaggtccc cttcttctcc    22560
accctcgaag gcgcctggat caccgaaccc gccctcgacg gcggctactg gtaccgcaac    22620
ctccgccatc gtgtgggctt cgccccggcc gtcgaaaccc tggccaccga cgaaggcttc    22680
acccacttcg tcgaggtcag cgcccacccc gtcctcacca tggcgctgcc cgagaccgtc    22740
accggactcg gcaccctccg ccgtgacaac ggcggacagc accgcctcac cacctccctc    22800
gccgaggcct gggccaacgg cctcaccgtc gactgggcct ctctcctccc caccacgacc    22860
acccaccccg atctgcccac ctacgccttc cagaccgagc gctactggcc gcagcccgac    22920
ctctccgccg ccggtgacat cacctccgcc ggtctcgggg cggccgagca cccgctgctc    22980
ggcgcggccg tggcgctcgc ggactccgac ggctgcctgc tcacggggag cctctccctc    23040
cgtacgcacc cctggctggc ggaccacgcg gtggccggca ccgtgctgct gccgggaacg    23100
gcgttcgtgg agctggcgtt ccgagccggg gaccaggtcg gttgcgatct ggtcgaggag    23160
ctcaccctcg acgcgccgct cgtgctgccc cgtcgtggcg cggtccgtgt gcagctgtcc    23220
gtcggcgcga gcgacgagtc cgggcgtcgt accttcgggc tctacgcgca cccggaggac    23280
gcgccgggcg aggcggagtg gacgcggcac gccaccggtg tgctggccgc ccgtgcggac    23340
cgcaccgccc ccgtcgccga cccggaggcc tggccgccgc cgggcgccga gccggtggac    23400
gtggacggtc tgtacgagcg cttcgcggcg aacggctacg gctacggccc cctcttccag    23460
ggcgtccgtg gtgtctggcg gcgtggcgac gaggtgttcg ccgacgtggc cctgccggcc    23520
gaggtcgccg gtgccgaggg cgcgcggttc ggccttcacc cggcgctgct cgacgccgcc    23580
gtgcaggcgg ccggtgcggg ccggggcgtt cggcgcgggc acgcggctgc cgttcgcctg    23640
gagcgggatc tcctgtacgc ggtcggcgcc accgccctcc gcgtgcggct ggcccccgcc    23700
ggcccggaca cggtgtccgt gagcgccgcc gactcctccg gcagccggt gttcgccgcg    23760
gactccctca cggtgctgcc cgtcgacccc gcgcagctgg cggccttcag cgacccgact    23820
ctggacgcgc tgcacctgct ggagtggacc gcctgggacg gtgccgcgca ggccctgccc    23880
ggcgcgtcg tgctgggcgg cgacgccgac ggtctcgccg cggcgctgcg cgccggtggc    23940
```

```
accgaggtcc tgtccttccc ggaccttacg gacctggtgg aggccgtcga ccggggcgag   24000 acccccggccc cggcgaccgt cctggtggcc tgcccccgccg ccggccccga tgggccggag   24060
catgtccgcg aggccctgca cgggtcgctc gcgctgatgc aggcctggct ggccgacgag   24120
cggttcaccg atgggcgcct ggtgctcgtg acccgcgacg cggtcgccgc ccgttccggc   24180
gacggcctgc ggtccacggg acaggccgcc gtctgggcc tcggccggtc cgcgcagacg   24240
gagagcccgg gccggttcgt cctgctcgac ctcgccgggg aagcccggac ggccggggac   24300
gccaccgccg gggacggcct gacgaccggg gacgccaccg tcggcggcac ctctggagac   24360
gccgccctcg gcagcgccct cgcgaccgcc ctcggctcgg gcgagccgca gctcgccctc   24420
cgggacgggg cgctcctcgt accccgcctg gcgcggggcc ccgcgcccgc cgcggccgac   24480
ggcctcgccg cggccgacgg cctcgccgct ctgccgctgc ccgccgctcc ggccctctgg   24540
cgtctggagc ccggtacgga cggcagcctg gagagcctca cggcggcgcc cggcgacgcc   24600
gagaccctcg ccccggagcc gctcggcccg ggacaggtcc gcatcgcgat ccgggccacc   24660
ggtctcaact tccgcgacgt cctgatcgcc ctcggcatgt accccgatcc ggcgctgatg   24720
ggcaccgagg gagccggcgt ggtcaccgcg accggccccg gcgtcacgca cctcgccccc   24780
ggcgaccggg tcatgggcct gctctccggc gcgtacgccc cggtcgtcgt ggcggacgcg   24840
cggaccgtcg cgcggatgcc cgaggggtgg acgttcgccc agggcgcctc cgtgccggtg   24900
gtgttcctga cggccgtcta cgccctgcgc gacctggcgg acgtcaagcc cggcgagcgc   24960
ctcctggtcc actccgccgc cggtggcgtg ggcatggccg ccgtgcagct cgcccggcac   25020 tgggcgtgg aggtccacgg cacggcgagt cacgggaagt gggacgccct gcgcgcgctc   25080
ggcctggacg acgcgcacat cgcctcctcc cgcaccctgg acttcgagtc cgcgttccgt   25140
gccgcttccg gcggggcggg catggacgtc gtactgaact cgctcgcccg cgagttcgtc   25200
gacgcctcgc tgcgcctgct cgggccgggc ggccggttcg tggagatggg gaagaccgac   25260
gtccgcgacg cggagcgggt cgccgccgac cacccccggtg tcggctaccg cgccttcgac   25320
ctgggcgagg ccgggccgga gcggatcggc gagatgctcg ccgaggtcat cgccctcttc   25380
gaggacgggg tgctccggca cctgcccgtc acgacctggg acgtgcgccg ggcccgcgac   25440
gccttccggc acgtcagcca ggcccgccac acgggcaagg tcgtcctcac gatgccgtcg   25500
ggcctcgacc cggagggtac ggtcctgctg accggcggca ccggtgcgct gggggggcatc   25560 gtggcccggc acgtggtggg cgagtggggc gtacgacgcc tgctgctcgt gagccggcgg   25620
ggcacggacg ccccgggcgc cggcgagctc gtgcacgagc tggaggccct gggagccgac   25680
gtctcggtgg ccgcgtgcga cgtcgccgac cgcgaagccc tcaccgccgt actcgactcg   25740
atccccgccg aacacccgct caccgcggtc gtccacacgg caggcgtcct ctccgacggc   25800 accctccccct cgatgacagc ggaggatgtg aacacgtac tgcgtcccaa ggtcgacgcc   25860
gcgttcctcc tcgacgaact cacctcgacg cccggctacg acctggcagc gttcgtcatg   25920
ttctcctccg ccgcgccgt cttcggtggc gcggggcagg gcgcctacgc cgccgccaac   25980 gccacccctcg acgccctcgc ctggcgccgc cggacagccg gactccccgc cctctccctc   26040
ggctggggcc tctgggccga ccagcggcg atgaccggcg gactcagcga caccgaccgc   26100
tcgcggctgg cccgttccgg ggcgacgccc atggacagcg agctgaccct gtccctcctg   26160
gacgcggcca tgcgccgcga cgacccgcg ctcgtcccga tcgccctgga cgtcgccgcg   26220
ctccgcgccc agcagcgcga cggcatgctg gcgccgctgc tcagcgggct caccccgcgga   26280
```

```
tcgcgggtcg gcggcgcgcc ggtcaaccag cgcagggcag ccgccggagg cgcgggcgag   26340
gcggacacgg acctcggcgg gcggctcgcc gcgatgacac cggacgaccg ggtcgcgcac   26400
ctgcgggacc tcgtccgtac gcacgtggcg accgtcctgg acacggcac cccgagccgg    26460 gtggacctgg agcgggcctt ccgcgacacc ggtttcgact cgctcaccgc cgtcgaactc   26520
cgcaaccgtc tcaacgccgc gaccgggctg cggctgccgg ccacgctggt cttcgaccac   26580 cccacccccgg gggagctcgc cgggcacctg ctcgacgaac tcgccacggc cgcgggcggg   26640
tcctgggcga aggcaccggg gtccggagac acggcctcgg cgaccgatcg gcagaccacg   26700
gcggccctcg ccgaactcga ccggctggaa ggcgtgctcg cctccctcgc gcccgccgcc   26760
ggcggccgtc cggagctcgc cgcccggctc agggcgctgg ccgcggccct gggggacgac   26820
ggcgacgacg ccaccgacct ggacgaggcg tccgacgacg acctcttctc cttcatcgac   26880
aaggagctgg gcgactccga cttctgacct gcccgacacc accggcacca ccggcaccac   26940
cagcccccct cacacacgga acacggaacg gacaggcgag aacgggagcc atggcgaaca   27000
acgaagacaa gctccgcgac tacctcaagc gcgtcaccgc cgagctgcag cagaacacca   27060
ggcgtctgcg cgagatcgag ggacgcacgc acgagccggt ggcgatcgtg ggcatggcct   27120
gccgcctgcc gggcggtgtc gcctcgcccg aggacctgtg gcagctggtg gccgggacg    27180 gggacgcgat ctcggagttc ccgcaggacc gcggctggga cgtggagggg ctgtacgacc   27240
ccgacccgga cgcgtccggc aggacgtact gccggtccgg cggattcctg cacgacgccg   27300
gcgagttcga cgccgacttc ttcgggatct cgcccgcgcg ggcccctcgcc atggaccgcg   27360 agcagcgact gtccctcacc accgcgtggg aggcgatcga gagcgcgggc atcgacccga   27420
cggccctgaa gggcagcggc ctcggcgtct tcgtcggcgg ctggcacacc ggctacacct   27480
cggggcagac caccgccgtg cagtcgcccg agctggaggg ccacctggtc agcggcgcgg   27540
cgctgggctt cctgtccggc cgtatcgcgt acgtcctcgg tacggacgga ccggccctga   27600
ccgtggacac ggcctgctcg tcctcgctgg tcgccctgca cctcgccgtg caggccctcc   27660
gcaagggcga gtgcgacatg gccctcgccg gtggtgtcac ggtcatgccc aacgcggacc   27720
tgttcgtgca gttcagccgg cagcgcgggc tggccgcgga cggccggtcg aaggcgttcg   27780
ccacctcggc ggacgcttc ggccccgcgg agggcgccgg agtcctgctg gtggagcgcc    27840
tgtcggacgc ccgccgcaac ggacaccgga tcctcgcggt cgtccgcggc agcgcggtca   27900
accaggacgc cgccagcaac ggcctcacgg ctccgcacgg gccctcccag cagcgcgtca   27960
tccgacgggc cctggcggac gcccggctcg cgccgggtga cgtggacgtc gtcgaggcgc   28020 acggcacgg cacgcggctc ggcgaccgc tcgaggcgca ggccctcatc gccacctacg    28080
gccaggagaa gagcagcgaa cagccgctga ggctgggcgc gttgaagtcg aacatcgggc   28140
acacgcaggc cgcggccggt gtcgcaggtg tcatcaagat ggtccaggcg atgcgccacg   28200
gactgctgcc gaagacgctg cacgtcgacg agccctcgga ccagatcgac tggtcggcgg   28260
gcacggtgga actcctcacc gaggccgtcg actggccgga gaagcaggac ggcgggctgc   28320
gccgcgcggc tgtctcctcc ttcggcatca gcgggacgaa cgcgcacgtc gtcctggagg   28380 aggcccggc ggtcgaggac tccccggccg tcgagccgcc ggccggtggc ggtgtggtgc    28440
cgtggccggt gtccgcgaag actccggccg cgctggacgc ccagatcggg cagctcgccg   28500
cgtacgcgga cggtcgtacg gacgtggatc cggcggtggc cgcccgcgcc ctggtcgaca   28560
gccgtacgga gatggagcac cgcgcggtcg cggtcggcga cagccgggag gcactgcggg   28620
acgccctgcg gatgccggaa ggactggtac gcggcacgtc ctcggacgtg ggccgggtgg   28680
```

-continued

```
cgttcgtctt ccccggccag ggcacgcagt gggccggcat gggcgccgaa ctccttgaca   28740
gctcaccgga gttcgctgcc tcgatggccg aatgcgagac cgcgctctcc cgctacgtcg   28800
actggtctct tgaagccgtc gtccgacagg aacccggcgc acccacgctc gaccgcgtcg   28860
acgtcgtcca gcccgtgacc ttcgctgtca tggtctcgct ggcgaaggtc tggcagcacc   28920
acggcatcac ccccaggcc gtcgtcggcc actcgcaggg cgagatcgcc gccgcgtacg   28980
tcgccggtgc actcaccctc gacgacgccg cccgcgtcgt caccctgcgc agcaagtcca   29040
tcgccgccca cctcgccggc aagggcggca tgatctccct cgccctcgac gaggcggccg   29100
tcctgaagcg actgagcgac ttcgacggac tctccgtcgc cgccgtcaac ggccccaccg   29160
ccaccgtcgt ctccggcgac ccgacccaga tcgaggaact cgcccgcacc tgcgaggccg   29220
acggcgtccg tgcgcggatc atcccggtcg actacgcctc ccacagccgg caggtcgaga   29280
tcatcgagaa ggagctggcc gaggtcctcg ccggactcgc cccgcaggct ccgcacgtgc   29340
cgttcttctc caccctcgaa ggcacctgga tcaccgagcc ggtgctcgac ggcacctact   29400
ggtaccgcaa cctgcgccat cgcgtgggct tcgccccgc cgtggagacc ttggcggttg   29460
acggcttcac ccacttcatc gaggtcagcg cccacccgt cctcaccatg accctccccg   29520
agaccgtcac cggcctcggc accctccgcc gcgaacaggg aggccaggag cgtctggtca   29580
cctcactcgc cgaagcctgg gccaacggcc tcaccatcga ctgggcgccc atcctcccca   29640
ccgcaaccgg ccaccacccc gagctcccca cctacgcctt ccagaccgag cgcttctggc   29700
tgcagagctc cgcgcccacc agcgccgccg acgactggcg ttaccgcgtc gagtggaagc   29760
cgctgacggc ctccggccag gcggaccgtgt ccgggcggtg gatcgtcgcc gtcgggagcg   29820
agccagaagc cgagctgctg ggcgcgctga aggccgcggg agcggaggtc gacgtactgg   29880
aagccggggc ggacgacgac cgtgaggccc tcgccgcccg gctcaccgca ctgacgaccg   29940
gcgacggctt caccggcgtg gtctcgctcc tcgacgacct cgtgccacag gtcgcctggg   30000
tgcaggcact cggcgacgcc ggaatcaagg cgccctgtg gtccgtcacc cagggcgcgg   30060
tctccgtcgg acgtctcgac accccgccg accccgaccg ggccatgctc tggggcctcg   30120
gccgcgtcgt cgcccttgag caccccgaac gctgggccgg cctcgtcgac ctccccgccc   30180
agcccgatgc cgccgccctc gcccacctcg tcaccgcact ctccggcgcc accggcgagg   30240
accagatcgc catccgcacc accggactcc acgcccgccg cctcgcccgc gcacccctcc   30300
acggacgtcg gcccacccgc gactggcagc cccacgcac cgtcctcatc accggcggca   30360
ccggagccct cggcagccac gccgcacgct ggatggccca ccacgagcc gaacacctcc   30420 tcctcgtcag ccgcagcggc gaacaagccc ccggagccac ccaactcacc gccgaactca   30480
ccgcatcggg cgcccgcgtc accatcgccg cctgcgacgt cgccgacccc cacgccatgc   30540
gcaccctcct cgacgccatc cccgccgaga cgccctcac cgccgtcgtc cacaccgccg   30600
gcgcaccggg cggcgatccg ctggacgtca ccggcccgga ggacatcgcc cgcatcctgg   30660
gcgcgaagac gagcggcgcc gaggtcctcg acgacctgct ccgcggcact ccgctggacg   30720
ccttcgtcct ctactcctcg aacgccgggg tctggggcag cggcagccag ggcgtctacg   30780
cggcggccaa cgcccacctc gacgcgctcg ccgcccggcg ccgcgccgg ggcgagacgg   30840 cgacctcggt cgcctggggc ctctgggccg gcgacggcat gggccggggc gccgacgacg   30900
cgtactggca gcgtcgcggc atccgtccga tgagcccga ccgcgcctg gacgaactgg   30960 ccaaggccct gagccacgac gagaccttcg tcgccgtggc cgatgtcgac tgggagcggt   31020
```

```
tcgcgcccgc gttcacggtg tcccgtccca gccttctgct cgacggcgtc ccggaggccc   31080
ggcaggcgct cgccgcaccc gtcggtgccc cggctcccgg cgacgccgcc gtggcgccga   31140
ccgggcagtc gtcggcgctg gccgcgatca ccgcgctccc cgagcccgag cgccggccga   31200
cgctcctcac cctcgtccgt acccacgcgg cggccgtact cggccattcc tccccgacc    31260 gggtggcccc cggccgtgcc ttcaccgagc tcggcttcga ctcgctgacg gccgtgcagc   31320
tccgcaacca gctctccacg gtggtcggca acaggctccc cgccaccacg gtcttcgacc   31380
acccgacgcc cgccgcactc gccgcgcacc tccacgaggc gtacctcgca ccggccgagc   31440
cggccccgac ggactgggag gggcgggtgc gccgggccct ggccgaactg cccctcgacc   31500
ggctgcggga cgcgggggtc ctcgacaccg tcctgcgcct caccggcatc gagcccgagc   31560
cgggttccgg cggttcggac ggcggcgccg ccgaccctgg tgcggagccg gaggcgtcga   31620
tcgacgacct ggacgccgag gccctgatcc ggatggctct cggcccccgt aacacctgac   31680
ccgaccgcgg tcctgcccca cgcgccgcac cccgcgcatc ccgcgcacca cccgccccca   31740
cacgcccaca accccatcca cgagcggaag accacaccca gatgacgagt tccaacgaac   31800
agttggtgga cgctctgcgc gcctctctca aggagaacga agaactccgg aaagagagcc   31860
gtcgccgggc cgaccgtcgg caggagccca tggcgatcgt cggcatgagc tgccggttcg   31920
cgggcggaat ccggtccccc gaggacctct ggacgcgcgt cgccgcgggc aaggacctgg   31980
tctccgaggt accggaggag cgcggctggg acatcgactc cctctacgac ccggtgcccg   32040
ggcgcaaggg cacgacgtac gtccgcaacg ccgcgttcct cgacgacgcc gccggattcg   32100
acgcggcctt cttcgggatc tcgccgcgcg aggccctcgc catggacccg cagcagcggc   32160
agctcctcga agcctcctgg gaggtcttcg agcgggccgg catcgacccc gcgtcggtcc   32220
gcggcaccga cgtcggcgtg tacgtgggct gtggctacca ggactacgcg ccggacatcc   32280
gggtcgcccc cgaaggcacc ggcggttacg tcgtcaccgg caactcctcc gccgtggcct   32340
ccgggcgcat cgcgtactcc ctcggcctgg agggacccgc cgtgaccgtg gacacggcgt   32400
gctcctcttc gctcgtcgcc ctgcacctcg ccctgaaggg cctgcggaac ggcgactgct   32460
cgacggcact cgtgggcggc gtggccgtcc tcgcgacgcc gggcgcgttc atcgagttca   32520
gcagccagca ggccatggcc gccgacggcc ggaccaaggg cttcgcctcg gcggcggacg   32580
gcctcgcctg gggcgagggc gtcgccgtac tcctcctcga acggctctcc gacgcgcggc   32640
gcaagggcca ccgggtcctg gccgtcgtgc gggcagcgc catcaaccag gacggcgcga   32700
gcaacggcct cacggctccg cacgggccct cccagcagca cctgatccgc caggccctgg   32760
ccgacgcgcg gctcacgtcg agcgacgtgg acgtcgtgga gggccacggc acggggaccc   32820
gtctcggcga cccgatcgag gcgcaggcgc tgctcgccac gtacgggcag gggcgcgccc   32880
cggggcagcc gctgcggctg gggacgctga agtcgaacat cgggcacacg caggccgctt   32940
cgggtgtcgc cggtgtcatc aagatggtgc aggcgctgcg ccacggggtg ctgccgaaga   33000
ccctgcacgt ggacgagccg acggaccagg tcgactggtc ggccggttcg gtcgagctgc   33060
tcaccgaggc cgtggactgg ccggagcggc cgggccggct ccgccgggcg ggcgtctccg   33120
cgttcggcgt gggcgggacg aacgcgcacg tcgtcctgga ggaggccccg gcggtcgagg   33180
agtcccctgc cgtcgagccg ccggccggtg gcggcgtggt gccgtggccg gtgtccgcga   33240
agacctcggc cgcactggac gcccagatcg ggcagctcgc cgcatacgcg gaagaccgca   33300
cggacgtgga tccggcggtg gccgcccgcg ccctggtcga cagccgtacg gcgatggagc   33360
accgcgcggt cgcggtcggc gacagccggg aggcactgcg ggacgccctg cggatgccgg   33420
```

```
aaggactggt acggggcacg gtcaccgatc cgggccgggt ggcgttcgtc ttccccggcc    33480
agggcacgca gtgggccggc atgggcgccg aactcctcga cagctcaccc gaattcgccg    33540
ccgccatggc cgaatgcgag accgcactct ccccgtacgt cgactggtct ctcgaagccg    33600
tcgtccgaca ggctcccagc gcaccgacac tcgaccgcgt cgacgtcgtc cagcccgtca    33660
ccttcgccgt catggtctcc ctcgccaagg tctggcagca ccacggcatc accccgagg     33720 ccgtcatcgg ccactcccag ggcgagatcg ccgccgcgta cgtcgccggt gccctcaccc    33780
tcgacgacgc cgctcgtgtc gtgacccctcc gcagcaagtc catcgccgcc cacctcgccg   33840
gcaagggcgg catgatctcc ctcgccctca gcgaggaagc cacccggcag cgcatcgaga    33900
acctccacgg actgtcgatc gccgccgtca acgggcctac cgccaccgtg gtttcgggcg    33960
accccaccca gatccaagaa cttgctcagg cgtgtgaggc cgacggcatc cgcgcacgga    34020
tcatccccgt cgactacgcc tcccacagcg cccacgtcga gaccatcgag aacgaactcg    34080
ccgacgtcct ggcggggttg tccccccaga caccccaggt cccccttcttc tccacccctcg   34140 aaggcacctg gatcaccgaa cccgccctcg acggcggcta ctggtaccgc aacctccgcc    34200
atcgtgtggg cttcgccccg gccgtcgaga ccctcgccac cgacgaaggc ttcacccact    34260
tcatcgaggt cagcgcccac cccgtcctca ccatgaccct ccccgacaag gtcaccggcc    34320 tggccacccct ccgacgcgag gacggcggac agcaccgcct caccacctcc cttgccgagg    34380
cctgggccaa cggcctcgcc ctcgactggg cctccctcct gccgccacg ggcgccctca     34440 gccccgccgt ccccgacctc ccgacgtacg ccttccagca ccgctcgtac tggatcagcc    34500
ccgcgggtcc cggcgaggcg cccgcgcaca ccgcttccgg gcgcgaggcc gtcgccgaga    34560
cggggctcgc gtggggcccg ggtgccgagg acctcgacga ggagggccgg cgcagcgccg    34620
tactcgcgat ggtgatgcgg caggcggcct ccgtgctccg gtgcgactcg cccgaagagg    34680
tccccgtcga ccgcccgctg cgggagatcg gcttcgactc gctgaccgcc gtcgacttcc    34740
gcaaccgcgt caaccggctg accggtctcc agctgccgcc caccgtcgtg ttccagcacc    34800
cgacgcccgt cgcgctcgcc gagcgcatca gcgacgagct ggccgagcgg aactgggccg    34860
tcgccgagcc gtcggatcac gagcaggcgg aggaggagaa ggccgccgct ccggcggggg    34920
cccgctccgg ggccgacacc ggcgccggcg ccgggatgtt ccgcgccctg ttccggcagg    34980
ccgtggagga cgaccggtac ggcgagttcc tcgacgtcct cgccgaagcc tccgcgttcc    35040
gcccgcagtt cgcctcgccc gaggcctgct cggagcggct cgacccggtg ctgctcgccg    35100
gcggtccgac ggaccgggcg gaaggccgtg ccgttctcgt cggctgcacc ggcaccgcgg    35160
cgaacggcgg cccgcacgag ttcctgcggc tcagcacctc cttccaggag gagcgggact    35220
tcctcgccgt acctctcccc ggctacggca cgggtacggg caccggcacg gccctcctcc    35280
cggccgatct cgacaccgcg ctcgacgccc aggcccgggc gatcctccgg gccgccgggg    35340 acgccccgt cgtcctgctc gggcactccg gcggcgccct gctcgcgcac gagctggcct    35400
tccgcctgga gcgggcgcac ggcgcgccgc cggccggat cgtcctggtc gacccctatc    35460
cgccgggcca tcaggagccc atcgaggtgt ggagcaggca gctgggcgag ggcctgttcg    35520
cgggcgagct ggagccgatg tccgatgcgc ggctgctggc catgggccgg tacgcgcggt    35580
tcctcgccgg cccgcggccg gccgcagca gcgcgcccgt gcttctggtc cgtgcctccg     35640
aaccgctggg cgactggcag gaggagcggg gcgactggcg tgcccactgg gaccttccgc    35700
acaccgtcgc ggacgtgccg ggcgaccact tcacgatgat gcgggaccac gcgccggccg    35760
```

-continued

```
tcgccgaggc cgtcctctcc tggctcgacg ccatcgaggg catcgagggg gcgggcaagt    35820
gaccgacaga cctctgaacg tggacagcgg actgtggatc cggcgcttcc accccgcgcc    35880
gaacagcgcg gtgcggctgg tctgcctgcc gcacgccggc ggctccgcca gctacttctt    35940
ccgcttctcg gaggagctgc acccctccgt cgaggccctg tcggtgcagt atccgggccg    36000
ccaggaccgg cgtgccgagc cgtgtctgga gagcgtcgag gagctcgccg agcatgtggt    36060
cgcggccacc gaaccctggt ggcaggaggg ccggctggcc ttcttcgggc acagcctcgg    36120
cgcctccgtc gccttcgaga cggcccgcat cctggaacag cggcacgggg tacgcccga    36180 gggcctgtac gtctccggtc ggcgcgcccc gtcgctggcg ccggaccggc tcgtccacca    36240
gctggacgac cgggcgttcc tggccgagat ccggcggctc agcggcaccg acgagcggtt    36300
cctccaggac gacgagctgc tgcggctggt gctgcccgcg ctgcgcagcg actacaaggc    36360
ggcggagacg tacctgcacc ggccgtccgc caagctcacc tgcccggtga tggccctggc    36420
cggcgaccgt gacccgaagg cgccgctgaa cgaggtggcc gagtggcgtc ggcacaccag    36480
cgggccgttc tgcctccggg cgtactccgg cggccacttc tacctcaacg accagtggca    36540
cgagatctgc aacgacatct ccgaccacct gctcgtcacc cgcggcgcgc ccgatgcccg    36600
cgtcgtgcag cccccgacca gccttatcga aggagcggcg aagagatggc agaacccacg    36660
gtgaccgacg acctgacggg ggcctcacg cagccccgc tgggccgcac cgtccgcgcg    36720
gtggccgacc gtgaactcgg cacccacctc ctggagaccc gcggcatcca ctggatcc      36778
```

<210> SEQ ID NO: 6
<211> LENGTH: 11877
<212> TYPE: PRT
<213> ORGANISM: Streptomyces venezuelae

<400> SEQUENCE: 6

```
Met Ala Met Arg Asp Ser Ile Pro Arg Arg Ala Asp Arg Asp Thr Leu
 1               5                   10                  15

Arg Arg Glu Leu Gly Gln Asn Phe Leu Gln Asp Asp Arg Ala Val Arg
            20                  25                  30

Asn Leu Val Thr His Val Glu Gly Asp Gly Arg Asn Val Leu Glu Ile
        35                  40                  45

Gly Pro Gly Lys Gly Ala Ile Thr Glu Glu Leu Val Arg Ser Phe Asp
    50                  55                  60

Thr Val Thr Val Val Glu Met Asp Pro His Trp Ala Ala His Val Arg
65                  70                  75                  80

Arg Lys Phe Glu Gly Glu Arg Val Thr Val Phe Gln Gly Asp Phe Leu
                85                  90                  95

Asp Phe Arg Ile Pro Arg Asp Ile Asp Thr Val Val Gly Asn Val Pro
            100                 105                 110

Phe Gly Ile Thr Thr Gln Ile Leu Arg Ser Leu Leu Glu Ser Thr Asn
        115                 120                 125

Trp Gln Ser Ala Ala Leu Ile Val Gln Trp Glu Val Ala Arg Lys Arg
    130                 135                 140

Ala Gly Arg Ser Gly Gly Ser Leu Leu Thr Thr Ser Trp Ala Pro Trp
145                 150                 155                 160

Tyr Glu Phe Ala Val His Asp Arg Val Arg Ala Ser Ser Phe Arg Pro
                165                 170                 175

Met Pro Arg Val Asp Gly Gly Val Leu Thr Ile Arg Arg Arg Pro Gln
            180                 185                 190
```

-continued

```
Pro Leu Leu Pro Glu Ser Ala Ser Arg Ala Phe Gln Asn Phe Ala Glu
        195                 200                 205
Ala Val Phe Thr Gly Pro Gly Arg Gly Leu Ala Glu Ile Leu Arg Arg
    210                 215                 220
His Ile Pro Lys Arg Thr Tyr Arg Ser Leu Ala Asp Arg His Gly Ile
225                 230                 235                 240
Pro Asp Gly Gly Leu Pro Lys Asp Leu Thr Leu Thr Gln Trp Ile Ala
                245                 250                 255
Leu Phe Gln Ala Ser Gln Pro Ser Tyr Ala Pro Gly Ala Pro Gly Thr
            260                 265                 270
Arg Met Pro Gly Gln Gly Gly Ala Gly Gly Arg Asp Tyr Asp Ser
        275                 280                 285
Glu Thr Ser Arg Ala Ala Val Pro Gly Ser Arg Arg Tyr Gly Pro Thr
    290                 295                 300
Arg Gly Gly Glu Pro Cys Ala Pro Arg Ala Gln Val Arg Gln Thr Lys
305                 310                 315                 320
Gly Arg Gln Gly Ala Arg Gly Ser Ser Tyr Gly Arg Arg Thr Gly Arg
                325                 330                 335
Met Ser Ser Ala Gly Ile Thr Arg Thr Gly Ala Arg Thr Pro Val Thr
            340                 345                 350
Gly Arg Gly Ala Ala Ala Trp Asp Thr Gly Glu Val Arg Val Arg Arg
        355                 360                 365
Gly Leu Pro Pro Ala Gly Pro Asp His Ala Glu His Ser Phe Ser Arg
    370                 375                 380
Ala Pro Thr Gly Asp Val Arg Ala Glu Leu Ile Arg Gly Glu Met Ser
385                 390                 395                 400
Thr Val Ser Lys Ser Glu Ser Glu Glu Phe Val Ser Val Ser Asn Asp
                405                 410                 415
Ala Gly Ser Ala His Gly Thr Ala Glu Pro Val Ala Val Gly Ile
            420                 425                 430
Ser Cys Arg Val Pro Gly Ala Arg Asp Pro Arg Glu Phe Trp Glu Leu
        435                 440                 445
Leu Ala Ala Gly Gly Gln Ala Val Thr Asp Val Pro Ala Asp Arg Trp
    450                 455                 460
Asn Ala Gly Asp Phe Tyr Asp Pro Asp Arg Ser Ala Pro Gly Arg Ser
465                 470                 475                 480
Asn Ser Arg Trp Gly Gly Phe Ile Glu Asp Val Asp Arg Phe Asp Ala
                485                 490                 495
Ala Phe Phe Gly Ile Ser Pro Arg Glu Ala Ala Glu Met Asp Pro Gln
            500                 505                 510
Gln Arg Leu Ala Leu Glu Leu Gly Trp Glu Ala Leu Glu Arg Ala Gly
        515                 520                 525
Ile Asp Pro Ser Ser Leu Thr Gly Thr Arg Thr Gly Val Phe Ala Gly
    530                 535                 540
Ala Ile Trp Asp Asp Tyr Ala Thr Leu Lys His Arg Gln Gly Gly Ala
545                 550                 555                 560
Ala Ile Thr Pro His Thr Val Thr Gly Leu His Arg Gly Ile Ile Ala
                565                 570                 575
Asn Arg Leu Ser Tyr Thr Leu Gly Leu Arg Gly Pro Ser Met Val Val
            580                 585                 590
Asp Ser Gly Gln Ser Ser Ser Leu Val Ala Val His Leu Ala Cys Glu
        595                 600                 605
```

-continued

```
Ser Leu Arg Arg Gly Glu Ser Glu Leu Ala Leu Ala Gly Gly Val Ser
    610                 615                 620

Leu Asn Leu Val Pro Asp Ser Ile Ile Gly Ala Ser Lys Phe Gly Gly
625                 630                 635                 640

Leu Ser Pro Asp Gly Arg Ala Tyr Thr Phe Asp Ala Arg Ala Asn Gly
                645                 650                 655

Tyr Val Arg Gly Glu Gly Gly Phe Val Val Leu Lys Arg Leu Ser
            660                 665                 670

Arg Ala Val Ala Asp Gly Asp Pro Val Leu Ala Val Ile Arg Gly Ser
            675                 680                 685

Ala Val Asn Asn Gly Gly Ala Ala Gln Gly Met Thr Thr Pro Asp Ala
690                 695                 700

Gln Ala Gln Glu Ala Val Leu Arg Glu Ala His Glu Arg Ala Gly Thr
705                 710                 715                 720

Ala Pro Ala Asp Val Arg Tyr Val Glu Leu His Gly Thr Gly Thr Pro
                725                 730                 735

Val Gly Asp Pro Ile Glu Ala Ala Ala Leu Gly Ala Ala Leu Gly Thr
            740                 745                 750

Gly Arg Pro Ala Gly Gln Pro Leu Leu Val Gly Ser Val Lys Thr Asn
            755                 760                 765

Ile Gly His Leu Glu Gly Ala Ala Gly Ile Ala Gly Leu Ile Lys Ala
    770                 775                 780

Val Leu Ala Val Arg Gly Arg Ala Leu Pro Ala Ser Leu Asn Tyr Glu
785                 790                 795                 800

Thr Pro Asn Pro Ala Ile Pro Phe Glu Leu Asn Leu Arg Val Asn
                805                 810                 815

Thr Glu Tyr Leu Pro Trp Glu Pro Glu His Asp Gly Gln Arg Met Val
            820                 825                 830

Val Gly Val Ser Ser Phe Gly Met Gly Gly Thr Asn Ala His Val Val
            835                 840                 845

Leu Glu Glu Ala Pro Gly Gly Cys Arg Gly Ala Ser Val Val Glu Ser
850                 855                 860

Thr Val Gly Gly Ser Ala Val Gly Gly Gly Val Val Pro Trp Val Val
865                 870                 875                 880

Ser Ala Lys Ser Ala Ala Leu Asp Ala Gln Ile Glu Arg Leu Ala
                885                 890                 895

Ala Phe Ala Ser Arg Asp Arg Thr Asp Gly Val Asp Ala Gly Ala Val
                900                 905                 910

Asp Ala Gly Ala Val Asp Ala Gly Ala Val Ala Arg Val Leu Ala Gly
            915                 920                 925

Gly Arg Ala Gln Phe Glu His Arg Ala Val Val Gly Ser Gly Pro
    930                 935                 940

Asp Asp Leu Ala Ala Ala Leu Ala Ala Pro Glu Gly Leu Val Arg Gly
945                 950                 955                 960

Val Ala Ser Gly Val Gly Arg Val Ala Phe Val Phe Pro Gly Gln Gly
                965                 970                 975

Thr Gln Trp Ala Gly Met Gly Ala Glu Leu Leu Asp Ser Ser Ala Val
            980                 985                 990

Phe Ala Ala Ala Met Ala Glu Cys Glu Ala Ala Leu Ser Pro Tyr Val
            995                 1000                1005

Asp Trp Ser Leu Glu Ala Val Val Arg Gln Ala Pro Gly Ala Pro Thr
    1010                1015                1020
```

```
Leu Glu Arg Val Asp Val Gln Pro Val Thr Phe Ala Val Met Val
1025                1030                1035                1040

Ser Leu Ala Arg Val Trp Gln His His Gly Val Thr Pro Gln Ala Val
            1045                1050                1055

Val Gly His Ser Gln Gly Glu Ile Ala Ala Ala Tyr Val Ala Gly Ala
            1060                1065                1070

Leu Ser Leu Asp Asp Ala Ala Arg Val Val Thr Leu Arg Ser Lys Ser
    1075                1080                1085

Ile Ala Ala His Leu Ala Gly Lys Gly Gly Met Leu Ser Leu Ala Leu
    1090                1095                1100

Ser Glu Asp Ala Val Leu Glu Arg Leu Ala Gly Phe Asp Gly Leu Ser
1105                1110                1115                1120

Val Ala Ala Val Asn Gly Pro Thr Ala Thr Val Val Ser Gly Asp Pro
                1125                1130                1135

Val Gln Ile Glu Glu Leu Ala Arg Ala Cys Glu Ala Asp Gly Val Arg
                1140                1145                1150

Ala Arg Val Ile Pro Val Asp Tyr Ala Ser His Ser Arg Gln Val Glu
            1155                1160                1165

Ile Ile Glu Ser Glu Leu Ala Glu Val Leu Ala Gly Leu Ser Pro Gln
    1170                1175                1180

Ala Pro Arg Val Pro Phe Phe Ser Thr Leu Glu Gly Ala Trp Ile Thr
1185                1190                1195                1200

Glu Pro Val Leu Asp Gly Gly Tyr Trp Tyr Arg Asn Leu Arg His Arg
                1205                1210                1215

Val Gly Phe Ala Pro Ala Val Glu Thr Leu Ala Thr Asp Glu Gly Phe
            1220                1225                1230

Thr His Phe Val Glu Val Ser Ala His Pro Val Leu Thr Met Ala Leu
    1235                1240                1245

Pro Gly Thr Val Thr Gly Leu Ala Thr Leu Arg Arg Asp Asn Gly Gly
    1250                1255                1260

Gln Asp Arg Leu Val Ala Ser Leu Ala Glu Ala Trp Ala Asn Gly Leu
1265                1270                1275                1280

Ala Val Asp Trp Ser Pro Leu Leu Pro Ser Ala Thr Gly His His Ser
            1285                1290                1295

Asp Leu Pro Thr Tyr Ala Phe Gln Thr Glu Arg His Trp Leu Gly Glu
            1300                1305                1310

Ile Glu Ala Leu Ala Pro Ala Gly Glu Pro Ala Val Gln Pro Ala Val
            1315                1320                1325

Leu Arg Thr Glu Ala Ala Glu Pro Ala Glu Leu Asp Arg Asp Glu Gln
    1330                1335                1340

Leu Arg Val Ile Leu Asp Lys Val Arg Ala Gln Thr Ala Gln Val Leu
1345                1350                1355                1360

Gly Tyr Ala Thr Gly Gly Gln Ile Glu Val Asp Arg Thr Phe Arg Glu
            1365                1370                1375

Ala Gly Cys Thr Ser Leu Thr Gly Val Asp Leu Arg Asn Arg Ile Asn
            1380                1385                1390

Ala Ala Phe Gly Val Arg Met Ala Pro Ser Met Ile Phe Asp Phe Pro
    1395                1400                1405

Thr Pro Glu Ala Leu Ala Glu Gln Leu Leu Leu Val Val His Gly Glu
    1410                1415                1420

Ala Ala Ala Asn Pro Ala Gly Ala Glu Pro Ala Pro Val Ala Ala Ala
1425                1430                1435                1440
```

-continued

```
Gly Ala Val Asp Glu Pro Val Ala Ile Val Gly Met Ala Cys Arg Leu
            1445                1450                1455

Pro Gly Gly Val Ala Ser Pro Glu Asp Leu Trp Arg Leu Val Ala Gly
            1460                1465                1470

Gly Gly Asp Ala Ile Ser Glu Phe Pro Gln Asp Arg Gly Trp Asp Val
            1475                1480                1485

Glu Gly Leu Tyr His Pro Asp Pro Glu His Pro Gly Thr Ser Tyr Val
            1490                1495                1500

Arg Gln Gly Gly Phe Ile Glu Asn Val Ala Gly Phe Asp Ala Ala Phe
1505                1510                1515                1520

Phe Gly Ile Ser Pro Arg Glu Ala Leu Ala Met Asp Pro Gln Gln Arg
            1525                1530                1535

Leu Leu Leu Glu Thr Ser Trp Glu Ala Val Glu Asp Ala Gly Ile Asp
            1540                1545                1550

Pro Thr Ser Leu Arg Gly Arg Gln Val Gly Val Phe Thr Gly Ala Met
            1555                1560                1565

Thr His Glu Tyr Gly Pro Ser Leu Arg Asp Gly Gly Glu Gly Leu Asp
            1570                1575                1580

Gly Tyr Leu Leu Thr Gly Asn Thr Ala Ser Val Met Ser Gly Arg Val
1585                1590                1595                1600

Ser Tyr Thr Leu Gly Leu Glu Gly Pro Ala Leu Thr Val Asp Thr Ala
            1605                1610                1615

Cys Ser Ser Ser Leu Val Ala Leu His Leu Ala Val Gln Ala Leu Arg
            1620                1625                1630

Lys Gly Glu Val Asp Met Ala Leu Ala Gly Gly Val Ala Val Met Pro
            1635                1640                1645

Thr Pro Gly Met Phe Val Glu Phe Ser Arg Gln Arg Gly Leu Ala Gly
            1650                1655                1660

Asp Gly Arg Ser Lys Ala Phe Ala Ala Ser Ala Asp Gly Thr Ser Trp
1665                1670                1675                1680

Ser Glu Gly Val Gly Val Leu Leu Val Glu Arg Leu Ser Asp Ala Arg
            1685                1690                1695

Arg Asn Gly His Gln Val Leu Ala Val Val Arg Gly Ser Ala Leu Asn
            1700                1705                1710

Gln Asp Gly Ala Ser Asn Gly Leu Thr Ala Pro Asn Gly Pro Ser Gln
            1715                1720                1725

Gln Arg Val Ile Arg Arg Ala Leu Ala Asp Ala Arg Leu Thr Thr Ser
            1730                1735                1740

Asp Val Asp Val Val Glu Ala His Gly Thr Gly Thr Arg Leu Gly Asp
1745                1750                1755                1760

Pro Ile Glu Ala Gln Ala Leu Ile Ala Thr Tyr Gly Gln Gly Arg Asp
            1765                1770                1775

Asp Glu Gln Pro Leu Arg Leu Gly Ser Leu Lys Ser Asn Ile Gly His
            1780                1785                1790

Thr Gln Ala Ala Ala Gly Val Ser Gly Val Ile Lys Met Val Gln Ala
            1795                1800                1805

Met Arg His Gly Leu Leu Pro Lys Thr Leu His Val Asp Glu Pro Ser
            1810                1815                1820

Asp Gln Ile Asp Trp Ser Ala Gly Ala Val Glu Leu Leu Thr Glu Ala
1825                1830                1835                1840

Val Asp Trp Pro Glu Lys Gln Asp Gly Gly Leu Arg Arg Ala Ala Val
            1845                1850                1855
```

-continued

Ser Ser Phe Gly Ile Ser Gly Thr Asn Ala His Val Val Leu Glu Glu
            1860                1865                1870

Ala Pro Val Val Val Glu Gly Ala Ser Val Val Glu Pro Ser Val Gly
            1875                1880                1885

Gly Ser Ala Val Gly Gly Val Thr Pro Trp Val Val Ser Ala Lys
            1890                1895                1900

Ser Ala Ala Ala Leu Asp Ala Gln Ile Glu Arg Leu Ala Ala Phe Ala
1905                1910                1915                1920

Ser Arg Asp Arg Thr Asp Asp Ala Asp Ala Gly Ala Val Asp Ala Gly
                    1925                1930                1935

Ala Val Ala His Val Leu Ala Asp Gly Arg Ala Gln Phe Glu His Arg
            1940                1945                1950

Ala Val Ala Leu Gly Ala Gly Ala Asp Asp Leu Val Gln Ala Leu Ala
            1955                1960                1965

Asp Pro Asp Gly Leu Ile Arg Gly Thr Ala Ser Gly Val Gly Arg Val
            1970                1975                1980

Ala Phe Val Phe Pro Gly Gln Gly Thr Gln Trp Ala Gly Met Gly Ala
1985                1990                1995                2000

Glu Leu Leu Asp Ser Ser Ala Val Phe Ala Ala Ala Met Ala Glu Cys
            2005                2010                2015

Glu Ala Ala Leu Ser Pro Tyr Val Asp Trp Ser Leu Glu Ala Val Val
            2020                2025                2030

Arg Gln Ala Pro Gly Ala Pro Thr Leu Glu Arg Val Asp Val Val Gln
            2035                2040                2045

Pro Val Thr Phe Ala Val Met Val Ser Leu Ala Arg Val Trp Gln His
            2050                2055                2060

His Gly Val Thr Pro Gln Ala Val Val Gly His Ser Gln Gly Glu Ile
2065                2070                2075                2080

Ala Ala Ala Tyr Val Ala Gly Ala Leu Pro Leu Asp Asp Ala Ala Arg
                    2085                2090                2095

Val Val Thr Leu Arg Ser Lys Ser Ile Ala Ala His Leu Ala Gly Lys
            2100                2105                2110

Gly Gly Met Leu Ser Leu Ala Leu Asn Glu Asp Ala Val Leu Glu Arg
            2115                2120                2125

Leu Ser Asp Phe Asp Gly Leu Ser Val Ala Ala Val Asn Gly Pro Thr
            2130                2135                2140

Ala Thr Val Val Ser Gly Asp Pro Val Gln Ile Glu Glu Leu Ala Gln
2145                2150                2155                2160

Ala Cys Lys Ala Asp Gly Phe Arg Ala Arg Ile Ile Pro Val Asp Tyr
                    2165                2170                2175

Ala Ser His Ser Arg Gln Val Glu Ile Ile Glu Ser Glu Leu Ala Gln
                    2180                2185                2190

Val Leu Ala Gly Leu Ser Pro Gln Ala Pro Arg Val Pro Phe Phe Ser
            2195                2200                2205

Thr Leu Glu Gly Thr Trp Ile Thr Glu Pro Val Leu Asp Gly Thr Tyr
            2210                2215                2220

Trp Tyr Arg Asn Leu Arg His Arg Val Gly Phe Ala Pro Ala Ile Glu
2225                2230                2235                2240

Thr Leu Ala Val Asp Glu Gly Phe Thr His Phe Val Glu Val Ser Ala
                    2245                2250                2255

His Pro Val Leu Thr Met Thr Leu Pro Glu Thr Val Thr Gly Leu Gly
            2260                2265                2270

```
Thr Leu Arg Arg Glu Gln Gly Gly Gln Glu Arg Leu Val Thr Ser Leu
        2275                2280                2285

Ala Glu Ala Trp Val Asn Gly Leu Pro Val Ala Trp Thr Ser Leu Leu
        2290                2295                2300

Pro Ala Thr Ala Ser Arg Pro Gly Leu Pro Thr Tyr Ala Phe Gln Ala
2305                2310                2315                2320

Glu Arg Tyr Trp Leu Glu Asn Thr Pro Ala Ala Leu Ala Thr Gly Asp
        2325                2330                2335

Asp Trp Arg Tyr Arg Ile Asp Trp Lys Arg Leu Pro Ala Ala Glu Gly
        2340                2345                2350

Ser Glu Arg Thr Gly Leu Ser Gly Arg Trp Leu Ala Val Thr Pro Glu
        2355                2360                2365

Asp His Ser Ala Gln Ala Ala Ala Val Leu Thr Ala Leu Val Asp Ala
        2370                2375                2380

Gly Ala Lys Val Glu Val Leu Thr Ala Gly Ala Asp Asp Asp Arg Glu
2385                2390                2395                2400

Ala Leu Ala Ala Arg Leu Thr Ala Leu Thr Thr Gly Asp Gly Phe Thr
        2405                2410                2415

Gly Val Val Ser Leu Leu Asp Gly Leu Val Pro Gln Val Ala Trp Val
        2420                2425                2430

Gln Ala Leu Gly Asp Ala Gly Ile Lys Ala Pro Leu Trp Ser Val Thr
        2435                2440                2445

Gln Gly Ala Val Ser Val Gly Arg Leu Asp Thr Pro Ala Asp Pro Asp
        2450                2455                2460

Arg Ala Met Leu Trp Gly Leu Gly Arg Val Val Ala Leu Glu His Pro
2465                2470                2475                2480

Glu Arg Trp Ala Gly Leu Val Asp Leu Pro Ala Gln Pro Asp Ala Ala
        2485                2490                2495

Ala Leu Ala His Leu Val Thr Ala Leu Ser Gly Ala Thr Gly Glu Asp
        2500                2505                2510

Gln Ile Ala Ile Arg Thr Thr Gly Leu His Ala Arg Arg Leu Ala Arg
        2515                2520                2525

Ala Pro Leu His Gly Arg Arg Pro Thr Arg Asp Trp Gln Pro His Gly
        2530                2535                2540

Thr Val Leu Ile Thr Gly Gly Thr Gly Ala Leu Gly Ser His Ala Ala
2545                2550                2555                2560

Arg Trp Met Ala His His Gly Ala Glu His Leu Leu Leu Val Ser Arg
        2565                2570                2575

Ser Gly Glu Gln Ala Pro Gly Ala Thr Gln Leu Thr Ala Glu Leu Thr
        2580                2585                2590

Ala Ser Gly Ala Arg Val Thr Ile Ala Ala Cys Asp Val Ala Asp Pro
        2595                2600                2605

His Ala Met Arg Thr Leu Leu Asp Ala Ile Pro Ala Glu Thr Pro Leu
        2610                2615                2620

Thr Ala Val Val His Thr Ala Gly Ala Leu Asp Asp Gly Ile Val Asp
2625                2630                2635                2640

Thr Leu Thr Ala Glu Gln Val Arg Arg Ala His Arg Ala Lys Ala Val
        2645                2650                2655

Gly Ala Ser Val Leu Asp Glu Leu Thr Arg Asp Leu Asp Leu Asp Ala
        2660                2665                2670

Phe Val Leu Phe Ser Ser Val Ser Ser Thr Leu Gly Ile Pro Gly Gln
        2675                2680                2685
```

```
Gly Asn Tyr Ala Pro His Asn Ala Tyr Leu Asp Ala Leu Ala Ala Arg
    2690                2695                2700

Arg Arg Ala Thr Gly Arg Ser Ala Val Ser Val Ala Trp Gly Pro Trp
2705                2710                2715                2720

Asp Gly Gly Gly Met Ala Ala Gly Asp Gly Val Ala Glu Arg Leu Arg
                2725                2730                2735

Asn His Gly Val Pro Gly Met Asp Pro Glu Leu Ala Leu Ala Ala Leu
            2740                2745                2750

Glu Ser Ala Leu Gly Arg Asp Glu Thr Ala Ile Thr Val Ala Asp Ile
            2755                2760                2765

Asp Trp Asp Arg Phe Tyr Leu Ala Tyr Ser Ser Gly Arg Pro Gln Pro
    2770                2775                2780

Leu Val Glu Glu Leu Pro Glu Val Arg Arg Ile Ile Asp Ala Arg Asp
2785                2790                2795                2800

Ser Ala Thr Ser Gly Gln Gly Gly Ser Ser Ala Gln Gly Ala Asn Pro
                2805                2810                2815

Leu Ala Glu Arg Leu Ala Ala Ala Pro Gly Glu Arg Thr Glu Ile
            2820                2825                2830

Leu Leu Gly Leu Val Arg Ala Gln Ala Ala Val Leu Arg Met Arg
            2835                2840                2845

Ser Pro Glu Asp Val Ala Ala Asp Arg Ala Phe Lys Asp Ile Gly Phe
    2850                2855                2860

Asp Ser Leu Ala Gly Val Glu Leu Arg Asn Arg Leu Thr Arg Ala Thr
2865                2870                2875                2880

Gly Leu Gln Leu Pro Ala Thr Leu Val Phe Asp His Pro Thr Pro Leu
                2885                2890                2895

Ala Leu Val Ser Leu Leu Arg Ser Glu Phe Leu Gly Asp Glu Glu Thr
            2900                2905                2910

Ala Asp Ala Arg Arg Ser Ala Ala Leu Pro Ala Thr Val Gly Ala Gly
            2915                2920                2925

Ala Gly Ala Gly Ala Gly Thr Asp Ala Asp Asp Pro Ile Ala Ile
            2930                2935                2940

Val Ala Met Ser Cys Arg Tyr Pro Gly Asp Ile Arg Ser Pro Glu Asp
2945                2950                2955                2960

Leu Trp Arg Met Leu Ser Glu Gly Gly Glu Gly Ile Thr Pro Phe Pro
                2965                2970                2975

Thr Asp Arg Gly Trp Asp Leu Asp Gly Leu Tyr Asp Ala Asp Pro Asp
                2980                2985                2990

Ala Leu Gly Arg Ala Tyr Val Arg Glu Gly Gly Phe Leu His Asp Ala
            2995                3000                3005

Ala Glu Phe Asp Ala Glu Phe Phe Gly Val Ser Pro Arg Glu Ala Leu
            3010                3015                3020

Ala Met Asp Pro Gln Gln Arg Met Leu Leu Thr Thr Ser Trp Glu Ala
3025                3030                3035                3040

Phe Glu Arg Ala Gly Ile Glu Pro Ala Ser Leu Arg Gly Ser Ser Thr
                3045                3050                3055

Gly Val Phe Ile Gly Leu Ser Tyr Gln Asp Tyr Ala Ala Arg Val Pro
            3060                3065                3070

Asn Ala Pro Arg Gly Val Glu Gly Tyr Leu Leu Thr Gly Ser Thr Pro
        3075                3080                3085

Ser Val Ala Ser Gly Arg Ile Ala Tyr Thr Phe Gly Leu Glu Gly Pro
    3090                3095                3100
```

```
Ala Thr Thr Val Asp Thr Ala Cys Ser Ser Leu Thr Ala Leu His
3105                3110                3115                3120

Leu Ala Val Arg Ala Leu Arg Ser Gly Glu Cys Thr Met Ala Leu Ala
                3125                3130                3135

Gly Gly Val Ala Met Met Ala Thr Pro His Met Phe Val Glu Phe Ser
                3140                3145                3150

Arg Gln Arg Ala Leu Ala Pro Asp Gly Arg Ser Lys Ala Phe Ser Ala
                3155                3160                3165

Asp Ala Asp Gly Phe Gly Ala Ala Glu Gly Val Gly Leu Leu Leu Val
                3170                3175                3180

Glu Arg Leu Ser Asp Ala Arg Arg Asn Gly His Pro Val Leu Ala Val
3185                3190                3195                3200

Val Arg Gly Thr Ala Val Asn Gln Asp Gly Ala Ser Asn Gly Leu Thr
                3205                3210                3215

Ala Pro Asn Gly Pro Ser Gln Gln Arg Val Ile Arg Gln Ala Leu Ala
                3220                3225                3230

Asp Ala Arg Leu Ala Pro Gly Asp Ile Asp Ala Val Glu Thr His Gly
                3235                3240                3245

Thr Gly Thr Ser Leu Gly Asp Pro Ile Glu Ala Gln Gly Leu Gln Ala
                3250                3255                3260

Thr Tyr Gly Lys Glu Arg Pro Ala Glu Arg Pro Leu Ala Ile Gly Ser
3265                3270                3275                3280

Val Lys Ser Asn Ile Gly His Thr Gln Ala Ala Gly Ala Ala Gly
                3285                3290                3295

Ile Ile Lys Met Val Leu Ala Met Arg His Gly Thr Leu Pro Lys Thr
                3300                3305                3310

Leu His Ala Asp Glu Pro Ser Pro His Val Asp Trp Ala Asn Ser Gly
                3315                3320                3325

Leu Ala Leu Val Thr Glu Pro Ile Asp Trp Pro Ala Gly Thr Gly Pro
                3330                3335                3340

Arg Arg Ala Ala Val Ser Ser Phe Gly Ile Ser Gly Thr Asn Ala His
3345                3350                3355                3360

Val Val Leu Glu Gln Ala Pro Asp Ala Ala Gly Glu Val Leu Gly Ala
                3365                3370                3375

Asp Glu Val Pro Glu Val Ser Glu Thr Val Ala Met Ala Gly Thr Ala
                3380                3385                3390

Gly Thr Ser Glu Val Ala Glu Gly Ser Glu Ala Ser Glu Ala Pro Ala
                3395                3400                3405

Ala Pro Gly Ser Arg Glu Ala Ser Leu Pro Gly His Leu Pro Trp Val
                3410                3415                3420

Leu Ser Ala Lys Asp Glu Gln Ser Leu Arg Gly Gln Ala Ala Ala Leu
3425                3430                3435                3440

His Ala Trp Leu Ser Glu Pro Ala Ala Asp Leu Ser Asp Ala Asp Gly
                3445                3450                3455

Pro Ala Arg Leu Arg Asp Val Gly Tyr Thr Leu Ala Thr Ser Arg Thr
                3460                3465                3470

Ala Phe Ala His Arg Ala Ala Val Thr Ala Ala Asp Arg Asp Gly Phe
                3475                3480                3485

Leu Asp Gly Leu Ala Thr Leu Ala Gln Gly Gly Thr Ser Ala His Val
                3490                3495                3500

His Leu Asp Thr Ala Arg Asp Gly Thr Thr Ala Phe Leu Phe Thr Gly
3505                3510                3515                3520
```

```
Gln Gly Ser Gln Arg Pro Gly Ala Gly Arg Glu Leu Tyr Asp Arg His
            3525                3530                3535

Pro Val Phe Ala Arg Ala Leu Asp Glu Ile Cys Ala His Leu Asp Gly
            3540                3545                3550

His Leu Glu Leu Pro Leu Leu Asp Val Met Phe Ala Ala Glu Gly Ser
            3555                3560                3565

Ala Glu Ala Ala Leu Leu Asp Glu Thr Arg Tyr Thr Gln Cys Ala Leu
            3570                3575                3580

Phe Ala Leu Glu Val Ala Leu Phe Arg Leu Val Glu Ser Trp Gly Met
3585                3590                3595                3600

Arg Pro Ala Ala Leu Leu Gly His Ser Val Gly Glu Ile Ala Ala Ala
            3605                3610                3615

His Val Ala Gly Val Phe Ser Leu Ala Asp Ala Ala Arg Leu Val Ala
            3620                3625                3630

Ala Arg Gly Arg Leu Met Gln Glu Leu Pro Ala Gly Gly Ala Met Leu
            3635                3640                3645

Ala Val Gln Ala Ala Glu Asp Glu Ile Arg Val Trp Leu Glu Thr Glu
            3650                3655                3660

Glu Arg Tyr Ala Gly Arg Leu Asp Val Ala Ala Val Asn Gly Pro Glu
3665                3670                3675                3680

Ala Ala Val Leu Ser Gly Asp Ala Asp Ala Ala Arg Glu Ala Glu Ala
            3685                3690                3695

Tyr Trp Ser Gly Leu Gly Arg Arg Thr Arg Ala Leu Arg Val Ser His
            3700                3705                3710

Ala Phe His Ser Ala His Met Asp Gly Met Leu Asp Gly Phe Arg Ala
            3715                3720                3725

Val Leu Glu Thr Val Glu Phe Arg Pro Ser Leu Thr Val Val Ser
            3730                3735                3740

Asn Val Thr Gly Leu Ala Ala Gly Pro Asp Asp Leu Cys Asp Pro Glu
3745                3750                3755                3760

Tyr Trp Val Arg His Val Arg Gly Thr Val Arg Phe Leu Asp Gly Val
            3765                3770                3775

Arg Val Leu Arg Asp Leu Gly Val Arg Thr Cys Leu Glu Leu Gly Pro
            3780                3785                3790

Asp Gly Val Leu Thr Ala Met Ala Ala Asp Gly Leu Ala Asp Thr Pro
            3795                3800                3805

Ala Asp Ser Ala Ala Gly Ser Pro Val Gly Ser Pro Ala Gly Ser Pro
            3810                3815                3820

Ala Asp Ser Ala Ala Gly Ala Leu Arg Pro Arg Pro Leu Leu Val Ala
3825                3830                3835                3840

Leu Leu Arg Arg Lys Arg Ser Glu Thr Glu Thr Val Ala Asp Ala Leu
            3845                3850                3855

Gly Arg Ala His Ala His Gly Thr Gly Pro Asp Trp His Ala Trp Phe
            3860                3865                3870

Ala Gly Ser Gly Ala His Arg Val Asp Leu Pro Thr Tyr Ser Phe Arg
            3875                3880                3885

Arg Asp Arg Tyr Trp Leu Asp Ala Pro Ala Ala Asp Thr Ala Val Asp
            3890                3895                3900

Thr Ala Gly Leu Gly Leu Gly Thr Ala Asp His Pro Leu Leu Gly Ala
3905                3910                3915                3920

Val Val Ser Leu Pro Asp Arg Asp Gly Leu Leu Leu Thr Gly Arg Leu
            3925                3930                3935
```

```
Ser Leu Arg Thr His Pro Trp Leu Ala Asp His Ala Val Leu Gly Ser
            3940                3945                3950

Val Leu Leu Pro Gly Ala Ala Met Val Glu Leu Ala Ala His Ala Ala
            3955                3960                3965

Glu Ser Ala Gly Leu Arg Asp Val Arg Glu Leu Thr Leu Leu Glu Pro
            3970                3975                3980

Leu Val Leu Pro Glu His Gly Val Glu Leu Arg Val Thr Val Gly
3985                3990                3995                4000

Ala Pro Ala Gly Glu Pro Gly Gly Glu Ser Ala Gly Asp Gly Ala Arg
                4005                4010                4015

Pro Val Ser Leu His Ser Arg Leu Ala Asp Ala Pro Ala Gly Thr Ala
            4020                4025                4030

Trp Ser Cys His Ala Thr Gly Leu Leu Ala Thr Asp Arg Pro Glu Leu
            4035                4040                4045

Pro Val Ala Pro Asp Arg Ala Ala Met Trp Pro Pro Gln Gly Ala Glu
            4050                4055                4060

Glu Val Pro Leu Asp Gly Leu Tyr Glu Arg Leu Asp Gly Asn Gly Leu
4065                4070                4075                4080

Ala Phe Gly Pro Leu Phe Gln Gly Leu Asn Ala Val Trp Arg Tyr Glu
            4085                4090                4095

Gly Glu Val Phe Ala Asp Ile Ala Leu Pro Ala Thr Thr Asn Ala Thr
            4100                4105                4110

Ala Pro Ala Thr Ala Asn Gly Gly Gly Ser Ala Ala Ala Ala Pro Tyr
            4115                4120                4125

Gly Ile His Pro Ala Leu Leu Asp Ala Ser Leu His Ala Ile Ala Val
            4130                4135                4140

Gly Gly Leu Val Asp Glu Pro Glu Leu Val Arg Val Pro Phe His Trp
4145                4150                4155                4160

Ser Gly Val Thr Val His Ala Ala Gly Ala Ala Ala Arg Val Arg
            4165                4170                4175

Leu Ala Ser Ala Gly Thr Asp Ala Val Ser Leu Ser Leu Thr Asp Gly
            4180                4185                4190

Glu Gly Arg Pro Leu Val Ser Val Glu Arg Leu Thr Leu Arg Pro Val
            4195                4200                4205

Thr Ala Asp Gln Ala Ala Ala Ser Arg Val Gly Gly Leu Met His Arg
            4210                4215                4220

Val Ala Trp Arg Pro Tyr Ala Leu Ala Ser Ser Gly Glu Gln Asp Pro
4225                4230                4235                4240

His Ala Thr Ser Tyr Gly Pro Thr Ala Val Leu Gly Lys Asp Glu Leu
            4245                4250                4255

Lys Val Ala Ala Ala Leu Glu Ser Ala Gly Val Glu Val Gly Leu Tyr
            4260                4265                4270

Pro Asp Leu Ala Ala Leu Ser Gln Asp Val Ala Ala Gly Ala Pro Ala
            4275                4280                4285

Pro Arg Thr Val Leu Ala Pro Leu Pro Ala Gly Pro Ala Asp Gly Gly
            4290                4295                4300

Ala Glu Gly Val Arg Gly Thr Val Ala Arg Thr Leu Glu Leu Leu Gln
4305                4310                4315                4320

Ala Trp Leu Ala Asp Glu His Leu Ala Gly Thr Arg Leu Leu Leu Val
            4325                4330                4335

Thr Arg Gly Ala Val Arg Asp Pro Glu Gly Ser Gly Ala Asp Asp Gly
            4340                4345                4350
```

-continued

```
Gly Glu Asp Leu Ser His Ala Ala Trp Gly Leu Val Arg Thr Ala
            4355                4360                4365
Gln Thr Glu Asn Pro Gly Arg Phe Gly Leu Leu Asp Leu Ala Asp Asp
    4370                4375                4380
Ala Ser Ser Tyr Arg Thr Leu Pro Ser Val Leu Ser Asp Ala Gly Leu
4385                4390                4395                4400
Arg Asp Glu Pro Gln Leu Ala Leu His Asp Gly Thr Ile Arg Leu Ala
                4405                4410                4415
Arg Leu Ala Ser Val Arg Pro Glu Thr Gly Thr Ala Ala Pro Ala Leu
            4420                4425                4430
Ala Pro Glu Gly Thr Val Leu Leu Thr Gly Gly Thr Gly Gly Leu Gly
            4435                4440                4445
Gly Leu Val Ala Arg His Val Val Gly Glu Trp Gly Val Arg Arg Leu
    4450                4455                4460
Leu Leu Val Ser Arg Arg Gly Thr Asp Ala Pro Gly Ala Asp Glu Leu
4465                4470                4475                4480
Val His Glu Leu Glu Ala Leu Gly Ala Asp Val Ser Val Ala Ala Cys
            4485                4490                4495
Asp Val Ala Asp Arg Glu Ala Leu Thr Ala Val Leu Asp Ala Ile Pro
            4500                4505                4510
Ala Glu His Pro Leu Thr Ala Val His Thr Ala Gly Val Leu Ser
            4515                4520                4525
Asp Gly Thr Leu Pro Ser Met Thr Thr Glu Asp Val Glu His Val Leu
            4530                4535                4540
Arg Pro Lys Val Asp Ala Ala Phe Leu Leu Asp Glu Leu Thr Ser Thr
4545                4550                4555                4560
Pro Ala Tyr Asp Leu Ala Ala Phe Val Met Phe Ser Ser Ala Ala Ala
            4565                4570                4575
Val Phe Gly Gly Ala Gly Gln Gly Ala Tyr Ala Ala Asn Ala Thr
            4580                4585                4590
Leu Asp Ala Leu Ala Trp Arg Arg Ala Ala Gly Leu Pro Ala Leu
            4595                4600                4605
Ser Leu Gly Trp Gly Leu Trp Ala Glu Thr Ser Gly Met Thr Gly Glu
    4610                4615                4620
Leu Gly Gln Ala Asp Leu Arg Arg Met Ser Arg Ala Gly Ile Gly Gly
4625                4630                4635                4640
Ile Ser Asp Ala Glu Gly Ile Ala Leu Leu Asp Ala Ala Leu Arg Asp
            4645                4650                4655
Asp Arg His Pro Val Leu Leu Pro Leu Arg Leu Asp Ala Ala Gly Leu
            4660                4665                4670
Arg Asp Ala Ala Gly Asn Asp Pro Ala Gly Ile Pro Ala Leu Phe Arg
            4675                4680                4685
Asp Val Val Gly Ala Arg Thr Val Arg Ala Arg Pro Ser Ala Ala Ser
            4690                4695                4700
Ala Ser Thr Thr Ala Gly Thr Ala Gly Thr Pro Gly Thr Ala Asp Gly
4705                4710                4715                4720
Ala Ala Glu Thr Ala Ala Val Thr Leu Ala Asp Arg Ala Ala Thr Val
                4725                4730                4735
Asp Gly Pro Ala Arg Gln Arg Leu Leu Leu Glu Phe Val Val Gly Glu
            4740                4745                4750
Val Ala Glu Val Leu Gly His Ala Arg Gly His Arg Ile Asp Ala Glu
            4755                4760                4765
```

-continued

```
Arg Gly Phe Leu Asp Leu Gly Phe Asp Ser Leu Thr Ala Val Glu Leu
    4770            4775                4780
Arg Asn Arg Leu Asn Ser Ala Gly Leu Ala Leu Pro Ala Thr Leu
4785            4790                4795                4800
Val Phe Asp His Pro Ser Pro Ala Ala Leu Ala Ser His Leu Asp Ala
                4805                4810                4815
Glu Leu Pro Arg Gly Ala Ser Asp Gln Asp Gly Ala Gly Asn Arg Asn
            4820                4825                4830
Gly Asn Glu Asn Gly Thr Thr Ala Ser Arg Ser Thr Ala Glu Thr Asp
        4835                4840                4845
Ala Leu Leu Ala Gln Leu Thr Arg Leu Glu Gly Ala Leu Val Leu Thr
    4850                4855                4860
Gly Leu Ser Asp Ala Pro Gly Ser Glu Glu Val Leu Glu His Leu Arg
4865                4870                4875                4880
Ser Leu Arg Ser Met Val Thr Gly Glu Thr Gly Thr Gly Thr Ala Ser
                4885                4890                4895
Gly Ala Pro Asp Gly Ala Gly Ser Gly Ala Glu Asp Arg Pro Trp Ala
            4900                4905                4910
Ala Gly Asp Gly Ala Gly Gly Ser Glu Asp Gly Ala Gly Val Pro
        4915                4920                4925
Asp Phe Met Asn Ala Ser Ala Glu Glu Leu Phe Gly Leu Leu Asp Gln
    4930                4935                4940
Asp Pro Ser Thr Asp Met Ser Thr Val Asn Glu Glu Lys Tyr Leu Asp
4945                4950                4955                4960
Tyr Leu Arg Arg Ala Thr Ala Asp Leu His Glu Ala Arg Gly Arg Leu
                4965                4970                4975
Arg Glu Leu Glu Ala Lys Ala Gly Glu Pro Val Ala Ile Val Gly Met
            4980                4985                4990
Ala Cys Arg Leu Pro Gly Gly Val Ala Ser Pro Glu Asp Leu Trp Arg
        4995                5000                5005
Leu Val Ala Gly Gly Glu Asp Ala Ile Ser Glu Phe Pro Gln Asp Arg
    5010                5015                5020
Gly Trp Asp Val Glu Gly Leu Tyr Asp Pro Asn Pro Glu Ala Thr Gly
5025                5030                5035                5040
Lys Ser Tyr Ala Arg Glu Ala Gly Phe Leu Tyr Glu Ala Gly Glu Phe
                5045                5050                5055
Asp Ala Asp Phe Phe Gly Ile Ser Pro Arg Glu Ala Leu Ala Met Asp
            5060                5065                5070
Pro Gln Gln Arg Leu Leu Leu Glu Ala Ser Trp Glu Ala Phe Glu His
        5075                5080                5085
Ala Gly Ile Pro Ala Ala Thr Ala Arg Gly Thr Ser Val Gly Val Phe
    5090                5095                5100
Thr Gly Val Met Tyr His Asp Tyr Ala Thr Arg Leu Thr Asp Val Pro
5105                5110                5115                5120
Glu Gly Ile Glu Gly Tyr Leu Gly Thr Gly Asn Ser Gly Ser Val Ala
                5125                5130                5135
Ser Gly Arg Val Ala Tyr Thr Leu Gly Leu Glu Gly Pro Ala Val Thr
            5140                5145                5150
Val Asp Thr Ala Cys Ser Ser Ser Leu Val Ala Leu His Leu Ala Val
        5155                5160                5165
Gln Ala Leu Arg Lys Gly Glu Val Asp Met Ala Leu Ala Gly Gly Val
    5170                5175                5180
```

-continued

```
Thr Val Met Ser Thr Pro Ser Thr Phe Val Glu Phe Ser Arg Gln Arg
5185                5190                5195                5200

Gly Leu Ala Pro Asp Gly Arg Ser Lys Ser Phe Ser Thr Ala Asp
                5205                5210                5215

Gly Thr Ser Trp Ser Glu Gly Val Gly Val Leu Leu Val Glu Arg Leu
                5220                5225                5230

Ser Asp Ala Arg Arg Lys Gly His Arg Ile Leu Ala Val Val Arg Gly
                5235                5240                5245

Thr Ala Val Asn Gln Asp Gly Ala Ser Ser Gly Leu Thr Ala Pro Asn
                5250                5255                5260

Gly Pro Ser Gln Gln Arg Val Ile Arg Ala Leu Ala Asp Ala Arg
5265                5270                5275                5280

Leu Thr Thr Ser Asp Val Asp Val Val Glu Ala His Gly Thr Gly Thr
                5285                5290                5295

Arg Leu Gly Asp Pro Ile Glu Ala Gln Ala Val Ile Ala Thr Tyr Gly
                5300                5305                5310

Gln Gly Arg Asp Gly Glu Gln Pro Leu Arg Leu Gly Ser Leu Lys Ser
                5315                5320                5325

Asn Ile Gly His Thr Gln Ala Ala Ala Gly Val Ser Gly Val Ile Lys
                5330                5335                5340

Met Val Gln Ala Met Arg His Gly Val Leu Pro Lys Thr Leu His Val
5345                5350                5355                5360

Glu Lys Pro Thr Asp Gln Val Asp Trp Ser Ala Gly Ala Val Glu Leu
                5365                5370                5375

Leu Thr Glu Ala Met Asp Trp Pro Asp Lys Gly Asp Gly Gly Leu Arg
                5380                5385                5390

Arg Ala Ala Val Ser Ser Phe Gly Val Ser Gly Thr Asn Ala His Val
                5395                5400                5405

Val Leu Glu Glu Ala Pro Ala Ala Glu Glu Thr Pro Ala Ser Glu Ala
                5410                5415                5420

Thr Pro Ala Val Glu Pro Ser Val Gly Ala Gly Leu Val Pro Trp Leu
5425                5430                5435                5440

Val Ser Ala Lys Thr Pro Ala Ala Leu Asp Ala Gln Ile Gly Arg Leu
                5445                5450                5455

Ala Ala Phe Ala Ser Gln Gly Arg Thr Asp Ala Ala Asp Pro Gly Ala
                5460                5465                5470

Val Ala Arg Val Leu Ala Gly Gly Arg Ala Glu Phe Glu His Arg Ala
                5475                5480                5485

Val Val Leu Gly Thr Gly Gln Asp Asp Phe Ala Gln Ala Leu Thr Ala
                5490                5495                5500

Pro Glu Gly Leu Ile Arg Gly Thr Pro Ser Asp Val Gly Arg Val Ala
5505                5510                5515                5520

Phe Val Phe Pro Gly Gln Gly Thr Gln Trp Ala Gly Met Gly Ala Glu
                5525                5530                5535

Leu Leu Asp Val Ser Lys Glu Phe Ala Ala Ala Met Ala Glu Cys Glu
                5540                5545                5550

Ser Ala Leu Ser Arg Tyr Val Asp Trp Ser Leu Glu Ala Val Val Arg
                5555                5560                5565

Gln Ala Pro Gly Ala Pro Thr Leu Glu Arg Val Asp Val Val Gln Pro
                5570                5575                5580

Val Thr Phe Ala Val Met Val Ser Leu Ala Lys Val Trp Gln His His
5585                5590                5595                5600
```

-continued

```
Gly Val Thr Pro Gln Ala Val Val Gly His Ser Gln Gly Glu Ile Ala
            5605                5610                5615

Ala Ala Tyr Val Ala Gly Ala Leu Thr Leu Asp Asp Ala Ala Arg Val
        5620                5625                5630

Val Thr Leu Arg Ser Lys Ser Ile Ala Ala His Leu Ala Gly Lys Gly
    5635                5640                5645

Gly Met Ile Ser Leu Ala Leu Ser Glu Glu Ala Thr Arg Gln Arg Ile
    5650                5655                5660

Glu Asn Leu His Gly Leu Ser Ile Ala Ala Val Asn Gly Pro Thr Ala
5665                5670                5675                5680

Thr Val Val Ser Gly Asp Pro Thr Gln Ile Gln Glu Leu Ala Gln Ala
            5685                5690                5695

Cys Glu Ala Asp Gly Val Arg Ala Arg Ile Ile Pro Val Asp Tyr Ala
            5700                5705                5710

Ser His Ser Ala His Val Glu Thr Ile Glu Ser Glu Leu Ala Glu Val
            5715                5720                5725

Leu Ala Gly Leu Ser Pro Arg Thr Pro Glu Val Pro Phe Phe Ser Thr
    5730                5735                5740

Leu Glu Gly Ala Trp Ile Thr Glu Pro Val Leu Asp Gly Thr Tyr Trp
5745                5750                5755                5760

Tyr Arg Asn Leu Arg His Arg Val Gly Phe Ala Pro Ala Val Glu Thr
            5765                5770                5775

Leu Ala Thr Asp Glu Gly Phe Thr His Phe Ile Glu Val Ser Ala His
            5780                5785                5790

Pro Val Leu Thr Met Thr Leu Pro Glu Thr Val Thr Gly Leu Gly Thr
            5795                5800                5805

Leu Arg Arg Glu Gln Gly Gly Gln Glu Arg Leu Val Thr Ser Leu Ala
    5810                5815                5820

Glu Ala Trp Thr Asn Gly Leu Thr Ile Asp Trp Ala Pro Val Leu Pro
5825                5830                5835                5840

Thr Ala Thr Gly His His Pro Glu Leu Pro Thr Tyr Ala Phe Gln Arg
            5845                5850                5855

Arg His Tyr Trp Leu His Asp Ser Pro Ala Val Gln Gly Ser Val Gln
            5860                5865                5870

Asp Ser Trp Arg Tyr Arg Ile Asp Trp Lys Arg Leu Ala Val Ala Asp
    5875                5880                5885

Ala Ser Glu Arg Ala Gly Leu Ser Gly Arg Trp Leu Val Val Val Pro
    5890                5895                5900

Glu Asp Arg Ser Ala Glu Ala Ala Pro Val Leu Ala Ala Leu Ser Gly
5905                5910                5915                5920

Ala Gly Ala Asp Pro Val Gln Leu Asp Val Ser Pro Leu Gly Asp Arg
            5925                5930                5935

Gln Arg Leu Ala Ala Thr Leu Gly Glu Ala Leu Ala Ala Gly Gly
        5940                5945                5950

Ala Val Asp Gly Val Leu Ser Leu Leu Ala Trp Asp Glu Ser Ala His
            5955                5960                5965

Pro Gly His Pro Ala Pro Phe Thr Arg Gly Thr Gly Ala Thr Leu Thr
        5970                5975                5980

Leu Val Gln Ala Leu Glu Asp Ala Gly Val Ala Ala Pro Leu Trp Cys
5985                5990                5995                6000

Val Thr His Gly Ala Val Ser Val Gly Arg Ala Asp His Val Thr Ser
            6005                6010                6015
```

-continued

```
Pro Ala Gln Ala Met Val Trp Gly Met Gly Arg Val Ala Ala Leu Glu
            6020                6025                6030

His Pro Glu Arg Trp Gly Gly Leu Ile Asp Leu Pro Ser Asp Ala Asp
            6035                6040                6045

Arg Ala Ala Leu Asp Arg Met Thr Thr Val Leu Ala Gly Gly Thr Gly
            6050                6055                6060

Glu Asp Gln Val Ala Val Arg Ala Ser Gly Leu Leu Ala Arg Arg Leu
6065                6070                6075                6080

Val Arg Ala Ser Leu Pro Ala His Gly Thr Ala Ser Pro Trp Trp Gln
            6085                6090                6095

Ala Asp Gly Thr Val Leu Val Thr Gly Ala Glu Glu Pro Ala Ala Ala
            6100                6105                6110

Glu Ala Ala Arg Arg Leu Ala Arg Asp Gly Ala Gly His Leu Leu Leu
            6115                6120                6125

His Thr Thr Pro Ser Gly Ser Glu Gly Ala Glu Gly Thr Ser Gly Ala
            6130                6135                6140

Ala Glu Asp Ser Gly Leu Ala Gly Leu Val Ala Glu Leu Ala Asp Leu
6145                6150                6155                6160

Gly Ala Thr Ala Thr Val Val Thr Cys Asp Leu Thr Asp Ala Glu Ala
            6165                6170                6175

Ala Ala Arg Leu Leu Ala Gly Val Ser Asp Ala His Pro Leu Ser Ala
            6180                6185                6190

Val Leu His Leu Pro Pro Thr Val Asp Ser Glu Pro Leu Ala Ala Thr
            6195                6200                6205

Asp Ala Asp Ala Leu Ala Arg Val Val Thr Ala Lys Ala Thr Ala Ala
            6210                6215                6220

Leu His Leu Asp Arg Leu Leu Arg Glu Ala Ala Ala Gly Gly Arg
6225                6230                6235                6240

Pro Pro Val Leu Val Leu Phe Ser Ser Val Ala Ala Ile Trp Gly Gly
            6245                6250                6255

Ala Gly Gln Gly Ala Tyr Ala Ala Gly Thr Ala Phe Leu Asp Ala Leu
            6260                6265                6270

Ala Gly Gln His Arg Ala Asp Gly Pro Thr Val Thr Ser Val Ala Trp
            6275                6280                6285

Ser Pro Trp Glu Gly Ser Arg Val Thr Glu Gly Ala Thr Gly Glu Arg
            6290                6295                6300

Leu Arg Arg Leu Gly Leu Arg Pro Leu Ala Pro Ala Thr Ala Leu Thr
6305                6310                6315                6320

Ala Leu Asp Thr Ala Leu Gly His Gly Asp Thr Ala Val Thr Ile Ala
            6325                6330                6335

Asp Val Asp Trp Ser Ser Phe Ala Pro Gly Phe Thr Thr Ala Arg Pro
            6340                6345                6350

Gly Thr Leu Leu Ala Asp Leu Pro Glu Ala Arg Arg Ala Leu Asp Glu
            6355                6360                6365

Gln Gln Ser Thr Thr Ala Ala Asp Asp Thr Val Leu Ser Arg Glu Leu
            6370                6375                6380

Gly Ala Leu Thr Gly Ala Glu Gln Gln Arg Met Gln Glu Leu Val
6385                6390                6395                6400

Arg Glu His Leu Ala Val Val Leu Asn His Pro Ser Pro Glu Ala Val
            6405                6410                6415

Asp Thr Gly Arg Ala Phe Arg Asp Leu Gly Phe Asp Ser Leu Thr Ala
            6420                6425                6430
```

-continued

```
Val Glu Leu Arg Asn Arg Leu Lys Asn Ala Thr Gly Leu Ala Leu Pro
        6435                6440                6445

Ala Thr Leu Val Phe Asp Tyr Pro Thr Pro Arg Thr Leu Ala Glu Phe
        6450                6455                6460

Leu Leu Ala Glu Ile Leu Gly Glu Gln Ala Gly Ala Gly Glu Gln Leu
6465                6470                6475                6480

Pro Val Asp Gly Val Asp Asp Glu Pro Val Ala Ile Val Gly Met
            6485                6490                6495

Ala Cys Arg Leu Pro Gly Gly Val Ala Ser Pro Glu Asp Leu Trp Arg
        6500                6505                6510

Leu Val Ala Gly Gly Glu Asp Ala Ile Ser Gly Phe Pro Gln Asp Arg
        6515                6520                6525

Gly Trp Asp Val Glu Gly Leu Tyr Asp Pro Asp Pro Asp Ala Ser Gly
        6530                6535                6540

Arg Thr Tyr Cys Arg Ala Gly Gly Phe Leu Asp Glu Ala Gly Glu Phe
6545                6550                6555                6560

Asp Ala Asp Phe Phe Gly Ile Ser Pro Arg Glu Ala Leu Ala Met Asp
        6565                6570                6575

Pro Gln Gln Arg Leu Leu Leu Glu Thr Ser Trp Glu Ala Val Glu Asp
        6580                6585                6590

Ala Gly Ile Asp Pro Thr Ser Leu Gln Gly Gln Gln Val Gly Val Phe
        6595                6600                6605

Ala Gly Thr Asn Gly Pro His Tyr Glu Pro Leu Leu Arg Asn Thr Ala
        6610                6615                6620

Glu Asp Leu Glu Gly Tyr Val Gly Thr Gly Asn Ala Ala Ser Ile Met
6625                6630                6635                6640

Ser Gly Arg Val Ser Tyr Thr Leu Gly Leu Glu Gly Pro Ala Val Thr
        6645                6650                6655

Val Asp Thr Ala Cys Ser Ser Ser Leu Val Ala Leu His Leu Ala Val
        6660                6665                6670

Gln Ala Leu Arg Lys Gly Glu Cys Gly Leu Ala Leu Ala Gly Gly Val
        6675                6680                6685

Thr Val Met Ser Thr Pro Thr Thr Phe Val Glu Phe Ser Arg Gln Arg
        6690                6695                6700

Gly Leu Ala Glu Asp Gly Arg Ser Lys Ala Phe Ala Ala Ser Ala Asp
6705                6710                6715                6720

Gly Phe Gly Pro Ala Glu Gly Val Gly Met Leu Leu Val Glu Arg Leu
            6725                6730                6735

Ser Asp Ala Arg Arg Asn Gly His Arg Val Leu Ala Val Val Arg Gly
        6740                6745                6750

Ser Ala Val Asn Gln Asp Gly Ala Ser Asn Gly Leu Thr Ala Pro Asn
        6755                6760                6765

Gly Pro Ser Gln Gln Arg Val Ile Arg Arg Ala Leu Ala Asp Ala Arg
        6770                6775                6780

Leu Thr Thr Ala Asp Val Asp Val Val Glu Ala His Gly Thr Gly Thr
6785                6790                6795                6800

Arg Leu Gly Asp Pro Ile Glu Ala Gln Ala Leu Ile Ala Thr Tyr Gly
            6805                6810                6815

Gln Gly Arg Asp Thr Glu Gln Pro Leu Arg Leu Gly Ser Leu Lys Ser
            6820                6825                6830

Asn Ile Gly His Thr Gln Ala Ala Ala Gly Val Ser Gly Ile Ile Lys
            6835                6840                6845
```

```
Met Val Gln Ala Met Arg His Gly Val Leu Pro Lys Thr Leu His Val
    6850                6855                6860

Asp Arg Pro Ser Asp Gln Ile Asp Trp Ser Ala Gly Thr Val Glu Leu
6865            6870                6875                6880

Leu Thr Glu Ala Met Asp Trp Pro Arg Lys Gln Glu Gly Gly Leu Arg
                6885                6890                6895

Arg Ala Ala Val Ser Ser Phe Gly Ile Ser Gly Thr Asn Ala His Ile
            6900                6905                6910

Val Leu Glu Glu Ala Pro Val Asp Glu Asp Ala Pro Ala Asp Glu Pro
        6915                6920                6925

Ser Val Gly Gly Val Val Pro Trp Leu Val Ser Ala Lys Thr Pro Ala
        6930                6935                6940

Ala Leu Asp Ala Gln Ile Gly Arg Leu Ala Ala Phe Ala Ser Gln Gly
6945                6950                6955                6960

Arg Thr Asp Ala Ala Asp Pro Gly Ala Val Ala Arg Val Leu Ala Gly
                6965                6970                6975

Gly Arg Ala Gln Phe Glu His Arg Ala Val Ala Leu Gly Thr Gly Gln
            6980                6985                6990

Asp Asp Leu Ala Ala Ala Leu Ala Ala Pro Glu Gly Leu Val Arg Gly
        6995                7000                7005

Val Ala Ser Gly Val Gly Arg Val Ala Phe Val Phe Pro Gly Gln Gly
    7010                7015                7020

Thr Gln Trp Ala Gly Met Gly Ala Glu Leu Leu Asp Val Ser Lys Glu
7025                7030                7035                7040

Phe Ala Ala Ala Met Ala Glu Cys Glu Ala Ala Leu Ala Pro Tyr Val
                7045                7050                7055

Asp Trp Ser Leu Glu Ala Val Val Arg Gln Ala Pro Gly Ala Pro Thr
            7060                7065                7070

Leu Glu Arg Val Asp Val Val Gln Pro Val Thr Phe Ala Val Met Val
        7075                7080                7085

Ser Leu Ala Lys Val Trp Gln His His Gly Val Thr Pro Gln Ala Val
    7090                7095                7100

Val Gly His Ser Gln Gly Glu Ile Ala Ala Tyr Val Ala Gly Ala
7105                7110                7115                7120

Leu Ser Leu Asp Asp Ala Ala Arg Val Val Thr Leu Arg Ser Lys Ser
                7125                7130                7135

Ile Gly Ala His Leu Ala Gly Gln Gly Gly Met Leu Ser Leu Ala Leu
            7140                7145                7150

Ser Glu Ala Ala Val Val Glu Arg Leu Ala Gly Phe Asp Gly Leu Ser
        7155                7160                7165

Val Ala Ala Val Asn Gly Pro Thr Ala Thr Val Val Ser Gly Asp Pro
    7170                7175                7180

Thr Gln Ile Gln Glu Leu Ala Gln Ala Cys Glu Ala Asp Gly Val Arg
7185                7190                7195                7200

Ala Arg Ile Ile Pro Val Asp Tyr Ala Ser His Ser Ala His Val Glu
                7205                7210                7215

Thr Ile Glu Ser Glu Leu Ala Asp Val Leu Ala Gly Leu Ser Pro Gln
            7220                7225                7230

Thr Pro Gln Val Pro Phe Phe Ser Thr Leu Glu Gly Ala Trp Ile Thr
        7235                7240                7245

Glu Pro Ala Leu Asp Gly Gly Tyr Trp Tyr Arg Asn Leu Arg His Arg
    7250                7255                7260
```

```
Val Gly Phe Ala Pro Ala Val Glu Thr Leu Ala Thr Asp Glu Gly Phe
7265                7270                7275                7280

Thr His Phe Val Glu Val Ser Ala His Pro Val Leu Thr Met Ala Leu
            7285                7290                7295

Pro Glu Thr Val Thr Gly Leu Gly Thr Leu Arg Arg Asp Asn Gly Gly
            7300                7305                7310

Gln His Arg Leu Thr Thr Ser Leu Ala Glu Ala Trp Ala Asn Gly Leu
            7315                7320                7325

Thr Val Asp Trp Ala Ser Leu Leu Pro Thr Thr Thr His Pro Asp
7330                7335                7340

Leu Pro Thr Tyr Ala Phe Gln Thr Glu Arg Tyr Trp Pro Gln Pro Asp
7345                7350                7355                7360

Leu Ser Ala Ala Gly Asp Ile Thr Ser Ala Gly Leu Gly Ala Ala Glu
            7365                7370                7375

His Pro Leu Leu Gly Ala Ala Val Ala Leu Ala Asp Ser Asp Gly Cys
            7380                7385                7390

Leu Leu Thr Gly Ser Leu Ser Leu Arg Thr His Pro Trp Leu Ala Asp
            7395                7400                7405

His Ala Val Ala Gly Thr Val Leu Leu Pro Gly Thr Ala Phe Val Glu
            7410                7415                7420

Leu Ala Phe Arg Ala Gly Asp Gln Val Gly Cys Asp Leu Val Glu Glu
7425                7430                7435                7440

Leu Thr Leu Asp Ala Pro Leu Val Leu Pro Arg Arg Gly Ala Val Arg
            7445                7450                7455

Val Gln Leu Ser Val Gly Ala Ser Asp Glu Ser Gly Arg Arg Thr Phe
            7460                7465                7470

Gly Leu Tyr Ala His Pro Glu Asp Ala Pro Gly Glu Ala Glu Trp Thr
            7475                7480                7485

Arg His Ala Thr Gly Val Leu Ala Ala Arg Ala Asp Arg Thr Ala Pro
            7490                7495                7500

Val Ala Asp Pro Glu Ala Trp Pro Pro Pro Gly Ala Glu Pro Val Asp
7505                7510                7515                7520

Val Asp Gly Leu Tyr Glu Arg Phe Ala Ala Asn Gly Tyr Gly Tyr Gly
            7525                7530                7535

Pro Leu Phe Gln Gly Val Arg Gly Val Trp Arg Arg Gly Asp Glu Val
            7540                7545                7550

Phe Ala Asp Val Ala Leu Pro Ala Glu Val Gly Ala Glu Gly Ala
            7555                7560                7565

Arg Phe Gly Leu His Pro Ala Leu Leu Asp Ala Val Gln Ala Ala
            7570                7575                7580

Gly Ala Gly Arg Gly Val Arg Arg Gly His Ala Ala Val Arg Leu
7585                7590                7595                7600

Glu Arg Asp Leu Leu Tyr Ala Val Gly Ala Thr Ala Leu Arg Val Arg
            7605                7610                7615

Leu Ala Pro Ala Gly Pro Asp Thr Val Ser Val Ser Ala Ala Asp Ser
            7620                7625                7630

Ser Gly Gln Pro Val Phe Ala Ala Asp Ser Leu Thr Val Leu Pro Val
            7635                7640                7645

Asp Pro Ala Gln Leu Ala Ala Phe Ser Asp Pro Thr Leu Asp Ala Leu
            7650                7655                7660

His Leu Leu Glu Trp Thr Ala Trp Asp Gly Ala Ala Gln Ala Leu Pro
7665                7670                7675                7680
```

```
Gly Ala Val Val Leu Gly Gly Asp Ala Asp Gly Leu Ala Ala Ala Leu
                7685                7690                7695

Arg Ala Gly Gly Thr Glu Val Leu Ser Phe Pro Asp Leu Thr Asp Leu
                7700                7705                7710

Val Glu Ala Val Asp Arg Gly Glu Thr Pro Ala Pro Ala Thr Val Leu
                7715                7720                7725

Val Ala Cys Pro Ala Ala Gly Pro Asp Gly Pro Glu His Val Arg Glu
                7730                7735                7740

Ala Leu His Gly Ser Leu Ala Leu Met Gln Ala Trp Leu Ala Asp Glu
7745                7750                7755                7760

Arg Phe Thr Asp Gly Arg Leu Val Leu Val Thr Arg Asp Ala Val Ala
                7765                7770                7775

Ala Arg Ser Gly Asp Gly Leu Arg Ser Thr Gly Gln Ala Ala Val Trp
                7780                7785                7790

Gly Leu Gly Arg Ser Ala Gln Thr Glu Ser Pro Gly Arg Phe Val Leu
                7795                7800                7805

Leu Asp Leu Ala Gly Glu Ala Arg Thr Ala Gly Asp Ala Thr Ala Gly
                7810                7815                7820

Asp Gly Leu Thr Thr Gly Asp Ala Thr Val Gly Gly Thr Ser Gly Asp
7825                7830                7835                7840

Ala Ala Leu Gly Ser Ala Leu Ala Thr Ala Leu Gly Ser Gly Glu Pro
                7845                7850                7855

Gln Leu Ala Leu Arg Asp Gly Ala Leu Leu Val Pro Arg Leu Ala Arg
                7860                7865                7870

Ala Ala Ala Pro Ala Ala Ala Asp Gly Leu Ala Ala Ala Asp Gly Leu
                7875                7880                7885

Ala Ala Leu Pro Leu Pro Ala Ala Pro Ala Leu Trp Arg Leu Glu Pro
                7890                7895                7900

Gly Thr Asp Gly Ser Leu Glu Ser Leu Thr Ala Ala Pro Gly Asp Ala
7905                7910                7915                7920

Glu Thr Leu Ala Pro Glu Pro Leu Gly Pro Gly Gln Val Arg Ile Ala
                7925                7930                7935

Ile Arg Ala Thr Gly Leu Asn Phe Arg Asp Val Leu Ile Ala Leu Gly
                7940                7945                7950

Met Tyr Pro Asp Pro Ala Leu Met Gly Thr Glu Gly Ala Gly Val Val
                7955                7960                7965

Thr Ala Thr Gly Pro Gly Val Thr His Leu Ala Pro Gly Asp Arg Val
7970                7975                7980

Met Gly Leu Leu Ser Gly Ala Tyr Ala Pro Val Val Ala Asp Ala
7985                7990                7995                8000

Arg Thr Val Ala Arg Met Pro Glu Gly Trp Thr Phe Ala Gln Gly Ala
                8005                8010                8015

Ser Val Pro Val Val Phe Leu Thr Ala Val Tyr Ala Leu Arg Asp Leu
                8020                8025                8030

Ala Asp Val Lys Pro Gly Glu Arg Leu Leu Val His Ser Ala Ala Gly
                8035                8040                8045

Gly Val Gly Met Ala Ala Val Gln Leu Ala Arg His Trp Gly Val Glu
                8050                8055                8060

Val His Gly Thr Ala Ser His Gly Lys Trp Asp Ala Leu Arg Ala Leu
8065                8070                8075                8080

Gly Leu Asp Asp Ala His Ile Ala Ser Ser Arg Thr Leu Asp Phe Glu
                8085                8090                8095
```

-continued

```
Ser Ala Phe Arg Ala Ala Ser Gly Gly Ala Gly Met Asp Val Val Leu
            8100                8105                8110
Asn Ser Leu Ala Arg Glu Phe Val Asp Ala Ser Leu Arg Leu Leu Gly
        8115                8120                8125
Pro Gly Gly Arg Phe Val Glu Met Gly Lys Thr Asp Val Arg Asp Ala
    8130                8135                8140
Glu Arg Val Ala Ala Asp His Pro Gly Val Gly Tyr Arg Ala Phe Asp
8145                8150                8155                8160
Leu Gly Glu Ala Gly Pro Glu Arg Ile Gly Glu Met Leu Ala Glu Val
                8165                8170                8175
Ile Ala Leu Phe Glu Asp Gly Val Leu Arg His Leu Pro Val Thr Thr
            8180                8185                8190
Trp Asp Val Arg Arg Ala Arg Asp Ala Phe Arg His Val Ser Gln Ala
        8195                8200                8205
Arg His Thr Gly Lys Val Val Leu Thr Met Pro Ser Gly Leu Asp Pro
    8210                8215                8220
Glu Gly Thr Val Leu Leu Thr Gly Gly Thr Gly Ala Leu Gly Gly Ile
8225                8230                8235                8240
Val Ala Arg His Val Val Gly Glu Trp Gly Val Arg Arg Leu Leu Leu
                8245                8250                8255
Val Ser Arg Arg Gly Thr Asp Ala Pro Gly Ala Gly Glu Leu Val His
            8260                8265                8270
Glu Leu Glu Ala Leu Gly Ala Asp Val Ser Val Ala Ala Cys Asp Val
        8275                8280                8285
Ala Asp Arg Glu Ala Leu Thr Ala Val Leu Asp Ser Ile Pro Ala Glu
    8290                8295                8300
His Pro Leu Thr Ala Val Val His Thr Ala Gly Val Leu Ser Asp Gly
8305                8310                8315                8320
Thr Leu Pro Ser Met Thr Ala Glu Asp Val Glu His Val Leu Arg Pro
                8325                8330                8335
Lys Val Asp Ala Ala Phe Leu Leu Asp Glu Leu Thr Ser Thr Pro Gly
            8340                8345                8350
Tyr Asp Leu Ala Ala Phe Val Met Phe Ser Ser Ala Ala Ala Val Phe
        8355                8360                8365
Gly Gly Ala Gly Gln Gly Ala Tyr Ala Ala Ala Asn Ala Thr Leu Asp
    8370                8375                8380
Ala Leu Ala Trp Arg Arg Arg Thr Ala Gly Leu Pro Ala Leu Ser Leu
8385                8390                8395                8400
Gly Trp Gly Leu Trp Ala Glu Thr Ser Gly Met Thr Gly Gly Leu Ser
                8405                8410                8415
Asp Thr Asp Arg Ser Arg Leu Ala Arg Ser Gly Ala Thr Pro Met Asp
            8420                8425                8430
Ser Glu Leu Thr Leu Ser Leu Leu Asp Ala Ala Met Arg Arg Asp Asp
        8435                8440                8445
Pro Ala Leu Val Pro Ile Ala Leu Asp Val Ala Ala Leu Arg Ala Gln
    8450                8455                8460
Gln Arg Asp Gly Met Leu Ala Pro Leu Leu Ser Gly Leu Thr Arg Gly
8465                8470                8475                8480
Ser Arg Val Gly Gly Ala Pro Val Asn Gln Arg Arg Ala Ala Ala Gly
                8485                8490                8495
Gly Ala Gly Glu Ala Asp Thr Asp Leu Gly Gly Arg Leu Ala Ala Met
            8500                8505                8510
```

-continued

```
Thr Pro Asp Asp Arg Val Ala His Leu Arg Asp Leu Val Arg Thr His
        8515                8520                8525

Val Ala Thr Val Leu Gly His Gly Thr Pro Ser Arg Val Asp Leu Glu
        8530                8535                8540

Arg Ala Phe Arg Asp Thr Gly Phe Asp Ser Leu Thr Ala Val Glu Leu
8545                8550                8555                8560

Arg Asn Arg Leu Asn Ala Ala Thr Gly Leu Arg Leu Pro Ala Thr Leu
        8565                8570                8575

Val Phe Asp His Pro Thr Pro Gly Glu Leu Ala Gly His Leu Leu Asp
        8580                8585                8590

Glu Leu Ala Thr Ala Ala Gly Gly Ser Trp Ala Glu Gly Thr Gly Ser
        8595                8600                8605

Gly Asp Thr Ala Ser Ala Thr Asp Arg Gln Thr Thr Ala Ala Leu Ala
        8610                8615                8620

Glu Leu Asp Arg Leu Glu Gly Val Leu Ala Ser Leu Ala Pro Ala Ala
8625                8630                8635                8640

Gly Gly Arg Pro Glu Leu Ala Ala Arg Leu Arg Ala Leu Ala Ala Ala
                8645                8650                8655

Leu Gly Asp Asp Gly Asp Asp Ala Thr Asp Leu Asp Glu Ala Ser Asp
                8660                8665                8670

Asp Asp Leu Phe Ser Phe Ile Asp Lys Glu Leu Gly Asp Ser Asp Phe
        8675                8680                8685

Met Ala Asn Asn Glu Asp Lys Leu Arg Asp Tyr Leu Lys Arg Val Thr
        8690                8695                8700

Ala Glu Leu Gln Gln Asn Thr Arg Arg Leu Arg Glu Ile Glu Gly Arg
8705                8710                8715                8720

Thr His Glu Pro Val Ala Ile Val Gly Met Ala Cys Arg Leu Pro Gly
                8725                8730                8735

Gly Val Ala Ser Pro Glu Asp Leu Trp Gln Leu Val Ala Gly Asp Gly
                8740                8745                8750

Asp Ala Ile Ser Glu Phe Pro Gln Asp Arg Gly Trp Asp Val Glu Gly
        8755                8760                8765

Leu Tyr Asp Pro Asp Pro Asp Ala Ser Gly Arg Thr Tyr Cys Arg Ser
8770                8775                8780

Gly Gly Phe Leu His Asp Ala Gly Glu Phe Asp Ala Asp Phe Phe Gly
8785                8790                8795                8800

Ile Ser Pro Arg Glu Ala Leu Ala Met Asp Pro Gln Gln Arg Leu Ser
                8805                8810                8815

Leu Thr Thr Ala Trp Glu Ala Ile Glu Ser Ala Gly Ile Asp Pro Thr
                8820                8825                8830

Ala Leu Lys Gly Ser Gly Leu Gly Val Phe Val Gly Trp His Thr
        8835                8840                8845

Gly Tyr Thr Ser Gly Gln Thr Thr Ala Val Gln Ser Pro Glu Leu Glu
        8850                8855                8860

Gly His Leu Val Ser Gly Ala Ala Leu Gly Phe Leu Ser Gly Arg Ile
8865                8870                8875                8880

Ala Tyr Val Leu Gly Thr Asp Gly Pro Ala Leu Thr Val Asp Thr Ala
                8885                8890                8895

Cys Ser Ser Ser Leu Val Ala Leu His Leu Ala Val Gln Ala Leu Arg
                8900                8905                8910

Lys Gly Glu Cys Asp Met Ala Leu Ala Gly Gly Val Thr Val Met Pro
        8915                8920                8925
```

-continued

```
Asn Ala Asp Leu Phe Val Gln Phe Ser Arg Gln Arg Gly Leu Ala Ala
    8930                8935                8940
Asp Gly Arg Ser Lys Ala Phe Ala Thr Ser Ala Asp Gly Phe Gly Pro
8945                8950                8955                8960
Ala Glu Gly Ala Gly Val Leu Leu Val Glu Arg Leu Ser Asp Ala Arg
                8965                8970                8975
Arg Asn Gly His Arg Ile Leu Ala Val Val Arg Gly Ser Ala Val Asn
            8980                8985                8990
Gln Asp Gly Ala Ser Asn Gly Leu Thr Ala Pro His Gly Pro Ser Gln
            8995                9000                9005
Gln Arg Val Ile Arg Arg Ala Leu Ala Asp Ala Arg Leu Ala Pro Gly
        9010                9015                9020
Asp Val Asp Val Val Glu Ala His Gly Thr Gly Thr Arg Leu Gly Asp
9025                9030                9035                9040
Pro Ile Glu Ala Gln Ala Leu Ile Ala Thr Tyr Gly Gln Glu Lys Ser
                9045                9050                9055
Ser Glu Gln Pro Leu Arg Leu Gly Ala Leu Lys Ser Asn Ile Gly His
                9060                9065                9070
Thr Gln Ala Ala Ala Gly Val Ala Gly Val Ile Lys Met Val Gln Ala
            9075                9080                9085
Met Arg His Gly Leu Leu Pro Lys Thr Leu His Val Asp Glu Pro Ser
        9090                9095                9100
Asp Gln Ile Asp Trp Ser Ala Gly Thr Val Glu Leu Leu Thr Glu Ala
9105                9110                9115                9120
Val Asp Trp Pro Glu Lys Gln Asp Gly Gly Leu Arg Arg Ala Ala Val
                9125                9130                9135
Ser Ser Phe Gly Ile Ser Gly Thr Asn Ala His Val Val Leu Glu Glu
            9140                9145                9150
Ala Pro Ala Val Glu Asp Ser Pro Ala Val Glu Pro Pro Ala Gly Gly
        9155                9160                9165
Gly Val Val Pro Trp Pro Val Ser Ala Lys Thr Pro Ala Ala Leu Asp
        9170                9175                9180
Ala Gln Ile Gly Gln Leu Ala Ala Tyr Ala Asp Gly Arg Thr Asp Val
9185                9190                9195                9200
Asp Pro Ala Val Ala Ala Arg Ala Leu Val Asp Ser Arg Thr Ala Met
                9205                9210                9215
Glu His Arg Ala Val Ala Val Gly Asp Ser Arg Glu Ala Leu Arg Asp
            9220                9225                9230
Ala Leu Arg Met Pro Glu Gly Leu Val Arg Gly Thr Ser Ser Asp Val
        9235                9240                9245
Gly Arg Val Ala Phe Val Phe Pro Gly Gln Gly Thr Gln Trp Ala Gly
        9250                9255                9260
Met Gly Ala Glu Leu Leu Asp Ser Ser Pro Glu Phe Ala Ala Ser Met
9265                9270                9275                9280
Ala Glu Cys Glu Thr Ala Leu Ser Arg Tyr Val Asp Trp Ser Leu Glu
                9285                9290                9295
Ala Val Val Arg Gln Pro Gly Ala Pro Thr Leu Asp Arg Val Asp
            9300                9305                9310
Val Val Gln Pro Val Thr Phe Ala Val Met Val Ser Leu Ala Lys Val
        9315                9320                9325
Trp Gln His His Gly Ile Thr Pro Gln Ala Val Val Gly His Ser Gln
        9330                9335                9340
```

```
Gly Glu Ile Ala Ala Ala Tyr Val Ala Gly Ala Leu Thr Leu Asp Asp
9345                9350                9355                9360

Ala Ala Arg Val Val Thr Leu Arg Ser Lys Ser Ile Ala Ala His Leu
            9365                9370                9375

Ala Gly Lys Gly Gly Met Ile Ser Leu Ala Leu Asp Glu Ala Ala Val
            9380                9385                9390

Leu Lys Arg Leu Ser Asp Phe Asp Gly Leu Ser Val Ala Ala Val Asn
            9395                9400                9405

Gly Pro Thr Ala Thr Val Val Ser Gly Asp Pro Thr Gln Ile Glu Glu
        9410                9415                9420

Leu Ala Arg Thr Cys Glu Ala Asp Gly Val Arg Ala Arg Ile Ile Pro
9425                9430                9435                9440

Val Asp Tyr Ala Ser His Ser Arg Gln Val Glu Ile Ile Glu Lys Glu
                9445                9450                9455

Leu Ala Glu Val Leu Ala Gly Leu Ala Pro Gln Ala Pro His Val Pro
            9460                9465                9470

Phe Phe Ser Thr Leu Glu Gly Thr Trp Ile Thr Glu Pro Val Leu Asp
            9475                9480                9485

Gly Thr Tyr Trp Tyr Arg Asn Leu Arg His Arg Val Gly Phe Ala Pro
        9490                9495                9500

Ala Val Glu Thr Leu Ala Val Asp Gly Phe Thr His Phe Ile Glu Val
9505                9510                9515                9520

Ser Ala His Pro Val Leu Thr Met Thr Leu Pro Glu Thr Val Thr Gly
                9525                9530                9535

Leu Gly Thr Leu Arg Arg Glu Gln Gly Gly Gln Glu Arg Leu Val Thr
            9540                9545                9550

Ser Leu Ala Glu Ala Trp Ala Asn Gly Leu Thr Ile Asp Trp Ala Pro
            9555                9560                9565

Ile Leu Pro Thr Ala Thr Gly His His Pro Glu Leu Pro Thr Tyr Ala
    9570                9575                9580

Phe Gln Thr Glu Arg Phe Trp Leu Gln Ser Ser Ala Pro Thr Ser Ala
9585                9590                9595                9600

Ala Asp Asp Trp Arg Tyr Arg Val Glu Trp Lys Pro Leu Thr Ala Ser
                9605                9610                9615

Gly Gln Ala Asp Leu Ser Gly Arg Trp Ile Val Ala Val Gly Ser Glu
            9620                9625                9630

Pro Glu Ala Glu Leu Leu Gly Ala Leu Lys Ala Ala Gly Ala Glu Val
            9635                9640                9645

Asp Val Leu Glu Ala Gly Ala Asp Asp Arg Glu Ala Leu Ala Ala
        9650                9655                9660

Arg Leu Thr Ala Leu Thr Thr Gly Asp Gly Phe Thr Gly Val Val Ser
9665                9670                9675                9680

Leu Leu Asp Asp Leu Val Pro Gln Val Ala Trp Val Gln Ala Leu Gly
            9685                9690                9695

Asp Ala Gly Ile Lys Ala Pro Leu Trp Ser Val Thr Gln Gly Ala Val
            9700                9705                9710

Ser Val Gly Arg Leu Asp Thr Pro Ala Asp Pro Asp Arg Ala Met Leu
            9715                9720                9725

Trp Gly Leu Gly Arg Val Val Ala Leu Glu His Pro Glu Arg Trp Ala
    9730                9735                9740

Gly Leu Val Asp Leu Pro Ala Gln Pro Asp Ala Ala Ala Leu Ala His
    9745                9750                9755                9760
```

-continued

```
Leu Val Thr Ala Leu Ser Gly Ala Thr Gly Glu Asp Gln Ile Ala Ile
            9765                9770                9775

Arg Thr Thr Gly Leu His Ala Arg Arg Leu Ala Arg Ala Pro Leu His
            9780                9785                9790

Gly Arg Arg Pro Thr Arg Asp Trp Gln Pro His Gly Thr Val Leu Ile
            9795                9800                9805

Thr Gly Gly Thr Gly Ala Leu Gly Ser His Ala Ala Arg Trp Met Ala
            9810                9815                9820

His His Gly Ala Glu His Leu Leu Val Ser Arg Ser Gly Glu Gln
9825                9830                9835                9840

Ala Pro Gly Ala Thr Gln Leu Thr Ala Glu Leu Thr Ala Ser Gly Ala
            9845                9850                9855

Arg Val Thr Ile Ala Ala Cys Asp Val Ala Asp Pro His Ala Met Arg
            9860                9865                9870

Thr Leu Leu Asp Ala Ile Pro Ala Glu Thr Pro Leu Thr Ala Val Val
            9875                9880                9885

His Thr Ala Gly Ala Pro Gly Gly Asp Pro Leu Asp Val Thr Gly Pro
9890                9895                9900

Glu Asp Ile Ala Arg Ile Leu Gly Ala Lys Thr Ser Gly Ala Glu Val
9905                9910                9915                9920

Leu Asp Asp Leu Leu Arg Gly Thr Pro Leu Asp Ala Phe Val Leu Tyr
            9925                9930                9935

Ser Ser Asn Ala Gly Val Trp Gly Ser Gly Ser Gln Gly Val Tyr Ala
            9940                9945                9950

Ala Ala Asn Ala His Leu Asp Ala Leu Ala Ala Arg Arg Ala Arg
            9955                9960                9965

Gly Glu Thr Ala Thr Ser Val Ala Trp Gly Leu Trp Ala Gly Asp Gly
    9970                9975                9980

Met Gly Arg Gly Ala Asp Asp Ala Tyr Trp Gln Arg Arg Gly Ile Arg
9985                9990                9995                10000

Pro Met Ser Pro Asp Arg Ala Leu Asp Glu Leu Ala Lys Ala Leu Ser
            10005                10010                10015

His Asp Glu Thr Phe Val Ala Val Ala Asp Val Asp Trp Glu Arg Phe
            10020                10025                10030

Ala Pro Ala Phe Thr Val Ser Arg Pro Ser Leu Leu Leu Asp Gly Val
            10035                10040                10045

Pro Glu Ala Arg Gln Ala Leu Ala Ala Pro Val Gly Ala Pro Ala Pro
    10050                10055                10060

Gly Asp Ala Ala Val Ala Pro Thr Gly Gln Ser Ser Ala Leu Ala Ala
10065                10070                10075                10080

Ile Thr Ala Leu Pro Glu Pro Glu Arg Arg Pro Ala Leu Leu Thr Leu
            10085                10090                10095

Val Arg Thr His Ala Ala Ala Val Leu Gly His Ser Ser Pro Asp Arg
            10100                10105                10110

Val Ala Pro Gly Arg Ala Phe Thr Glu Leu Gly Phe Asp Ser Leu Thr
            10115                10120                10125

Ala Val Gln Leu Arg Asn Gln Leu Ser Thr Val Val Gly Asn Arg Leu
    10130                10135                10140

Pro Ala Thr Thr Val Phe Asp His Pro Thr Pro Ala Ala Leu Ala Ala
    10145                10150                10155                10160

His Leu His Glu Ala Tyr Leu Ala Pro Ala Glu Pro Ala Pro Thr Asp
            10165                10170                10175
```

-continued

```
Trp Glu Gly Arg Val Arg Arg Ala Leu Ala Glu Leu Pro Leu Asp Arg
        10180               10185               10190

Leu Arg Asp Ala Gly Val Leu Asp Thr Val Leu Arg Leu Thr Gly Ile
        10195               10200               10205

Glu Pro Glu Pro Gly Ser Gly Gly Ser Asp Gly Gly Ala Ala Asp Pro
10210               10215               10220

Gly Ala Glu Pro Glu Ala Ser Ile Asp Asp Leu Asp Ala Glu Ala Leu
10225               10230               10235               10240

Ile Arg Met Ala Leu Gly Pro Arg Asn Thr Met Thr Ser Ser Asn Glu
        10245               10250               10255

Gln Leu Val Asp Ala Leu Arg Ala Ser Leu Lys Glu Asn Glu Glu Leu
        10260               10265               10270

Arg Lys Glu Ser Arg Arg Arg Ala Asp Arg Arg Gln Glu Pro Met Ala
        10275               10280               10285

Ile Val Gly Met Ser Cys Arg Phe Ala Gly Gly Ile Arg Ser Pro Glu
        10290               10295               10300

Asp Leu Trp Asp Ala Val Ala Ala Gly Lys Asp Leu Val Ser Glu Val
10305               10310               10315               10320

Pro Glu Glu Arg Gly Trp Asp Ile Asp Ser Leu Tyr Asp Pro Val Pro
        10325               10330               10335

Gly Arg Lys Gly Thr Thr Tyr Val Arg Asn Ala Ala Phe Leu Asp Asp
        10340               10345               10350

Ala Ala Gly Phe Asp Ala Ala Phe Phe Gly Ile Ser Pro Arg Glu Ala
        10355               10360               10365

Leu Ala Met Asp Pro Gln Gln Arg Gln Leu Leu Glu Ala Ser Trp Glu
        10370               10375               10380

Val Phe Glu Arg Ala Gly Ile Asp Pro Ala Ser Val Arg Gly Thr Asp
10385               10390               10395               10400

Val Gly Val Tyr Val Gly Cys Gly Tyr Gln Asp Tyr Ala Pro Asp Ile
            10405               10410               10415

Arg Val Ala Pro Glu Gly Thr Gly Gly Tyr Val Val Thr Gly Asn Ser
            10420               10425               10430

Ser Ala Val Ala Ser Gly Arg Ile Ala Tyr Ser Leu Gly Leu Glu Gly
        10435               10440               10445

Pro Ala Val Thr Val Asp Thr Ala Cys Ser Ser Ser Leu Val Ala Leu
        10450               10455               10460

His Leu Ala Leu Lys Gly Leu Arg Asn Gly Asp Cys Ser Thr Ala Leu
10465               10470               10475               10480

Val Gly Gly Val Ala Val Leu Ala Thr Pro Gly Ala Phe Ile Glu Phe
            10485               10490               10495

Ser Ser Gln Gln Ala Met Ala Ala Asp Gly Arg Thr Lys Gly Phe Ala
        10500               10505               10510

Ser Ala Ala Asp Gly Leu Ala Trp Gly Glu Gly Val Ala Val Leu Leu
        10515               10520               10525

Leu Glu Arg Leu Ser Asp Ala Arg Arg Lys Gly His Arg Val Leu Ala
        10530               10535               10540

Val Val Arg Gly Ser Ala Ile Asn Gln Asp Gly Ala Ser Asn Gly Leu
10545               10550               10555               10560

Thr Ala Pro His Gly Pro Ser Gln Gln His Leu Ile Arg Gln Ala Leu
            10565               10570               10575

Ala Asp Ala Arg Leu Thr Ser Ser Asp Val Asp Val Val Glu Gly His
            10580               10585               10590
```

```
Gly Thr Gly Thr Arg Leu Gly Asp Pro Ile Glu Ala Gln Ala Leu Leu
    10595              10600              10605

Ala Thr Tyr Gly Gln Gly Arg Ala Pro Gly Gln Pro Leu Arg Leu Gly
    10610              10615              10620

Thr Leu Lys Ser Asn Ile Gly His Thr Gln Ala Ala Ser Gly Val Ala
10625              10630              10635              10640

Gly Val Ile Lys Met Val Gln Ala Leu Arg His Gly Val Leu Pro Lys
            10645              10650              10655

Thr Leu His Val Asp Glu Pro Thr Asp Gln Val Asp Trp Ser Ala Gly
        10660              10665              10670

Ser Val Glu Leu Leu Thr Glu Ala Val Asp Trp Pro Glu Arg Pro Gly
    10675              10680              10685

Arg Leu Arg Arg Ala Gly Val Ser Ala Phe Gly Val Gly Gly Thr Asn
    10690              10695              10700

Ala His Val Val Leu Glu Glu Ala Pro Ala Val Glu Glu Ser Pro Ala
10705              10710              10715              10720

Val Glu Pro Pro Ala Gly Gly Gly Val Val Pro Trp Pro Val Ser Ala
            10725              10730              10735

Lys Thr Ser Ala Ala Leu Asp Ala Gln Ile Gly Gln Leu Ala Ala Tyr
        10740              10745              10750

Ala Glu Asp Arg Thr Asp Val Asp Pro Ala Val Ala Ala Arg Ala Leu
    10755              10760              10765

Val Asp Ser Arg Thr Ala Met Glu His Arg Ala Val Ala Val Gly Asp
    10770              10775              10780

Ser Arg Glu Ala Leu Arg Asp Ala Leu Arg Met Pro Glu Gly Leu Val
10785              10790              10795              10800

Arg Gly Thr Val Thr Asp Pro Gly Arg Val Ala Phe Val Phe Pro Gly
        10805              10810              10815

Gln Gly Thr Gln Trp Ala Gly Met Gly Ala Glu Leu Leu Asp Ser Ser
            10820              10825              10830

Pro Glu Phe Ala Ala Ala Met Ala Glu Cys Glu Thr Ala Leu Ser Pro
        10835              10840              10845

Tyr Val Asp Trp Ser Leu Glu Ala Val Val Arg Gln Ala Pro Ser Ala
    10850              10855              10860

Pro Thr Leu Asp Arg Val Asp Val Val Gln Pro Val Thr Phe Ala Val
    10865              10870              10875              10880

Met Val Ser Leu Ala Lys Val Trp Gln His His Gly Ile Thr Pro Glu
            10885              10890              10895

Ala Val Ile Gly His Ser Gln Gly Glu Ile Ala Ala Tyr Val Ala
        10900              10905              10910

Gly Ala Leu Thr Leu Asp Asp Ala Ala Arg Val Val Thr Leu Arg Ser
    10915              10920              10925

Lys Ser Ile Ala Ala His Leu Ala Gly Lys Gly Gly Met Ile Ser Leu
    10930              10935              10940

Ala Leu Ser Glu Glu Ala Thr Arg Gln Arg Ile Glu Asn Leu His Gly
10945              10950              10955              10960

Leu Ser Ile Ala Ala Val Asn Gly Pro Thr Ala Thr Val Val Ser Gly
            10965              10970              10975

Asp Pro Thr Gln Ile Gln Glu Leu Ala Gln Ala Cys Glu Ala Asp Gly
        10980              10985              10990

Ile Arg Ala Arg Ile Ile Pro Val Asp Tyr Ala Ser His Ser Ala His
    10995              11000              11005
```

-continued

```
Val Glu Thr Ile Glu Asn Glu Leu Ala Asp Val Leu Ala Gly Leu Ser
    11010               11015               11020

Pro Gln Thr Pro Gln Val Pro Phe Phe Ser Thr Leu Glu Gly Thr Trp
11025               11030               11035               11040

Ile Thr Glu Pro Ala Leu Asp Gly Gly Tyr Trp Tyr Arg Asn Leu Arg
        11045               11050               11055

His Arg Val Gly Phe Ala Pro Ala Val Glu Thr Leu Ala Thr Asp Glu
        11060               11065               11070

Gly Phe Thr His Phe Ile Glu Val Ser Ala His Pro Val Leu Thr Met
    11075               11080               11085

Thr Leu Pro Asp Lys Val Thr Gly Leu Ala Thr Leu Arg Arg Glu Asp
    11090               11095               11100

Gly Gly Gln His Arg Leu Thr Thr Ser Leu Ala Glu Ala Trp Ala Asn
11105               11110               11115               11120

Gly Leu Ala Leu Asp Trp Ala Ser Leu Leu Pro Ala Thr Gly Ala Leu
        11125               11130               11135

Ser Pro Ala Val Pro Asp Leu Pro Thr Tyr Ala Phe Gln His Arg Ser
        11140               11145               11150

Tyr Trp Ile Ser Pro Ala Gly Pro Gly Glu Ala Pro Ala His Thr Ala
    11155               11160               11165

Ser Gly Arg Glu Ala Val Ala Glu Thr Gly Leu Ala Trp Gly Pro Gly
    11170               11175               11180

Ala Glu Asp Leu Asp Glu Glu Gly Arg Arg Ser Ala Val Leu Ala Met
11185               11190               11195               11200

Val Met Arg Gln Ala Ala Ser Val Leu Arg Cys Asp Ser Pro Glu Glu
        11205               11210               11215

Val Pro Val Asp Arg Pro Leu Arg Glu Ile Gly Phe Asp Ser Leu Thr
        11220               11225               11230

Ala Val Asp Phe Arg Asn Arg Val Asn Arg Leu Thr Gly Leu Gln Leu
        11235               11240               11245

Pro Pro Thr Val Val Phe Gln His Pro Thr Pro Val Ala Leu Ala Glu
    11250               11255               11260

Arg Ile Ser Asp Glu Leu Ala Glu Arg Asn Trp Ala Val Ala Glu Pro
11265               11270               11275               11280

Ser Asp His Glu Gln Ala Glu Glu Lys Ala Ala Pro Ala Gly
        11285               11290               11295

Ala Arg Ser Gly Ala Asp Thr Gly Ala Gly Ala Gly Met Phe Arg Ala
        11300               11305               11310

Leu Phe Arg Gln Ala Val Glu Asp Asp Arg Tyr Gly Glu Phe Leu Asp
        11315               11320               11325

Val Leu Ala Glu Ala Ser Ala Phe Arg Pro Gln Phe Ala Ser Pro Glu
    11330               11335               11340

Ala Cys Ser Glu Arg Leu Asp Pro Val Leu Leu Ala Gly Gly Pro Thr
11345               11350               11355               11360

Asp Arg Ala Glu Gly Arg Ala Val Leu Val Gly Cys Thr Gly Thr Ala
        11365               11370               11375

Ala Asn Gly Gly Pro His Glu Phe Leu Arg Leu Ser Thr Ser Phe Gln
        11380               11385               11390

Glu Glu Arg Asp Phe Leu Ala Val Pro Leu Pro Gly Tyr Gly Thr Gly
        11395               11400               11405

Thr Gly Thr Gly Thr Ala Leu Leu Pro Ala Asp Leu Asp Thr Ala Leu
    11410               11415               11420
```

```
Asp Ala Gln Ala Arg Ala Ile Leu Arg Ala Ala Gly Asp Ala Pro Val
    11425               11430               11435               11440

Val Leu Leu Gly His Ser Gly Gly Ala Leu Leu Ala His Glu Leu Ala
            11445               11450               11455

Phe Arg Leu Glu Arg Ala His Gly Ala Pro Pro Ala Gly Ile Val Leu
    11460               11465               11470

Val Asp Pro Tyr Pro Pro Gly His Gln Glu Pro Ile Glu Val Trp Ser
        11475               11480               11485

Arg Gln Leu Gly Glu Gly Leu Phe Ala Gly Glu Leu Glu Pro Met Ser
    11490               11495               11500

Asp Ala Arg Leu Leu Ala Met Gly Arg Tyr Ala Arg Phe Leu Ala Gly
11505               11510               11515               11520

Pro Arg Pro Gly Arg Ser Ser Ala Pro Val Leu Leu Val Arg Ala Ser
            11525               11530               11535

Glu Pro Leu Gly Asp Trp Gln Glu Glu Arg Gly Asp Trp Arg Ala His
    11540               11545               11550

Trp Asp Leu Pro His Thr Val Ala Asp Val Pro Gly Asp His Phe Thr
        11555               11560               11565

Met Met Arg Asp His Ala Pro Ala Val Ala Glu Ala Val Leu Ser Trp
    11570               11575               11580

Leu Asp Ala Ile Glu Gly Ile Glu Gly Ala Gly Lys Met Thr Asp Arg
11585               11590               11595               11600

Pro Leu Asn Val Asp Ser Gly Leu Trp Ile Arg Arg Phe His Pro Ala
            11605               11610               11615

Pro Asn Ser Ala Val Arg Leu Val Cys Leu Pro His Ala Gly Gly Ser
        11620               11625               11630

Ala Ser Tyr Phe Phe Arg Phe Ser Glu Glu Leu His Pro Ser Val Glu
    11635               11640               11645

Ala Leu Ser Val Gln Tyr Pro Gly Arg Gln Asp Arg Arg Ala Glu Pro
    11650               11655               11660

Cys Leu Glu Ser Val Glu Glu Leu Ala Glu His Val Val Ala Ala Thr
11665               11670               11675               11680

Glu Pro Trp Trp Gln Glu Gly Arg Leu Ala Phe Phe Gly His Ser Leu
            11685               11690               11695

Gly Ala Ser Val Ala Phe Glu Thr Ala Arg Ile Leu Glu Gln Arg His
        11700               11705               11710

Gly Val Arg Pro Glu Gly Leu Tyr Val Ser Gly Arg Arg Ala Pro Ser
    11715               11720               11725

Leu Ala Pro Asp Arg Leu Val His Gln Leu Asp Asp Arg Ala Phe Leu
    11730               11735               11740

Ala Glu Ile Arg Arg Leu Ser Gly Thr Asp Glu Arg Phe Leu Gln Asp
11745               11750               11755               11760

Asp Glu Leu Leu Arg Leu Val Leu Pro Ala Leu Arg Ser Asp Tyr Lys
            11765               11770               11775

Ala Ala Glu Thr Tyr Leu His Arg Pro Ser Ala Lys Leu Thr Cys Pro
        11780               11785               11790

Val Met Ala Leu Ala Gly Asp Arg Asp Pro Lys Ala Pro Leu Asn Glu
    11795               11800               11805

Val Ala Glu Trp Arg Arg His Thr Ser Gly Pro Phe Cys Leu Arg Ala
    11810               11815               11820

Tyr Ser Gly Gly His Phe Tyr Leu Asn Asp Gln Trp His Glu Ile Cys
11825               11830               11835               11840
```

```
Asn Asp Ile Ser Asp His Leu Leu Val Thr Arg Gly Ala Pro Asp Ala
            11845               11850               11855

Arg Val Val Gln Pro Pro Thr Ser Leu Ile Glu Gly Ala Ala Lys Arg
            11860               11865               11870

Trp Gln Asn Pro Arg
        11875

<210> SEQ ID NO: 7
<211> LENGTH: 1248
<212> TYPE: DNA
<213> ORGANISM: Streptomyces venezuelae

<400> SEQUENCE: 7
gtgaaaagcg ccttatccga cctcgcattc ttcggcggcc ccgccgcttt cgaccagccg      60
ctcctcgtgg ggcggcccaa ccgcatcgac cgcgccaggc tgtacgagcg gctcgaccgg     120
gccctcgaca gccagtggct gtccaacggc ggcccgctcg tccgcgagtt cgaggagcgc     180
gtcgccgggc tcgccggggt ccggcatgcc gtggccacct gcaacgccac ggccgggctc     240
cagctcctcg cgcacgccgc cggcctcacc ggcgaagtga tcatgccgtc gatgacgttc     300
gccgccaccc cgcacgcact cgctggatc ggcctcaccc cggtcttcgc cgacatcgac     360
ccggacaccg gcaacctcga cccggaccag gtggccgccg cggtcacacc ccgcacctcg     420
gccgtcgtcg gcgtccacct ctggggccgc ccctgcgccg ccgaccagct gcggaaggtc     480
gccgacgagc acggcctgcg gctgtacttc gacgccgcgc acgccctcgg ctgcgcggtc     540
gacggccggc ccgccggcag cctcggcgac gccgaggtct tcagcttcca cgccaccaag     600
gccgtcaacg ccttcgaggg cggcgccgtc gtcaccgacg acgccgacct cgccgcccgg     660
atccgcgccc tccacaactt cggcttcgac ctgcccggcg gcagccccgc cggcgggacc     720
aacgccaaga tgagcgaggc cgccgccgcc atgggcctca cctccctcga cgcgtttccc     780
gaggtcatcg accggaaccg gcgcaaccac gccgcctacc gcgagcacct cgcggacctc     840
cccggcgtcc tcgtcgccga ccacgaccgc acggcctca caaccacca gtacgtgatc     900 gtcgagatcg acgaggccac caccggcatc caccgcgacc tcgtcatgga ggtcctgaag     960
gccgaaggcg tgcacacccg cgcctacttc tcgccgggct gccacgagct ggagccgtac    1020
cgcgggcagc cgcacgcccc gctgccgcac accgaacgcc tcgccgcgcg cgtgctgtcc    1080
ctgccgaccg gcaccgccat cggcgacgac gacatccgcc gggtcgccga cctgctgcgt    1140
ctctgcgcga cccgcggccg cgaactgacc gcgcgccacc gcgacacggc ccccgccccg    1200
ctcgcggccc cccagacatc cacgcccacg attggacgct cccgatga             1248

<210> SEQ ID NO: 8
<211> LENGTH: 415
<212> TYPE: PRT
<213> ORGANISM: Streptomyces venezuelae

<400> SEQUENCE: 8

Met Lys Ser Ala Leu Ser Asp Leu Ala Phe Phe Gly Gly Pro Ala Ala
  1               5                  10                  15

Phe Asp Gln Pro Leu Leu Val Gly Arg Pro Asn Arg Ile Asp Arg Ala
              20                  25                  30

Arg Leu Tyr Glu Arg Leu Asp Arg Ala Leu Asp Ser Gln Trp Leu Ser
          35                  40                  45

Asn Gly Gly Pro Leu Val Arg Glu Phe Glu Glu Arg Val Ala Gly Leu
      50                  55                  60
```

```
Ala Gly Val Arg His Ala Val Ala Thr Cys Asn Ala Thr Ala Gly Leu
 65                  70                  75                  80

Gln Leu Leu Ala His Ala Ala Gly Leu Thr Gly Glu Val Ile Met Pro
                 85                  90                  95

Ser Met Thr Phe Ala Ala Thr Pro His Ala Leu Arg Trp Ile Gly Leu
            100                 105                 110

Thr Pro Val Phe Ala Asp Ile Asp Pro Asp Thr Gly Asn Leu Asp Pro
            115                 120                 125

Asp Gln Val Ala Ala Val Thr Pro Arg Thr Ser Ala Val Val Gly
        130                 135                 140

Val His Leu Trp Gly Arg Pro Cys Ala Ala Asp Gln Leu Arg Lys Val
145                 150                 155                 160

Ala Asp Glu His Gly Leu Arg Leu Tyr Phe Asp Ala Ala His Ala Leu
                165                 170                 175

Gly Cys Ala Val Asp Gly Arg Pro Ala Gly Ser Leu Gly Asp Ala Glu
                180                 185                 190

Val Phe Ser Phe His Ala Thr Lys Ala Val Asn Ala Phe Glu Gly Gly
                195                 200                 205

Ala Val Val Thr Asp Asp Ala Asp Leu Ala Ala Arg Ile Arg Ala Leu
        210                 215                 220

His Asn Phe Gly Phe Asp Leu Pro Gly Gly Ser Pro Ala Gly Gly Thr
225                 230                 235                 240

Asn Ala Lys Met Ser Glu Ala Ala Ala Met Gly Leu Thr Ser Leu
                245                 250                 255

Asp Ala Phe Pro Glu Val Ile Asp Arg Asn Arg Arg Asn His Ala Ala
            260                 265                 270

Tyr Arg Glu His Leu Ala Asp Leu Pro Gly Val Leu Val Ala Asp His
                275                 280                 285

Asp Arg His Gly Leu Asn Asn His Gln Tyr Val Ile Val Glu Ile Asp
        290                 295                 300

Glu Ala Thr Thr Gly Ile His Arg Asp Leu Val Met Glu Val Leu Lys
305                 310                 315                 320

Ala Glu Gly Val His Thr Arg Ala Tyr Phe Ser Pro Gly Cys His Glu
                325                 330                 335

Leu Glu Pro Tyr Arg Gly Gln Pro His Ala Pro Leu Pro His Thr Glu
            340                 345                 350

Arg Leu Ala Ala Arg Val Leu Ser Leu Pro Thr Gly Thr Ala Ile Gly
        355                 360                 365

Asp Asp Asp Ile Arg Arg Val Ala Asp Leu Leu Arg Leu Cys Ala Thr
370                 375                 380

Arg Gly Arg Glu Leu Thr Ala Arg His Arg Asp Thr Ala Pro Ala Pro
385                 390                 395                 400

Leu Ala Ala Pro Gln Thr Ser Thr Pro Thr Ile Gly Arg Ser Arg
                405                 410                 415

<210> SEQ ID NO: 9
<211> LENGTH: 1458
<212> TYPE: DNA
<213> ORGANISM: Streptomyces venezuelae

<400> SEQUENCE: 9
atgaccgccc ccgcccttct cgccaccgcc ccggccgaac gctgcgcgca ccccggagcc    60
gatctggggg cggcggtcca cgccgtcggc cagaccctcg ccgccggcgg cctcgtgccg   120
cccgacgagg ccggaacgac cgcccgccac ctcgtccggc tcgccgtgcg ctacggcaac   180
```

```
agcccttca ccccgctgga ggaggcccgc cacgacctgg gcgtcgaccg ggacgccttc      240
cggcgcctcc tcgccctgtt cgggcaggtc ccggagctcc gcaccgcggt cgagaccggc      300
cccgccgggg cgtactggaa gaacaccctg ctcccgctcg aacagcgcgg cgtcttcgac      360
gcggcgctcg ccaggaagcc cgtcttcccg tacagcgtcg gcctctaccc cggcccgacc      420
tgcatgttcc gctgccactt ctgcgtccgt gtgaccggcg cccgctacga cccgtccgcc      480
ctcgacgccg gcaacgccat gttccggtcg gtcatcgacg agatacccgc gggcaacccc      540
tcggcgatgt acttctccgg cggcctggag ccgctcacca cccccggcct cgggagcctg      600
gccgcgcacg ccaccgacca cggcctgcgg cccaccgtct acacgaactc cttcgcgctc      660
accgagcgca ccctggagcg ccagcccggc tctggggcc tgcacgccat ccgcacctcg      720
ctctacggcc tcaacgacga ggagtacgag cagaccaccg caagaaggc cgccttccgc      780 cgcgtccgcg agaacctgcg ccgcttccag cagctgcgcg ccgagcgcga gtcgccgatc      840
aacctcggct cgcctacat cgtgctcccg ggccgtgcct cccgcctgct cgacctggtc      900
gacttcatcg ccgacctcaa cgacgccggg cagggcagga cgatcgactt cgtcaacatt      960
cgcgaggact acagcggccg tgacgacggc aagctgccgc aggaggagcg ggccgagctc     1020
caggaggccc tcaacgcctt cgaggagcgg gtccgcgagc gcaccccgg actccacatc     1080 gactacggct acgccctgaa cagcctgcgc accggggccg acgccgaact gctgcggatc     1140
aagcccgcca ccatgcggcc caccgcgcac ccgcaggtcg cggtgcaggt cgatctcctc     1200
ggcgacgtgt acctgtaccg cgaggccggc ttccccgacc tggacggcgc gacccgctac     1260
atcgcgggcc gcgtgacccc cgacacctcc ctcaccgagg tcgtcaggga cttcgtcgag     1320
cgcggcggcg aggtggcggc cgtcgacggc gacgagtact tcatggacgg cttcgatcag     1380
gtcgtcaccg cccgcctgaa ccagctggag cgcgacgccg cggacggctg ggaggaggcc     1440
cgcggcttcc tgcgctga                                                   1458
```

<210> SEQ ID NO: 10
<211> LENGTH: 485
<212> TYPE: PRT
<213> ORGANISM: Streptomyces venezuelae

<400> SEQUENCE: 10

```
Met Thr Ala Pro Ala Leu Ser Ala Thr Ala Pro Ala Glu Arg Cys Ala
 1               5                  10                  15

His Pro Gly Ala Asp Leu Gly Ala Ala Val His Ala Val Gly Gln Thr
                20                  25                  30

Leu Ala Ala Gly Gly Leu Val Pro Pro Asp Glu Ala Gly Thr Thr Ala
            35                  40                  45

Arg His Leu Val Arg Leu Ala Val Arg Tyr Gly Asn Ser Pro Phe Thr
        50                  55                  60

Pro Leu Glu Glu Ala Arg His Asp Leu Gly Val Asp Arg Asp Ala Phe
    65                  70                  75                  80

Arg Arg Leu Leu Ala Leu Phe Gly Gln Val Pro Glu Leu Arg Thr Ala
                85                  90                  95

Val Glu Thr Gly Pro Ala Gly Ala Tyr Trp Lys Asn Thr Leu Leu Pro
                100                 105                 110

Leu Glu Gln Arg Gly Val Phe Asp Ala Ala Leu Ala Arg Lys Pro Val
            115                 120                 125

Phe Pro Tyr Ser Val Gly Leu Tyr Pro Gly Pro Thr Cys Met Phe Arg
        130                 135                 140
```

-continued

```
Cys His Phe Cys Val Arg Val Thr Gly Ala Arg Tyr Asp Pro Ser Ala
145                 150                 155                 160

Leu Asp Ala Gly Asn Ala Met Phe Arg Ser Val Ile Asp Glu Ile Pro
                165                 170                 175

Ala Gly Asn Pro Ser Ala Met Tyr Phe Ser Gly Gly Leu Glu Pro Leu
            180                 185                 190

Thr Asn Pro Gly Leu Gly Ser Leu Ala Ala His Ala Thr Asp His Gly
        195                 200                 205

Leu Arg Pro Thr Val Tyr Thr Asn Ser Phe Ala Leu Thr Glu Arg Thr
    210                 215                 220

Leu Glu Arg Gln Pro Gly Leu Trp Gly Leu His Ala Ile Arg Thr Ser
225                 230                 235                 240

Leu Tyr Gly Leu Asn Asp Glu Glu Tyr Glu Gln Thr Thr Gly Lys Lys
                245                 250                 255

Ala Ala Phe Arg Arg Val Arg Glu Asn Leu Arg Arg Phe Gln Gln Leu
            260                 265                 270

Arg Ala Glu Arg Glu Ser Pro Ile Asn Leu Gly Phe Ala Tyr Ile Val
        275                 280                 285

Leu Pro Gly Arg Ala Ser Arg Leu Leu Asp Leu Val Asp Phe Ile Ala
    290                 295                 300

Asp Leu Asn Asp Ala Gly Gln Gly Arg Thr Ile Asp Phe Val Asn Ile
305                 310                 315                 320

Arg Glu Asp Tyr Ser Gly Arg Asp Asp Gly Lys Leu Pro Gln Glu Glu
                325                 330                 335

Arg Ala Glu Leu Gln Glu Ala Leu Asn Ala Phe Glu Glu Arg Val Arg
            340                 345                 350

Glu Arg Thr Pro Gly Leu His Ile Asp Tyr Gly Tyr Ala Leu Asn Ser
        355                 360                 365

Leu Arg Thr Gly Ala Asp Ala Glu Leu Leu Arg Ile Lys Pro Ala Thr
    370                 375                 380

Met Arg Pro Thr Ala His Pro Gln Val Ala Val Gln Val Asp Leu Leu
385                 390                 395                 400

Gly Asp Val Tyr Leu Tyr Arg Glu Ala Gly Phe Pro Asp Leu Asp Gly
                405                 410                 415

Ala Thr Arg Tyr Ile Ala Gly Arg Val Thr Pro Asp Thr Ser Leu Thr
            420                 425                 430

Glu Val Val Arg Asp Phe Val Glu Arg Gly Gly Glu Val Ala Ala Val
        435                 440                 445

Asp Gly Asp Glu Tyr Phe Met Asp Gly Phe Asp Gln Val Val Thr Ala
    450                 455                 460

Arg Leu Asn Gln Leu Glu Arg Asp Ala Ala Asp Gly Trp Glu Glu Ala
465                 470                 475                 480

Arg Gly Phe Leu Arg
                485
```

<210> SEQ ID NO: 11
<211> LENGTH: 879
<212> TYPE: DNA
<213> ORGANISM: Streptomyces venezuelae

<400> SEQUENCE: 11

| | | | | |
|---|---|---|---|---|
| atgaagggaa tagtcctggc cggcgggagc ggaactcggc tgcatccggc gacctcggtc | | | | 60 |
| atttcgaagc agattcttcc ggtctacaac aaaccgatga tctactatcc gctgtcggtt | | | | 120 |

-continued

```
ctcatgctcg gcggtattcg cgagattcaa atcatctcga cccccagca catcgaactc      180 ttccagtcgc ttctcggaaa cggcaggcac ctgggaatag aactcgacta tgcggtccag      240
aaagagcccg caggaatcgc ggacgcactt ctcgtcggag ccgagcacat cggcgacgac      300
acctgcgccc tgatcctggg cgacaacatc ttccacgggc ccggcctcta cacgctcctg      360
cgggacagca tcgcgcgcct cgacggctgc gtgctcttcg gctacccggt caaggacccc      420
gagcggtacg gcgtcgccga ggtggacgcg acgggccggc tgaccgacct cgtcgagaag      480
cccgtcaagc cgcgctccaa cctcgccgtc accggcctct acctctacga caacgacgtc      540
gtcgacatcg ccaagaacat ccggccctcg ccgcgcggcg agctggagat caccgacgtc      600
aaccgcgtct acctggagcg gggccgggcc gaactcgtca acctgggccg cggcttcgcc      660
tggctggaca ccggcaccca cgactcgctc ctgcgggccg cccagtacgt ccaggtcctg      720
gaggagcggc agggcgtctg gatcgcgggc cttgaggaga tcgccttccg catgggcttc      780
atcgacgccg aggcctgtca cggcctggga gaaggcctct cccgcaccga gtacggcagc      840
tatctgatgg agatcgccgg ccgcgaggga gccccgtga                              879
```

<210> SEQ ID NO: 12
<211> LENGTH: 292
<212> TYPE: PRT
<213> ORGANISM: Streptomyces venezuelae

<400> SEQUENCE: 12

```
Met Lys Gly Ile Val Leu Ala Gly Gly Ser Gly Thr Arg Leu His Pro
 1               5                  10                  15

Ala Thr Ser Val Ile Ser Lys Gln Ile Leu Pro Val Tyr Asn Lys Pro
                20                  25                  30

Met Ile Tyr Tyr Pro Leu Ser Val Leu Met Leu Gly Gly Ile Arg Glu
            35                  40                  45

Ile Gln Ile Ile Ser Thr Pro Gln His Ile Glu Leu Phe Gln Ser Leu
        50                  55                  60

Leu Gly Asn Gly Arg His Leu Gly Ile Glu Leu Asp Tyr Ala Val Gln
 65                  70                  75                  80

Lys Glu Pro Ala Gly Ile Ala Asp Ala Leu Leu Val Gly Ala Glu His
                85                  90                  95

Ile Gly Asp Asp Thr Cys Ala Leu Ile Leu Gly Asp Asn Ile Phe His
            100                 105                 110

Gly Pro Gly Leu Tyr Thr Leu Leu Arg Asp Ser Ile Ala Arg Leu Asp
        115                 120                 125

Gly Cys Val Leu Phe Gly Tyr Pro Val Lys Asp Pro Glu Arg Tyr Gly
    130                 135                 140

Val Ala Glu Val Asp Ala Thr Gly Arg Leu Thr Asp Leu Val Glu Lys
145                 150                 155                 160

Pro Val Lys Pro Arg Ser Asn Leu Ala Val Thr Gly Leu Tyr Leu Tyr
                165                 170                 175

Asp Asn Asp Val Val Asp Ile Ala Lys Asn Ile Arg Pro Ser Pro Arg
            180                 185                 190

Gly Glu Leu Glu Ile Thr Asp Val Asn Arg Val Tyr Leu Glu Arg Gly
        195                 200                 205

Arg Ala Glu Leu Val Asn Leu Gly Arg Gly Phe Ala Trp Leu Asp Thr
    210                 215                 220

Gly Thr His Asp Ser Leu Leu Arg Ala Ala Gln Tyr Val Gln Val Leu
225                 230                 235                 240
```

```
Glu Glu Arg Gln Gly Val Trp Ile Ala Gly Leu Glu Glu Ile Ala Phe
            245                 250                 255

Arg Met Gly Phe Ile Asp Ala Glu Ala Cys His Gly Leu Gly Glu Gly
            260                 265                 270

Leu Ser Arg Thr Glu Tyr Gly Ser Tyr Leu Met Glu Ile Ala Gly Arg
            275                 280                 285

Glu Gly Ala Pro
        290

<210> SEQ ID NO: 13
<211> LENGTH: 1014
<212> TYPE: DNA
<213> ORGANISM: Streptomyces venezuelae

<400> SEQUENCE: 13
gtgcggcttc tggtgaccgg aggtgcgggc ttcatcggct cgcacttcgt gcggcagctc     60
ctcgccgggg cgtaccccga cgtgcccgcc gatgaggtga tcgtcctgga cagcctcacc    120
tacgcgggca accgcgccaa cctcgccccg gtggacgcgg accgcgacgc gcgcttcgtc    180
cacggcgaca tccgcgacgc cggcctcctc gcccgggaac tgcgcggcgt ggacgccatc    240
gtccacttcg cggccgagag ccacgtggac cgctccatcg cgggcgcgtc cgtgttcacc    300
gagaccaacg tgcagggcac gcagacgctg ctccagtgcc cgtcgacgc cggcgtcggc    360
cgggtcgtgc acgtctccac cgacgaggtg tacgggtcga tcgactccgg ctcctggacc    420
gagagcagcc cgctggagcc caactcgccc tacgcggcgt ccaaggccgg ctccgacctc    480
gttgcccgcg cctaccaccg gacgtacggc ctcgacgtac ggatcacccg ctgctgcaac    540
aactacgggc cgtaccagca ccccgagaag ctcatccccc tcttcgtgac gaacctcctc    600
gacggcggga cgctcccgct gtacggcgac ggcgcgaacg tccgcgagtg ggtgcacacc    660
gacgaccact gccggggcat cgcgctcgtc ctcgcgggcg gccgggccgg cgagatctac    720
cacatcggcg gcggcctgga gctgaccaac cgcgaactca ccggcatcct cctggactcg    780
ctcgcgccgc actggtcctc ggtccggaag gtcgccgacc gcaagggcca cgacctgcgc    840
tactccctcg acggcggcga gatcgagcgc gagctcggct accgccgca ggtctccttc    900
gcggacggcc tcgcgcggac cgtccgctgg taccgggaga accgcggctg gtgggagccg    960
ctcaaggcga ccgccccgca gctgcccgcc accgccgtgg aggtgtccgc gtga         1014

<210> SEQ ID NO: 14
<211> LENGTH: 337
<212> TYPE: PRT
<213> ORGANISM: Streptomyces venezuelae

<400> SEQUENCE: 14

Met Arg Leu Leu Val Thr Gly Gly Ala Gly Phe Ile Gly Ser His Phe
  1               5                  10                  15

Val Arg Gln Leu Leu Ala Gly Ala Tyr Pro Asp Val Pro Ala Asp Glu
                 20                  25                  30

Val Ile Val Leu Asp Ser Leu Thr Tyr Ala Gly Asn Arg Ala Asn Leu
             35                  40                  45

Ala Pro Val Asp Ala Asp Pro Arg Leu Arg Phe Val His Gly Asp Ile
         50                  55                  60

Arg Asp Ala Gly Leu Leu Ala Arg Glu Leu Arg Gly Val Asp Ala Ile
 65                  70                  75                  80

Val His Phe Ala Ala Glu Ser His Val Asp Arg Ser Ile Ala Gly Ala
                 85                  90                  95
```

```
Ser Val Phe Thr Glu Thr Asn Val Gln Gly Thr Gln Thr Leu Leu Gln
            100                 105                 110
Cys Ala Val Asp Ala Gly Val Gly Arg Val Val His Val Ser Thr Asp
        115                 120                 125
Glu Val Tyr Gly Ser Ile Asp Ser Gly Ser Trp Thr Glu Ser Ser Pro
    130                 135                 140
Leu Glu Pro Asn Ser Pro Tyr Ala Ala Ser Lys Ala Gly Ser Asp Leu
145                 150                 155                 160
Val Ala Arg Ala Tyr His Arg Thr Tyr Gly Leu Asp Val Arg Ile Thr
                165                 170                 175
Arg Cys Cys Asn Asn Tyr Gly Pro Tyr Gln His Pro Glu Lys Leu Ile
            180                 185                 190
Pro Leu Phe Val Thr Asn Leu Leu Asp Gly Gly Thr Leu Pro Leu Tyr
        195                 200                 205
Gly Asp Gly Ala Asn Val Arg Glu Trp Val His Thr Asp Asp His Cys
    210                 215                 220
Arg Gly Ile Ala Leu Val Leu Ala Gly Gly Arg Ala Gly Glu Ile Tyr
225                 230                 235                 240
His Ile Gly Gly Gly Leu Glu Leu Thr Asn Arg Glu Leu Thr Gly Ile
                245                 250                 255
Leu Leu Asp Ser Leu Gly Ala Asp Trp Ser Ser Val Arg Lys Val Ala
            260                 265                 270
Asp Arg Lys Gly His Asp Leu Arg Tyr Ser Leu Asp Gly Gly Glu Ile
        275                 280                 285
Glu Arg Glu Leu Gly Tyr Arg Pro Gln Val Ser Phe Ala Asp Gly Leu
    290                 295                 300
Ala Arg Thr Val Arg Trp Tyr Arg Glu Asn Arg Gly Trp Trp Glu Pro
305                 310                 315                 320
Leu Lys Ala Thr Ala Pro Gln Leu Pro Ala Thr Ala Val Glu Val Ser
                325                 330                 335
Ala
```

<210> SEQ ID NO: 15
<211> LENGTH: 1140
<212> TYPE: DNA
<213> ORGANISM: Streptomyces venezuelae

<400> SEQUENCE: 15

```
gtgagcagcc gcgccgagac ccccgcgtc cccttcctcg acctcaaggc cgcctacgag      60
gagctccgcg cggagaccga cgccgcgatc gcccgcgtcc tcgactcggg gcgctacctc     120
ctcggacccg aactcgaagg attcgaggcg gagttcgccg cgtactgcga gacggaccac     180
gccgtcggcg tgaacagcgg gatggacgcc ctccagctcg ccctccgcgg cctcggcatc     240
ggacccgggg acgaggtgat cgtcccctcg cacacgtaca tcgccagctg gctcgcggtg     300
tccgccaccg gcgcgacccc cgtgcccgtc gagccgcacg aggaccaccc caccctggac     360
ccgctgctcg tcgagaaggc gatcacccc cgcacccggg cgctcctccc cgtccacctc     420
tacgggcacc ccgccgacat ggacgccctc cgcgagctcg cggaccggca cggcctgcac     480
atcgtcgagg acgccgcgca ggcccacggc gcccgctacc ggggccggcg gatcggcgcc     540
gggtcgtcgg tggccgcgtt cagcttctac ccgggcaaga acctcggctg cttcggcgac     600
ggcggcgccg tcgtcaccgg cgaccccgag ctcgccgaac ggctccggat gctccgcaac     660
tacggctcgc ggcagaagta cagccacgag acgaagggca ccaactcccg cctggacgag     720
```

```
atgcaggccg ccgtgctgcg gatccggctc gcccacctgg acagctggaa cggccgcagg    780
tcggcgctgg ccgcggagta cctctccggg ctcgccggac tgcccggcat cggcctgccg    840
gtgaccgcgc ccgacaccga cccggtctgg cacctcttca ccgtgcgcac cgagcgccgc    900
gacgagctgc gcagccacct cgacgcccgc ggcatcgaca ccctcacgca ctacccggta    960
cccgtgcacc tctcgcccgc ctacgcgggc gaggcaccgc cggaaggctc gctcccgcgc   1020
gccgagagct tcgcgcggca ggtcctcagc ctgccgatcg gcccgcacct ggagcgcccg   1080
caggcgctgc gggtgatcga cgccgtgcgc gaatgggccg agcgggtcga ccaggcctag   1140
```

<210> SEQ ID NO: 16
<211> LENGTH: 379
<212> TYPE: PRT
<213> ORGANISM: Streptomyces venezuelae

<400> SEQUENCE: 16

```
Met Ser Ser Arg Ala Glu Thr Pro Arg Val Pro Phe Leu Asp Leu Lys
  1               5                  10                  15

Ala Ala Tyr Glu Glu Leu Arg Ala Glu Thr Asp Ala Ala Ile Ala Arg
             20                  25                  30

Val Leu Asp Ser Gly Arg Tyr Leu Leu Gly Pro Glu Leu Glu Gly Phe
         35                  40                  45

Glu Ala Glu Phe Ala Ala Tyr Cys Glu Thr Asp His Ala Val Gly Val
     50                  55                  60

Asn Ser Gly Met Asp Ala Leu Gln Leu Ala Leu Arg Gly Leu Gly Ile
 65                  70                  75                  80

Gly Pro Gly Asp Glu Val Ile Val Pro Ser His Thr Tyr Ile Ala Ser
                 85                  90                  95

Trp Leu Ala Val Ser Ala Thr Gly Ala Thr Pro Val Pro Val Glu Pro
            100                 105                 110

His Glu Asp His Pro Thr Leu Asp Pro Leu Leu Val Glu Lys Ala Ile
        115                 120                 125

Thr Pro Arg Thr Arg Ala Leu Leu Pro Val His Leu Tyr Gly His Pro
    130                 135                 140

Ala Asp Met Asp Ala Leu Arg Glu Leu Ala Asp Arg His Gly Leu His
145                 150                 155                 160

Ile Val Glu Asp Ala Ala Gln Ala His Gly Ala Arg Tyr Arg Gly Arg
                165                 170                 175

Arg Ile Gly Ala Gly Ser Ser Val Ala Ala Phe Ser Phe Tyr Pro Gly
            180                 185                 190

Lys Asn Leu Gly Cys Phe Gly Asp Gly Gly Ala Val Val Thr Gly Asp
        195                 200                 205

Pro Glu Leu Ala Glu Arg Leu Arg Met Leu Arg Asn Tyr Gly Ser Arg
    210                 215                 220

Gln Lys Tyr Ser His Glu Thr Lys Gly Thr Asn Ser Arg Leu Asp Glu
225                 230                 235                 240

Met Gln Ala Ala Val Leu Arg Ile Arg Leu Ala His Leu Asp Ser Trp
                245                 250                 255

Asn Gly Arg Arg Ser Ala Leu Ala Ala Glu Tyr Leu Ser Gly Leu Ala
            260                 265                 270

Gly Leu Pro Gly Ile Gly Leu Pro Val Thr Ala Pro Asp Thr Asp Pro
        275                 280                 285

Val Trp His Leu Phe Thr Val Arg Thr Glu Arg Arg Asp Glu Leu Arg
    290                 295                 300
```

```
Ser His Leu Asp Ala Arg Gly Ile Asp Thr Leu Thr His Tyr Pro Val
305                 310                 315                 320

Pro Val His Leu Ser Pro Ala Tyr Ala Gly Glu Ala Pro Pro Glu Gly
            325                 330                 335

Ser Leu Pro Arg Ala Glu Ser Phe Ala Arg Gln Val Leu Ser Leu Pro
        340                 345                 350

Ile Gly Pro His Leu Glu Arg Pro Gln Ala Leu Arg Val Ile Asp Ala
            355                 360                 365

Val Arg Glu Trp Ala Glu Arg Val Asp Gln Ala
        370                 375

<210> SEQ ID NO: 17
<211> LENGTH: 714
<212> TYPE: DNA
<213> ORGANISM: Streptomyces venezuelae

<400> SEQUENCE: 17
gtgtacgaag tcgaccacgc cgacgtctac gacctcttct acctgggtcg cggcaaggac      60
tacgccgccg aggcctccga catcgccgac ctggtgcgct cccgtacccc cgaggcctcc     120
tcgctcctgg acgtggcctg cggtacgggc acgcatctgg agcacttcac caaggagttc     180
ggcgacaccc ccggcctgga gctgtccgag acatgctca cccacgcccg caagcggctg      240
cccgacgcca cgctccacca gggcgacatg cgggacttcc ggctcggccg gaagttctcc     300
gccgtggtca gcatgttcag ctccgtcggc tacctgaaga cgaccgagga actcggcgcg     360
gccgtcgcct cgttcgcgga gcacctggag cccggtggcg tcgtcgtcgt cgagccgtgg     420
tggttcccgg agaccttcgc cgacggctgg gtcagcgccg acgtcgtccg ccgtgacggg     480
cgcaccgtgg cccgtgtctc gcactcggtg cgggagggga acgcgacgcg catggaggtc     540
cacttcaccg tggccgaccc gggcaagggc gtgcggcact ctccgacgt ccatctcatc      600 accctgttcc accaggccga gtacgaggcc gcgttcacgg ccgccgggct gcgcgtcgag     660
tacctggagg gcggcccgtc gggccgtggc ctcttcgtcg gcgtccccgc ctga           714

<210> SEQ ID NO: 18
<211> LENGTH: 237
<212> TYPE: PRT
<213> ORGANISM: Streptomyces venezuelae

<400> SEQUENCE: 18

Met Tyr Glu Val Asp His Ala Asp Val Tyr Asp Leu Phe Tyr Leu Gly
1               5                   10                  15

Arg Gly Lys Asp Tyr Ala Ala Glu Ala Ser Asp Ile Ala Asp Leu Val
            20                  25                  30

Arg Ser Arg Thr Pro Glu Ala Ser Ser Leu Leu Asp Val Ala Cys Gly
        35                  40                  45

Thr Gly Thr His Leu Glu His Phe Thr Lys Glu Phe Gly Asp Thr Ala
    50                  55                  60

Gly Leu Glu Leu Ser Glu Asp Met Leu Thr His Ala Arg Lys Arg Leu
65                  70                  75                  80

Pro Asp Ala Thr Leu His Gln Gly Asp Met Arg Asp Phe Arg Leu Gly
            85                  90                  95

Arg Lys Phe Ser Ala Val Val Ser Met Phe Ser Ser Val Gly Tyr Leu
        100                 105                 110

Lys Thr Thr Glu Glu Leu Gly Ala Ala Val Ala Ser Phe Ala Glu His
    115                 120                 125
```

Leu Glu Pro Gly Gly Val Val Val Glu Pro Trp Trp Phe Pro Glu
            130                 135                 140

Thr Phe Ala Asp Gly Trp Val Ser Ala Asp Val Arg Arg Asp Gly
145                 150                 155                 160

Arg Thr Val Ala Arg Val Ser His Ser Val Arg Glu Gly Asn Ala Thr
                165                 170                 175

Arg Met Glu Val His Phe Thr Val Ala Asp Pro Gly Lys Gly Val Arg
            180                 185                 190

His Phe Ser Asp Val His Leu Ile Thr Leu Phe His Gln Ala Glu Tyr
        195                 200                 205

Glu Ala Ala Phe Thr Ala Ala Gly Leu Arg Val Glu Tyr Leu Glu Gly
    210                 215                 220

Gly Pro Ser Gly Arg Gly Leu Phe Val Gly Val Pro Ala
225                 230                 235

<210> SEQ ID NO: 19
<211> LENGTH: 1281
<212> TYPE: DNA
<213> ORGANISM: Streptomyces venezuelae

<400> SEQUENCE: 19
atgcgcgtcc tgctgaccte gttcgcacat cacacgcact actacggcct ggtgcccctg      60
gcctgggcgc tgctcgccgc cgggcacgag gtgcgggtcg ccagccagcc cgcgctcacg     120
gacaccatca ccgggtccgg gctcgccgcg gtgccggtcg caccgaccga cctcatccac     180
gagtaccggg tgcggatggc gggcgagccg cgcccgaacc atccggcgat cgccttcgac     240
gaggcccgtc ccgagccgct ggactgggac acgccctcg gcatcgaggc gatcctcgcc      300
ccgtacttcc atctgctcgc caacaacgac tcgatggtcg acgacctcgt cgacttcgcc     360
cggtcctggc agccggacct ggtgctgtgg gagccgacga cctacgcggg cgccgtcgcc     420
gcccaggtca ccggtgccgc gcacgcccgg gtcctgtggg ggcccgacgt gatgggcagc     480
gcccgccgca agttcgtcgc gctgcgggac cggcagccgc cgagcaccg cgaggacccc      540 accgcggagt ggctgacgtg gacgctcgac cggtacggcg cctccttcga agaggagctg     600
ctcaccggcc agttcacgat cgacccgacc ccgccgagcc tgcgcctcga cacgggcctg     660
ccgaccgtcg ggatgcgtta tgttccgtac aacggcacgt cggtcgtgcc ggactggctg     720
agtgagccgc ccgcgcggcc ccgggtctgc ctgacccctcg gcgtctccgc gcgtgaggtc     780
ctcggcggcg acggcgtctc gcagggcgac atcctggagg cgctcgccga cctcgacatc     840
gagctcgtcg ccacgctcga cgcgagtcag gcgccgaga tccgcaacta cccgaagcac      900
acccggttca cggacttcgt gccgatgcac gcgctcctgc cgagctgctc ggcgatcatc     960
caccacggcg gggcgggcac ctacgcgacc gccgtgatca acgcggtgcc gcaggtcatg    1020
ctcgccgagc tgtgggacgc gccggtcaag gcgcgggccg tcgccgagca gggggcgggg    1080
ttcttcctgc cgccggccga gctcacgccg caggccgtgc gggacgccgt cgtccgcatc    1140
ctcgacgacc cctcggtcgc caccgccgcg caccggctgc gcgaggagac cttcggcgac    1200 cccacccccgg ccgggatcgt ccccgagctg gagcggctcg ccgcgcagca ccgccgcccg    1260
ccggccgacg cccggcactg a                                             1281

<210> SEQ ID NO: 20
<211> LENGTH: 426
<212> TYPE: PRT

<213> ORGANISM: Streptomyces venezuelae

<400> SEQUENCE: 20

```
Met Arg Val Leu Leu Thr Ser Phe Ala His His Thr His Tyr Tyr Gly
 1               5                  10                  15
Leu Val Pro Leu Ala Trp Ala Leu Leu Ala Ala Gly His Glu Val Arg
             20                  25                  30
Val Ala Ser Gln Pro Ala Leu Thr Asp Thr Ile Thr Gly Ser Gly Leu
         35                  40                  45
Ala Ala Val Pro Val Gly Thr Asp His Leu Ile His Glu Tyr Arg Val
     50                  55                  60
Arg Met Ala Gly Glu Pro Arg Pro Asn His Pro Ala Ile Ala Phe Asp
 65                  70                  75                  80
Glu Ala Arg Pro Glu Pro Leu Asp Trp Asp His Ala Leu Gly Ile Glu
                 85                  90                  95
Ala Ile Leu Ala Pro Tyr Phe His Leu Leu Ala Asn Asn Asp Ser Met
            100                 105                 110
Val Asp Asp Leu Val Asp Phe Ala Arg Ser Trp Gln Pro Asp Leu Val
        115                 120                 125
Leu Trp Glu Pro Thr Thr Tyr Ala Gly Ala Val Ala Ala Gln Val Thr
    130                 135                 140
Gly Ala Ala His Ala Arg Val Leu Trp Gly Pro Asp Val Met Gly Ser
145                 150                 155                 160
Ala Arg Arg Lys Phe Val Ala Leu Arg Asp Arg Gln Pro Pro Glu His
                165                 170                 175
Arg Glu Asp Pro Thr Ala Glu Trp Leu Thr Trp Thr Leu Asp Arg Tyr
            180                 185                 190
Gly Ala Ser Phe Glu Glu Leu Leu Thr Gly Gln Phe Thr Ile Asp
        195                 200                 205
Pro Thr Pro Pro Ser Leu Arg Leu Asp Thr Gly Leu Pro Thr Val Gly
    210                 215                 220
Met Arg Tyr Val Pro Tyr Asn Gly Thr Ser Val Val Pro Asp Trp Leu
225                 230                 235                 240
Ser Glu Pro Pro Ala Arg Pro Arg Val Cys Leu Thr Leu Gly Val Ser
                245                 250                 255
Ala Arg Glu Val Leu Gly Gly Asp Gly Val Ser Gln Gly Asp Ile Leu
            260                 265                 270
Glu Ala Leu Ala Asp Leu Asp Ile Glu Leu Val Ala Thr Leu Asp Ala
        275                 280                 285
Ser Gln Arg Ala Glu Ile Arg Asn Tyr Pro Lys His Thr Arg Phe Thr
    290                 295                 300
Asp Phe Val Pro Met His Ala Leu Leu Pro Ser Cys Ser Ala Ile Ile
305                 310                 315                 320
His His Gly Gly Ala Gly Thr Tyr Ala Thr Ala Val Ile Asn Ala Val
                325                 330                 335
Pro Gln Val Met Leu Ala Glu Leu Trp Asp Ala Pro Val Lys Ala Arg
            340                 345                 350
Ala Val Ala Glu Gln Gly Ala Gly Phe Phe Leu Pro Pro Ala Glu Leu
        355                 360                 365
Thr Pro Gln Ala Val Arg Asp Ala Val Arg Ile Leu Asp Asp Pro
    370                 375                 380
Ser Val Ala Thr Ala Ala His Arg Leu Arg Glu Glu Thr Phe Gly Asp
385                 390                 395                 400
```

```
Pro Thr Pro Ala Gly Ile Val Pro Glu Leu Glu Arg Leu Ala Ala Gln
            405                 410                 415
His Arg Arg Pro Pro Ala Asp Ala Arg His
            420                 425
```

<210> SEQ ID NO: 21
<211> LENGTH: 1209
<212> TYPE: DNA
<213> ORGANISM: Streptomyces venezuelae

<400> SEQUENCE: 21

```
gtgaccgacg acctgacggg ggccctcacg cagcccccgc tgggccgcac cgtccgcgcg      60
gtggccgacc gtgaactcgg cacccacctc ctggagaccc gcggcatcca ctggatccac     120
gccgcgaacg gcgacccgta cgccaccgtg ctgcgcggcc aggcggacga cccgtatccc     180
gcgtacgagc gggtgcgtgc ccgcggcgcg ctctccttca gcccgacggg cagctgggtc     240
accgccgatc acgccctggc ggcgagcatc ctctgctcga cggacttcgg ggtctccggc     300
gccgacggcg tcccggtgcc gcagcaggtc ctctcgtacg ggagggctg tccgctggag     360
cgcgagcagg tgctgccggc ggccggtgac gtgccggagg gcgggcagcg tgccgtggtc     420
gaggggatcc accgggagac gctggagggt ctcgcgccgg acccgtcggc gtcgtacgcc     480
ttcgagctgc tgggcggttt cgtccgcccg gcggtgacgg ccgctgccgc cgccgtgctg     540
ggtgttcccg cggaccggcg cgcggacttc gcggatctgc tggagcggct ccggccgctg     600
tccgacagcc tgctggcccc gcagtccctg cggacggtac gggcggcgga cggcgcgctg     660
gccgagctca cggcgctgct cgccgattcg gacgactccc ccggggccct gctgtcggcg     720
ctcggggtca ccgcagccgt ccagctcacc gggaacgcgg tgctcgcgct cctcgcgcat     780
cccgagcagt ggcgggagct gtgcgaccgg cccgggctcg cggcggccgc ggtggaggag     840
accctccgct acgacccgcc ggtgcagctc gacgcccggg tggtccgcgg ggagacggag     900
ctggcgggcc ggcggctgcc ggccggggcg catgtcgtcg tcctgaccgc cgcgaccggc     960
cgggaccccg aggtcttcac ggacccggag cgcttcgacc tcgcgcgccc cgacgccgcc    1020
gcgcacctcg cgctgcaccc cgccggtccg tacgccccgg tggcgtccct ggtccggctt    1080
caggcggagg tcgcgctgcg gaccctggcc gggcgtttcc ccgggctgcg gcaggcgggg    1140
gacgtgctcc gccccgccg cgcgcctgtc ggccgcgggc cgctgagcgt cccggtcagc    1200
agctcctga                                                           1209
```

<210> SEQ ID NO: 22
<211> LENGTH: 402
<212> TYPE: PRT
<213> ORGANISM: Streptomyces venezuelae

<400> SEQUENCE: 22

```
Met Thr Asp Asp Leu Thr Gly Ala Leu Thr Gln Pro Pro Leu Gly Arg
1               5                   10                  15
Thr Val Arg Ala Val Ala Asp Arg Glu Leu Gly Thr His Leu Leu Glu
            20                  25                  30
Thr Arg Gly Ile His Trp Ile His Ala Ala Asn Gly Asp Pro Tyr Ala
        35                  40                  45
Thr Val Leu Arg Gly Gln Ala Asp Asp Pro Tyr Pro Ala Tyr Glu Arg
    50                  55                  60
Val Arg Ala Arg Gly Ala Leu Ser Phe Ser Pro Thr Gly Ser Trp Val
65                  70                  75                  80
```

```
Thr Ala Asp His Ala Leu Ala Ala Ser Ile Leu Cys Ser Thr Asp Phe
             85                  90                  95

Gly Val Ser Gly Ala Asp Gly Val Pro Val Pro Gln Gln Val Leu Ser
            100                 105                 110

Tyr Gly Glu Gly Cys Pro Leu Glu Arg Glu Gln Val Leu Pro Ala Ala
            115                 120                 125

Gly Asp Val Pro Glu Gly Gly Gln Arg Ala Val Glu Gly Ile His
            130                 135                 140

Arg Glu Thr Leu Glu Gly Leu Ala Pro Asp Pro Ser Ala Ser Tyr Ala
145                 150                 155                 160

Phe Glu Leu Leu Gly Gly Phe Val Arg Pro Ala Val Thr Ala Ala Ala
                165                 170                 175

Ala Ala Val Leu Gly Val Pro Ala Asp Arg Arg Ala Asp Phe Ala Asp
            180                 185                 190

Leu Leu Glu Arg Leu Arg Pro Leu Ser Asp Ser Leu Leu Ala Pro Gln
            195                 200                 205

Ser Leu Arg Thr Val Arg Ala Ala Asp Gly Ala Leu Ala Glu Leu Thr
210                 215                 220

Ala Leu Leu Ala Asp Ser Asp Asp Ser Pro Gly Ala Leu Leu Ser Ala
225                 230                 235                 240

Leu Gly Val Thr Ala Ala Val Gln Leu Thr Gly Asn Ala Val Leu Ala
            245                 250                 255

Leu Leu Ala His Pro Glu Gln Trp Arg Glu Leu Cys Asp Arg Pro Gly
            260                 265                 270

Leu Ala Ala Ala Val Glu Glu Thr Leu Arg Tyr Asp Pro Pro Val
            275                 280                 285

Gln Leu Asp Ala Arg Val Val Arg Gly Glu Thr Glu Leu Ala Gly Arg
            290                 295                 300

Arg Leu Pro Ala Gly Ala His Val Val Leu Thr Ala Ala Thr Gly
305                 310                 315                 320

Arg Asp Pro Glu Val Phe Thr Asp Pro Glu Arg Phe Asp Leu Ala Arg
            325                 330                 335

Pro Asp Ala Ala Ala His Leu Ala Leu His Pro Ala Gly Pro Tyr Gly
            340                 345                 350

Pro Val Ala Ser Leu Val Arg Leu Gln Ala Glu Val Ala Leu Arg Thr
            355                 360                 365

Leu Ala Gly Arg Phe Pro Gly Leu Arg Gln Ala Gly Asp Val Leu Arg
            370                 375                 380

Pro Arg Arg Ala Pro Val Gly Arg Gly Pro Leu Ser Val Pro Val Ser
385                 390                 395                 400

Ser Ser
```

<210> SEQ ID NO: 23
<211> LENGTH: 2430
<212> TYPE: DNA
<213> ORGANISM: Streptomyces venezuelae

<400> SEQUENCE: 23

```
gtgacaggta agacccgaat accgcgtgtc cgccgcggcc gcaccacgcc cagggccttc    60
accctggccg tcgtcggcac cctgctggcg ggcaccaccg tggcggccgc cgctcccggc   120
gccgccgaca cggccaatgt tcagtacacg agccgggcgg cggagctcgt cgcccagatg   180
acgctcgacg agaagatcag cttcgtccac tgggcgctgg accccgaccg gcagaacgtc   240
ggctaccttc ccggcgtgcc gcgtctgggc atcccggagc tgcgtgccgc cgacggcccg   300
```

```
aacggcatcc gcctggtggg gcagaccgcc accgcgctgc ccgcgccggt cgccctggcc      360
agcaccttcg acgacaccat ggccgacagc tacggcaagg tcatgggccg cgacggtcgc      420
gcgctcaacc aggacatggt cctgggcccg atgatgaaca catccgggt gccgcacggc       480 ggccggaact acgagacctt cagcgaggac cccctggtct cctcgcgcac cgcggtcgcc      540
cagatcaagg gcatccaggg tgcgggtctg atgaccacgc ccaagcactt cgcggccaac      600
aaccaggaga caaccgcttc tccgtgaac gccaatgtcg acgagcagac gctccgcgag       660
atcgagttcc cggcgttcga ggcgtcctcc aaggccggcg cggcctcctt catgtgtgcc      720
tacaacggcc tcaacgggaa gccgtcctgc ggcaacgacg agctcctcaa caacgtgctg      780
cgcacgcagt ggggcttcca gggctgggtg atgtccgact ggctcgccac cccgggcacc      840
gacgccatca ccaagggcct cgaccaggag atgggcgtcg agctccccgg cgacgtcccg      900
aagggcgagc cctcgccgcc ggccaagttc ttcggcgagg cgctgaagac ggccgtcctg      960
aacggcacgg tccccgaggc ggccgtgacg cggtcggcgg agcggatcgt cggccagatg     1020
gagaagttcg gtctgctcct cgccactccg gcgccgcgc ccgagcgcga caaggcgggt      1080
gcccaggcgg tgtcccgcaa ggtcgccgag aacggcgcgg tgctcctgcg caacgagggc     1140
caggccctgc cgctcgccgg tgacgccggc aagagcatcg cggtcatcgg cccgacggcc     1200
gtcgacccca aggtcaccgg cctgggcagc gcccacgtcg tcccggactc ggcggcggcg     1260
ccactcgaca ccatcaaggc ccgcgcgggt gcgggtgcga cggtgacgta cgagacgggt     1320
gaggagacct tcgggacgca gatcccggcg gggaacctca gcccggcgtt caaccagggc     1380
caccagctcg agccgggcaa ggcggggggcg ctgtacgacg gcacgctgac cgtgcccgcc    1440
gacggcgagt accgcatcgc ggtccgtgcc accggtggtt acgccacggt gcagctcggc     1500
agccacacca tcgaggccgg tcaggtctac ggcaaggtga gcagcccgct cctcaagctg     1560
accaagggca cgcacaagct cacgatctcg ggcttcgcga tgagtgccac cccgctctcc     1620
ctggagctgg gctgggtgac gccggcggcg gccgacgcga cgatcgcgaa ggccgtggag     1680
tcggcgcgga aggcccgtac ggcggtcgtc ttcgcctacg acgacggcac cgagggcgtc     1740
gaccgtccga acctgtcgct gccgggtacg caggacaagc tgatctcggc tgtcgcggac     1800
gccaacccga acacgatcgt ggtcctcaac accggttcgt cggtgctgat gccgtggctg     1860
tccaagaccc gcgcggtcct ggacatgtgg tacccgggcc aggcgggcgc cgaggccacc     1920
gccgcgctgc tctacggtga cgtcaacccg agcggcaagc tcacgcagag cttcccggcc     1980
gccgagaacc agcacgcggt cgccggcgac ccgacaagct acccggcgt cgacaaccag      2040 cagacgtacc gcgagggcat ccacgtcggg taccgctggt tcgacaagga gaacgtcaag     2100
ccgctgttcc cgttcgggca cggcctgtcg tacacctcgt tcacgcagag cgccccgacc     2160
gtcgtgcgta cgtccacggg tggtctgaag gtcacgtca cggtccgcaa cagcgggaag      2220
cgcgccggcc aggaggtcgt ccaggcgtac ctcggtgcca gcccgaacgt gacggctccg     2280
caggcgaaga gaagctcgt gggctacacg aaggtctcgc tcgccgcggg cgaggcgaag      2340
acggtgacgg tgaacgtcga ccgccgtcag ctgcagaccg gttcgtcctc cgccgacctg     2400
cggggcagcg ccacggtcaa cgtctggtga                                      2430
```

<210> SEQ ID NO: 24
<211> LENGTH: 809
<212> TYPE: PRT

-continued

<213> ORGANISM: Streptomyces venezuelae

<400> SEQUENCE: 24

```
Met Thr Gly Lys Thr Arg Ile Pro Arg Val Arg Arg Gly Arg Thr Thr
 1               5                  10                  15
Pro Arg Ala Phe Thr Leu Ala Val Val Gly Thr Leu Leu Ala Gly Thr
                20                  25                  30
Thr Val Ala Ala Ala Pro Gly Ala Ala Asp Thr Ala Asn Val Gln
             35                  40                  45
Tyr Thr Ser Arg Ala Ala Glu Leu Val Ala Gln Met Thr Leu Asp Glu
 50                  55                  60
Lys Ile Ser Phe Val His Trp Ala Leu Asp Pro Asp Arg Gln Asn Val
 65                  70                  75                  80
Gly Tyr Leu Pro Gly Val Pro Arg Leu Gly Ile Pro Glu Leu Arg Ala
                 85                  90                  95
Ala Asp Gly Pro Asn Gly Ile Arg Leu Val Gly Gln Thr Ala Thr Ala
                100                 105                 110
Leu Pro Ala Pro Val Ala Leu Ala Ser Thr Phe Asp Asp Thr Met Ala
            115                 120                 125
Asp Ser Tyr Gly Lys Val Met Gly Arg Asp Gly Arg Ala Leu Asn Gln
130                 135                 140
Asp Met Val Leu Gly Pro Met Met Asn Asn Ile Arg Val Pro His Gly
145                 150                 155                 160
Gly Arg Asn Tyr Glu Thr Phe Ser Glu Asp Pro Leu Val Ser Ser Arg
                165                 170                 175
Thr Ala Val Ala Gln Ile Lys Gly Ile Gln Gly Ala Gly Leu Met Thr
            180                 185                 190
Thr Ala Lys His Phe Ala Ala Asn Asn Gln Glu Asn Asn Arg Phe Ser
            195                 200                 205
Val Asn Ala Asn Val Asp Glu Gln Thr Leu Arg Glu Ile Glu Phe Pro
210                 215                 220
Ala Phe Glu Ala Ser Ser Lys Ala Gly Ala Ala Ser Phe Met Cys Ala
225                 230                 235                 240
Tyr Asn Gly Leu Asn Gly Lys Pro Ser Cys Gly Asn Asp Glu Leu Leu
                245                 250                 255
Asn Asn Val Leu Arg Thr Gln Trp Gly Phe Gln Gly Trp Val Met Ser
                260                 265                 270
Asp Trp Leu Ala Thr Pro Gly Thr Asp Ala Ile Thr Lys Gly Leu Asp
            275                 280                 285
Gln Glu Met Gly Val Glu Leu Pro Gly Asp Val Pro Lys Gly Glu Pro
290                 295                 300
Ser Pro Pro Ala Lys Phe Phe Gly Glu Ala Leu Lys Thr Ala Val Leu
305                 310                 315                 320
Asn Gly Thr Val Pro Glu Ala Ala Val Thr Arg Ser Ala Glu Arg Ile
                325                 330                 335
Val Gly Gln Met Glu Lys Phe Gly Leu Leu Leu Ala Thr Pro Ala Pro
            340                 345                 350
Arg Pro Glu Arg Asp Lys Ala Gly Ala Gln Ala Val Ser Arg Lys Val
            355                 360                 365
Ala Glu Asn Gly Ala Val Leu Leu Arg Asn Glu Gly Gln Ala Leu Pro
370                 375                 380
Leu Ala Gly Asp Ala Gly Lys Ser Ile Ala Val Ile Gly Pro Thr Ala
385                 390                 395                 400
```

```
-continued

Val Asp Pro Lys Val Thr Gly Leu Gly Ser Ala His Val Val Pro Asp
            405                 410                 415

Ser Ala Ala Ala Pro Leu Asp Thr Ile Lys Ala Arg Ala Gly Ala Gly
            420                 425                 430

Ala Thr Val Thr Tyr Glu Thr Gly Glu Glu Thr Phe Gly Thr Gln Ile
            435                 440                 445

Pro Ala Gly Asn Leu Ser Pro Ala Phe Asn Gln Gly His Gln Leu Glu
450                 455                 460

Pro Gly Lys Ala Gly Ala Leu Tyr Asp Gly Thr Leu Thr Val Pro Ala
465                 470                 475                 480

Asp Gly Glu Tyr Arg Ile Ala Val Arg Ala Thr Gly Tyr Ala Thr
            485                 490                 495

Val Gln Leu Gly Ser His Thr Ile Glu Ala Gly Gln Val Tyr Gly Lys
            500                 505                 510

Val Ser Ser Pro Leu Leu Lys Leu Thr Lys Gly Thr His Lys Leu Thr
            515                 520                 525

Ile Ser Gly Phe Ala Met Ser Ala Thr Pro Leu Ser Leu Glu Leu Gly
530                 535                 540

Trp Val Thr Pro Ala Ala Ala Asp Ala Thr Ile Ala Lys Ala Val Glu
545                 550                 555                 560

Ser Ala Arg Lys Ala Arg Thr Ala Val Val Phe Ala Tyr Asp Asp Gly
            565                 570                 575

Thr Glu Gly Val Asp Arg Pro Asn Leu Ser Leu Pro Gly Thr Gln Asp
            580                 585                 590

Lys Leu Ile Ser Ala Val Ala Asp Ala Asn Pro Asn Thr Ile Val Val
            595                 600                 605

Leu Asn Thr Gly Ser Ser Val Leu Met Pro Trp Leu Ser Lys Thr Arg
            610                 615                 620

Ala Val Leu Asp Met Trp Tyr Pro Gly Gln Ala Gly Ala Glu Ala Thr
625                 630                 635                 640

Ala Ala Leu Leu Tyr Gly Asp Val Asn Pro Ser Gly Lys Leu Thr Gln
            645                 650                 655

Ser Phe Pro Ala Ala Glu Asn Gln His Ala Val Ala Gly Asp Pro Thr
            660                 665                 670

Ser Tyr Pro Gly Val Asp Asn Gln Gln Thr Tyr Arg Glu Gly Ile His
            675                 680                 685

Val Gly Tyr Arg Trp Phe Asp Lys Glu Asn Val Lys Pro Leu Phe Pro
690                 695                 700

Phe Gly His Gly Leu Ser Tyr Thr Ser Phe Thr Gln Ser Ala Pro Thr
705                 710                 715                 720

Val Val Arg Thr Ser Thr Gly Gly Leu Lys Val Thr Val Thr Val Arg
            725                 730                 735

Asn Ser Gly Lys Arg Ala Gly Gln Glu Val Val Gln Ala Tyr Leu Gly
            740                 745                 750

Ala Ser Pro Asn Val Thr Ala Pro Gln Ala Lys Lys Leu Val Gly
            755                 760                 765

Tyr Thr Lys Val Ser Leu Ala Ala Gly Glu Ala Lys Thr Val Thr Val
770                 775                 780

Asn Val Asp Arg Arg Gln Leu Gln Thr Gly Ser Ser Ser Ala Asp Leu
785                 790                 795                 800

Arg Gly Ser Ala Thr Val Asn Val Trp
                            805
```

```
<210> SEQ ID NO: 25
<211> LENGTH: 9
<212> TYPE: PRT
<213> ORGANISM: Artificial Sequence
<220> FEATURE:
<223> OTHER INFORMATION: A consensus sequence.
<220> FEATURE:
<221> NAME/KEY: VARIANT
<222> LOCATION: (4)...(4)
<223> OTHER INFORMATION: Residue 4 is either V or I.

<400> SEQUENCE: 25

Leu Leu Asp Val Ala Cys Gly Thr Gly
  1               5

<210> SEQ ID NO: 26
<211> LENGTH: 1011
<212> TYPE: DNA
<213> ORGANISM: Streptomyces venezuelae

<400> SEQUENCE: 26
atggcaatgc gcgactccat accgaggcga gcggaccgcg acacccttcg ccgcgaatta      60
ggccagaact tccttcagga cgacagagcc gtgcgcaatc tcgtcacgca tgtcgagggg     120
gacggtagga acgttctcga atcggcccc ggaaagggcg cgataaccga ggagttggtg     180
cgctccttcg acaccgtgac ggtcgtggag atggacccgc actgggccgc gcatgtgcgg    240
cggaaattcg aagggagag ggtcaccgta ttccagggtg atttcctcga cttccgcatt     300
ccgcgcgata tcgacaccgt cgtcggaaac gttcccttcg gcatcacgac ccagattctc    360
cggagtctcc tggaatcgac gaactggcag tcggcggccc tgatagtgca gtgggaggtc    420
gcccgcaaac gcgccggtcg cagcggcgga tcgctcctca cgacctcctg gcccccctgg    480
tacgagttcg cggtccacga ccgcgtccgc gcctcgtcgt tccgtccgat gccccgcgtc    540
gacggcggcg tcctgacgat caggcgacgc ccccagcccc tgctgcccga gagcgcgagc    600
cgcgccttcc agaacttcgc cgaagccgtc ttcaccggcc ccggacgggg cctcgcggag    660
atcctccggc gccacatccc caagcggacc taccgttccc tcgccgaccg ccacggaatt    720
ccggacggcg gactgccgaa ggacctcacg ctcacccaat ggatcgccct tttccaggcc    780
tcccagccga gttacgcgcc gggggcgccc ggcacgcgca tgccgggcca gggcggtggc    840
gccggcggca gggactatga ctcggagacg agcagggccg ccgtgcccgg gagccgcaga    900
tacggcccca cgcgcggcgg cgaaccctgc gcaccccgcg cacaggtccg gcagaccaag    960
ggccgccagg gcgcgcgagg ctcgtcgtac ggacgccgca cgggccgtta g            1011

<210> SEQ ID NO: 27
<211> LENGTH: 336
<212> TYPE: PRT
<213> ORGANISM: Streptomyces venezuelae

<400> SEQUENCE: 27

Met Ala Met Arg Asp Ser Ile Pro Arg Arg Ala Asp Arg Asp Thr Leu
  1               5                  10                  15

Arg Arg Glu Leu Gly Gln Asn Phe Leu Gln Asp Asp Arg Ala Val Arg
                 20                  25                  30

Asn Leu Val Thr His Val Glu Gly Asp Gly Arg Asn Val Leu Glu Ile
             35                  40                  45

Gly Pro Gly Lys Gly Ala Ile Thr Glu Glu Leu Val Arg Ser Phe Asp
         50                  55                  60
```

```
Thr Val Thr Val Val Glu Met Asp Pro His Trp Ala His Val Arg
 65                  70                  75                  80

Arg Lys Phe Glu Gly Glu Arg Val Thr Val Phe Gln Gly Asp Phe Leu
                 85                  90                  95

Asp Phe Arg Ile Pro Arg Asp Ile Asp Thr Val Val Gly Asn Val Pro
            100                 105                 110

Phe Gly Ile Thr Thr Gln Ile Leu Arg Ser Leu Leu Glu Ser Thr Asn
        115                 120                 125

Trp Gln Ser Ala Ala Leu Ile Val Gln Trp Glu Val Ala Arg Lys Arg
    130                 135                 140

Ala Gly Arg Ser Gly Gly Ser Leu Leu Thr Thr Ser Trp Ala Pro Trp
145                 150                 155                 160

Tyr Glu Phe Ala Val His Asp Arg Val Arg Ala Ser Ser Phe Arg Pro
                165                 170                 175

Met Pro Arg Val Asp Gly Gly Val Leu Thr Ile Arg Arg Arg Pro Gln
            180                 185                 190

Pro Leu Leu Pro Glu Ser Ala Ser Arg Ala Phe Gln Asn Phe Ala Glu
        195                 200                 205

Ala Val Phe Thr Gly Pro Gly Arg Gly Leu Ala Glu Ile Leu Arg Arg
    210                 215                 220

His Ile Pro Lys Arg Thr Tyr Arg Ser Leu Ala Asp Arg His Gly Ile
225                 230                 235                 240

Pro Asp Gly Gly Leu Pro Lys Asp Leu Thr Leu Thr Gln Trp Ile Ala
                245                 250                 255

Leu Phe Gln Ala Ser Gln Pro Ser Tyr Ala Pro Gly Ala Pro Gly Thr
            260                 265                 270

Arg Met Pro Gly Gln Gly Gly Ala Gly Gly Arg Asp Tyr Asp Ser
        275                 280                 285

Glu Thr Ser Arg Ala Ala Val Pro Gly Ser Arg Arg Tyr Gly Pro Thr
    290                 295                 300

Arg Gly Gly Glu Pro Cys Ala Pro Arg Ala Gln Val Arg Gln Thr Lys
305                 310                 315                 320

Gly Arg Gln Gly Ala Arg Gly Ser Ser Tyr Gly Arg Arg Thr Gly Arg
                325                 330                 335

<210> SEQ ID NO: 28
<211> LENGTH:
<212> TYPE:
<213> ORGANISM:

<400> SEQUENCE: 28

This Sequence is intentionally skipped

<210> SEQ ID NO: 29
<211> LENGTH:
<212> TYPE:
<213> ORGANISM:

<400> SEQUENCE: 29

This Sequence is intentionally skipped

<210> SEQ ID NO: 30
<211> LENGTH: 13842
<212> TYPE: DNA
<213> ORGANISM: Streptomyces venezuelae

<400> SEQUENCE: 30
```

-continued

```
atgtcttcag ccggaattac caggaccggt gcgagaacac cggtgacagg gcgtggggcg      60
gcagcgtggg acacggggga agtgcgggtc cgacggggt tgcccctgc cggccccgat       120
catgcggagc actccttctc tcgtgctcct accggtgatg tgcgcgccga attgattcgt    180
ggagagatgt cgacagtgtc caagagtgag tccgaggaat tcgtgtccgt gtcgaacgac    240
gccggttccg cgcacggcac agcggaaccc gtcgccgtcg tcggcatctc ctgccgggtg   300
cccggcgccc gggacccgag agagttctgg gaactcctgg cggcaggcgg ccaggccgtc    360
accgacgtcc ccgcggaccg ctggaacgcc ggcgacttct acgacccgga ccgctccgcc    420
cccgccgct cgaacagccg gtggggcggg ttcatcgagg acgtcgaccg gttcgacgcc     480
gccttcttcg gcatctcgcc ccgcgaggcc gcggagatgg accgcagca gcggctcgcc    540
ctggagctgg gctgggaggc cctggagcgc gccgggatcg accgtcctc gctcaccggc    600
acccgcaccg cgtcttcgc cggcgccatc tgggacgact acgccaccct gaagcaccgc    660
cagggcggcg ccgcgatcac cccgcacacc gtcaccggcc tccaccgcgg catcatcgcg   720
aaccgactct cgtacacgct cgggctccgc ggccccagca tggtcgtcga ctccggccag   780
tcctcgtcgc tcgtcgccgt ccacctcgcg tgcgagagcc tgcggcgcgg cgagtccgag   840
ctcgccctcg ccggcggcgt ctcgctcaac ctggtgccgg acagcatcat cggggcgagc   900
aagttcggcg gcctctcccc cgacggccgc gcctacacct tcgacgcgcg cgccaacggc   960
tacgtacgcg gcgagggcgg cggtttcgtc gtcctgaagc gcctctcccg ggccgtcgcc  1020
gacggcgacc cggtgctcgc cgtgatccgg ggcagcgccg tcaacaacgg cggcgccgcc  1080
cagggcatga cgaccccga cgcgcaggcg caggaggcc tgctccgcga ggcccacgag    1140
cgggccggga ccgcgccggc cgacgtgcgg tacgtcgagc tgcacggcac cggcacccc   1200
gtgggcgacc cgatcgaggc cgctgcgctc ggcgccgccc tcggcaccgg ccgcccggcc  1260
ggacagccgc tcctggtcgg ctcggtcaag acgaacatcg gccacctgga gggcgcggcc   1320
ggcatcgccg gcctcatcaa ggccgtcctg cggtccgcg gtcgcgcgct gcccgccagc   1380
ctgaactacg agaccccgaa cccggcgatc ccgttcgagg aactgaacct ccgggtgaac  1440
acggagtacc tgccgtggga gccggagcac gacgggcagc ggatggtcgt cggcgtgtcc  1500
tcgttcggca tgggcggcac gaacgcgcat gtcgtgctcg aagaggcccc cggggggttgt  1560
cgaggtgctt cggtcgtgga gtcgacggtc ggcgggtcgg cggtcggcgg cggtgtggtg  1620
ccgtgggtgg tgtcggcgaa gtccgctgcc gcgctggacg cgcagatcga gcggcttgcc  1680
gcgttcgcct cgcgggatcg tacgatggt gtcgacgcgg gcgctgtcga tgcgggtgct   1740
gtcgatgcgg gtgctgtcgc tcgcgtactg gccggcgggc gtgctcagtt cgagcaccgg  1800
gccgtcgtcg tcggcagcgg gccggacgat ctggcggcag cgctggccgc gcctgagggt  1860
ctggtccggg gcgtggcttc cggtgtcggg cgagtggcgt tcgtgttccc cgggcagggc  1920
acgcagtggg ccggcatggg tgccgaactg ctggactctt ccgcggtgtt cgcggcggcc  1980
atggccgaat gcgaggccgc actctccccg tacgtcgact ggtcgctgga ggccgtcgta  2040
cggcaggccc ccgtgcgcc cacgctggag cgggtcgatg tcgtgcagcc tgtgacgttc   2100
gccgtcatgg tctcgctggc tcgcgtgtgg cagcaccacg gggtgacgcc ccaggcggtc   2160
gtcggccact cgcagggcga gatcgccgcc gcgtacgtcg ccggtgccct gagcctggac   2220
gacgccgctc gtgtcgtgac cctgcgcagc aagtccatcg ccgcccacct cgccggcaag  2280
ggcggcatgc tgtccctcgc gctgagcgag gacgccgtcc tggagcgact ggccgggttc   2340
```

```
gacgggctgt ccgtcgccgc tgtgaacggg cccaccgcca ccgtggtctc cggtgacccc    2400
gtacagatcg aagagcttgc tcgggcgtgt gaggccgatg gggtccgtgc gcgggtcatt    2460
cccgtcgact acgcgtccca cagccggcag gtcgagatca tcgagagcga gctcgccgag    2520
gtcctcgccg ggctcagccc gcaggctccg cgcgtgccgt tcttctcgac actcgaaggc    2580
gcctggatca ccgagcccgt gctcgacggg ggctactggt accgcaacct cgccatcgt     2640 gtgggcttcg ccccggccgt cgagaccctg gccaccgacg agggcttcac ccacttcgtc    2700
gaggtcagcg cccacccccgt cctcaccatg gccctccccg gaccgtcac cggtctggcg     2760 accctgcgtc gcgacaacgg cggtcaggac cgcctagtcg cctccctcgc cgaagcatgg    2820
gccaacggac tcgcggtcga ctggagcccg ctcctcccct ccgcgaccgg ccaccactcc    2880
gacctcccca cctacgcgtt ccagaccgag cgccactggc tgggcgagat cgaggcgctc    2940 gcccggcgg gcgagccggc ggtgcagccc gccgtcctcc gcacggaggc ggccgagccg      3000
gcggagctcg accgggacga gcagctgcgc gtgatcctgg acaaggtccg ggcgcagacg    3060
gcccaggtgc tggggtacgc gacaggcggg cagatcgagg tcgaccggac cttccgtgag    3120
gccggttgca cctccctgac cggcgtggac ctgcgcaacc ggatcaacgc cgccttcggc    3180
gtacggatgg cgccgtccat gatcttcgac ttccccaccc ccgaggctct cgcggagcag    3240
ctgctcctcg tcgtgcacgg ggaggcggcg gcgaacccgg ccggtgcgga gccggctccg    3300
gtggcggcgg ccggtgccgt cgacgagccg gtggcgatcg tcggcatggc ctgccgcctg    3360 cccgtgggg tcgcctcgcc ggaggacctg tggcggctgg tggccggcgg cggggacgcg     3420
atctcggagt tcccgcagga ccgcggctgg gacgtggagg ggctgtacca cccggatccg    3480
gagcaccccg gcacgtcgta cgtccgccag ggcggtttca tcgagaacgt cgccggcttc    3540
gacgcggcct tcttcgggat ctcgccgcgc gaggccctcg ccatggaccc gcagcagcgg    3600
ctcctcctcg aaacctcctg ggaggccgtc gaggacgccg ggatcgaccc gacctccctg    3660
cggggacggc aggtcggcgt cttcactggg gcgatgaccc acgagtacgg gccgagcctg    3720
cgggacggcg gggaaggcct cgacggctac ctgctgaccg gcaacacggc cagcgtgatg    3780
tcgggccgcg tctcgtacac actcggcctt gagggccccg ccctgacggt ggacacggcc    3840
tgctcgtcgt cgctggtcgc cctgcacctc gccgtgcagg ccctgcgcaa gggcgaggtc    3900
gacatggcgc tcgccggcgg cgtggccgtg atgcccacgc ccgggatgtt cgtcgagttc    3960
agccggcagc gcgggctggc cggggacggc cggtcgaagg cgttcgccgc gtcggcggac    4020
ggcaccagct ggtccgaggg cgtcggcgtc ctcctcgtcg agcgcctgtc ggacgcccgc    4080
cgcaacggac accaggtcct cgcggtcgtc cgcggcagcg ccttgaacca ggacggcgcg    4140
agcaacggcc tcacggctcc gaacgggccc tcgcagcagc gcgtcatccg gcgcgcgctg    4200
gcggacgccc ggctgacgac ctccgacgtg gacgtcgtcg aggcacacgg cacgggcacg    4260
cgactcggcg acccgatcga ggcgcaggcc ctgatcgcca cctacggcca gggccgtgac    4320
gacgaacagc cgctgcgcct cggtcgttg aagtccaaca tcgggcacac ccaggccgcg     4380
gccggcgtct ccggtgtcat caagatggtc caggcgatgc gccacggact gctgccgaag    4440
acgctgcacg tcgacgagcc ctcggaccag atcgactggt cggctggcgc cgtgaactc     4500 ctcaccgagg ccgtcgactg gccggagaag caggacggcg ggctgcgccg ggccgccgtc    4560
tcctccttcg ggatcagcgg caccaatgcg catgtggtgc tcgaagaggc cccggtggtt    4620
gtcgagggtg cttcggtcgt cgagccgtcg gttggcgggt cggcggtcgg cggcggtgtg    4680
acgccttggg tggtgtcggc gaagtccgct gccgcgctcg acgcgcagat cgagcggctt    4740
```

-continued

```
gccgcattcg cctcgcggga tcgtacggat gacgccgacg ccggtgctgt cgacgcgggc   4800
gctgtcgctc acgtactggc tgacgggcgt gctcagttcg agcaccgggc cgtcgcgctc   4860
ggcgccgggg cggacgacct cgtacaggcg ctggccgatc cggacgggct gatacgcgga   4920
acggcttccg gtgtcgggcg agtggcgttc gtgttccccg gtcagggcac gcagtgggct   4980
ggcatgggtg ccgaactgct ggactcttcc gcggtgttcg cggcggccat ggccgagtgt   5040
gaggccgcgc tgtccccgta cgtcgactgg tcgctggagg ccgtcgtacg gcaggccccc   5100
ggtgcgccca cgctggagcg ggtcgatgtc gtgcagcctg tgacgttcgc cgtcatggtc   5160
tcgctggctc gcgtgtggca gcaccacggt gtgacgcccc aggcggtcgt cggccactcg   5220
cagggcgaga tcgccgccgc gtacgtcgcc ggagccctgc ccctggacga cgccgcccgc   5280
gtcgtcaccc tgcgcagcaa gtccatcgcc gcccacctcg ccggcaaggg cggcatgctg   5340
tccctcgcgc tgaacgagga cgccgtcctg gagcgactga gtgacttcga cgggctgtcc   5400
gtcgccgccg tcaacgggcc caccgccact gtcgtgtcgg gtgacccgt acagatcgaa    5460 gagcttgctc aggcgtgcaa gcggacgga ttccgcgcgc ggatcattcc cgtcgactac    5520
gcgtcccaca gccggcaggt cgagatcatc gagagcgagc tcgcccaggt cctcgccggt   5580
ctcagcccgc aggcccgcg cgtgccgttc ttctcgacgc tcgaaggcac ctggatcacc    5640
gagcccgtcc tcgacggcac ctactggtac cgcaacctcc gtcaccgcgt cggcttcgcc   5700
cccgccatcg agaccctggc cgtcgacgag ggcttcacgc acttcgtcga ggtcagcgcc   5760 cacccccgtcc tcaccatgac cctccccgag accgtcaccg gcctcggcac cctccgtcgc   5820
gaacagggag gccaagagcg tctggtcacc tcgctcgccg aggcgtgggt caacgggctt   5880
cccgtggcat ggacttcgct cctgcccgcc acggcctccc gccccggtct gcccacctac   5940
gccttccagg ccgagcgcta ctggctcgag aacactcccg ccgccctggc caccggcgac   6000
gactggcgct accgcatcga ctggaagcgc ctcccggccg ccgaggggtc cgagcgcacc   6060
ggcctgtccg gccgctggct cgccgtcacg ccggaggacc actccgcgca ggccgccgcc   6120
gtgctcaccg cgctggtcga cgccggggcg aaggtcgagg tgctgacggc cggggcggac   6180
gacgaccgtg aggccctcgc cgcccggctc accgcactga cgaccggtga cggcttcacc   6240
ggcgtggtct cgctcctcga cggactcgta ccgcaggtcg cctgggtcca ggcgctcggc   6300
gacgccggaa tcaaggcgcc cctgtggtcc gtcacccagg gcgcggtctc cgtcggacgt   6360
ctcgacaccc ccgccgaccc cgaccgggcc atgtctctggg gcctcggccg cgtcgtcgcc   6420
cttgagcacc ccgaacgctg gccggcctc gtcgacctcc ccgcccagcc cgatgccgcc    6480
gccctcgccc acctcgtcac cgcactctcc ggcgccaccg cgaggacca gatcgccatc     6540 cgcaccaccg gactccacgc ccgccgcctc gcccgcgcac ccctccacgg acgtcggccc    6600
acccgcgact ggcagcccca cggcaccgtc tcatcaccg cggcaccgg agccctcggc      6660 agccacgccg cacgctggat ggccaccac ggagccgaac acctcctcct cgtcagccgc     6720
agcggcgaac aagcccccgg agccacccaa ctcaccgccg aactcaccgc atcgggcgcc    6780
cgcgtcacca tcgccgcctg cgacgtcgcc gaccccacg ccatgcgcac cctcctcgac     6840 gccatcccg ccgagacgcc cctcaccgcc gtcgtccaca ccgccggcgc gctcgacgac      6900
ggcatcgtgg acacgctgac cgccgagcag gtccggcggg cccaccgtgc gaaggccgtc     6960
ggcgcctcgg tgctcgacga gctgaccccgg gacctcgacc tcgacgcgtt cgtgctcttc     7020
tcgtccgtgt cgagcactct gggcatcccc ggtcagggca actacgcccc gcacaacgcc    7080
```

-continued

```
tacctcgacg ccctcgcggc tcgccgccgg gccaccggcc ggtccgccgt ctcgtggcc    7140 tggggaccgt gggacggtgg cggcatggcc gccggtgacg gcgtggccga gcggctgcgc   7200
aaccacggcg tgcccggcat ggacccggaa ctcgccctgg ccgcactgga gtccgcgctc   7260
ggccgggacg agaccgcgat caccgtcgcg gacatcgact gggaccgctt ctacctcgcg   7320
tactcctccg gtcgcccgca gccctcgtc gaggagctgc cgaggtgcg cgcatcatc     7380 gacgcacggg acagcgccac gtccggacag ggcgggagct ccgcccaggg cgccaacccc   7440
ctggccgagc ggctggccgc cgcggctccc ggcgagcgta cggagatcct cctcggtctc   7500
gtacgggcgc aggccgccgc cgtgctccgg atgcgttcgc cggaggacgt cgccgccgac   7560
cgcgccttca aggacatcgg cttcgactcg ctcgccggtg tcgagctgcg caacaggctg   7620
acccgggcga ccgggctcca gctgcccgcg acgctcgtct tcgaccaccc gacgccgctg   7680
gccctcgtgt cgctgctccg cagcgagttc ctcggtgacg aggagacggc ggacgcccgg   7740
cggtccgcgg cgctgcccgc gactgtcggt gccggtgccg gcgccggcgc cggcaccgat   7800
gccgacgacg atccgatcgc gatcgtcgcg atgagctgcc gctacccgg tgacatccgc    7860 agcccggagg acctgtggcg gatgctgtcc gagggcggcg agggcatcac gccgttcccc   7920
accgaccgcg gctgggacct cgacggcctg tacgacgccg acccgacgc gctcggcagg    7980 gcgtacgtcc gcgagggcgg gttcctgcac gacgcggccg agttcgacgc ggagttcttc   8040
ggcgtctcgc cgcgcgaggc gctggccatg gacccgcagc agcggatgct cctgacgacg   8100
tcctgggagg ccttcgagcg ggccggcatc gagcggcat cgctgcgcgg cagcagcacc    8160
ggtgtcttca tcggcctctc ctaccaggac tacgcggccc gcgtcccgaa cgccccgcgt   8220
ggcgtggagg gttacctgct gaccggcagc acgccgagcg tcgcgtcggg ccgtatcgcg   8280
tacaccttcg gtctcgaagg gcccgcgacg accgtcgaca ccgcctgctc gtcgtcgctg   8340
accgccctgc acctggcggt gcgggcgctg cgcagcggcg agtgcacgat ggcgctcgcc   8400
ggtggcgtgg cgatgatggc gaccccgcac atgttcgtgg agttcagccg tcagcgggcg   8460
ctcgccccga acgccgcag caaggccttc tcggcggacg ccgacgggtt cggcgccgcg   8520
gagggcgtcg gcctgctgct cgtggagcgg ctctcggacg cgcggcgcaa cggtcacccg   8580
gtgctcgccg tggccgcgg taccgccgtc aaccaggacg cgccagcaa cgggctgacc     8640 gcgcccaacg gaccctcgca gcagcgggtg atccggcagg cgctcgccga cgcccggctg   8700
gcacccggcg acatcgacgc cgtcgagacg cacggcacgg gaacctcgct gggcgacccc   8760
atcgaggccc agggcctcca ggccacgtac ggcaaggagc ggcccgcgga acggccgctc   8820
gccatcggct ccgtgaagtc caacatcgga cacacccagg ccgcggccgg tgcggcgggc   8880
atcatcaaga tggtcctcgc gatgcgccac ggcacctgc cgaagaccct ccacgccgac    8940
gagccgagcc cgcacgtcga ctgggcgaac agcggcctgg ccctcgtcac cgagccgatc   9000
gactggccgg ccggcaccgg tccgcgccgc gccgccgtct cctccttcgg catcagcggg   9060
acgaacgcgc acgtcgtgct ggagcaggcg ccggatgctg ctggtgaggt gcttggggcc   9120
gatgaggtgc ctgaggtgtc tgagacggta gcgatggctg gacggctgg gacctccgag    9180 gtcgctgagg gctctgaggc ctccgaggcc ccgcgcccc ccggcagccg tgaggcgtcc     9240
ctccccgggc acctgccctg ggtgctgtcc gccaaggacg agcagtcgct gcgcggccag   9300
gccgccgccc tgcacgcgtg gctgtccgag cccgccgccg acctgtccgga cgcggacgga   9360 ccggcccgcc tgcgggacgt cgggtacacg ctcgccacga gccgtaccgc cttcgcgcac   9420
cgcgccgccg tgaccgccgc cgaccgggac gggttcctgg acgggctggc cacgctggcc   9480
```

```
cagggcggca cctcggccca cgtccacctg gacaccgccc gggacggcac caccgcgttc   9540
ctcttcaccg gccagggcag tcagcgcccc ggcgccggcc gtgagctgta cgaccggcac   9600
cccgtcttcg cccgggcgct cgacgagatc tgcgccacc tcgacggtca cctcgaactg    9660
cccctgctcg acgtgatgtt cgcggccgag ggcagcgcgg aggccgcgct gctcgacgag   9720
acgcggtaca cgcagtgcgc gctgttcgcc ctggaggtcg cgctcttccg gctcgtcgag   9780
agctggggca tgcggccggc cgcactgctc ggtcactcgg tcggcgagat cgccgccgcg   9840
cacgtcgccg gtgtgttctc gctcgccgac gccgccgcc tggtcgccgc gcgcggccgg    9900
ctcatgcagg agctgcccgc cggtggcgcg atgctcgccg tccaggccgc ggaggacgag   9960
atccgcgtgt ggctggagac ggaggagcgg tacgcgggac gtctgacgt cgccgccgtc   10020
aacggccccg aggccgccgt cctgtccggc gacgcggacg cggcgcggga ggcggaggcg   10080
tactggtccg ggctcggccg caggaccgc gcgctgcggg tcagccacgc cttccactcc    10140
gcgcacatgg acggcatgct cgacgggttc cgcgccgtcc tggagacggt ggagttccgg   10200
cgcccctccc tgaccgtggt ctcgaacgtc accggcctgg ccgccggccc ggacgacctg   10260
tgcgaccccg agtactgggt ccggcacgtc cgcggcaccg tccgcttcct cgacggcgtc   10320
cgtgtcctgc gcgacctcgg cgtgcggacc tgcctggagc tgggcccga cggggtcctc    10380
accgccatgg cggccgacgg cctcgcggac accccgcgg attccgctgc cggctccccc    10440
gtcggctctc ccgccggctc tcccgccgac tccgccgccg gcgcgctccg gccccggccg   10500
ctgctcgtgg cgctgctgcg ccgcaagcgg tcggagaccg agaccgtcgc ggacgccctc   10560
ggcagggcgc acgcccacgg caccggaccc gactggcacg cctggttcgc cggctccggg   10620
gcgcaccgcg tggacctgcc cacgtactcc ttccggcgcg accgctactg gctggacgcc   10680
ccggcggccg acaccgcggt ggacaccgcc ggcctcggtc tcggcaccgc cgaccacccg   10740
ctgctcggcg ccgtggtcag ccttccggac cgggacggcc tgctgctcac cggccgcctc   10800
tccctgcgca cccacccgtg gctcgcggac cacgccgtcc tggggagcgt cctgctcccc   10860
ggcgccgcga tggtcgaact cgccgcgcac gctgcggagt ccgccggtct gcgtgacgtg   10920
cgggagctga ccctccttga accgctggta ctgcccgagc acgtggcgt cgagctgcgc    10980
gtgacggtcg gggcgccggc cggagagccc ggtggcgagt cggccgggga cggcgcacgg   11040
cccgtctccc tccactcgcg gctcgccgac gcgcccgccg gtaccgcctg gtcctgccac   11100
gcgaccggtc tgctggccac cgaccggccc gagcttcccg tcgcgcccga ccgtgcggcc   11160
atgtggccgc gcagggcgc cgaggaggtg ccgctcgacg gtctctacga gcggctcgac    11220
gggaacggcc tcgccttcgg tccgctgttc caggggctga acgcggtgtg gcggtacgag   11280
ggtgaggtct cgccgacat cgcgctcccc gccaccacga atgcgaccgc gcccgcgacc    11340
gcgaacggcg gcgggagtgc ggcggcggcc ccctacggca tccacccccgc cctgctcgac   11400
gcttcgctgc acgccatcgc ggtcggcggt ctcgtcgacg agcccgagct cgtccgcgtc   11460
cccttccact ggacggtgt caccgtgcac gcggccggtg ccgcggcggc ccgggtccgt    11520
ctcgcctccg cggggacgga cgccgtctcg ctgtccctga cggacggcga gggacgcccg   11580
ctggtctccg tggaacggct cacgctgcgc ccggtcaccg ccgatcaggc ggcggcgagc   11640
cgcgtcggcg ggctgatgca ccgggtggcc tggcgtccgt acgccctcgc ctcgtccggc   11700
gaacaggacc cgcacgccac ttcgtacggg ccgaccgcc tcctcggcaa ggacgagctg    11760
aaggtcgccg ccgccctgga gtccgcgggc gtcgaagtcg ggctctaccc cgacctggcc   11820
```

-continued

```
gcgctgtccc aggacgtggc ggccggcgcc ccggcgcccc gtaccgtcct tgcgccgctg    11880
cccgcgggtc cgccgacggc cggcgcggag ggtgtacggg gcacggtggc ccggacgctg    11940
gagctgctcc aggcctggct ggccgacgag cacctcgcgg gcacccgcct gctcctggtc    12000
acccgcggtg cggtgcggga ccccgagggg tccggcgccg acgatggcgg cgaggacctg    12060
tcgcacgcgg ccgcctgggg tctcgtacgg accgcgcaga ccgagaaccc cggccgcttc    12120
ggccttctcg acctggccga cgacgcctcg tcgtaccgga ccctgccgtc ggtgctctcc    12180
gacgcgggcc tgcgcgacga accgcagctc gccctgcacg acggcaccat caggctggcc    12240
cgcctggcct ccgtccggcc cgagaccggc accgccgcac cggcgctcgc cccggagggc    12300
acggtcctgc tgaccggcgg caccggcggc ctgggcggac tggtcgcccg gcacgtggtg    12360
ggcgagtggg gcgtacgacg cctgctgctg gtgagccggc ggggcacgga cgccccgggc    12420
gccgacgagc tcgtgcacga gctggaggcc ctgggagccg acgtctcggt ggccgcgtgc    12480
gacgtcgccg accgcgaagc cctcaccgcc gtactcgacg ccatccccgc cgaacacccg    12540
ctcaccgcgg tcgtccacac ggcaggcgtc ctctccgacg gcaccctccc gtccatgacg    12600
acggaggacg tggaacacgt actgcggccc aaggtcgacg ccgcgttcct cctcgacgaa    12660
ctcacctcga cgcccgcata cgacctggca gcgttcgtca tgttctcctc cgccgccgcc    12720
gtcttcggtg gcgcggggca gggcgcctac gccgccgcca acgccaccct cgacgccctc    12780
gcctggcgcc gccgggcagc cggactcccc gccctctccc tcggctgggg cctctgggcc    12840
gagaccagcg gcatgaccgg cgagctcggc caggcggacc tgcgccggat gagccgcgcg    12900
ggcatcggcg ggatcagcga cgccgagggc atcgcgctcc tcgacgccgc cctccgcgac    12960
gaccgccacc cggtcctgct gccccctgcgg ctcgacgccg ccgggctgcg ggacgcggcc    13020
gggaacgacc cggccggaat cccggcgctc ttccgggacg tcgtcggcgc caggaccgtc    13080
cgggcccggc cgtccgcggc ctccgcctcg acgacagccg ggacgccgg cacgccgggg    13140 acggcggacg gcgcggcgga aacggcggcg gtcacgctcg ccgaccgggc cgccaccgtg    13200
gacgggcccc acggcagcg cctgctgctc gagttcgtcg tcggcgaggt cgccgaagta    13260
ctcggccacg cccgcggtca ccggatcgac gccgaacggg gcttcctcga cctcggcttc    13320
gactccctga ccgccgtcga actccgcaac cggctcaact ccgccggtgg cctcgccctc    13380
ccggcgaccc tggtcttcga ccacccaagc ccggcggcac tcgcctccca cctggacgcc    13440
gagctgccgc gcgcgcctc ggaccaggac ggagccggga accggaacgg gaacgagaac    13500
gggacgacgg cgtcccggag caccgccgag acggacgcgc tgctggcaca actgacccgc    13560
ctggaaggcg ccttggtgct gacgggcctc tcggacgccc ccgggagcga agaagtcctg    13620
gagcacctgc ggtccctgcg ctcgatggtc acgggcgaga ccgggaccgg gaccgcgtcc    13680
ggagccccgg acggcgccgg gtccggcgcc gaggaccggc cctgggcggc cggggacgga    13740
gccgggggcg ggagtgagga cggcgcggga gtgccggact tcatgaacgc ctcggccgag    13800
gaactcttcg gcctcctcga ccaggacccc agcacggact ga                      13842
```

<210> SEQ ID NO: 31
<211> LENGTH: 4613
<212> TYPE: PRT
<213> ORGANISM: Streptomyces venezuelae

<400> SEQUENCE: 31

Met Ser Ser Ala Gly Ile Thr Arg Thr Gly Ala Arg Thr Pro Val Thr
  1               5                  10                  15

-continued

```
Gly Arg Gly Ala Ala Ala Trp Asp Thr Gly Glu Val Arg Val Arg Arg
             20                  25                  30

Gly Leu Pro Pro Ala Gly Pro Asp His Ala Glu His Ser Phe Ser Arg
         35                  40                  45

Ala Pro Thr Gly Asp Val Arg Ala Glu Leu Ile Arg Gly Glu Met Ser
     50                  55                  60

Thr Val Ser Lys Ser Glu Ser Glu Glu Phe Val Ser Val Ser Asn Asp
 65                  70                  75                  80

Ala Gly Ser Ala His Gly Thr Ala Glu Pro Val Ala Val Gly Ile
                 85                  90                  95

Ser Cys Arg Val Pro Gly Ala Arg Asp Pro Arg Glu Phe Trp Glu Leu
                100                 105                 110

Leu Ala Ala Gly Gly Gln Ala Val Thr Asp Val Pro Ala Asp Arg Trp
            115                 120                 125

Asn Ala Gly Asp Phe Tyr Asp Pro Asp Arg Ser Ala Pro Gly Arg Ser
        130                 135                 140

Asn Ser Arg Trp Gly Gly Phe Ile Glu Asp Val Asp Arg Phe Asp Ala
145                 150                 155                 160

Ala Phe Phe Gly Ile Ser Pro Arg Glu Ala Ala Glu Met Asp Pro Gln
                165                 170                 175

Gln Arg Leu Ala Leu Glu Leu Gly Trp Glu Ala Leu Glu Arg Ala Gly
            180                 185                 190

Ile Asp Pro Ser Ser Leu Thr Gly Thr Arg Thr Gly Val Phe Ala Gly
        195                 200                 205

Ala Ile Trp Asp Asp Tyr Ala Thr Leu Lys His Arg Gln Gly Gly Ala
210                 215                 220

Ala Ile Thr Pro His Thr Val Thr Gly Leu His Arg Gly Ile Ile Ala
225                 230                 235                 240

Asn Arg Leu Ser Tyr Thr Leu Gly Leu Arg Gly Pro Ser Met Val Val
                245                 250                 255

Asp Ser Gly Gln Ser Ser Ser Leu Val Ala Val His Leu Ala Cys Glu
            260                 265                 270

Ser Leu Arg Arg Gly Glu Ser Glu Leu Ala Leu Ala Gly Gly Val Ser
        275                 280                 285

Leu Asn Leu Val Pro Asp Ser Ile Ile Gly Ala Ser Lys Phe Gly Gly
    290                 295                 300

Leu Ser Pro Asp Gly Arg Ala Tyr Thr Phe Asp Ala Arg Ala Asn Gly
305                 310                 315                 320

Tyr Val Arg Gly Glu Gly Gly Phe Val Val Leu Lys Arg Leu Ser
                325                 330                 335

Arg Ala Val Ala Asp Gly Asp Pro Val Leu Ala Val Ile Arg Gly Ser
            340                 345                 350

Ala Val Asn Asn Gly Gly Ala Ala Gln Gly Met Thr Thr Pro Asp Ala
        355                 360                 365

Gln Ala Gln Glu Ala Val Leu Arg Glu Ala His Glu Arg Ala Gly Thr
    370                 375                 380

Ala Pro Ala Asp Val Arg Tyr Val Glu Leu His Gly Thr Gly Thr Pro
385                 390                 395                 400

Val Gly Asp Pro Ile Glu Ala Ala Leu Gly Ala Ala Leu Gly Thr
                405                 410                 415

Gly Arg Pro Ala Gly Gln Pro Leu Leu Val Gly Ser Val Lys Thr Asn
            420                 425                 430
```

```
Ile Gly His Leu Glu Gly Ala Ala Gly Ile Ala Gly Leu Ile Lys Ala
            435                 440                 445

Val Leu Ala Val Arg Gly Arg Ala Leu Pro Ala Ser Leu Asn Tyr Glu
450                 455                 460

Thr Pro Asn Pro Ala Ile Pro Phe Glu Glu Leu Asn Leu Arg Val Asn
465                 470                 475                 480

Thr Glu Tyr Leu Pro Trp Glu Pro Glu His Asp Gly Gln Arg Met Val
                485                 490                 495

Val Gly Val Ser Ser Phe Gly Met Gly Gly Thr Asn Ala His Val Val
                500                 505                 510

Leu Glu Glu Ala Pro Gly Gly Cys Arg Gly Ala Ser Val Val Glu Ser
            515                 520                 525

Thr Val Gly Gly Ser Ala Val Gly Gly Val Val Pro Trp Val Val
            530                 535                 540

Ser Ala Lys Ser Ala Ala Ala Leu Asp Ala Gln Ile Glu Arg Leu Ala
545                 550                 555                 560

Ala Phe Ala Ser Arg Asp Arg Thr Asp Gly Val Asp Ala Gly Ala Val
                565                 570                 575

Asp Ala Gly Ala Val Asp Ala Gly Ala Val Ala Arg Val Leu Ala Gly
            580                 585                 590

Gly Arg Ala Gln Phe Glu His Arg Ala Val Val Gly Ser Gly Pro
            595                 600                 605

Asp Asp Leu Ala Ala Ala Leu Ala Ala Pro Glu Gly Leu Val Arg Gly
            610                 615                 620

Val Ala Ser Gly Val Gly Arg Val Ala Phe Val Phe Pro Gly Gln Gly
625                 630                 635                 640

Thr Gln Trp Ala Gly Met Gly Ala Glu Leu Leu Asp Ser Ser Ala Val
                645                 650                 655

Phe Ala Ala Met Ala Glu Cys Glu Ala Ala Leu Ser Pro Tyr Val
                660                 665                 670

Asp Trp Ser Leu Glu Ala Val Arg Gln Ala Pro Gly Ala Pro Thr
            675                 680                 685

Leu Glu Arg Val Asp Val Val Gln Pro Val Thr Phe Ala Val Met Val
            690                 695                 700

Ser Leu Ala Arg Val Trp Gln His His Gly Val Thr Pro Gln Ala Val
705                 710                 715                 720

Val Gly His Ser Gln Gly Glu Ile Ala Ala Tyr Val Ala Gly Ala
                725                 730                 735

Leu Ser Leu Asp Asp Ala Ala Arg Val Val Thr Leu Arg Ser Lys Ser
                740                 745                 750

Ile Ala Ala His Leu Ala Gly Lys Gly Gly Met Leu Ser Leu Ala Leu
            755                 760                 765

Ser Glu Asp Ala Val Leu Glu Arg Leu Ala Gly Phe Asp Gly Leu Ser
            770                 775                 780

Val Ala Ala Val Asn Gly Pro Thr Ala Thr Val Val Ser Gly Asp Pro
785                 790                 795                 800

Val Gln Ile Glu Glu Leu Ala Arg Ala Cys Glu Ala Asp Gly Val Arg
                805                 810                 815

Ala Arg Val Ile Pro Val Asp Tyr Ala Ser His Ser Arg Gln Val Glu
                820                 825                 830

Ile Ile Glu Ser Glu Leu Ala Glu Val Leu Ala Gly Leu Ser Pro Gln
            835                 840                 845
```

-continued

```
Ala Pro Arg Val Pro Phe Phe Ser Thr Leu Glu Gly Ala Trp Ile Thr
850                 855                 860

Glu Pro Val Leu Asp Gly Gly Tyr Trp Tyr Arg Asn Leu Arg His Arg
865                 870                 875                 880

Val Gly Phe Ala Pro Ala Val Glu Thr Leu Ala Thr Asp Glu Gly Phe
                885                 890                 895

Thr His Phe Val Glu Val Ser Ala His Pro Val Leu Thr Met Ala Leu
            900                 905                 910

Pro Gly Thr Val Thr Gly Leu Ala Thr Leu Arg Arg Asp Asn Gly Gly
            915                 920                 925

Gln Asp Arg Leu Val Ala Ser Leu Ala Glu Ala Trp Ala Asn Gly Leu
        930                 935                 940

Ala Val Asp Trp Ser Pro Leu Leu Pro Ser Ala Thr Gly His His Ser
945                 950                 955                 960

Asp Leu Pro Thr Tyr Ala Phe Gln Thr Glu Arg His Trp Leu Gly Glu
                965                 970                 975

Ile Glu Ala Leu Ala Pro Ala Gly Glu Pro Ala Val Gln Pro Ala Val
            980                 985                 990

Leu Arg Thr Glu Ala Ala Glu Pro Ala Glu Leu Asp Arg Asp Glu Gln
            995                 1000                1005

Leu Arg Val Ile Leu Asp Lys Val Arg Ala Gln Thr Ala Gln Val Leu
    1010                1015                1020

Gly Tyr Ala Thr Gly Gly Gln Ile Glu Val Asp Arg Thr Phe Arg Glu
1025                1030                1035                1040

Ala Gly Cys Thr Ser Leu Thr Gly Val Asp Leu Arg Asn Arg Ile Asn
                1045                1050                1055

Ala Ala Phe Gly Val Arg Met Ala Pro Ser Met Ile Phe Asp Phe Pro
            1060                1065                1070

Thr Pro Glu Ala Leu Ala Glu Gln Leu Leu Leu Val Val His Gly Glu
            1075                1080                1085

Ala Ala Ala Asn Pro Ala Gly Ala Glu Pro Ala Pro Val Ala Ala Ala
        1090                1095                1100

Gly Ala Val Asp Glu Pro Val Ala Ile Val Gly Met Ala Cys Arg Leu
1105                1110                1115                1120

Pro Gly Gly Val Ala Ser Pro Glu Asp Leu Trp Arg Leu Val Ala Gly
                1125                1130                1135

Gly Gly Asp Ala Ile Ser Glu Phe Pro Gln Asp Arg Gly Trp Asp Val
            1140                1145                1150

Glu Gly Leu Tyr His Pro Asp Pro Glu His Pro Gly Thr Ser Tyr Val
            1155                1160                1165

Arg Gln Gly Gly Phe Ile Glu Asn Val Ala Gly Phe Asp Ala Ala Phe
        1170                1175                1180

Phe Gly Ile Ser Pro Arg Glu Ala Leu Ala Met Asp Pro Gln Gln Arg
1185                1190                1195                1200

Leu Leu Leu Glu Thr Ser Trp Glu Ala Val Glu Asp Ala Gly Ile Asp
                1205                1210                1215

Pro Thr Ser Leu Arg Gly Arg Gln Val Gly Val Phe Thr Gly Ala Met
            1220                1225                1230

Thr His Glu Tyr Gly Pro Ser Leu Arg Asp Gly Gly Glu Gly Leu Asp
            1235                1240                1245

Gly Tyr Leu Leu Thr Gly Asn Thr Ala Ser Val Met Ser Gly Arg Val
1250                1255                1260
```

-continued

```
Ser Tyr Thr Leu Gly Leu Glu Gly Pro Ala Leu Thr Val Asp Thr Ala
1265                1270                1275                1280

Cys Ser Ser Ser Leu Val Ala Leu His Leu Ala Val Gln Ala Leu Arg
            1285                1290                1295

Lys Gly Glu Val Asp Met Ala Leu Ala Gly Val Ala Val Met Pro
        1300                1305                1310

Thr Pro Gly Met Phe Val Glu Phe Ser Arg Gln Arg Gly Leu Ala Gly
            1315                1320                1325

Asp Gly Arg Ser Lys Ala Phe Ala Ala Ser Ala Asp Gly Thr Ser Trp
        1330                1335                1340

Ser Glu Gly Val Gly Val Leu Leu Val Glu Arg Leu Ser Asp Ala Arg
1345                1350                1355                1360

Arg Asn Gly His Gln Val Leu Ala Val Val Arg Gly Ser Ala Leu Asn
                1365                1370                1375

Gln Asp Gly Ala Ser Asn Gly Leu Thr Ala Pro Asn Gly Pro Ser Gln
            1380                1385                1390

Gln Arg Val Ile Arg Arg Ala Leu Ala Asp Ala Arg Leu Thr Thr Ser
        1395                1400                1405

Asp Val Asp Val Val Glu Ala His Gly Thr Gly Thr Arg Leu Gly Asp
        1410                1415                1420

Pro Ile Glu Ala Gln Ala Leu Ile Ala Thr Tyr Gly Gln Gly Arg Asp
1425                1430                1435                1440

Asp Glu Gln Pro Leu Arg Leu Gly Ser Leu Lys Ser Asn Ile Gly His
                1445                1450                1455

Thr Gln Ala Ala Ala Gly Val Ser Gly Val Ile Lys Met Val Gln Ala
                1460                1465                1470

Met Arg His Gly Leu Leu Pro Lys Thr Leu His Val Asp Glu Pro Ser
        1475                1480                1485

Asp Gln Ile Asp Trp Ser Ala Gly Ala Val Glu Leu Leu Thr Glu Ala
            1490                1495                1500

Val Asp Trp Pro Glu Lys Gln Asp Gly Gly Leu Arg Arg Ala Ala Val
1505                1510                1515                1520

Ser Ser Phe Gly Ile Ser Gly Thr Asn Ala His Val Val Leu Glu Glu
            1525                1530                1535

Ala Pro Val Val Val Glu Gly Ala Ser Val Val Glu Pro Ser Val Gly
            1540                1545                1550

Gly Ser Ala Val Gly Gly Gly Val Thr Pro Trp Val Val Ser Ala Lys
        1555                1560                1565

Ser Ala Ala Ala Leu Asp Ala Gln Ile Glu Arg Leu Ala Ala Phe Ala
    1570                1575                1580

Ser Arg Asp Arg Thr Asp Asp Ala Asp Ala Gly Ala Val Asp Ala Gly
1585                1590                1595                1600

Ala Val Ala His Val Leu Ala Asp Gly Arg Ala Gln Phe Glu His Arg
                1605                1610                1615

Ala Val Ala Leu Gly Ala Gly Ala Asp Asp Leu Val Gln Ala Leu Ala
            1620                1625                1630

Asp Pro Asp Gly Leu Ile Arg Gly Thr Ala Ser Gly Val Gly Arg Val
        1635                1640                1645

Ala Phe Val Phe Pro Gly Gln Gly Thr Gln Trp Ala Gly Met Gly Ala
        1650                1655                1660

Glu Leu Leu Asp Ser Ser Ala Val Phe Ala Ala Ala Met Ala Glu Cys
1665                1670                1675                1680
```

-continued

```
Glu Ala Ala Leu Ser Pro Tyr Val Asp Trp Ser Leu Glu Ala Val Val
             1685                1690                1695

Arg Gln Ala Pro Gly Ala Pro Thr Leu Glu Arg Val Asp Val Val Gln
        1700                1705                1710

Pro Val Thr Phe Ala Val Met Val Ser Leu Ala Arg Val Trp Gln His
        1715                1720                1725

His Gly Val Thr Pro Gln Ala Val Gly His Ser Gln Gly Glu Ile
    1730                1735                1740

Ala Ala Ala Tyr Val Ala Gly Ala Leu Pro Leu Asp Asp Ala Ala Arg
1745                1750                1755                1760

Val Val Thr Leu Arg Ser Lys Ser Ile Ala Ala His Leu Ala Gly Lys
             1765                1770                1775

Gly Gly Met Leu Ser Leu Ala Leu Asn Glu Asp Ala Val Leu Glu Arg
             1780                1785                1790

Leu Ser Asp Phe Asp Gly Leu Ser Val Ala Ala Val Asn Gly Pro Thr
             1795                1800                1805

Ala Thr Val Val Ser Gly Asp Pro Val Gln Ile Glu Glu Leu Ala Gln
    1810                1815                1820

Ala Cys Lys Ala Asp Gly Phe Arg Ala Arg Ile Ile Pro Val Asp Tyr
1825                1830                1835                1840

Ala Ser His Ser Arg Gln Val Glu Ile Ile Glu Ser Glu Leu Ala Gln
             1845                1850                1855

Val Leu Ala Gly Leu Ser Pro Gln Ala Pro Arg Val Pro Phe Phe Ser
             1860                1865                1870

Thr Leu Glu Gly Thr Trp Ile Thr Glu Pro Val Leu Asp Gly Thr Tyr
             1875                1880                1885

Trp Tyr Arg Asn Leu Arg His Arg Val Gly Phe Ala Pro Ala Ile Glu
    1890                1895                1900

Thr Leu Ala Val Asp Glu Gly Phe Thr His Phe Val Glu Val Ser Ala
1905                1910                1915                1920

His Pro Val Leu Thr Met Thr Leu Pro Glu Thr Val Thr Gly Leu Gly
             1925                1930                1935

Thr Leu Arg Arg Glu Gln Gly Gly Gln Glu Arg Leu Val Thr Ser Leu
             1940                1945                1950

Ala Glu Ala Trp Val Asn Gly Leu Pro Val Ala Trp Thr Ser Leu Leu
             1955                1960                1965

Pro Ala Thr Ala Ser Arg Pro Gly Leu Pro Thr Tyr Ala Phe Gln Ala
    1970                1975                1980

Glu Arg Tyr Trp Leu Glu Asn Thr Pro Ala Ala Leu Ala Thr Gly Asp
1985                1990                1995                2000

Asp Trp Arg Tyr Arg Ile Asp Trp Lys Arg Leu Pro Ala Ala Glu Gly
             2005                2010                2015

Ser Glu Arg Thr Gly Leu Ser Gly Arg Trp Leu Ala Val Thr Pro Glu
             2020                2025                2030

Asp His Ser Ala Gln Ala Ala Val Leu Thr Ala Leu Val Asp Ala
             2035                2040                2045

Gly Ala Lys Val Glu Val Leu Thr Ala Gly Ala Asp Asp Arg Glu
    2050                2055                2060

Ala Leu Ala Ala Arg Leu Thr Ala Leu Thr Thr Gly Asp Gly Phe Thr
2065                2070                2075                2080

Gly Val Val Ser Leu Leu Asp Gly Leu Val Pro Gln Val Ala Trp Val
             2085                2090                2095
```

```
Gln Ala Leu Gly Asp Ala Gly Ile Lys Ala Pro Leu Trp Ser Val Thr
              2100                2105                2110
Gln Gly Ala Val Ser Val Gly Arg Leu Asp Thr Pro Ala Asp Pro Asp
          2115                2120                2125
Arg Ala Met Leu Trp Gly Leu Gly Arg Val Val Ala Leu Glu His Pro
      2130                2135                2140
Glu Arg Trp Ala Gly Leu Val Asp Leu Pro Ala Gln Pro Asp Ala Ala
2145                2150                2155                2160
Ala Leu Ala His Leu Val Thr Ala Leu Ser Gly Ala Thr Gly Glu Asp
              2165                2170                2175
Gln Ile Ala Ile Arg Thr Thr Gly Leu His Ala Arg Arg Leu Ala Arg
          2180                2185                2190
Ala Pro Leu His Gly Arg Arg Pro Thr Arg Asp Trp Gln Pro His Gly
      2195                2200                2205
Thr Val Leu Ile Thr Gly Gly Thr Gly Ala Leu Gly Ser His Ala Ala
          2210                2215                2220
Arg Trp Met Ala His His Gly Ala Glu His Leu Leu Leu Val Ser Arg
2225                2230                2235                2240
Ser Gly Glu Gln Ala Pro Gly Ala Thr Gln Leu Thr Ala Glu Leu Thr
              2245                2250                2255
Ala Ser Gly Ala Arg Val Thr Ile Ala Ala Cys Asp Val Ala Asp Pro
          2260                2265                2270
His Ala Met Arg Thr Leu Leu Asp Ala Ile Pro Ala Glu Thr Pro Leu
      2275                2280                2285
Thr Ala Val Val His Thr Ala Gly Ala Leu Asp Asp Gly Ile Val Asp
          2290                2295                2300
Thr Leu Thr Ala Glu Gln Val Arg Arg Ala His Arg Ala Lys Ala Val
2305                2310                2315                2320
Gly Ala Ser Val Leu Asp Glu Leu Thr Arg Asp Leu Asp Leu Asp Ala
              2325                2330                2335
Phe Val Leu Phe Ser Ser Val Ser Ser Thr Leu Gly Ile Pro Gly Gln
          2340                2345                2350
Gly Asn Tyr Ala Pro His Asn Ala Tyr Leu Asp Ala Leu Ala Ala Arg
      2355                2360                2365
Arg Arg Ala Thr Gly Arg Ser Ala Val Ser Val Ala Trp Gly Pro Trp
          2370                2375                2380
Asp Gly Gly Gly Met Ala Ala Gly Asp Gly Val Ala Glu Arg Leu Arg
2385                2390                2395                2400
Asn His Gly Val Pro Gly Met Asp Pro Glu Leu Ala Leu Ala Ala Leu
              2405                2410                2415
Glu Ser Ala Leu Gly Arg Asp Glu Thr Ala Ile Thr Val Ala Asp Ile
          2420                2425                2430
Asp Trp Asp Arg Phe Tyr Leu Ala Tyr Ser Ser Gly Arg Pro Gln Pro
      2435                2440                2445
Leu Val Glu Glu Leu Pro Glu Val Arg Arg Ile Ile Asp Ala Arg Asp
          2450                2455                2460
Ser Ala Thr Ser Gly Gln Gly Gly Ser Ser Ala Gln Gly Ala Asn Pro
2465                2470                2475                2480
Leu Ala Glu Arg Leu Ala Ala Ala Pro Gly Glu Arg Thr Glu Ile
              2485                2490                2495
Leu Leu Gly Leu Val Arg Ala Gln Ala Ala Ala Val Leu Arg Met Arg
          2500                2505                2510
```

-continued

```
Ser Pro Glu Asp Val Ala Ala Asp Arg Ala Phe Lys Asp Ile Gly Phe
    2515                2520                2525

Asp Ser Leu Ala Gly Val Glu Leu Arg Asn Arg Leu Thr Arg Ala Thr
2530                2535                2540

Gly Leu Gln Leu Pro Ala Thr Leu Val Phe Asp His Pro Thr Pro Leu
2545                2550                2555                2560

Ala Leu Val Ser Leu Leu Arg Ser Glu Phe Leu Gly Asp Glu Glu Thr
    2565                2570                2575

Ala Asp Ala Arg Arg Ser Ala Ala Leu Pro Ala Thr Val Gly Ala Gly
            2580                2585                2590

Ala Gly Ala Gly Ala Gly Thr Asp Ala Asp Asp Pro Ile Ala Ile
        2595                2600                2605

Val Ala Met Ser Cys Arg Tyr Pro Gly Asp Ile Arg Ser Pro Glu Asp
    2610                2615                2620

Leu Trp Arg Met Leu Ser Glu Gly Gly Glu Gly Ile Thr Pro Phe Pro
2625                2630                2635                2640

Thr Asp Arg Gly Trp Asp Leu Asp Gly Leu Tyr Asp Ala Asp Pro Asp
            2645                2650                2655

Ala Leu Gly Arg Ala Tyr Val Arg Glu Gly Gly Phe Leu His Asp Ala
        2660                2665                2670

Ala Glu Phe Asp Ala Glu Phe Phe Gly Val Ser Pro Arg Glu Ala Leu
    2675                2680                2685

Ala Met Asp Pro Gln Gln Arg Met Leu Leu Thr Thr Ser Trp Glu Ala
    2690                2695                2700

Phe Glu Arg Ala Gly Ile Glu Pro Ala Ser Leu Arg Gly Ser Ser Thr
2705                2710                2715                2720

Gly Val Phe Ile Gly Leu Ser Tyr Gln Asp Tyr Ala Ala Arg Val Pro
            2725                2730                2735

Asn Ala Pro Arg Gly Val Glu Gly Tyr Leu Leu Thr Gly Ser Thr Pro
        2740                2745                2750

Ser Val Ala Ser Gly Arg Ile Ala Tyr Thr Phe Gly Leu Glu Gly Pro
    2755                2760                2765

Ala Thr Thr Val Asp Thr Ala Cys Ser Ser Ser Leu Thr Ala Leu His
    2770                2775                2780

Leu Ala Val Arg Ala Leu Arg Ser Gly Glu Cys Thr Met Ala Leu Ala
2785                2790                2795                2800

Gly Gly Val Ala Met Met Ala Thr Pro His Met Phe Val Glu Phe Ser
            2805                2810                2815

Arg Gln Arg Ala Leu Ala Pro Asp Gly Arg Ser Lys Ala Phe Ser Ala
        2820                2825                2830

Asp Ala Asp Gly Phe Gly Ala Ala Glu Gly Val Gly Leu Leu Leu Val
    2835                2840                2845

Glu Arg Leu Ser Asp Ala Arg Arg Asn Gly His Pro Val Leu Ala Val
    2850                2855                2860

Val Arg Gly Thr Ala Val Asn Gln Asp Gly Ala Ser Asn Gly Leu Thr
2865                2870                2875                2880

Ala Pro Asn Gly Pro Ser Gln Gln Arg Val Ile Arg Gln Ala Leu Ala
            2885                2890                2895

Asp Ala Arg Leu Ala Pro Gly Asp Ile Asp Ala Val Glu Thr His Gly
        2900                2905                2910

Thr Gly Thr Ser Leu Gly Asp Pro Ile Glu Ala Gln Gly Leu Gln Ala
    2915                2920                2925
```

-continued

```
Thr Tyr Gly Lys Glu Arg Pro Ala Glu Arg Pro Leu Ala Ile Gly Ser
        2930                2935                2940
Val Lys Ser Asn Ile Gly His Thr Gln Ala Ala Gly Ala Ala Gly
2945                2950                2955                2960
Ile Ile Lys Met Val Leu Ala Met Arg His Gly Thr Leu Pro Lys Thr
            2965                2970                2975
Leu His Ala Asp Glu Pro Ser Pro His Val Asp Trp Ala Asn Ser Gly
            2980                2985                2990
Leu Ala Leu Val Thr Glu Pro Ile Asp Trp Pro Ala Gly Thr Gly Pro
            2995                3000                3005
Arg Arg Ala Ala Val Ser Ser Phe Gly Ile Ser Gly Thr Asn Ala His
3010                3015                3020
Val Val Leu Glu Gln Ala Pro Asp Ala Gly Glu Val Leu Gly Ala
3025                3030                3035                3040
Asp Glu Val Pro Glu Val Ser Glu Thr Val Ala Met Ala Gly Thr Ala
            3045                3050                3055
Gly Thr Ser Glu Val Ala Glu Gly Ser Glu Ala Ser Glu Ala Pro Ala
            3060                3065                3070
Ala Pro Gly Ser Arg Glu Ala Ser Leu Pro Gly His Leu Pro Trp Val
            3075                3080                3085
Leu Ser Ala Lys Asp Glu Gln Ser Leu Arg Gly Gln Ala Ala Ala Leu
            3090                3095                3100
His Ala Trp Leu Ser Glu Pro Ala Ala Asp Leu Ser Asp Ala Asp Gly
3105                3110                3115                3120
Pro Ala Arg Leu Arg Asp Val Gly Tyr Thr Leu Ala Thr Ser Arg Thr
            3125                3130                3135
Ala Phe Ala His Arg Ala Ala Val Thr Ala Ala Asp Arg Asp Gly Phe
            3140                3145                3150
Leu Asp Gly Leu Ala Thr Leu Ala Gln Gly Gly Thr Ser Ala His Val
            3155                3160                3165
His Leu Asp Thr Ala Arg Asp Gly Thr Thr Ala Phe Leu Phe Thr Gly
            3170                3175                3180
Gln Gly Ser Gln Arg Pro Gly Ala Gly Arg Glu Leu Tyr Asp Arg His
3185                3190                3195                3200
Pro Val Phe Ala Arg Ala Leu Asp Glu Ile Cys Ala His Leu Asp Gly
            3205                3210                3215
His Leu Glu Leu Pro Leu Leu Asp Val Met Phe Ala Ala Glu Gly Ser
            3220                3225                3230
Ala Glu Ala Ala Leu Leu Asp Glu Thr Arg Tyr Thr Gln Cys Ala Leu
            3235                3240                3245
Phe Ala Leu Glu Val Ala Leu Phe Arg Leu Val Glu Ser Trp Gly Met
3250                3255                3260
Arg Pro Ala Ala Leu Leu Gly His Ser Val Gly Glu Ile Ala Ala Ala
3265                3270                3275                3280
His Val Ala Gly Val Phe Ser Leu Ala Asp Ala Ala Arg Leu Val Ala
            3285                3290                3295
Ala Arg Gly Arg Leu Met Gln Glu Leu Pro Ala Gly Gly Ala Met Leu
            3300                3305                3310
Ala Val Gln Ala Ala Glu Asp Glu Ile Arg Val Trp Leu Glu Thr Glu
            3315                3320                3325
Glu Arg Tyr Ala Gly Arg Leu Asp Val Ala Ala Val Asn Gly Pro Glu
            3330                3335                3340
```

-continued

```
Ala Ala Val Leu Ser Gly Asp Ala Asp Ala Ala Arg Glu Ala Glu Ala
3345             3350             3355             3360

Tyr Trp Ser Gly Leu Gly Arg Arg Thr Arg Ala Leu Arg Val Ser His
             3365             3370             3375

Ala Phe His Ser Ala His Met Asp Gly Met Leu Asp Gly Phe Arg Ala
         3380             3385             3390

Val Leu Glu Thr Val Glu Phe Arg Arg Pro Ser Leu Thr Val Val Ser
     3395             3400             3405

Asn Val Thr Gly Leu Ala Ala Gly Pro Asp Asp Leu Cys Asp Pro Glu
     3410             3415             3420

Tyr Trp Val Arg His Val Arg Gly Thr Val Arg Phe Leu Asp Gly Val
3425             3430             3435             3440

Arg Val Leu Arg Asp Leu Gly Val Arg Thr Cys Leu Glu Leu Gly Pro
             3445             3450             3455

Asp Gly Val Leu Thr Ala Met Ala Ala Asp Gly Leu Ala Asp Thr Pro
         3460             3465             3470

Ala Asp Ser Ala Ala Gly Ser Pro Val Gly Ser Pro Ala Gly Ser Pro
         3475             3480             3485

Ala Asp Ser Ala Ala Gly Ala Leu Arg Pro Arg Pro Leu Leu Val Ala
     3490             3495             3500

Leu Leu Arg Arg Lys Arg Ser Glu Thr Glu Thr Val Ala Asp Ala Leu
3505             3510             3515             3520

Gly Arg Ala His Ala His Gly Thr Gly Pro Asp Trp His Ala Trp Phe
             3525             3530             3535

Ala Gly Ser Gly Ala His Arg Val Asp Leu Pro Thr Tyr Ser Phe Arg
         3540             3545             3550

Arg Asp Arg Tyr Trp Leu Asp Ala Pro Ala Ala Asp Thr Ala Val Asp
         3555             3560             3565

Thr Ala Gly Leu Gly Leu Gly Thr Ala Asp His Pro Leu Leu Gly Ala
     3570             3575             3580

Val Val Ser Leu Pro Asp Arg Asp Gly Leu Leu Leu Thr Gly Arg Leu
3585             3590             3595             3600

Ser Leu Arg Thr His Pro Trp Leu Ala Asp His Ala Val Leu Gly Ser
             3605             3610             3615

Val Leu Leu Pro Gly Ala Ala Met Val Glu Leu Ala Ala His Ala Ala
         3620             3625             3630

Glu Ser Ala Gly Leu Arg Asp Val Arg Glu Leu Thr Leu Leu Glu Pro
         3635             3640             3645

Leu Val Leu Pro Glu His Gly Gly Val Glu Leu Arg Val Thr Val Gly
     3650             3655             3660

Ala Pro Ala Gly Glu Pro Gly Gly Glu Ser Ala Gly Asp Gly Ala Arg
3665             3670             3675             3680

Pro Val Ser Leu His Ser Arg Leu Ala Asp Ala Pro Ala Gly Thr Ala
             3685             3690             3695

Trp Ser Cys His Ala Thr Gly Leu Leu Ala Thr Asp Arg Pro Glu Leu
         3700             3705             3710

Pro Val Ala Pro Asp Arg Ala Ala Met Trp Pro Pro Gln Gly Ala Glu
         3715             3720             3725

Glu Val Pro Leu Asp Gly Leu Tyr Glu Arg Leu Asp Gly Asn Gly Leu
     3730             3735             3740

Ala Phe Gly Pro Leu Phe Gln Gly Leu Asn Ala Val Trp Arg Tyr Glu
3745             3750             3755             3760
```

-continued

```
Gly Glu Val Phe Ala Asp Ile Ala Leu Pro Ala Thr Thr Asn Ala Thr
                3765                3770                3775
Ala Pro Ala Thr Ala Asn Gly Gly Ser Ala Ala Ala Pro Tyr
            3780                3785                3790
Gly Ile His Pro Ala Leu Leu Asp Ala Ser Leu His Ala Ile Ala Val
                3795                3800                3805
Gly Gly Leu Val Asp Glu Pro Glu Leu Val Arg Val Pro Phe His Trp
                3810                3815                3820
Ser Gly Val Thr Val His Ala Gly Ala Ala Ala Arg Val Arg
3825                3830                3835                3840
Leu Ala Ser Ala Gly Thr Asp Ala Val Ser Leu Ser Leu Thr Asp Gly
                3845                3850                3855
Glu Gly Arg Pro Leu Val Ser Val Glu Arg Leu Thr Leu Arg Pro Val
                3860                3865                3870
Thr Ala Asp Gln Ala Ala Ala Ser Arg Val Gly Gly Leu Met His Arg
                3875                3880                3885
Val Ala Trp Arg Pro Tyr Ala Leu Ala Ser Ser Gly Glu Gln Asp Pro
                3890                3895                3900
His Ala Thr Ser Tyr Gly Pro Thr Ala Val Leu Gly Lys Asp Glu Leu
3905                3910                3915                3920
Lys Val Ala Ala Ala Leu Glu Ser Ala Gly Val Glu Val Gly Leu Tyr
                3925                3930                3935
Pro Asp Leu Ala Ala Leu Ser Gln Asp Val Ala Ala Gly Ala Pro Ala
                3940                3945                3950
Pro Arg Thr Val Leu Ala Pro Leu Pro Ala Gly Pro Ala Asp Gly Gly
                3955                3960                3965
Ala Glu Gly Val Arg Gly Thr Val Ala Arg Thr Leu Glu Leu Leu Gln
                3970                3975                3980
Ala Trp Leu Ala Asp Glu His Leu Ala Gly Thr Arg Leu Leu Leu Val
3985                3990                3995                4000
Thr Arg Gly Ala Val Arg Asp Pro Glu Gly Ser Gly Ala Asp Asp Gly
                4005                4010                4015
Gly Glu Asp Leu Ser His Ala Ala Ala Trp Gly Leu Val Arg Thr Ala
                4020                4025                4030
Gln Thr Glu Asn Pro Gly Arg Phe Gly Leu Leu Asp Leu Ala Asp Asp
                4035                4040                4045
Ala Ser Ser Tyr Arg Thr Leu Pro Ser Val Leu Ser Asp Ala Gly Leu
                4050                4055                4060
Arg Asp Glu Pro Gln Leu Ala Leu His Asp Gly Thr Ile Arg Leu Ala
4065                4070                4075                4080
Arg Leu Ala Ser Val Arg Pro Glu Thr Gly Thr Ala Ala Pro Ala Leu
                4085                4090                4095
Ala Pro Glu Gly Thr Val Leu Leu Thr Gly Gly Thr Gly Gly Leu Gly
                4100                4105                4110
Gly Leu Val Ala Arg His Val Val Gly Glu Trp Gly Val Arg Arg Leu
                4115                4120                4125
Leu Leu Val Ser Arg Arg Gly Thr Asp Ala Pro Gly Ala Asp Glu Leu
                4130                4135                4140
Val His Glu Leu Glu Ala Leu Gly Ala Asp Val Ser Val Ala Ala Cys
4145                4150                4155                4160
Asp Val Ala Asp Arg Glu Ala Leu Thr Ala Val Leu Asp Ala Ile Pro
                4165                4170                4175
```

-continued

```
Ala Glu His Pro Leu Thr Ala Val Val His Thr Ala Gly Val Leu Ser
            4180                4185                4190

Asp Gly Thr Leu Pro Ser Met Thr Thr Glu Asp Val Glu His Val Leu
            4195                4200                4205

Arg Pro Lys Val Asp Ala Ala Phe Leu Leu Asp Glu Leu Thr Ser Thr
            4210                4215                4220

Pro Ala Tyr Asp Leu Ala Ala Phe Val Met Phe Ser Ser Ala Ala Ala
4225                4230                4235                4240

Val Phe Gly Gly Ala Gly Gln Gly Ala Tyr Ala Ala Ala Asn Ala Thr
            4245                4250                4255

Leu Asp Ala Leu Ala Trp Arg Arg Ala Ala Gly Leu Pro Ala Leu
            4260                4265                4270

Ser Leu Gly Trp Gly Leu Trp Ala Glu Thr Ser Gly Met Thr Gly Glu
            4275                4280                4285

Leu Gly Gln Ala Asp Leu Arg Arg Met Ser Arg Ala Gly Ile Gly Gly
            4290                4295                4300

Ile Ser Asp Ala Glu Gly Ile Ala Leu Leu Asp Ala Ala Leu Arg Asp
4305                4310                4315                4320

Asp Arg His Pro Val Leu Leu Pro Leu Arg Leu Asp Ala Ala Gly Leu
            4325                4330                4335

Arg Asp Ala Ala Gly Asn Asp Pro Ala Gly Ile Pro Ala Leu Phe Arg
            4340                4345                4350

Asp Val Val Gly Ala Arg Thr Val Arg Ala Arg Pro Ser Ala Ala Ser
            4355                4360                4365

Ala Ser Thr Thr Ala Gly Thr Ala Gly Thr Pro Gly Thr Ala Asp Gly
            4370                4375                4380

Ala Ala Glu Thr Ala Ala Val Thr Leu Ala Asp Arg Ala Ala Thr Val
4385                4390                4395                4400

Asp Gly Pro Ala Arg Gln Arg Leu Leu Leu Glu Phe Val Val Gly Glu
            4405                4410                4415

Val Ala Glu Val Leu Gly His Ala Arg Gly His Arg Ile Asp Ala Glu
            4420                4425                4430

Arg Gly Phe Leu Asp Leu Gly Phe Asp Ser Leu Thr Ala Val Glu Leu
            4435                4440                4445

Arg Asn Arg Leu Asn Ser Ala Gly Gly Leu Ala Leu Pro Ala Thr Leu
            4450                4455                4460

Val Phe Asp His Pro Ser Pro Ala Ala Leu Ala Ser His Leu Asp Ala
4465                4470                4475                4480

Glu Leu Pro Arg Gly Ala Ser Asp Gln Asp Gly Ala Gly Asn Arg Asn
            4485                4490                4495

Gly Asn Glu Asn Gly Thr Thr Ala Ser Arg Ser Thr Ala Glu Thr Asp
            4500                4505                4510

Ala Leu Leu Ala Gln Leu Thr Arg Leu Glu Gly Ala Leu Val Leu Thr
            4515                4520                4525

Gly Leu Ser Asp Ala Pro Gly Ser Glu Glu Val Leu Glu His Leu Arg
            4530                4535                4540

Ser Leu Arg Ser Met Val Thr Gly Glu Thr Gly Thr Gly Thr Ala Ser
4545                4550                4555                4560

Gly Ala Pro Asp Gly Ala Gly Ser Gly Ala Glu Asp Arg Pro Trp Ala
            4565                4570                4575

Ala Gly Asp Gly Ala Gly Gly Gly Ser Glu Asp Gly Ala Gly Val Pro
            4580                4585                4590
```

Asp Phe Met Asn Ala Ser Ala Glu Glu Leu Phe Gly Leu Leu Asp Gln
    4595                4600                4605

Asp Pro Ser Thr Asp
    4610

<210> SEQ ID NO: 32
<211> LENGTH: 11220
<212> TYPE: DNA
<213> ORGANISM: Streptomyces venezuelae

<400> SEQUENCE: 32

| | | |
|---|---|---|
| gtgtccacgg tgaacgaaga gaagtacctc gactacctgc gtcgtgccac ggcggacctc | 60 |
| cacgaggccc gtggccgcct ccgcgagctg gaggcgaagg cgggcgagcc ggtggcgatc | 120 |
| gtcggcatgg cctgccgcct gcccggcggc gtcgcctcgc ccgaggacct gtggcggctg | 180 |
| gtggccggcg gcgaggacgc gatctcggag ttcccccagg accgcggctg ggacgtggag | 240 |
| ggcctgtacg acccgaaccc ggaggccacg ggcaagagtt acgcccgcga ggccggattc | 300 |
| ctgtacgagg cgggcgagtt cgacgccgac ttcttcggga tctcgccgcg cgaggccctc | 360 |
| gccatggacc cgcagcagcg tctcctcctg gaggcctcct gggaggcgtt cgagcacgcc | 420 |
| gggatcccgg cggccaccgc gcgcggcacc tcggtcggcg tcttcaccgg cgtgatgtac | 480 |
| cacgactacg ccacccgtct caccgatgtc ccggagggca tcgagggcta cctgggcacc | 540 |
| ggcaactccg gcagtgtcgc ctcgggccgc gtcgcgtaca cgcttggcct ggagggggccg | 600 |
| gccgtcacgg tcgacaccgc ctgctcgtcc tcgctggtcg ccctgcacct cgccgtgcag | 660 |
| gccctgcgca gggcgaggt cgacatggcg ctcgccggcg gcgtgacggt catgtcgacg | 720 |
| cccagcacct tcgtcgagtt cagccgtcag cgcgggctgg cgccggacgg ccggtcgaag | 780 |
| tccttctcgt cgacggccga cggcaccagc tggtccgagg gcgtcggcgt cctcctcgtc | 840 |
| gagcgcctgt ccgacgcgcg tcgcaagggc catcggatcc tcgccgtggt ccggggcacc | 900 |
| gccgtcaacc aggacggcgc cagcagcggc ctcacggctc gaacgggcc gtcgcagcag | 960 |
| cgcgtcatcc gacgtgccct ggcggacgcc cggctcacga cctccgacgt ggacgtcgtc | 1020 |
| gaggcccacg gcacgggtac gcgactcggc gacccgatcg aggcgcaggc cgtcatcgcc | 1080 |
| acgtacgggc agggccgtga cggcgaacag ccgctgcgcc tcgggtcgtt gaagtccaac | 1140 |
| atcggacaca cccaggccgc cgccggtgtc tccggcgtga tcaagatggt ccaggcgatg | 1200 |
| cgccacggcg tcctgccgaa gacgctccac gtggagaagc cgacgaccag gtggactgg | 1260 |
| tccgcgggcg cggtcgagct gctcaccgag gccatggact ggccggacaa gggcgacggc | 1320 |
| ggactgcgca gggccgcggt ctcctccttc ggcgtcagcg gacgaacgc gcacgtcgtg | 1380 |
| ctcgaagagg ccccggcggc cgaggagacc cctgcctccg aggcgacccc ggccgtcgag | 1440 |
| ccgtcggtcg gcgccggcct ggtgccgtgg ctggtgtcgg cgaagactcc ggccgcgctg | 1500 |
| gacgcccaga tcggacgcct cgccgcgttc gcctcgcagg gccgtacgga cgccgccgat | 1560 |
| ccgggcgcgg tcgctcgcgt actgccggc gggcgcgccg agttcgagca ccgggccgtc | 1620 |
| gtgctcggca ccggacagga cgatttcgcg caggcgctga ccgctccgga aggactgata | 1680 |
| cgcggcacgc cctcggacgt gggccgggtg cgttcgtgt tccccggtca gggcacgcag | 1740 |
| tgggccggga tgggcgccga actcctcgac gtgtcgaagg agttcgcggc ggccatggcc | 1800 |
| gagtgcgaga gcgcgctctc ccgctatgtc gactggcgc tggaggccgt cgtccggcag | 1860 |
| gcgccgggcg cgcccacgct ggagcgggtc gacgtcgtcc agcccgtgac cttcgctgtc | 1920 |
| atggtttcgc tggcgaaggt ctggcagcac cacggcgtga cgccgcaggc cgtcgtcggc | 1980 |

```
cactcgcagg gcgagatcgc cgccgcgtac gtcgccggtg ccctcaccct cgacgacgcc    2040
gcccgcgtcg tcaccctgcg cagcaagtcc atcgccgccc acctcgccgg caagggcggc    2100
atgatctccc tcgccctcag cgaggaagcc acccggcagc gcatcgagaa cctccacgga    2160
ctgtcgatcg ccgccgtcaa cggccccacc gccaccgtgg tttcgggcga ccccacccag    2220
atccaagagc tcgctcaggc gtgtgaggcc gacgggtcc gcgcacggat catccccgtc     2280
gactacgcct cccacagcgc ccacgtcgag accatcgaga gcgaactcgc cgaggtcctc    2340
gccgggctca gcccgcggac acctgaggtg ccgttcttct cgacactcga aggcgcctgg    2400
atcaccgagc cggtgctcga cggcacctac tggtaccgca acctccgcca ccgcgtcggc    2460
ttcgcccccg ccgtcgagac cctcgccacc gacgaaggct caccccactt catcgaggtc    2520
agcgcccacc ccgtcctcac catgacccct cccgagaccg tcaccggcct cggcacccct   2580
cgccgcgaac agggaggcca ggagcgtctg gtcacctcac tcgccgaagc ctggaccaac    2640
ggcctcacca tcgactgggc gcccgtcctc ccaccgcaa ccggccacca ccccgagctc     2700
cccacctacg ccttccagcg ccgtcactac tggctccacg actcccccgc cgtccagggc    2760
tccgtgcagg actcctggcg ctaccgcatc gactggaagc gcctcgcggt cgccgacgcg    2820
tccgagcgcg ccgggctgtc cgggcgctgg ctcgtcgtcg tccccgagga ccgttccgcc    2880
gaggccgccc cggtgctcgc cgcgctgtcc ggcgccggcg ccgacccgt acagctggac     2940 gtgtcccgc tgggcgaccg gcagcggctc gccgcgacgc tgggcgaggc cctggcggcg     3000
gccggtggag ccgtcgacgg cgtcctctcg ctgctcgcgt gggacgagag cgcgcacccc   3060 ggccacccg ccccttcac ccgggcacc ggcgccaccc tcaccctggt gcaggcgctg       3120
gaggacgccg gcgtcgccgc cccgctgtgg tgcgtgaccc acggcgcggt gtccgtcggc    3180
cgggccgacc acgtcacctc ccccgcccag gccatggtgt ggggcatggg ccgggtcgcc    3240
gccctggagc accccgagcg gtggggcggc ctgatcgacc tgccctcgga cgccgaccgg    3300
gcggccctgg accgcatgac cacggtcctc gccggcggta cgggtgagga ccaggtcgcg   3360
gtacgcgcct ccgggctgct cgcccgccgc ctcgtccgcg cctccctccc ggcgcacggc    3420
acggcttcgc cgtggtggca ggccgacggc acggtgctcg tcaccggtgc cgaggagcct    3480
gcggccgccg aggccgcacg ccggctggcc cgcgacggcg ccggacacct cctcctccac   3540
accaccccct ccggcagcga aggcgccgaa ggcacctccg gtgccgccga ggactccggc    3600
ctcgccgggc tcgtcgccga actcgcggac ctggcgcga cggccaccgt cgtgacctgc     3660
gacctcacgg acgcggaggc ggccgcccgg ctgctcgccg gcgtctccga cgcgcacccg    3720
ctcagcgccg tcctccacct gccgcccacc gtcgactccg agccgctcgc cgcgaccgac    3780
gcggacgcgc tcgcccgtgt cgtgaccgcg aaggccaccg ccgcgctcca cctggaccgc    3840
ctcctgcggg aggccgcggc tgccggaggc cgtccgcccc tcctggtcct cttctcctcg    3900
gtcgccgcga tctggggcgg cgccggtcag ggcgcgtacg ccgccggtac ggccttcctc    3960
gacgccctcg ccggtcagca ccgggccgac ggccccaccg tgacctcggt ggcctggagc    4020
ccctgggagg gcagccgcgt caccgagggt gcgaccgggg agcggctgcg ccgcctcggc    4080
ctgcgccccc tcgcccccgc gacggcgctc accgccctgg acaccgcgct cggccacggc    4140
gacaccgccg tcacgatcgc cgacgtcgac tggtcgagct tcgcccccgg cttcaccacg    4200
gcccggccgg gcaccctcct cgccgatctg cccgaggcgc gccgcgcgct cgacgagcag    4260
cagtcgacga cggccgccga cgacaccgtc ctgagccgcg agctcggtgc gctcaccggc    4320
```

```
gccgaacagc agcgccgtat gcaggagttg gtccgcgagc acctcgccgt ggtcctcaac    4380
caccccctccc ccgaggccgt cgacacgggg cgggccttcc gtgacctcgg attcgactcg   4440
ctgacggcgg tcgagctccg caaccgcctc aagaacgcca ccggcctggc cctcccggcc    4500
actctggtct tcgactaccc gaccccccgg acgctggcgg agttcctcct cgcggagatc    4560
ctgggcgagc aggccggtgc cggcgagcag cttccggtgg acggcggggt cgacgacgag    4620
cccgtcgcga tcgtcggcat ggcgtgccgc ctgccgggcg gtgtcgcctc gccggaggac    4680
ctgtggcggc tggtggccgg cggcgaggac gcgatctccg gcttcccgca ggaccgcggc    4740
tgggacgtgg aggggctgta cgacccggac ccggacgcgt ccgggcggac gtactgccgt    4800
gccggtggct tcctcgacga ggcgggcgag ttcgacgccg acttcttcgg gatctcgccg    4860
cgcgaggccc tcgccatgga cccgcagcag cggctcctcc tggagacctc ctgggaggcc    4920
gtcgaggacg ccgggatcga cccgacctcc cttcaggggc agcaggtcgg cgtgttcgcg    4980
ggcaccaacg gccccccacta cgagccgctg ctccgcaaca ccgccgagga tcttgagggt    5040
tacgtcggga cgggcaacgc cgccagcatc atgtcgggcc gtgtctcgta caccctcggc    5100
ctggagggcc cggccgtcac ggtcgacacc gcctgctcct cctcgctggt cgccctgcac    5160
ctcgccgtgc aggccctgcg caagggcgaa tgcggactgg cgctcgcggg cggtgtgacg    5220
gtcatgtcga cgcccacgac gttcgtggag ttcagccggc agcgcgggct cgcggaggac    5280
ggccggtcga aggcgttcgc cgcgtcggcg gacggcttcg gcccggcgga gggcgtcggc    5340
atgctcctcg tcgagcgcct gtcggacgcc cgccgcaacg acaccgtgt gctggcggtc    5400
gtgcgcggca gcgcggtcaa ccaggacggc gcgagcaacg gcctgaccgc cccgaacggg    5460
ccctcgcagc agcgcgtcat ccggcgcgcg ctcgcggacg cccgactgac gaccgccgac    5520
gtggacgtcg tcgaggccca cggcacgggc acgcgactcg gcgacccgat cgaggcacag    5580
gccctcatcg ccacctacgg ccaggggcgc gacaccgaac agccgctgcg cctggggtcg    5640
ttgaagtcca acatcggaca cacccaggcc gccgccggtg tctccggcat catcaagatg    5700
gtccaggcga tgcgccacgg cgtcctgccg aagacgctcc acgtggaccg gccgtcggac    5760
cagatcgact ggtcggcggg cacggtcgag ctgctcaccg aggccatgga ctggccgagg    5820
aagcaggagg gcgggctgcg ccgcgcggcc gtctcctcct tcggcatcag cggcacgaac    5880
gcgcacatcg tgctcgaaga agccccggtc gacgaggacg ccccggcgga cgagccgtcg    5940
gtcggcggtg tggtgccgtg gctcgtgtcc gcgaagactc cggccgcgct ggacgcccag    6000
atcggacgcc tcgccgcgtt cgcctcgcag ggccgtacgg acgccgccga tccgggcgcg    6060
gtcgctcgcg tactggccgg cgggcgtgcg cagttcgagc accgggccgt cgcgctcggc    6120
accggacagg acgacctggc ggccgcactg gccgcgcctg agggtctggt ccggggtgtg    6180
gcctccggtg tgggtcgagt ggcgttcgtg ttcccgggac agggcacgca gtgggccggg    6240
atgggtgccg aactcctcga cgtgtcgaag gagttcgcgg cggccatggc cgagtgcgag    6300
gccgcgctcc tccgtacgt ggactggtcg ctggaggcc tcgtccgaca ggcccccggc    6360
gcgcccacgc tggagcgggt cgatgtcgtc cagcccgtga cgttcgccgt catggtctcg    6420
ctggcgaagg tctggcagca ccacgggtg acccgcaag ccgtcgtcgg ccactcgcag    6480
ggcgagatcg ccgccgcgta cgtcgccggt gccctgagcc tggacgacgc cgctcgtgtc    6540
gtgaccctgc gcagcaagtc catcggcgcc cacctcgcgg gccagggcgg catgctgtcc    6600
ctcgcgctga gcgaggcggc cgttgtggag cgactggccg ggttcgacgg gctgtccgtc    6660
gccgccgtca cgggcctac cgccaccgtg gtttcgggcg accgacccca gatccaagag    6720
```

```
ctcgctcagg cgtgtgaggc cgacggggtc cgcgcacgga tcatccccgt cgactacgcc   6780
tcccacagcg cccacgtcga gaccatcgag agcgaactcg ccgacgtcct ggcggggttg   6840 tcccccaga caccccaggt cccttcttc tccaccctcg aaggcgcctg gatcaccgaa    6900 ccgccctcg acggcggcta ctggtaccgc aacctccgcc atcgtgtggg cttcgccccg   6960
gccgtcgaaa ccctggccac cgacgaaggc ttcacccact tcgtcgaggt cagcgcccac   7020
cccgtcctca ccatggcgct gcccgagacc gtcaccggac tcggcaccct ccgccgtgac   7080
aacggcggac agcaccgcct caccacctcc ctcgccgagg cctgggccaa cggcctcacc   7140
gtcgactggg cctctctcct ccccaccacg accacccacc ccgatctgcc cacctacgcc   7200
ttccagaccg agcgctactg gccgcagccc gacctctccg ccgccggtga catcacctcc   7260
gccggtctcg gggcggccga gcacccgctg ctcggcgcgg ccgtggcgct cgcggactcc   7320
gacggctgcc tgctcacggg gagcctctcc ctccgtacgc acccctggct ggcggaccac   7380
gcggtggccg gcaccgtgct gctgccggga acggcgttcg tggagctggc gttccgagcc   7440
ggggaccagg tcggttgcga tctggtcgag gagctcaccc tcgacgcgcc gctcgtgctg   7500
ccccgtcgtg gcgcggtccg tgtgcagctg tccgtcggcg cgagcgacga gtccgggcgt   7560
cgtaccttcg ggctctacgc gcacccgag gacgcgccgg gcgaggcgga gtggacgcgg   7620
cacgccaccg gtgtgctggc cgcccgtgcg gaccgcaccg ccccgtcgc cgacccggag   7680 gcctggccgc cgccgggcgc cgagccgtg gacgtggacg tctgtacga gcgcttcgcg   7740 gcgaacggct acggctacgg cccctcttc cagggcgtcc gtggtgtctg gcggcgtggc   7800
gacgaggtgt tcgccgacgt ggccctgccg gccgaggtcg ccggtgccga gggcgcgcgg   7860
ttcggccttc acccggcgct gctcgacgcc gccgtgcagg cggccggtgc gggccggggc   7920
gttcggcgcg ggcacgcggc tgccgttcgc ctggagcggg atctcctgta cgcggtcggc   7980
gccaccgccc tccgcgtgcg gctggccccc gccggcccgg acacggtgtc cgtgagcgcc   8040
gccgactcct ccgggcagcc ggtgttcgcc gcggactccc tcacggtgct gcccgtcgac   8100
cccgcgcagc tggcggcctt cagcgacccg actctggacg cgctgcacct gctggagtgg   8160
accgcctggg acggtgccgc gcaggccctg cccggcgcgg tcgtgctggg cggcgacgcc   8220
gacggtctcg ccgcggcgct gcgcgccggt ggcaccgagg tcctgtcctt cccggaccct   8280
acggacctgg tggaggccgt cgaccggggc gagacccgg ccccgcgac cgtcctggtg   8340 gcctgccccg ccgccggccc cgatgggccg gagcatgtcc gcgaggccct gcacgggtcg   8400
ctcgcgctga tgcaggcctg gctggccgac gagcggttca ccgatgggcg cctggtgctc   8460
gtgacccgcg acgcggtcgc cgcccgttcc ggcgacggcc tgcggtccac gggacaggcc   8520
gccgtctggg gcctcggccg gtccgcgcag acggagagcc cgggccggtt cgtcctgctc   8580
gacctcgccg gggaagcccg gacggccggg gacgccaccg ccggggacgg cctgacgacc   8640
ggggacgcca ccgtcggcgg cacctctgga gacgccgccc tcggcagcgc cctcgcgacc   8700
gccctcggct cggcgagcc gcagctcgcc ctccgggacg gggcgctcct cgtacccgc   8760 ctggcgcggg ccgccgcgcc cgccgcggcc gacggcctcg ccgcggccga cggcctcgcc   8820
gctctgccgc tgcccgccgc tccggccctc tggcgtctgg agcccggtac ggacggcagc   8880
ctggagagcc tcacggcggc gcccggcgac gccgagaccc tcgccccgga gccgctcggc   8940
ccgggacagg tccgcatcgc gatcgggcc accggtctca acttccgcga cgtcctgatc   9000
gccctcggca tgtaccccga tccggcgctg atgggcaccg agggagccgg cgtggtcacc   9060
```

-continued

```
gcgaccggcc ccggcgtcac gcacctcgcc cccggcgacc gggtcatggg cctgctctcc    9120
ggcgcgtacg ccccggtcgt cgtggcggac gcgcggaccg tcgcgcggat gcccgagggg    9180
tggacgttcg cccagggcgc ctccgtgccg gtggtgttcc tgacgccgt ctacgccctg     9240 cgcgacctgg cggacgtcaa gcccggcgag cgcctcctgg tccactccgc cgccggtggc    9300
gtgggcatgg ccgccgtgca gctcgccgg cactggggcg tggaggtcca cggcacggcg     9360
agtcacggga agtgggacgc cctgcgcgcg ctcggcctgg acgacgcgca catcgcctcc    9420
tcccgcaccc tggacttcga gtccgcgttc cgtgccgctt ccggcggggc gggcatggac    9480
gtcgtactga actcgctcgc ccgcgagttc gtcgacgcct cgctgcgcct gctcgggccg    9540
ggcggccggt tcgtggagat ggggaagacc gacgtccgcg acgcggagcg ggtcgccgcc    9600 gaccacccg gtgtcggcta ccgcgccttc gacctgggcg aggccgggcc ggagcggatc     9660
ggcgagatgc tcgccgaggt catcgccctc ttcgaggacg gggtgctccg gcacctgccc    9720
gtcacgacct gggacgtgcg ccgggcccgc gacgccttcc ggcacgtcag ccaggcccgc    9780
cacacgggca aggtcgtcct cacgatgccg tcgggcctcg accggagggg tacggtcctg    9840
ctgaccggcg gcaccggtgc gctggggggc atcgtggccc ggcacgtggt gggcgagtgg    9900
ggcgtacgac gcctgctgct cgtgagccgg cgggcacgg acgccccggg cgccggcgag    9960
ctcgtgcacg agctggaggc cctggagcc gacgtctcgg tggccgcgtg cgacgtcgcc    10020
gaccgcgaag ccctcaccgc cgtactcgac tcgatccccg ccgaacaccc gctcaccgcg    10080
gtcgtccaca cggcaggcgt cctctccgac ggcaccctcc cctcgatgac agcggaggat    10140
gtggaacacg tactgcgtcc caaggtcgac gccgcgttcc tcctcgacga actcacctcg    10200
acgcccggct acgacctggc agcgttcgtc atgttctcct ccgccgccgc cgtcttcggt    10260
ggcgcggggc agggcgccta cgccgccgcc aacgccaccc tcgacgccct cgcctggcgc    10320
cgccggacag ccggactccc cgccctctcc ctcggctggg gcctctgggc cgagaccagc    10380
ggcatgaccg gcggactcag cgacaccgac cgctcgcggc tggcccgttc cggggcgacg    10440
cccatggaca gcgagctgac cctgtccctc ctggacgcgg ccatgcgccg cgacgacccg    10500
gcgctcgtcc cgatcgccct ggacgtcgcc gcgctccgcg cccagcagcg cgacggcatg    10560
ctggcgccgt tgctcagcgg gctcaccgc ggatgcgggg tcggcggcgc gccggtcaac     10620
cagcgcaggg cagccgccgg aggcgcgggc gaggcggaca cggacctcgg cgggcggctc    10680
gccgcgatga caccggacga ccgggtcgcg cacctgcggg acctcgtccg tacgcacgtg    10740
gcgaccgtcc tgggacacgg cacccgagc cgggtggacc tggagcgggc cttccgcgac     10800
accggtttcg actcgctcac cgccgtcgaa ctccgcaacc gtctcaacgc cgcgaccggg    10860
ctgcggctgc cggccacgct ggtcttcgac caccccaccc cggggagct cgccgggcac     10920 ctgctcgacg aactcgccac ggccgcgggc gggtcctggg cggaaggcac cgggtccgga    10980
gacacggcct cggcgaccga tcggcagacc acggcggccc tcgccgaact cgaccggctg    11040
gaaggcgtgc tcgcctccct cgcgcccgcc gccggcggcc gtccggagct cgccgcccgg    11100
ctcagggcgc tggccgcggc cctggggac gacggcgacg acgccaccga cctggacgag     11160
gcgtccgacg acgacctctt ctccttcatc gacaaggagc tgggcgactc cgacttctga    11220
```

<210> SEQ ID NO: 33
<211> LENGTH: 3739
<212> TYPE: PRT
<213> ORGANISM: Streptomyces venezuelae

<400> SEQUENCE: 33

-continued

```
Met Ser Thr Val Asn Glu Glu Lys Tyr Leu Asp Tyr Leu Arg Arg Ala
 1               5                  10                 15

Thr Ala Asp Leu His Glu Ala Arg Gly Arg Leu Arg Glu Leu Glu Ala
            20                  25                 30

Lys Ala Gly Glu Pro Val Ala Ile Val Gly Met Ala Cys Arg Leu Pro
            35                  40                 45

Gly Gly Val Ala Ser Pro Glu Asp Leu Trp Arg Leu Val Ala Gly Gly
    50                  55                  60

Glu Asp Ala Ile Ser Glu Phe Pro Gln Asp Arg Gly Trp Asp Val Glu
65                  70                  75                  80

Gly Leu Tyr Asp Pro Asn Pro Glu Ala Thr Gly Lys Ser Tyr Ala Arg
                85                  90                 95

Glu Ala Gly Phe Leu Tyr Glu Ala Gly Glu Phe Asp Ala Asp Phe Phe
                100                 105                110

Gly Ile Ser Pro Arg Glu Ala Leu Ala Met Asp Pro Gln Gln Arg Leu
            115                 120                 125

Leu Leu Glu Ala Ser Trp Glu Ala Phe Glu His Ala Gly Ile Pro Ala
    130                 135                 140

Ala Thr Ala Arg Gly Thr Ser Val Gly Val Phe Thr Gly Val Met Tyr
145                 150                 155                 160

His Asp Tyr Ala Thr Arg Leu Thr Asp Val Pro Glu Gly Ile Glu Gly
                165                 170                 175

Tyr Leu Gly Thr Gly Asn Ser Gly Ser Val Ala Ser Gly Arg Val Ala
            180                 185                 190

Tyr Thr Leu Gly Leu Glu Gly Pro Ala Val Thr Val Asp Thr Ala Cys
        195                 200                 205

Ser Ser Ser Leu Val Ala Leu His Leu Ala Val Gln Ala Leu Arg Lys
210                 215                 220

Gly Glu Val Asp Met Ala Leu Ala Gly Gly Val Thr Val Met Ser Thr
225                 230                 235                 240

Pro Ser Thr Phe Val Glu Phe Ser Arg Gln Arg Gly Leu Ala Pro Asp
                245                 250                 255

Gly Arg Ser Lys Ser Phe Ser Ser Thr Ala Asp Gly Thr Ser Trp Ser
            260                 265                 270

Glu Gly Val Gly Val Leu Leu Val Glu Arg Leu Ser Asp Ala Arg Arg
        275                 280                 285

Lys Gly His Arg Ile Leu Ala Val Val Arg Gly Thr Ala Val Asn Gln
        290                 295                 300

Asp Gly Ala Ser Ser Gly Leu Thr Ala Pro Asn Gly Pro Ser Gln Gln
305                 310                 315                 320

Arg Val Ile Arg Arg Ala Leu Ala Asp Ala Arg Leu Thr Thr Ser Asp
                325                 330                 335

Val Asp Val Val Glu Ala His Gly Thr Gly Thr Arg Leu Gly Asp Pro
                340                 345                 350

Ile Glu Ala Gln Ala Val Ile Ala Thr Tyr Gly Gln Gly Arg Asp Gly
            355                 360                 365

Glu Gln Pro Leu Arg Leu Gly Ser Leu Lys Ser Asn Ile Gly His Thr
    370                 375                 380

Gln Ala Ala Ala Gly Val Ser Gly Val Ile Lys Met Val Gln Ala Met
385                 390                 395                 400

Arg His Gly Val Leu Pro Lys Thr Leu His Val Glu Lys Pro Thr Asp
                405                 410                 415
```

```
Gln Val Asp Trp Ser Ala Gly Ala Val Glu Leu Leu Thr Glu Ala Met
            420                 425                 430

Asp Trp Pro Asp Lys Gly Asp Gly Gly Leu Arg Arg Ala Ala Val Ser
            435                 440                 445

Ser Phe Gly Val Ser Gly Thr Asn Ala His Val Val Leu Glu Glu Ala
            450                 455                 460

Pro Ala Ala Glu Glu Thr Pro Ala Ser Glu Ala Thr Pro Ala Val Glu
465                 470                 475                 480

Pro Ser Val Gly Ala Gly Leu Val Pro Trp Leu Val Ser Ala Lys Thr
            485                 490                 495

Pro Ala Ala Leu Asp Ala Gln Ile Gly Arg Leu Ala Ala Phe Ala Ser
            500                 505                 510

Gln Gly Arg Thr Asp Ala Ala Asp Pro Gly Ala Val Ala Arg Val Leu
            515                 520                 525

Ala Gly Gly Arg Ala Glu Phe Glu His Arg Ala Val Val Leu Gly Thr
            530                 535                 540

Gly Gln Asp Asp Phe Ala Gln Ala Leu Thr Ala Pro Glu Gly Leu Ile
545                 550                 555                 560

Arg Gly Thr Pro Ser Asp Val Gly Arg Val Ala Phe Val Phe Pro Gly
            565                 570                 575

Gln Gly Thr Gln Trp Ala Gly Met Gly Ala Glu Leu Leu Asp Val Ser
            580                 585                 590

Lys Glu Phe Ala Ala Ala Met Ala Glu Cys Glu Ser Ala Leu Ser Arg
            595                 600                 605

Tyr Val Asp Trp Ser Leu Glu Ala Val Val Arg Gln Ala Pro Gly Ala
            610                 615                 620

Pro Thr Leu Glu Arg Val Asp Val Val Gln Pro Val Thr Phe Ala Val
625                 630                 635                 640

Met Val Ser Leu Ala Lys Val Trp Gln His His Gly Val Thr Pro Gln
            645                 650                 655

Ala Val Val Gly His Ser Gln Gly Glu Ile Ala Ala Tyr Val Ala
            660                 665                 670

Gly Ala Leu Thr Leu Asp Asp Ala Ala Arg Val Val Thr Leu Arg Ser
            675                 680                 685

Lys Ser Ile Ala Ala His Leu Ala Gly Lys Gly Met Ile Ser Leu
            690                 695                 700

Ala Leu Ser Glu Glu Ala Thr Arg Gln Arg Ile Glu Asn Leu His Gly
705                 710                 715                 720

Leu Ser Ile Ala Ala Val Asn Gly Pro Thr Ala Thr Val Val Ser Gly
            725                 730                 735

Asp Pro Thr Gln Ile Gln Glu Leu Ala Gln Ala Cys Glu Ala Asp Gly
            740                 745                 750

Val Arg Ala Arg Ile Ile Pro Val Asp Tyr Ala Ser His Ser Ala His
            755                 760                 765

Val Glu Thr Ile Glu Ser Glu Leu Ala Glu Val Leu Ala Gly Leu Ser
            770                 775                 780

Pro Arg Thr Pro Glu Val Pro Phe Phe Ser Thr Leu Glu Gly Ala Trp
785                 790                 795                 800

Ile Thr Glu Pro Val Leu Asp Gly Thr Tyr Trp Tyr Arg Asn Leu Arg
            805                 810                 815

His Arg Val Gly Phe Ala Pro Ala Val Glu Thr Leu Ala Thr Asp Glu
            820                 825                 830
```

-continued

```
Gly Phe Thr His Phe Ile Glu Val Ser Ala His Pro Val Leu Thr Met
            835                 840                 845

Thr Leu Pro Glu Thr Val Thr Gly Leu Gly Thr Leu Arg Arg Glu Gln
    850                 855                 860

Gly Gly Gln Glu Arg Leu Val Thr Ser Leu Ala Glu Ala Trp Thr Asn
865                 870                 875                 880

Gly Leu Thr Ile Asp Trp Ala Pro Val Leu Pro Thr Ala Thr Gly His
                885                 890                 895

His Pro Glu Leu Pro Thr Tyr Ala Phe Gln Arg Arg His Tyr Trp Leu
            900                 905                 910

His Asp Ser Pro Ala Val Gln Gly Ser Val Gln Asp Ser Trp Arg Tyr
            915                 920                 925

Arg Ile Asp Trp Lys Arg Leu Ala Val Ala Asp Ala Ser Glu Arg Ala
    930                 935                 940

Gly Leu Ser Gly Arg Trp Leu Val Val Pro Glu Asp Arg Ser Ala
945                 950                 955                 960

Glu Ala Ala Pro Val Leu Ala Ala Leu Ser Gly Ala Gly Ala Asp Pro
                965                 970                 975

Val Gln Leu Asp Val Ser Pro Leu Gly Asp Arg Gln Arg Leu Ala Ala
            980                 985                 990

Thr Leu Gly Glu Ala Leu Ala Ala Gly Gly Ala Val Asp Gly Val
            995                 1000                1005

Leu Ser Leu Leu Ala Trp Asp Glu Ser Ala His Pro Gly His Pro Ala
    1010                1015                1020

Pro Phe Thr Arg Gly Thr Gly Ala Thr Leu Thr Leu Val Gln Ala Leu
1025                1030                1035                1040

Glu Asp Ala Gly Val Ala Ala Pro Leu Trp Cys Val Thr His Gly Ala
                1045                1050                1055

Val Ser Val Gly Arg Ala Asp His Val Thr Ser Pro Ala Gln Ala Met
            1060                1065                1070

Val Trp Gly Met Gly Arg Val Ala Ala Leu Glu His Pro Glu Arg Trp
        1075                1080                1085

Gly Gly Leu Ile Asp Leu Pro Ser Asp Ala Asp Arg Ala Ala Leu Asp
    1090                1095                1100

Arg Met Thr Thr Val Leu Ala Gly Gly Thr Gly Glu Asp Gln Val Ala
1105                1110                1115                1120

Val Arg Ala Ser Gly Leu Leu Ala Arg Arg Leu Val Arg Ala Ser Leu
            1125                1130                1135

Pro Ala His Gly Thr Ala Ser Pro Trp Trp Gln Ala Asp Gly Thr Val
                1140                1145                1150

Leu Val Thr Gly Ala Glu Glu Pro Ala Ala Glu Ala Ala Arg Arg
            1155                1160                1165

Leu Ala Arg Asp Gly Ala Gly His Leu Leu His Thr Thr Pro Ser
    1170                1175                1180

Gly Ser Glu Gly Ala Glu Gly Thr Ser Gly Ala Ala Glu Asp Ser Gly
1185                1190                1195                1200

Leu Ala Gly Leu Val Ala Glu Leu Ala Asp Leu Gly Ala Thr Ala Thr
                1205                1210                1215

Val Val Thr Cys Asp Leu Thr Asp Ala Glu Ala Ala Arg Leu Leu
            1220                1225                1230

Ala Gly Val Ser Asp Ala His Pro Leu Ser Ala Val Leu His Leu Pro
            1235                1240                1245
```

```
                                -continued

Pro Thr Val Asp Ser Glu Pro Leu Ala Ala Thr Asp Ala Asp Ala Leu
   1250                1255                1260

Ala Arg Val Val Thr Ala Lys Ala Thr Ala Ala Leu His Leu Asp Arg
1265                1270                1275                1280

Leu Leu Arg Glu Ala Ala Ala Gly Gly Arg Pro Val Leu Val
                    1285                1290                1295

Leu Phe Ser Ser Val Ala Ala Ile Trp Gly Ala Gly Gln Gly Ala
            1300                1305                1310

Tyr Ala Ala Gly Thr Ala Phe Leu Asp Ala Leu Ala Gly Gln His Arg
        1315                1320                1325

Ala Asp Gly Pro Thr Val Thr Ser Val Ala Trp Ser Pro Trp Glu Gly
        1330                1335                1340

Ser Arg Val Thr Glu Gly Ala Thr Gly Glu Arg Leu Arg Arg Leu Gly
1345                1350                1355                1360

Leu Arg Pro Leu Ala Pro Ala Thr Ala Leu Thr Ala Leu Asp Thr Ala
                1365                1370                1375

Leu Gly His Gly Asp Thr Ala Val Thr Ile Ala Asp Val Asp Trp Ser
            1380                1385                1390

Ser Phe Ala Pro Gly Phe Thr Thr Ala Arg Pro Gly Thr Leu Leu Ala
            1395                1400                1405

Asp Leu Pro Glu Ala Arg Arg Ala Leu Asp Gln Gln Ser Thr Thr
        1410                1415                1420

Ala Ala Asp Asp Thr Val Leu Ser Arg Glu Leu Gly Ala Leu Thr Gly
1425                1430                1435                1440

Ala Glu Gln Gln Arg Arg Met Gln Glu Leu Val Arg Glu His Leu Ala
                1445                1450                1455

Val Val Leu Asn His Pro Ser Pro Glu Ala Val Asp Thr Gly Arg Ala
                1460                1465                1470

Phe Arg Asp Leu Gly Phe Asp Ser Leu Thr Ala Val Glu Leu Arg Asn
        1475                1480                1485

Arg Leu Lys Asn Ala Thr Gly Leu Ala Leu Pro Ala Thr Leu Val Phe
    1490                1495                1500

Asp Tyr Pro Thr Pro Arg Thr Leu Ala Glu Phe Leu Leu Ala Glu Ile
1505                1510                1515                1520

Leu Gly Glu Gln Ala Gly Ala Gly Glu Gln Leu Pro Val Asp Gly Gly
                1525                1530                1535

Val Asp Asp Glu Pro Val Ala Ile Val Gly Met Ala Cys Arg Leu Pro
                1540                1545                1550

Gly Gly Val Ala Ser Pro Glu Asp Leu Trp Arg Leu Val Ala Gly Gly
            1555                1560                1565

Glu Asp Ala Ile Ser Gly Phe Pro Gln Asp Arg Gly Trp Asp Val Glu
    1570                1575                1580

Gly Leu Tyr Asp Pro Asp Pro Asp Ala Ser Gly Arg Thr Tyr Cys Arg
1585                1590                1595                1600

Ala Gly Gly Phe Leu Asp Glu Ala Gly Glu Phe Asp Ala Asp Phe Phe
                1605                1610                1615

Gly Ile Ser Pro Arg Glu Ala Leu Ala Met Asp Pro Gln Gln Arg Leu
            1620                1625                1630

Leu Leu Glu Thr Ser Trp Glu Ala Val Glu Asp Ala Gly Ile Asp Pro
        1635                1640                1645

Thr Ser Leu Gln Gly Gln Gln Val Gly Val Phe Ala Gly Thr Asn Gly
    1650                1655                1660
```

```
Pro His Tyr Glu Pro Leu Leu Arg Asn Thr Ala Glu Asp Leu Glu Gly
1665                1670                1675                1680

Tyr Val Gly Thr Gly Asn Ala Ala Ser Ile Met Ser Gly Arg Val Ser
                1685                1690                1695

Tyr Thr Leu Gly Leu Glu Gly Pro Ala Val Thr Val Asp Thr Ala Cys
            1700                1705                1710

Ser Ser Ser Leu Val Ala Leu His Leu Ala Val Gln Ala Leu Arg Lys
        1715                1720                1725

Gly Glu Cys Gly Leu Ala Leu Ala Gly Val Thr Val Met Ser Thr
    1730                1735                1740

Pro Thr Thr Phe Val Glu Phe Ser Arg Gln Arg Gly Leu Ala Glu Asp
1745                1750                1755                1760

Gly Arg Ser Lys Ala Phe Ala Ala Ser Ala Asp Gly Phe Gly Pro Ala
                1765                1770                1775

Glu Gly Val Gly Met Leu Leu Val Glu Arg Leu Ser Asp Ala Arg Arg
            1780                1785                1790

Asn Gly His Arg Val Leu Ala Val Val Arg Gly Ser Ala Val Asn Gln
        1795                1800                1805

Asp Gly Ala Ser Asn Gly Leu Thr Ala Pro Asn Gly Pro Ser Gln Gln
    1810                1815                1820

Arg Val Ile Arg Arg Ala Leu Ala Asp Ala Arg Leu Thr Thr Ala Asp
1825                1830                1835                1840

Val Asp Val Val Glu Ala His Gly Thr Gly Thr Arg Leu Gly Asp Pro
                1845                1850                1855

Ile Glu Ala Gln Ala Leu Ile Ala Thr Tyr Gly Gln Gly Arg Asp Thr
            1860                1865                1870

Glu Gln Pro Leu Arg Leu Gly Ser Leu Lys Ser Asn Ile Gly His Thr
        1875                1880                1885

Gln Ala Ala Ala Gly Val Ser Gly Ile Ile Lys Met Val Gln Ala Met
    1890                1895                1900

Arg His Gly Val Leu Pro Lys Thr Leu His Val Asp Arg Pro Ser Asp
1905                1910                1915                1920

Gln Ile Asp Trp Ser Ala Gly Thr Val Glu Leu Leu Thr Glu Ala Met
                1925                1930                1935

Asp Trp Pro Arg Lys Gln Glu Gly Gly Leu Arg Arg Ala Ala Val Ser
            1940                1945                1950

Ser Phe Gly Ile Ser Gly Thr Asn Ala His Ile Val Leu Glu Glu Ala
        1955                1960                1965

Pro Val Asp Glu Asp Ala Pro Ala Asp Glu Pro Ser Val Gly Gly Val
    1970                1975                1980

Val Pro Trp Leu Val Ser Ala Lys Thr Pro Ala Ala Leu Asp Ala Gln
1985                1990                1995                2000

Ile Gly Arg Leu Ala Ala Phe Ala Ser Gln Gly Arg Thr Asp Ala Ala
                2005                2010                2015

Asp Pro Gly Ala Val Ala Arg Val Leu Ala Gly Gly Arg Ala Gln Phe
            2020                2025                2030

Glu His Arg Ala Val Ala Leu Gly Thr Gly Gln Asp Asp Leu Ala Ala
        2035                2040                2045

Ala Leu Ala Ala Pro Glu Gly Leu Val Arg Gly Val Ala Ser Gly Val
    2050                2055                2060

Gly Arg Val Ala Phe Val Phe Pro Gly Gln Gly Thr Gln Trp Ala Gly
2065                2070                2075                2080
```

-continued

```
Met Gly Ala Glu Leu Leu Asp Val Ser Lys Glu Phe Ala Ala Met
                2085                2090                2095

Ala Glu Cys Glu Ala Ala Leu Ala Pro Tyr Val Asp Trp Ser Leu Glu
            2100                2105                2110

Ala Val Val Arg Gln Ala Pro Gly Ala Pro Thr Leu Glu Arg Val Asp
            2115                2120                2125

Val Val Gln Pro Val Thr Phe Ala Val Met Val Ser Leu Ala Lys Val
        2130                2135                2140

Trp Gln His His Gly Val Thr Pro Gln Ala Val Val Gly His Ser Gln
2145            2150                2155                2160

Gly Glu Ile Ala Ala Ala Tyr Val Ala Gly Ala Leu Ser Leu Asp Asp
                2165                2170                2175

Ala Ala Arg Val Val Thr Leu Arg Ser Lys Ser Ile Gly Ala His Leu
            2180                2185                2190

Ala Gly Gln Gly Gly Met Leu Ser Leu Ala Leu Ser Glu Ala Ala Val
            2195                2200                2205

Val Glu Arg Leu Ala Gly Phe Asp Gly Leu Ser Val Ala Ala Val Asn
        2210                2215                2220

Gly Pro Thr Ala Thr Val Val Ser Gly Asp Pro Thr Gln Ile Gln Glu
2225            2230                2235                2240

Leu Ala Gln Ala Cys Glu Ala Asp Gly Val Arg Ala Arg Ile Ile Pro
            2245                2250                2255

Val Asp Tyr Ala Ser His Ser Ala His Val Glu Thr Ile Glu Ser Glu
            2260                2265                2270

Leu Ala Asp Val Leu Ala Gly Leu Ser Pro Gln Thr Pro Gln Val Pro
            2275                2280                2285

Phe Phe Ser Thr Leu Glu Gly Ala Trp Ile Thr Glu Pro Ala Leu Asp
        2290                2295                2300

Gly Gly Tyr Trp Tyr Arg Asn Leu Arg His Arg Val Gly Phe Ala Pro
2305            2310                2315                2320

Ala Val Glu Thr Leu Ala Thr Asp Glu Gly Phe Thr His Phe Val Glu
                2325                2330                2335

Val Ser Ala His Pro Val Leu Thr Met Ala Leu Pro Glu Thr Val Thr
            2340                2345                2350

Gly Leu Gly Thr Leu Arg Arg Asp Asn Gly Gly Gln His Arg Leu Thr
        2355                2360                2365

Thr Ser Leu Ala Glu Ala Trp Ala Asn Gly Leu Thr Val Asp Trp Ala
        2370                2375                2380

Ser Leu Leu Pro Thr Thr Thr His Pro Asp Leu Pro Thr Tyr Ala
2385            2390                2395                2400

Phe Gln Thr Glu Arg Tyr Trp Pro Gln Pro Asp Leu Ser Ala Ala Gly
            2405                2410                2415

Asp Ile Thr Ser Ala Gly Leu Gly Ala Ala Glu His Pro Leu Leu Gly
            2420                2425                2430

Ala Ala Val Ala Leu Ala Asp Ser Asp Gly Cys Leu Leu Thr Gly Ser
        2435                2440                2445

Leu Ser Leu Arg Thr His Pro Trp Leu Ala Asp His Ala Val Ala Gly
        2450                2455                2460

Thr Val Leu Leu Pro Gly Thr Ala Phe Val Glu Leu Ala Phe Arg Ala
2465            2470                2475                2480

Gly Asp Gln Val Gly Cys Asp Leu Val Glu Glu Leu Thr Leu Asp Ala
                2485                2490                2495
```

-continued

```
Pro Leu Val Leu Pro Arg Arg Gly Ala Val Arg Val Gln Leu Ser Val
        2500                2505                2510

Gly Ala Ser Asp Glu Ser Gly Arg Arg Thr Phe Gly Leu Tyr Ala His
    2515                2520                2525

Pro Glu Asp Ala Pro Gly Glu Ala Glu Trp Thr Arg His Ala Thr Gly
    2530                2535                2540

Val Leu Ala Ala Arg Ala Asp Arg Thr Ala Pro Val Ala Asp Pro Glu
2545                2550                2555                2560

Ala Trp Pro Pro Gly Ala Glu Pro Val Asp Val Asp Gly Leu Tyr
            2565                2570                2575

Glu Arg Phe Ala Ala Asn Gly Tyr Gly Tyr Gly Pro Leu Phe Gln Gly
    2580                2585                2590

Val Arg Gly Val Trp Arg Arg Gly Asp Glu Val Phe Ala Asp Val Ala
    2595                2600                2605

Leu Pro Ala Glu Val Ala Gly Ala Glu Gly Ala Arg Phe Gly Leu His
    2610                2615                2620

Pro Ala Leu Leu Asp Ala Ala Val Gln Ala Ala Gly Ala Gly Arg Gly
2625                2630                2635                2640

Val Arg Arg Gly His Ala Ala Ala Val Arg Leu Glu Arg Asp Leu Leu
            2645                2650                2655

Tyr Ala Val Gly Ala Thr Ala Leu Arg Val Arg Leu Ala Pro Ala Gly
            2660                2665                2670

Pro Asp Thr Val Ser Val Ser Ala Ala Asp Ser Ser Gly Gln Pro Val
            2675                2680                2685

Phe Ala Ala Asp Ser Leu Thr Val Leu Pro Val Asp Pro Ala Gln Leu
    2690                2695                2700

Ala Ala Phe Ser Asp Pro Thr Leu Asp Ala Leu His Leu Leu Glu Trp
2705                2710                2715                2720

Thr Ala Trp Asp Gly Ala Ala Gln Ala Leu Pro Gly Ala Val Val Leu
            2725                2730                2735

Gly Gly Asp Ala Asp Gly Leu Ala Ala Ala Leu Arg Ala Gly Gly Thr
            2740                2745                2750

Glu Val Leu Ser Phe Pro Asp Leu Thr Asp Leu Val Glu Ala Val Asp
    2755                2760                2765

Arg Gly Glu Thr Pro Ala Pro Ala Thr Val Leu Val Ala Cys Pro Ala
    2770                2775                2780

Ala Gly Pro Asp Gly Pro Glu His Val Arg Glu Ala Leu His Gly Ser
2785                2790                2795                2800

Leu Ala Leu Met Gln Ala Trp Leu Ala Asp Glu Arg Phe Thr Asp Gly
            2805                2810                2815

Arg Leu Val Leu Val Thr Arg Asp Ala Val Ala Ala Arg Ser Gly Asp
            2820                2825                2830

Gly Leu Arg Ser Thr Gly Gln Ala Ala Val Trp Gly Leu Gly Arg Ser
            2835                2840                2845

Ala Gln Thr Glu Ser Pro Gly Arg Phe Val Leu Leu Asp Leu Ala Gly
    2850                2855                2860

Glu Ala Arg Thr Ala Gly Asp Ala Thr Ala Gly Asp Gly Leu Thr Thr
2865                2870                2875                2880

Gly Asp Ala Thr Val Gly Gly Thr Ser Gly Asp Ala Ala Leu Gly Ser
            2885                2890                2895

Ala Leu Ala Thr Ala Leu Gly Ser Gly Glu Pro Gln Leu Ala Leu Arg
            2900                2905                2910
```

```
Asp Gly Ala Leu Leu Val Pro Arg Leu Ala Arg Ala Ala Pro Ala
        2915                2920                2925
Ala Ala Asp Gly Leu Ala Ala Asp Gly Leu Ala Ala Leu Pro Leu
        2930                2935                2940
Pro Ala Ala Pro Ala Leu Trp Arg Leu Glu Pro Gly Thr Asp Gly Ser
2945                2950                2955                2960
Leu Glu Ser Leu Thr Ala Ala Pro Gly Asp Ala Glu Thr Leu Ala Pro
        2965                2970                2975
Glu Pro Leu Gly Pro Gly Gln Val Arg Ile Ala Ile Arg Ala Thr Gly
        2980                2985                2990
Leu Asn Phe Arg Asp Val Leu Ile Ala Leu Gly Met Tyr Pro Asp Pro
        2995                3000                3005
Ala Leu Met Gly Thr Glu Gly Ala Gly Val Val Thr Ala Thr Gly Pro
        3010                3015                3020
Gly Val Thr His Leu Ala Pro Gly Asp Arg Val Met Gly Leu Leu Ser
3025                3030                3035                3040
Gly Ala Tyr Ala Pro Val Val Ala Asp Ala Arg Thr Val Ala Arg
        3045                3050                3055
Met Pro Glu Gly Trp Thr Phe Ala Gln Gly Ala Ser Val Pro Val Val
        3060                3065                3070
Phe Leu Thr Ala Val Tyr Ala Leu Arg Asp Leu Ala Asp Val Lys Pro
        3075                3080                3085
Gly Glu Arg Leu Leu Val His Ser Ala Gly Gly Val Gly Met Ala
        3090                3095                3100
Ala Val Gln Leu Ala Arg His Trp Gly Val Glu Val His Gly Thr Ala
3105                3110                3115                3120
Ser His Gly Lys Trp Asp Ala Leu Arg Ala Leu Gly Leu Asp Asp Ala
        3125                3130                3135
His Ile Ala Ser Ser Arg Thr Leu Asp Phe Glu Ser Ala Phe Arg Ala
        3140                3145                3150
Ala Ser Gly Gly Ala Gly Met Asp Val Val Leu Asn Ser Leu Ala Arg
        3155                3160                3165
Glu Phe Val Asp Ala Ser Leu Arg Leu Leu Gly Pro Gly Gly Arg Phe
        3170                3175                3180
Val Glu Met Gly Lys Thr Asp Val Arg Asp Ala Glu Arg Val Ala Ala
3185                3190                3195                3200
Asp His Pro Gly Val Gly Tyr Arg Ala Phe Asp Leu Gly Glu Ala Gly
        3205                3210                3215
Pro Glu Arg Ile Gly Glu Met Leu Ala Glu Val Ile Ala Leu Phe Glu
        3220                3225                3230
Asp Gly Val Leu Arg His Leu Pro Val Thr Thr Trp Asp Val Arg Arg
        3235                3240                3245
Ala Arg Asp Ala Phe Arg His Val Ser Gln Ala Arg His Thr Gly Lys
        3250                3255                3260
Val Val Leu Thr Met Pro Ser Gly Leu Asp Pro Glu Gly Thr Val Leu
3265                3270                3275                3280
Leu Thr Gly Gly Thr Gly Ala Leu Gly Gly Ile Val Ala Arg His Val
        3285                3290                3295
Val Gly Glu Trp Gly Val Arg Arg Leu Leu Leu Val Ser Arg Arg Gly
        3300                3305                3310
Thr Asp Ala Pro Gly Ala Gly Glu Leu Val His Glu Leu Glu Ala Leu
        3315                3320                3325
```

-continued

```
Gly Ala Asp Val Ser Val Ala Ala Cys Asp Val Ala Asp Arg Glu Ala
    3330                3335                3340

Leu Thr Ala Val Leu Asp Ser Ile Pro Ala Glu His Pro Leu Thr Ala
3345                3350                3355                3360

Val Val His Thr Ala Gly Val Leu Ser Asp Gly Thr Leu Pro Ser Met
                3365                3370                3375

Thr Ala Glu Asp Val Glu His Val Leu Arg Pro Lys Val Asp Ala Ala
            3380                3385                3390

Phe Leu Leu Asp Glu Leu Thr Ser Thr Pro Gly Tyr Asp Leu Ala Ala
        3395                3400                3405

Phe Val Met Phe Ser Ser Ala Ala Ala Val Phe Gly Gly Ala Gly Gln
    3410                3415                3420

Gly Ala Tyr Ala Ala Ala Asn Ala Thr Leu Asp Ala Leu Ala Trp Arg
3425                3430                3435                3440

Arg Arg Thr Ala Gly Leu Pro Ala Leu Ser Leu Gly Trp Gly Leu Trp
                3445                3450                3455

Ala Glu Thr Ser Gly Met Thr Gly Gly Leu Ser Asp Thr Asp Arg Ser
                3460                3465                3470

Arg Leu Ala Arg Ser Gly Ala Thr Pro Met Asp Ser Glu Leu Thr Leu
        3475                3480                3485

Ser Leu Leu Asp Ala Ala Met Arg Arg Asp Asp Pro Ala Leu Val Pro
    3490                3495                3500

Ile Ala Leu Asp Val Ala Ala Leu Arg Ala Gln Gln Arg Asp Gly Met
3505                3510                3515                3520

Leu Ala Pro Leu Leu Ser Gly Leu Thr Arg Gly Ser Arg Val Gly Gly
                3525                3530                3535

Ala Pro Val Asn Gln Arg Arg Ala Ala Gly Gly Ala Gly Glu Ala
                3540                3545                3550

Asp Thr Asp Leu Gly Gly Arg Leu Ala Ala Met Thr Pro Asp Arg
        3555                3560                3565

Val Ala His Leu Arg Asp Leu Val Arg Thr His Val Ala Thr Val Leu
    3570                3575                3580

Gly His Gly Thr Pro Ser Arg Val Asp Leu Glu Arg Ala Phe Arg Asp
3585                3590                3595                3600

Thr Gly Phe Asp Ser Leu Thr Ala Val Glu Leu Arg Asn Arg Leu Asn
            3605                3610                3615

Ala Ala Thr Gly Leu Arg Leu Pro Ala Thr Leu Val Phe Asp His Pro
        3620                3625                3630

Thr Pro Gly Glu Leu Ala Gly His Leu Leu Asp Glu Leu Ala Thr Ala
    3635                3640                3645

Ala Gly Gly Ser Trp Ala Glu Gly Thr Gly Ser Gly Asp Thr Ala Ser
    3650                3655                3660

Ala Thr Asp Arg Gln Thr Thr Ala Ala Leu Ala Glu Leu Asp Arg Leu
3665                3670                3675                3680

Glu Gly Val Leu Ala Ser Leu Ala Pro Ala Ala Gly Gly Arg Pro Glu
            3685                3690                3695

Leu Ala Ala Arg Leu Arg Ala Leu Ala Ala Ala Leu Gly Asp Asp Gly
                3700                3705                3710

Asp Asp Ala Thr Asp Leu Asp Glu Ala Ser Asp Asp Leu Phe Ser
            3715                3720                3725

Phe Ile Asp Lys Glu Leu Gly Asp Ser Asp Phe
    3730                3735
```

-continued

<210> SEQ ID NO: 34
<211> LENGTH: 4689
<212> TYPE: DNA
<213> ORGANISM: Streptomyces venezuelae

<400> SEQUENCE: 34

| | | | | | |
|---|---|---|---|---|---|
| atggcgaaca | acgaagacaa | gctccgcgac | tacctcaagc | gcgtcaccgc | cgagctgcag | 60 |
| cagaacacca | ggcgtctgcg | cgagatcgag | ggacgcacgc | acgagccggt | ggcgatcgtg | 120 |
| ggcatggcct | ccgcctgcc | gggcggtgtc | gcctcgcccg | aggacctgtg | gcagctggtg | 180 |
| gccggggacg | gggacgcgat | ctcggagttc | cgcaggacc | gcggctggga | cgtggagggg | 240 |
| ctgtacgacc | ccgacccgga | cgcgtccggc | aggacgtact | gccggtccgg | cggattcctg | 300 |
| cacgacgccg | gcgagttcga | cgccgacttc | ttcgggatct | cgccgcgcga | ggccctcgcc | 360 |
| atggacccgc | agcagcgact | gtccctcacc | accgcgtggg | aggcgatcga | gagcgcgggc | 420 |
| atcgacccga | cggccctgaa | gggcagcggc | ctcgcgtct | tcgtcggcgg | ctggcacacc | 480 |
| ggctacacct | cggggcagac | caccgccgtg | cagtcgcccg | agctggaggg | ccacctggtc | 540 |
| agcggcgcg | cgctgggctt | cctgtccggc | cgtatcgcgt | acgtcctcgg | tacgacgga | 600 |
| ccggccctga | ccgtggacac | ggcctgctcg | tcctcgctgg | tcgccctgca | cctcgccgtg | 660 |
| caggccctcc | gcaagggcga | gtgcgacatg | gccctcgccg | tggtgtcac | ggtcatgccc | 720 |
| aacgcggacc | tgttcgtgca | gttcagccgg | cagcgcgggc | tggccgcgga | cggccggtcg | 780 |
| aaggcgttcg | ccacctcggc | ggacggcttc | ggccccgcgg | agggcgccgg | agtcctgctg | 840 |
| gtggagcgcc | tgtcggacgc | ccgccgcaac | ggacaccgga | tcctcgcggt | cgtccgcggc | 900 |
| agcgcggtca | accaggacgg | cgccagcaac | ggcctcacgg | ctccgcacgg | gccctcccag | 960 |
| cagcgcgtca | tccgacgggc | cctggcggac | gcccggctcg | cgccgggtga | cgtggacgtc | 1020 |
| gtcgaggcgc | acggcacggg | cacgcggctc | ggcgacccga | tcgaggcgca | ggccctcatc | 1080 |
| gccacctacg | gccaggagaa | gagcagcgaa | cagccgctga | ggctgggcgc | gttgaagtcg | 1140 |
| aacatcgggc | acacgcaggc | cgcggccggt | gtcgcaggtg | tcatcaagat | ggtccaggcg | 1200 |
| atgcgccacg | gactgctgcc | gaagacgctg | cacgtcgacg | agccctcgga | ccagatcgac | 1260 |
| tggtcgcgg | gcacggtgga | actcctcacc | gaggccgtcg | actggccgga | gaagcaggac | 1320 |
| ggcgggctgc | gccgcgcggc | tgtctcctcc | ttcggcatca | gcgggacgaa | cgcgcacgtc | 1380 |
| gtcctgagg | aggccccggc | ggtcgaggac | tccccggccg | tcgagccgcc | ggccggtggc | 1440 |
| ggtgtggtgc | cgtggccggt | gtccgcgaag | actccggccg | cgctggacgc | ccagatcggg | 1500 |
| cagctcgccg | cgtacgcgga | cggtcgtacg | gacgtggatc | cggcggtggc | cgcccgcgcc | 1560 |
| ctggtcgaca | gccgtacggc | gatggagcac | cgcgcggtcg | cggtcggcga | cagccgggag | 1620 |
| gcactgcggg | acgccctgcg | gatgccggaa | ggactggtac | gcggcacgtc | ctcggacgtg | 1680 |
| ggccgggtgg | cgttcgtctt | ccccggccag | ggcacgcagt | gggccggcat | gggcgccgaa | 1740 |
| ctccttgaca | gctcaccgga | gttcgctgcc | tcgatggccg | aatgcgagac | cgcgctctcc | 1800 |
| cgctacgtcg | actggtctct | tgaagccgtc | gtccgacagg | aacccggcgc | acccacgctc | 1860 |
| gaccgcgtcg | acgtcgtcca | gcccgtgacc | ttcgctgtca | tggtctcgct | ggcgaaggtc | 1920 |
| tggcagcacc | acgcatcac | ccccaggcc | gtcgtcggcc | actcgcaggg | cgagatcgcc | 1980 |
| gccgcgtacg | tcgccggtgc | actcaccctc | gacgacgccg | cccgcgtcgt | caccctgcgc | 2040 |
| agcaagtcca | tcgccgccca | cctcgccggc | aagggcggca | tgatctccct | cgccctcgac | 2100 |
| gaggcggccg | tcctgaagcg | actgagcgac | ttcgacggac | tctccgtcgc | cgccgtcaac | 2160 |

-continued

```
ggccccaccg ccaccgtcgt ctccggcgac ccgacccaga tcgaggaact cgcccgcacc    2220
tgcgaggccg acggcgtccg tgcgcggatc atcccggtcg actacgcctc ccacagccgg    2280
caggtcgaga tcatcgagaa ggagctggcc gaggtcctcg ccggactcgc cccgcaggct    2340
ccgcacgtgc cgttcttctc caccctcgaa ggcacctgga tcaccgagcc ggtgctcgac    2400
ggcacctact ggtaccgcaa cctgcgccat cgcgtgggct cgcccccgc cgtggagacc    2460 ttggcggttg acggcttcac ccacttcatc gaggtcagcg cccacccgt cctcaccatg    2520 accctccccg agaccgtcac cggcctcggc accctccgcc gcgaacaggg aggccaggag    2580
cgtctggtca cctcactcgc cgaagcctgg gccaacggcc tcaccatcga ctgggcgccc    2640
atcctcccca ccgcaaccgg ccaccacccc gagctcccca cctacgcctt ccagaccgag    2700
cgcttctggc tgcagagctc cgcgcccacc agcgccgccg acgactggcg ttaccgcgtc    2760
gagtggaagc cgctgacggc ctccggccag gcggacctgt ccgggcggtg gatcgtcgcc    2820
gtcgggagcg agccagaagc cgagctgctg ggcgcgctga aggccgcggg agcggaggtc    2880
gacgtactgg aagccggggc ggacgacgac cgtgaggccc tcgccgcccg gctcaccgca    2940
ctgacgaccg gcgacggctt caccggcgtg gtctcgctcc tcgacgacct cgtgccacag    3000
gtcgcctggg tgcaggcact cggcgacgcc ggaatcaagg cgccctgtg gtccgtcacc    3060 cagggcgcgg tctccgtcgg acgtctcgac accccgccg accccgaccg gccatgctc    3120 tgggcctcg ccgcgtcgt cgcccttgag caccccgaac gctgggccgg cctcgtcgac    3180
ctccccgccc agcccgatgc cgccgccctc gcccacctcg tcaccgcact ctccggcgcc    3240
accggcgagg accagatcgc catccgcacc accggactcc acgcccgccg cctcgcccgc    3300
gcacccctcc acgacgtcg gcccaccgc gactggcagc cccacggcac cgtcctcatc    3360
accggcggca ccggagccct cggcagccac gccgcacgct ggatggccca ccacggagcc    3420
gaacacctcc tcctcgtcag ccgcagcggc gaacaagccc ccggagccac ccaactcacc    3480
gccgaactca ccgcatcggg cgcccgcgtc accatcgccg cctgcgacgt cgccgacccc    3540
cacgccatgc gcaccctcct cgacgccatc cccgccgaga cgccctcac cgccgtcgtc    3600 cacaccgccg gcgcaccggg cggcgatccg ctggacgtca ccggcccgga ggacatcgcc    3660
cgcatcctgg gcgcgaagac gagcggcgcc gaggtcctcg acgacctgct ccgcggcact    3720
ccgctggacg ccttcgtcct ctactcctcg aacgccgggg tctggggcag cggcagccag    3780
ggcgtctacg cggcggccaa cgcccacctc gacgcgctcg ccgcccggcg ccgcgcccgg    3840
ggcgagacgg cgacctcggt cgcctggggc ctctgggccg gcgacggcat gggccggggc    3900
gccgacgacg cgtactggca gcgtcgcggc atccgtccga tgagcccga ccgcgccctg    3960 gacgaactgg ccaaggccct gagccacgac gagaccttcg tcgccgtggc cgatgtcgac    4020
tgggagcggt tcgcgcccgc gttcacggtg tcccgtccca gccttctgct cgacggcgtc    4080
ccggaggccc ggcaggcgct cgccgcaccc gtcggtgccc cggctcccgg cgacgccgcc    4140
gtggcgccga ccgggcagtc gtcggcgctg gccgcgatca ccgcgctccc cgagcccgag    4200
cgccggccgg cgctcctcac cctcgtccgt acccacgcgg cggccgtact cggccattcc    4260
tcccccgacc gggtggcccc cggccgtgcc ttcaccgagc tcggcttcga ctcgctgacg    4320
gccgtgcagc tccgcaacca gctctccacg gtggtcggca caggctcccc cgccaccacg    4380
gtcttcgacc acccgacgcc cgccgcactc gccgcgcacc tccacgaggc gtacctcgca    4440
ccggccgagc cggcccgac ggactgggag gggcgggtgc gccgggccct ggccgaactg    4500
cccctcgacc ggctgcggga cgcgggggtc ctcgacaccg tcctgcgcct caccggcatc    4560
```

```
gagcccgagc cgggttccgg cggttcggac ggcggcgccg ccgaccctgg tgcggagccg   4620
gaggcgtcga tcgacgacct ggacgccgag gccctgatcc ggatggctct cggcccccgt   4680
aacacctga                                                           4689
```

<210> SEQ ID NO: 35
<211> LENGTH: 1562
<212> TYPE: PRT
<213> ORGANISM: Streptomyces venezuelae

<400> SEQUENCE: 35

```
Met Ala Asn Asn Glu Asp Lys Leu Arg Asp Tyr Leu Lys Arg Val Thr
  1               5                  10                  15

Ala Glu Leu Gln Gln Asn Thr Arg Arg Leu Arg Glu Ile Glu Gly Arg
             20                  25                  30

Thr His Glu Pro Val Ala Ile Val Gly Met Ala Cys Arg Leu Pro Gly
         35                  40                  45

Gly Val Ala Ser Pro Glu Asp Leu Trp Gln Leu Val Ala Gly Asp Gly
     50                  55                  60

Asp Ala Ile Ser Glu Phe Pro Gln Asp Arg Gly Trp Asp Val Glu Gly
 65                  70                  75                  80

Leu Tyr Asp Pro Asp Pro Asp Ala Ser Gly Arg Thr Tyr Cys Arg Ser
                 85                  90                  95

Gly Gly Phe Leu His Asp Ala Gly Glu Phe Asp Ala Asp Phe Phe Gly
            100                 105                 110

Ile Ser Pro Arg Glu Ala Leu Ala Met Asp Pro Gln Gln Arg Leu Ser
        115                 120                 125

Leu Thr Thr Ala Trp Glu Ala Ile Glu Ser Ala Gly Ile Asp Pro Thr
    130                 135                 140

Ala Leu Lys Gly Ser Gly Leu Gly Val Phe Val Gly Gly Trp His Thr
145                 150                 155                 160

Gly Tyr Thr Ser Gly Gln Thr Thr Ala Val Gln Ser Pro Glu Leu Glu
                165                 170                 175

Gly His Leu Val Ser Gly Ala Ala Leu Gly Phe Leu Ser Gly Arg Ile
            180                 185                 190

Ala Tyr Val Leu Gly Thr Asp Gly Pro Ala Leu Thr Val Asp Thr Ala
        195                 200                 205

Cys Ser Ser Ser Leu Val Ala Leu His Leu Ala Val Gln Ala Leu Arg
    210                 215                 220

Lys Gly Glu Cys Asp Met Ala Leu Ala Gly Gly Val Thr Val Met Pro
225                 230                 235                 240

Asn Ala Asp Leu Phe Val Gln Phe Ser Arg Gln Arg Gly Leu Ala Ala
                245                 250                 255

Asp Gly Arg Ser Lys Ala Phe Ala Thr Ser Ala Asp Gly Phe Gly Pro
            260                 265                 270

Ala Glu Gly Ala Gly Val Leu Leu Val Glu Arg Leu Ser Asp Ala Arg
        275                 280                 285

Arg Asn Gly His Arg Ile Leu Ala Val Val Arg Gly Ser Ala Val Asn
    290                 295                 300

Gln Asp Gly Ala Ser Asn Gly Leu Thr Ala Pro His Gly Pro Ser Gln
305                 310                 315                 320

Gln Arg Val Ile Arg Arg Ala Leu Ala Asp Ala Arg Leu Ala Pro Gly
                325                 330                 335
```

-continued

```
Asp Val Asp Val Val Glu Ala His Gly Thr Gly Thr Arg Leu Gly Asp
            340                 345                 350

Pro Ile Glu Ala Gln Ala Leu Ile Ala Thr Tyr Gly Gln Glu Lys Ser
            355                 360                 365

Ser Glu Gln Pro Leu Arg Leu Gly Ala Leu Lys Ser Asn Ile Gly His
            370                 375                 380

Thr Gln Ala Ala Ala Gly Val Ala Gly Val Ile Lys Met Val Gln Ala
385                 390                 395                 400

Met Arg His Gly Leu Leu Pro Lys Thr Leu His Val Asp Glu Pro Ser
                405                 410                 415

Asp Gln Ile Asp Trp Ser Ala Gly Thr Val Glu Leu Leu Thr Glu Ala
            420                 425                 430

Val Asp Trp Pro Glu Lys Gln Asp Gly Gly Leu Arg Arg Ala Ala Val
            435                 440                 445

Ser Ser Phe Gly Ile Ser Gly Thr Asn Ala His Val Val Leu Glu Glu
            450                 455                 460

Ala Pro Ala Val Glu Asp Ser Pro Ala Val Glu Pro Pro Ala Gly Gly
465                 470                 475                 480

Gly Val Val Pro Trp Pro Val Ser Ala Lys Thr Pro Ala Ala Leu Asp
                485                 490                 495

Ala Gln Ile Gly Gln Leu Ala Ala Tyr Ala Asp Gly Arg Thr Asp Val
            500                 505                 510

Asp Pro Ala Val Ala Ala Arg Ala Leu Val Asp Ser Arg Thr Ala Met
            515                 520                 525

Glu His Arg Ala Val Ala Val Gly Asp Ser Arg Glu Ala Leu Arg Asp
            530                 535                 540

Ala Leu Arg Met Pro Glu Gly Leu Val Arg Gly Thr Ser Ser Asp Val
545                 550                 555                 560

Gly Arg Val Ala Phe Val Phe Pro Gly Gln Gly Thr Gln Trp Ala Gly
                565                 570                 575

Met Gly Ala Glu Leu Leu Asp Ser Ser Pro Glu Phe Ala Ala Ser Met
            580                 585                 590

Ala Glu Cys Glu Thr Ala Leu Ser Arg Tyr Val Asp Trp Ser Leu Glu
            595                 600                 605

Ala Val Val Arg Gln Glu Pro Gly Ala Pro Thr Leu Asp Arg Val Asp
            610                 615                 620

Val Val Gln Pro Val Thr Phe Ala Val Met Val Ser Leu Ala Lys Val
625                 630                 635                 640

Trp Gln His His Gly Ile Thr Pro Gln Ala Val Val Gly His Ser Gln
                645                 650                 655

Gly Glu Ile Ala Ala Ala Tyr Val Ala Gly Ala Leu Thr Leu Asp Asp
            660                 665                 670

Ala Ala Arg Val Val Thr Leu Arg Ser Lys Ser Ile Ala Ala His Leu
            675                 680                 685

Ala Gly Lys Gly Gly Met Ile Ser Leu Ala Leu Asp Glu Ala Ala Val
            690                 695                 700

Leu Lys Arg Leu Ser Asp Phe Asp Gly Leu Ser Val Ala Ala Val Asn
705                 710                 715                 720

Gly Pro Thr Ala Thr Val Val Ser Gly Asp Pro Thr Gln Ile Glu Glu
                725                 730                 735

Leu Ala Arg Thr Cys Glu Ala Asp Gly Val Arg Ala Arg Ile Ile Pro
            740                 745                 750
```

-continued

```
Val Asp Tyr Ala Ser His Ser Arg Gln Val Glu Ile Ile Glu Lys Glu
        755                 760                 765
Leu Ala Glu Val Leu Ala Gly Leu Ala Pro Gln Ala Pro His Val Pro
        770                 775                 780
Phe Phe Ser Thr Leu Glu Gly Thr Trp Ile Thr Glu Pro Val Leu Asp
785                 790                 795                 800
Gly Thr Tyr Trp Tyr Arg Asn Leu Arg His Arg Val Gly Phe Ala Pro
                805                 810                 815
Ala Val Glu Thr Leu Ala Val Asp Gly Phe Thr His Phe Ile Glu Val
                820                 825                 830
Ser Ala His Pro Val Leu Thr Met Thr Leu Pro Glu Thr Val Thr Gly
                835                 840                 845
Leu Gly Thr Leu Arg Arg Glu Gln Gly Gly Gln Glu Arg Leu Val Thr
        850                 855                 860
Ser Leu Ala Glu Ala Trp Ala Asn Gly Leu Thr Ile Asp Trp Ala Pro
865                 870                 875                 880
Ile Leu Pro Thr Ala Thr Gly His His Pro Glu Leu Pro Thr Tyr Ala
                885                 890                 895
Phe Gln Thr Glu Arg Phe Trp Leu Gln Ser Ser Ala Pro Thr Ser Ala
                900                 905                 910
Ala Asp Asp Trp Arg Tyr Arg Val Glu Trp Lys Pro Leu Thr Ala Ser
        915                 920                 925
Gly Gln Ala Asp Leu Ser Gly Arg Trp Ile Val Ala Val Gly Ser Glu
        930                 935                 940
Pro Glu Ala Glu Leu Leu Gly Ala Leu Lys Ala Ala Gly Ala Glu Val
945                 950                 955                 960
Asp Val Leu Glu Ala Gly Ala Asp Asp Arg Glu Ala Leu Ala Ala
                965                 970                 975
Arg Leu Thr Ala Leu Thr Thr Gly Asp Gly Phe Thr Gly Val Val Ser
                980                 985                 990
Leu Leu Asp Asp Leu Val Pro Gln Val Ala Trp Val Gln Ala Leu Gly
        995                 1000                1005
Asp Ala Gly Ile Lys Ala Pro Leu Trp Ser Val Thr Gln Gly Ala Val
        1010                1015                1020
Ser Val Gly Arg Leu Asp Thr Pro Ala Asp Pro Asp Arg Ala Met Leu
1025                1030                1035                1040
Trp Gly Leu Gly Arg Val Val Ala Leu Glu His Pro Glu Arg Trp Ala
                1045                1050                1055
Gly Leu Val Asp Leu Pro Ala Gln Pro Asp Ala Ala Ala Leu Ala His
                1060                1065                1070
Leu Val Thr Ala Leu Ser Gly Ala Thr Gly Glu Asp Gln Ile Ala Ile
        1075                1080                1085
Arg Thr Thr Gly Leu His Ala Arg Arg Leu Ala Arg Ala Pro Leu His
        1090                1095                1100
Gly Arg Arg Pro Thr Arg Asp Trp Gln Pro His Gly Thr Val Leu Ile
1105                1110                1115                1120
Thr Gly Gly Thr Gly Ala Leu Gly Ser His Ala Ala Arg Trp Met Ala
                1125                1130                1135
His His Gly Ala Glu His Leu Leu Leu Val Ser Arg Ser Gly Glu Gln
                1140                1145                1150
Ala Pro Gly Ala Thr Gln Leu Thr Ala Glu Leu Thr Ala Ser Gly Ala
        1155                1160                1165
```

```
Arg Val Thr Ile Ala Ala Cys Asp Val Ala Asp Pro His Ala Met Arg
    1170                1175                1180

Thr Leu Leu Asp Ala Ile Pro Ala Glu Thr Pro Leu Thr Ala Val Val
1185                1190                1195                1200

His Thr Ala Gly Ala Pro Gly Gly Asp Pro Leu Asp Val Thr Gly Pro
                1205                1210                1215

Glu Asp Ile Ala Arg Ile Leu Gly Ala Lys Thr Ser Gly Ala Glu Val
            1220                1225                1230

Leu Asp Asp Leu Leu Arg Gly Thr Pro Leu Asp Ala Phe Val Leu Tyr
        1235                1240                1245

Ser Ser Asn Ala Gly Val Trp Gly Ser Gly Ser Gln Gly Val Tyr Ala
    1250                1255                1260

Ala Ala Asn Ala His Leu Asp Ala Leu Ala Ala Arg Arg Arg Ala Arg
1265                1270                1275                1280

Gly Glu Thr Ala Thr Ser Val Ala Trp Gly Leu Trp Ala Gly Asp Gly
                1285                1290                1295

Met Gly Arg Gly Ala Asp Asp Ala Tyr Trp Gln Arg Arg Gly Ile Arg
            1300                1305                1310

Pro Met Ser Pro Asp Arg Ala Leu Asp Glu Leu Ala Lys Ala Leu Ser
        1315                1320                1325

His Asp Glu Thr Phe Val Ala Val Ala Asp Val Asp Trp Glu Arg Phe
    1330                1335                1340

Ala Pro Ala Phe Thr Val Ser Arg Pro Ser Leu Leu Leu Asp Gly Val
1345                1350                1355                1360

Pro Glu Ala Arg Gln Ala Leu Ala Ala Pro Val Gly Ala Pro Ala Pro
                1365                1370                1375

Gly Asp Ala Ala Val Ala Pro Thr Gly Gln Ser Ser Ala Leu Ala Ala
            1380                1385                1390

Ile Thr Ala Leu Pro Glu Pro Glu Arg Arg Pro Ala Leu Leu Thr Leu
        1395                1400                1405

Val Arg Thr His Ala Ala Val Leu Gly His Ser Ser Pro Asp Arg
    1410                1415                1420

Val Ala Pro Gly Arg Ala Phe Thr Glu Leu Gly Phe Asp Ser Leu Thr
1425                1430                1435                1440

Ala Val Gln Leu Arg Asn Gln Leu Ser Thr Val Val Gly Asn Arg Leu
                1445                1450                1455

Pro Ala Thr Thr Val Phe Asp His Pro Thr Pro Ala Ala Leu Ala Ala
            1460                1465                1470

His Leu His Glu Ala Tyr Leu Ala Pro Ala Glu Pro Ala Pro Thr Asp
        1475                1480                1485

Trp Glu Gly Arg Val Arg Arg Ala Leu Ala Glu Leu Pro Leu Asp Arg
    1490                1495                1500

Leu Arg Asp Ala Gly Val Leu Asp Thr Val Leu Arg Leu Thr Gly Ile
1505                1510                1515                1520

Glu Pro Glu Pro Gly Ser Gly Gly Ser Asp Gly Gly Ala Ala Asp Pro
                1525                1530                1535

Gly Ala Glu Pro Glu Ala Ser Ile Asp Asp Leu Asp Ala Glu Ala Leu
            1540                1545                1550

Ile Arg Met Ala Leu Gly Pro Arg Asn Thr
        1555                1560

<210> SEQ ID NO: 36
<211> LENGTH: 4041
<212> TYPE: DNA
```

<213> ORGANISM: Streptomyces venezuelae

<400> SEQUENCE: 36

| | | | | | |
|---|---|---|---|---|---|
| atgacgagtt | ccaacgaaca | gttggtggac | gctctgcgcg | cctctctcaa | ggagaacgaa | 60 |
| gaactccgga | aagagagccg | tcgccgggcc | gaccgtcggc | aggagcccat | ggcgatcgtc | 120 |
| ggcatgagct | gccggttcgc | gggcggaatc | cggtcccccg | aggacctctg | gacgccgtc | 180 |
| gccgcgggca | aggacctggt | ctccgaggta | ccggaggagc | gcggctggga | catcgactcc | 240 |
| ctctacgacc | cggtgcccgg | gcgcaagggc | acgacgtacg | tccgcaacgc | cgcgttcctc | 300 |
| gacgacgccg | ccggattcga | cgcggccttc | ttcgggatct | cgccgcgcga | ggccctcgcc | 360 |
| atggaccccgc | agcagcggca | gctcctcgaa | gcctcctggg | aggtcttcga | gcgggccggc | 420 |
| atcgaccccg | cgtcggtccg | cggcaccgac | gtcggcgtgt | acgtgggctg | tggctaccag | 480 |
| gactacgcgc | cggacatccg | ggtcgccccc | gaaggcaccg | gcggttacgt | cgtcaccggc | 540 |
| aactcctccg | ccgtggcctc | cgggcgcatc | gcgtactccc | tcggcctgga | gggacccgcc | 600 |
| gtgaccgtgg | acacggcgtg | ctcctcttcg | ctcgtcgccc | tgcacctcgc | cctgaagggc | 660 |
| ctgcggaacg | gcgactgctc | gacggcactc | gtgggcggcg | tggccgtcct | cgcgacgccg | 720 |
| ggcgcgttca | tcgagttcag | cagccagcag | gccatggccg | ccgacggccg | gaccaagggc | 780 |
| ttcgcctcgg | cggcggacgg | cctcgcctgg | ggcgagggcg | tcgccgtact | cctcctcgaa | 840 |
| cggctctccg | acgcgcggcg | caagggccac | cgggtcctgg | ccgtcgtgcg | cggcagcgcc | 900 |
| atcaaccagg | acgcgcgag | caacggcctc | acggctccgc | acgggccctc | ccagcagcac | 960 |
| ctgatccgcc | aggccctggc | cgacgcgcg | ctcacgtcga | gcgacgtgga | cgtcgtggag | 1020 |
| ggccacggca | cggggacccg | tctcggcgac | ccgatcgagg | cgcaggcgct | gctcgccacg | 1080 |
| tacgggcagg | ggcgcgcccc | ggggcagccg | ctgcggctgg | ggacgctgaa | gtcgaacatc | 1140 |
| gggcacacgc | aggccgcttc | gggtgtcgcc | ggtgtcatca | agatggtgca | ggcgctgcgc | 1200 |
| cacggggtgc | tgccgaagac | cctgcacgtg | gacgagccga | cggaccaggt | cgactggtcg | 1260 |
| gccggttcgg | tcgagctgct | caccgaggcc | gtggactggc | cggagcggcc | gggccggctc | 1320 |
| cgccgggcgg | gcgtctccgc | gttcggcgtg | ggcgggacga | acgcgcacgt | cgtcctggag | 1380 |
| gaggccccgg | cggtcgagga | gtcccctgcc | gtcgagccgc | cggccggtgg | cggcgtggtg | 1440 |
| ccgtggccgg | tgtccgcgaa | gacctcggcc | gcactggacg | cccagatcgg | gcagctcgcc | 1500 |
| gcatacgcgc | aagaccgcac | ggacgtggat | ccggcggtgg | ccgcccgcgc | cctggtcgac | 1560 |
| agccgtacgg | cgatggagca | ccgcgcggtc | gcggtcggcg | acagccggga | ggcactgcgg | 1620 |
| gacgccctgc | ggatgccgga | aggactggta | cggggcacgg | tcaccgatcc | gggccgggtg | 1680 |
| gcgttcgtct | tccccggcca | gggcacgcag | tgggccggca | tgggcgccga | actcctcgac | 1740 |
| agctcacccg | aattcgccgc | cgccatggcc | gaatgcgaga | ccgcactctc | cccgtacgtc | 1800 |
| gactggtctc | tcgaagccgt | cgtccgacag | gctcccagcg | caccgacact | cgaccgcgtc | 1860 |
| gacgtcgtcc | agcccgtcac | cttcgccgtc | atggtctccc | tcgccaaggt | ctggcagcac | 1920 |
| cacggcatca | ccccgaggc | cgtcatcggc | cactcccagg | gcgagatcgc | cgccgcgtac | 1980 |
| gtcgccggtg | ccctcacccct | cgacgacgcc | gctcgtgtcg | tgaccctccg | cagcaagtcc | 2040 |
| atcgccgccc | acctcgccgg | caagggcggc | atgatctccc | tcgccctcag | cgaggaagcc | 2100 |
| acccggcagc | gcatcgagaa | cctccacgga | ctgtcgatcg | ccgccgtcaa | cgggcctacc | 2160 |
| gccaccgtgg | tttcgggcga | ccccacccag | atccaagaac | ttgctcaggc | gtgtgaggcc | 2220 |
| gacggcatcc | gcgcacggat | catccccgtc | gactacgcct | cccacagcgc | ccacgtcgag | 2280 |

```
accatcgaga acgaactcgc cgacgtcctg gcggggttgt ccccccagac accccaggtc   2340
cccttcttct ccaccctcga aggcacctgg atcaccgaac ccgccctcga cggcggctac   2400
tggtaccgca acctccgcca tcgtgtgggc ttcgccccgg ccgtcgagac cctcgccacc   2460
gacgaaggct tcacccactt catcgaggtc agcgcccacc ccgtcctcac catgaccctc   2520
cccgacaagg tcaccggcct ggccaccctc cgacgcgagg acggcggaca gcaccgcctc   2580
accacctccc ttgccgaggc ctgggccaac ggcctcgccc tcgactgggc ctccctcctg   2640
cccgccacgg gcgccctcag ccccgccgtc ccgacctcc cgacgtacgc cttccagcac   2700
cgctcgtact ggatcagccc cgcgggtccc ggcgaggcgc ccgcgcacac cgcttccggg   2760
cgcgaggccg tcgccgagac ggggctcgcg tggggcccgg gtgccgagga cctcgacgag   2820
gagggccggc gcagcgccgt actcgcgatg gtgatgcggc aggcggcctc cgtgctccgg   2880
tgcgactcgc ccgaagaggt ccccgtcgac cgcccgctgc gggagatcgg cttcgactcg   2940
ctgaccgccg tcgacttccg caaccgcgtc aaccggctga ccggtctcca gctgccgccc   3000
accgtcgtgt tccagcaccc gacgcccgtc gcgctcgccg agcgcatcag cgacgagctg   3060
gccgagcgga actgggccgt cgccgagccg tcggatcacg agcaggcgga ggaggagaag   3120
gccgccgctc cggcggggc ccgctccggg gccgacaccg gcgccggcgc cgggatgttc   3180
cgcgccctgt tccggcaggc cgtggaggac gaccggtacg gcgagttcct cgacgtcctc   3240
gccgaagcct ccgcgttccg cccgcagttc gcctcgcccg aggcctgctc ggagcggctc   3300
gacccggtgc tgctcgccgg cggtccgacg gaccgggcgg aaggccgtgc cgttctcgtc   3360
ggctgcaccg gcaccgcggc gaacggcggc ccgcacgagt tcctgcggct cagcacctcc   3420
ttccaggagg agcgggactt cctcgccgta cctctccccg gctacggcac gggtacgggc   3480
accggcacgg ccctcctccc ggccgatctc gacaccgcgc tcgacgccca ggcccgggcg   3540
atcctccggg ccgccgggga cgccccggtc gtcctgctcg ggcactccgg cggcgccctg   3600
ctcgcgcacg agctggcctt ccgcctggag cgggcgcacg gcgcgccgcc ggccgggatc   3660
gtcctggtcg accccctatcc gccgggccat caggagccca tcgaggtgtg gagcaggcag   3720
ctgggcgagg gcctgttcgc gggcgagctg gagccgatgt ccgatgcgcg gctgctggcc   3780
atgggccggt acgcgcggtt cctcgccggc ccgcggccgg gccgcagcag cgcgcccgtg   3840
cttctggtcc gtgcctccga accgctgggc gactggcagg aggagcgggg cgactggcgt   3900
gcccactggg accttccgca caccgtcgcg gacgtgccgg gcgaccactt cacgatgatg   3960
cgggaccacg cgccggccgt cgccgaggcc gtcctctcct ggctcgacgc catcgagggc   4020
atcgaggggg cgggcaagtg a                                            4041
```

<210> SEQ ID NO: 37
<211> LENGTH: 1346
<212> TYPE: PRT
<213> ORGANISM: Streptomyces venezuelae

<400> SEQUENCE: 37

```
Met Thr Ser Ser Asn Glu Gln Leu Val Asp Ala Leu Arg Ala Ser Leu
 1               5                  10                  15

Lys Glu Asn Glu Glu Leu Arg Lys Glu Ser Arg Arg Arg Ala Asp Arg
            20                  25                  30

Arg Gln Glu Pro Met Ala Ile Val Gly Met Ser Cys Arg Phe Ala Gly
        35                  40                  45
```

-continued

```
Gly Ile Arg Ser Pro Glu Asp Leu Trp Asp Ala Val Ala Ala Gly Lys
     50                  55                  60

Asp Leu Val Ser Glu Val Pro Glu Glu Arg Gly Trp Asp Ile Asp Ser
 65                  70                  75                  80

Leu Tyr Asp Pro Val Pro Gly Arg Lys Gly Thr Thr Tyr Val Arg Asn
                 85                  90                  95

Ala Ala Phe Leu Asp Asp Ala Ala Gly Phe Asp Ala Ala Phe Phe Gly
            100                 105                 110

Ile Ser Pro Arg Glu Ala Leu Ala Met Asp Pro Gln Gln Arg Gln Leu
            115                 120                 125

Leu Glu Ala Ser Trp Glu Val Phe Glu Arg Ala Gly Ile Asp Pro Ala
        130                 135                 140

Ser Val Arg Gly Thr Asp Val Gly Val Tyr Val Gly Cys Gly Tyr Gln
145                 150                 155                 160

Asp Tyr Ala Pro Asp Ile Arg Val Ala Pro Glu Gly Thr Gly Gly Tyr
                165                 170                 175

Val Val Thr Gly Asn Ser Ser Ala Val Ala Ser Gly Arg Ile Ala Tyr
            180                 185                 190

Ser Leu Gly Leu Glu Gly Pro Ala Val Thr Val Asp Thr Ala Cys Ser
        195                 200                 205

Ser Ser Leu Val Ala Leu His Leu Ala Leu Lys Gly Leu Arg Asn Gly
    210                 215                 220

Asp Cys Ser Thr Ala Leu Val Gly Gly Val Ala Val Leu Ala Thr Pro
225                 230                 235                 240

Gly Ala Phe Ile Glu Phe Ser Ser Gln Gln Ala Met Ala Ala Asp Gly
                245                 250                 255

Arg Thr Lys Gly Phe Ala Ser Ala Ala Asp Gly Leu Ala Trp Gly Glu
            260                 265                 270

Gly Val Ala Val Leu Leu Leu Glu Arg Leu Ser Asp Ala Arg Arg Lys
        275                 280                 285

Gly His Arg Val Leu Ala Val Val Arg Gly Ser Ala Ile Asn Gln Asp
    290                 295                 300

Gly Ala Ser Asn Gly Leu Thr Ala Pro His Gly Pro Ser Gln Gln His
305                 310                 315                 320

Leu Ile Arg Gln Ala Leu Ala Asp Ala Arg Leu Thr Ser Ser Asp Val
                325                 330                 335

Asp Val Val Glu Gly His Gly Thr Gly Thr Arg Leu Gly Asp Pro Ile
            340                 345                 350

Glu Ala Gln Ala Leu Leu Ala Thr Tyr Gly Gln Gly Arg Ala Pro Gly
        355                 360                 365

Gln Pro Leu Arg Leu Gly Thr Leu Lys Ser Asn Ile Gly His Thr Gln
    370                 375                 380

Ala Ala Ser Gly Val Ala Gly Val Ile Lys Met Val Gln Ala Leu Arg
385                 390                 395                 400

His Gly Val Leu Pro Lys Thr Leu His Val Asp Glu Pro Thr Asp Gln
                405                 410                 415

Val Asp Trp Ser Ala Gly Ser Val Glu Leu Leu Thr Glu Ala Val Asp
            420                 425                 430

Trp Pro Glu Arg Pro Gly Arg Leu Arg Arg Ala Gly Val Ser Ala Phe
        435                 440                 445

Gly Val Gly Gly Thr Asn Ala His Val Val Leu Glu Glu Ala Pro Ala
    450                 455                 460
```

```
Val Glu Glu Ser Pro Ala Glu Pro Ala Gly Gly Val Val
465                 470             475             480

Pro Trp Pro Val Ser Ala Lys Thr Ser Ala Leu Asp Ala Gln Ile
                485             490                 495

Gly Gln Leu Ala Ala Tyr Ala Glu Asp Arg Thr Asp Val Asp Pro Ala
            500             505             510

Val Ala Ala Arg Ala Leu Val Asp Ser Arg Thr Ala Met Glu His Arg
            515             520             525

Ala Val Ala Val Gly Asp Ser Arg Glu Ala Leu Arg Asp Ala Leu Arg
530             535             540

Met Pro Glu Gly Leu Val Arg Gly Thr Val Thr Asp Pro Gly Arg Val
545             550             555             560

Ala Phe Val Phe Pro Gly Gln Gly Thr Gln Trp Ala Gly Met Gly Ala
                565             570             575

Glu Leu Leu Asp Ser Ser Pro Glu Phe Ala Ala Met Ala Glu Cys
            580             585             590

Glu Thr Ala Leu Ser Pro Tyr Val Asp Trp Ser Leu Glu Ala Val Val
            595             600             605

Arg Gln Ala Pro Ser Ala Pro Thr Leu Asp Arg Val Asp Val Val Gln
610             615             620

Pro Val Thr Phe Ala Val Met Val Ser Leu Ala Lys Val Trp Gln His
625             630             635             640

His Gly Ile Thr Pro Glu Ala Val Ile Gly His Ser Gln Gly Glu Ile
                645             650             655

Ala Ala Ala Tyr Val Ala Gly Ala Leu Thr Leu Asp Asp Ala Ala Arg
            660             665             670

Val Val Thr Leu Arg Ser Lys Ser Ile Ala Ala His Leu Ala Gly Lys
            675             680             685

Gly Gly Met Ile Ser Leu Ala Leu Ser Glu Glu Ala Thr Arg Gln Arg
690             695             700

Ile Glu Asn Leu His Gly Leu Ser Ile Ala Ala Val Asn Gly Pro Thr
705             710             715             720

Ala Thr Val Val Ser Gly Asp Pro Thr Gln Ile Gln Glu Leu Ala Gln
                725             730             735

Ala Cys Glu Ala Asp Gly Ile Arg Ala Arg Ile Ile Pro Val Asp Tyr
            740             745             750

Ala Ser His Ser Ala His Val Glu Thr Ile Glu Asn Glu Leu Ala Asp
            755             760             765

Val Leu Ala Gly Leu Ser Pro Gln Thr Pro Gln Val Pro Phe Phe Ser
770             775             780

Thr Leu Glu Gly Thr Trp Ile Thr Glu Pro Ala Leu Asp Gly Gly Tyr
785             790             795             800

Trp Tyr Arg Asn Leu Arg His Arg Val Gly Phe Ala Pro Ala Val Glu
                805             810             815

Thr Leu Ala Thr Asp Glu Gly Phe Thr His Phe Ile Glu Val Ser Ala
            820             825             830

His Pro Val Leu Thr Met Thr Leu Pro Asp Lys Val Thr Gly Leu Ala
            835             840             845

Thr Leu Arg Arg Glu Asp Gly Gly Gln His Arg Leu Thr Thr Ser Leu
850             855             860

Ala Glu Ala Trp Ala Asn Gly Leu Ala Leu Asp Trp Ala Ser Leu Leu
865             870             875             880
```

-continued

```
Pro Ala Thr Gly Ala Leu Ser Pro Ala Val Pro Asp Leu Pro Thr Tyr
            885                 890                 895

Ala Phe Gln His Arg Ser Tyr Trp Ile Ser Pro Ala Gly Pro Gly Glu
            900                 905                 910

Ala Pro Ala His Thr Ala Ser Gly Arg Glu Ala Val Ala Glu Thr Gly
            915                 920                 925

Leu Ala Trp Gly Pro Gly Ala Glu Asp Leu Asp Glu Glu Gly Arg Arg
            930                 935                 940

Ser Ala Val Leu Ala Met Val Met Arg Gln Ala Ala Ser Val Leu Arg
945                 950                 955                 960

Cys Asp Ser Pro Glu Glu Val Pro Val Asp Arg Pro Leu Arg Glu Ile
            965                 970                 975

Gly Phe Asp Ser Leu Thr Ala Val Asp Phe Arg Asn Arg Val Asn Arg
            980                 985                 990

Leu Thr Gly Leu Gln Leu Pro Pro Thr Val Val Phe Gln His Pro Thr
            995                 1000                1005

Pro Val Ala Leu Ala Glu Arg Ile Ser Asp Glu Leu Ala Glu Arg Asn
            1010                1015                1020

Trp Ala Val Ala Glu Pro Ser Asp His Glu Gln Ala Glu Glu Glu Lys
1025                1030                1035                1040

Ala Ala Ala Pro Ala Gly Ala Arg Ser Gly Ala Asp Thr Gly Ala Gly
            1045                1050                1055

Ala Gly Met Phe Arg Ala Leu Phe Arg Gln Ala Val Glu Asp Asp Arg
            1060                1065                1070

Tyr Gly Glu Phe Leu Asp Val Leu Ala Glu Ala Ser Ala Phe Arg Pro
            1075                1080                1085

Gln Phe Ala Ser Pro Glu Ala Cys Ser Glu Arg Leu Asp Pro Val Leu
            1090                1095                1100

Leu Ala Gly Gly Pro Thr Asp Arg Ala Glu Gly Arg Ala Val Leu Val
1105                1110                1115                1120

Gly Cys Thr Gly Thr Ala Ala Asn Gly Gly Pro His Glu Phe Leu Arg
            1125                1130                1135

Leu Ser Thr Ser Phe Gln Glu Glu Arg Asp Phe Leu Ala Val Pro Leu
            1140                1145                1150

Pro Gly Tyr Gly Thr Gly Thr Gly Thr Gly Thr Ala Leu Leu Pro Ala
            1155                1160                1165

Asp Leu Asp Thr Ala Leu Asp Ala Gln Ala Arg Ala Ile Leu Arg Ala
            1170                1175                1180

Ala Gly Asp Ala Pro Val Val Leu Leu Gly His Ser Gly Gly Ala Leu
1185                1190                1195                1200

Leu Ala His Glu Leu Ala Phe Arg Leu Glu Arg Ala His Gly Ala Pro
            1205                1210                1215

Pro Ala Gly Ile Val Leu Val Asp Pro Tyr Pro Pro Gly His Gln Glu
            1220                1225                1230

Pro Ile Glu Val Trp Ser Arg Gln Leu Gly Glu Gly Leu Phe Ala Gly
            1235                1240                1245

Glu Leu Glu Pro Met Ser Asp Ala Arg Leu Leu Ala Met Gly Arg Tyr
            1250                1255                1260

Ala Arg Phe Leu Ala Gly Pro Arg Gly Arg Ser Ser Ala Pro Val
1265                1270                1275                1280

Leu Leu Val Arg Ala Ser Glu Pro Leu Gly Asp Trp Gln Glu Glu Arg
            1285                1290                1295
```

-continued

Gly Asp Trp Arg Ala His Trp Asp Leu Pro His Thr Val Ala Asp Val
            1300                1305                1310

Pro Gly Asp His Phe Thr Met Met Arg Asp His Ala Pro Ala Val Ala
        1315                1320                1325

Glu Ala Val Leu Ser Trp Leu Asp Ala Ile Glu Gly Ile Glu Gly Ala
    1330                1335                1340

Gly Lys
1345

<210> SEQ ID NO: 38
<211> LENGTH: 1251
<212> TYPE: DNA
<213> ORGANISM: Streptomyces venezuelae

<400> SEQUENCE: 38

```
gtgcgccgta cccagcaggg aacgaccgct tctcccccgg tactcgacct cggggccctg      60
gggcaggatt tcgcggccga tccgtatccg acgtacgcga gactgcgtgc cgagggtccg     120
gcccaccggg tgcgcacccc cgaggggggac gaggtgtggc tggtcgtcgg ctacgaccgg    180
gcgcgggcgg tcctcgccga tccccggttc agcaaggact ggcgcaactc cacgactccc    240
ctgaccgagg ccgaggccgc gctcaaccac aacatgctgg agtccgaccc gccgcggcac    300
acccggctgc gcaagctggt ggcccgtgag ttcaccatgc gccgggtcga gttgctgcgg    360
ccccgggtcc aggagatcgt cgacgggctc gtggacgcca tgctggcggc gcccgacggc    420
cgcgccgatc tgatggagtc cctggcctgg ccgctgccga tcaccgtgat ctccgaactc    480
ctcggcgtgc ccgagccgga ccgcgccgcc ttccgcgtct ggaccgacgc cttcgtcttc    540
ccggacgatc ccgcccaggc ccagaccgcc atggccgaga tgagcggcta tctctcccgg    600
ctcatcgact ccaagcgcgg gcaggacggc gaggacctgc tcagcgcgct cgtgcggacc    660
agcgacgagg acggctcccg gctgacctcc gaggagctgc tcggtatggc ccacatcctg    720
ctcgtcgcgg ggcacgagac cacggtcaat ctgatcgcca acggcatgta cgcgctgctc    780
tcgcaccccg accagctggc cgccctgcgg gccgacatga cgctcttgga cggcgcggtg    840
gaggagatgt tgcgctacga gggcccggtg gaatccgcga cctaccgctt cccggtcgag    900
cccgtcgacc tggacggcac ggtcatcccg gccggtgaca cggtcctcgt cgtcctggcc    960
gacgcccacc gcacccccga gcgcttcccg gacccgcacc gcttcgacat ccgccgggac   1020
accgccggcc atctcgcctt cggccacggc atccacttct gcatcggcgc ccccttggcc   1080
cggttggagg cccggatcgc cgtccgcgcc cttctcgaac gctgcccgga cctcgccctg   1140
gacgtctccc ccggcgaact cgtgtggtat ccgaacccga tgattcgcgg gctcaaggcc   1200
ctgccgatcc gctggcggcg aggacgggag gcgggccgcc gtaccggttg a            1251
```

<210> SEQ ID NO: 39
<211> LENGTH: 416
<212> TYPE: PRT
<213> ORGANISM: Streptomyces venezuelae

<400> SEQUENCE: 39

Met Arg Arg Thr Gln Gln Gly Thr Thr Ala Ser Pro Pro Val Leu Asp
 1               5                  10                  15

Leu Gly Ala Leu Gly Gln Asp Phe Ala Ala Asp Pro Tyr Pro Thr Tyr
            20                  25                  30

Ala Arg Leu Arg Ala Glu Gly Pro Ala His Arg Val Arg Thr Pro Glu
        35                  40                  45

```
Gly Asp Glu Val Trp Leu Val Val Gly Tyr Asp Arg Ala Arg Ala Val
 50                  55                  60

Leu Ala Asp Pro Arg Phe Ser Lys Asp Trp Arg Asn Ser Thr Thr Pro
 65                  70                  75                  80

Leu Thr Glu Ala Glu Ala Ala Leu Asn His Asn Met Leu Glu Ser Asp
                 85                  90                  95

Pro Pro Arg His Thr Arg Leu Arg Lys Leu Val Ala Arg Glu Phe Thr
                100                 105                 110

Met Arg Arg Val Glu Leu Leu Arg Pro Arg Val Gln Glu Ile Val Asp
            115                 120                 125

Gly Leu Val Asp Ala Met Leu Ala Ala Pro Asp Gly Arg Ala Asp Leu
130                 135                 140

Met Glu Ser Leu Ala Trp Pro Leu Pro Ile Thr Val Ile Ser Glu Leu
145                 150                 155                 160

Leu Gly Val Pro Glu Pro Asp Arg Ala Ala Phe Arg Val Trp Thr Asp
                165                 170                 175

Ala Phe Val Phe Pro Asp Asp Pro Ala Gln Ala Gln Thr Ala Met Ala
                180                 185                 190

Glu Met Ser Gly Tyr Leu Ser Arg Leu Ile Asp Ser Lys Arg Gly Gln
            195                 200                 205

Asp Gly Glu Asp Leu Leu Ser Ala Leu Val Arg Thr Ser Asp Glu Asp
210                 215                 220

Gly Ser Arg Leu Thr Ser Glu Glu Leu Leu Gly Met Ala His Ile Leu
225                 230                 235                 240

Leu Val Ala Gly His Glu Thr Thr Val Asn Leu Ile Ala Asn Gly Met
                245                 250                 255

Tyr Ala Leu Leu Ser His Pro Asp Gln Leu Ala Ala Leu Arg Ala Asp
                260                 265                 270

Met Thr Leu Leu Asp Gly Ala Val Glu Glu Met Leu Arg Tyr Glu Gly
            275                 280                 285

Pro Val Glu Ser Ala Thr Tyr Arg Phe Pro Val Glu Pro Val Asp Leu
290                 295                 300

Asp Gly Thr Val Ile Pro Ala Gly Asp Thr Val Leu Val Leu Ala
305                 310                 315                 320

Asp Ala His Arg Thr Pro Glu Arg Phe Pro Asp Pro His Arg Phe Asp
                325                 330                 335

Ile Arg Arg Asp Thr Ala Gly His Leu Ala Phe Gly His Gly Ile His
            340                 345                 350

Phe Cys Ile Gly Ala Pro Leu Ala Arg Leu Glu Ala Arg Ile Ala Val
            355                 360                 365

Arg Ala Leu Leu Glu Arg Cys Pro Asp Leu Ala Leu Asp Val Ser Pro
370                 375                 380

Gly Glu Leu Val Trp Tyr Pro Asn Pro Met Ile Arg Gly Leu Lys Ala
385                 390                 395                 400

Leu Pro Ile Arg Trp Arg Arg Gly Arg Glu Ala Gly Arg Arg Thr Gly
                405                 410                 415
```

<210> SEQ ID NO: 40
<211> LENGTH: 2787
<212> TYPE: DNA
<213> ORGANISM: Streptomyces venezuelae

<400> SEQUENCE: 40

-continued

```
atgaatctgg tggaacgcga cggggagata gcccatctca gggccgttct tgacgcatcc    60
gccgcaggtg acgggacgct cttactcgtc tccggaccgg ccggcagcgg gaagacggag   120
ctgctgcggt cgctccgccg gctggccgcc gagcgggaga ccccgtctg gtcggtccgg    180
gcgctgccgg gtgaccgcga catccccctg gcgtcctct gccagttact ccgcagcgcc    240
gaacaacacg gtgccgacac ctccgccgtc cgcgacctgc tggacgccgc ctcgcggcgg   300
gccggaaacc tcacctcccc cgccgacgcg ccgctccgcg tcgacgagac acaccgcctg   360
cacgactggc tgctctccgt ctcccgccgc accccgttcc tcgtcgccgt cgacgacctg   420
acccacgccg acaccgcgtc cctgaggttc ctcctgtact cgccgccca ccacgaccag    480
ggcggcatcg gcttcgtcat gaccgagcgg gcctcgcagc gcgccggata ccgggtgttc   540
cgcgccgagc tgctccgcca ccgcactgc cgcaacatgt ggctctccgg gcttcccccc    600
agcggggtac gccagttact cgcccactac tacggccccg aggccgccga gcggcgggcc   660
cccgcgtacc acgcgacgac cggcgggaac ccgctgctcc tgcgggcgct gacccaggac   720
cggcaggcct cccacaccac cctcggcgcg gccggcggcg acgagcccgt ccacggcgac   780
gccttcgccc aggccgtcct cgactgcctg caccgcagcg ccgagggcac actggagacc   840
gcccgctggc tcgcggtcct cgaacagtcc gacccgctcc tggtggagcg gctcacggga   900
acgaccgccg ccgccgtcga gcgccacatc caggagctcg ccgccatcgg cctcctggac   960
gaggacggca ccctgggaca gcccgcgatc cgcgaggccg ccctccagga cctgccggcc  1020
ggcgagcgca ccgaactgca ccggcgcgcc gcggagcagc tgcaccggga cggcgccgac  1080
gaggacaccg tggcccgcca cctgctggtc ggcggcgccc ccgacgctcc ctgggcgctg  1140
cccctgctcg aacggggcgc gcagcaggcc ctgttcgacg accgactcga cgacgccttc  1200
cggatcctcg agttcgccgt gcggtcgagc accgacaaca cccagctggc ccgcctcgcc  1260
ccacacctgg tcgcggcctc ctggcggatg aacccgcaca tgacgacccg ggccctcgca  1320
ctcttcgacc ggctcctgag cggtgaactg ccgcccagcc acccggtcat ggccctgatc  1380
cgctgcctcg tctggtacgg gcggctgccc gaggccgccg acgcgctgtc ccggctgcgg  1440
cccagctccg acaacgatgc cttggagctg tcgctcaccc ggatgtggct cgcggcgctg  1500
tgcccgccgc tcctggagtc cctgccggcc acgccggagc cggagcgggg tcccgtcccc  1560
gtacggctcg cgccgcggac gaccgcgctc caggcccagg ccggcgtctt ccagcggggc  1620
ccggacaacg cctcggtcgc gcaggccgaa cagatcctgc agggctgccg gctgtcggag  1680
gagacgtacg aggccctgga gacggccctc ttggtcctcg tccacgccga ccggctcgac  1740
cgggcgctgt tctggtcgga cgccctgctc gccgaggccg tggagcggcg gtcgctcggc  1800
tgggaggcgg tcttcgccgc gacccgggcg atgatcgcga tccgctgcgg cgacctcccg  1860
acggcgcggg agcgggccga gctggcgctc tcccacgcgg cgccggagag ctggggcctc  1920
gccgtgggca tgcccctctc cgcgctgctg ctcgcctgca cggaggccgg cgagtacgaa  1980
caggcggagc gggtcctgcg gcagccggtg ccggacgcga tgttcgactc gcggcacggc  2040
atggagtaca tgcacgcccg gggccgctac tggctggcga cgggccggct gcacgcggcg  2100
ctgggcgagt tcatgctctg cggggagatc ctgggcagct ggaacctcga ccagccctcg  2160
atcgtgccct ggcggaccct cgccgccgag gtgtacctgc ggctcggcaa ccgccagaag  2220
gccagggcgc tggccgaggc ccagctcgcc ctggtgcgcg ccgggcgctc ccgcacccgg  2280
ggtctcaccc tgcgggtcct ggcggcggcg gtggacggcc agcaggcgga gcggctgcac  2340
```

```
gccgaggcgg tcgacatgct gcacgacagc ggcgaccggc tcgaacacgc ccgcgcgctc    2400
gccgggatga gccgccacca gcaggcccag ggggacaact accgggcgag gatgacggcg    2460
cggctcgccg cgacatggc gtgggcctgc ggcgcgtacc cgctggccga ggagatcgtg    2520
ccgggccgcg cggccgccg ggcgaaggcg gtgagcacgg agctggaact gccgggcggc    2580
ccggacgtcg gcctgctctc ggaggccgaa cgccgggtgg cggccctggc agcccgagga    2640
ttgacgaacc gccagatagc gcgccggctc tgcgtcaccg cgagcacggt cgaacagcac    2700
ctgacgcgcg tctaccgcaa actgaacgtg acccgccgag cagacctccc gatcagcctc    2760
gcccaggaca agtccgtcac ggcctga                                        2787

<210> SEQ ID NO: 41
<211> LENGTH: 928
<212> TYPE: PRT
<213> ORGANISM: Streptomyces venezuelae

<400> SEQUENCE: 41

Met Asn Leu Val Glu Arg Asp Gly Glu Ile Ala His Leu Arg Ala Val
 1               5                  10                  15

Leu Asp Ala Ser Ala Ala Gly Asp Gly Thr Leu Leu Val Ser Gly
                20                  25                  30

Pro Ala Gly Ser Gly Lys Thr Glu Leu Leu Arg Ser Leu Arg Arg Leu
            35                  40                  45

Ala Ala Glu Arg Glu Thr Pro Val Trp Ser Val Arg Ala Leu Pro Gly
        50                  55                  60

Asp Arg Asp Ile Pro Leu Gly Val Leu Cys Gln Leu Leu Arg Ser Ala
65                  70                  75                  80

Glu Gln His Gly Ala Asp Thr Ser Ala Val Arg Asp Leu Leu Asp Ala
                85                  90                  95

Ala Ser Arg Arg Ala Gly Asn Leu Thr Ser Pro Ala Asp Ala Pro Leu
            100                 105                 110

Arg Val Asp Glu Thr His Arg Leu His Asp Trp Leu Leu Ser Val Ser
        115                 120                 125

Arg Arg Thr Pro Phe Leu Val Ala Val Asp Asp Leu Thr His Ala Asp
130                 135                 140

Thr Ala Ser Leu Arg Phe Leu Leu Tyr Cys Ala Ala His His Asp Gln
145                 150                 155                 160

Gly Gly Ile Gly Phe Val Met Thr Glu Arg Ala Ser Gln Arg Ala Gly
                165                 170                 175

Tyr Arg Val Phe Arg Ala Glu Leu Leu Arg Gln Pro His Cys Arg Asn
            180                 185                 190

Met Trp Leu Ser Gly Leu Pro Pro Ser Gly Val Arg Gln Leu Leu Ala
        195                 200                 205

His Tyr Tyr Gly Pro Glu Ala Ala Glu Arg Arg Ala Pro Ala Tyr His
    210                 215                 220

Ala Thr Thr Gly Gly Asn Pro Leu Leu Leu Arg Ala Leu Thr Gln Asp
225                 230                 235                 240

Arg Gln Ala Ser His Thr Thr Leu Gly Ala Ala Gly Asp Glu Pro
                245                 250                 255

Val His Gly Asp Ala Phe Ala Gln Ala Val Leu Asp Cys Leu His Arg
            260                 265                 270

Ser Ala Glu Gly Thr Leu Glu Thr Ala Arg Trp Leu Ala Val Leu Glu
        275                 280                 285
```

-continued

```
Gln Ser Asp Pro Leu Leu Val Glu Arg Leu Thr Gly Thr Thr Ala Ala
    290                 295                 300

Ala Val Glu Arg His Ile Gln Glu Leu Ala Ala Ile Gly Leu Leu Asp
305                 310                 315                 320

Glu Asp Gly Thr Leu Gly Gln Pro Ala Ile Arg Glu Ala Ala Leu Gln
                325                 330                 335

Asp Leu Pro Ala Gly Glu Arg Thr Glu Leu His Arg Arg Ala Ala Glu
            340                 345                 350

Gln Leu His Arg Asp Gly Ala Asp Glu Asp Thr Val Ala Arg His Leu
        355                 360                 365

Leu Val Gly Gly Ala Pro Asp Ala Pro Trp Ala Leu Pro Leu Leu Glu
    370                 375                 380

Arg Gly Ala Gln Gln Ala Leu Phe Asp Asp Arg Leu Asp Asp Ala Phe
385                 390                 395                 400

Arg Ile Leu Glu Phe Ala Val Arg Ser Ser Thr Asp Asn Thr Gln Leu
                405                 410                 415

Ala Arg Leu Ala Pro His Leu Val Ala Ala Ser Trp Arg Met Asn Pro
            420                 425                 430

His Met Thr Thr Arg Ala Leu Ala Leu Phe Asp Arg Leu Leu Ser Gly
        435                 440                 445

Glu Leu Pro Pro Ser His Pro Val Met Ala Leu Ile Arg Cys Leu Val
    450                 455                 460

Trp Tyr Gly Arg Leu Pro Glu Ala Ala Asp Ala Leu Ser Arg Leu Arg
465                 470                 475                 480

Pro Ser Ser Asp Asn Asp Ala Leu Glu Leu Ser Leu Thr Arg Met Trp
                485                 490                 495

Leu Ala Ala Leu Cys Pro Pro Leu Leu Glu Ser Leu Pro Ala Thr Pro
            500                 505                 510

Glu Pro Glu Arg Gly Pro Val Pro Val Arg Leu Ala Pro Arg Thr Thr
        515                 520                 525

Ala Leu Gln Ala Gln Ala Gly Val Phe Gln Arg Gly Pro Asp Asn Ala
    530                 535                 540

Ser Val Ala Gln Ala Glu Gln Ile Leu Gln Gly Cys Arg Leu Ser Glu
545                 550                 555                 560

Glu Thr Tyr Glu Ala Leu Glu Thr Ala Leu Leu Val Leu Val His Ala
                565                 570                 575

Asp Arg Leu Asp Arg Ala Leu Phe Trp Ser Asp Ala Leu Leu Ala Glu
            580                 585                 590

Ala Val Glu Arg Arg Ser Leu Gly Trp Glu Ala Val Phe Ala Ala Thr
        595                 600                 605

Arg Ala Met Ile Ala Ile Arg Cys Gly Asp Leu Pro Thr Ala Arg Glu
    610                 615                 620

Arg Ala Glu Leu Ala Leu Ser His Ala Ala Pro Glu Ser Trp Gly Leu
625                 630                 635                 640

Ala Val Gly Met Pro Leu Ser Ala Leu Leu Leu Ala Cys Thr Glu Ala
                645                 650                 655

Gly Glu Tyr Glu Gln Ala Glu Arg Val Leu Arg Gln Pro Val Pro Asp
            660                 665                 670

Ala Met Phe Asp Ser Arg His Gly Met Glu Tyr Met His Ala Arg Gly
        675                 680                 685

Arg Tyr Trp Leu Ala Thr Gly Arg Leu His Ala Ala Leu Gly Glu Phe
    690                 695                 700
```

-continued

| | | | | | | | | | | | | | | |
|---|---|---|---|---|---|---|---|---|---|---|---|---|---|---|
| Met | Leu | Cys | Gly | Glu | Ile | Leu | Gly | Ser | Trp | Asn | Leu | Asp | Gln | Pro | Ser |
| 705 | | | | | 710 | | | | | 715 | | | | | 720 |

Ile Val Pro Trp Arg Thr Ser Ala Ala Glu Val Tyr Leu Arg Leu Gly
                    725                    730                    735

Asn Arg Gln Lys Ala Arg Ala Leu Ala Glu Ala Gln Leu Ala Leu Val
            740                    745                    750

Arg Pro Gly Arg Ser Arg Thr Arg Gly Leu Thr Leu Arg Val Leu Ala
          755                    760                    765

Ala Ala Val Asp Gly Gln Gln Ala Glu Arg Leu His Ala Glu Ala Val
770                    775                    780

Asp Met Leu His Asp Ser Gly Asp Arg Leu Glu His Ala Arg Ala Leu
785                    790                    795                    800

Ala Gly Met Ser Arg His Gln Gln Ala Gln Gly Asp Asn Tyr Arg Ala
          805                    810                    815

Arg Met Thr Ala Arg Leu Ala Gly Asp Met Ala Trp Ala Cys Gly Ala
          820                    825                    830

Tyr Pro Leu Ala Glu Ile Val Pro Gly Arg Gly Arg Arg Ala
          835                    840                    845

Lys Ala Val Ser Thr Glu Leu Glu Leu Pro Gly Gly Pro Asp Val Gly
          850                    855                    860

Leu Leu Ser Glu Ala Glu Arg Arg Val Ala Ala Leu Ala Ala Arg Gly
865                    870                    875                    880

Leu Thr Asn Arg Gln Ile Ala Arg Arg Leu Cys Val Thr Ala Ser Thr
            885                    890                    895

Val Glu Gln His Leu Thr Arg Val Tyr Arg Lys Leu Asn Val Thr Arg
          900                    905                    910

Arg Ala Asp Leu Pro Ile Ser Leu Ala Gln Asp Lys Ser Val Thr Ala
          915                    920                    925

<210> SEQ ID NO: 42
<211> LENGTH: 846
<212> TYPE: DNA
<213> ORGANISM: Streptomyces venezuelae

<400> SEQUENCE: 42

| | | |
|---|---|---|
| gtgaccgaca gacctctgaa cgtggacagc ggactgtgga tccggcgctt ccaccccgcg | 60 |
| ccgaacagcg cggtgcggct ggtctgcctg ccgcacgccg gcggctccgc cagctacttc | 120 |
| ttccgcttct cggaggagct gcaccccctcc gtcgaggccc tgtcggtgca gtatccgggc | 180 |
| cgccaggacc ggcgtgccga ccgtgtctg gagagcgtcg aggagctcgc cgagcatgtg | 240 |
| gtcgcggcca ccgaaccctg gtggcaggag gccggctgg ccttcttcgg gcacagcctc | 300 |
| ggcgcctccg tcgccttcga cggcccgc atcctggaac agcggcacgg ggtacggccc | 360 |
| gagggcctgt acgtctccgg tcggcgcgcc ccgtcgctgg cgccgaccg gctcgtccac | 420 |
| cagctggacg accgggcgtt cctggccgag atccggcggc tcagcggcac cgacgagcgg | 480 |
| ttcctccagg acgacgagct gctgcggctg gtgctgcccg cgctgcgcag cgactacaag | 540 |
| gcggcggaga cgtacctgca ccggccgtcc gccaagctca cctgcccggt gatggccctg | 600 |
| gccggcgacc gtgacccgaa ggcgccgctg aacgaggtgg ccgagtggcg tcggcacacc | 660 |
| agcgggccgt tctgcctccg ggcgtactcc ggcggccact tctacctcaa cgaccagtgg | 720 |
| cacgagatct gcaacgacat ctccgaccac ctgctcgtca cccgcggcgc gcccgatgcc | 780 |
| cgcgtcgtgc agccccccgac cagccttatc gaaggagcgg cgaagagatg gcagaaccca | 840 |
| cggtga | 846 |

```
<210> SEQ ID NO: 43
<211> LENGTH: 281
<212> TYPE: PRT
<213> ORGANISM: Streptomyces venezuelae

<400> SEQUENCE: 43
```

Met Thr Asp Arg Pro Leu Asn Val Asp Ser Gly Leu Trp Ile Arg Arg
 1               5                  10                  15

Phe His Pro Ala Pro Asn Ser Ala Val Arg Leu Val Cys Leu Pro His
                20                  25                  30

Ala Gly Gly Ser Ala Ser Tyr Phe Phe Arg Phe Ser Glu Glu Leu His
            35                  40                  45

Pro Ser Val Glu Ala Leu Ser Val Gln Tyr Pro Gly Arg Gln Asp Arg
        50                  55                  60

Arg Ala Glu Pro Cys Leu Glu Ser Val Glu Glu Leu Ala Glu His Val
65                  70                  75                  80

Val Ala Ala Thr Glu Pro Trp Trp Gln Glu Gly Arg Leu Ala Phe Phe
                85                  90                  95

Gly His Ser Leu Gly Ala Ser Val Ala Phe Glu Thr Ala Arg Ile Leu
               100                 105                 110

Glu Gln Arg His Gly Val Arg Pro Glu Gly Leu Tyr Val Ser Gly Arg
           115                 120                 125

Arg Ala Pro Ser Leu Ala Pro Asp Arg Leu Val His Gln Leu Asp Asp
130                 135                 140

Arg Ala Phe Leu Ala Glu Ile Arg Arg Leu Ser Gly Thr Asp Glu Arg
145                 150                 155                 160

Phe Leu Gln Asp Asp Glu Leu Leu Arg Leu Val Leu Pro Ala Leu Arg
               165                 170                 175

Ser Asp Tyr Lys Ala Ala Glu Thr Tyr Leu His Arg Pro Ser Ala Lys
           180                 185                 190

Leu Thr Cys Pro Val Met Ala Leu Ala Gly Asp Arg Asp Pro Lys Ala
           195                 200                 205

Pro Leu Asn Glu Val Ala Glu Trp Arg Arg His Thr Ser Gly Pro Phe
       210                 215                 220

Cys Leu Arg Ala Tyr Ser Gly Gly His Phe Tyr Leu Asn Asp Gln Trp
225                 230                 235                 240

His Glu Ile Cys Asn Asp Ile Ser Asp His Leu Leu Val Thr Arg Gly
               245                 250                 255

Ala Pro Asp Ala Arg Val Val Gln Pro Pro Thr Ser Leu Ile Glu Gly
           260                 265                 270

Ala Ala Lys Arg Trp Gln Asn Pro Arg
275                 280

DNA ENCODING METHYMYCIN AND PIKROMYCIN

STATEMENT OF GOVERNMENT RIGHTS

This invention was made with a grant from the Government of the United States of America (grants GM48562, GM35906 and GM54346 from the National Institutes of Health and a grant from the Office of Naval Research). The Government may have certain rights in the invention.

BACKGROUND OF THE INVENTION

Polyhydroxyalkanoates (PHAs) are one class of biodegradable polymers. The first identified member of the PHAs thermoplastics was polyhydroxybutyrate (PHB), the polymeric ester of D(-)-3-hydroxybutyrate. The biosynthetic pathway of PHB in the gram negative bacterium *Alcaligenes eutrophus* is depicted in FIG. 1. PHAs related to PHB differ in the structure of the pendant arm, R (FIG. 2). For example, $R=CH_3$ in PHB, while $R=CH_2CH_3$ in polyhydroxyvalerate, and $R=(CH_2)_4CH_3$ in polyhydroxyoctanoate.

The genes responsible for PHB synthesis in *A. eutrophus* have been cloned and sequenced. (Peoples et al., *J. Biol. Chem.*, 264, 15293 (1989); Peoples et al., *J. Biol. Chem.*, 264, 15298 (1989)). Three enzymes: β-ketothiolase (phbA), acetoacetyl-CoA reductase (phbB), and PHB synthase (phbC) are involved in the conversion of acetyl-CoA to PHB. The PHB synthase gene encodes a protein of $M_r=63,900$ which is active when introduced into *E. coli* (Peoples et al., *J. Biol. Chem.*, 264, 15298 (1989)).

Although PHB represents the archetypical form of a biodegradable thermoplastic, its physical properties preclude significant use of the homopolymer form. Pure PHB is highly crystalline and, thus, very brittle. However, unique physical properties resulting form the structural characteristics of the R groups in a PHA copolymer may result in a polymer with more desirable characteristics. These characteristics include altered crystallinity, UV weathering resistance, glass to rubber transition temperature ($T_g$), melting temperature of the crystalline phase, rigidity and durability (Holmes et al., EPO 00052 459; Anderson et al., *Microbiol. Rev.*, 54, 450 (1990)). Thus, these polyesters behave as thermoplastics, with melting temperatures of 50–180° C., which can be processed by conventional extension and molding equipment.

Traditional strategies for producing random PHA copolymers involve feeding short- and long-chain fatty acid monomers to bacterial cultures. However, this technology is limited by the monomer units which can be incorporated into a polymer by the endogenous PHA synthase and the expense of manufacturing PHAs by existing fermentation methods (Haywood et al., *FEMS Microbiol. Lett.*, 57, 1 (1989); Poi et al., *Int. J. Biol. Macromol.*, 12, 106 (1990); Steinbuchel et al., In: *Novel Biomaterials from Biological Sources*. D. Byron (ed.), MacMillan, N.Y. (1991); Valentin et al., *Appl. Microbiol. Biotechnical*, 36, 507 (1992)).

The production of diverse hydroxyacylCoA monomers for homo- and co-polymeric PHAs also occurs in some bacteria through the reduction and condensation pathway of fatty acids. This pathway employs a fatty acid synthase (FAS) which condenses malonate and acetate. The resulting β-keto group undergoes three processing steps, β-keto reduction, dehydration, and enoyl reduction, to yield a fully saturated butyryl unit. However, this pathway provides only a limited array of PHA monomers which vary in alkyl chain length but not in the degree of alkyl group branching, saturation, or functionalization along the acyl chain.

The biosynthesis of polyketides, such as erythromycin, is mechanistically related to formation of long-chain fatty acids. However, polyketides, in contrast to FASs, retain ketone, hydroxyl, or olefinic functions and contain methyl or ethyl side groups interspersed along an acyl chain comparable in length to that of common fatty acids. This asymmetry in structure implies that the polyketide synthase (PKS), the enzyme system responsible for formation of these molecules, although mechanistically related to a FAS, results in an end product that is structurally very different than that of a long-chain fatty acid.

Because PHAs are biodegradable polymers that have the versatility to replace petrochemical-based thermoplastics, it is desirable that new, more economical methods be provided for the production of defined PHAs. Thus, what is needed are methods to produce recombinant PHA monomer synthases for the generation of PHA polymers.

SUMMARY OF THE INVENTION

The present invention provides a method of preparing a polyhydroxyalkanoate synthase. The method comprises introducing an expression cassette into a non-plant eukaryotic cell. The expression cassette comprises a DNA molecule encoding a polyhydroxyalkanoate synthase, e.g., a polyhydroxybutyrate synthase, operably linked to a promoter functional in the non-plant eukaryotic cell. The DNA molecule may be obtained from a bacterium such as *Alcaligenes eutrophus*. The DNA molecule encoding the polyhydroxyalkanoate synthase is then expressed in the cell. Thus, another embodiment of the invention provides a purified recombinant polyhydroxybutyrate synthase isolated from a host cell which expresses the synthase.

Another embodiment of the invention is a method of preparing a polyhydroxyalkanoate polymer. The method comprises introducing a first expression cassette and a second expression cassette into a eukaryotic cell. The first expression cassette comprises a DNA segment encoding a fatty acid synthase in which the dehydrase activity has been inactivated that is operably linked to a promoter functional in the eukaryotic cell, e.g., an insect cell. The inactivation preferably is via a mutation in the catalytic site of the dehydrase. The second expression cassette comprises a DNA segment encoding a polyhydroxyalkanoate synthase operably linked to a promoter functional in the eukaryotic cell. The expression cassettes may be on the same or separate molecules. The DNA segments in the expression cassettes are expressed in the cell so as to yield a polyhydroxyalkanoate polymer.

Another embodiment of the invention is a baculovirus expression cassette comprising a nucleic acid molecule encoding a polyhydroxyalkanoate synthase operably linked to a promoter functional in an insect cell. Preferably, the nucleic acid molecule is obtained from a bacterium, e.g., *Alcaligenes eutrophus*.

The present invention also provides an expression cassette comprising a nucleic acid molecule encoding a polyhydroxyalkanoate monomer synthase operably linked to a promoter functional in a host cell. The nucleic acid molecule comprises a plurality of DNA segments. Thus, the nucleic acid molecule comprises at least a first and a second DNA segment. No more than one DNA segment is derived from the eryA gene cluster of *Saccharopolyspora erythraea*. The first DNA segment encodes a first module and the second DNA segment encodes a second module, wherein the DNA segments together encode a polyhydroxyalkanoate monomer synthase. The source of at least one DNA segment is preferably bacterial DNA. It is preferred that the first DNA segment encodes the first module form the vep gene cluster and the second DNA segment encodes module 7 from the tyl P gene cluster. The nucleic acid molecule may optionally further comprise a third DNA segment encoding a polyhydroxyalkanoate synthase. Alternatively, a second nucleic acid molecule encoding a polyhydroxyalkanoate synthase may be introduced into the host cell.

Also provided is an isolated and purified DNA molecule. The DNA molecule comprises a plurality of DNA segments. Thus, the DNA molecule comprises at least a first and a second DNA segment. The first DNA segment encodes a first module and the second DNA segment encodes a second module. No more than one DNA segment is derived from the eryA gene cluster of *Saccharopolyspora erythraea*. Also, it is preferred that no more than one module is derived from the gene cluster from *Streptomyces hygroscopicus* that encodes rapamycin or the gene cluster that encodes spiramycin. Together the DNA segments encode a recombinant polyhydroxyalkanoate monomer synthase. A preferred embodiment of the invention employs a first DNA segment derived from the vep gene cluster of Streptomyces. Another preferred embodiment of the invention employs a second DNA segment derived from the tyl gene cluster of Streptomyces. A further preferred embodiment of the isolated DNA molecule of the invention includes a DNA segment encoding a polyhydroxyalkanoate synthase.

Yet another preferred embodiment is an isolated DNA molecule of the invention wherein the second DNA segment comprises a DNA encoding a thioesterase which is located at the 3' end of the second DNA segment. More preferably, the second DNA segment comprises a DNA encoding an acyl carrier protein which is located 5' to the DNA encoding the thioesterase. Even more preferably, the second DNA segment comprises a DNA encoding a linker region, wherein the DNA encoding the linker region is located between the DNA encoding the acyl carrier protein and the DNA encoding the thioesterase.

Another embodiment of the isolated DNA molecule of the invention comprises a first DNA segment comprising DNA encoding two acyl transferases, wherein the DNA encoding the first acyl transferase is 5' to the DNA encoding the second acyl transferase. Preferably, the second acyl transferase adds acyl groups to malonylCoA.

Other embodiments of the isolated DNA molecule include a first DNA segment comprising a DNA encoding a dehydrase, a first DNA segment comprising a DNA encoding a dehydrase and an enoyl reductase, a second DNA segment comprising a DNA encoding an inactive dehydrase, or a first DNA segment comprising a DNA encoding an acyl transferase. A preferred acyl transferase binds an acyl CoA substrate.

A further embodiment of the isolated DNA molecule includes a first DNA segment encoding a first module and a second DNA segment encoding a second module, wherein the DNA segments together encode a recombinant polyhydroxyalkanoate monomer synthase, and wherein no more than one DNA segment is derived from the eryA gene cluster of *Saccharopolyspora erythraea*. Also preferably, at least one DNA segment is derived from the vep gene cluster or the tyl gene cluster. In one preferred embodiment, the first DNA segment encodes the first module from the vep gene cluster and the second DNA segment encodes module 7 from the tyl gene cluster.

Yet another embodiment of the invention is a method of providing a polyhydroxyalkanoate monomer. The method comprises introducing a DNA molecule into a host cell. The DNA molecule comprises a DNA segment encoding a recombinant polyhydroxyalkanoate monomer synthase operably linked to a promoter functional in the host cell. The DNA encoding the recombinant polyhydroxyalkanoate monomer synthase, which synthase comprises at least a first module and a second module, is expressed in the host cell so as to generate a polyhydroxyalkanoate monomer. Preferably, the first DNA segment encodes the first module from the vep gene cluster and the second DNA segment encodes module 7 from the tyl P gene cluster. Also preferably, the DNA molecule further comprises a DNA segment encoding a polyhydroxyalkanoate synthase.

Also provided is a method of preparing a polyhydroxyalkanoate polymer. The method comprises introducing a first DNA molecule and a second DNA molecule into a host cell. The first DNA molecule comprises a DNA segment encoding a recombinant polyhydroxyalkanoate monomer synthase. The recombinant polyhydroxyalkanoate monomer synthase comprises a plurality of modules. Thus, the monomer synthase comprises at least a first module and a second module. The first DNA molecule is operably linked to a promoter functional in a host cell. The second DNA molecule comprises a DNA segment encoding a polyhydroxyalkanoate synthase operably linked to a promoter functional in the host cell. The DNAs encoding the recombinant polyhydroxyalkanoate monomer synthase and polyhydroxyalkanoate synthase are expressed in the host cell so as to generate a polyhydroxyalkanoate polymer.

Yet another embodiment of the invention is an isolated and purified DNA molecule. The DNA molecule comprises a plurality of DNA segments. That is, the DNA molecule comprises at least a first and a second DNA segment. The first DNA segment encodes a fatty acid synthase and the second DNA segment encodes a module of a polyketide synthase. A preferred embodiment of the invention employs a second DNA segment encoding a module which comprises a β-ketoacyl synthase amino-terminal to an acyltransferase which is amino-terminal to a ketoreductase which is amino-terminal to an acyl carrier protein which is amino-terminal to a thioesterase. Other preferred embodiments of the invention include a second DNA segment that is 3' to the DNA encoding the fatty acid synthase, a first DNA segment encoding a fatty acid synthase and a second DNA segment encoding a module of a polyketide synthase, or a second DNA segment that is separated from the first DNA segment by a DNA encoding a linker region. Preferred linker regions include the linker region from tyl ORF1 $ACP_1$-$KS_2$, tyl ORF1 $ACP_2$-$KS_3$, tyl ORF3 $ACP_5$-$KS_6$, eryA ORF1 $ACP_1$-$KS_1$, eryA ORF1 $ACP_2$-$KS_2$, eryA ORF2 $ACP_3$-$KS_4$, and eryA ORF2 $ACP5$-$KS_6$.

The invention also provides a method of preparing a polyhydroxyalkanoate monomer. The method comprises introducing a DNA molecule comprising a plurality of DNA segments into a host cell, e.g., an insect cell, a Streptomyces cell or a Pseudomonas cell. Thus, the DNA molecule comprises at least a first and a second DNA segment. The first DNA segment encodes a fatty acid synthase operably linked to a promoter functional in the host cell. Preferably, the fatty acid synthase is eukaryotic in origin. Alternatively, the fatty acid synthase is prokaryotic in origin. The second DNA segment encodes a polyketide synthase. Preferably, the second DNA segment encodes the tyl module F. The second DNA segment is located 3' to the first DNA segment. The first DNA segment is linked to the second DNA segment so that the encoded protein is expressed as a fusion protein. The DNA molecule is then expressed in the host cell so as to generate a polyhydroxyalkanoate monomer.

Another embodiment of the invention is an expression cassette comprising a DNA molecule comprising a DNA segment encoding a fatty acid synthase and a polyhydroxyalkanoate synthase.

Also provided is a method of providing a polyhydroxyalkanoate monomer synthase. The method comprises introducing an expression cassette into a host cell. The expression cassette comprises a DNA molecule encoding a polyhydroxyalkanoate monomer synthase operably linked to a promoter functional in the host cell. The monomer synthase comprises a plurality of modules. Thus, the monomer synthase comprises at least a first and second module which together encode the monomer synthase. Optionally, the expression cassette further comprises a second DNA molecule encoding a polyhydroxyalkanoate synthase.

A further embodiment of the invention is an isolated and purified DNA molecule comprising a DNA segment which encodes a *Streptomyces venezuelae* polyketide synthase, e.g., a polyhydroxyalkanoate monomer synthase, a biologically active variant or subunit (fragment) thereof. Preferably, the DNA segment encodes a polypeptide having an amino acid sequence comprising SEQ ID NO:2. Preferably, the DNA segment comprises SEQ ID NO:1. The DNA molecules of the invention are double stranded or single stranded. A preferred embodiment of the invention is a DNA molecule that has at least about 70%, more preferably at least about 80%, and even more preferably at least about 90%, but less than 100%, contiguous sequence identity to the DNA segment comprising SEQ ID NO:1, e.g., a "variant" DNA molecule. A variant DNA molecule of the invention can be prepared by methods well known to the art, including oligonucleotide-mediated mutagenesis. See Adelman et al., *DNA*, 2, 183 (1983) and Sambrook et al., *Molecular Cloning: A Laboratory Manual* (1989).

The invention also provides an isolated, purified polyhydroxyalkanoate monomer synthase, e.g., a polypeptide having an amino acid sequence comprising SEQ ID NO:2, a biologically active subunit, or a biologically active variant thereof. Thus, the invention provides a variant polypeptide having at least about 80%, more preferably at least about 90%, and even more preferably at least about 95%, but less than 100%, contiguous amino acid sequence identity to the polypeptide having an amino acid sequence comprising SEQ ID NO:2. A preferred variant polypeptide, or a subunit of a polypeptide, of the invention includes a variant or subunit polypeptide having at least about 10%, more preferably at least about 50%, and even more preferably at least about 90%, the activity of the polypeptide having the amino acid sequence comprising SEQ ID NO:2. Preferably, a variant polypeptide of the invention has one or more conservative amino acid substitutions relative to the polypeptide having the amino acid sequence comprising SEQ ID NO:2. For example, conservative substitutions include aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. The biological activity of a polypeptide of the invention can be measured by methods well known to the art, including but not limited to, methods described hereinbelow.

The invention also provides an isolated and purified nucleic acid segment comprising a nucleic acid sequence comprising a sugar (desosamine) biosynthetic gene cluster, a biologically active variant or fragment thereof, wherein the nucleic acid sequence is not derived from the eryC gene cluster of *Saccharopolyspora erythraea*. As described hereinbelow, the desosamine biosynthetic gene cluster from *Streptomycyes venezuelae* was isolated, cloned and sequenced. The isolated nucleic acid segment comprising the gene cluster preferably includes a nucleic acid sequence comprising SEQ ID NO:3, or a fragment or variant thereof. The cluster was found to encode nine polypeptides including DesI (e.g., SEQ ID NO:8 encoded by SEQ ID NO:7), DesII (e.g., SEQ ID NO:10 encoded by SEQ ID NO:9), DesIII (e.g., SEQ ID NO:12 encoded by SEQ ID NO:11), DesIV (e.g., SEQ ID NO:14 encoded by SEQ ID NO:13), DesV (e.g., SEQ ID NO:16 encoded by SEQ ID NO:15), DesVI (e.g., SEQ ID NO:18 encoded by SEQ ID NO:17), DesVII (e.g., SEQ ID NO:20 encoded by SEQ ID NO:19), DesVIII (e.g., SEQ ID NO:22 encoded by SEQ ID NO:21), and DesR (e.g., SEQ ID NO:24 encoded by SEQ ID NO:23) (see FIG. 24). It is also preferred that the nucleic acid segment of the invention encoding DesR is not derived from the eryB gene cluster of *Saccharopolyspora erythraea* or the oleD gene from *Streptomyces antibioticus*.

The invention also provides a variant polypeptide having at least about 80%, more preferably at least about 90%, and even more preferably at least about 95%, but less than 100%, contiguous amino acid sequence identity to the polypeptide having an amino acid sequence comprising SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or a fragment thereof. A preferred variant polypeptide, or a subunit or fragment of a polypeptide, of the invention includes a variant or subunit polypeptide having at least about 1%, more preferably at least about 10%, and even more preferably at least about 50%, the activity of the polypeptide having the amino acid sequence comprising SEQ ID NO:8, SEQ ID NO:10, SEQ ID NO:12, SEQ ID NO:14, SEQ ID NO:16, SEQ ID NO:18, SEQ ID NO:20, SEQ ID NO:22, or SEQ ID NO:24. Thus, for example, the glycosyltransferase activity of a polypeptide of SEQ ID NO:20 can be compared to a variant of SEQ ID NO:20 having at least one amino acid substitution, insertion, or deletion relative to SEQ ID NO:20.

A variant nucleic acid sequence of the invention has at least about 80%, more preferably at least about 90%, and even more preferably at least about 95%, but less than 100%, contiguous nucleic acid sequence identity to a nucleic acid sequence comprising SEQ ID NO:3, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or a fragment thereof.

Also provided is an expression cassette comprising a nucleic acid sequence comprising a desosamine biosynthetic gene cluster, a biologically active variant or fragment thereof operably linked to a promoter functional in a host cell, as well as host cells comprising an expression cassette of the invention. Thus, the expression cassettes of the invention are useful to express individual genes within the cluster, e.g., the desR gene which encodes a glycosidase or the desVII gene which encodes a glycosyltransferase having relaxed substrate specificity for polyketides and deoxysugars, i.e., the glycosyltransferase processes sugar substrates other than TDP-desosamine. Thus, the desVII gene can be employed in combinatorial biology approaches to synthesize a library of macrolide compounds having various polyketide and deoxysugar structures. Moreover, the expression of a glycosylase in a host cell which synthesizes a macrolide antibiotic may be useful in a method to reduce toxicity of, e.g., inactivate, the antibiotic. For example, a host cell which produces the antibiotic is transformed with an expression cassette encoding the glycosyltransferase. The recombinant glycosyltransferase is expressed in an amount that reversibly inactivates the antibiotic. To activate the antibiotic, the antibiotic, preferably the isolated antibiotic which is recovered from the host cell, is contacted with an appropriate native or recombinant glycosidase.

Preferably, the nucleic acid segment encoding desosamine in the expression cassette of the invention is not derived form the eryC gene cluster of *Saccharopolyspora erythraea*. Preferred host cells are prokaryotic cells, although eukaryotic host cells are also envisioned. These host cells are useful to express desosamine, analogs or derivatives thereof. Also provided is an expression cassette or host cell comprising antisense sequences from at least a portion of the desosamine biosynthetic gene cluster.

Another embodiment of the invention is a recombinant host cell, e.g., a bacterial cell, in which a portion of a nucleic acid sequence encoding desosamine in the host chromosome is disrupted, e.g., deleted or interrupted (e.g., by an insertion) with heterologous sequences, or substituted with a variant nucleic acid sequence of the invention, preferably so as to result in a decrease or lack of desosamine synthesis, and/or so as to result in the synthesis of an analog or derivative of desosamine. Preferably, the nucleic acid sequence which is disrupted is not derived from the eryC gene cluster of *Saccharopolyspora erythraea*. Thus, the recombinant host cell of the invention has at least one gene, i.e., desI, desII, desIII, desIV, desV, desVI, desVII, desVIII or desR, which is disrupted. One embodiment of the invention includes a recombinant host cell in which the desVI gene, which encodes an N-methyltransferase, is disrupted, for example, by replacement with an antibiotic resistance gene. Preferably, such a host cell produces an aglycone having an N-acetylated aminodeoxy sugar, 10-deoxymethylonide, a compound of formula (7), a compound of formula (8), or a combination thereof. Thus, the deletion or disruption of the desVI gene may be useful in a method for preparing novel sugars.

Another preferred embodiment of the invention is a recombinant bacterial host cell in which the desR gene, which encodes a glycosidase such as β-glucosidase, is disrupted. Preferably, the host cell synthesizes C-2' β-glucosylated macrolide antibiotics, for example, a compound of formula (13), a compound of formula (14), or a combination thereof. Therefore, the invention further provides a compound of formula (8), (9), (13) or (14). It will be appreciated by those skilled in the art that each atom of the compounds of the invention having a chiral center may exist in and be isolated in optically active and racemic forms. Some compounds may exhibit polymorphism. It is to be understood that the present invention encompasses any racemic, optically active, polymorphic or stereoisomeric form, or mixtures thereof, of a compound of the invention, which possess the useful properties described herein, it being well known in the art how to prepare optically active forms (for example, by resolution of the racemic form by recrystallization techniques, by synthesis from optically active starting materials, by chiral synthesis, or by chromatographic separation using a chiral stationary phase) and how to determine activity using the standard tests described herein, or using other similar tests which are well known in the art.

Further provided is an isolated and purified nucleic acid segment comprising a nucleic acid sequence comprising a macrolide biosynthetic gene cluster (the "met/pik" or "pik" gene cluster) encoding methymycin, pikomycin, neomethymycin, narbomycin, or a combination thereof, or a biologically active variant or fragment thereof. It is preferred that the nucleic acid segment comprises SEQ ID NO:5, or a fragment or variant thereof. It is also preferred that the isolated and purified nucleic acid segment is from Streptomyces sp., such as *Streptomyces venezuelae* (e.g., ATCC 15439, MCRL 0306, SC 2366 or 3629), *Streptomyces narbonensis, Streptomyces eurocidicus, Streptomyces zaomyceticus* (MCRL 0405), *Streptomyces flavochromogens,* Streptomyces sp. AM400, and *Streptomyces felleus,* although isolated and purified nucleic acid from other organisms which produce methymycin, narbomycin, neomethymycin and/or pikomycin are also within the scope of the invention. The cloned genes can be introduced into an expression system and genetically manipulated so as to yield novel macrolide antibiotics, e.g., ketolides, as well as monomers for polyhydroxyalkanoate (PHA) biopolymers. Preferably, the nucleic acid sequence encodes PikR1 (e.g., SEQ ID NO:27 encoded by SEQ ID NO:26), PikR2 (e.g., SEQ ID NO:29 encoded by SEQ ID NO:28), PikAI (e.g., SEQ ID NO:31 encoded by SEQ ID NO:30), PikAII (e.g., SEQ ID NO:33 encoded by SEQ ID NO:32), PikAIII (e.g., SEQ ID NO:35 encoded by SEQ ID NO:34), PikAIV (e.g., SEQ ID NO:37 encoded by SEQ ID NO:36), PikB (which is the desosamine gene cluster described above), PikC (e.g., SEQ ID NO:39 encoded by SEQ ID NO:38), and PikD (e.g., SEQ ID NO:41 encoded by SEQ ID NO:40), a variant or a fragment thereof.

The invention also provides a variant polypeptide having at least about 80%, more preferably at least about 90%, and even more preferably at least about 95%, but less than 100%, contiguous amino acid sequence identity to the polypeptide having an amino acid sequence comprising SEQ ID NO:27, SEQ ID NO:31, SEQ ID NO:33, SEQ ID NO:35, SEQ ID NO:37, SEQ ID NO:39, SEQ ID NO:41, or a fragment thereof. A preferred variant polypeptide, or a subunit of a polypeptide, of the invention includes a variant or subunit polypeptide having at least about 1%, more preferably at least about 10%, and even more preferably at least about 50%, the activity of the polypeptide having the amino acid sequence comprising SEQ ID NO:27, SEQ ID NO:31, SEQ ID NO:33, SEQ ID NO:35, SEQ ID NO:37, SEQ ID NO:39, or SEQ ID NO:41. The activities of polypeptides of the macrolide biosynthetic pathway of the invention are described below.

A variant nucleic acid sequence of the pik biosynthetic gene cluster of the invention has at least about 80%, more preferably at least about 90%, and even more preferably at least about 95%, but less than 100%, contiguous nucleic acid sequence identity to a nucleic acid sequence comprising SEQ ID NO:5, SEQ ID NO:26, SEQ ID NO:30, SEQ ID NO:32, SEQ ID NO:34, SEQ ID NO:36, SEQ ID NO:38, SEQ ID NO:40, or a fragment thereof.

The pikA gene encodes a polyketide synthase which synthesizes macrolactone 10-deoxymethonolide and narbolide, pikB encodes desosamine synthases which catalyze the formation and transfer of a deoxysugar moiety onto aglycones, the pikC gene encodes a P450 hydoxylase which catalyzes the conversion of YC-17 and narbomycin into methymycin, neomethymycin, and pikromycin, and the pikR1, pikR2 (possibly one for a 12-membered ring and the other for a 14-membered ring) and desR genes which encode enzymes associated with bacterial self-protection. Thus, the isolated nucleic acid molecule of the invention encodes four active macrolide antibiotics two of which have a 12-membered ring while the other two have a 14-membered ring. The regulation of the synthesis of 12- or 14-membered rings may be the result of the sequences in the spacer region between modules 5 and 6, as discussed below. Thus, the genetic mechanism underlying the alternative termination of polyketide synthesis may be useful to prepare novel antibiotics and PHA monomers.

The invention further provides isolated and purified nucleic acid segments, e.g., in the form of an expression cassette, for each of the individual genes in the macrolide biosynthetic gene cluster. For example, the invention provides an isolated and purified pikAV gene that encodes a thioesterase II. In particular, the thioesterase is useful to enhance the structural diversity of antibiotics and in PHA production, as the thioesterase modulates chain release and cyclization. For example, a thioesterase II gene having acyl-ACP coenzyme A transferase activity (e.g., a mutant pik TEII, bacterial, fungal or plant medium-chain-length thioesterase, an animal fatty acid thioesterase or a thioesterase from a polyketide synthase) is introduced at the end of a recombinant monomer synthase (see FIG. 36), which, in the presence of a PHA synthase, e.g., phaC1, produces a novel polyhydroxyalkanoate polymer. Alternatively, in the absence of a TEII domain, a fusion of a portion of PKS gene cluster with a PHA synthase may result in the transfer of an acyl chain from the PHA to the polymerase.

Also provided is a pikC gene that encodes a hydroxylase which is active at two positions on a 12-membered ring or at one position on a 14-membered ring. Such a gene may be particularly useful to prepare novel compounds through bioconversion or biotransformation.

The invention also provides an expression cassette comprising a nucleic acid segment comprising a macrolide biosynthetic gene cluster encoding methymycin, pikomycin, neomethymycin, narbomycin, or a combination thereof, or a biologically active variant or fragment thereof, operably linked to a promoter functional in a host cell. Further provided is a host cell comprising the nucleic acid segment encoding methymycin, pikomycin, neomethymycin, narbomycin, or a combination thereof, or a biologically active variant or fragment thereof. Moreover, the invention provides isolated and purified polypeptides of the invention, preferably obtained from host cells having the nucleic acid molecules of the invention. In addition, expression cassettes and host cells comprising antisense sequences of at least a portion of the macrolide biosynthetic gene cluster of the invention are envisioned.

Yet another embodiment of the invention is a recombinant host cell, e.g., a bacterial cell, in which a portion of the macrolide biosynthetic gene cluster of the invention is disrupted or replaced with a heterologous sequence or a variant nucleic acid segment of the invention, preferably so as to result in a decrease or lack of methymycin, pikomycin, neomethymycin, narbomycin, or a combination thereof, and/or so as to result in the synthesis of novel macrolides. Therefore, the invention provides a recombinant host cell in which a pikAI gene, a pikAII gene, a pikAIII gene (12-membered rings), a pikIV gene (14-membered rings), a pikB gene cluster, a pikAV gene, a pikC gene, a pikD gene, a pikR1 gene, a pikR2 gene, or a combination thereof, is disrupted or replaced. A preferred embodiment of the invention is a host cell wherein the pikB (e.g., the desVI and desV genes), pikAI, pikAV or pikC gene, is disrupted.

Moreover, as the nucleic acid segment comprising the macrolide biosynthetic gene cluster of the invention encodes a polyketide synthase, modules of that synthase are useful in methods to prepare recombinant polyhydroxyalkanoate monomer synthases and polymers in addition to macrolide antibiotics and derivatives thereof.

Thus, the invention provides an isolated and purified DNA molecule comprising a first DNA segment encoding a first module and a second DNA segment encoding a second module, wherein the DNA segments together encode a recombinant polyhydroxyalkanoate monomer synthase, and wherein at least one DNA segment is derived from the pikA gene cluster of *Streptomyces venezuelae*. Preferably, no more than one DNA segment is derived from the eryA gene cluster of *Saccharopolyspora erythraea*. In one embodiment of the invention, the 3' most DNA segment of the isolated DNA molecule of the invention encodes a thioesterase II. Also provided is an expression cassette comprising a nucleic acid molecule encoding the polyhydroxyalkanoate monomer synthase operably linked to a promoter functional in a host cell.

Yet another embodiment of the invention is a method of providing a polyhydroxyalkanoate monomer. The method comprises introducing into a host cell a DNA molecule comprising a DNA segment encoding a recombinant polyhydroxyalkanoate monomer synthase operably linked to a promoter functional in the host cell. The recombinant polyhydroxyalkanoate monomer synthase comprises a first module and a second module, wherein at least one DNA segment is derived from the pikA gene cluster of *Streptomyces venezuelae*. The DNA encoding the recombinant polyhydroxyalkanoate monomer synthase is then expressed in the host cell so as to generate a polyhydroxyalkanoate monomer. Optionally, a a second DNA molecule may be introduced into the host cell. The second DNA molecule comprises a DNA segment encoding a polyhydroxyalkanoate synthase operably linked to a promoter functional in the host cell. The two DNA molecules are expressed in the host cell so as to generate a polyhydroxyalkanoate polymer.

Another embodiment of the invention is an isolated and purified DNA molecule comprising a first DNA segment encoding a fatty acid synthase and a second DNA segment encoding a module from the pikA gene cluster of *Streptomyces venezuelae*. Such a DNA molecule can be employed in a method of providing a polyhydroxyalkanoate monomer. Thus, a DNA molecule comprising a first DNA segment encoding a fatty acid synthase and a second DNA segment encoding a polyketide synthase is introduced into a host cell. The first DNA segment is 5' to the second DNA segment and the first DNA segment is operably linked to a promoter functional in the host cell. The first DNA segment is linked to the second DNA segment so that the linked DNA segments express a fusion protein. The DNA molecule is expressed in the host cell so as to generate a polyhydroxyalkanoate monomer.

Further provided is a method of providing a polyhydroxyalkanoate monomer synthase. The method comprises introducing an expression cassette comprising a DNA molecule encoding a polyhydroxyalkanoate synthase operably linked to a promoter functional in a host cell. The DNA molecule comprises a first DNA segment encoding a first module and a second DNA segment encoding a second module wherein the DNA segments together encode a polyhydroxyalkanoate monomer synthase. At least one DNA segment is derived from the pikA gene cluster of *Streptomyces venezuelae*. The DNA molecule is expressed in the host cell. Optionally, the DNA molecule further comprises a DNA segment encoding a polyhydroxyalkanoate synthase. Alternatively, a second, separate DNA molecule encoding a polyhydroxyalkanoate synthase is introduced into the host cell.

Also provided is a method for directing the biosynthesis of specific glycosylation-modified polyketides by genetic manipulation of a polyketide-producing microorganism. The method comprises introducing into a polyketide-producing microorganism a DNA sequence encoding enzymes in desosamine biosynthesis, e.g., a DNA sequence comprising SEQ ID NO:3, a variant or fragment thereof, so as to yield a microorganism that produces specific glycosylation-modified polyketides. Alternatively, an anti-sense DNA sequence of the invention may be employed. Then the glycosylation-modified polyketides are isolated from the microorganism. It is preferred that the DNA sequence is modified so as to result in the inactivation of at least one enzymatic activity in sugar biosynthesis or in the attachment of the sugar to a polyketide.

Thus, the modules encoded by the nucleic acid segments of the invention may be employed in the methods described hereinabove to prepare polyhydroxyalkanoates of varied chain length or having various side chain substitutions and/or to prepare glycosylated biopolymers. Therefore, the compounds produced by the recombinant host cells of the invention are useful as biopolymers, e.g., in packaging or biomedical applications, or to engineer PHA monomer synthases; pharmaceuticals such as chemotherapeutic agents, immunosuppressants, agents to treat asthma, chronic obstructive pulmonary disease as well as other diseases involving respiratory inflammation, cholesterol-lowering agents, or macrolide-based antibiotics which are active against a variety of organisms, e.g., bacteria, including multi-drug-resistant pneumococci and other respiratory pathogens, as well as viral and parasitic pathogens; or as crop protection agents (e.g., fungicides or insecticides) via expression of polyketides in plants. Methods employing these compounds, e.g., to treat a mammal, bird or fish in need of such therapy, such as a patient having a bacterial infection, are also envisioned.

As used herein, a "linker region" is an amino acid sequence present in a multifunctional protein which is less well conserved in an amino acid sequence than an amino acid sequence with catalytic activity.

As used herein, an "extender unit" catalytic or enzymatic domain is an acyl transferase in a module that catalyzes chain elongation by adding 2–4 carbon units to an acyl chain and is located carboxy-terminal to another acyl transferase. For example, an extender unit with methylmalonylCoA specificity adds acyl groups to a methylmalonylCoA molecule.

As used herein, a "polyhydroxyalkanoate" or "PHA" polymer includes, but is not limited to, linked units of related, preferably heterologous, hydroxyalkanoates such as 3-hydroxybutyrate, 3-hydroxyvalerate, 3-hydroxycaproate, 3-hydroxyheptanoate, 3-hydroxyhexanoate, 3-hydroxyoctanoate, 3-hydroxyundecanoate, and 3-hydroxydodecanoate, and their 4-hydroxy and 5-hydroxy counterparts.

As used herein, a "Type I polyketide synthase" is a single polypeptide with a single set of iteratively used active sites. This is in contrast to a Type II polyketide synthase which employs active sites on a series of polypeptides.

As used herein, a "recombinant" nucleic acid or protein molecule is a molecule where the nucleic acid molecule which encodes the protein has been modified in vitro, so that its sequence is not naturally occurring, or corresponds to naturally occurring sequences that are not positioned as they would be positioned in a genome which has not been modified.

A "recombinant" host cell of the invention has a genome that has been manipulated in vitro so as to alter, e.g., decrease or disrupt, or, alternatively, increase, the function or activity of at least one gene in the macrolide or desosamine biosynthetic gene cluster of the invention.

As used herein, a "multifunctional protein" is one where two or more enzymatic activities are present on a single polypeptide.

As used herein, a "module" is one of a series of repeated units in a multifunctional protein, such as a Type I polyketide synthase or a fatty acid synthase.

As used herein, a "premature termination product" is a product which is produced by a recombinant multifunctional protein which is different than the product produced by the non-recombinant multifunctional protein. In general, the product produced by the recombinant multifunctional protein has fewer acyl groups.

As used herein, a DNA that is "derived from" a gene cluster is a DNA that has been isolated and purified in vitro from genomic DNA, or synthetically prepared on the basis of the sequence of genomic DNA.

As used herein, the pik gene cluster includes sequences encoding a polyketide synthase (pikA), desosamine biosynthetic enzymes (pikB, also referred to as des), a cytochrome P450 (pikC), regulatory factors (pikD) and enzymes for cellular self-resistance (pikR).

As used herein, the terms "isolated and/or purified" refer to in vitro isolation of a DNA or polypeptide molecule from its natural cellular environment, and from association with other components of the cell, such as nucleic acid or polypeptide, so that is can be sequenced, replicated and/or expressed. Moreover, the DNA may encode more than one recombinant Type I polyketide synthase and/or fatty acid synthase. For example, "an isolated DNA molecule encoding a polyhydroxyalkanoate monomer synthase" is RNA or DNA containing greater than 7, preferably 15, and more preferably 20 or more sequential nucleotide bases that encode a biologically active polypeptide, fragment, or variant thereof, that is complementary to the non-coding, or complementary to the coding strand, of a polyhydroxyalkanoate monomer synthase RNA, or hybridizes to the RNA or DNA encoding the polyhydroxyalkanoate monomer synthase and remains stably bound under stringent conditions, as defined by methods well known to the art, e.g., in Sambrook et al., supra.

An "antibiotic" as used herein is a substance produced by a microorganism which, either naturally or with limited chemical modification, will inhibit the growth of or kill another microorganism or eukaryotic cell.

An "antibiotic biosynthetic gene" is a nucleic acid, e.g., DNA, segment or sequence that encodes an enzymatic activity which is necessary for an enzymatic reaction in the process of converting primary metabolites into antibiotics.

An "antibiotic biosynthetic pathway" includes the entire set of antibiotic biosynthetic genes necessary for the process of converting primary metabolites into antibiotics. These genes can be isolated by methods well known to the art, e.g., see U.S. Pat. No. 4,935,340.

Antibiotic-producing organisms include any organism, including, but not limited to, Actinoplanes, Actinomadura, Bacillus, Cephalosporium, Micromonospora, Penicillium, Nocardia, and Streptomyces, which either produces an antibiotic or contains genes which, if expressed, would produce an antibiotic.

An antibiotic resistance-conferring gene is a DNA segment that encodes an enzymatic or other activity which confers resistance to an antibiotic.

The term "polyketide" as used herein refers to a large and diverse class of natural products, including but not limited to antibiotic, antifungal, anticancer, and anti-helminthic compounds. Antibiotics include, but are not limited to anthracyclines and macrolides of different types (polyenes and avermectins as well as classical macrolides such as erythromycins). Macrolides are produced by, for example, *S. erytheus, S. antibioticus, S. venezuelae, S. fradiae* and *S. narbonensis.*

The term "glycosylated polyketide" refers to any polyketide that contains one or more sugar residues.

The term "glycosylation-modified polyketide" refers to a polyketide having a changed glycosylation pattern or configuration relative to that particular polyketide's unmodified or native state.

The term "polyketide-producing microorganism" as used herein includes any microorganism that can produce a polyketide naturally or after being suitably engineered (i.e., genetically). Examples of actinomycetes that naturally produce polyketides include but are not limited to *Micromonospora rosaria, Micromonospora megalomicea, Saccharopolyspora erythraea, Streptomyces antibioticus, Streptomyces albereticuli, Streptomyces ambofaciens, Streptomyces avermitilis, Streptomycesfradiae, Streptomyces griseus, Streptomyces hydroscopicus, Streptomyces tsukulubaensis, Streptomyces mycarofasciens, Streptomyces platenesis, Streptomycesviolaceoniger, Streptomyces violaceoniger, Streptomyces thermotolerans, Streptomyces rimosus, Streptomyces peucetius, Streptomyces coelicolor, Streptomyces glaucescens, Streptomyces roseofulvus, Streptomyces cinnamonensis, Streptomyces curacoi, and Amycolatopsis mediterranei* (see Hopwood, D. A. and Sherman, D. H., *Annu. Rev. Genet.*, 24:37–66 (1990), incorporated herein by reference). Other examples of polyketide-producing microorganisms that produce polyketides naturally include various Actinomadura, Dactylosporangium and Nocardia strains.

The term "sugar biosynthesis genes" as used herein refers to nucleic acid sequences from organisms such as *Streptomyces venezuelae* that encode sugar biosynthesis enzymes and is intended to include sequences of DNA from other polyketide-producing microorganisms which are identical or analogous to those obtained from *Streptomyces venezuelae.*

The term "sugar biosynthesis enzymes" as used herein refers to polypeptides which are involved in the biosynthesis and/or attachment of polyketide-associated sugars and their derivatives and intermediates.

The term "polyketide-associated sugar" refers to a sugar that is known to attach to polyketides or that can be attached to polyketides by the processes described herein.

The term "sugar derivative" refers to a sugar which is naturally associated with a polyketide but which is altered relative to the unmodified or native state, including but not limited to, N-3-α-desdimethyl D-desosamine.

The term "sugar intermediate" refers to an intermediate compound produced in a sugar biosynthesis pathway.

BRIEF DESCRIPTION OF THE FIGURES

FIG. 2. Molecular structure of common bacterial PHAs. Most of the known PHAs are polymers of 3-hydroxy acids possessing the general formula shown. For example, $R=CH_3$ in PHB, $T=CH_2CH_3$ in polyhydroxyvalerate (PHV), and $R=(CH_2)_4CH_3$ in polyhydroxyoctanoate (PHO).

FIG. 6. Strategy for producing a recombinant PHA monomer synthase by domain replacement.

FIG. 8. N-terminal analysis of PHA synthase purified from insect cells. (a) The expected N-terminal 25 amino acid sequence of *A. eutrophus* PHA synthase. (b&c) The two N-terminal sequences determined for the *A. eutrophus* PHA synthase produced in insect cells. The bolded sequences are the actual N-termini determined.

DETAILED DESCRIPTION OF THE INVENTION

Figure 1:
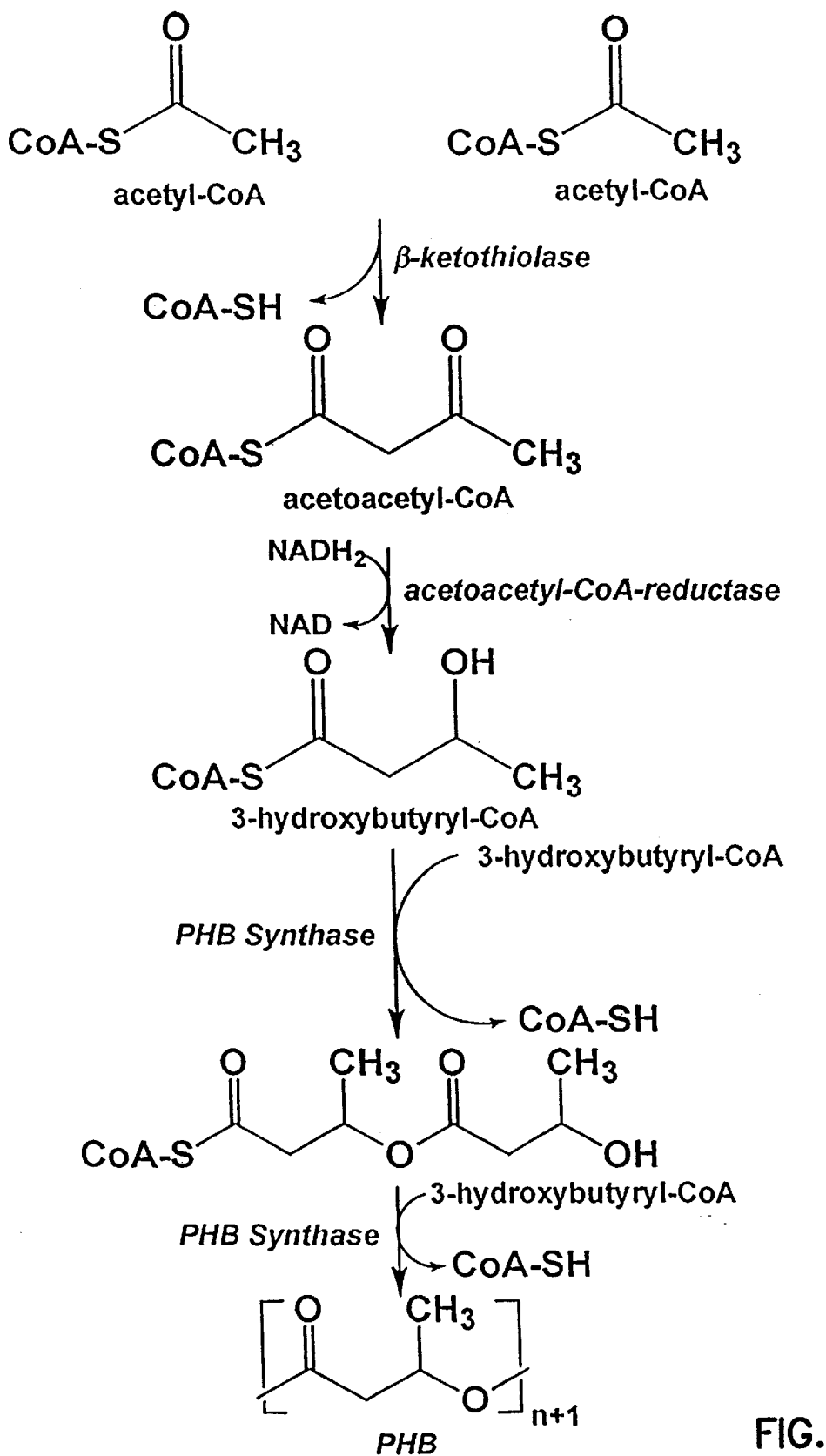
FIG. 1. The PHB biosynthetic pathway in *A. eutrophus.*
Figure 3:
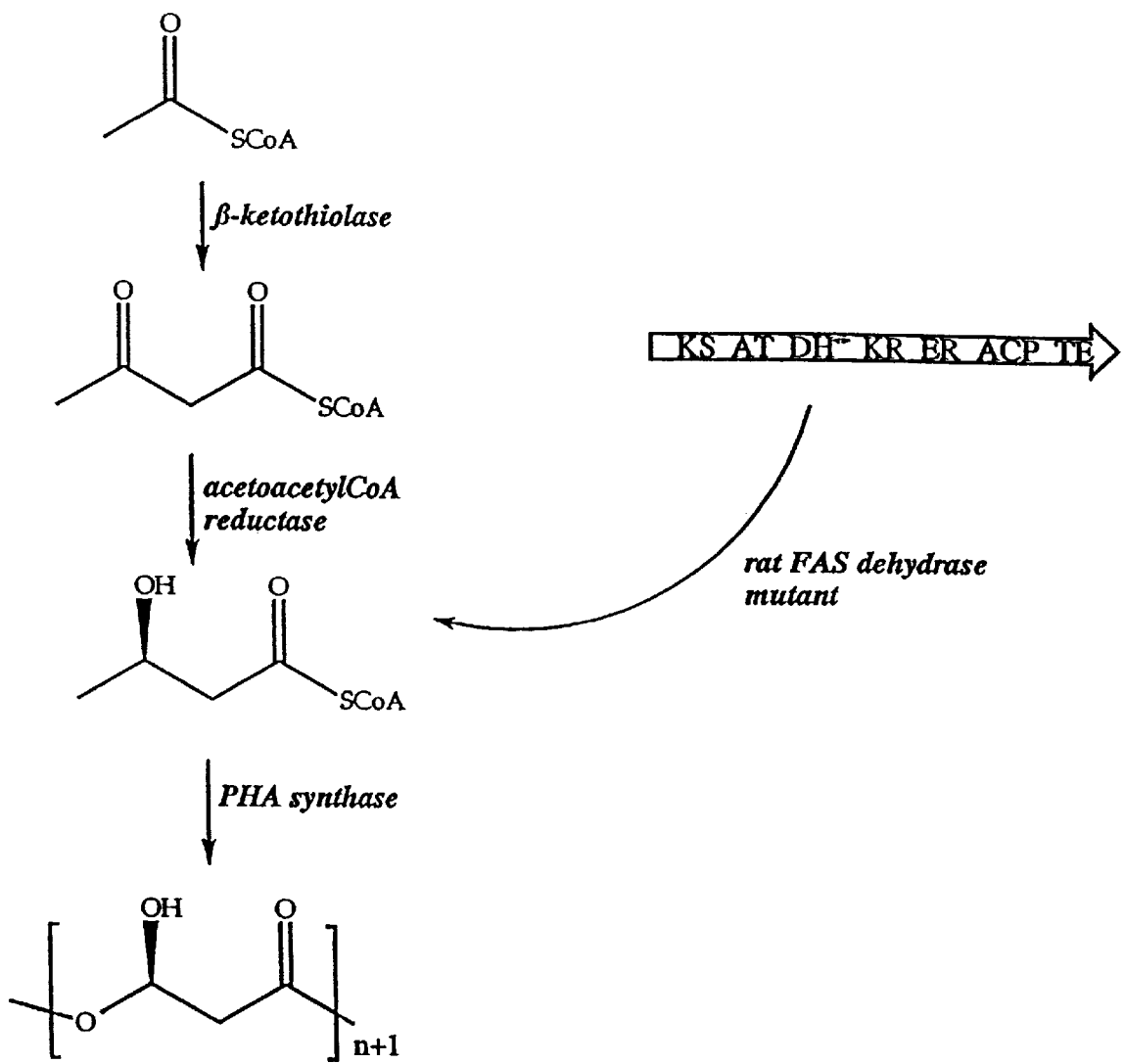
FIG. 3. Comparison of the natural and recombinant pathways for PHB synthesis. The three enzymatic steps of PHB synthesis in bacteria involving 3-ketothiolase, acetoacetyl-CoA reductase, and PHB synthase are shown on the left. The two enzymatic steps involved in PHB synthesis in the pathway in Sf21 cells containing a rat fatty acid synthase with an inactivated dehydrase domain (ratFAS206) are shown on the right.

The invention described herein can be used for the production of a diverse range of biodegradable PHA polymers through genetic redesign of DNA encoding a FAS or a PKS such as that found in Streptomyces spp. Type I PKS polypeptide to provide a recombinant PHA monomer synthase. Different PHA synthases can then be tested for their ability to polymerize the monomers produced by the recombinant PHA synthase into a biodegradable polymer. The invention also provides a method by which various PHA synthases can be tested for their specificity with respect to different monomer substrates.

The potential uses and applications of PHAs produced by PHA monomer synthases and PHA synthases include both medical and industrial applications. Medical applications of PHAs include surgical pins, sutures, staples, swabs, wound dressings, blood vessel replacements, bone replacements and plates, stimulation of bone growth by piezoelectric properties, and biodegradable carrier for long-term dosage of pharmaceuticals. Industrial applications of PHAs include disposable items such as baby diapers, packaging containers, bottles, wrappings, bags, and films, and biodegradable carriers for long-term dosage of herbicides, fungicides, insecticides, or fertilizers.

In animals, the biosynthesis of fatty acids de novo from malonyl-CoA is catalyzed by FAS. For example, the rat FAS is a homodimer with a subunit structure consisting of 2505 amino acid residues having a molecular weight of 272,340 Da. Each subunit consists of seven catalytic activities in separate physical domains (Amy et al., *Proc. Natl. Acad. Sci. USA*, 86, 3114 (1989)). The physical location of six of the catalytic activities, ketoacyl synthase (KS), malonyl/acetyltransferase (M/AT), enoyl reductase (ER), ketoreductase (KR), acyl carrier protein (ACP), and thioesterase (TE), has been established by (1) the identification of the various active site residues within the overall amino acid sequence by isolation of catalytically active fragments from limited proteolytic digests of the whole FAS, (2) the identification of regions within the FAS that exhibit sequence similarity with various monofunctional proteins, (3) expression of DNA encoding an amino acid sequence with catalytic activity to produce recombinant proteins, and (4) the identification of DNA that does not encode catalytic activity, i.e., DNA encoding a linker region. (Smith et al., *Proc. Natl. Acad. Sci. USA*, 73, 1184 (1976); Tsukamoto et al., *J. Biol. Chem.*, 263, 16225 (1988); Rangan et al., *J. Biol. Chem.*, 266, 19180 (1991)).

The seventh catalytic activity, dehydrase (DH), was identified as physically residing between AT and ER by an amino acid comparison of FAS with the amino acid sequences encoded by the three open reading frames of the eryA polyketide synthase (PKS) gene cluster of *Saccharopolyspora erythraea*. The three polypeptides that comprise this PKS are constructed from "modules" which resemble animal FAS, both in terms of their amino acid sequence and in the ordering of the constituent domains (Donadio et al., *Gene*, 111, 51 (1992); Benh et al., *Eur. J. Biochem.*, 204, 39 (1992)).

One embodiment of the invention employs a FAS in which the DH is inactivated (FAS DH-). The FAS DH- employed in this embodiment of the invention is preferably a eukaryotic FAS DH- and, more preferably, a mammalian FAS DH-. The most preferred embodiment of the invention is a FAS where the active site in the DH has been inactivated by mutation. For example, Joshi et al. (*J. Biol. Chem.*, 268, 22508 (1993)) changed the His$^{878}$ residue in the rat FAS to an alanine residue by site-directed mutagenesis. In vitro studies showed that a FAS with this change (ratFAS206) produced 3-hydroxybutyrylCoA as a premature termination product from acetyl-CoA, malonyl-CoA and NADPH.

As shown below, a FAS DH- effectively replaces the β-ketothiolase and acetoacetyl-CoA reductase activities of the natural pathway by producing D(-)-3-hydroxybutyrate as a premature termination product, rather than the usual 16-carbon product, palmitic acid. This premature termination product can then be incorporated into PHB by a PHB synthase (See Example 2).

Another embodiment of the invention employs a recombinant Streptomyces spp. PKS to produce a variety of β-hydroxyCoA esters that can serve as monomers for a PHA synthase. One example of a DNA encoding a Type I PKS is the eryA gene cluster, which governs the synthesis of erythromycin aglycone deoxyerythronolide B (DEB). The gene cluster encodes six repeated units, termed modules or synthase units (SUs). Each module or SU, which comprises a series of putative FAS-like activities, is responsible for one of the six elongation cycles required for DEB formation. Thus, the processive synthesis of asymmetric acyl chains found in complex polyketides is accomplished through the use of a programmed protein template, where the nature of the chemical reactions occurring at each point is determined by the specificities in each SU.

Two other Type I PKS are encoded by the tyl (tylosin) (FIG. 4) and met (methymycin) (FIG. 5) gene clusters. The macrolide multifunctional synthases encoded by tyl and met provide a greater degree of metabolic diversity than that found in the eryA gene cluster. The PKSs encoded by the eryA gene cluster only catalyze chain elongation with methylmalonylCoA, as opposed to tyl and met PKSs, which catalyze chain elongation with malonylCoA, methylmalonylCoA and ethylmalonylCoA. Specifically, the tyl PKS includes two malonylCoA extender units and one ethylmalonylCoA extender unit, and the met PKS includes one malonylCoA extender unit. Thus, a preferred embodiment of the invention includes, but is not limited to, replacing catalytic activities encoded in met PKS open reading frame 1 (ORF1) to provide a DNA encoding a protein that possesses the required keto group processing capacity and short-chain acylCoA ester starter and extender unit specificity necessary to provide a saturated β-hydroxyhexanoylCoA or unsaturated β-hydroxyhexenoylCoA monomer.

In order to manipulate the catalytic specificities within each module, DNA encoding a catalytic activity must remain undisturbed. To identify the amino acid sequences between the amino acid sequences with catalytic activity, the "linker regions," amino acid sequences of related modules, preferably those encoded by more than one gene cluster, are compared. Linker regions are amino acid sequences which are less well conserved than amino acid sequences with catalytic activity. Witkowski et al., *Eur. J. Biochem.*, 19, 571 (1991).

In an alternative embodiment of the invention, to provide a DNA encoding a Type I PKS module with a TE and lacking a functional DH, a DNA encoding a module F, containing KS, MT, KR, ACP, and TE catalytic activities, is introduced at the 3' end of a DNA encoding a first module (FIG. 6). Module F introduces the final (R)-3-hydroxyl acyl group at the final step of PHA monomer synthesis, as a result of the presence of a TE domain. DNA encoding a module F is not present in the eryA PKS gene cluster (Donadio et al., supra, 1991).

A DNA encoding a recombinant monomer synthase is inserted into an expression vector. The expression vector employed varies depending on the host cell to be transformed with the expression vector. That is, vectors are employed with transcription, translation and/or post-translational signals, such as targeting signals, necessary for efficient expression of the genes in various host cells into which the vectors are introduced. Such vectors are constructed and transformed into host cells by methods well known in the art. See Sambrook et al., *Molecular Cloning: A Laboratory Manual*, Cold Spring Harbor (1989). Preferred host cells for the vectors of the invention include insect, bacterial, and plant cells. Preferred insect cells include *Spodoptera frugiperda* cells such as Sf21, and *Trichoplusia* ni cells. Preferred bacterial cells include *Escherichia coli*, Streptomyces and Pseudomonas. Preferred plant cells include monocot and dicot cells, such as maize, rice, wheat, tobacco, legumes, carrot, squash, canola, soybean, potato, and the like.

Moreover, the appropriate subcellular compartment in which to locate the enzyme in eukaryotic cells must be considered when constructing eukaryotic expression vectors. Two factors are important: the site of production of the acetyl-CoA substrate, and the available space for storage of the PHA polymer. To direct the enzyme to a particular subcellular location, targeting sequences may be added to the sequences encoding the recombinant molecules.

The baculovirus system is particularly amenable to the introduction of DNA encoding a recombinant FAS or a PKS monomer synthase because an increasing variety of transfer plasmids are becoming available which can accommodate a large insert, and the virus can be propagated to high titers. Moreover, insect cells are adapted readily to suspension culture, facilitating relatively large-scale recombinant protein production. Further, recombinant proteins tend to be produced exclusively as soluble proteins in insect cells, thus, obviating the need for refolding, a task that might be particularly daunting in the case of a large multifunctional protein. The Sf21/baculovirus system has routinely expressed milligram quantities of catalytically active recombinant fatty acid synthase. Finally, the baculovirus/insect cell system provides the ability to construct and analyze different synthase proteins for the ability to polymerize monomers into unique biodegradable polymers.

A further embodiment of the invention is the introduction of at least one DNA encoding a PHA synthase and a DNA encoding a PHA monomer synthase into a host cell. Such synthases include, but are not limited to, *A. eutrophus* 3-hydroxy, 4-hydroxy, and 5-hydroxy alkanoate synthases, *Rhodococcus ruber* $C_3-C_5$ hydroxyalkanoate synthases, *Pseudomonas oleororans* $C_6-C_{14}$ hydroxyalkanoate synthases, *P. putida* $C_6-C_{14}$ hydroxyalkanoate synthases, *P. aeruginosa* $C_5-C_{10}$ hydroxyalkanoate synthases, *P. resinovorans* $C_4-C_{10}$ hydroxyalkanoate synthases, *Rhodospirillum rubrum* $C_4-C_7$ hydroxyalkanoate syntheses, *R. gelatinorus* $C_4-C_7$, *Thiocapsa pfennigii* $C_4-C_8$ hydroxyalkanoate synthases, and *Bacillus megaterium* $C_4-C_5$ hydroxyalkanoate synthases.

The introduction of DNA(S) encoding more than one PHA synthase may be necessary to produce a particular PHA polymer due to the specificities exhibited by different PHA synthases. As multifunctional proteins are altered to produce unusual monomeric structures, synthase specificity may be problematic for particular substrates. Although the *A. eutrophus* PHB synthase utilizes only C4 and C5 compounds as substrates, it appears to be a good prototype synthase for initial studies since it is known to be capable of producing copolymers of 3-hydroxybutyrate and 4-hydroxybutyrate (Kunioka et al., *Macromolecules*, 22, 694 (1989)) as well as copolymers of 3-hydroxyvalerate, 3-hydroxybutyrate, and 5-hydroxyvalerate (Doi et al., *Macromolecules*, 19, 2860 (1986)). Other synthases, especially those of *Pseudomonas aeruginosa* (Timm et al., *Eur. J. Biochem.*, 209, 15 (1992)) and *Rhodococcus ruber* (Pieper et al., *FEMS Microbiol. Lett.*, 96, 73 (1992)), can also be employed in the practice of the invention. Synthase specificity may be alterable through molecular biological methods.

In yet another embodiment of the invention, a DNA encoding a FAS and a PHA synthase can be introduced into a single expression vector, obviating the need to introduce the genes into a host cell individually.

A further embodiment of the invention is the generation of a DNA encoding a recombinant multifunctional protein, which comprises a FAS, of either eukaryotic or prokaryotic origin, and a PKS module F. Module F will carry out the final chain extension to include two additional carbons and the reduction of the β-keto group, which results in a (R)-3-hydroxy acyl CoA moiety.

To produce this recombinant protein, DNA encoding the FAS TE is replaced with a DNA encoding a linker region which is normally found in the ACP-KS interdomain region of bimodular ORFs. DNA encoding a module F is then inserted 3' to the DNA encoding the linker region. Different linker regions, such as those described below which vary in length and amino acid composition, can be tested to determine which linker most efficiently mediates or allows the required transfer of the nascent saturated fatty acid intermediate to module F for the final chain elongation and keto reduction steps. The resulting DNA encoding the protein can then be tested for expression of long-chain β-hydroxy fatty acids in insect cells, such as Sf21 cells, or Streptomyces, or Pseudomonas. The expected 3-hydroxy C-18 fatty acid can serve as a potential substrate for PHA synthases which are able to accept long-chain alkyl groups. A preferred embodiment of the invention is a FAS that has a chain length specificity between 4–22 carbons.

Examples of linker regions that can be employed in this embodiment of the invention include, but are not limited to, the ACP-KS linker regions encoded by the tyl ORFI ($ACP_1$-$KS_2$; $ACP_2$-$KS_3$), and ORF3 ($ACP_1$-$KS_6$), and eryA ORFI ($ACP_1$-$KS_1$; $ACP_2$-$KS_2$), ORF2 ($ACP_3$-$KS_4$) and ORF3 ($ACP_1$-$KS_6$).

This approach can also be used to produce shorter chain fatty acid groups by limiting the ability of the FAS unit to generate long-chain fatty acids. Mutagenesis of DNA encoding various FAS catalytic activities, starting with the KS, may result in the synthesis of short-chain (R)-3-hydroxy fatty acids.

The PHA polymers are then recovered from the biomass. Large-scale solvent extraction can be used, but is expensive. An alternative method involving heat shock with subsequent enzymatic and detergent digestive processes is also available (Byron, *Trend Biotechnical*, 5, 246 (1987); Holmes, In: *Developments in Crystalline Polymers*, D. C. Bassett (ed.), pp. 1–65 (1988)). PHB and other PHAs are readily extracted from microorganisms by chlorinated hydrocarbons. Refluxing with chloroform has been extensively used; the resulting solution is filtered to remove debris and concentrated, and the polymer is precipitated with methanol or ethanol, leaving low-molecular-weight lipids in solution. Longer side-chain PHAs show a less restricted solubility than PHB and are, for example, soluble in acetone. Other strategies adopted include the use of ethylene carbonate and propylene carbonate as disclosed by Lafferty et al. (*Chem. Rundschau*, 30, 14 (1977)) to extract PHB from biomass. Scandola et al. (*Int. J. Biol. Microbiol.*, 10, 373 (1988)) reported that 1 M HCl-chloroform extraction of *Rhizobium meliloti* yielded PHB of $M_W=6\times10^4$ compared with $1.4\times10^6$ when acetone was used.

Methods are well known in the art for the determination of the PHB or PHA content of microorganisms, the composition of PHAs, and the distribution of the monomer units in the polymer. Gas chromatography and high-pressure liquid chromatography are widely used for quantitative PHB analysis. See Anderson et al., *Microbiol. Rev.*, 54, 450 (1990) for a review of such methods. NMR techniques can also be used to determine polymer composition, and the distribution of monomer units.

Figures 9, 31:
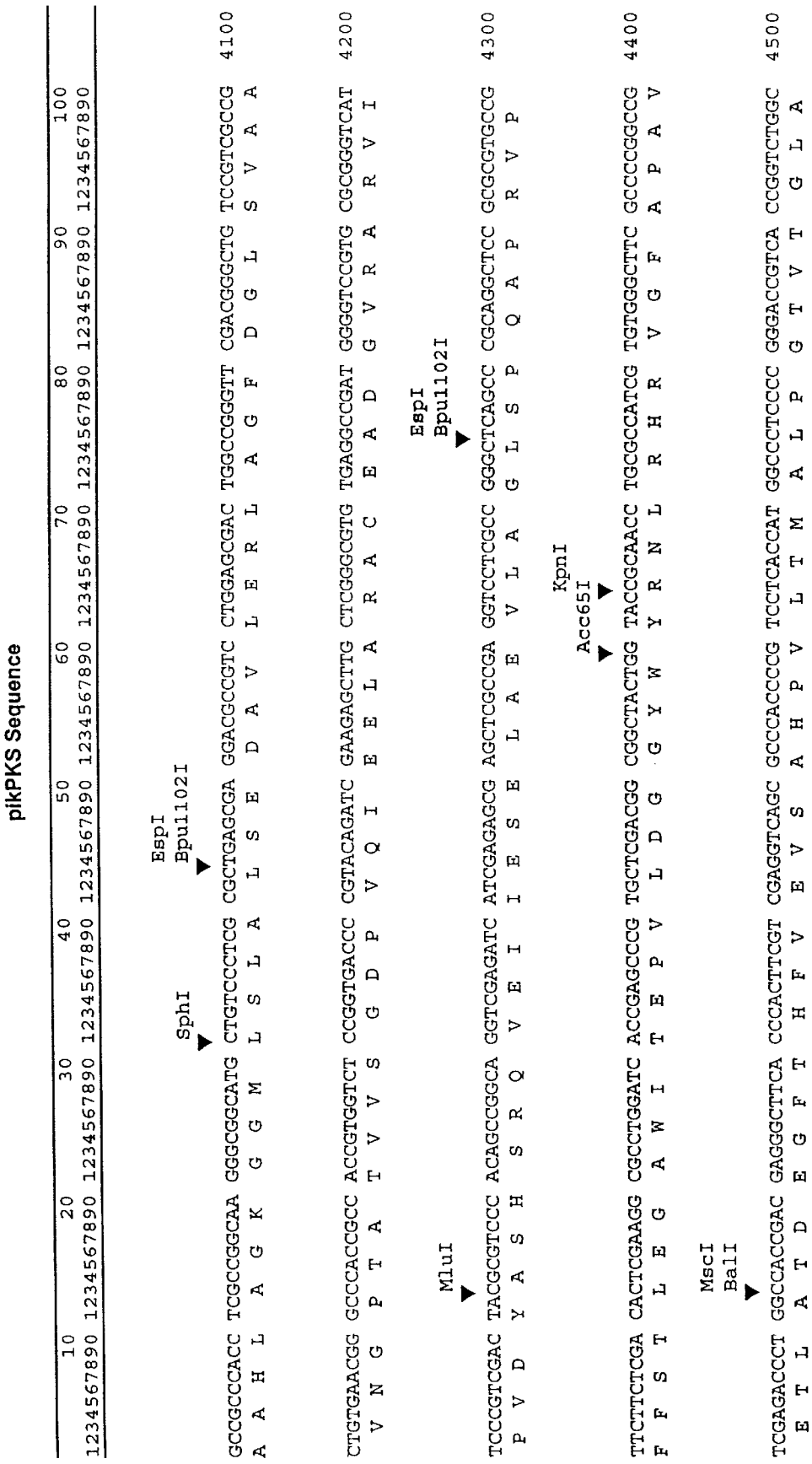
FIG. 31. Nucleotide sequence (SEQ ID NO:5) and inferred amino acid sequence (SEQ ID NO:6) of the pik gene cluster.
Figures 10, 31:
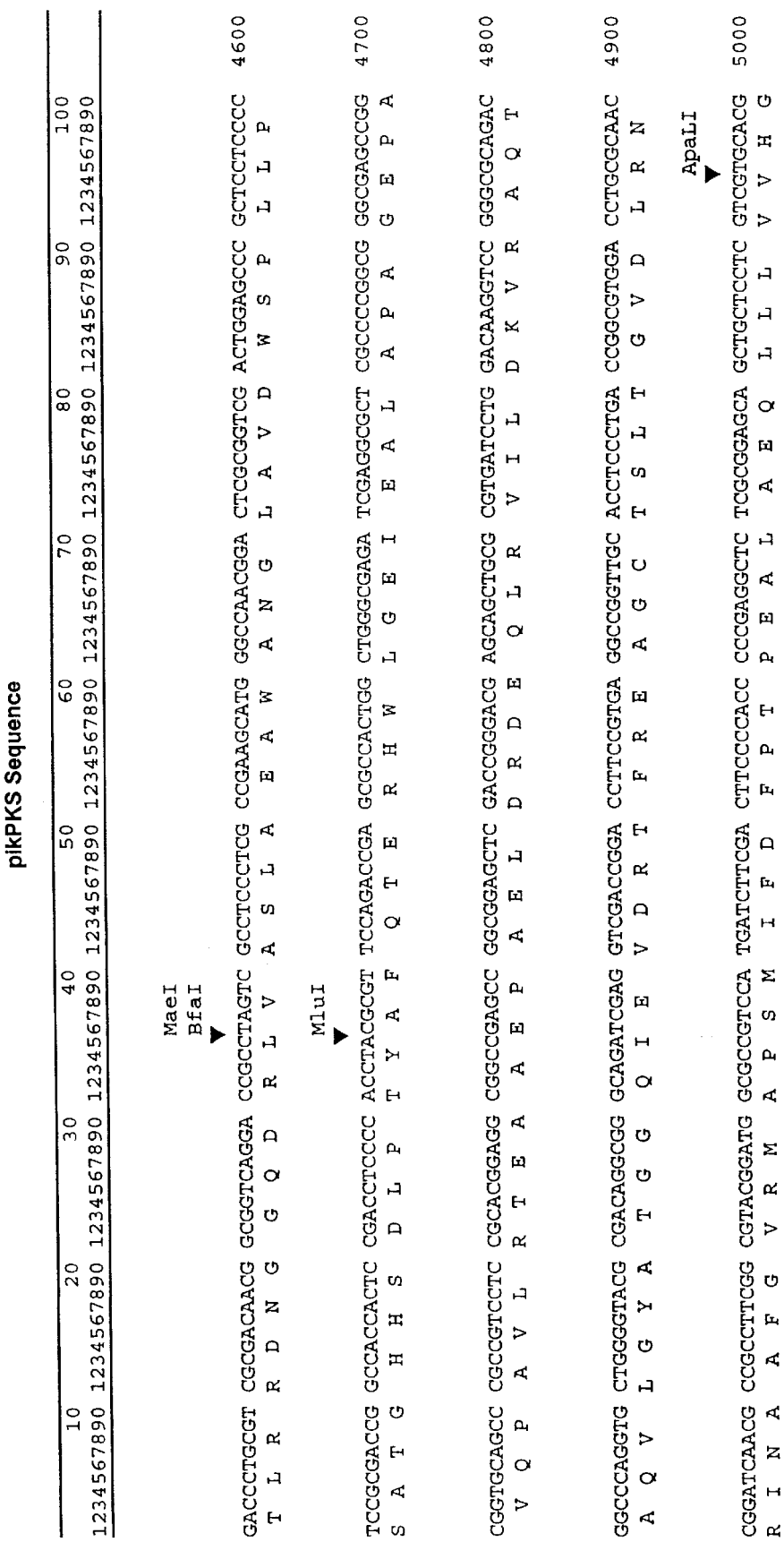
Figures 13, 31:
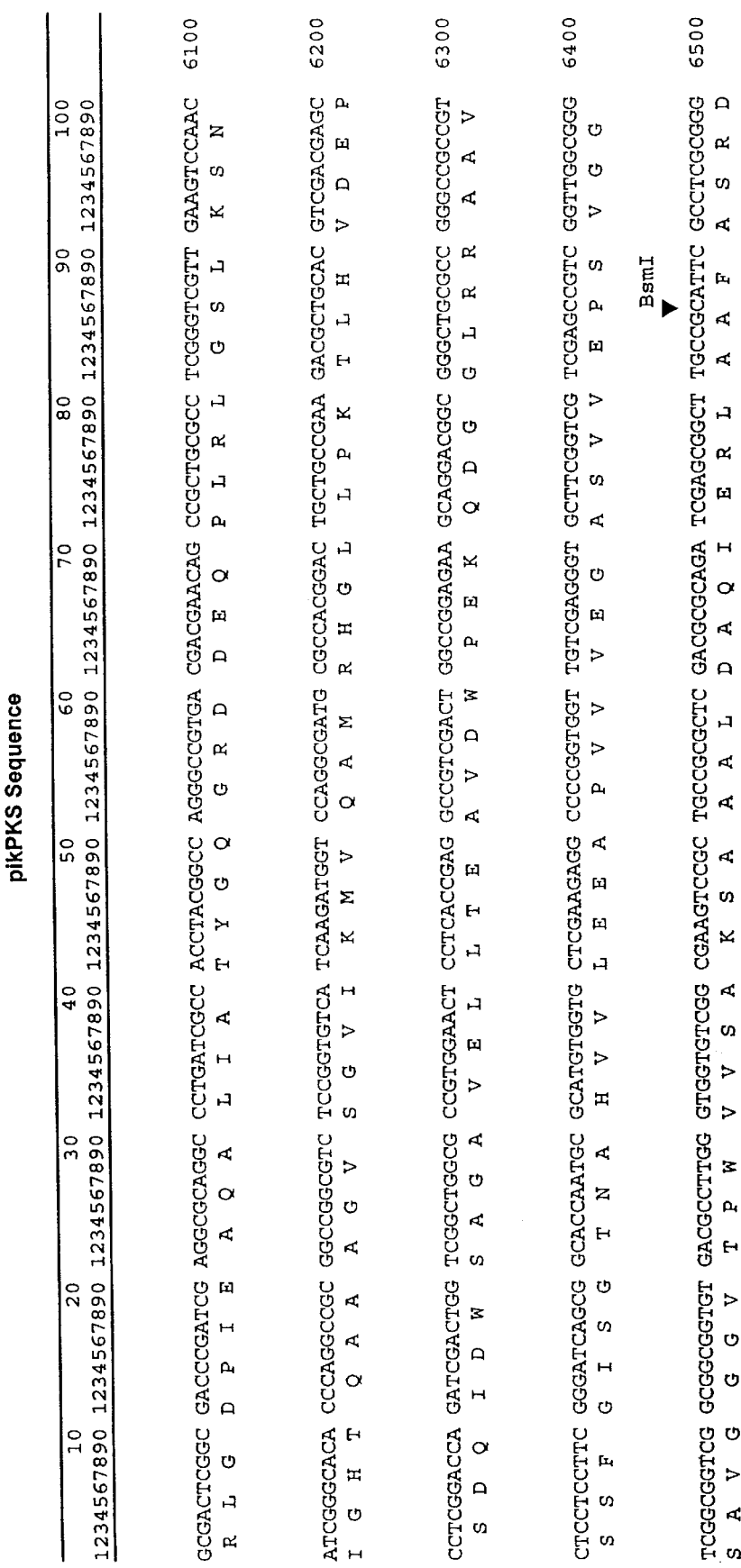
Figures 20, 31:
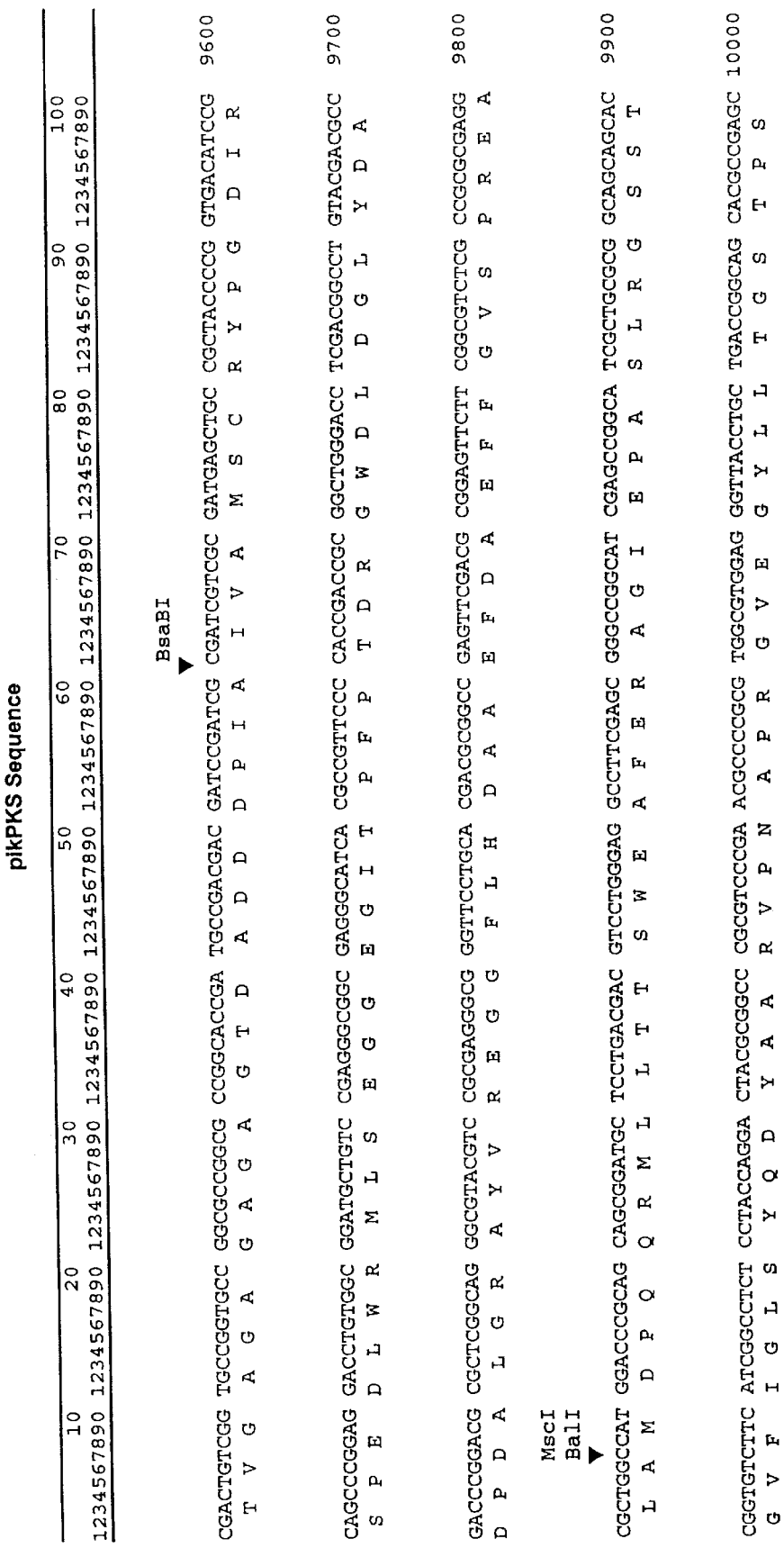
Figures 21, 31:
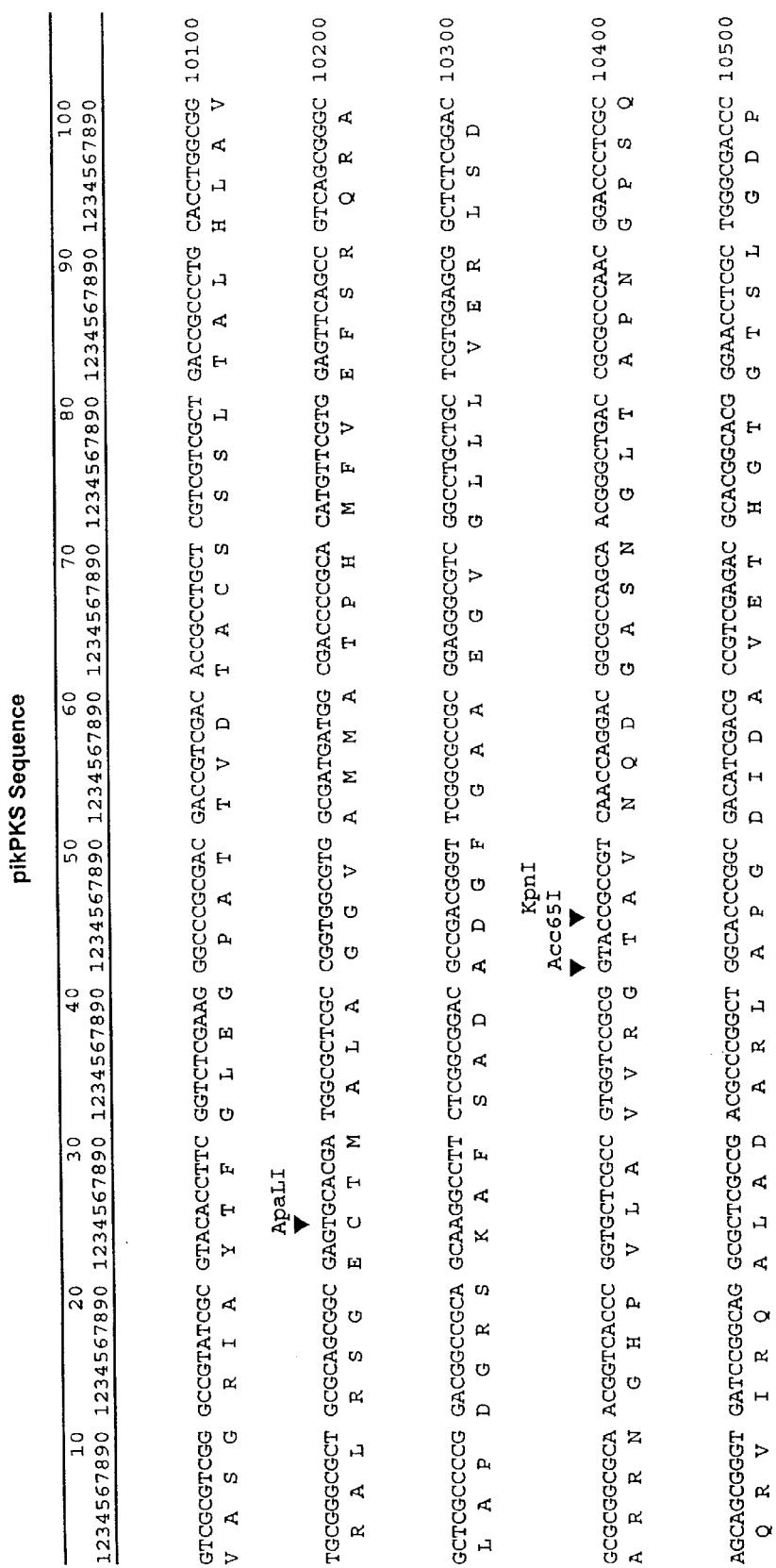
Figures 27, 31:
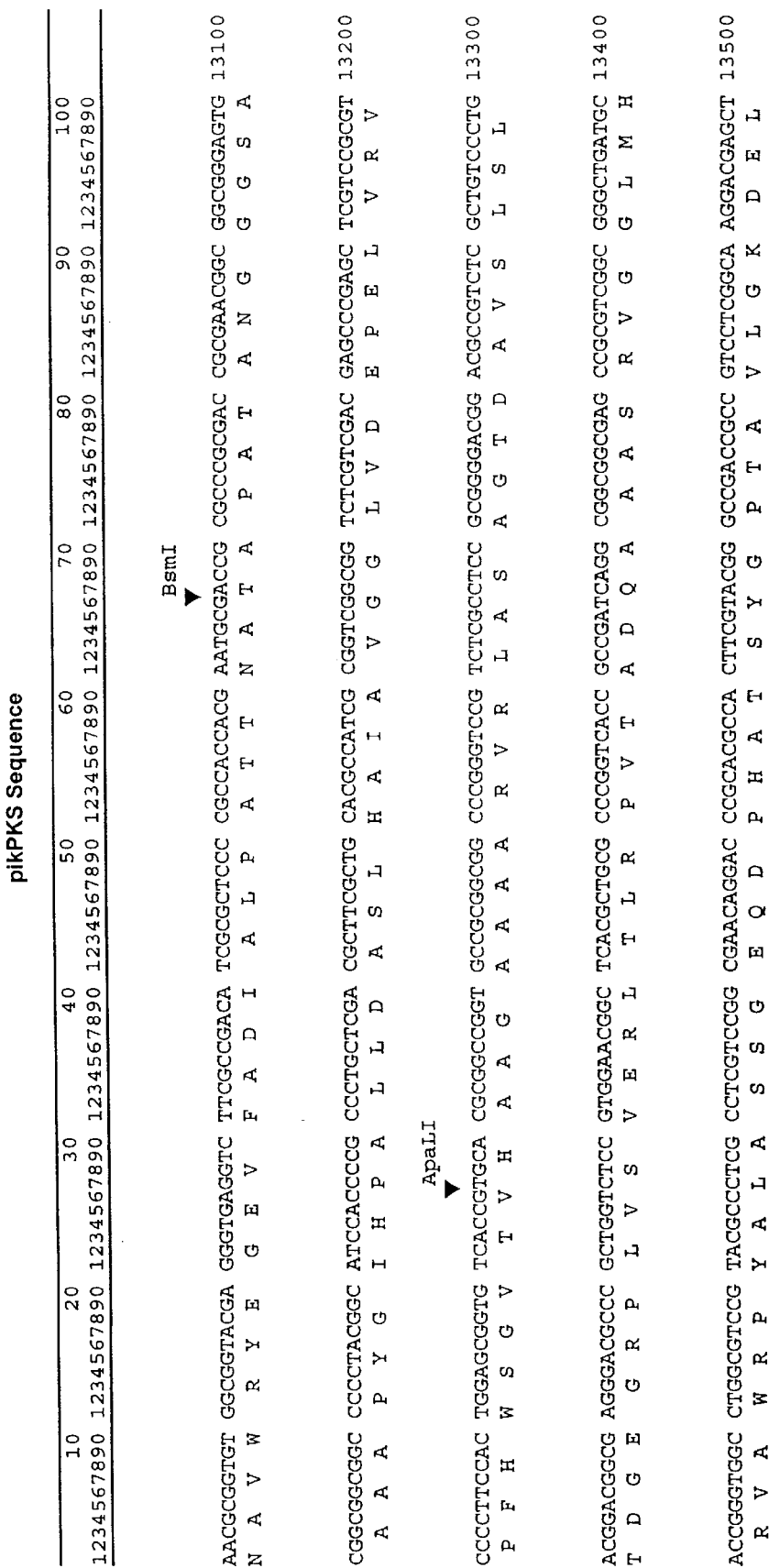
Figures 28, 31:
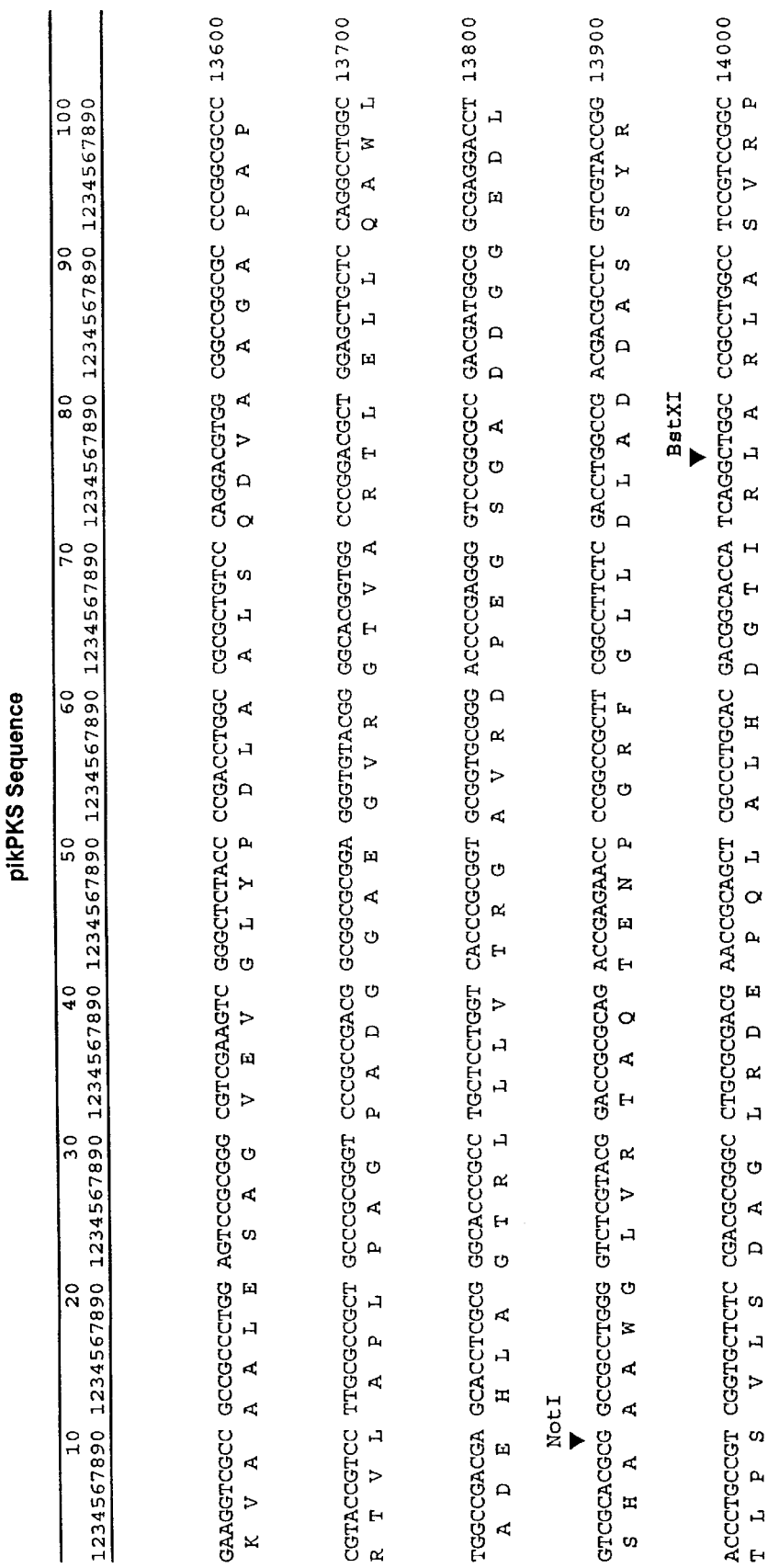
Figures 30, 31:
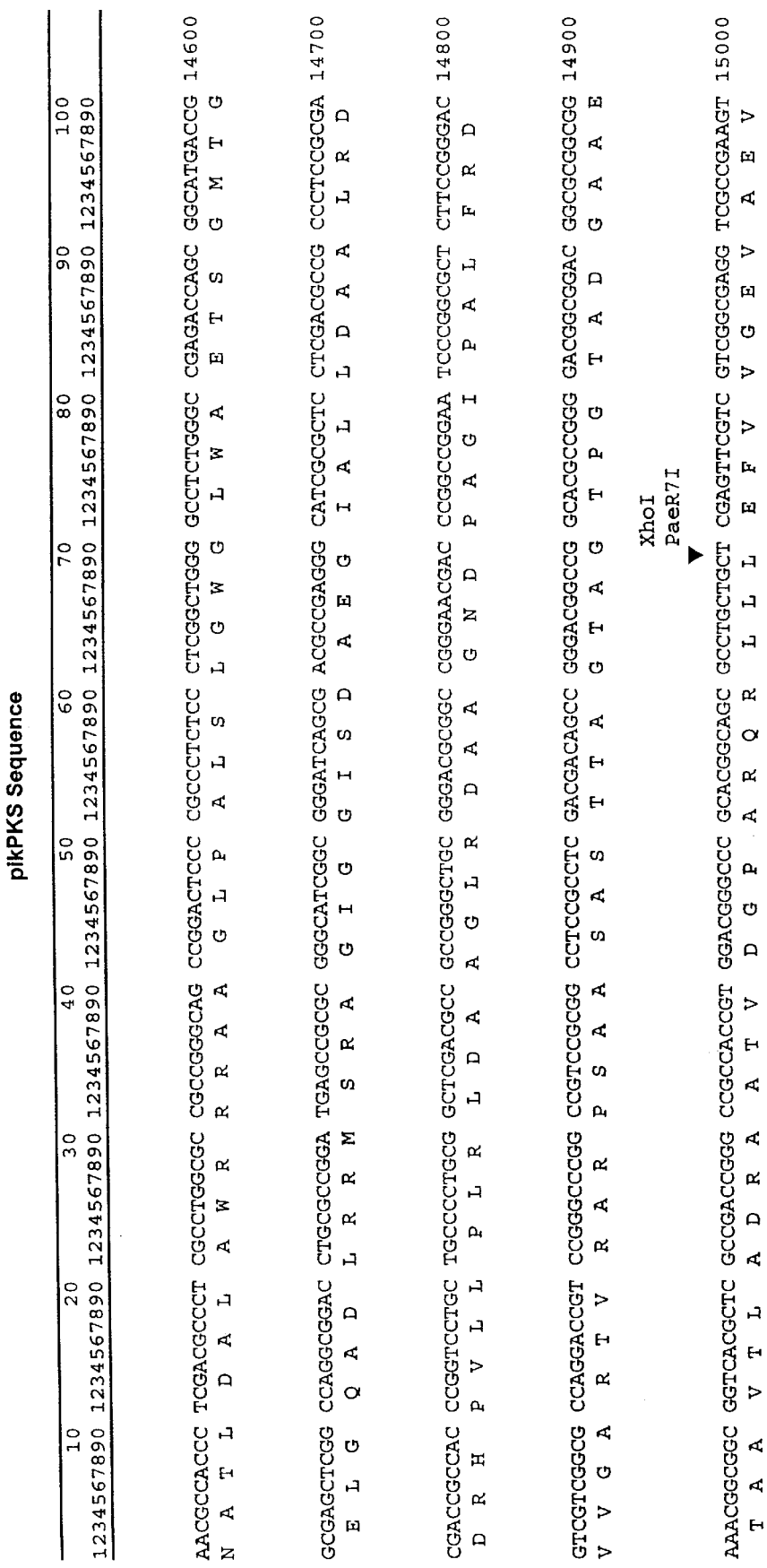
Figures 31, 32, 33:
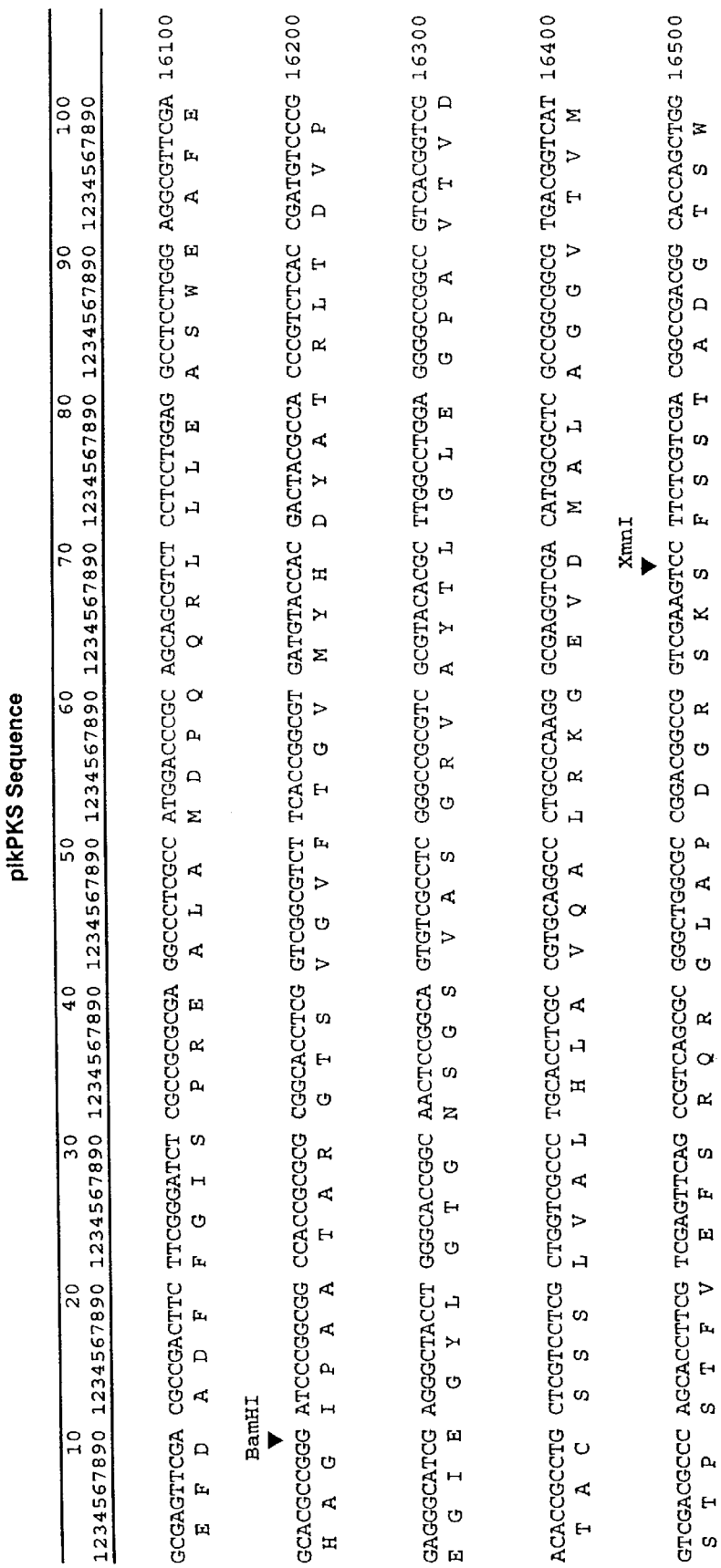
FIG. 32. Nucleotide sequence (SEQ ID NO:3) and inferred amino acid sequence (SEQ ID NO:4) of the desosamine gene cluster.
FIG. 33. *S. venezuelae* AX916 construct useful to prepare a polyketide having a shorter chain length compared to wild-type pikA. pik module 2 is fused to pik module 5, and module 3 and 4 are deleted, so as to encode a three module PKS which produces two macrolides, a triketide and a tetraketide.
Figures 31, 32, 33, 34:
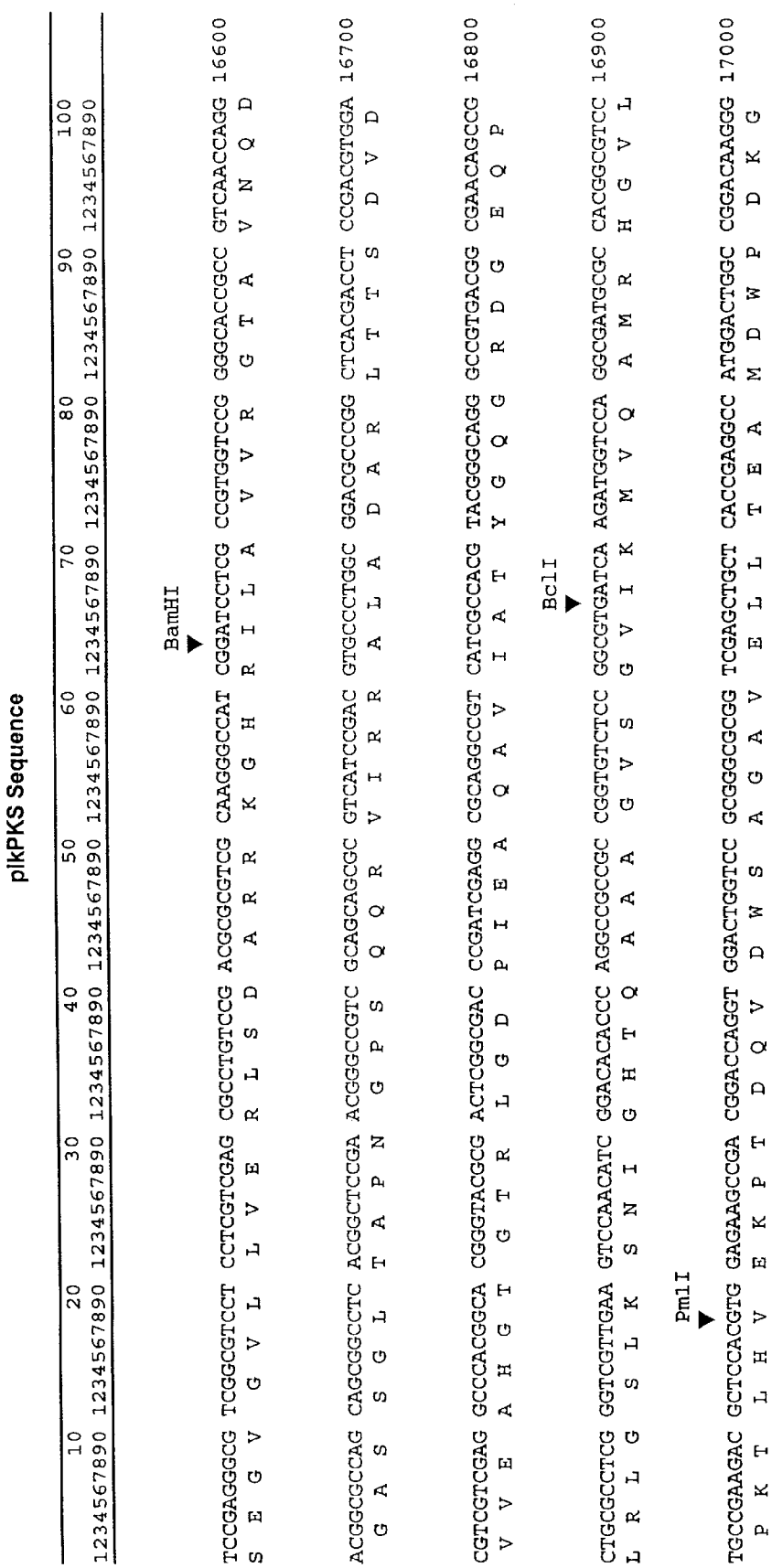
FIG. 34. Recombinant PiKS having a wild-type thioesterase II.
Figures 31, 32, 33, 34, 35:
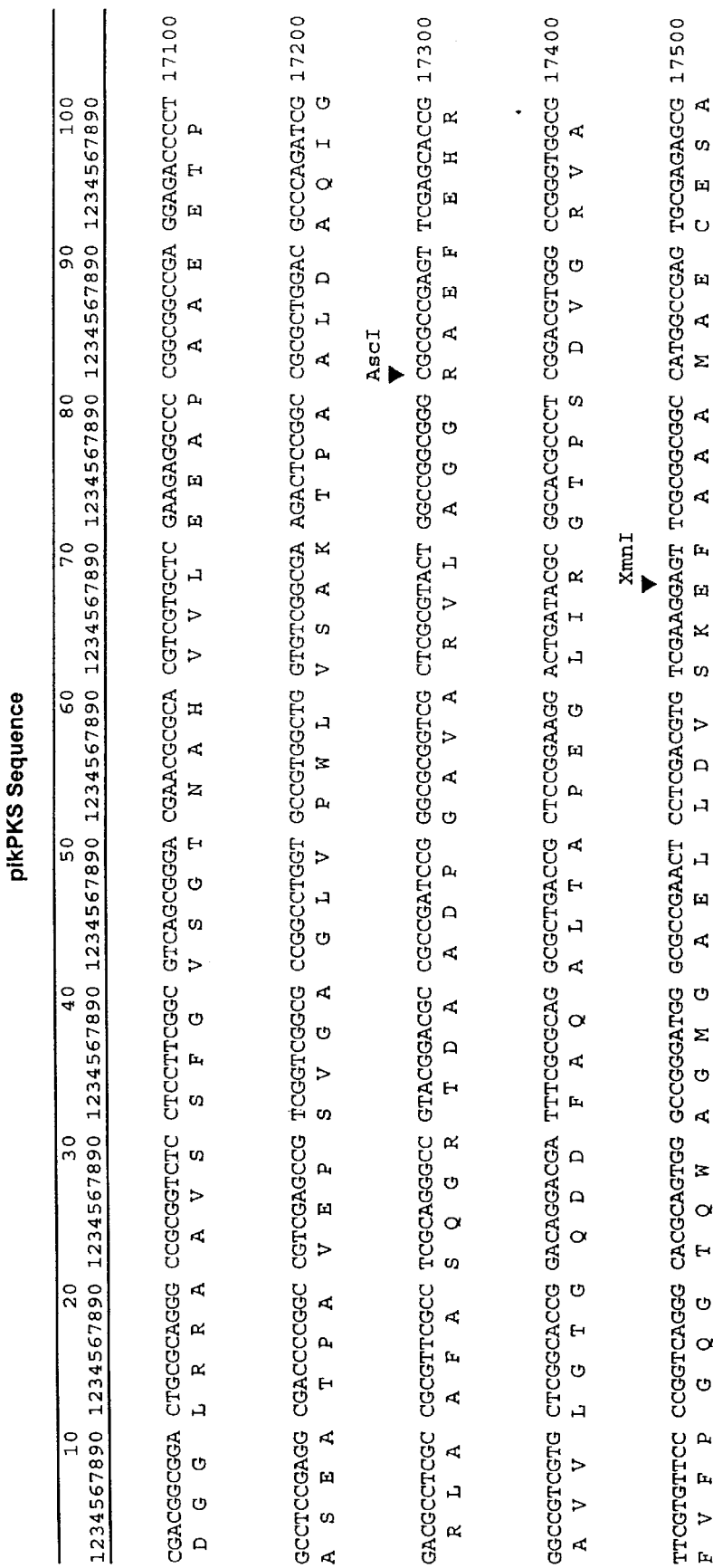
FIG. 35. pAX703 construct, an expression and complementation vector. The PikTEII gene can be replaced with an EcoRI-NsiI fragment. The phaC 1 gene can be replaced with a PacI-DraI fragment.
Figures 31, 32, 33, 34, 35, 36, 37, 38, 39, 40, 41, 42:
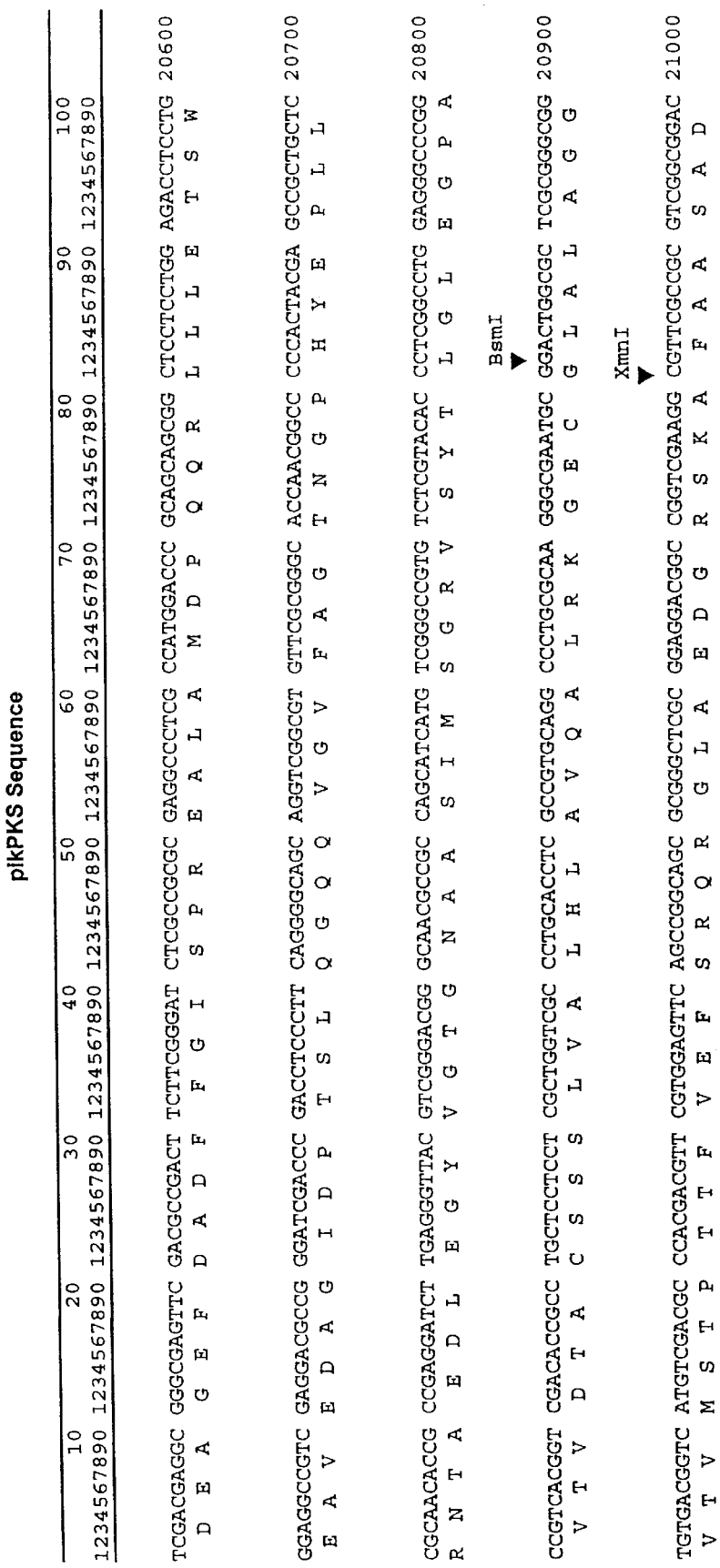
FIG. 36. Strategy for C7 polymer production. mTEII is a mutant pikTEII, an acyl-ACP CoA transferase; phaC1 is a PHA polymerase 1 from *P. olivarus* which may have racemase activity. In a strain having these constructs, AX916, a PHA polymer is produced.
FIG. 37. Strategy for C5 polymer production. A PHA polymerase gene phaC 1 is directly fused to pik module 2, so as to result in a fusion that transfers an acyl chain from the PKS protein directly to the polymerase by the prosthetic group on the ACP domain of the PKS.
FIG. 38. Codons for specified amino acids.
FIG. 39. Exemplary and preferred amino acid substitutions.
Figures 31, 32, 33, 34, 35, 36, 37, 38, 39, 40, 41, 42, 43, 44:
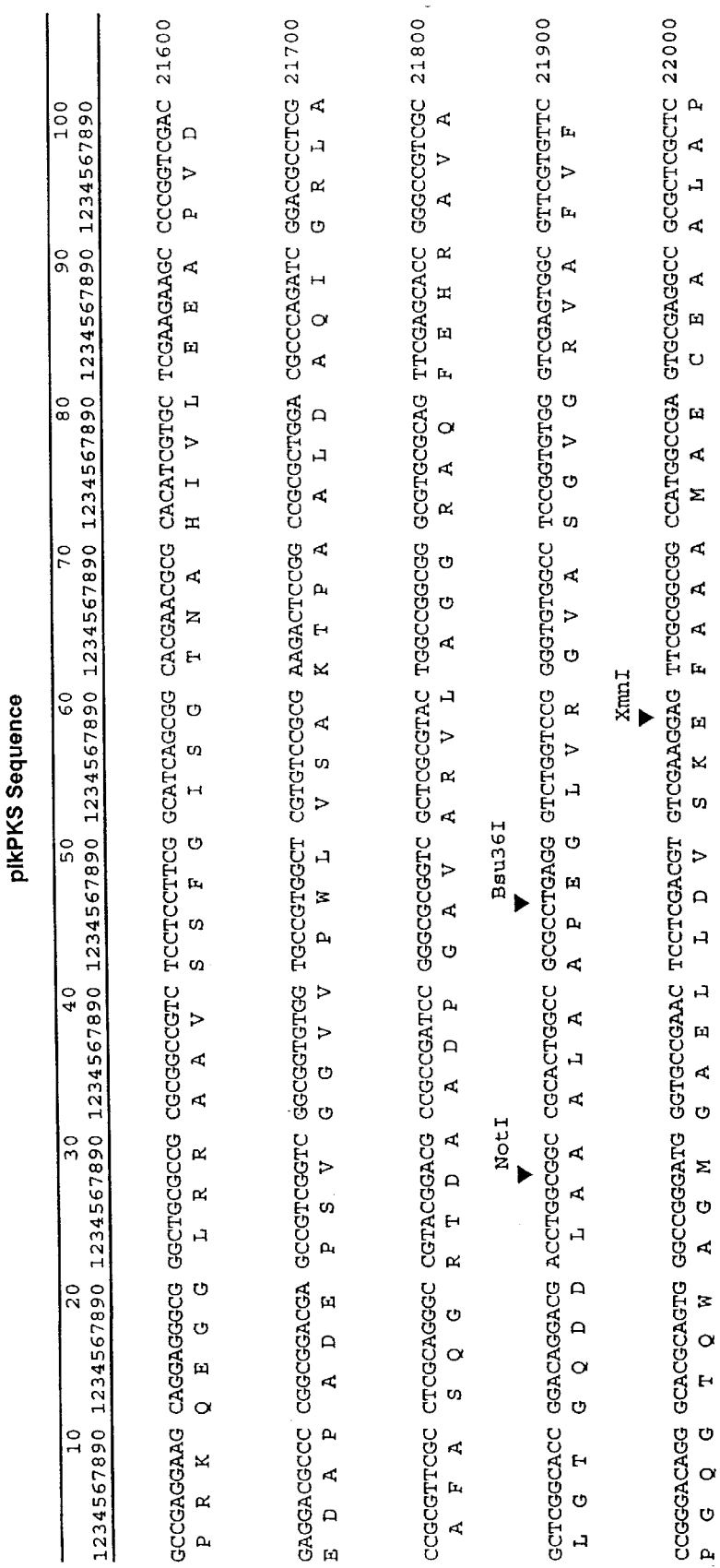
Figures 31, 32, 33, 34, 35, 36, 37, 38, 39, 40, 41, 42, 43, 44, 45:
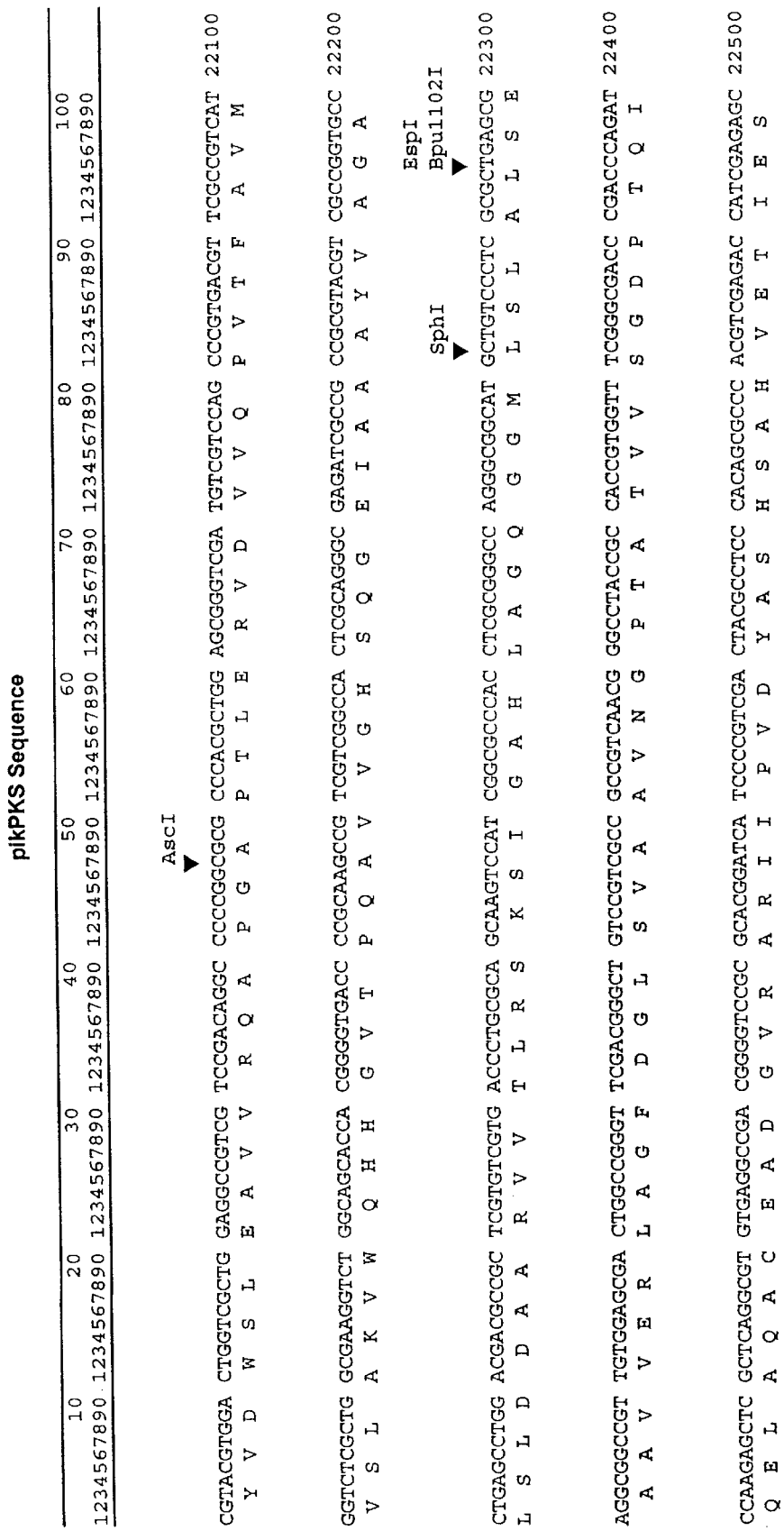
Figures 31, 32, 33, 34, 35, 36, 37, 38, 39, 40, 41, 42, 43, 44, 45, 46:
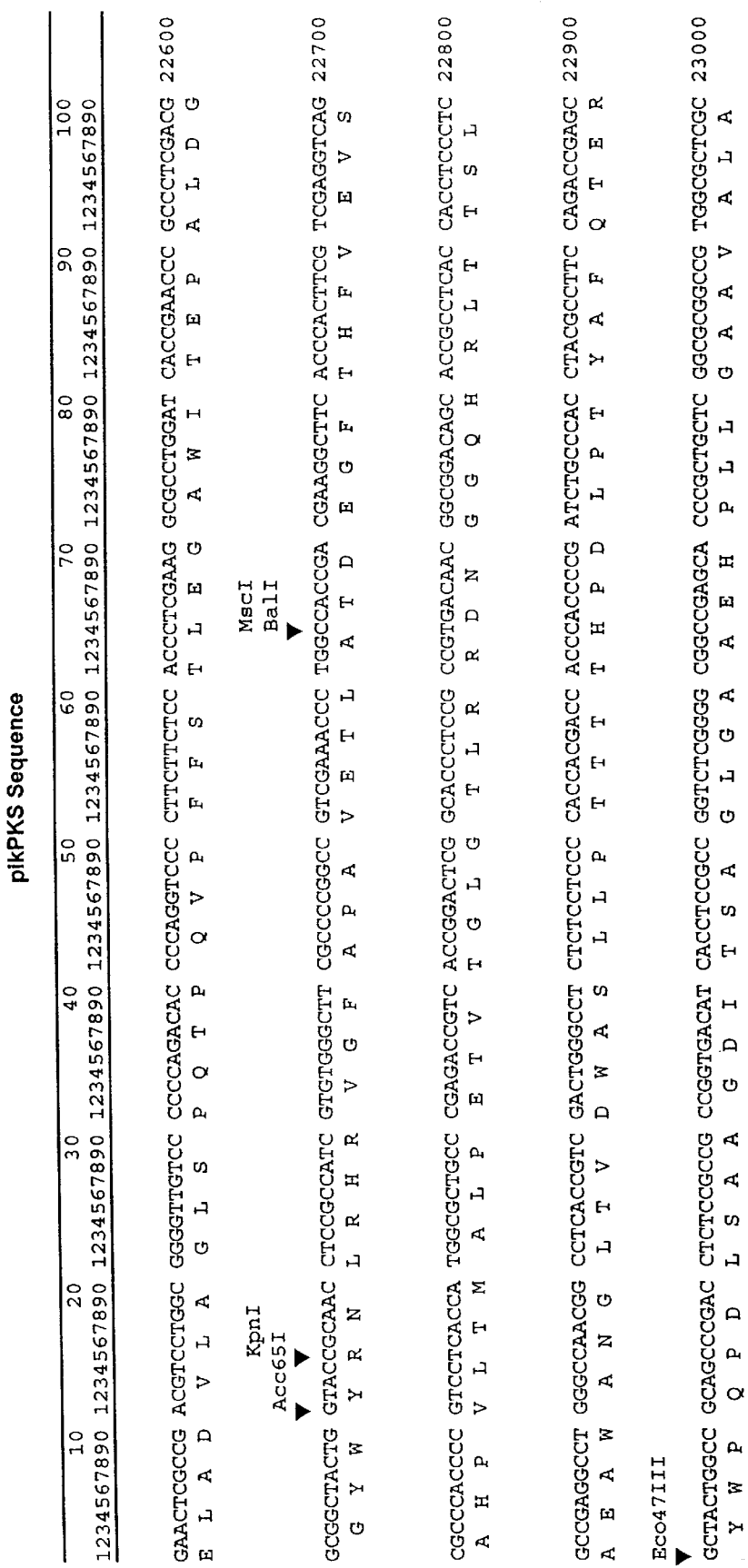
Figures 31, 32, 33, 34, 35, 36, 37, 38, 39, 40, 41, 42, 43, 44, 45, 46, 47, 48, 49, 50, 51, 52, 53:
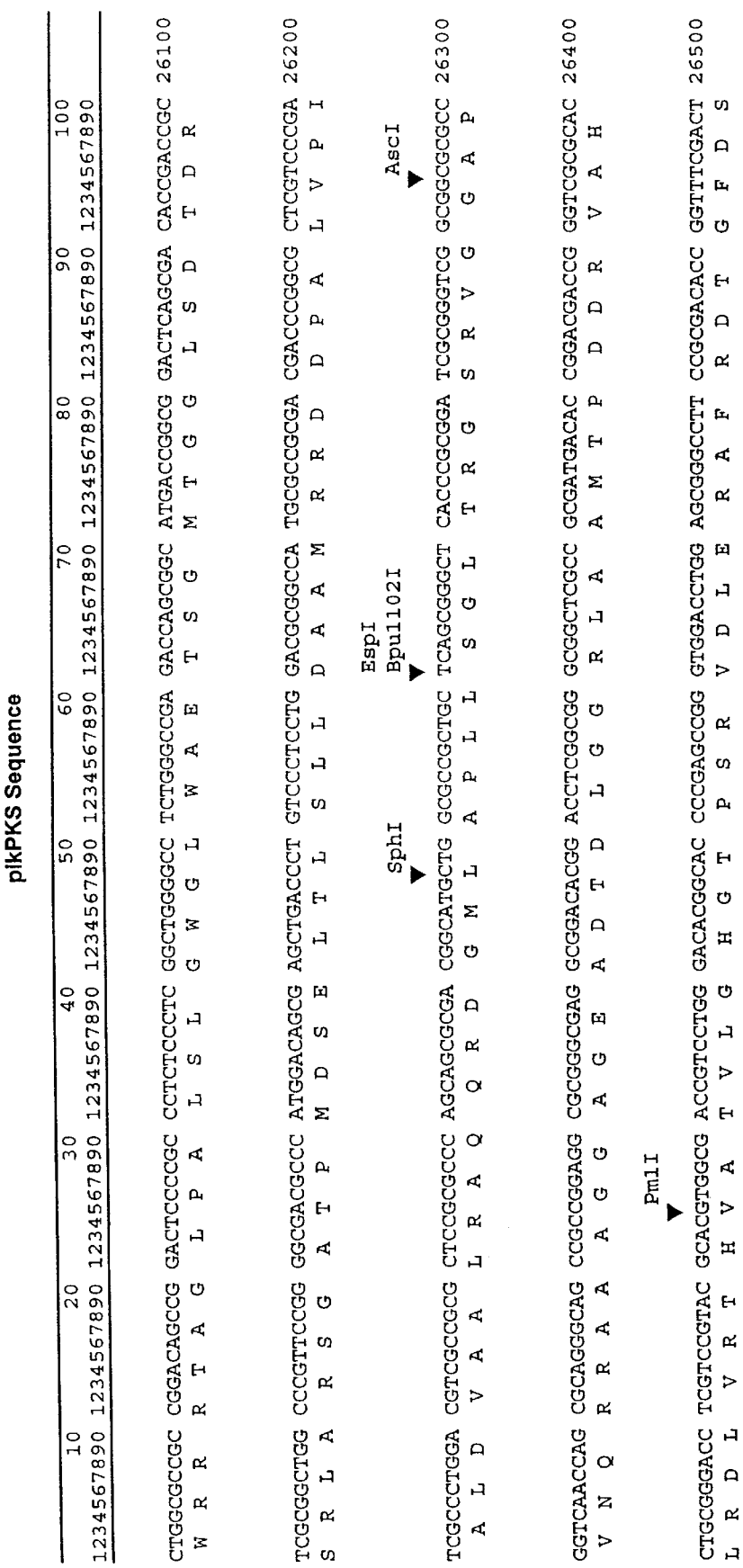
Figures 31, 32, 33, 34, 35, 36, 37, 38, 39, 40, 41, 42, 43, 44, 45, 46, 47, 48, 49, 50, 51, 52, 53, 54, 55:
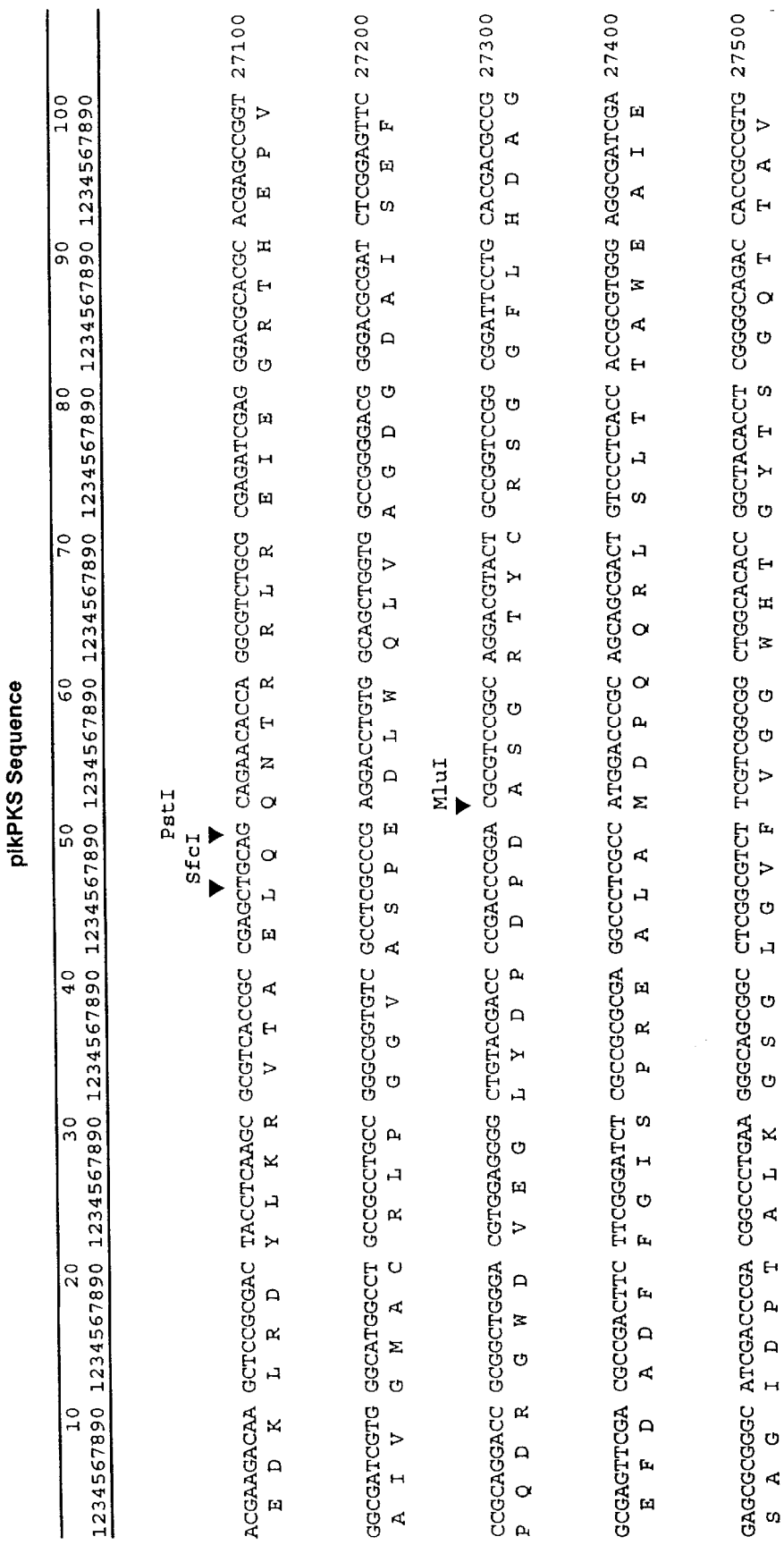
Figures 31, 32, 33, 34, 35, 36, 37, 38, 39, 40, 41, 42, 43, 44, 45, 46, 47, 48, 49, 50, 51, 52, 53, 54, 55, 56:
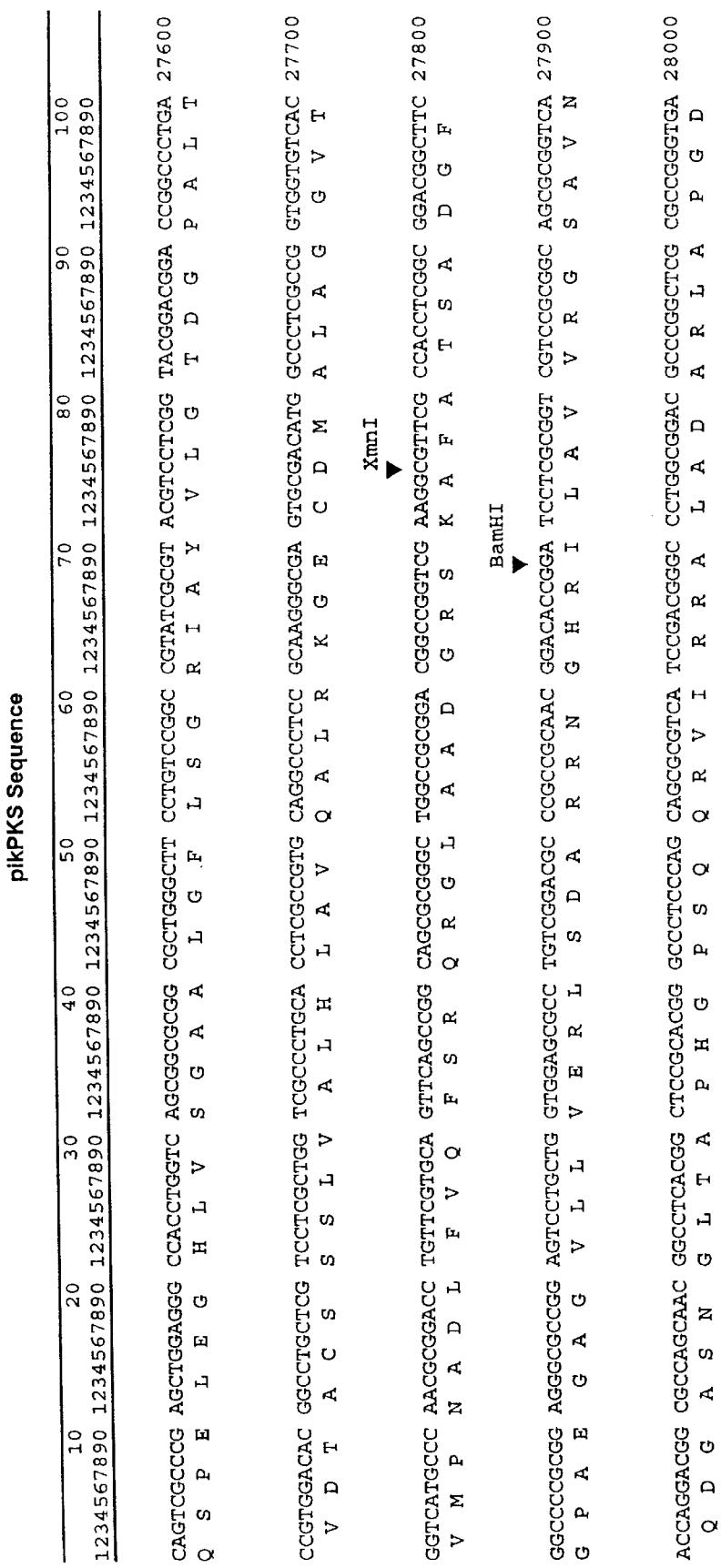
Figures 31, 32, 33, 34, 35, 36, 37, 38, 39, 40, 41, 42, 43, 44, 45, 46, 47, 48, 49, 50, 51, 52, 53, 54, 55, 56, 57, 58:
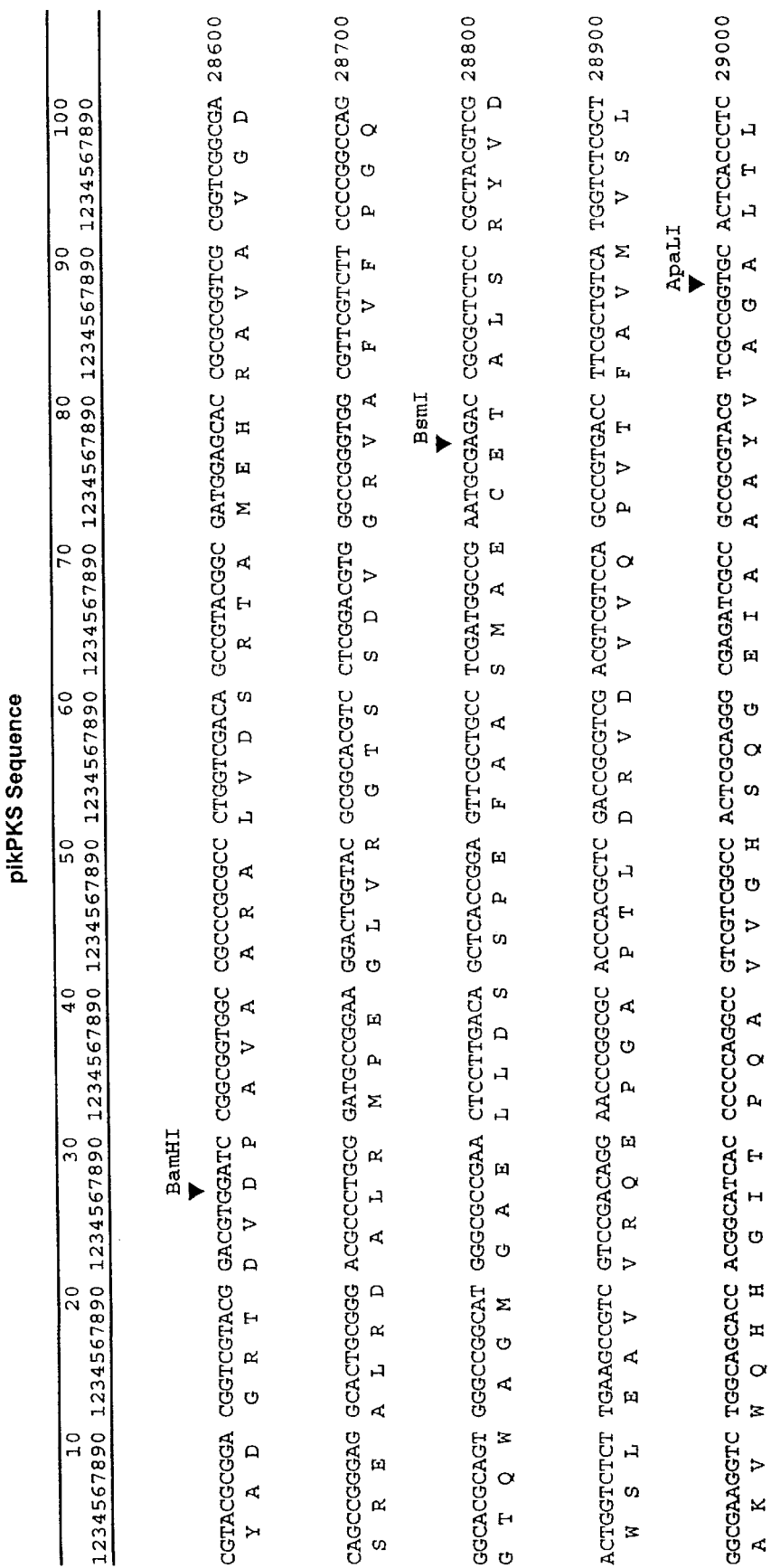
Figures 31, 32, 33, 34, 35, 36, 37, 38, 39, 40, 41, 42, 43, 44, 45, 46, 47, 48, 49, 50, 51, 52, 53, 54, 55, 56, 57, 58, 59:
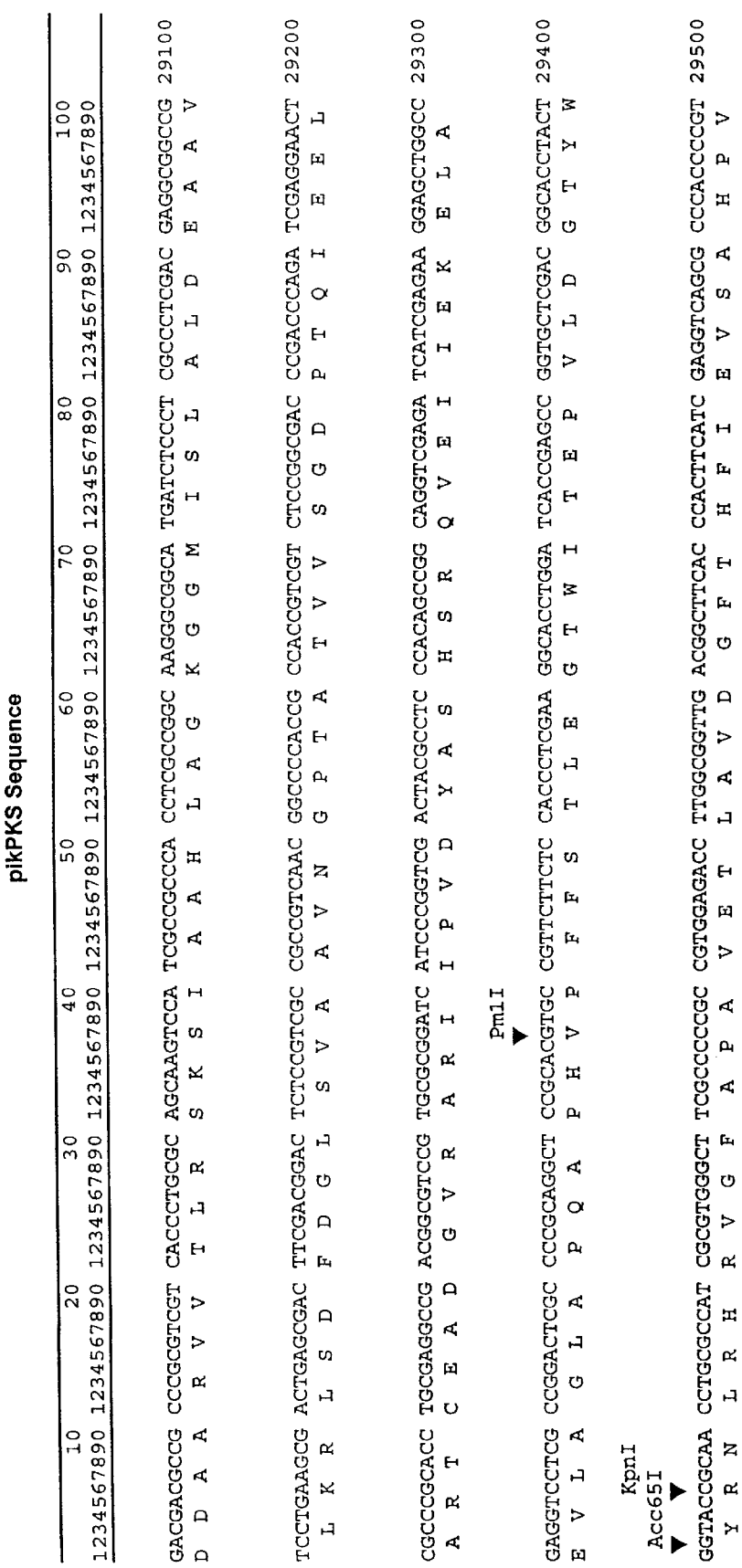
Figures 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61:
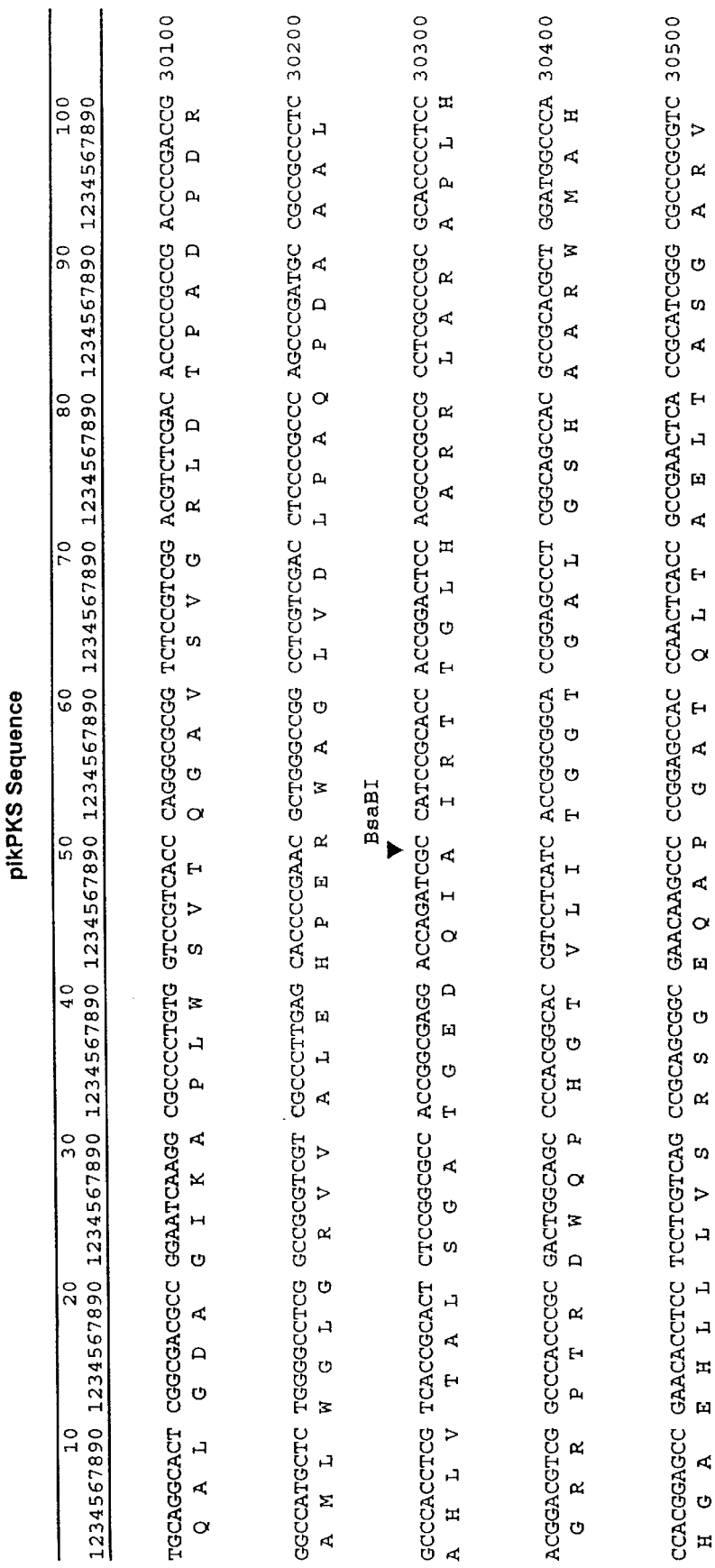
Figures 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62:
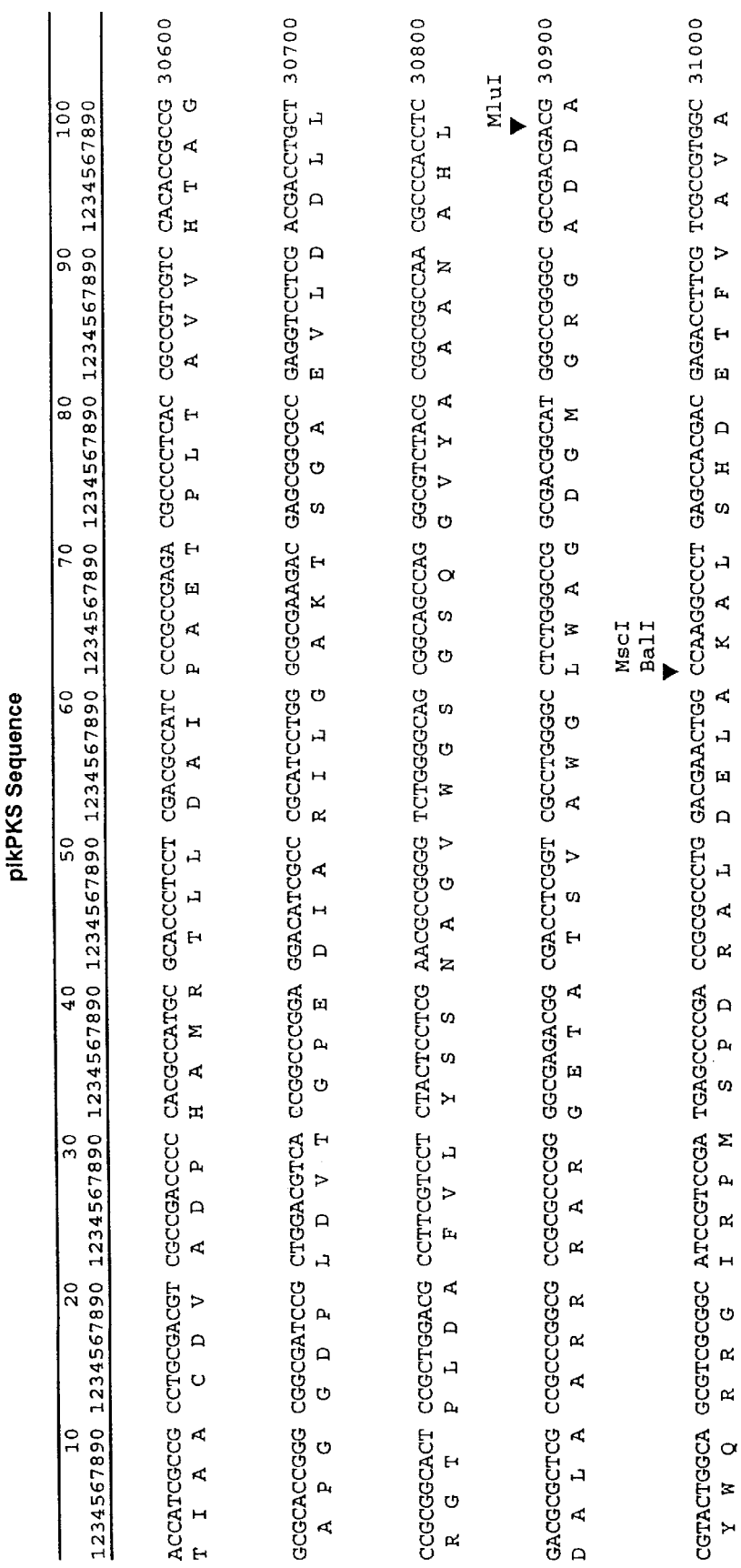
Figures 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68:
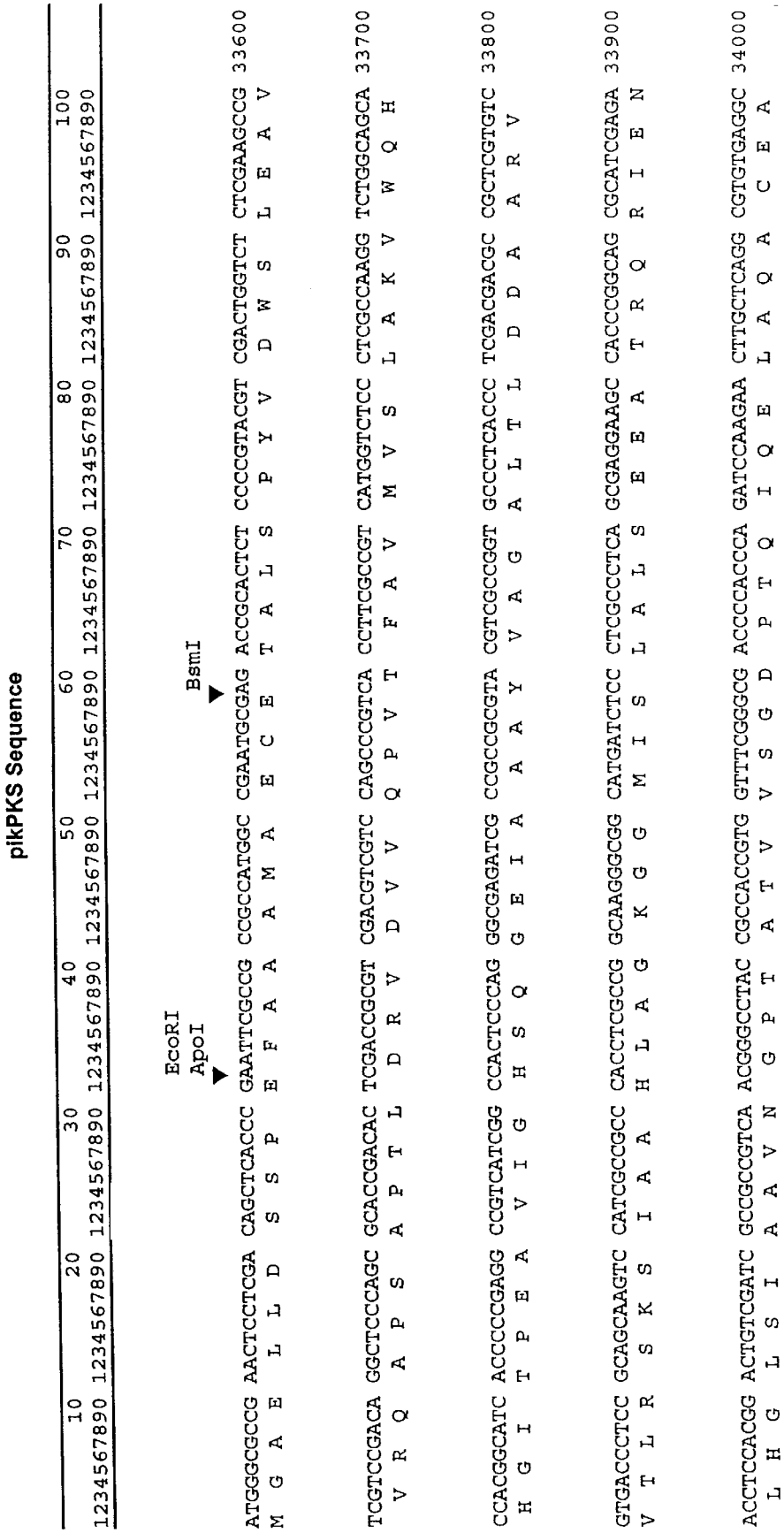
Figures 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69:
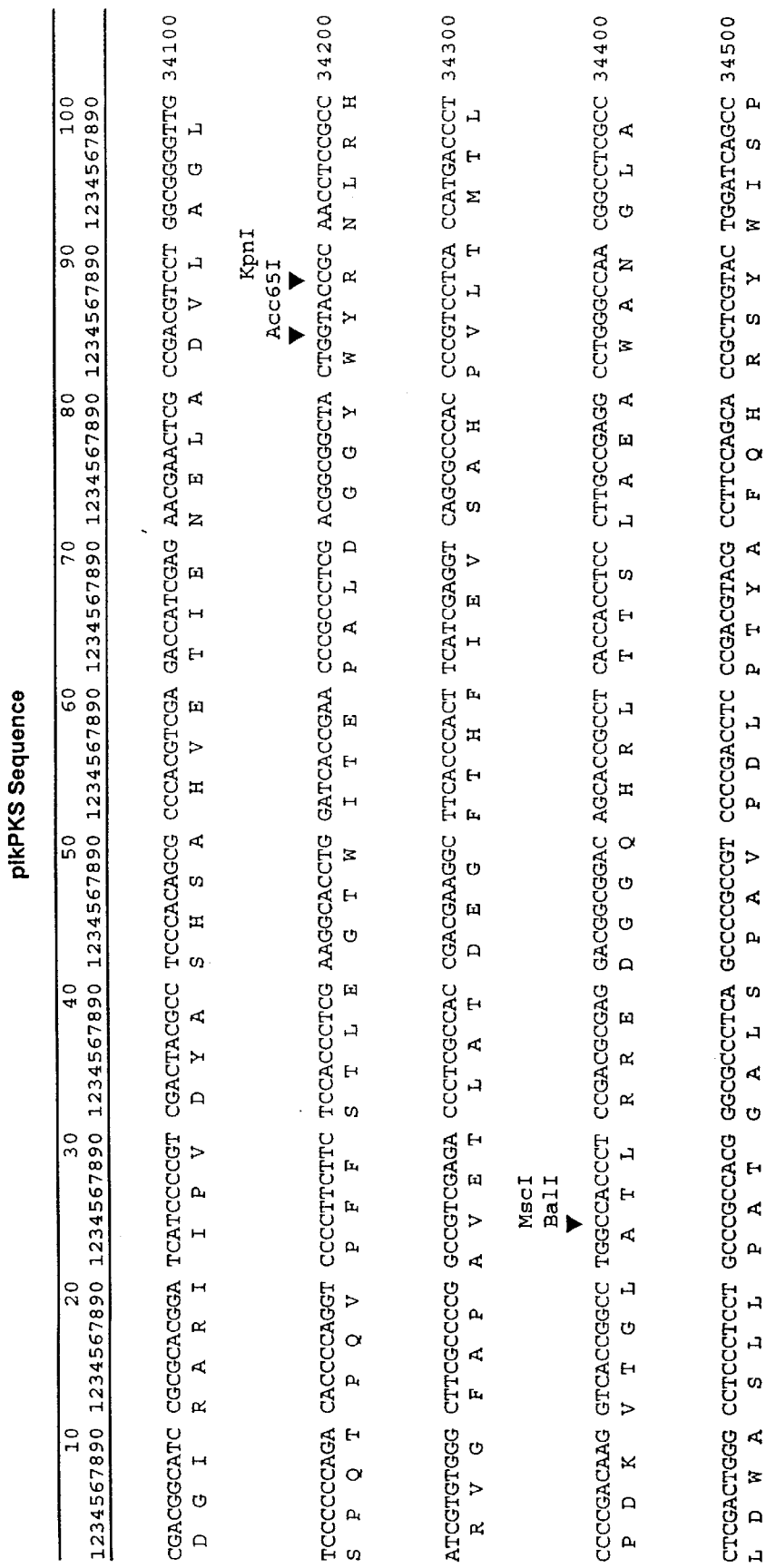
Figures 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71:
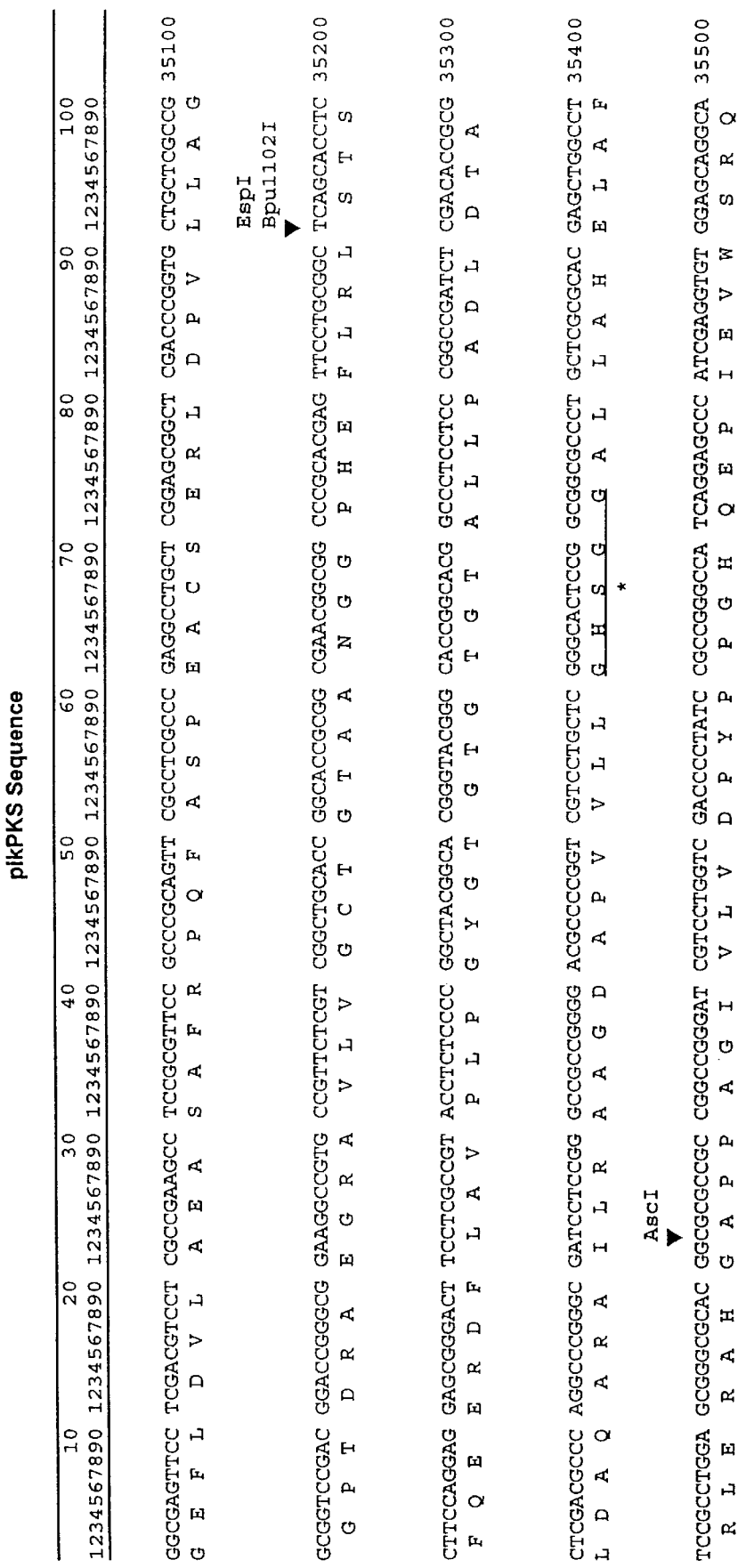
Figures 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72:
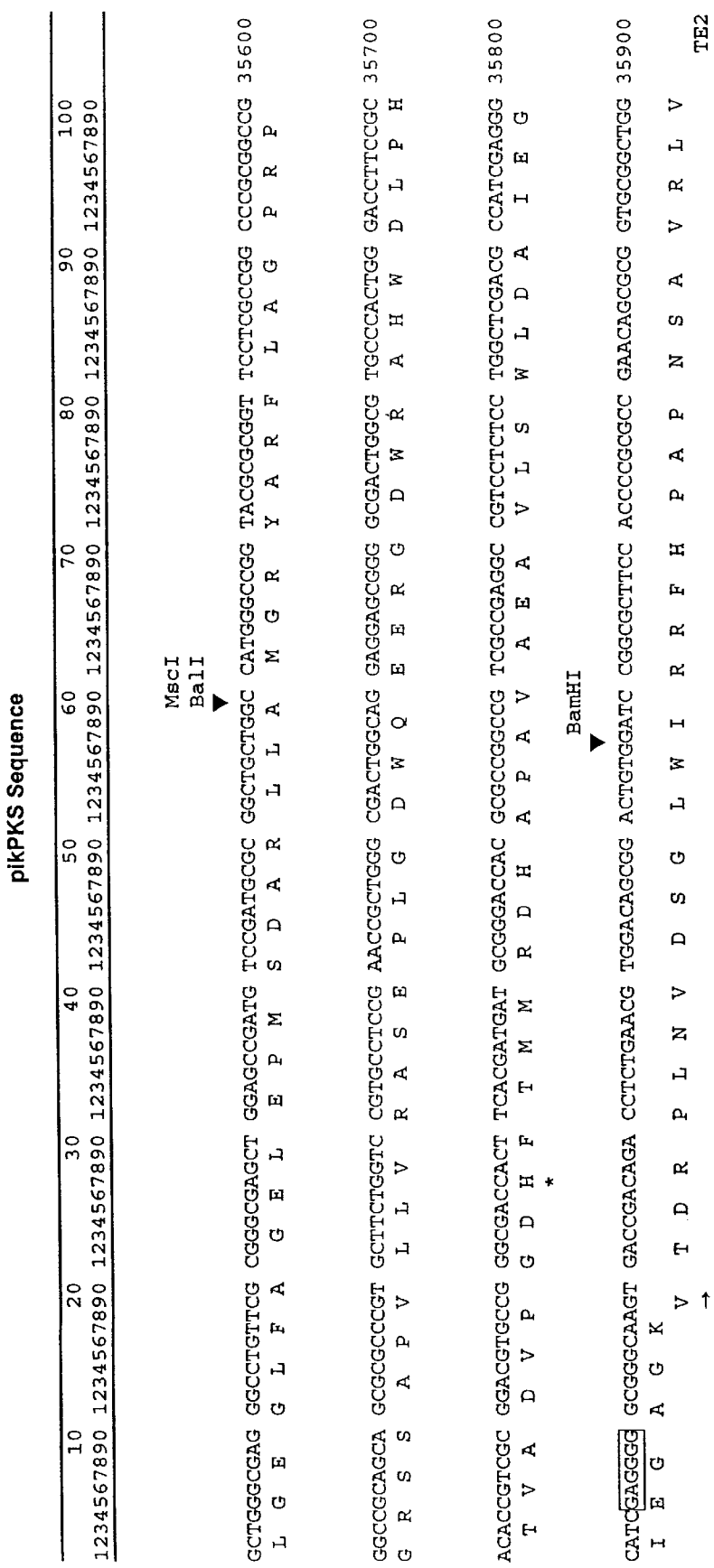
Figures 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74:
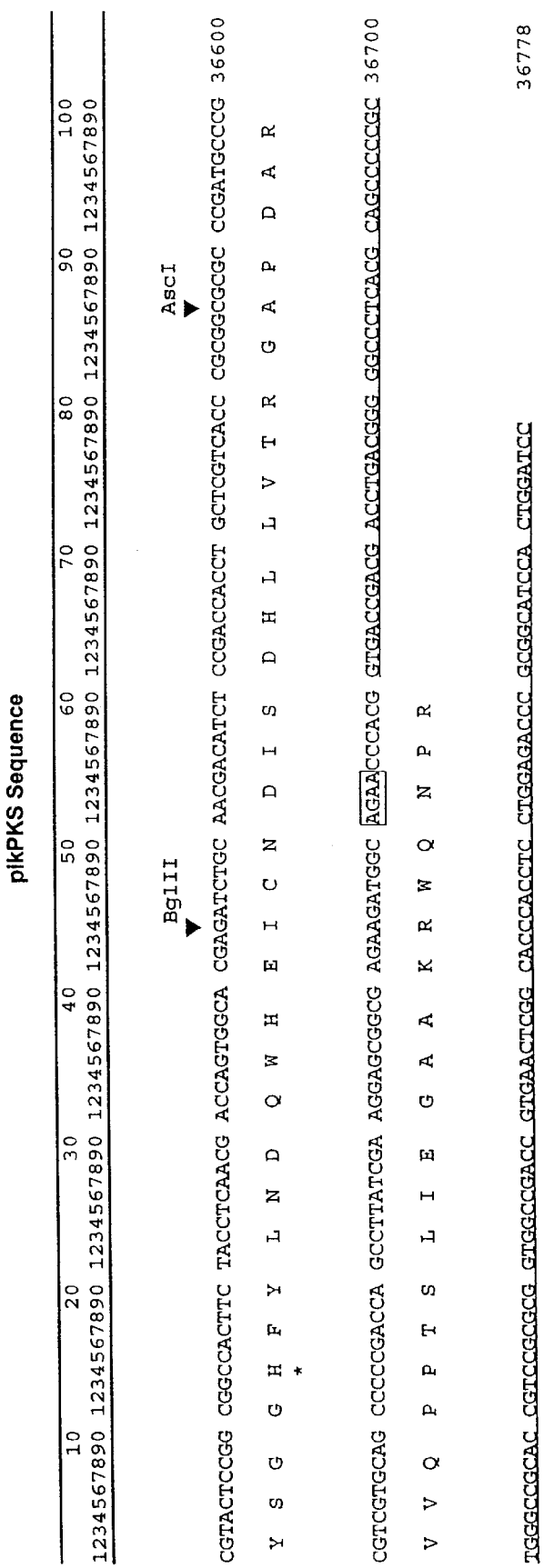

Preparation of Variant Nucleic Acid Molecules and Variant Polypeptides of the Invention The present invention also contemplates nucleic acid sequences which hybridize under stringent hybridization conditions to the nucleic acid sequences set forth herein. Stringent hybridization conditions are well known in the art and define a degree of sequence identity greater than about 80 to about 90%. Thus, nucleic acid sequences encoding variant polypeptides (FIG. 38), or nucleic acid sequences having conservative (silent) nucleotide substitutions (FIG. 37), are within the scope of the invention. Preferably, variant polypeptides encoded by the nucleic acid sequences of the invention are biologically active. The present invention also contemplates naturally occurring allelic variations and mutations of the nucleic acid sequences described herein.

As is well known in the art, because of the degeneracy of the genetic code, there are numerous other DNA and RNA molecules that can code for the same polypeptides as those encoded by the exemplified biosynthetic genes and fragments thereof. The present invention, therefore, contemplates those other DNA and RNA molecules which, on expression, encode the polypeptides of, for example, portions of SEQ ID NO:4 or SEQ ID NO:6. Having identified the amino acid residue sequence encoded by a sugar biosynthetic or macrolide biosynthetic gene, and with knowledge of all triplet codons for each particular amino acid residue, it is possible to describe all such encoding RNA and DNA sequences. DNA and RNA molecules other than those specifically disclosed herein and, which molecules are characterized simply by a change in a codon for a particular amino acid, are within the scope of this invention.

The 20 common amino acids and their representative abbreviations, symbols and codons are well known in the art (see, for example, *Molecular Biology of the Cell,* Second Edition, B. Alberts et al., Garland Publishing Inc., New York and London, 1989). As is also well known in the art, codons constitute triplet sequences of nucleotides in mRNA molecules and as such, are characterized by the base uracil (U) in place of base thymidine (T) which is present in DNA molecules. A simple change in a codon for the same amino acid residue within a polynucleotide will not change the structure of the encoded polypeptide. By way of example, it can be seen from SEQ ID NO:6 that a TCT codon for serine exists at nucleotide positions 1735-1737. However, it can also be seen from that same sequence that serine can be encoded by a TCA codon (see, e.g., nucleotide positions 1738–1740) and a TCC codon (see, e.g., nucleotide positions 1874–1876). Substitution of the latter codons for serine with the TCT codon for serine or vice versa, does not substantially alter the DNA sequence of SEQ ID NO:6 and results in production of the same polypeptide. In a similar manner, substitutions of the recited codons with other equivalent codons can be made in a like manner without departing from the scope of the present invention.

A nucleic acid molecule, segment or sequence of the present invention can also be an RNA molecule, segment or sequence. An RNA molecule contemplated by the present invention corresponds to, is complementary to or hybridizes under stringent conditions to any of the DNA sequences set forth herein. Exemplary and preferred RNA molecules are mRNA molecules that encode sugar biosynthetic or macrolide biosynthetic enzymes of this invention.

Mutations can be made to the native nucleic acid sequences of the invention and such mutants used in place of the native sequence, so long as the mutants are able to function with other sequences to collectively catalyze the synthesis of an identifiable polyketide or macrolides. Such mutations can be made to the native sequences using conventional techniques such as by preparing synthetic oligonucleotides including the mutations and inserting the mutated sequence into the gene using restriction endonuclease digestion. (See, e.g., Kunkel, T. A. *Proc. Natl. Acad. Sci. USA* (1985) 82:448; Geisselsoder et al. *BioTechiques* (1987) 5:786.) Alternatively, the mutations can be effected using a mismatched primer (generally 10–20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, *Methods Enzymol.,* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al., *Proc. Natl. Acad. Sci. USA* (1982) 79:6409. PCR mutagenesis will also find use for effecting the desired mutations.

Random mutagenesis of the nucleotide sequence can be accomplished by several different techniques known in the art, such as by altering sequences within restriction endonuclease sites, inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, hydroxylamine, agents which damage or remove bases thereby preventing normal basepairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

Large populations of random enzyme variants can be constructed in vivo using "recombination-enhanced mutagenesis." This method employs two or more pools of, for example, $10^6$ mutants each of the wild-type encoding nucleotide sequence that are generated using any convenient mutagenesis technique and then inserted into cloning vectors.

The gene sequences can be inserted into one or more expression vectors, using methods known to those of skill in the art. Expression vectors may include control sequences operably linked to the desired genes. Suitable expression systems for use with the present invention include systems which function in eukaryotic and prokaryotic host cells. Prokaryotic systems are preferred, and in particular, systems compatible with Streptomyces spp. are of particular interest. Control elements for use in such systems include promoters, optionally containing operator sequences, and ribosome binding sites. Particularly useful promoters include control sequences derived from the gene clusters of the invention. However, other bacterial promoters, such as those derived from sugar metabolizing enzymes, such as galactose, lactose (lac) and maltose, will also find use in the expression cassettes encoding desosamine. Additional examples include promoter sequences derived from biosynthetic enzymes such as tryptophan (trp), the β-lactamase (bla)

promoter system, bacteriophage lambda PL, and T5. In addition, synthetic promoters, such as the tac promoter (U.S. Pat. No. 4,551,433), which do not occur in nature, also function in bacterial host cells.

Other regulatory sequences may also be desirable which allow for regulation of expression of the genes relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid. Alternatively, several polyketides are naturally colored and this characteristic provides a built-in marker for selecting cells successfully transformed by the present constructs.

The various subunits of interest can be cloned into one or more recombinant vectors as individual cassettes, with separate control elements, or under the control of, e.g., a single promoter. The subunits can include flanking restriction sites to allow for the easy deletion and insertion of other subunits so that hybrid PKSs can be generated. The design of such unique restriction sites is known to those of skill in the art and can be accomplished using the techniques described above, such as site-directed mutagenesis and PCR.

For sequences generated by random mutagenesis, the choice of vector depends on the pool of mutant sequences, i.e., donor or recipient, with which they are to be employed. Furthermore, the choice of vector determines the host cell to be employed in subsequent steps of the claimed method. Any transducible cloning vector can be used as a cloning vector for the donor pool of mutants. It is preferred, however, that phagemids, cosmids, or similar cloning vectors be used for cloning the donor pool of mutant encoding nucleotide sequences into the host cell. Phagemids and cosmids, for example, are advantageous vectors due to the ability to insert and stably propagate therein larger fragments of DNA than in M13 phage and λ phage, respectively. Phagemids which will find use in this method generally include hybrids between plasmids and filamentous phage cloning vehicles. Cosmids which will find use in this method generally include λ phage-based vectors into which cos sites have been inserted. Recipient pool cloning vectors can be any suitable plasmid. The cloning vectors into which pools of mutants are inserted may be identical or may be constructed to harbor and express different genetic markers (see, e.g., Sambrook et al., supra). The utility of employing such vectors having different marker genes may be exploited to facilitate a determination of successful transduction.

Thus, for example, the cloning vector employed may be a phagemid and the host cell may be $E.$ $coli.$ Upon infection of the host cell which contains a phagemid, single-stranded phagemid DNA is produced, packaged and extruded from the cell in the form of a transducing phage in a manner similar to other phage vectors. Thus, clonal amplification of mutant encoding nucleotide sequences carried by phagemids is accomplished by propagating the phagemids in a suitable host cell.

Following clonal amplification, the cloned donor pool of mutants is infected with a helper phage to obtain a mixture of phage particles containing either the helper phage genome or phagemids mutant alleles of the wild-type encoding nucleotide sequence.

Infection, or transfection, of host cells with helper phage is generally accomplished by methods well known in the art (see., e.g., Sambrook et al., supra; and Russell et al. (1986) *Gene* 4:333–338).

The helper phage may be any phage which can be used in combination with the cloning phage to produce an infective transducing phage. For example, if the cloning vector is a cosmid, the helper phage will necessarily be a λ phage. Preferably, the cloning vector is a phagemid and the helper phage is a filamentous phage, and preferably phage M13.

If desired after infecting the phagemid with helper phage and obtaining a mixture of phage particles, the transducing phage can be separated from helper phage based on size difference (Barnes et al. (1983) *Methods Enzymol.* 101:98–122), or other similarly effective technique.

The entire spectrum of cloned donor mutations can now be transduced into clonally amplified recipient cells into which has been transduced or transformed a pool of mutant encoding nucleotide sequences. Recipient cells which may be employed in the method disclosed and claimed herein may be, for example, $E.$ $coli,$ or other bacterial expression systems which are not recombination deficient. A recombination deficient cell is a cell in which recombinatorial events is greatly reduced, such as rec⁻ mutants of $E.$ $coli$ (see, Clark et al. (1965) *Proc. Natl. Acad. Sci. USA* 53:451–459).

These transductants can now be selected for the desired expressed protein property or characteristic and, if necessary or desirable, amplified. Optionally, if the phagemids into which each pool of mutants is cloned are constructed to express different genetic markers, as described above, transductants may be selected by way of their expression of both donor and recipient plasmid markers.

The recombinants generated by the above-described methods can then be subjected to selection or screening by any appropriate method, for example, enzymatic or other biological activity.

The above cycle of amplification, infection, transduction, and recombination may be repeated any number of times using additional donor pools cloned on phagemids. As above, the phagemids into which each pool of mutants is cloned may be constructed to express a different marker gene. Each cycle could increase the number of distinct mutants by up to a factor of $10^{6.}$ Thus, if the probability of occurrence of an inter-allelic recombination event in any individual cell is f (a parameter that is actually a function of the distance between the recombining mutations), the transduced culture from two pools of $10^6$ allelic mutants will express up to $10^{12}$ distinct mutants in a population of $10^{12}/f$ cells.

I. EXPERIMENTAL PROCEDURES

Materials and Methods

Materials.

Sodium R-(−)-3-hydroxybutyrate, coenzyme-A, ethylchloroformate, pyridine and diethyl ether were purchased from Sigma Chemical Co. Amberlite IR-120 was purchased from Mallinckrodt Inc. 6-O-(N-Heptylcarbamoyl)methyl α-D-glycopyranoside (Hecameg) was obtained from Vegatec (Villeejuif, France). Two-piece spectrophotometer cells with pathlengths of 0.1 (#20/0-Q-1) and 0.01 cm (#20/0-Q-0.1) were obtained from Starna Cells Inc. (Atascadero, Calif.). Rabbit anti-*A. eutrophus* PHA synthase antibody was a gracious gift from Dr. F. Srienc and S. Stoup (Biological Process Technology Institute, University of Minnesota). Sf21 cells and *T. ni* cells were kindly provided by Greg Franzen (R&D Systems, Minneapolis, Minn.) and Stephen Harsch (Department of Veterinary Pathobiology, University of Minnesota), respectively.

Plasmid pFAS206 and a recombinant baculoviral clone encoding FAS206 (Joshi et al., *J. Biol. Chem.*, 268, 22508 (1993)) were generous gifts of A. Joshi and S. Smith. Plasmid pAet41 (Peoples et al., *J. Biol. Chem.*, 264, 15298 (1989)), the source of the *A. eutrophus* PHB synthase, was obtained from A. Sinskey. Baculovirus transfer vector, pBacPAK9, and linearized baculoviral DNA, were obtained from Clontech Inc. (Palo Alto, Calif.). Restriction enzymes, T4 DNA ligase, *E. coli* DH5 a competent cells, molecular weight standards, lipofectin reagent, Grace's insect cell medium, fetal bovine serum (FBS), and antibiotic/antimycotic reagent were obtained from GIBCO-BRL (Grand Island, N.Y.). Tissue culture dishes were obtained from Corning Inc. Spinner flasks were obtained from Bellco Glass Inc. Seaplaque agarose GTG was obtained from FMC Bioproducts Inc.

Methods

Preparation of R-3HBCoA.

R-(−)-3 HBCoA was prepared by the mixed anhydride method described by Haywood et al., *FEMS Microbiol. Lett*, 57, 1 (1989). 60 mg (0.58 nmol) of R-(−)-3 hydroxybutyric acid was freeze dried and added to a solution of 72 mg of pyridine in 10 ml diethyl ether at 0° C. Ethylchloroformate (100 mg) was added, and the mixture was allowed to stand at 4° C. for 60 minutes. Insoluble pyridine hydrochloride was removed by centrifugation. The resulting anhydride was added, dropwise with mixing, to a solution of 100 mg coenzyme-A (0.13 mmol) in 4 ml 0.2 M potassium bicarbonate, pH 8.0 at 0° C. The reaction was monitored by the nitroprusside test of Stadtman, *Meth. Enzymol.*, 3, 931 (1957), to ensure sufficient anhydride was added to esterify all the coenzyme-A. The concentration of R-3-HBCoA was determined by measuring the absorbance at 260 nm (e=16.8 nM$^{-1}$ cm$^{-1}$; 18).

Construction of pBP—phC.

The phbC gene (approximately 1.8 kb) was excised from pAet41 (Peoples et al., *J. Biol. Chem.*, 264, 15293 (1989)) by digestion with BstBI and StuI, purified as described by Williams et al. (*Gene*, 109, 445 (1991)), and ligated to pBacPAK9 digested with BstBI and StuI. This resulted in pBP-phbC, the baculovirus transfer vector used in formation of recombinant baculovirus particles carrying phbC.

Large-scale expression of PHA Synthase.

A 1 L culture of *T. ni* cells (1.2×10$^6$ cells/ml) in logarithmic growth was infected by the addition of 50 ml recombinant viral stock solution (2.5×10$^8$ pfu/ml) resulting in a multiplicity of infection (MOI) of 10. This infected culture was split between two Bellco spinners (350 ml/500 ml spinner, 700 ml/1 L spinner) to facilitate oxygenation of the culture. These cultures were incubated at 28° C. and stirred at 60 rpm for 60 hours. Infected cells were harvested by centrifugation at 1000×g for 10 minutes at 4° C. Cells were flash frozen in liquid N$_2$ and stored in 4 equal aliquots, at −80° C. until purification.

Insect Cell Maintenance and Recombinant Baculovirus Formation.

Sf21 cells were maintained at 26–28° C. in Grace's insect cell medium supplemented with 10% FBS, 1.0% pluronic F68, and 1.0% antibiotic/antimycotic (GIBCO-BRL). Cells were typically maintained in suspension at 0.2–2.0×10$^6$/ml in 60 ml total culture volume in 100 ml spinner flasks at 55–65 rpm. Cell viability during the culture period was typically 95–100%. The procedures for use of the transfer vector and baculovirus were essentially those described by the manufacturer (Clontech, Inc.). Purified pBP-phbC and linearized baculovirus DNA were used for cotransfection of Sf21 cells using the liposome-mediated method (Felgner et al., *Proc. Natl. Acad. Sci. USA*, 84, 7413 (1987)) utilizing Lipofectin (GIBCO-BRL). Four days later cotransfection supernatants were utilized for plaque purification. Recombinant viral clones were purified from plaque assay plates containing 1.5% Seaplaque GTG after 5–7 days at 28° C. Recombinant viral clone stocks were then amplified in T25-flask cultures (4 ml, 3×10$^6$/ml on day 0) for 4 days; infected cells were determined by their morphology and size and then screened by SDS/PAGE using 10% polyacrylamide gels (Laemmli, *Nature*, 227, 680 (1970)) for production of PHA synthase.

Purification of PHA Synthase from BTI-TN-5BI-4 *T. ni* cells.

Purification of PHA synthase was performed according to the method of Germgross et al., *Biochemistry*, 33, 9311 (1994) with the following alterations. One aliquot (110 mg protein) of frozen cells was thawed on ice and resuspended in 10 mM KPi (pH 7.2), 5% glycerol, and 0.05% Hecameg (Buffer A) containing the following protease inhibitors at the indicated final concentrations: benzamidine (2 mM), phenylmethylsulfonyl fluoride (PMSF, 0.4 mM), pepstatin (2 mg/ml), leupeptin (2.5 mg/ml), and Na-p-tosyl-1-lysine chloromethyl ketone (TLCK, 2 mM). EDTA was omitted at this stage due to its incompatibility with hydroxylapatite (HA). This mixture was homogenized with three series of 10 strokes each in two Thomas homogenizers while partially submerged in an ice bath and then sonicated for 2 minutes in a Branson Sonifier 250 at 30% cycle, 30% power while on ice. All subsequent procedures were carried out at 4° C.

The lysate was immediately centrifuged at 100000×g in a Beckman 50.2Ti rotor for 80 minutes, and the resulting supernatant (10.5 ml, 47 mg) was immediately filtered through a 0.45 mm Uniflow filter (Schleicher and Schuell Inc., Keene, N.H.) to remove any remaining insoluble matter. Aliquots of the soluble fraction (1.5 ml, 7 mg) were loaded onto a 5 ml BioRad Econo-Pac HTP column that had been equilibrated with Buffer A (+protease inhibitor mix) attached to a BioRad Econo-system, and the column was washed with 30 ml Buffer A. All chromatographic steps were carried out at a flow rate of 0.8 ml/minute. PHA synthase was eluted form the HA column with a 32×32 ml linear gradient from 10 to 300 mM KPi.

Fraction collection tubes were prepared by addition of 30 ml of 100 mM EDTA to provide a metalloprotease inhibitor at 1 mM immediately after HA chromatography. PHA synthase was eluted in a broad peak between 110–180 mM KPi. Fractions (3 ml) containing significant PHA synthase activity were pooled and stored at 0° C. until the entire soluble fraction had been run through the chromatographic process. Pooled fractions then were concentrated at 4° C. by use of a Centriprep-30 concentrator (Amicon) to 3.8 mg/ml. Aliquots (0.5 ml) were either flash frozen and stored in liquid N$_2$ or glycerol was added to a final concentration of 50% and samples (1.9 mg/ml) were stored at −20° C.

Western Analysis.

Samples of *T. ni* cells were fractionated by SDS-PAGE on 10% polyacrylamide gels, and the proteins then were transferred to 0.2 mm nitrocellulose membranes using a BioRad Transblot SD Semi-Dry electrophoretic transfer cell according to the manufacturer. Proteins were transferred for 1 hour at 15 V. The membrane was rinsed with doubly distilled H$_2$O, dried, and treated with phosphate-buffered saline (PBS) containing 0.05% Tween-20 (PBS-Tween) and 3% nonfat dry milk to block non-specific binding sites. Primary antibody (rabbit anti-PHA synthase) was applied in fresh blocking solution and incubated at 25° C. for 2 hours. Membranes were then washed four times for 10 minutes with PBS-Tween followed by the addition of horseradish peroxidase-conjugated goat-anti-rabbit antibody (Boehringer-Mannheim) diluted 10,000× in fresh blocking solution and incubated at 25° C. for 1 hour. Membranes were washed finally in three changes (10 minutes) of PBS, and the immobilized peroxidase label was detected using the chemiluminescent LumiGLO substrate kit (Kirkegaard and Perry, Gaithersburg, Md.) and X-ray film.

N-Terminal Analysis.

Approximately 10 mg of purified PHA synthase was run on a 10% SDS-polyacrylamide gel, transferred to PVDF (Immobilon-PSQ, Millipore Corporation, Bedford, Mass.), stained with Amido Black, and sequenced on a 494 Procise Protein Sequencer (Perkin-Elmer, Applied Biosystems Division, Foster City, Calif.).

Double-Infection Protocol.

Four 100 ml spinner flasks were each inoculated with $8 \times 10^7$ cells in 50 ml of fresh insect medium. To flask 1, an additional 20 ml of fresh insect medium was added (uninfected control); to flask 2, 10 ml BacPAK6::phbC viral stock ($1 \times 10^8$ pfu/ml) and 10 ml fresh insect medium were added; to flask 3, 10 ml BacPAK6::FAS206 viral stock ($1 \times 10^8$ pfu/ml) and 10 ml fresh insect medium were added; and to flask 4, 10 ml BacPAK6::phbC viral stock ($1 \times 10^8$ pfu/ml) and 10 ml BacPAK6::FAS206 viral stock ($1 \times 10^8$ pfu/ml) were added. These viral infections were carried out at a multiplicity of infection of approximately 10. Cultures were maintained under normal growth conditions and 15 ml samples were removed at 24, 48, and 72 hour time points. Cells were collected by gentle centrifugation at 1000×g for 5 minutes, the medium was discarded, and the cells were immediately stored at −70° C.

PHA Synthase Assays.

Coenzyme A released by PHA synthase in the process of polymerization was monitored precisely as described by Gemgross et al. (supra) using 5,5'-dithiobis (2-nitrobenzoic acid, DTNB) (Ellman, *Arch. Biochem. Biophys.*, 8, 70 (1959)).

The presence of HBCoA was monitored spectrophotometrically. Assays were performed at 25° C. in a Hewlett Packard 8452A diode array spectrophotometer equipped with a water-jacketed cell holder. Two-piece Starna Spectrosil spectrophotometer cells with pathlengths of 0.1 and 0.01 cm were employed to avoid errors arising from the compression of the absorbance scale at higher values. Absorbance was monitored at 232 nm, and $E_{232}$ nm of $4.5 \times 10^3$ $M^{-1}$ $cm^{-1}$ was used in calculations. One unit (U) of enzyme is the amount required to hydrolyze 1 mmol of substrate $minute^{-1}$. Buffer (0.15 M KPi, pH 7.2) and substrate were equilibrated to 25° C. and then combined in an Eppendorf tube also at 25° C. Enzyme was added and mixed once in the pipet tip used to transfer the entire mixture to the spectrophotometer cell. The two-piece cell was immediately assembled, placed in the spectrophotometer with the cell holder (type CH) adapted for the standard 10 mm pathlength cell holder of the spectrophotometer. Manipulations of sample, from mixing to initiation of monitoring, took only 10–15 seconds. Absorbance was continually monitored for up to 10 minutes. Calibration of reactions was against a solution of buffer and enzyme (no substrate) which led to absorbance values that represented substrate only.

PHB Assay.

PHB was assayed from Sf21 cell samples according to the propanolysis method of Riis et al., *J. Chromo.*, 445, 285 (1988). Cell pellets were thawed on ice, resuspended in 1 ml cold $ddH_2O$ and transferred to 5 ml screwtop test tubes with teflon seals. Two ml of $ddH_2O$ were added, the cells were washed and centrifuged and then 3 ml of acetone were added and the cells washed and centrifuged. The samples were then desiccated by placing them in a 94° C. oven for 12 hours. The following day 0.5 ml of 1,2-dichloroethane, 0.5 ml acidified propanol (20 ml HCl, 80 ml 1-propanol) and 50 ml benzoic acid standard were added and the sealed tubes were heated to 100° C. in a boiling water bath for 2 hours with periodic vortexing. The tubes were cooled to room temperature and the organic phase was used for gas-chromatographic (GC) analysis using a Hewlett Packard 5890A gas chromatograph equipped with a Hewlett Packard 7673A automatic injector and a fused silica capillary column, DB-WAX 30W of 30 meter length. Positive samples were further subjected to GC-mass spectrometric (MS) analysis for the presence of propylhydroxybutyrate using a Kratos MS25 GC/MS. The following parameters were used: source temperature, 210° C.; voltage, 70 eV; and accelerating voltage, 4 KeV.

Catalytic Activities

Ketoacyl synthase (KS) activity was assessed radiochemically by the condensation-$^{14}CO_2$ exchange reaction (Smith et al., *PNAS USA*, 73, 1184 (1976)).

Transferase (AT) activity was assayed, using malonyl-CoA as donor and pantetheine as acceptor, by determining spectrophotometrically the free CoA released in a coupled ATP citrate-lyase-malate dehydrogenase reaction (see, Rangen et al., *J. Biol. Chem.*, 266, 19180 (1991).

Ketoreductase (KR) was assayed spectrophotometrically at 340 nm: assay systems contained 0.1 M potassium phosphate buffer (pH 7), 0.15 mM NADPH, enzyme and either 10 mM trans-1-decalone or 0.1 mM acetoacetyl-CoA substrate.

Dehydrase (DH) activity was assayed spectrophotometrically at 270 nm using S-DL-β-hydyroxybutyryl N-acetylcysteamine as substrate (Kumar et al., *J. Biol. Chem.*, 245, 4732 (1970)).

Enoyl reductase (ER) activity was assayed spectrophotometrically at 340 nm essentially as described by Strom et al. (*J. Biol. Chem.*, 254, 8159 (1979)); the assay system contained 0.1 M potassium phosphate buffer (pH 7), 0.15 mM NADPH, 0.375 nM crotonoyl-CoA, 20 µM CoA and enzyme.

Thioesterase (TE) activity was assessed radiochemically by extracting and assaying the [$^{14}C$]pahnitic acid formed from [1-$^{14}C$]palmitoyl-CoA during a 3 minute incubation Smith, *Meth. Enzymol.*, 71C, 181 (1981); the assay was in a final volume of 0.1 ml, 25 mM potassium phosphate buffer (pH 8), 20 µM [1-$^{14}C$]palmitoyl-CoA (20 nCi) and enzyme.

Assay of overall fatty acid synthase activity was performed spectrophotometrically as described previously by Smith et al. (*Meth. Enzymol.*, 35, 65 (1975)). All enzyme activities were assayed at 37° C. except the transferase, which was assayed at 20° C. Activity units indicate nmol of substrate consumed/minute. All assays were conducted, at a minimum, at two different protein concentrations with the appropriate enzyme and substrate blanks included.

II. EXAMPLES

Example 1

Expression of *A. Eutrophus* PHA Synthase using a Baculovirus System

Recent work has shown that PHA synthase from *A. eutrophus* can be overexpressed in *E. coli*, in the absence of 3-ketothiolase and acetoacetyl-CoA reductase (Gerngross et al., supra) and can be expressed in plants (See Poirier et al., *Biotech*, 13, 142 (1995) for a review). Isolation of the soluble form of PHA synthase provides opportunities to examine the mechanistic details of the priming and initiation reactions. Because the baculovirus system has been successful for the expression of a number of prokaryotic genes as soluble proteins, and insect cells, unlike bacterial expression systems, carry out a wide array of post-translational modifications, the baculovirus expression system appeared ideal for the expression of large quantities of soluble PHA synthase, a protein that must be modified by phosphopantetheine in order to be catalytically active (Germgross et al., supra).

Purification of PHA Synthase.

The purification procedure employed for PHA synthase is a modification of Germgross et al. (supra) involving the elimination of the second liquid chromatographic step and inclusion of a protease-inhibitor cocktail in all buffers. All steps were carried out on ice or at 4° C. except where noted. Frozen cells were thawed on ice in 10 ml of Buffer A (10 mM KPi, pH 7.2, 05% glycerol, and 0.05% Hecameg) and then immediately homogenized prior to centrifugation and HA chromatography.

The results of these efforts are summarized in Table 1 and FIG. 7. A prominent band at 64 kDa is visible in total, soluble, and HA eluate protein samples fractionated by SDS/PAGE (lanes 4, 5, and 6 of FIG. 7, respectively). The initial specific activity of the isolated PHA synthase was 20-fold higher than previous attempts at expression and purification of this polypeptide. Approximately 1000 units of PHB synthase have been purified, based on calculations from the direct spectrophotometric assay detailed below, with an overall recovery of activity of 70%. The large proportion of synthase present in the membrane fraction, and the fact that over 90% of the initial activity was found in the soluble fraction, suggest either that the synthase in the membrane fraction is in an inactive form or that the direct assay is not applicable to the initial, 12 U/mg, crude extract.

TABLE 1

Purification of PHA Synthase

| sample | total units | vol (mL) | (mg) | (mg/ml) | protein specific activity | recovery |
|---|---|---|---|---|---|---|
| total protein | 1430 | 11.5 | 113 | 9.8 | 12.7 | 100 |
| soluble protein | 1340 | 10.5 | 47 | 4.5 | 28.6 | 93 |
| pooled HA fractions | 1020 | 7.9 | 30 | 3.8 | 34.2 | 71 |

Figures 7A, 7B:
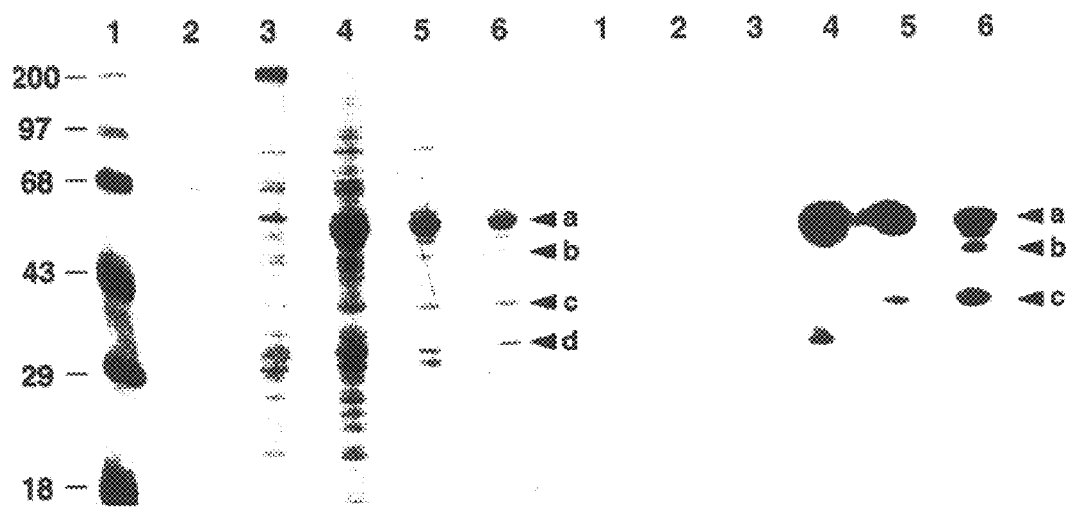
FIG. 7. (A) 10% SDS-PAGE gel showing samples from various stages of the purification of PHA synthase; lane 1, molecular weight markers; lane 2, total protein of uninfected insect cells; lane 3, total protein or insect cells expressing a rat FAS (200 kDa; Joshi et al., *Biochem. J.*, 296, 143 (1993)); lane 4, total protein of insect cells expressing PHA synthase; lane 5, soluble protein from sample in lane 4; lane 6, pooled hydroxylapatite (HA) fractions containing PHA synthase. (B) Western analysis of an identical gel using rabbit-α-PHA synthase antibody as probe. Bands designated with arrows are: a, intact PHB synthase with N-terminal alanine at residue 7 and serine at residue 10 (A7/S10); b, 44 kDa fragment of PHB synthase with N-terminal alanine at residue 181 and asparagine at residue 185 (A181/N185); c, PHB synthase fragment of approximately 30 kDa apparently blocked based on resistance to Edman degradation; d, 22 kDa fragment with N-terminal glycine at residue 187 (G187). Band d apparently does not react with rabbit-α-PHB synthase antibody (B, lane 6). The band of similar size in B, lane 4 was not further identified.

N-terminal sequencing of the 64 kDa protein confirmed its identity as PHA synthase (FIG. 8). Two prominent N-termini, at amino acid residue 7 (alanine) and residue 10 (serine) were obtained in a 3:2 ratio. This heterogeneous N-terminus presumably is the result of aminopeptidase activity. Western analysis using a rabbit-anti-PHA synthase antibody corroborated the results of the sequencing and indicated the presence of at least three bands that resulted from proteolysis of PHA synthase (FIG. 7B, lanes 4–6). The antibody was specific for PHA synthase since neither *T. ni* nor baculoviral proteins showed reactivity (FIG. 7B, lanes 2 and 3). N-terminal protein sequencing (FIG. 8) showed directly that the 44 kDa (band b) and 32 kDa (band d) proteins were derived from PHA synthase (fragments beginning at A181/N185 and at G387, respectively). The 35–40 kDa (band c) protein gave low sequencing yields and may contain a blocked N-terminus. Inspection of FIG. 7B suggests that most degradation occurs following cell disruption since the total protein sample of this gel (lane 4) was prepared by boiling intact cells directly in SDS sample buffer while the HA sample (lane 6) went through the purification procedure described above.

Assay of Synthase Activity.

Figure 9:
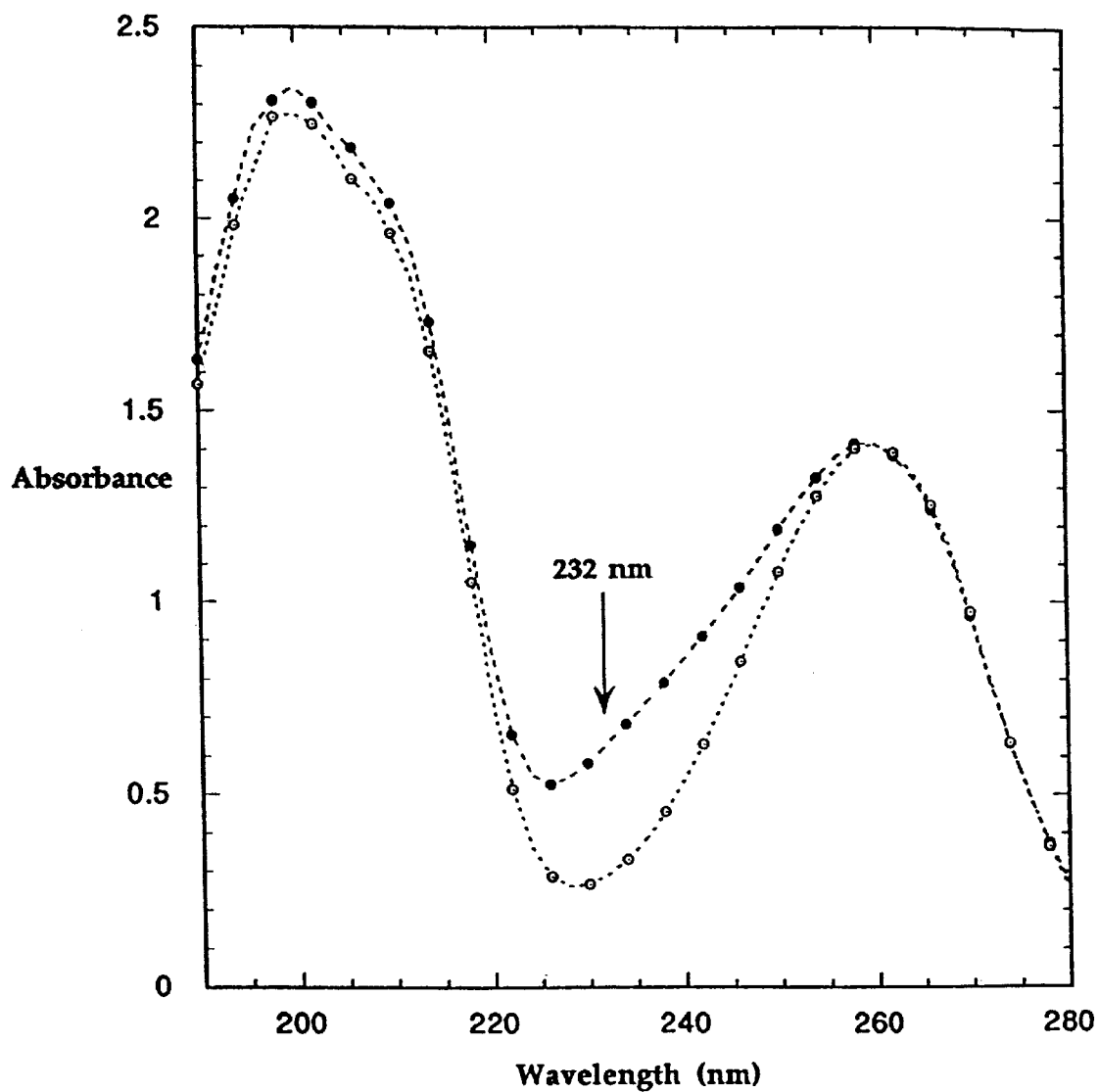
FIG. 9. Spectrophotometric scans of substrate, 3-hydroxybutyrate CoA (HBCOA) and product, CoA. The wavelength at which the direct spectrophotometric assays were carried out (232 nm) is denoted by the arrow; substrate, HBCoA (●) and product, CoA (○).

Due to the significant level of expression obtained using the baculovirus system, the synthase activity could be assayed spectrophotometrically by monitoring hydrolysis of the thioester bond at 232 nm, the wavelength at which there is a maximum decrease in absorbance upon hydrolysis. The difference between substrate (HBCOA) and product (CoA) at this wavelength is shown in FIG. 9. Absorbance of HBCoA and CoA at 232 nm occurs at a trough between two well-separated peaks. Assays were carried out at pH 7.2 for comparative analysis with previous studies (Gerngross et al., supra). Substrate (R-(−)3-HBCoA) substrate for these studies was prepared using the mixed anhydride method (Haywood et al., supra), and its concentration was determined by measuring $A_{260}$. The short pathlength cells (0.1 cm and 0.01 cm) allowed use of relatively high reaction concentrations while conserving substrate and enzyme. Assay results showed an initial lag period of 60 seconds prior to the linear decrease in $A_{232}$, and velocities were determined from the slope of these linear regions of the assay curves. The length of the lag period was variable and was inversely related to enzyme concentration. These data are consistent with those using PHA synthase purified from *E. coli* (Gemgross et al., supra).

Figure 10:
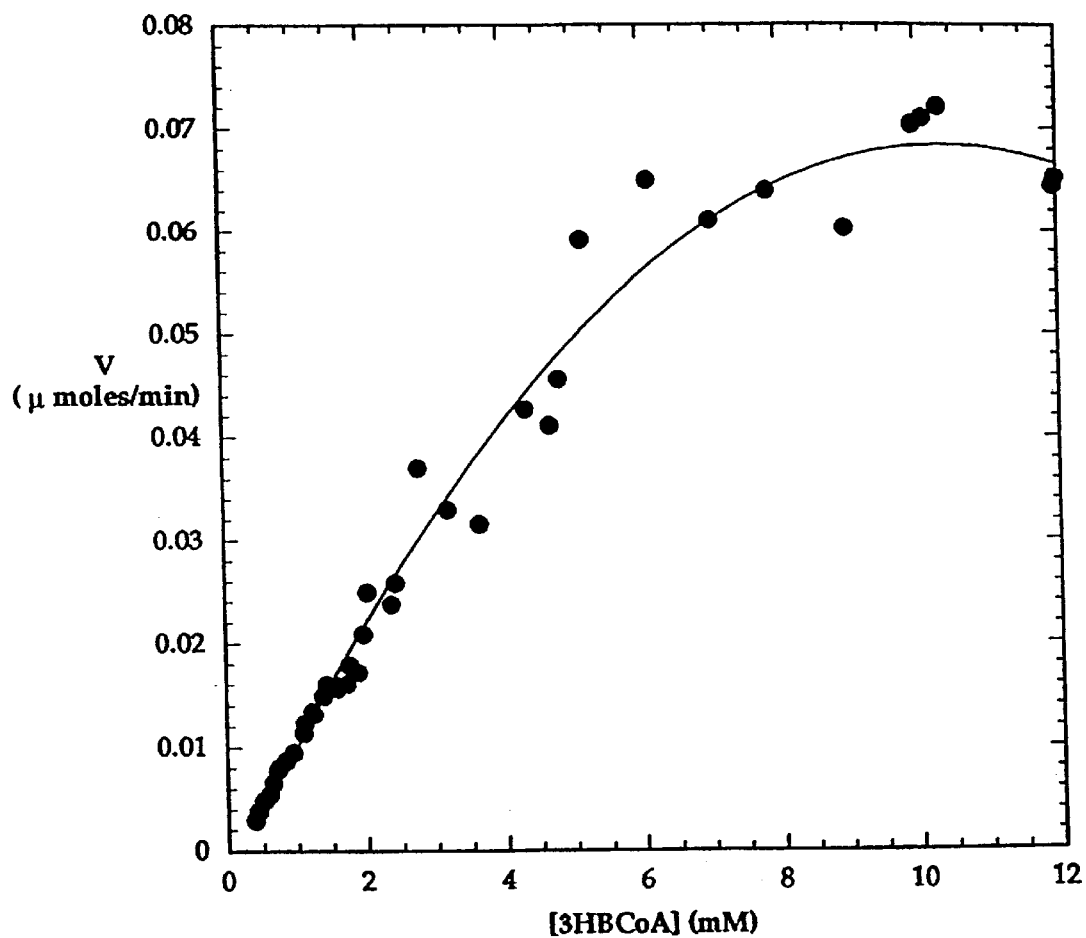
FIG. 10. Velocity of the hydrolysis of HBCoA as a function of substrate concentration. Assays were carried out in 40 or 200 µl assay volumes with enzyme concentration remaining constant at 0.95 mg/ml (3.8 µg/40 µl assay). Velocities were calculated from the linear portions of the assay curves subsequent to the characteristic lag period. The substrate concentration at half-optimal velocity, the apparent $K_m$ value, was estimated to be 2.5 mM from this data.
Figure 11:
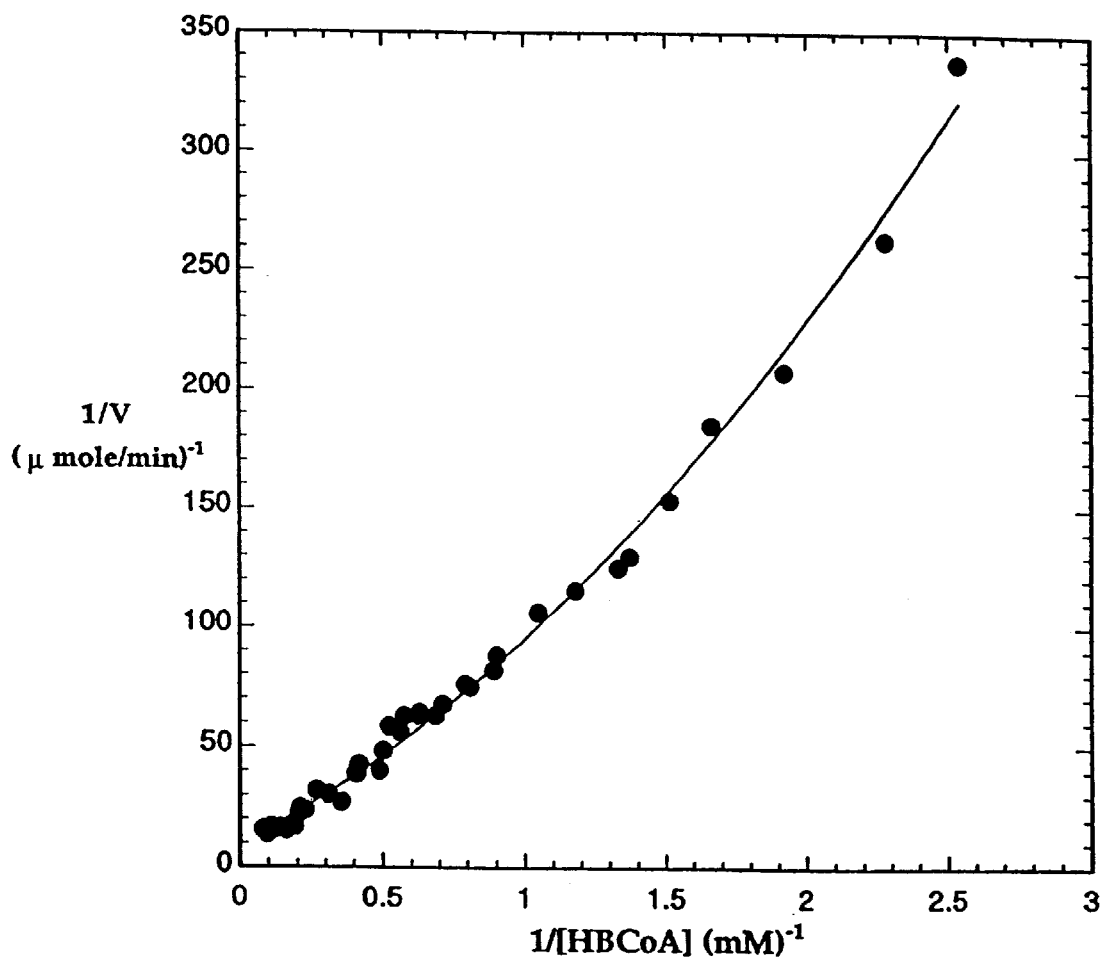
FIG. 11. Double reciprocal plot of velocity versus substrate concentration. The concave upward shape of this plot is similar to results obtained by Fukui et al. (*Arch. Microbiol.*, 110, 149 (1976)) with granular PHA synthase from *Z. ramigera.*
Figure 12:
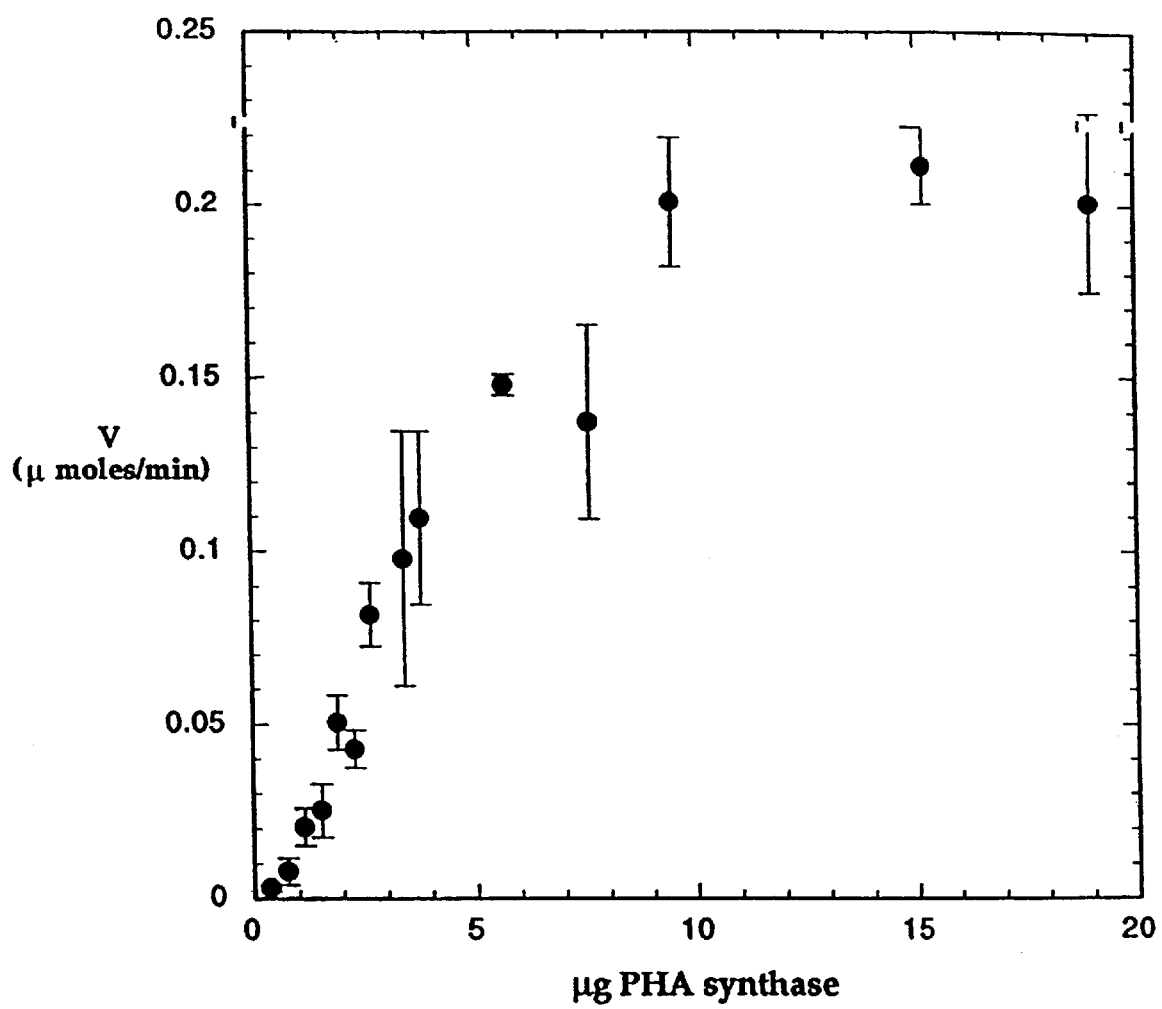
FIG. 12. Velocity of the hydrolysis of HBCoA as a function of enzyme concentration. Assays were carried out in 40 µl assay volumes with the concentration HBCoA remaining constant at 8 µM.
Figure 13:
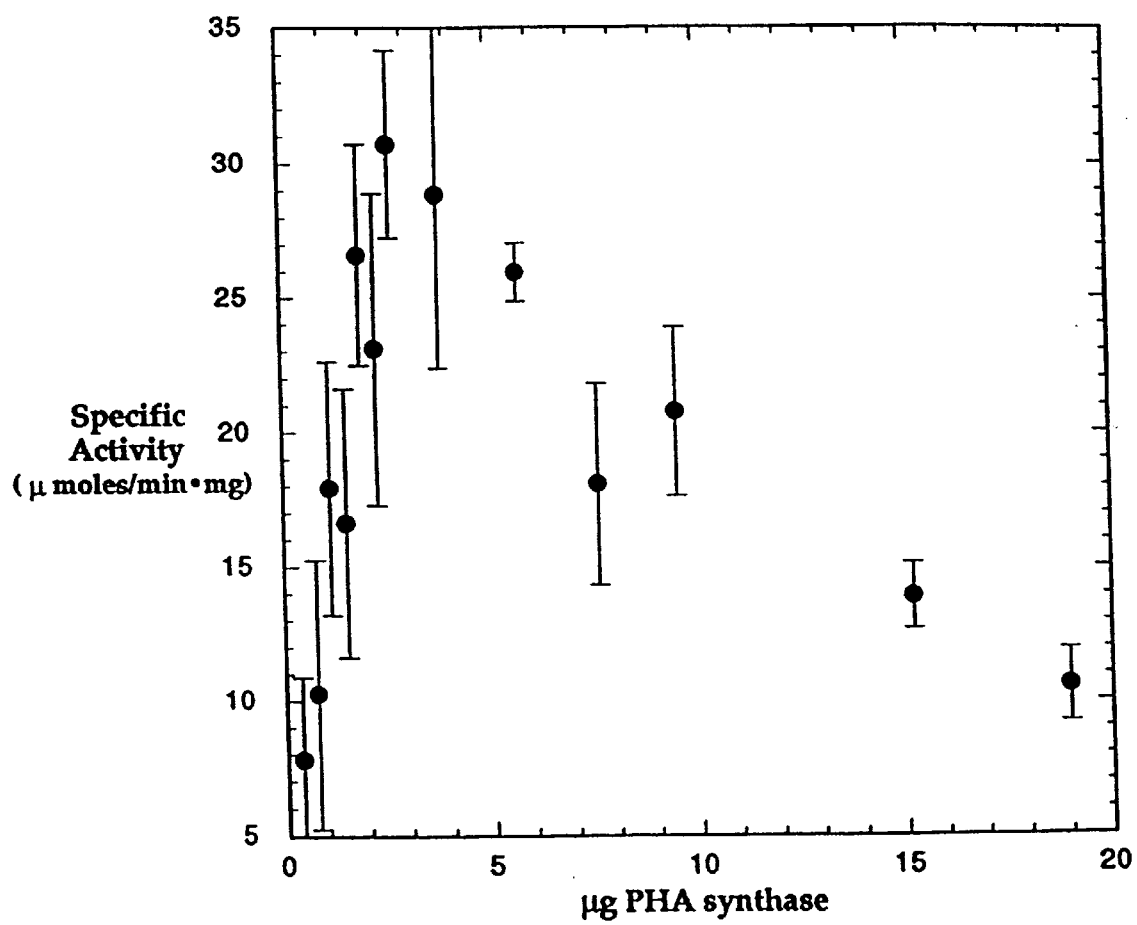
FIG. 13. Specific activity of PHA synthase as a function of enzyme concentration.
Figure 14:
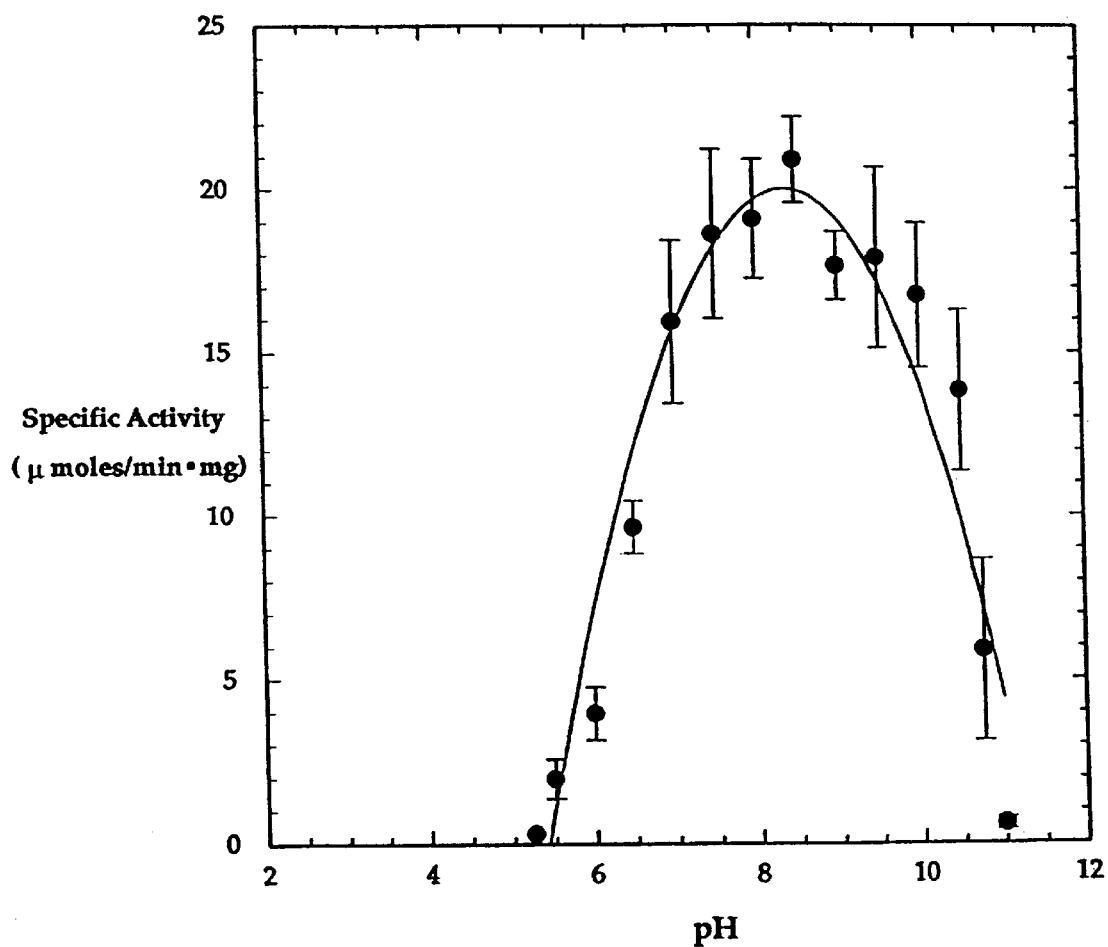
FIG. 14. pH activity curve for soluble PHA synthase produced using the baculovirus system. Reactions were carried out in the presence of 200 mM $P_i$. Buffers of pH<10 were prepared with potassium phosphate, while buffers of pH>10 were prepared with the appropriate proportion of $Na_3PO_4$.

FIGS. 10 and 11 show the V versus S and 1/V versus 1/S plots, respectively. The double reciprocal plot was concave upward which is similar to results obtained from studies of the granular PHA synthase from *Zooglea ramigera* (Fukui et al., *Arch. Microbiol.*, 110, 149 (1976)) and suggests a complex reaction mechanism. Examinations of velocity and specific activity as a function of enzyme concentration are shown in FIGS. 12 and 13. These results confirm that specific activity of the synthase depends upon enzyme concentration. The pH activity curve for *A. eutrophus* PHA synthase purified from *T. ni* cells is shown in FIG. 14. The curve shows a broad activity maximum centered around pH 8.5. This result agrees well with prior work on the *A. eutrophus* PHB synthase although it is significantly different than results obtained for the PHB synthase from *Z. ramigera* for which the optimum was determined to be pH 7.0.

Figure 15:
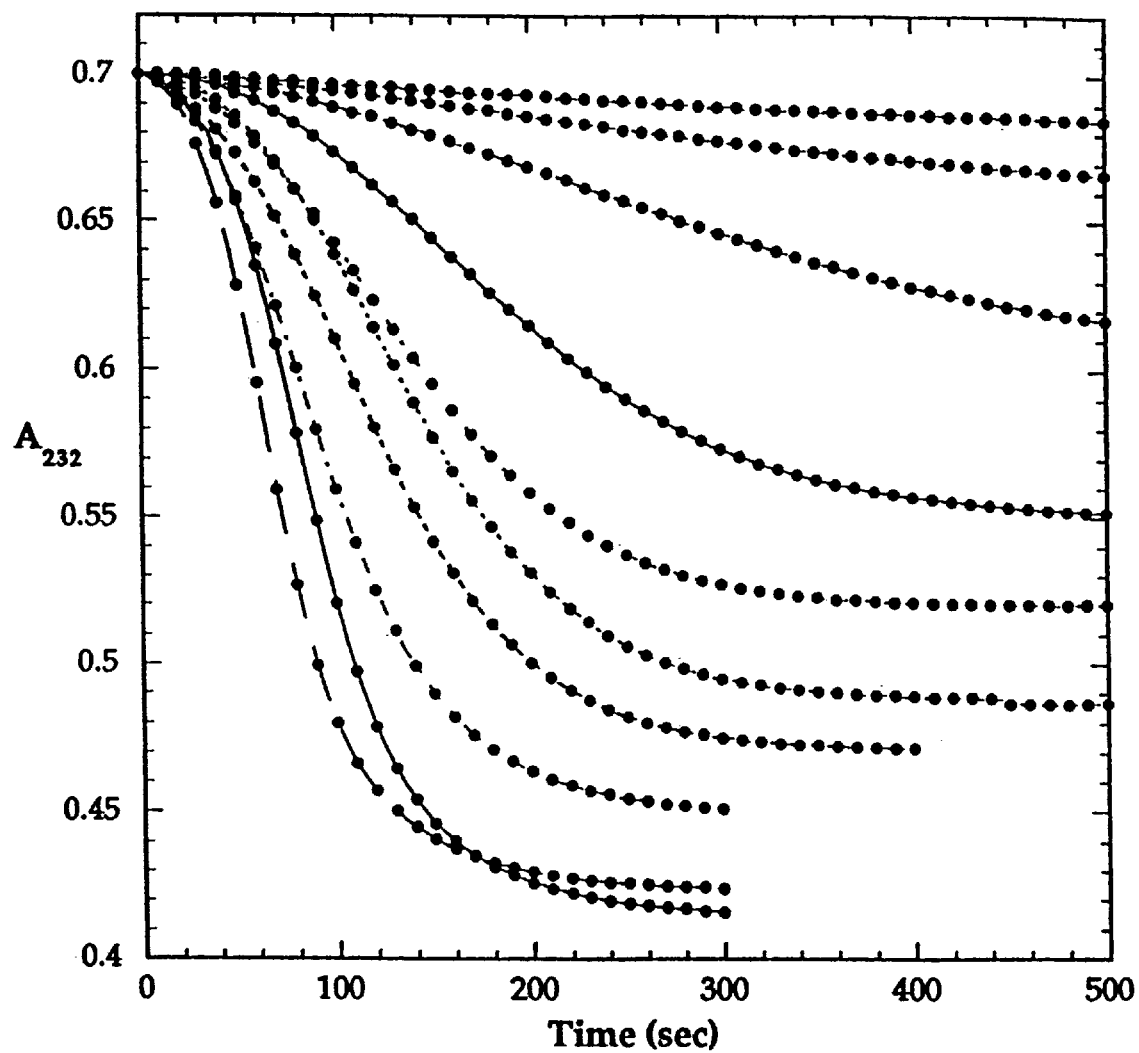
FIG. 15. Assays of the hydrolysis of HBCoA with varying amounts of PHA synthase. Assays were carried out in 40 μl assay volumes with the concentration of HBCoA remaining constant at 8 μM. Initial $A_{232}$ values, originally between 0.62 and 0.77, were normalized to 0.70. Enzyme amounts used in these assays were, from the uppermost curve, 0.38, 0.76, 1.14, 1.52, 1.90, 2.28, 2.66, 3.02, 3.42, 7.6, and 15.2 μg, respectively.

The effect of varying enzyme concentration in the presence of a fixed amount of substrate revealed an intriguing trend (FIG. 15). From these data it appears that the extent of polymerization is dependent on the amount of enzyme included in the reaction mixture. This could be explained if there is a "terminal length" limitation of the polymer, which, once reached, cannot be extended any further. If this is the case, it would also suggest that termination of the polymerization reaction, the release of the synthase from the polymer, and/or reinitiation of polymerization by the newly released synthase are relatively slow events since no evidence of these reactions are seen within the time course of these studies. The phenomenon observed in FIG. 15 is not the result of decay of the enzyme over the course of the assay since virtually identical results are obtained following a 10 minute preincubation of the synthase at 25° C.

It must also be noted that comparisons of the direct spectrophotometric assays used here and the more common assay involving the use of Ellman's reagent, DTNB, (Ellman, supra) in the formation of thiolate of coenzyme-A showed that the values determined by the direct method were approximately 70% of the values determined using Ellman's reagent. This may be due to phase separation occurring in the cuvettes as the relatively insoluble polymer is formed. In support of this notion, a faint haze or opalescence in the cuvette developed during the course of the reaction, particularly at higher substrate concentrations.

PHA synthase purified from insect cells appears to be relatively stable. Examination of activity following storage, in liquid $N_2$ and at −20° C. in the presence of 50% glycerol showed that approximately 50% of synthase activity remained after 7 weeks when stored in liquid $N_2$ and approximately 75% of synthase activity remained after 7 weeks when stored at −20° C. in the presence of 50% glycerol.

The expression of PHA synthase from A. eutrophus in a baculovirus expression system results in the synthase constituting approximately 50% of total protein 60 hours post-infection; however, approximately 50–75% of the synthase is observed in the membrane-associated fraction. This elevated level of expression allowed purification of the soluble PHA synthase using a single chromatographic step on HA. The purity of this preparation is estimated to be approximately 90% (intact PHA synthase and 3 proteolysis products).

The initial specific activity of 12 U/mg was approximately 20-fold higher than the most successful previous efforts at overexpression of A. eutrophus PHA synthase. The synthase reported here was isolated from a 250 ml culture with 70% recovery which represents an improvement of 500-fold (1000 U/64 U×8 L/0.25 L) when compared to an 8 L E. coli culture with 40% recovery. This high expression level should provide sufficient PHA synthase for extensive structural, functional, and mechanistic studies. Furthermore, it is clear that the baculovirus expression system is an attractive option for isolation of other PHA synthases from various sources.

PHA synthase produced in the baculovirus system was of sufficient potency to allow direct spectrophotometric analysis of the hydrolysis of the thioester bond of HBCoA at 232 nm. These assays revealed a lag period of approximately 60 seconds, the length of which was variable and inversely related to enzyme concentration. Such a lag period presumably reflects a slow step in the reaction, perhaps correlating to dimerization of the enzyme, the priming, and/or initiation steps in formation of PHB. Size exclusion chromatographic examination of the PHB synthase native MW indicated two forms of the synthase. One form showed a MW of approximately 100–160 kDa and the other showed a MW of approximately 50–80 kDA; these two forms likely represent the dimer and monomer of PHA synthase, respectively. Similar results have been reported previously in which two forms of approximately 60 and 130 kDa were observed. Comparisons of the direct assay reported here and the indirect assay using DTNB revealed that the former resulted in values that were 70% of the values determined by the DTNB indirect assay. Although the reason for this difference has not been examined in detail, it is probable that the apparent phase separation that occurred upon P1B formation in the short pathlength cuvettes used, particularly with high [HBCoA], results in this discrepancy.

Enzymatic analyses of the PHA synthase have found that the enzyme has a broad pH optimum centered at pH 8.5; however, the studies described herein have been performed at pH 7.2 to provide comparative values with the results of others. Moreover, the specific activity of this enzyme is dependent upon enzyme concentration which confirms and extends earlier results (Gerngross et al., supra).

In studies intended to examine the dependence of activity upon enzyme concentration, it became apparent that the extent of the polymerization reaction is dependent on the amount of enzyme included in the reaction mixture. Specifically, decreasing the amount of enzyme leads not only to decreased velocity of reaction but also to a decreased extent of condensation (FIG. 15). One possible explanation is that the enzyme is thermally labile; however, identical assays in which the enzyme is preincubated at 25° C. for 10 minutes prior to initiation of the reaction had similar results. Another possibility is that a terminal-length of the polymer is reached precluding further condensations until the particular synthase molecule is released from the terminal-length polymer.

This work clearly demonstrates the value of the baculovirus expression system for the production of A. eutrophus PHA synthase and for the potential application to studies of other PHA synthases. Furthermore, the high level of expression obtained using the baculoviral system should allow convenient analysis for substrate-specificity and structure-function studies of PHA synthases from relatively crude insect cell extracts.

Example 2

Co-expression of Rat FAS Dehydraae Mutant cDNA and PHB Synthase Gene in Insect Cells Expression of a rat FAS DH- cDNA in Sf9 cells has been reported previously (Rangan et al., J. Biol. Chem., 266, 19180 (1991); Joshi et al., Biochem. J., 296, 143 (1993)). Once activity of the phbC gene product had been established in insect cells (see Example 1), baculovirus clones containing the rat FAS DH- cDNA and BacPAK6::phbC were employed in a double-infection strategy to determine if PHB would be produced in insect cells. It was not known if an intracellular pool of R(−)-3-hydroxybutyrate would be stable or available as a substrate for the PHB synthase. In order for the R-(−)-3-hydroxybutyrylCoA to be available as a substrate, the R-(−)-3-hydroxybutyrylCoA released from rat FAS DH- protein must be trapped by the PHB synthase and incorporated into a polymer at a rate faster than oxidation, which would regenerate acetylCoA. It was also not known if the stereochemical configuration of the 3-hydroxyl group, which must be in the R form, would be recognized as a substrate by PHB synthase. Fortunately, previous biochemical studies on eukaryotic FASs indicated that the R form of 3-hydroxybutyrylCoA would be generated (Wakil et al., J. Biol. Chem., 237, 687 (1962)).

Figure 16:
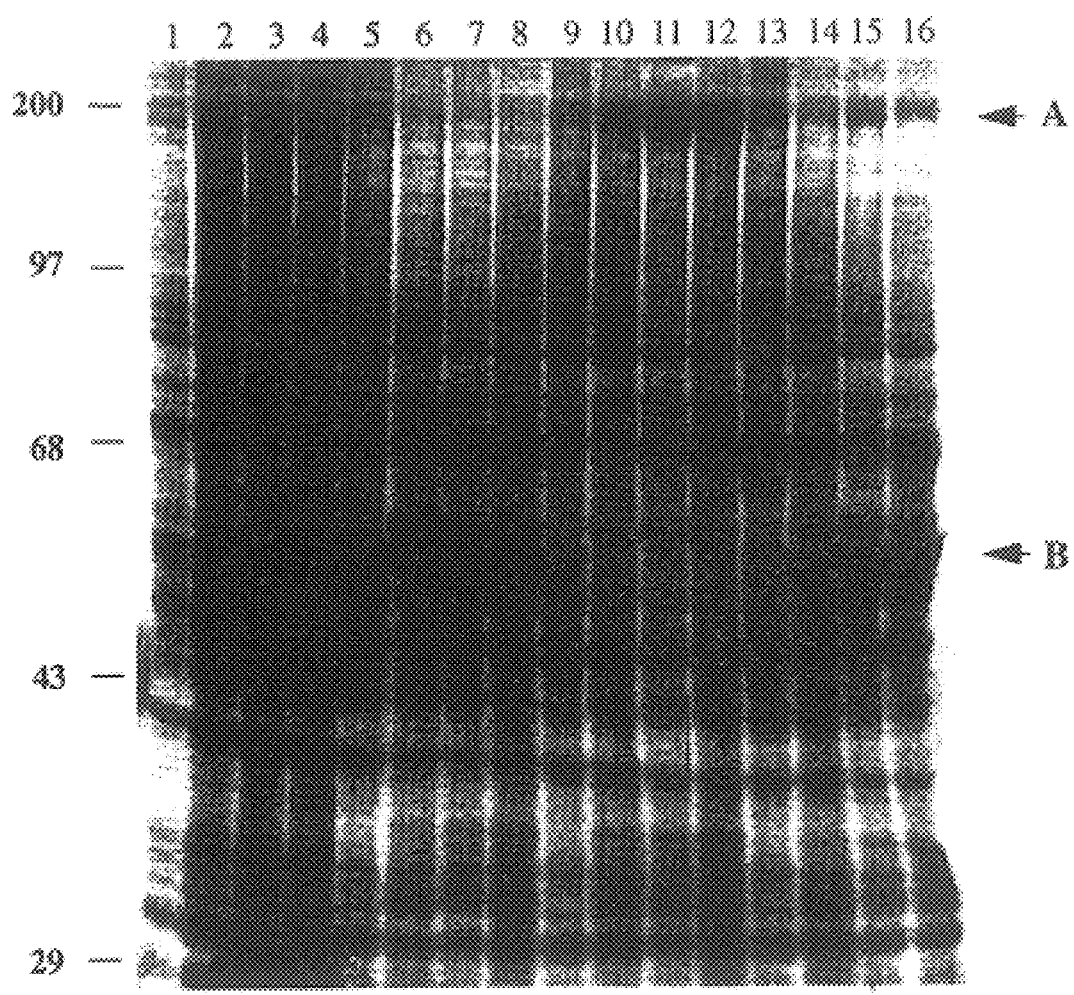
FIG. 16. SDS/PAGE analysis of proteins synthesized at various time points during infection of Sf21 cells. Approximately 0.5 mg of total cellular protein from various samples was fractionated on a 10% polyacrylamide gel. Samples include: uninfected cells, lanes 1–4, days 0, 1, 2, 3, respectively; infection with BacPAK6::phbC alone, lanes 5–8, days, 0, 1, 2, 3, respectively, infection with baculoviral clone containing ratFAS206 alone, lanes 9–12, days 0, 1, 2, 3, respectively; and ratFAS206 and BacPAK6 infected cells, lanes 13–16, days 0, 1, 2, 3, respectively. A=mobility of FAS, B=mobility of PHA synthase. Molecular weight standard lanes are marked M.

SDS-PAGE of protein samples from a time course of uninfected, single-infected, and dual-infected Sf21 cells was performed (FIG. 16). From these data, it is clear that the rat FAS DH mutant and PHB synthase polypeptides are efficiently co-expressed in Sf21 cells. However, co-expression results in ~50% reduced levels of both polypeptides compared to Sf21 cells that are producing the individual proteins. Western analysis using anti-rat FAS (Rangan et al., supra) and anti-PHA synthase antibodies confirmed simultaneous production of the corresponding proteins.

To provide further evidence that PHB was being synthesized in insect cells, T. ni cells which had been infected with a baculovirus vector encoding rat FAS DHO and/or a baculovirus vector encoding PHA synthase were analyzed for the presence of granules. Infected cells were fixed in paraformaldehyde and incubated with anti-PHA synthase antibodies (Williams et al., Protein Exp. Purif., 7, 203 (1996)). Granules were observed only in doubly infected cells (Williams et al., App. Environ. Micro., 62, 2540 (1996)).

Characterization of PHB Production in Insect Cells.

Figure 17:
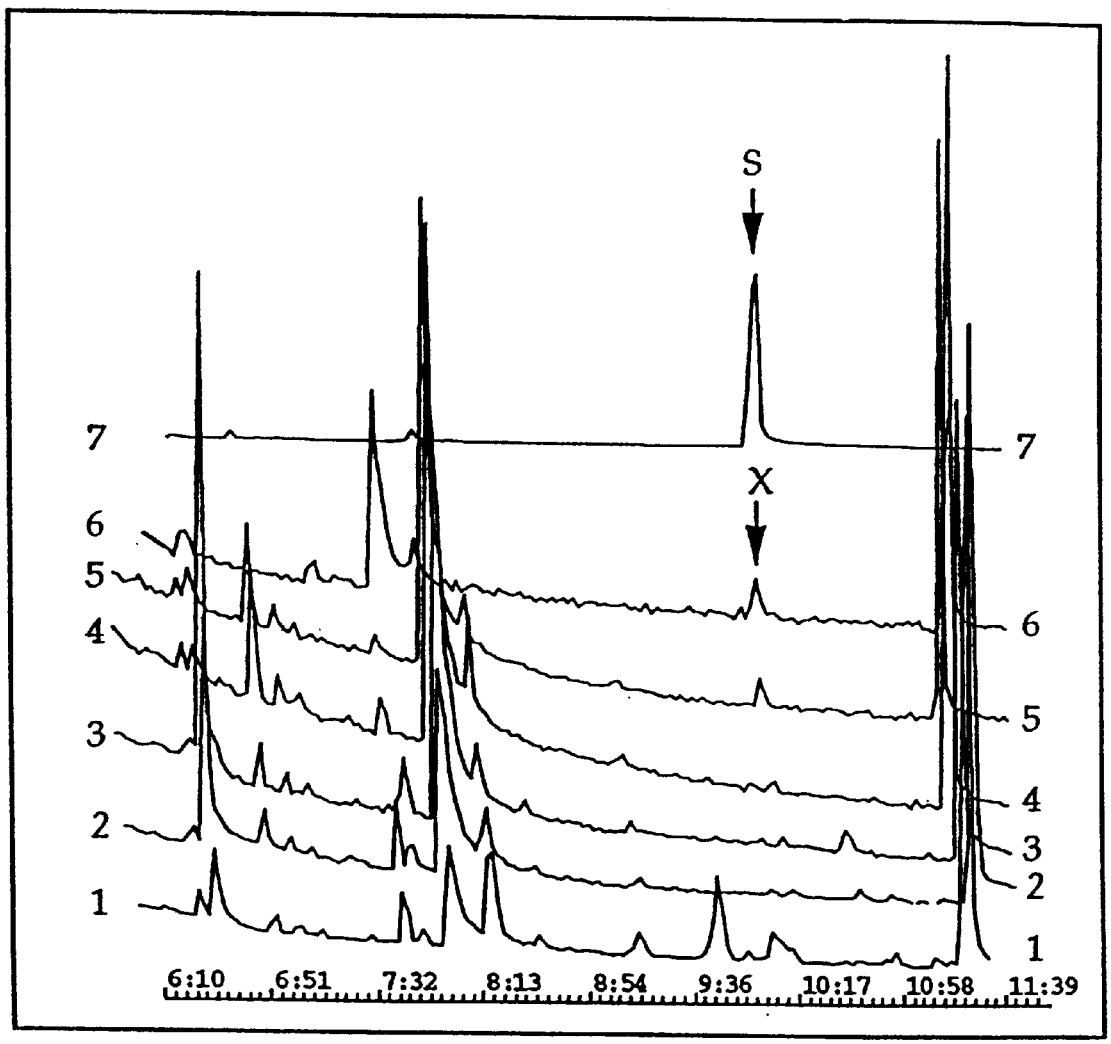
FIG. 17. Gas chromatographic evidence for PHB accumulation in Sf21 cells. Gas chromatograms from various samples are superimposed. PHB standard (Sigma) is chromatogram #7 showing a propylhydroxybutyrate elution time of 10.043 minutes (s, arrow). The gas chromatograms of extracts of the uninfected (#1); singly infected with rat-FAS206 (#2, day 3); and singly infected with PHA synthase (#3, day 3) are shown at the bottom of the figure. Gas chromatograms of extracts of dual-infected cells at day 1 (#4), 2 (#5), and 3 (#6) are also shown exhibiting a peak eluting at 10.096 minutes (x, arrow). The peak of dual-infected, day 3 extract (#6) was used for mass spectrometry (MS) analysis.
Figure 18:
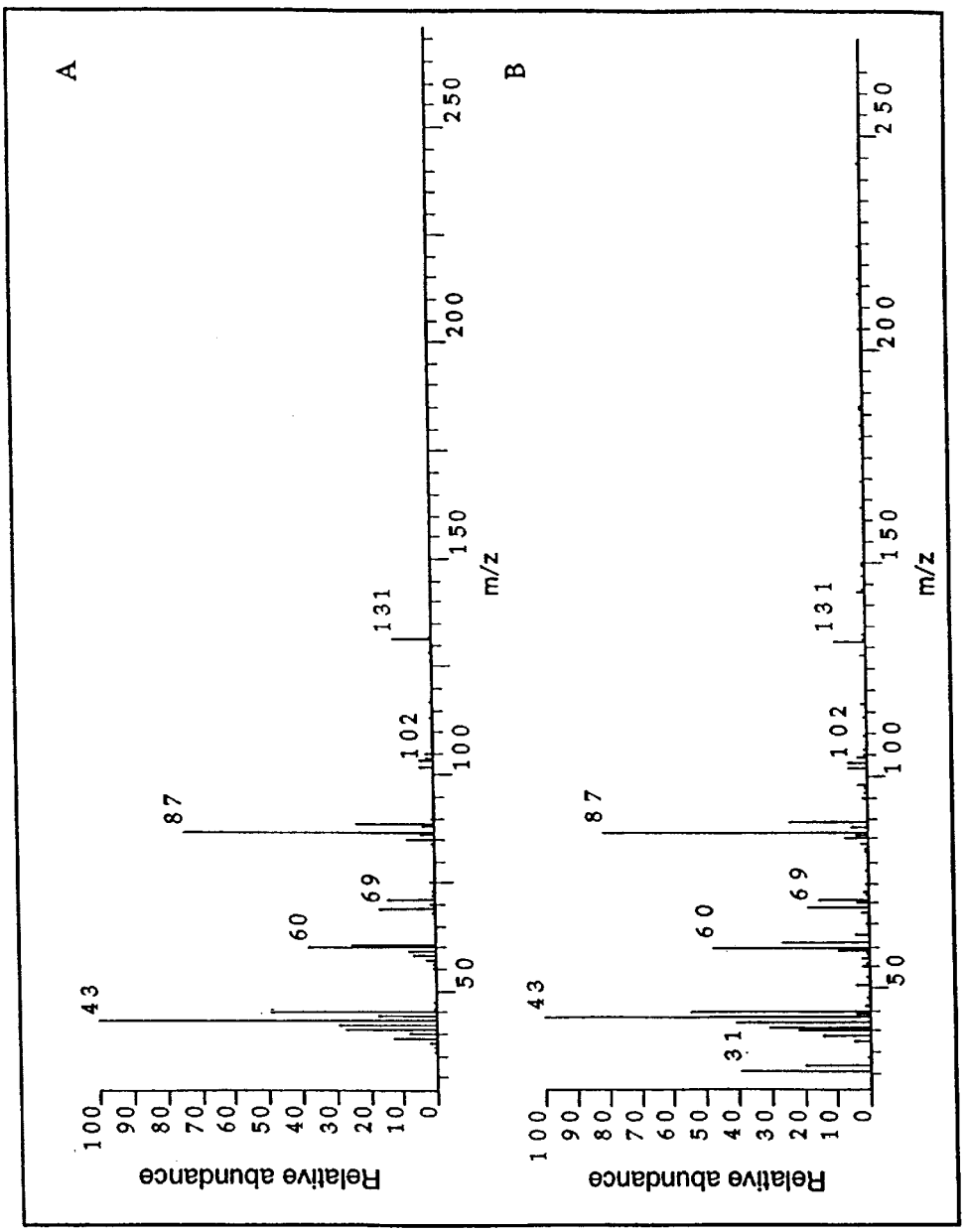
FIG. 18. Gas chromatography-mass spectrometry analysis of PHB. The characteristic fragmentation of propylhydroxybutyrate at m/z of 43, 60, 87, and 131 is shown. A) standard PHB from bacteria (Sigma), and B) peak X from ratFAS206 and BacPAK6: phbC baculovirus infected, day 3 (#6, FIG. 17) Sf21 cells expressing rat FAS dehydrase inactivated protein and PHA synthase.

In order to determine if de novo synthesis of PHB was occurring in Sf21 cells that co-express the rat FAS DH mutant and PHB synthase, fractions of these samples were extracted, the extract subjected to propanolysis, and analyzed for the presence of propylhydroxybutyrate by gas chromatography (FIG. 17). A unique peak with a retention time that coincided with a propylhydroxybutyrate standard was detected only in the double infection samples at 48 and 72 hours, in contrast to the individually expressed gene products and uninfected controls, which were negative. These samples were analyzed further by GC/MS to confirm the identity of the product. FIG. 18 shows mass spectroscopy data corresponding to the material obtained from peak 10.1 in the gas chromatograph compared to a propylhydroxybutyrate standard. The results show that PHB synthesis is occurring only in Sf21 cells co-expressing the rat FAS DH mutant cDNA and the phbC gene from *A. eutrophus*. Integration of the peak in the gas chromatograph corresponding to propylhydroxybutyrate revealed that approximately 1 mg of PHB was isolated from 1 liter culture of Sf21 cells (approximately 600 mg dry cell weight of Sf21 cells). Thus, the ratFAS206 protein effectively replaces the β-ketothiolase and acetoacetyl-CoA reductase functions, resulting in the production of PHB by a novel pathway.

The approach described here provides a new strategy to combine metabolic pathways that are normally engaged in primary anabolic functions for production of polyesters. The premature termination of the normal fatty acid biosynthetic pathway to provide suitably modified acylCoA monomers for use in PHA synthesis can be applied to both prokaryotic and eukaryotic expression since the formation of polymer will not be dependent on specialized feedstocks. Thus, once a recombinant PHA monomer synthase is introduced into a prokaryotic or eukaryotic system, and co-expressed with the appropriate PHA synthase, novel bipolymer formation can occur.

Example 3

Cloning and Sequencing of the Vep ORFI PKS Gene Cluster

Figures 19, 32:
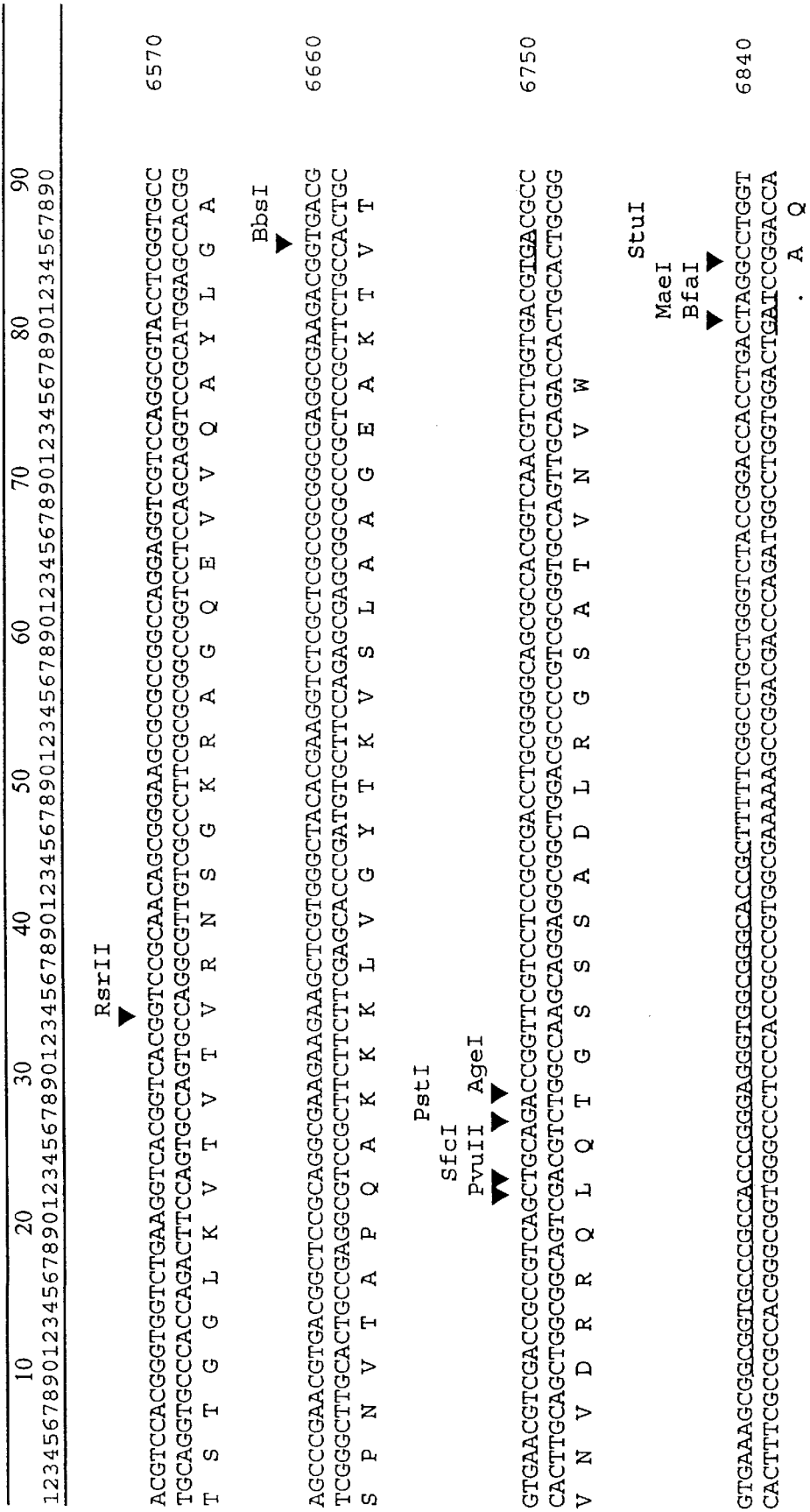
FIG. 19. Map of the vep (*Streptomyces venezuelae* polyene encoding) gene cluster.
Figures 21, 32:
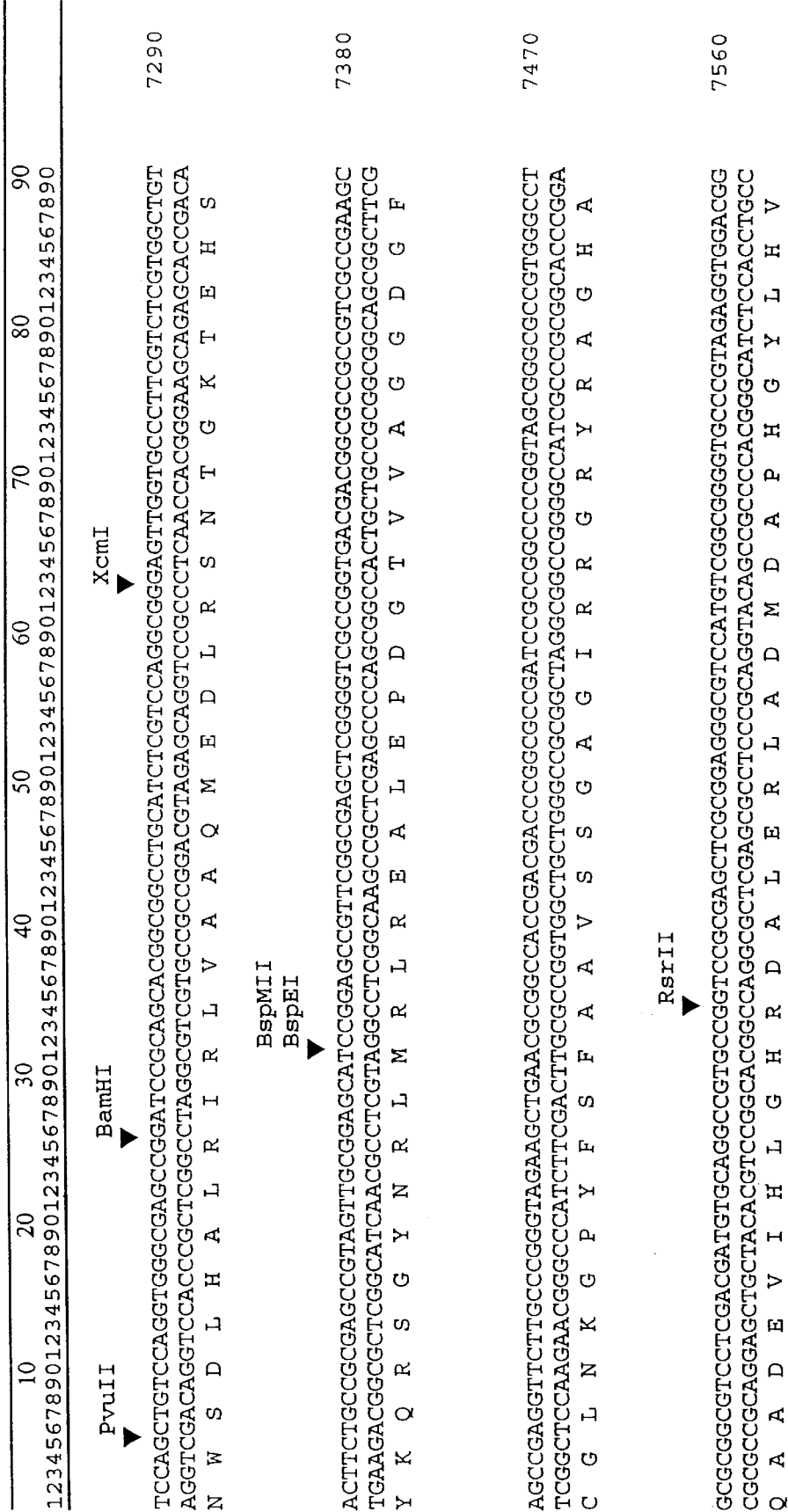
Figures 22, 32:
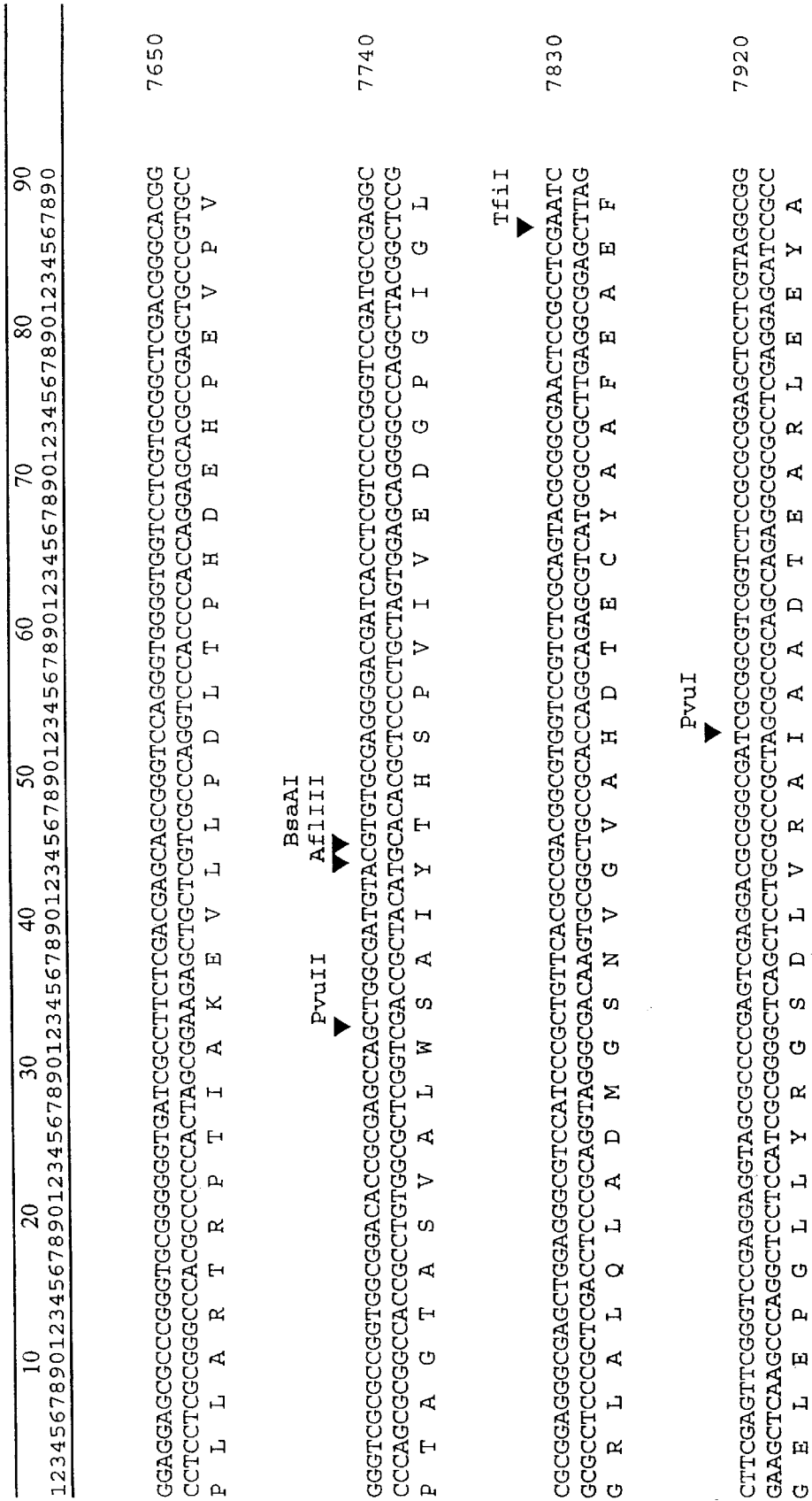
FIG. 22. Cloning protocol for pDHS505.
Figures 23, 32:
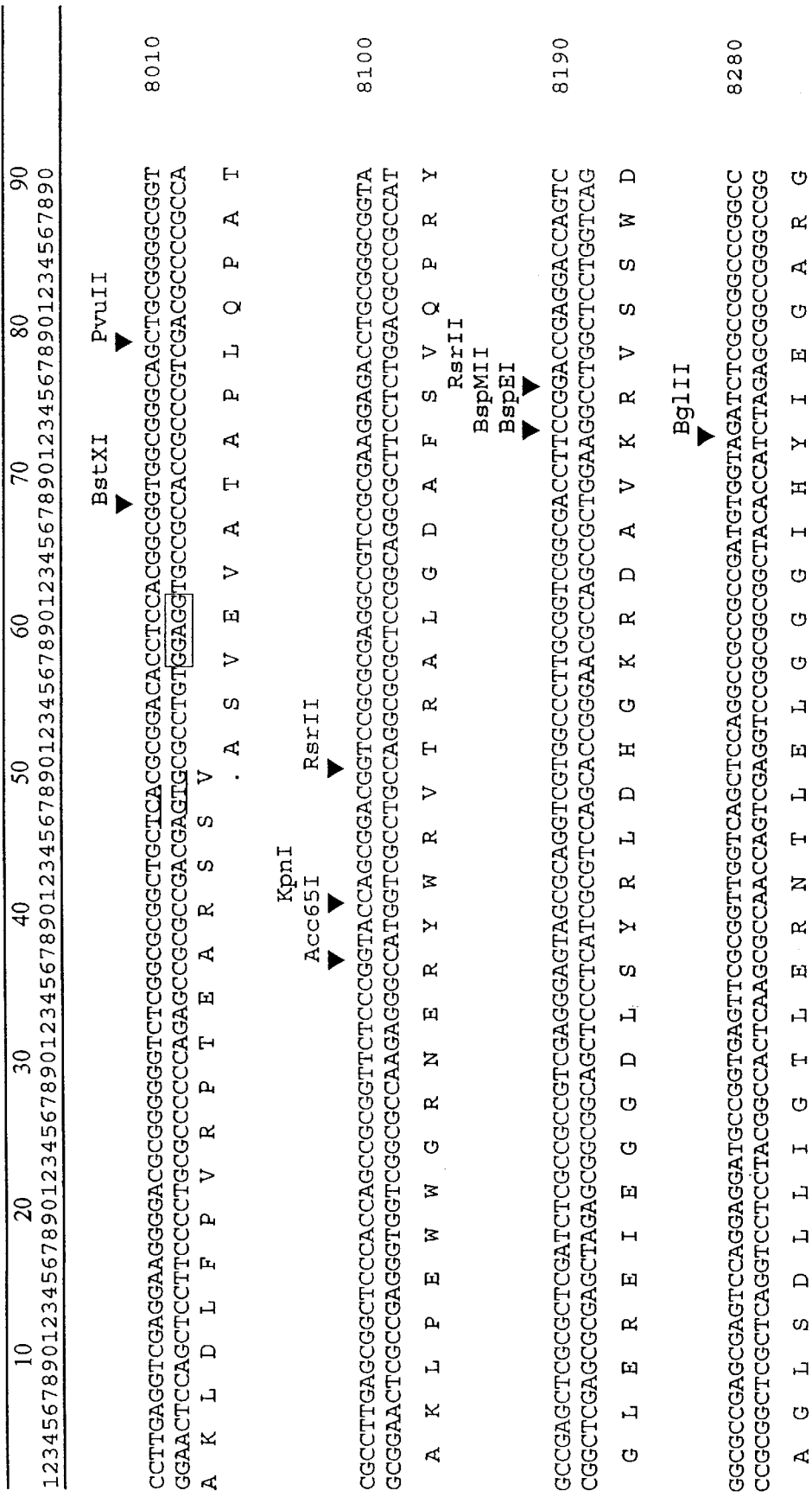
FIG. 23. Nucleotide sequence (SEQ ID NO:1) and corresponding amino acid sequence (SEQ ID NO:2) of vep ORFI.
Figure 34:
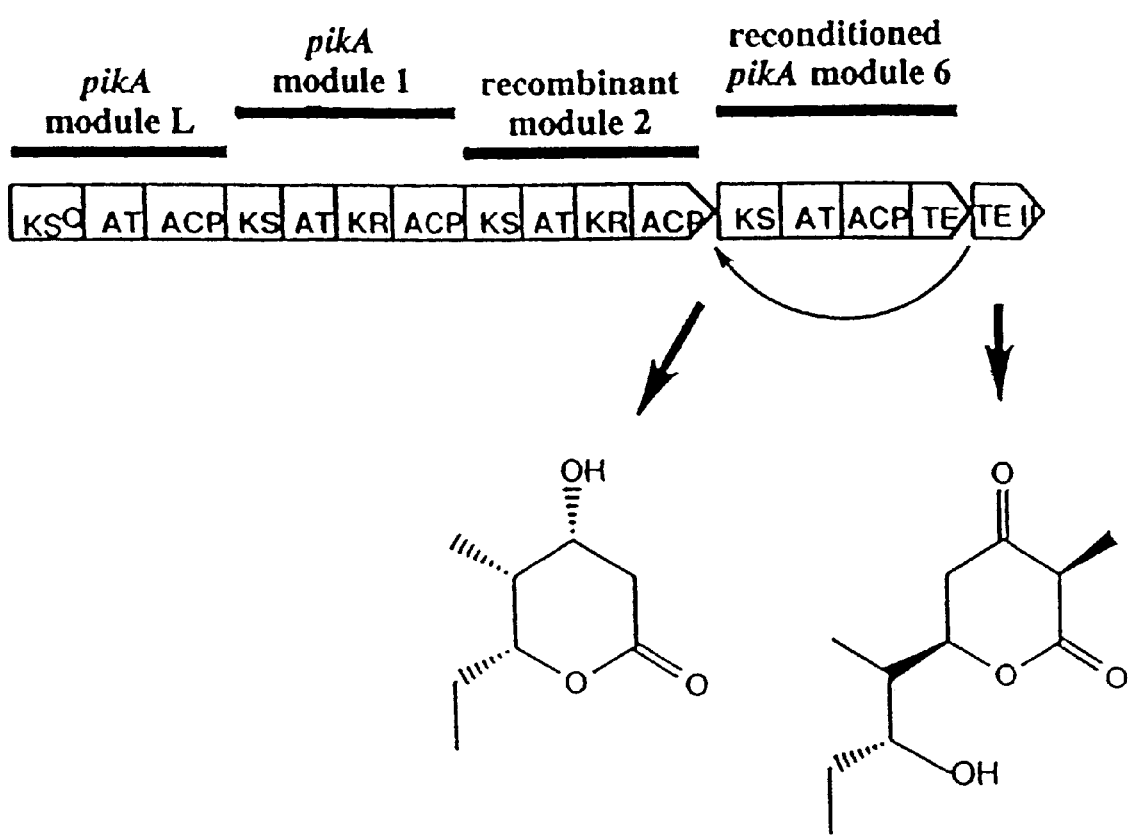
Figure 35:
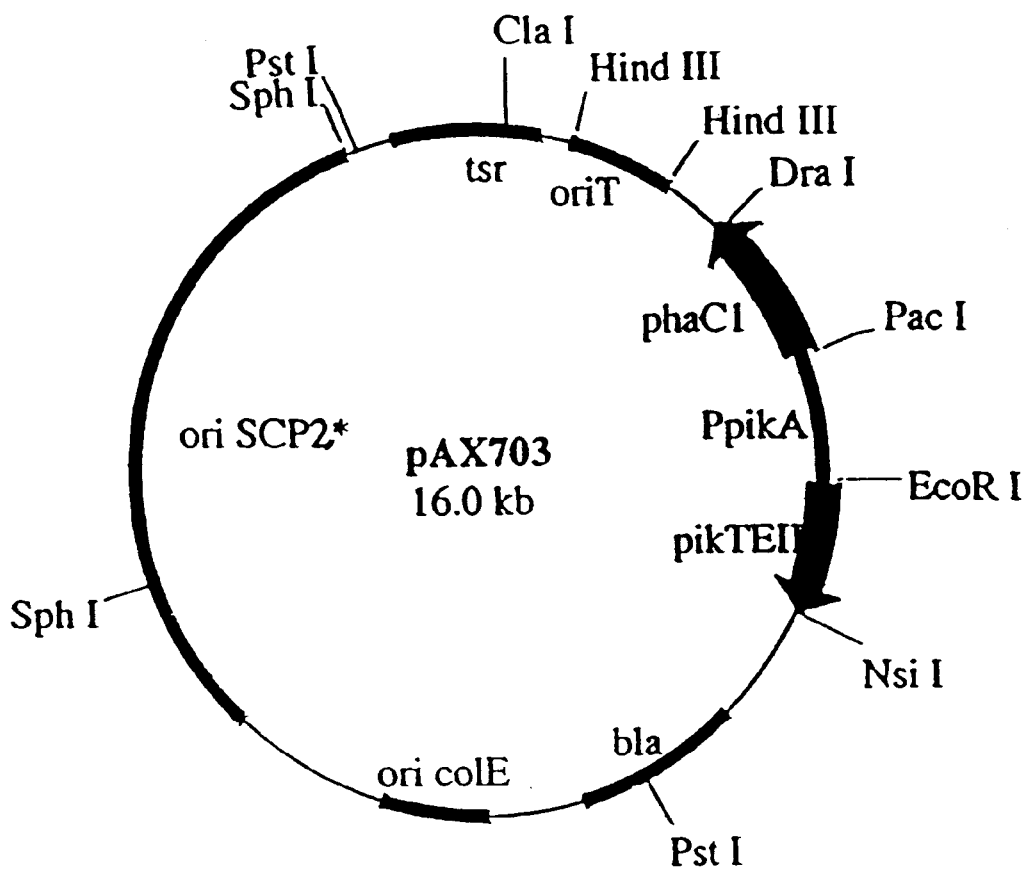
Figure 36:
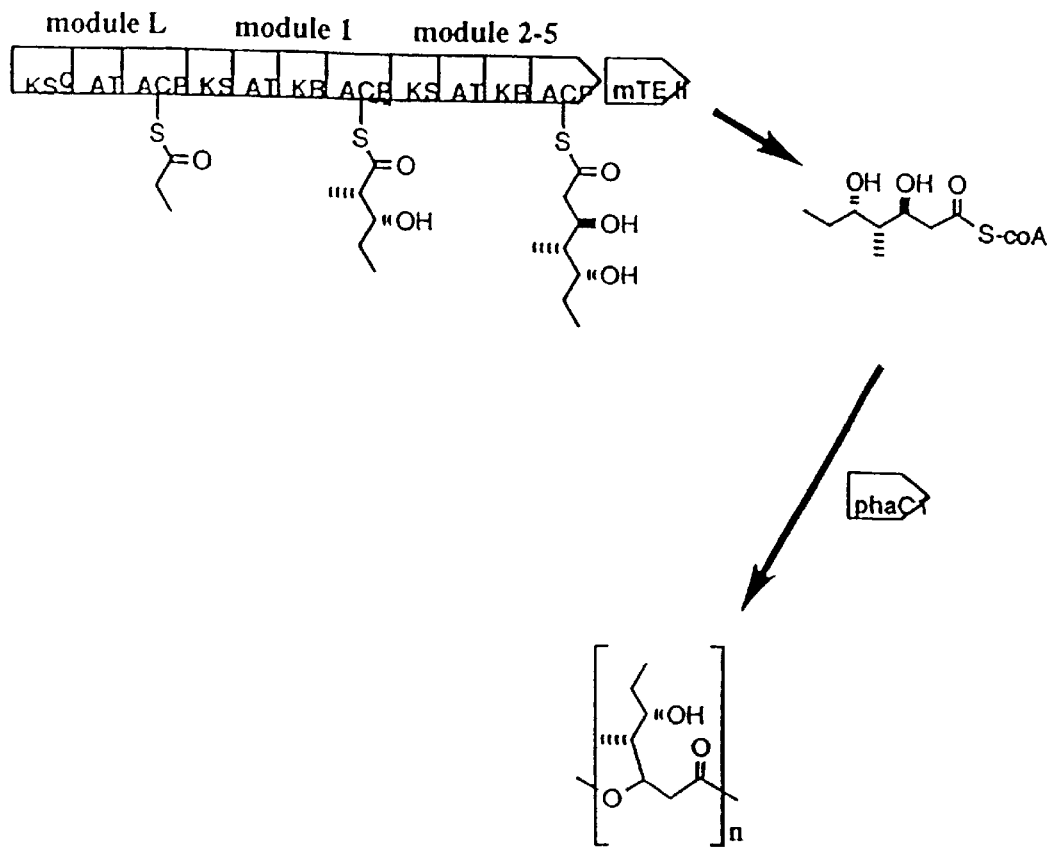
Figure 37:
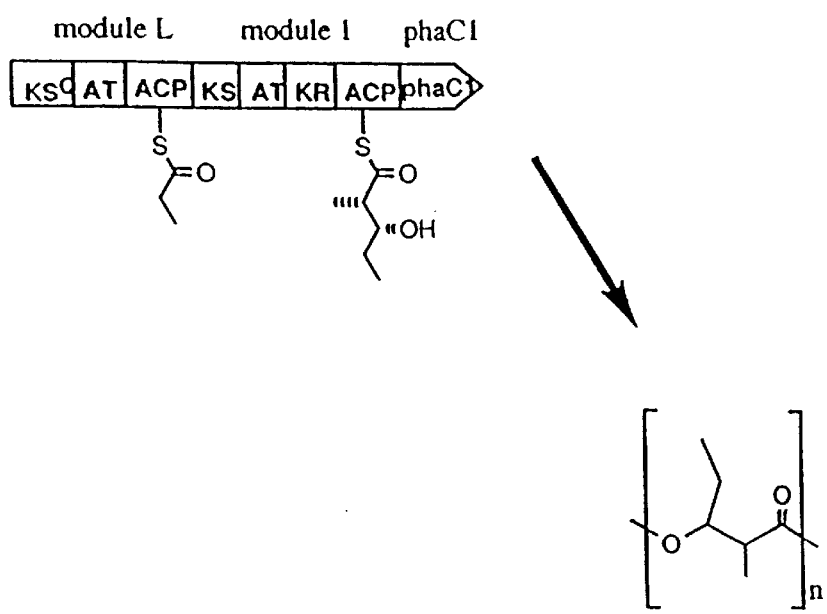

The entire PKS cluster form *Streptomyces venezuelae* was cloned using a heterologous hybridization strategy. A 1.2 kb DNA fragment that hybridized strongly to a DNA encoding an eryA PKS β-ketoacyl synthase domain was cloned and used to generate a plasmid for gene disruption. This method generated a mutant strain blocked in the synthesis of the antibiotic. A *S. venezuelae* genomic DNA library was generated and used to clone a cosmid containing the complete methymycin aglycone PKS DNA. Fine-mapping analysis was performed to identify the order and sequence of catalytic domains along the multifunctional PKS (FIG. 19). DNA sequence analysis of the vep ORFI showed that the order of catalytic domains is $KS^Q$/AT/ACP/KS/AT/KR/ACP/KS/AT/DH/KR/ACP. The complete DNA sequence, and corresponding amino acid sequence, of the vep ORFI is shown in FIG. 23 (SEQ ID NO:1 and SEQ ID NO:2, respectively).

The sequence data indicated that the PKS gene cluster encodes a polyene of twelve carbons. The vep gene cluster contains 5 polyketide synthase modules, with a loading module at its 5' end and an ending domain at its 3' end. Each of the sequenced modules includes a keto-ACP (KS), an acyltransferase (AT), a dehydratase (DH), a keto-reductase (KR), and an acyl carrier protein domain. The six acyltransferase domains in the cluster are responsible for the incorporation of six acetyl-CoA moieties into the product. The loading module contains a $KS^Q$, an AT and an ACP domain. $KS^Q$ refers to a domain that is homologous to a KS domain except that the active site cysteine (C) is replaced by glutamine (Q). There is no counterpart to the $KS^Q$ domain in the PKS clusters which have been previously characterized.

The ending domain (ED) is an enzyme which is responsible for the attachment of the nascent polyketide chain onto another molecule. The amino acid sequence of ED resembles an enzyme, HetM, which is involved in Anabaena heterocyst formation. The homology between vep and HetM suggests that the polypeptide encoded by the vep gene cluster may synthesize a polyene-containing composition which is present in the spore coat or cell wall of its natural host, *S. venezuelae*.

Example 4

Preparation of a Vector Encoding a Saturated β-hydroxyhexanoyl CoA Monomer or an Unsaturated β-hydroxyhexanoy CoA Monomer To provide a recombinant monomer synthase that generates a saturated β-hydroxyhexanoylCoA or unsaturated β-hydroxyhexanoylCoA monomer, the linear correspondence between the genetic organization of the Type I macrolide PKS and the catalytic domain organization in the multifunctional proteins is assessed (Donadio et al., supra, 1991; Katz et al., *Ann. Rev. Microbiol.*, 47, 875 (1993)). First, a DNA encoding a TE is added to the 3' end of an ORFI of a Type I PKS, preferably the met ORFI (FIG. 6) as recently described by Cortes et al. (*Science*, 268, 1487 (1995)) in the erythromycin system. To ensure that the DNA encoding the TE is completely active, DNA encoding a linker region separating a normal ACP-TE region in a PKS, for example, the one found in met PKS ORF5 (FIG. 5), will be incorporated into the DNA. The resulting vector can be introduced into a host cell and the TE activity, rate of release of the CoA product, and identity of the fatty acid chain determined.

The acyl chain that is most likely to be released is the CoA ester, specifically the 3-hydroxy-4-methyl heptenoylCoA ester, since the fully elongated chain is presumably released in this form prior to macrolide cyclization. If the CoA form of the acyl chain is not observed, then a gene encoding a CoA ligase will be cloned and co-expressed in the host cell to catalyze formation of the desired intermediate.

There is clear precedent for release of the predicted premature termination products from mutant strains of macrolide-producing Streptomyces that produce intermediates in macrolide synthesis (Huber et al., *Antimicrob. Agents Chemother.*, 34, 1535 (1990); Kinoshita et al., *J. Chem. Soc., Chem. Comm.*, 14, 943 (1988)). The structure of these intermediates is consistent with the linear organization of functional domains in macrolide PKSs, particularly those related to eryA, tyl, and met. Other known PKS gene clusters include, but are not limited to, the gene cluster encoding 6-methylsalicylic acid synthase (Beck et al., *Eur. J. Biochem.*, 192, 487 (1990)), soraphen A (Schupp et al., *J. Bacteriol.*, 171, 3673 (1995)), and sterigmatocystin (Yu et al., *J. Bacteriol.*, 177, 4792 (1995)).

Figure 4:
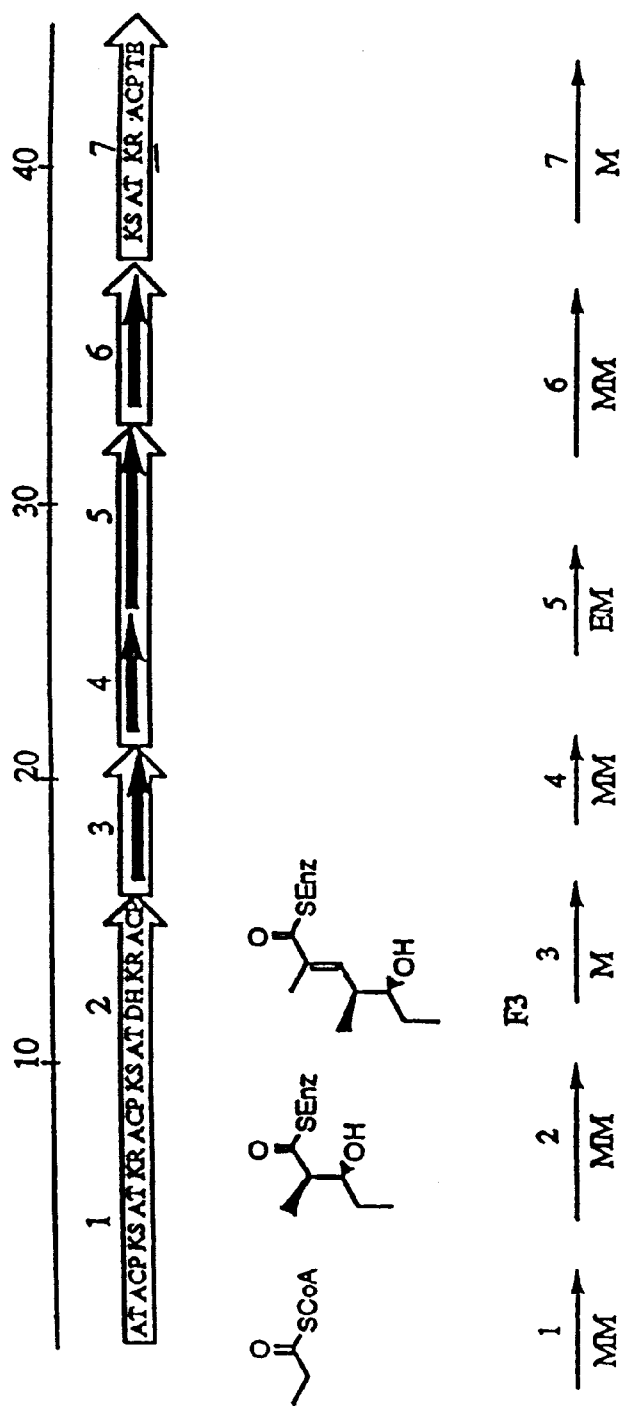
FIG. 4. Schematic diagram of the molecular organization of the tyl polyketide synthase (PKS) gene cluster. Open arrows correspond to individual open reading frames (ORFs) and numbers above an ORF denote a multifunctional module or synthase unit (SU). AT=acyltransferase; ACP=acyl carrier protein; KS=β-ketoacyl synthase; KR=ketoreductase; DH=dehydrase; ER=enoyl reductase; TE=thioesterase; MM=methylmalonylCoA; M=malonyl CoA; EM=ethylmalonyl CoA. Module 7 in tyl is also known as Module F.
Figure 5:
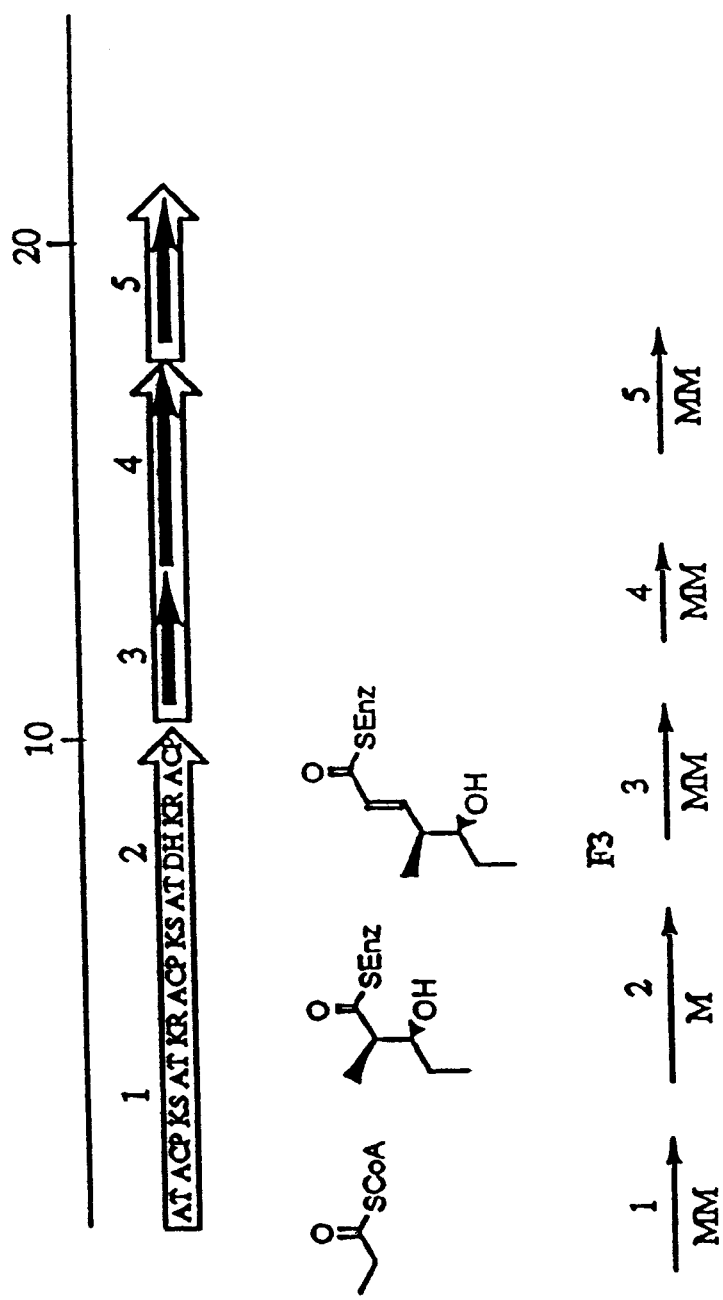
FIG. 5. Schematic diagram of the molecular organization of the met PKS gene cluster.

Once the release of the 3-hydroxy-4-methyl heptenoyl-CoA ester is established, DNA encoding the extender unit AT in met module 1 is replaced to change the specificity from methylmalonylCoA to malonylCoA (FIGS. 4–6). This change eliminates methyl group branching in the β-hydroxy acyl chain. While comparison of known AT amino acid sequences shows high overall amino acid sequence conservation, distinct regions are readily apparent where significant deletions or insertions have occurred. For example, comparison of malonyl and methylmalonyl amino acid sequences reveals a 37 amino acid deletion in the central region of the malonyltransferase. Thus, to change the specificity of the methylmalonyl transferase to malonyl transferase, the met ORFI DNA encoding the 37 amino acid sequence of MMT will be deleted, and the resulting gene will be tested in a host cell for production of the desmethyl species, 3-hydroxyheptenoylCoA. Alternatively, the DNA encoding the entire MMT can be replaced with a DNA encoding an intact MT to affect the desired chain construction.

After replacing MMT with MT, DNA encoding DH/ER will be introduced into DNA encoding met ORFI module 1. This modification results in a multifunctional protein that generates a methylene group at C-3 of the acyl chain (FIG. 6). The DNA encoding DH/ER will be PCR amplified from the available eryA or tyl PKS sequences, including the DNA encoding the required linker regions, employing a primer pair to conserved sequences 5' and 3' of the DNA encoding DH/ER. The PCR fragment will then be cloned into the met ORFI. The result is a DNA encoding a multifunctional protein (MT*DH/ER*TE*). This protein possesses the full complement of keto group processing steps and results in the production of heptenoylCoA.

The DNA encoding dehydrase in met module 2 is then inactivated, using site-directed mutagenesis in a scheme similar to that used to generate the rat FAS DH- described above (Joshi et al., *J. Biol. Chem.*, 268, 22508 (1993)). This preserves the required (R)-3-hydroxy group which serves as the substrate for PHA synthases and results in (R)-3-hydroxyheptanoylCoA species.

The final domain replacement will involve the DNA encoding the starter unit acyltransferase in met module 1 (FIG. 5), to change the specificity from propionyl CoA to acetyl CoA. This shortens the (R)-3-hydroxy acyl chain from heptanoyl to hexanoyl. The DNA encoding the catalytic domain will need to be generated based on a FAS or 6-methylsalicylic acid synthase model (Beck et al., *Eur. J. Biochem*, 192, 487 (1990)) or by using site-directed mutagenesis to alter the specificity of the resident met PKS propionyltransferase sequence. Limiting the initiator species to acetylCoA can result in the use of this starter unit by the monomer synthase. Previous work with macrolide synthases have shown that some are able to accept a wide range of starter unit carboxylic acids. This is particularly well documented for avermectin synthase, where over 60 new compounds have been produced by altering the starter unit substrate in precursor feeding studies (Dutton et al., *J. Antibiotics*, 44, 357 (1991)).

Example 5

Figure 20:
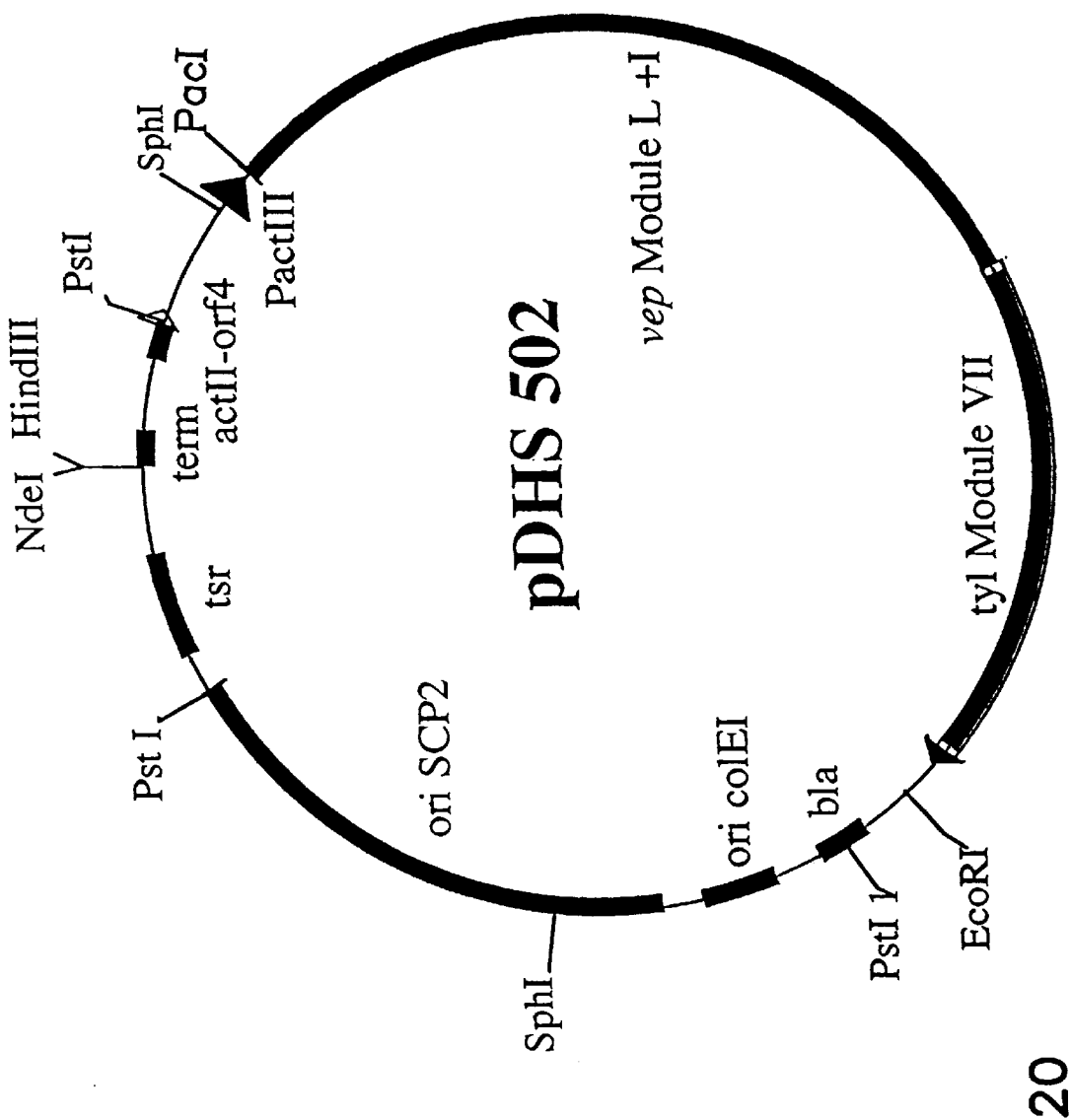
FIG. 20. Plasmid map of pDHS502.
Figure 21:
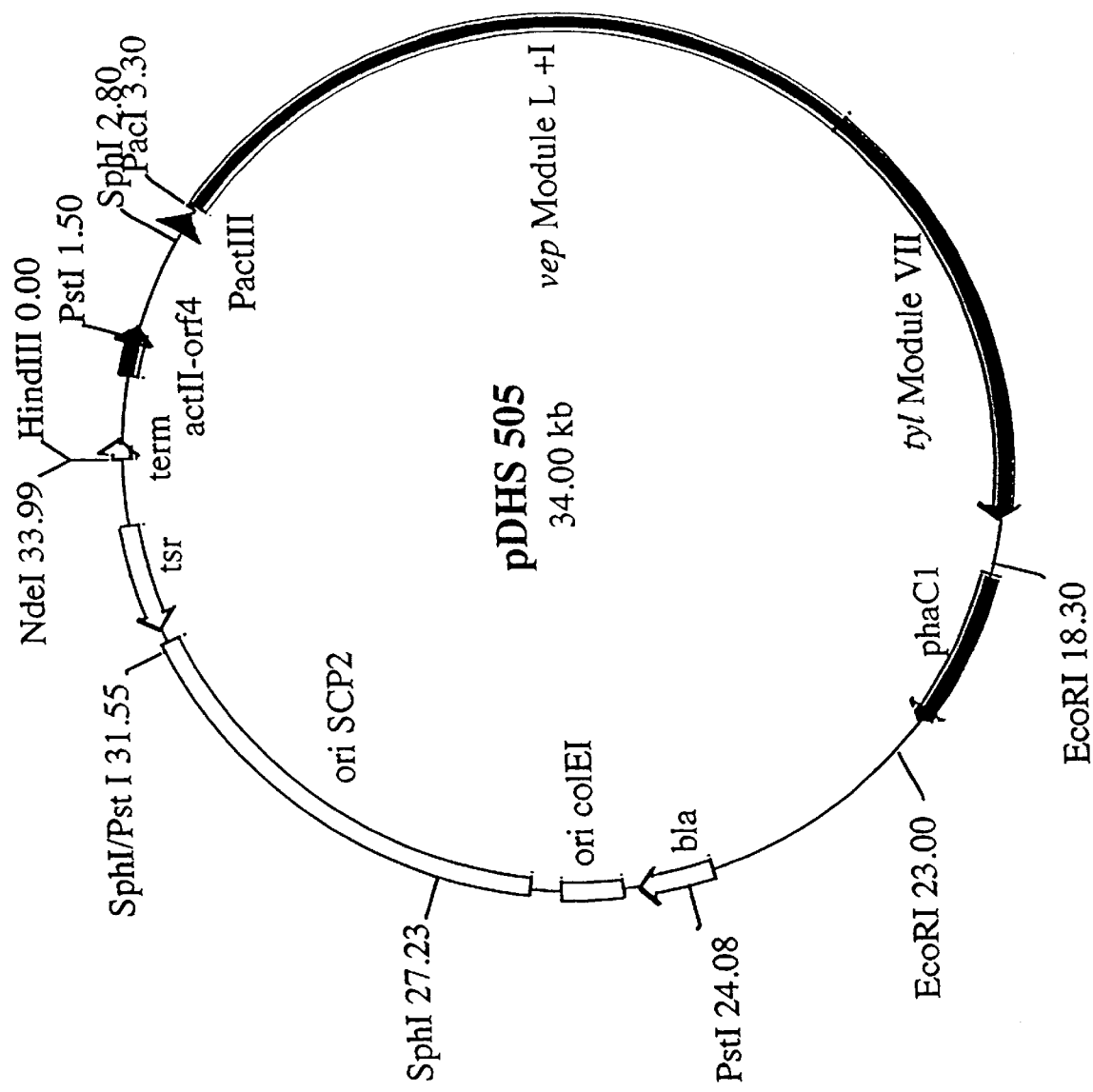
FIG. 21. Plasmid map of pDHS505.

Preparation of a Vector Encoding a Recombinant Monomer Synthase that Synthesizes 3-hydroxyl-4-hexenoic Acid To provide a recombinant monomer synthase that synthesizes 3-hydroxyl-4-hexenoic acid, a precursor for polyhydroxyhexenoate, the DNA segment encoding the loading and the first module of the vep gene cluster was linked to the DNA segment encoding module 7 of the tyl gene cluster so as to yield a recombinant DNA molecule encoding a fusion polypeptide which has no amino acid differences relative to the corresponding amino acid sequence of the parent modules. The fusion polypeptide catalyzes the synthesis of 3-hydroxyl-4-hexenoic acid. The recombinant DNA molecule was introduced into SCP2, a Streptomyces vector, under the control of the act promoter (pDHS502, FIG. 20). A polyhydroxyalkanoate polymerase gene, phaC1 from *Pseudomonas oleavorans*, was then introduced downstream of the recombinant PKS cluster (pDHS505; FIGS. 22 and 23). The DNA segment encoding the polyhydroxyalkanoate polymerase is linked to the DNA segment encoding the recombinant PKS synthase so as to yield a fusion polypeptide which synthesizes polyhydroxyhexenoate in Streptomyces. Polyhydroxyhexenoate, a biodegradable thermoplastic, is not naturally synthesized in Streptomyces, or as a major product in any other organism. Moreover, the unsaturated double bond in the side chain of polyhydroxyhexenoate may result in a polymer which has superior physical properties as a biodegradable thermoplastic over the known polyhydroxyalkanoates.

Example 6

Deletion of the desR Gene of the Desosamine Biosynthetic Gene Cluster

As some macrolides have more than one attached sugar moiety, the assignment of sugar biosynthetic genes to the appropriate sugar biosynthetic pathway can be quite difficult. Since methymycin (a compound of formula (1)) and neomethymycin (a compound of formula (2)) (FIG. 24) (Donin et al., 1953; Djerassi et al., 1956), two closely related macrolide antibiotics produced by *Streptomyces venezuelae*, contain desosamine as their sole sugar component, the organization of the sugar biosynthetic genes in the methymycin/neomethymycin gene cluster may be less complicated. Thus, this system was chosen for the study of the biosynthesis of desosamine, a N,N-dimethylamino-3,4,6-trideoxyhexose, which also exists in the erythromycin structure (Flinn et al., 1954).

Figure 24:
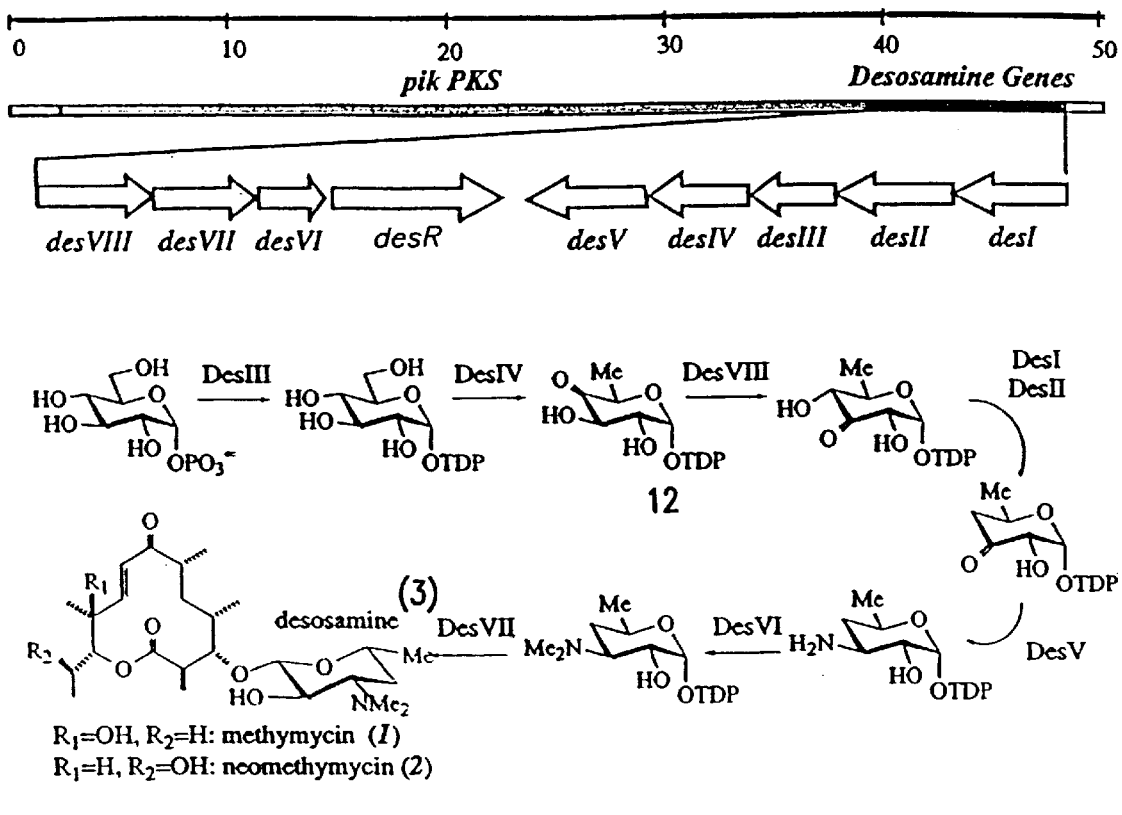
FIG. 24. Schematic diagram of the desosamine biosynthetic pathway and the enzymatic activity associated with each of the desosamine biosynthetic polypeptides.

To study the formation of this unusual sugar, a DNA library was constructed by partially digesting the genomic DNA of *S. venezuelae* (ATCC 15439) with Sau3A I into 35–40 kb fragments which were ligated into the cosmid vector pNJ1 (Tuan et al., 1990). The recombinant DNA was packaged into bacteriophage X which was used to transfect *E. coli* DH5α. The resulting cosmid library was screened for desired clones using the tylA1 and tylA2 genes from the tylosin biosynthetic cluster as probes (Baltz et al., 1988; Merson-Davies et al., 1994). These two probes are specific for sugar biosynthetic genes whose products catalyze the first two steps universally followed by all unusual 6-deoxyhexoses studied thus far. The initial reaction involves conversion of glucose-1-phosphate to TDP-D-glucose by α-D-glucose-1-phosphate thymidylyltransferase (TylA1) and subsequently, TDP-D-glucose is transformed to TDP-4-keto-6-deoxy-D-glucose by TDP-D-glucose 4,6-dehydratase (TylA2). Three cosmids were found to contain genes homologous to tylA1 and tylA2. Further analysis of these cosmids led to the identification of nine open reading frames (ORFs) downstream of the PKS genes (FIG. 24). Based on sequence similarities to other sugar biosynthetic genes, especially those derived form the erythromycin cluster (Gaisser et al., 1997; Summers et al., 1997), eight of these nine ORFs are believed to be involved in the biosynthesis of TDP-D-desosamine. Interestingly, the ery cluster lacks homologs of the tylA1 and tylA2 genes that are responsible for the first two steps in desosamine pathway. It is possible that the erythromycin biosynthetic machinery may rely on a general cellular pool of TDP-4-keto-6-deoxy-D-glucose for mycarose and desosamine formation. Depicted in FIG. 24 is a biosynthetic pathway for TDP-D-desosamine.

Although eight of the nine ORFs have been assigned to desosamine formation, the presence of desR, which shows strong sequence homology to glucosidases (as high as 39% identity and 46% similarity) (Castle et al., 1998), within the desosamine gene cluster is puzzling. To investigate the function of DesR relative to the biosynthesis of methymycin/neomethymycin, a disruption plasmid (pBL1005) derived from pKC1139 (containing an apramycin resistance marker) (Bierman et al., 1992) was constructed in which a 1.0 kb NcoI/XhoI fragment of the desR gene was deleted and replaced by the thiostrepton resistance (tsr) gene (1.1 kb) (Bibb et al., 1985) via blunt-end ligation. This plasmid was used to transform *E. coli* S17-1, which serves as the donor strain to introduce the pBL1005 construct through conjugal transfer into the wild-type *S. venezuelae* (Bierman et al., 1992). The double crossover mutants in which chromosomal desR had been replaced with the disrupted gene were selected according to their thiostrepton-resistant and apramycin-sensitive characteristics. Southern blot hybridization analysis was used to confirm the gene replacement.

The desired mutant was first grown at 29° C. in seed medium for 48 hours, and then inoculated and grown in vegetative medium for another 48 hours (Cane et al., 1993). After the fermentation broth was centrifuged at 10,000 g to remove cellular debris and mycelia, the supernatant was adjusted to pH 9.5 with concentrated KOH, and extracted with an equivolume of chloroform (four times). The organic layer was dried over sodium sulfate and evaporated to dryness. The amber oil-like crude products were first subjected to flash chromatography on silica gel using a gradient of 0–40% methanol in chloroform, followed by HPLC purification on a $C_{18}$ column eluted isocratically with 45% acetonitrile in 57 mM ammonium acetate (pH 6.7). In addition to methymycin (a compound of formula (1)) and neomethymycin (a compound of formula (2)), two new products were isolated. The yield of a compound of formula (13) and a compound of formula (14) was each in the range of 5–10 mg/L of fermentation broth. However, a compound of formula (1) and a compound of formula (2) remained to be the major products. High-resolution FAB-MS revealed that both compounds have identical molecular compositions that differ from methymycin/neomethymycin by an extra hexose. The chemical nature of these two new compounds were elucidated to be C-2' β-glucosylated methymycin and neomethymycin (a compound of formula (13) and formula (14), respectively) by extensive spectral analysis.

The spectral data of (13): $^1$H NMR (acetone-$d_6$) δ 6.56 (1H, d, J=16.0, 9-H), 6.46 (1H, d, J=16.0, 8-H), 4.67 (1H, dd, J=10.8, 2.0, 11-H), 4.39 (1H, d, J=7.5, 1'-H), 4.32 (1H, d, J=8.0, 1"-H), 3.99 (1H, dd, J=11.5, 2.5, 6"-H), 3.72 (1H, dd, J=11.5, 5.5, 6"-H), 3.56 (1H, m, 5'-H), 3.52 (1H, d, J=10.0, 3-H), 3.37 (1H, t, J=8.5, 3"-H), 3.33 (1H, m, 5"-H), 3.28 (1H, t, J=8.5, 4"-H), 3.23 (1H, dd, J=10.5, 7.5, 2'-H), 3.15 (1H, dd, J=8.5, 8.0, 2"-H), 3.10 (1H, m, 2-H), 2.75 (1H, 3'-H, buried under $H_2O$ peak), 2.42 (1H, m, 6H), 2.28 (6H, s, $NMe_2$), 1.95 (1H, m, 12-H), 1.9 (1H, m, 5-H), 1.82 (1H, m, 4'-H), 1.50 (1H, m, 12-H), 1.44 (3H, d, J=7.0, 2-Me), 1.4 (1H, m, 5-H), 1.34 (3H, s, 10-Me), 1.3 (1H, m, 4-H), 1.25 (1H, m, 4'-H), 1.20 (3H, d, J=6.0, 5'-Me), 1.15 (3H, d, J=7.0, 6-Me), 0.95 (3H, d, J=6.0, 4-Me), 0.86 (3H, t, J=7.5, 12-Me). High-resolution FAB-MS: calc for $C_{31}H_{54}NO_{12}$ $(M+H)^+$ 632.3646, found 632.3686.

Spectral data of (14): $^1$H NMR (acetone-$d_6$) δ 6.69 (1H, dd, J=16.0, 5.5 Hz, 9-H), 6.55 (1H, dd, J=16.0, 1.3, 8-H), 4.71 (1H, dd, J 9.0, 2.0, 11-H), 4.37 (1H, d, J=7.0, 1'-H), 4.31 (1H, d, J=8.0, 1"-H), 3.97 (1H, dd, J=11.5, 2.5, 6"-H), 3.81 (1H, dq, J=9.0, 6.0, 12-H), 3.72 (1H, dd, J=11.5, 5.0, 6"-H), 3.56 (1H, m, 5'-H), 3.50 (1H, bd, J=10.0, 3-H), 3.36 (1H, t, J=8.5, 3"-H), 3.32 (1H, m, 5"-H), 3.30 (1H, t, J=8.5, 4"-H), 3.23 (1H, dd, J=10.2, 7.0, 2'-H), 3.13, (1H, dd, J=8.5, 8.0, 2"-H), 3.09 (1H, m, 2-H), 3.08 (1H, m, 10-H), 2.77 (1H, ddd, J=12.5, 10.2, 4.5, 3'-H), 2.41 (1H, m, 6-H), 2.28 (6H, s, $NMe_2$), 1.89 (1H, t, J=13.0, 5-H), 1.83 (1H, ddd, J=12.5, 4.5, 1.5,4'-H), 1.41 (3H, d, J=7.0, 2-Me), 1.3 (1H, m, 4-H), 1.25 (1H, m, 5-H), 1.2 (1H, m, 4'-H, 1.20 (3H, d, J=6.0,5'-Me), 1.17 (6H, d, J=7.0,6-Me, 10-Me), 1.12 (3H, d, J=6.0, 12-Me), 0.96 (3H, d, J=6.0, 4-Me). $^{13}$C NMR (acetone-$d_6$) δ 204.1 (C-7), 175.8 (C-1), 148.2 (C-9), 126.7 (C-8), 108.3 (C-1"), 104.2 (C-1'), 85.1 (C-3), 83.0 (C-2'), 78.2 (C-3"), 78.1 (C-5"), 76.6 (C-2"), 76.4 (C-1), 71.8 (C-4"), 69.3 (C-5'), 66.1 (C-12), 66.0 (C-3'), 63.7 (C-6"), 46.2 (C-6), 44.4 (C-2), 40.8 ($NMe_2$), 36.4 (C-10), 34.7 (C-5), 34.0 (C-4), 29.5 (C-4'), 21.5 (5'-Me), 21.5 (12-Me), 17.9 (6-Me), 17.7 (4-Me), 17.2 (2-Me), 9.9 (10-Me). High-resolution FAB-MS: calc for $C_{31}H_{54}NO_{12}$ $(M+H)^+$ 632.3646, found 632.3648.

The coupling constant (d, J=8.0 Hz) of the anomeric hydrogen (1"-H) of the added glucose and the magnitude of the downfield shift (11.8 ppm) of C-2' of desosamine are all consistent with the assigned C-2' β-configuration (Seo et al., 1978).

The antibiotic activity of a compound of formula (13) and (14) against *Streptococcus pyogenes* was examined by separately applying 20 μL of each sample (1.6 mM in MeOH) to sterilized filter paper discs which were placed onto the surface of *S. pyogenes* grown on Mueller-Hinton agar plates (Mangahas, 1996). After being grown overnight at 37° C., the plates of the controls (a compound of formula (1) and (2)) showed clearly visible inhibition zones. In contrast, no such clearings were discernible around the discs of a compound of formula (13) and (14). Evidently, β-glucosylation at C-2' of desosamine in methymycin/neomethymycin renders these antibiotics inactive.

It should be noted that similar phenomena involving inactivation of macrolide antibiotics by glycosylation are known (Celmer et al., 1985; Kuo et al., 1989; Sasaki et al., 1996). For example, it was found that when erythromycin was given to *Streptomyces lividans,* which contains a macrolide glycosyltransferase (MgtA), the bacterium was able to defend itself by glycosylating the drug (Cundliffe, 1992; Jenkins et al., 1991). Such a macrolide glycosyltransferase activity has been detected in 15 out of a total of 32 actinomycete strains producing various polyketide antibiotics (Sasaki et al., 1996). Interestingly, the co-existence of a macrolide glycosyltransferase (OleD) capable of deactivating oleandomycin by glucosylation (Hernandez et al., 1993), and an extracellular β-glucosidase capable of removing the added glucose from the deactivated oleandomycin in *Streptomyces antibioticus* (Vilches et al., 1992) has led to the speculation of glycosylation as a possible self-resistance mechanism in *S. antibioticus*. Although the genes of the aforementioned glycosyltransferases have been cloned in a few cases, such as mgtA of *S. lividans* and oleD of *S. antibioticus,* the whereabouts of macrolide β-glycosidase genes remain obscure. Interestingly, the recently released eryBI sequence, which is part of the erythromycin biosynthetic cluster, is highly homologous to desR (55% identity) (Gaisser et al., 1997).

Figure 25:
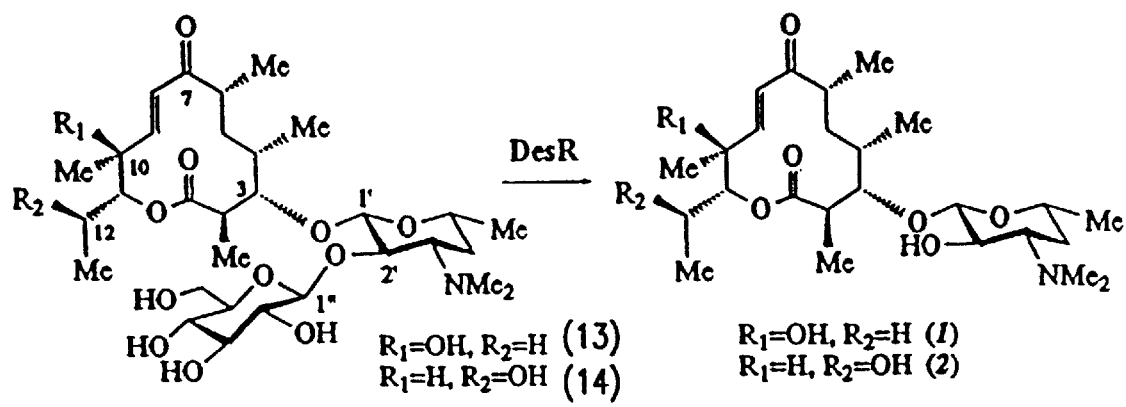
FIG. 25. Schematic of the conversion of the inactive (diglycosylated) form of methymycin and pikromycin to the active form of methymycin and pikromycin.

The discovery of desR, a macrolide β-glucosidase gene, within the desosamine gene cluster is thus significant, and the accumulation of deactivated compounds of formula (13) and (14) after desR disruption provides direct molecular evidence indicating that a similar self-defense mechanism via glycosylation/deglycosylation may also be operative in *S. venezuelae*. However, because a significant amount of methymycin and neomethymycin also exist in the fermentation broth of the mutant strain, glucosylation of desosamine may not be the primary self-resistance mechanism in *S. venezuelae*. Indeed, an rRNA methyltransferase gene found upstream from the PKS genes in this cluster may confer the primary self-resistance protection. Thus, these results are consistent with the fact that antibiotic producing organisms generally have more than one defensive option (Cundliffe, 1989). In light of this observation, it is conceivable that methymycin/neomethymycin may be produced in part as the inert diglycosides (a compound of formula (13) or (14)), and the macrolide β-glucosidase encoded by desR is responsible for transforming methymycin/neomethymycin from their dormant state to their active form. Supporting this idea, the translated desR gene has a leader sequence characteristic of secretory proteins (von Heijne, 1986; von Heijne, 1989). Thus, DesR may be transported through the cell membrane and hydrolyze the modified antibiotics extracellularly to activate them (FIG. 25).

Summary

Inspired by the complex assembly and the enzymology of aminodeoxy sugars that are frequently found as essential components of macrolide antibiotics, the entire desosamine biosynthetic gene cluster from the methymycin and neomethymycin producing strain *Streptomyces venezuelae* was cloned, sequenced, and mapped. Eight of the nine mapped genes were assigned to the biosynthesis of TDP-D-desosamine based on sequence similarities to those derived from the erythromycin cluster. The remaining gene, designated desR, showed strong sequence homology to β-glucosidases.

To investigate the function of the encoded protein (DesR), a disruption mutant was constructed in which a NcoI/XhoI fragment of the desR gene was deleted and replaced by the thiostrepton resistance (tsr) gene. In addition to methymycin and neomethymycin, two new products were isolated from the fermentation of the mutant strain. These two new compounds, which are biologically inactive, were found to be C-2' β-glucosylated methymycin and neomethymycin. Since the translated desR gene has a leader sequence characteristic of secretory proteins, the DesR protein may be an extracellular β-glucosidase capable of removing the added glucose from the modified antibiotics to activate them. Thus, the occurrence of desR within the desosamine gene cluster and the accumulation of deactivated glucosylated methymycin/neomethymycin upon disruption of desR provide strong molecular evidence suggesting that a self-resistance mechanism via glucosylation may be operative in *S. venezuelae*.

Thus, the desR gene can be used as a probe to identify homologs in other antibiotic biosynthetic pathways. Deletion of the corresponding macrolide glycosidase gene in other antibiotic biosynthetic pathways may lead to the accumulation of the glycosylated products which may be used as prodrugs with reduced cytotoxicity. Glycosylation also holds promise as a tool to regulate and/or minimize the potential toxicity associated with new macrolide antibiotics produced by genetically engineered microorganisms. Moreover, the availability of macrolide glycosidases, which can be used for the activation of newly formed antibiotics that have been deliberately deactivated by engineered glycosyltransferases, may be useful in the development of novel antibiotics using the combinatorial biosynthetic approach (Hopwood et al., 1990; Katz et al., 1993; Hutch-inson et al., 1995; Carreras et al., 1997; Kramer et al., 1996; Khosla et al., 1996; Jacobsen et al., 1997; Marsden et al., 1998).

Example 7

Deletion of the desVI Gene of the Desosamine Biosynthetic Gene Cluster

The emergence of pathogenic bacteria resistant to many commonly used antibiotics poses a serious threat to human health and has been the impetus of the present resurgent search for new antimicrobial agents (Box et al., 1997; Davies, 1996; Service, 1995). Since the first report on using genetic engineering techniques to create "hybrid" polyketides (Hopwood et al., 1995), the potential of manipulating the genes governing the biosynthesis of secondary metabolites to create new bioactive compounds, especially macrolide antibiotics, has received much attention (Kramer et al., 1996; Khosla et al., 1996). This class of clinically important drugs consists of two essential structural components: a polyketide aglycone and the appended deoxy sugars (Omura, 1984). The aglycone is synthesized via sequential condensations of acyl thioesters catalyzed by a highly organized multi-enzyme complex, polyketide synthase (PKS) (Hopwood et al., 1990; Katz, 1993; Hutchinson et al., 1995; Carreras et al., 1997). Recent advances in the understanding of the polyketide biosynthesis have allowed recombination of the PKS genes to construct an impressive array of novel skeletons (Kramer et al., 1996; Khosla et al., 1996; Hopwood et al., 1990; Katz, 1993; Hutchinson et al., 1995; Carreras et al., 1997; Epp et al., 1989; Donadio et al., 1993; Arisawa et al., 1994; Jacobsen et al., 1997; Marsden et al., 1998). Without the sugar components, however, these new compounds are usually biologically impotent. Hence, if one plans to make new macrolide antibiotics by a combinatorial biosynthetic approach, two immediate challenges must be overcome: assembling a repertoire of novel sugar structures and then having the capacity to couple these sugars to the structurally diverse macrolide aglycones.

Unfortunately, knowledge of the formation of the unusual sugars in these antibiotics remains limited (Liu et al., 1994; Kirschning et al., 1997; Johnson et al., 1998). Part of the reason for this comes from the fact that the sugar genes are generally scattered at both ends of the PKS genes. Such an organization within the macrolide biosynthetic gene cluster makes it difficult to distinguish the sugar genes from those encoding regulatory proteins or aglycone modification enzymes that are also interspersed in the same regions. The task can be made even more formidable if the macrolides contain multiple sugar components. In view of the "scattered" nature of the sugar biosynthetic genes, the antibiotic methymycin (a compound of formula (1) in FIG. 24) and its co-metabolite, neomethymycin (a compound of formula (2) in FIG. 24)), of *Streptomyces venezuelae* present themselves as an attractive system to study the formation of deoxy sugars (Donin et al., 1953; Djerassi et al., 1956). First, they carry D-desosamine (a compound of formula (3)) a prototypical aminodeoxy sugar that also exists in erythromycin. Second, since desosamine is the only sugar attached to the macrolactone of formula (1) and (2), identification of the sugar biosynthetic genes within the methymycin/neomethymycin gene cluster should be possible with much more certainty.

Figure 26:
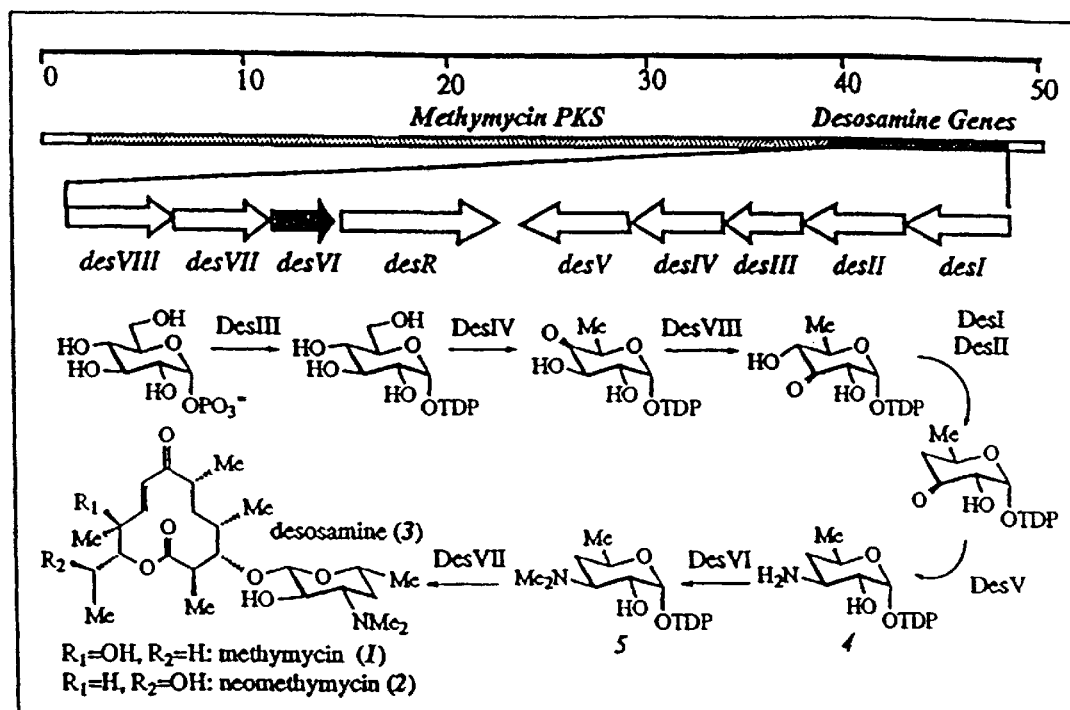
FIG. 26. Schematic diagram of the desosamine biosynthetic pathway.

A 10 kb stretch of DNA downstream from the methymycin/neomethymycin gene cluster, which is about 60 kb in length, was found to harbor the entire desosamine biosynthetic gene cluster (FIG. 26). Among the nine open reading frames (ORFs) mapped in this segment, eight are likely to be involved in desosamine formation, while the remaining one, desR, encodes a macrolide β-glycosidase that may be involved in a self-resistance mechanism. Their identities, shown in FIG. 26, are assigned based on sequence similarities to other sugar biosynthetic genes (Gaisser et al., 1997; Summers et al., 1997). The proposed pathway is well founded on literature precedent and mechanistic intuition for the construction of aminodeoxy sugars (Liu et al., 1994; Kirschning et al., 1997; Johnson et al., 1998).

To determine whether new methymycin/neomethymycin analogues carrying modified sugars could be generated by altering the desosamine biosynthetic genes, the desVI gene, which has been predicted to encode the N-methyltransferase, was chosen as a target (Gaisser et al., 1997; Summers et al., 1997). The deduced desVI product is most closely related to that of eryCVI from the erythromycin producing strain *Saccharopolyspora erythraea* (70% identity), and also strongly resembles the predicted products of rdmD from the rhodomycin cluster of *Streptomyces purpurascens* (Niemi et al., 1995), srmX from the spiromycin cluster of *Streptomyces ambofaciens* (Geistlich et al., 1992), and tylM1 from the tylosin cluster of Streptomycesfradiae (Gandecha et al., 1997). All of these enzymes contain the consensus sequence LLDV(I)ACGTG (SEQ ID NO:25) (Gaisser et al., 1997; Summers et al., 1997), near their N-terminus, which is part of the S-adenosylmethionine binding site (Ingrosso et al., 1989; Haydock et al., 1991).

The deletion of desVI should have little polar effect (Lin et al., 1984) on the expression of other desosamine biosynthetic genes because the ORF (desR) lying immediately downstream from desVI is not directly involved in desosamine formation, and those lying further downstream are transcribed in the opposite direction. Second, since N,N-dimethylation is almost certainly the last step in the desosamine biosynthetic pathway (Liu et al., 1994; Kirschning et al., 1997; Johnson et al., 1998; Gaisser et al., 1997; Summers et al., 1997), perturbing this step may lead to the accumulation of a compound of formula (4), which stands the best chance among all other intermediates of being recognized by the glycosyltransferase (DesVII) for successful linkage to the macrolactone of formula (6) (FIG. 25). Deletion and/or disruption of a single biosynthetic gene often affects the pathway at more than one specific step. In fact, disruption of eryCVI, the desVI equivalent in the erythromycin cluster, which has been predicted to encode a similar N-methylase to make desosamine in erythromycin (Gaisser et al., 1997; Summers et al., 1997), led to the accumulation of an intermediate devoid of the entire desosamine moiety (Summers et al., 1997).

A plasmid pBL3001, in which desVI was replaced by the thiostrepton gene (tsr) (Bibb et al., 1985), was constructed and introduced into wild type *S. venezuelae* by conjugal transfer using *E. coli* S17-1 (Bierman et al., 1992). Two identical double crossover mutants, KdesVI-21 and KdesVI-22 with phenotypes of thiostrepton resistance (Thio$^R$) and apamycin sensitivity (Apm$^s$) were obtained. Southern blot hybridization using tsr or a 1.1 kb HincII fragment from the desVII region further confirmed that the desVI gene was indeed replaced by tsr on the chromosome of these mutants. The KdesVI-21 mutant was first grown at 29° C. in seed medium (100 mL) for 48 hours, and then inoculated and grown in vegetative medium (3 L) for another 48 hours (Cane et al., 1993). The fermentation broth was centrifuged to remove the cellular debris and mycelia, and the supernatant was adjusted to pH 9.5 with concentrated KOH, followed by extraction with chloroform. No methymycin or neomethymycin was found; instead, the 10-deoxymethynolide (6) (350 mg) (Lambalot et al., 1992) and two new macrolides containing an N-acetylated amino sugar, a compound of formula (7) (20 mg) and a compound of formula (8) (15 mg), were isolated. Their structures were determined by spectral analyses and high-resolution MS.

Spectral data of formula 7 are: $^1$H NMR (CDCl$_3$) δ 6.62 (1H, d, J=16.0, H-9), 6.22 (1H, d, J=16.0, H-8), 5.75 (1 H, d, J=7.5, N—H), 4.75 (1H, dd, J=10.8, 2.2, H-11), 4.28 (1H, d, J=7.5, H-1'), 3.95 (1H, m, H-3'), 3.64 (1H, d, J=10.5, H-3), 3.56 (1H, m, H-5'), 3.16 (1H, dd, J=10.0, 7.5, H-2'), 2.84 (1H, dq, J=10.5, 7.0, H-2), 2.55 (1H, m, H-6), 2.02 (3H, s, NAc), 1.95 (1H, m, H-12), 1.90 (1H, m, H-4'), 1.66 (1H, m, H-5), 1.50 (1H, m, H-12), 1.41 (3H, d, J=7.0, 2-Me), 1.40 (1H, m, H-5), 1.34 (3H, s, 10-Me), 1.25 (1H, m, H-4), 1.22 (1H, m, H-4'), 1.21 (3H, d, J=6.0, H-6'), 1.17 (3H, d, J=7.0, 6-Me), 1.01 (3H, d, J=6.5, 4-Me), 0.89 (3H, t, J=7.2, 12-Me); $^{13}$C NMR (CDCl$_3$) δ 204.3 (C-7), 175.1 (C-1), 171.8 (Me—C=O), 149.1 (C-9), 125.3 (C-8), 104.4 (C-1'), 85.4 (C-3), 76.3 (C-11), 75.4 (C-2'), 74.1 (C-10), 68.6 (C-5'), 51.9 (C-3'), 45.0 (C-6), 44.0 (C-2), 38.5 (C-4'), 33.8 (C-5), 33.3 (C-4), 23.1 (Me—C=O), 21.1 (C-12), 20.6 (C-6'), 19.2 (10-Me), 17.5 (6-Me), 17.2 (4-Me), 16.2 (2-Me), 10.6 (12-Me). High-resolution FABMS: calc for C$_{25}$H$_{43}$O$_8$N (M+H)$^+$ 484.2910, found 484.2903.

Spectral data of formula 8 are: $^1$H NMR (CDCl$_3$) δ 6.76 (11H, dd, J=16.0, 5.5, H-9), 6.44 (11H, dd, J=16.0, 1.5, H-8), 5.50 (11H, d, J=6.5, N—H), 4.80 (1H, dd, J=9.0, 2.0, H-11), 4.28 (1H, d, J=7.5, H-1'), 3.95 (1H, m, H-3'), 3.88 (1H, m, H-12), 3.62 (1H, d, J=11.0, H-3), 3.57 (1H, m, H-5'), 3.18 (1H, dd, J=10.0, 7.5, H-2'), 3.06 (1H, m, H-10), 2.86 (1H, dq, J=11.0, 7.0, H-2), 2.54 (1H, m, H-6), 2.04 (3H, s, NAc), 1.98 (1H, m, H-4'), 1.67 (1H, m, H-5), 1.40 (1H, m, H-5), 1.39 (3H, d, J=7.0, 2-Me), 1.25 (1H, m, H-4), 1.22 (1H, m, H-4'), 1.22 (3H, d, J=6.0, H-6'), 1.21 (3H, d, J=6.0, 6-Me), 1.19 (3H, d, J=7.0, 12-Me), 1.16 (3H, d, J=6.5, 10-Me), 1.01 (3H, d, J=6.5, 4-Me); $^{13}$C NMR (CDCl$_3$) δ 205.1 (C-7), 174.6 (C-1), 171.9 (Me—C=O), 147.2 (C-9), 126.2 (C-8), 104.4 (C-1'), 85.3 (C-3), 75.7 (C-11), 75.4 (C-2'), 68.7 (C-5'), 66.4 (C-12), 52.0 (C-3'), 45.1 (C-6), 43.8 (C-2), 38.6 (C-4'), 35.4 (C-10), 34.1 (C-5), 33.4 (C-4), 23.1 (Me—C=O), 21.0 (12-Me), 20.7 (C-6'), 17.7 (6-Me), 17.4 (4-Me), 16.1 (2-Me), 9.8 (10-Me). High-resolution FABMS: calc for C$_{25}$H$_{43}$O$_8$N (M+H)$^+$ 484.2910, found 484.2892.

Figure 27:
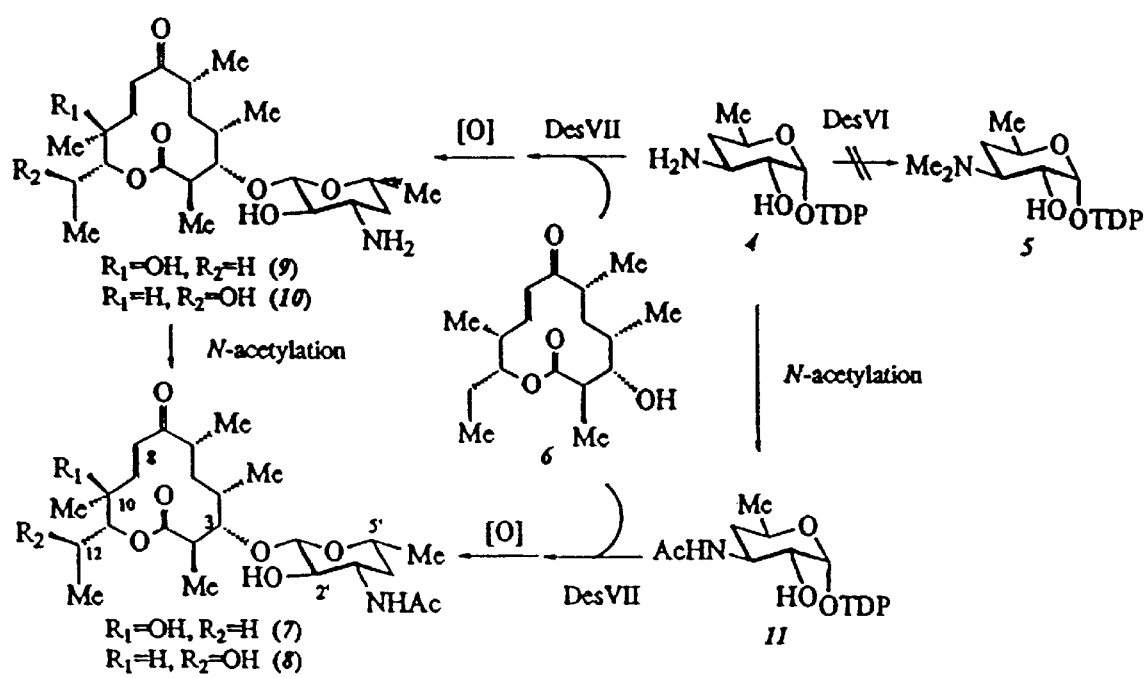
FIG. 27. Pathway for the synthesis of a compound of formula 7 and 8 in desVI⁻ mutants of Streptomyces.

The fact that compounds of formula (7) and (8) bearing modified desosamine are produced by the desVI-deletion mutant is a thrilling discovery. However, this result is also somewhat surprising since the sugar component in the products is expected to be the aminodeoxy hexose (4). As illustrated in FIG. 27, it is possible that a compound of formula (7) and (8) are derived from the predicted compound of formula (9) and (10), respectively, by a post-synthetic nonspecific acetylation of the attached aminodeoxy sugar. It is also conceivable that N-acetylation of (4) occurs first, followed by coupling of the resulting sugar (11) to the 10-deoxymethynolide (6). Nevertheless, the lack of N-methylation of the sugar component in these new products provides convincing evidence sustaining the assignment of desVI as the N-methyltransferase gene. Most significantly, the production of a compound of formula (7) and (8) by the desVI-deletion mutant attests to the fact that the glycosyltransferase (DesVII) in methymycin/neomethymycin pathway is capable of recognizing and processing sugar substrates other than TDP-desosamine (5).

Since both compounds of formula (7) and (8) are new compounds synthesized in vivo by the *S. venezuelae* mutant strain, the observed N-acetylation might be a necessary step for self-protection (Cundliffe, 1989). In view of these results, the potential toxicity associated with new macrolide antibiotics produced by genetically engineered microorganisms can be minimized and newly formed antibiotics that have been deactivated (either deliberately or not) during production can be activated. Such an approach can be part of an overall strategy for the development of novel antibiotics using the combinatorial biosynthetic approach. Indeed, purified compounds of formula (7) and (8) are inactive against *Streptococcus pyogenes* grown on Mueller-Hinton agar plates (Mangahas, 1996), while the controls (a compound of formula (1) and (2)) show clearly visible inhibition zones.

It should be pointed out that a few glycosyltransferases involved in the biosynthesis of antibiotics have been shown to have relaxed specificity towards modified macrolactones (Jacobsen et al., 1997; Marsden et al., 1998; Weber et al., 1991). However, a similar relaxed specificity toward sugar substrates has only been reported for the daunorubicin glycosyltransferase, which is able to recognize a modified daunosamine and catalyze its coupling to the aglycone, ε-rhodomycinone (Madduri et al., 1998). Thus, the fact that the methymycin/neomethymycin glycosyltransferase can also tolerate structural variants of its sugar substrate indicates that at least some glycosyltransferases in antibiotic biosynthetic pathways may be useful to create biologically active hybrid natural products via genetic engineering.

Summary

The appended sugars in macrolide antibiotics are indispensable to the biological activities of these clinically important drugs. Therefore, the development of new antibiotics via a biological combinatorial approach requires detailed knowledge of the biosynthesis of these unusual sugars, as well as the ability to manipulate the biosynthetic genes to create novel sugars that can be incorporated into the final macrolide structures. A targeted deletion of the desVI gene of *Streptomyces venezuelae*, which has been predicted to encode an N-methyltransferase based on sequence comparison, was prepared to determine whether new methymycin/neomethymycin analogues bearing modified sugars can be generated by altering the desosamine biosynthetic genes. Growth of the *S. venezuelae* deletion mutant strain resulted in the accumulation of a methymycin/neomethymycin analogue carrying an N-acetylated aminodeoxy sugar. Isolation and characterization of these derivatives not only provide the first direct evidence confirming the identity of desVI as the N-methyltransferase gene, but also demonstrate the feasibility of preparing novel sugars by the gene deletion approach. Most significantly, the results also revealed that the glycosyltransferase of methymycin/neomethymycin exhibits a relaxed specificity towards its sugar substrates.

Example 8

Cloning and Sequencing of the Met/Pik Biosynthetic Gene Cluster Materials and Methods Bacterial Strains and Media.

*E. coli* DH5α was used as a cloning host. *E. coli* LE392 was the host for a cosmid library derived from *S. venezuelae* genomic DNA. LB medium was used in *E. coil* propagation. *Streptomyces venezuelae* ATCC 15439 was obtained as a freeze-dried pellet from ATCC. Media for vegetative growth and antibiotic production were used as described (Lambalot et al., 1992). Briefly, SGGP liquid medium was for propagation of *S. venezuelae* mycelia. Sporulation agar (SPA) was used for production of *S. venezuelae* spores. Methymycin production was conducted in either SCM or vegetative medium and pikromycin production was performed in Suzuki glucose-peptone medium.

Vectors, DNA Manipulation and Cosmid Library Construction.

pUC119 was the routine cloning vector, and pNJ1 was the cosmid vector used for genomic DNA library construction. Plasmid vectors for gene disruption were either pGM160 (Muth et al., 1989) or pKC1139 (Bierman et al., 1992). Plasmid, cosmid, and genomic DNA preparation, restriction digestion, fragment isolation, and cloning were performed using standard procedures (Sambrook et al., 1989; Hopwood et al., 1985). The cosmid library was made according to instructions from the Packagene λ-packaging system (Promega).

DNA Sequencing and Analysis.

An Exonuclease III (ExoIII) nested deletion series combined with PCR-based double stranded DNA sequencing was employed to sequence the pik cluster. The ExoIII procedure followed the Erase-a-Base protocol (Stratagene) and DNA sequencing reactions were performed using the Dye Primer Cycle Sequencing Ready Reaction Kit (Applied Biosystems). The nucleotide sequences were read from an ABI PRISM 377 sequencer on both DNA strands. DNA and deduced protein sequence analyses were performed using GeneWorks and GCG sequence analysis package. All analyses were performed using the specific program default parameters.

Gene Disruption.

A replicative plasmid-mediated homologous recombination approach was developed to conduct gene disruption in *S. venezuelae*. Plasmids for insertional inactivation were constructed by cloning a kanamycin resistance marker into target genes, and plasmid for gene deletion/replacement was constructed by replacing the target gene with a kanamycin or thiostrepton resistance gene in the plasmid. Disruption plasmids were introduced into *S. venezuelae* by either PEG-mediated protoplast transformation (Hopwood et al., 1985) or RK2-mediated conjugation (Bierman et al., 1992). Then, spores from individual transformants or transconjugants were cultured on non-selective plates to induce recombination. The cycle was repeated three times to enhance the opportunity for recombination. Double crossovers yielding targeted gene disruption mutants were selected and screened using the appropriate combination of antibiotics and finally confirmed by Southern hybridization.

Antibiotic Extraction and Analysis.

Methymycin, pikromycin, and related compounds were extracted following published procedures (Cane et al., 1993). Thin layer chromatography (TLC) was routinely used to detect methymycin, neomethymycin, narbomycin and pikromycin. Further purification was conducted using flash column chromatography and HPLC, and the purified compounds were analyzed by $^1$H, $^{13}$C NMR spectroscopy and MS spectrometry.

Results

Cloning and Identification of the pik Cluster.

Figure 28:
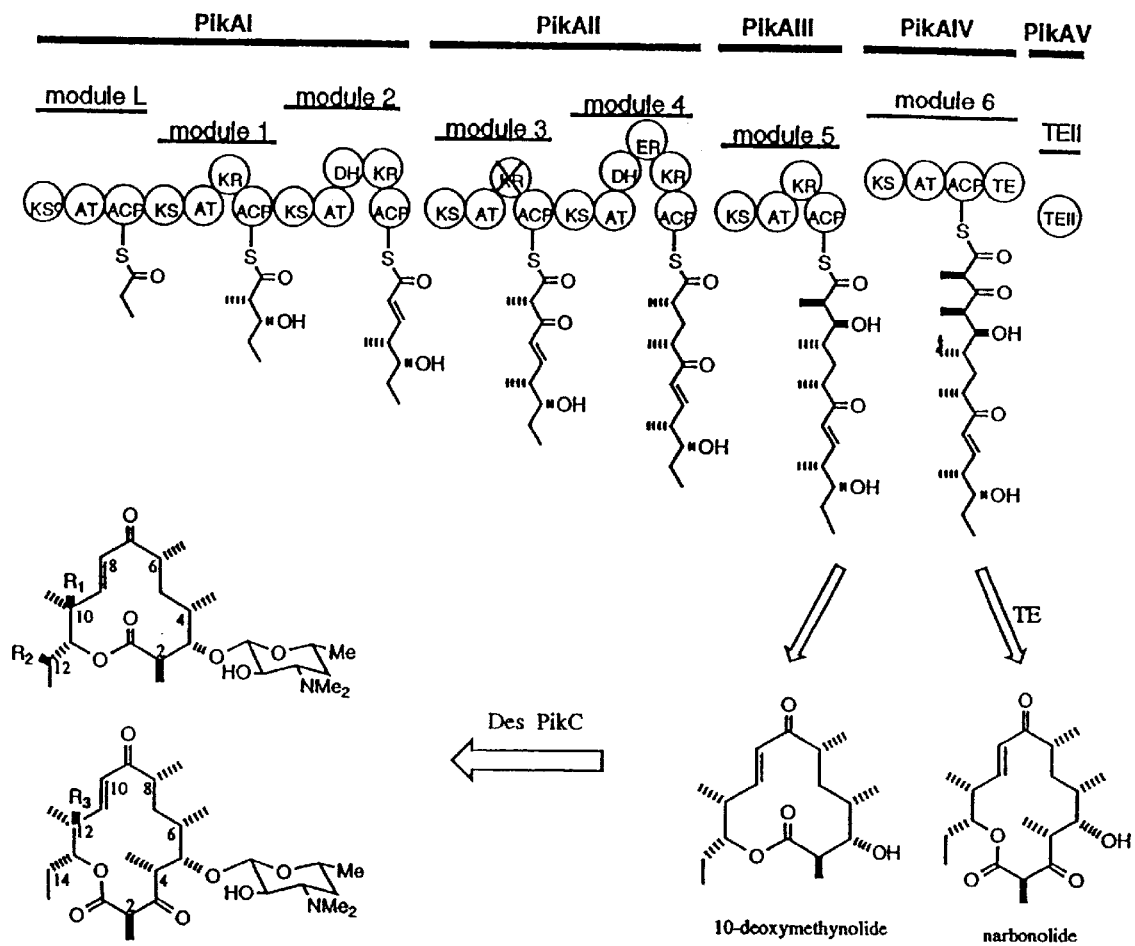
FIG. 28. The methymycin/pikromycin biosynthetic gene cluster and the structure and biosynthesis of methymycin, neomethymycin, narbomycin, and pikromycin in *S. venezuelae*. Methymycin: $R_1$=OH, $R_2$=H, neomethymycin: $R_1$=H, $R_2$=OH; narbomycin $R_3$=H, pikromycin $R_3$=OH. Each circle represents an enzymatic domain in PKS protein. ACP, acyl carrier protein; KS, β-ketoacyl-ACP synthase; $KS^Q$, a KS-like domain; AT, acyltransferase; KR, β-ketoacyl ACP reductase; DH, β-hydroxyl-thioester dehydratase; ER, enoyl reductase; TEI, thioesterase domain; TEII, type II thioesterase. Des represents all eight enzymes in desosamine synthesis and transfer which include DesI, DesII, DesIII, DesIV, DesV, DesVI, DesVIII, and Des VII.

Heterologous hybridization was used to identify genes for methymycin, neomethymycin, narbomycin and pikromycin biosynthesis in *S. venezuelae*. Initial Southern blot hybridization analysis using a type I PKS DNA probe revealed two multifunctional PKS clusters of uncharacterized function in the genome. Since these four antibiotics are all comprised of an identical desosamine residue, a tylA1 α-D-glucose-1-phosphate thymidylyltransferase DNA probe (for mycaminose/mycorose/mycinose biosynthesis in the tylosin pathway) (Merson-Davies et al., 1994) was used to locate the corresponding biosynthetic gene cluster(s). This analysis established that only one of the PKS pathways contained a cluster of desosamine biosynthetic genes. Nine overlapping cosmid clones were isolated spanning over 80 kilobases (kb) on the bacterial chromosome that encompassed the entire gene cluster (pik) for methymycin, neomethymycin, narbomycin and pikromycin biosynthesis (FIG. 28). Through subsequent gene disruption, the other PKS cluster (vep, devoid of linked desosamine biosynthetic genes) was found to play no role in production of methymycin, neomethymycin, narbomycin or pikromycin.

Nucleotide Sequence of the pik Cluster.

The nucleotide sequence of the pik cluster was completely determined and shown to contain 18 open reading frames (ORFs) that span approximately 60 kb. Central to the cluster are four large ORFs, pikAI, pikAII, pikAIII, and pikAIV, encoding a multifunctional PKS (FIG. 28). Analysis of the six modules comprising the pik PKS indicated that it would specify production of narbonolide, the 14-membered ring aglycone precursor of narbomycin and pikromycin (FIG. 28).

Figure 29:
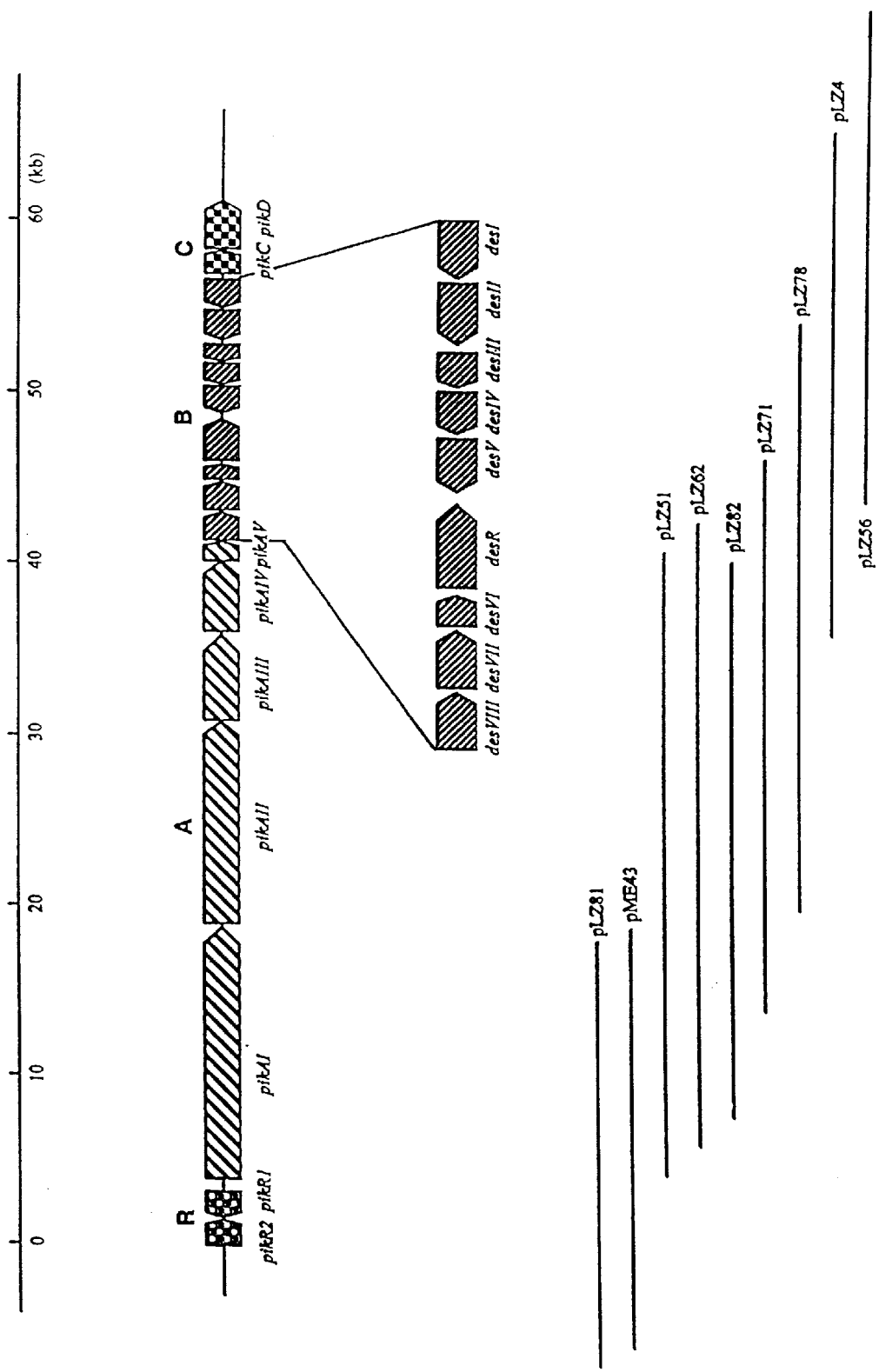
FIG. 29. Organization of the pik cluster in *S. venezuelae*. Each arrow represents an open reading frame (ORF). The direction of transcription and relative sizes of the ORFs deduced from nucleotide sequence are indicated. The cluster is composed of four genetic loci: pikA, pikB (des), pikC, and pikR. Cosmid clones are denoted as overlapping lines.

Initial analysis unveiled two significant architectural differences in the pikA-encoded PKS. First, compared with eryA (Donadio et al., 1998) and oleA (Swan et al., 1994), two PKS clusters that produce 14-membered ring macrolides erythromycin and oleadomycin similar to pikromycin, the presence of separate ORFs, pikAIII and pikAIV, encoding Pik module 5 and Pik module 6 (as individual modules) as opposed to one bimodular protein as in eryAIII and oleAII is striking. Secondly, the presence of a type II thioesterase immediately downstream of the type I PKS cluster is also unprecedented (FIG. 28). These two characteristics suggest that pikA may produce the 12-membered ring macrolactone 10-deoxymethynolide as well. Indeed, the domain organization of PikAI–AIII (module L-5) is consistent with the predicted biosynthesis of 10-deoxymethynolide except for the absence of a TE function at the C-terminus of Pik module 5 (PikAIII). The lack of a TE domain in PikAIII may be compensated by the type II TE (encoded by pikAV) immediately downstream of pikAIV. Consistent with the supposition that two distinct polyketide ring systems are assembled from the pik PKS, two macrolide-lincosamide-streptogramin B type resistant genes, pikR1 and pikR2, are found upstream of the pik PKS (FIG. 29), which presumably provide cellular self-protection for *S. venezuelae*.

The genetic locus for desosamine biosynthesis and glycosyl transfer are immediately downstream of pikA. Seven genes, desI, desII, desIII, desIV, desV, desVI, and desVIII, are responsible for the biosynthesis of the deoxysugar, and the eighth gene, desVII, encodes a glycosyltransferase that apparently catalyzes transfer of desosamine onto the alternate (12- and 14-membered ring) polyketide aglycones. The existence of only one set of desosamine genes indicates that DesVIII can accept both 10-deoxymethynolide and narbonolide as substrates (Jacobsen et al., 1997). The largest ORF in the des locus, desR, encodes a β-glycosidase that is involved in a drug inactivation-reactivation cycle for bacterial self-protection.

Figure 30:
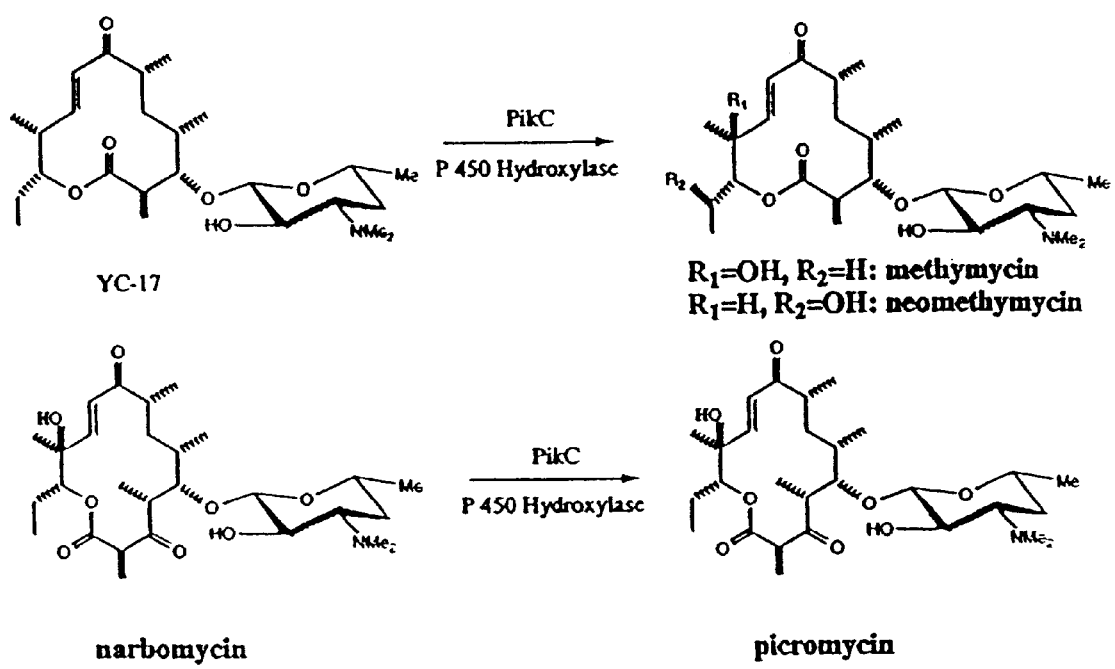
FIG. 30. Conversion of YC-17 and narbomycin by PikC P450 hydroxylase.

Just downstream of the des locus is a gene (pikC) encoding a cytochrome P450 hydroxylase similar to eryF (Andersen et al., 1992), and eryK (Stassi et al., 1993), PikC, and a gene pikD) encoding a putative regulator protein, PikD (FIG. 28). Interestingly, PikC is the only P450 hydroxylase identified in the entire pik cluster, suggesting that the enzyme can accept both 12- and 14-membered ring macrolide substrates and, more remarkably, it is active on both C-10 and C-12 of the YC-17 (12-membered ring intermediate) to produce methymycin and neomethymycin (FIG. 30). PikD is a putative regulatory protein similar to ORFH in the rapamycin gene cluster (Schwecke et al., 1995).

The combined functionality coded by the eighteen genes in the pik cluster predicts biosynthesis of methymycin, neomethymycin, narbomycin and pikromycin (Table 2). Flanking the pik cluster locus are genes presumably involved in primary metabolism and genes that may be involved in both primary and secondary metabolism. An S-adenosyl-methionine synthase gene is located downstream of pikD that may help to provide the methyl group in desosamine synthesis. A threonine dehydratase gene was identified upstream of pikR1 that may provide precursors for polyketide biosynthesis. It is not apparent that any of these genes are dedicated to antibiotic biosynthesis and they are not directly linked to the pik cluster.

TABLE 2

Deduced function of ORFs in the pik cluster

| Polypeptide (ORF) | Amino acids, no. | Proposed function of sequence similarity detected | | | | | |
|---|---|---|---|---|---|---|---|
| PikAI | 4,613 | PKS | | | | | |
| Loading module | | $KS^Q$ | AT(P) | | | | ACP |
| Module 1 | | KS | AT(P) | | | KR | ACP |
| Module 2 | | KS | AT(A) | DH | | KR | ACP |
| PikAII | 3,739 | PKS | | | | | |
| Module 3 | | KS | AT(P) | | | $KR^0$ | ACP |
| Module 4 | | KS | AT(P) | DH | ER | KR | ACP |
| PikAIII | 1,562 | PKS | | | | | |
| Module 5 | | KS | AT(P) | | | KR | ACP |
| PikAIV | 1,346 | PKS | | | | | |
| Module 6 | | KS | AT(P) | | | ACP | TE |
| PikAV | 281 | Thioesterase II (TEII) | | | | | |
| DesI | 415 | 4-Dehydrase | | | | | |
| DesII | 485 | Reductase? | | | | | |
| DesIII | 292 | α-D-Glucose-1-phosphate thymidylyltransferase | | | | | |
| DesIV | 337 | TDP-glucose 4,6-dehydratase | | | | | |
| DesV | 379 | Transaminase | | | | | |
| DesVI | 237 | N,N-dimethyltransferase | | | | | |
| DesVII | 426 | Glycosyl transferase | | | | | |
| DesVIII | 402 | Tautomerase? | | | | | |
| DesR | 809 | β-Glucosidase (involved in resistance mechanism) | | | | | |
| PikC | 418 | P450 hydroxylase | | | | | |
| PikD | 945? | Putative regulator | | | | | |
| PikR1 | 336 | rRNA methyltransferase (mls resistance) | | | | | |
| PikR2 | 288? | rRNA methyltransferase (mls resistance) | | | | | |

AT(A), acyltransferase incorporating an acetate extender unit; AT(P), acyltransferase incorporating a propionate extender unit. $KR^0$, an inactive KR. Enzymes of uncertain function are denoted with a question mark.

TABLE 3

Summary of mutational analyses of the pik cluster

| | | | Antibiotic production/ Intermediate accumulation | |
|---|---|---|---|---|
| Mutant | Type of mutation | Target gene | Met & neomethymycin | Pikromycin |
| AX903 | Insertion | pikAI | No/No | No/No |
| LZ3001 | Deletion/ replacement | desVI | No/ 10-deoxymethynolide | No/narbonolide |
| LZ4001 | Deletion/ replacement | desV | No/ 10-deoxymethynolide | No/narbonolide |
| AX905 | Deletion/ replacement | pikAV | <5%/No | <5%/No |
| AX906 | Insertion | pikC | No/YC-17 | No/narbomycin |

Mutational Analysis of the pik Cluster.

Extensive disruption of genes in the pik cluster were carried out to address the role of key enzymes in antibiotic production (Table 3). First, PikAI, the first putative enzyme involved in the biosynthesis of 10-deoxymethynolide and narbonolide was inactivated by insertional mutagenesis. The resulting mutant, AX903, produced neither methymycin or neomethymycin, nor narbomycin or pikromycin, indicating that pikA encodes a PKS required for both 12- and 14-membered ring macrolactone formation.

Second, deletion of both desVI and desV abolished methymycin, neomethymycin, narbomycin and pikromycin production, and the resulting mutants, LZ3001 and LZ4001, accumulate 10-deoxymethynolide and narbonolide in their culture broth, indicating that enzymes for desosamine synthesis and transfer are also shared by the 12- and 14-membered ring macrolides.

In order to understand the mechanism of polyketide chain termination at PikAIII (PIKAIII (module 5) is presumed to be the termination point in construction of 10-deoxymethynolide), the pik TEII gene, pikA V, was deleted. The deletion/replacement mutant, AX905, produces less than 5% of methymycin, eomethymycin, and less than 5% of pikromycin compared to wild type S. venezuelae. This abrogation in product formation occurs without significant accumulation of the expected aglycone intermediates, suggesting that pik TEII is involved in the termination of 12- as well as 14-membered ring macrolides at PikAIII and PikAIV, respectively. Although the polar effects may influence the observed phenotype in AX905, this has been ruled out after the consideration of mutant LZ3001, in which mutation in an enzyme downstream of pikAV accumulated 10-deoxymethynolide and narbonolide. The fact that mutant AX905 failed to accumulate these intermediates suggested that the polyketide chains were not efficiently released from this PKS protein in the absence of Pik TEII. Therefore, Pik TEII plays a crucial role in polyketide chain release and cyclization, and it presumably provides the mechanism for alternative termination in pik polyketide biosynthesis.

Finally, disruption of pikC confirmed that PikC is the sole enzyme catalyzing hydroxylation of both YC-17 (at C-10 and C-12) and narbomycin (at C-12). The relaxed substrate specificity of PikC and its regional specificity at C-10 and C-12 provide another layer of metabolite diversity in the pik-encoded biosynthetic system.

The work described herein has established that methymycin, neomethymycin, narbomycin and pikromycin biosynthesis is encoded by the pik cluster in S. venezuelae. Three key enzymes as well as the unique architecture of the cluster enable this relatively compact system to produce multiple macrolide antibiotics. Foremost, the presence of pik module 5 and 6 as separate proteins, PikAIII and PikAIV, and the activity of pik TEII enable the bacterium to terminate the polyketide chain at two different points of assembly, thereby producing two macrolactones of different ring size. Second, DesVII, the glycosyltransferase in the pik cluster, can accept both 12- and 14-membered ring macrolactones as substrates. Finally, PikC, the P450 hydroxylase, has a remarkable substrate and regiochemical specificity that introduces another layer of diversity into the system.

It is interesting to consider that pikA evolved in a line analogous to eryA and oleA since each of these PKSs specify the synthesis of 14-membered ring macrolactones. Therefore, pik may have acquired the capacity to generate methymycin when a mutation in the primordial pikAIII-pikAIV linker region caused splitting of Pik module 5 and 6 into two separate gene products. This notion is raised by two features of the nucleotide sequence. First, the intergenic region between pikAIII and pikAIV, which is 105 bp, may be the remanent of an intramodular linker peptide of 35 amino acids. Moreover, the potential for independently regulated expression of pikAIV is implied by the presence of a 100 nucleotide region at the 5' end of the gene that is relatively AT-rich (62% as comparing 74% G+C content in coding region). Thus, as the mutation in an original ORF encoding the bimodular multifunctional protein (PikAIII–PikAIV) occurred, so too may have evolved a mechanism for regulated synthesis of the new gene product (PikAIV).

The role of Pik TEII in alternative termination of polyketide chain elongation intermediates provides a unique aspect of diversity generation in natural product biosynthesis. Engineered polyketides of different chain length are typically generated by moving the TE catalytic domain to alternate positions in a modular PKS (Cortes et al., 1995). Repositioning of the TE domain necessarily abolishes production of the original full-length polyketide so only one macrolide is produced each time. In contrast to the fixed-position TE domain, the independent Pik TEII polypeptide presumably has the flexibility to catalyze termination at different stages of polyketide assembly, therefore enabling the system to produce multiple products of variant chain length. Combinatorial biology technologies can now exploit this system for generating molecular diversity through construction of novel PKS systems with TEIIs for simultaneous production of several new molecules as opposed to the TE domains alone that limit catalysis to a single termination step.

It is noteworthy that sequences similar to Pik TEII are found in almost all known polyketide and non-ribosomal polypeptide biosynthetic systems (Marahiel et al., 1997). Currently, the pik TEII is the first to be characterized in a modular PKS. However, recent work on a TEII gene in the lipopeptide surfactin biosynthetic cluster (Schneider et al., 1998) demonstrated that srf-TEII plays an important role in polypeptide chain release, and may suggest that srf-TEII reacts at multiple stages in peptide assembly as well (Marahiel et al., 1997).

The enzymes involved in post-polyketide assembly of 10-deoxymethynolide and narbonolide are particularly intriguing, especially the glycosyltransferase, DesVII, and P450 hydroxylase, PikC. Both have the remarkable ability to accept substrates with significant structural variability. Moreover, disruption of desVI demonstrated that DesVII also tolerates variations in deoxysugar structure (Example 6). Likewise, PikC has recently been shown to convert YC-17 to methymycin/neomethymycin and narbomycin to pikromycin in vitro.

Targeted gene disruption of ORF 1 abolished both pikromycin and methymycin production, indicating that the single cluster is responsible for biosynthesis of both antibiotics. Deletion of the TE2 gene substantially reduced methymycin and pikromycin production, which demonstrates that TE2, in contrast to the position-fixed TE1 domain, has the capacity to release polyketide chain at different points during the assembly process, thereby producing polyketides of different chain length.

The results described above were unexpected in that it was surprising that one PKS cluster produces two macrolides which differ in the number of atoms in their ring structure, that module 5 and module 6 of the PKS are in ORFs that are separated by a spacer region, that PikAIII lacked TE, that there was a Type II thioesterase, that TEI domain was not separate, and that 2 resistance genes were identified which may be specific for either a 12- or 14-membered ring.

With eighteen genes spanning less than 60 kb of DNA capable of producing four active macrolide antibiotics, the pik cluster represents the least complex yet most versatile modular PKS system so far investigated. This simplicity provides the basis for a compelling expression system in which novel active ketoside products are engineered and produced with considerable facility for discovery of a diverse range of new biologically active compounds.

Summary

Complex polyketide synthesis follows a processive reaction mechanism, and each module within a PKS harbors a string of three to six enzymatic domains that catalyze reactions in nearly linear order as described in particular detail for the erythromycin-producing PKS (Katz, 1997; Khosla, 1997; Staunton et al. 1997). The combined set of PKS modules and catalytic domains along with genes that encode enzymes for post-polyketide tailoring (e.g., glycosyl transferases, hydroxylases) typically limits a biosynthetic system to the generation of a single polyketide product.

Combinatorial biology involves the genetic manipulation of multistep biosynthetic pathways to create molecular diversity in natural products for use in novel drug discovery. PKSs represent one of the most amenable systems for combinatorial technologies because of their inherent genetic organization and ability to produce polyketide metabolites, a large group of natural products generated by bacteria (primarily actinomycetes and myxobacteria) and fungi with diverse structures and biological activities. Complex polyketides are produced by multifunctional PKSs involving a mechanism similar to long-chain fatty acid synthesis in animals (Hopwood et al., 1990). Pioneering studies (Cortes et al., 1990; Donadio et al., 1991) on the erythromycin PKS in *Saccharopolyspora erythraea* revealed a modular organization. Characterization of this multidomain protein system, followed by molecular analysis of rapamycin (Aparicio et al., 1996), FK506 (Motamedi et al., 1997), soraphen A (Schupp et al., 1995), niddamycin (Kakavas et al., 1997), and rifamycin (August et al., 1998) PKSs, demonstrated a co-linear relationship between modular structure of a multifunctional bacterial PKS and the structure of its polyketide product.

In a survey of microbial systems capable of generating unusual metabolite structural variability, *Streptomyces venezuelae* ATCC 15439 is notable in its ability to produce two distinct groups of macrolide antibiotics. Methymycin and neomethymycin are derived from the 12-membered ring macrolactone 10-deoxymethynolide, while narbomycin and pikromycin are derived from the 14 -membered ring macrolactone, narbonolide. The cloning and characterization of the biosynthetic gene cluster for these antibiotics reveals the key role of a type II thioesterase in forming a metabolic branch through which polyketides of different chain length are generated by the pikromycin multifunctional polyketide synthase (PKS). Immediately downstream of the PKS genes (pikA) are a set of genes for desosamine (des) biosynthesis and macrolide ring hydroxylation. The glycosyl transferase (encoded by desVIII) has the remarkable ability to catalyze glycosylation of both the 12- and 14-membered ring macrolactones. Moreover, the pikC-encoded P450 hydroxylase provides yet another layer of structural variability by introducing regiochemical diversity into the macrolide ring systems.

Example 9

Strategies Employing Modular PKS as PHA Monomer Providers

One strategy to exploit modular PKSs, e.g., modules of pikA or a FAS, to provide PHA monomers is to harvest polyketide intermediates as CoA derivatives using a TEII which is converted to an acyl-CoA transferase (mTEII). PikTEII is a small enzyme (281 amino acids) encoded by pikAV in *S. venezuelae*. The primary function of the wild-type enzyme is to catalyze the release of a polyketide chain at the fifth module in the pikA pathway as 10-deoxymethonolide. The enzyme most likely binds to the fifth module (PikAIII) ACP (ACP5) and releases the acyl chain attached to it. This relationship, TEII and its cognate ACP5, can be exploited to produce a polyketide having different chain lengths by moving Pik ACP5 to a different position in the cluster. For example, by moving ACP5 into the second module in place of ACP2, a triketide instead of hexoketide may be produced by the cluster. Further, moving KR5 together with ACP5 into the second module, and replacing the DH, KR, and ACP domains, a 3-hydroxyl triketide is produced that is structurally suitable as PHA monomer. A mutant TEII (mTEII) catalyzes the release of the triketide as CoA form. The triketide-CoA, 3,5-dihydroxyl-4-methylheptonyl-CoA, is a substrate for PHA polymerase, e.g., PhaC1 from *P. olivarus,* which, in turn, can incorporate the monomer into a polymer.

A second strategy includes the harvesting of a polyketide intermediate as a CoA derivative using a TEI which has been converted to an acyl-CoA transferase (mTE). Thus, the second strategy for 3-hydroxyacyl-CoA monomer production is to exploit the TE domain (TEI) within the PKS module. It has been demonstrated that the TE domain can release polyketide intermediates attached to the ACP domain within the same module. Moving the TEI to a different position in a PKS cluster results in the production of a polyketide having a different chain length. Similarly, a mutant TEI (mTEI) (i.e., one which is an acyl-CoA transferase) releases the polyketide intermediate to acyl-CoA, which then is polymerized by PHA synthetase. Preferably, a mutant TE domain in the pikA gene cluster is moved into pik module 1, fusing it immediately downstream of ACP1. The recombinant enzyme produces 2-(S)-methyl-3(R)-hydroxylveleratyl-CoA, which is a suitable substrate for PHA polymerase PhaC1. Therefore, the coexpression of the polymerase with the recombinant PKS produces a polymer.

A third strategy is to directly collect polyketide intermediates as substrates for PHA synthesis by fusing a PHA polymerase with a polyketide synthase. The first two strategies produce 3-hydroxylacyl-CoA as a substrate for PHA synthesis by employing a mutant PKS enzyme (TEI or TEII). As PHA polymerase may be active on acyl-ACP itself if the acyl-ACP is properly oriented, the third strategy fuses a PHA polymerase downstream of an ACP in a PKS protein. The PHA synthetase then serves as a domain within the chimeric multifunctional enzyme in place of a TE domain. The PKS portion of the protein catalyzes the synthesis of a 3-hydroxylacyl-ACP intermediate and then the PHA synthetase domain accepts it as substrate and adds the 3-hydroxylacyl monomer to the growing polyhydroxyalkanoate chain. The process regenerates ACP function so that the reaction can go on repeatedly to synthesize a PHA of multiple units. For example, a phaC1 gene is fused directly downstream of pik ACP1 so as to produce a chimeric enzyme that catalyzes the synthesis of a polymer.

The strategies described above can produce PHAs of complex structure, and having superior properties. In addition, the structure can be easily fine-tuned by modifying the PKS gene, thus resulting in PHAs having desired properties or functions.

REFERENCES

Andersen, J. R., Hutchinson, C. R. *J. Bacteriol.,* 174:725–735 (1992).

Aparicio, J. F., Molnar, I., Schwecke, T., Konig, A., Haydock, S. F., Khaw, L. E., Staunton, J., Leadlay, P. F. *Gene,* 169:9–16 (1996).

Arisawa, A., Kawamura, N., Takeda, K., Tsunekawa, H., Okamura, K., Okamoto, R. *Appl. Environ. Microbiol.,* 60:2657–2660 (1994).

August, P. R., Tang, L., Yoon, Y. J., Ning, S., Muller, R., Yu, T. W., Taylor, M., Hoffmann, D., Kim, C. G., Zhang, X., Hutchinson, C. R. & Floss, H. G. *Chem. Biol.*, 5:69–79 (1998).

Baltz, R. H., Seno, E. T. *Annu. Rev. Microbiol.*, 42:547–574 (1988).

Bibb, M. J., Bibb, M. J., Ward, J. M., Cohen, S. N. *Mol. Gen. Genet.*, 199:26–36 (1985).

Bierman, M., Logan, R., O'Brien, K., Seno, G., Nagaraja, R., Schoner, B. E. *Gene*, 116:43–49 (1992).

Box, R. P. *Clin. Infect. Dis.*, 24:S151 (1997).

Cane, D. E., Lambalot, R. H., Prabhakaran, P. C., Ott, W. R. *J. Am. Chem. Soc.*, 115:522–526 (1993).

Carreras, C. W., Pieper, R., Khosla, C. In *Bioorganic Chemistry Deoxysugars, Polyketides & Related Classes: Synthesis, Biosynthesis, Enzymes*, Rohr, J. (ed.), Springer:Berlin, 85–126 (1997).

Castle, L. A., Smith, K. D., Morris, R. O. *J. Bacteriol.*, 174:1478–1486 (1992).

Celmer, W. D., Nagel, A. A., Wadlow, J. W., Tatematsu, H., Ikenaga, S., Nakanishi, S. Abstracts of Papers of 24th Intersci. Conf. on Antimicrob. Agents Chemother., No. 1142, Washington, D.C. (1985).

Cortes, J. Haydock, S. F., Roberts, G. A., Bevitt, D. J., Leadlay, P. F. *Nature*, 348:176–8 (1990).

Cortes, J., Wiesmann, K. E., Roberts, G. A., Brown, M. J., Staunton, J., Leadlay, P. F. *Science*, 268:1487–9 (1995).

Cundliffe, E. C. *Annu. Rev. Microbiol.*, 43:207–233 (1989).

Cundliffe, E. *Antimicrob. Agents Chemother.*, 36:348–352 (1992).

Davies, J. *Nature*, 3×3:219–220 (1996).

Djerassi, C., Zderic, J. A. *J. Am. Chem. Soc.*, 78:6390–6395 (1956).

Donadio, S., McAlpine, J. B., Sheldon, P. J., Jackson, M., Katz, L. *Proc. Natl. Acad. Sci. U.S.A.*, 90:7119–7123 (1993).

Donadio, S., Staver, M. J., McAlpine, J. B., Swanson, S. J., Katz, L. *Science*, 252:675–9 (1991).

Donadio, S., Katz, L. *Gene*, 111:51–60 (1992).

Donin, M. N., Pagano, J., Dutcher, J. D., McKee, C. M. *Antibiotics Annu.*, 1:179–185 (1953–1954).

Epp, J., Huber, M. L. B., Tuner, J. R., Goodson, T., Schoner, B. E. *Gene*, 85:293–301 (1989).

Flinn, E. H., Sigal, M. V., Jr., Wiley, P. F., Gerzon, K. *J. Am. Chem. Soc.*, 76:3121–3131 (1954).

Gaisser, S., Bohm, G. A., Cortés, J., Leadlay, P. F. *Mol. Gen. Genet.*, 256:239–251 (1997).

Gandecha, A. R., Large, S. L., Cundliffe, E. *Gene*, 184:197–203 (1997).

Geistlich, M., Losick, R., Turner, J. R., Rao, R. N. *Mol. Microbiol.*, 6:2019–2029 (1992).

Haydock, S. F., Dowson, J. A., Dhillon, N., Roberts, G. A., Cortés, J., Leadlay, P. F. *Mol. Gen. Genet.*, 230:120–128 (1991).

Hernandez, C., Olano, C., Mendez, C., Salas, J. A. *Gene*, 134:139–140 (1993).

Hopwood, D. A., Sherman, D. H. *Annu. Rev. Genet.*, 24:37–66 (1990).

Hopwood, D. A., Malpartida, F., Kieser, H. M., Ikeda, H., Duncan, J., Fujii, I., Rudd, B. A., Floss, H. G., Omura, S. *Nature*, 314:642–644 (1985).

Hopwood, D. A., Bibb, M. J., Chater, K. J., Kieser, T., Bruton, C. J., Kieser, H. M., Lydiate, D. J., Smith, C. P., Ward, J. M., Schrempf, H., *Genetic Manipulation of Streptoyces: A Laboratory Manual* (The John Innes Foundation) (1985).

Hori et al., *Chem. Comm.*, 304 (1971).

Hutchinson, C. R., Fujii, I. *Annu. Rev. Microbiol.*, 49:201–238 (1995).

Ingrosso, D., Fowler, A. V., Bleibaum, J., Clarke, S. *J. Biol. Chem.*, 264:20130–20139 (1989).

Jacobsen, J. R., Hutchinson, C. R., Cane, D. E., Khosla, C. *Science*, 277:367–369 (1997).

Jenksins, G., Cundliffe, E. *Gene*, 18, 55–62 (1991).

Kakavas, S. J., Katz, L., Stassi, D. *J. Bacteriol.*, 179:7515–22 (1997).

Katz, L., Donadio, S. *Annu. Rev. Microbiol.*, 47:875–912 (1993).

Katz, L., *Chem. Rev.*, 97:2557–2575 (1997).

Khosla, C., *Chem. Rev.*, 97:2577–2590 (1997).

Khosla, C., Zawada, R. J. *Trends Biotechnol.*, 14:335–341 (1996).

Kirschning, A., Bechthold, A. F. -W., Rohr, J. In *Bioorganic Chemistry Deoxysugars, Polyketides & Related Classes: Synthesis, Biosynthesis, Enzymes*, Rohr, J. (ed.), Springer:Berlin 1–84 (1997).

Kramer, P. J., Khosla, C. *Annu. N.Y. Acad. Sci.*, 799:32–45 (1996).

Kuo, M. -S., Chirby, D. G., Argoudelis, A. D., Cialdella, J. I., Coats, J. H., Marshall, V. P. *Antimicrob. Agents Chemother.*, 33:2089–2091 (1989).

Lambalot, R. H., Cane, D. E. *J. Antibiot.*, 45:1981–1982 (1992).

Lin, E. C. C., Goldstein, R., Syvanen, M. *Bacteria, Plasmids, and Phages, An Introduction to Molecular Biology*, Harvard University Press:Cambridge, p. 123 (1984).

Liu, H. -w., Thorson, J. S. *Annu. Rev. Microbiol.*, 48:223–256 (1994).

Madduri, K., Kennedy, J., Rivola, G., Inventi-Solari, A., Filippini, S., Zanuso, G., Colombo, A. L., Gewain, K. M., Occi, J. L., MacNeil, D. J., Hutchinson, C. R. *Nature Biotech.*, 16:69–74 (1998).

Mangahas, F. R. MS Thesis, University of Minnesota, 1996.

Marahiel, M. A., Stachelhaus, T., Mootz, H. D., *Chem. Rev.*, 97:2651–2673 (1997).

Marsden, A. F. A., Wilkinson, B., Cortés, J., Dunster, N. J., Staunton, J., Leadlay, P. F. *Science*, 279:199–201 (1998).

Merson-Davies, L. A., Cundliffe, E. *Mol. Microbiol.*, 13:349–355 (1994).

Merson-Davies, L. A., Cundliffe, E. *Mol. Microbiol.*, 13:347–355 (1994).

Motamedi, H., Cai, S. J., Shafiee, A., Elliston, K. O. *Eur. J. Biochem.*, 244:74–80 (1997).

Muth, G., Nubhaumer, B., Wohlleben, W., Puhler, A. *Mol. Gene. Genet.*, 219:341–348 (1989).

Niemi, J., Mantsala, P. *J. Bacteriol.*, 177:2942–2945 (1995).

Omura, S. (ed.) *Macrolide Antibiotics, Chemistry, Biology, and Practice*, Academic Press:New York (1984).

Omuras et al., *J. Antibio.*, 29, 316 (1971).

Sambrook, J., Fritsch, E. F., Maniatis, T. *Molecular Cloning: A Laboratory Manual* (Cold Spring Harbor Laboratory Press), 2nd edition (1989).

Sasaki, J., Mizoue, K., Morimoto, S., Omura, S. *J. Antibiotics*, 49:1110–1118 (1996).

Schneider, A., Marahiel, M. A., *Arch. Microbiol.*, 169:404–410 (1998).

Schupp, T., Toupet, C., Cluzel, B., Neff, S., Hill, S., Beck, J. J., Ligon, J. M., *J. Bacteriol.*, 177:3673–9 (1995).

Schwecke, T., Aparicio, J. F., Molnar, I., Konig, A., Khaw, L. E., Haydock, S. F., Oliynyk, M., Caffrey, P., Cortes, J., Lester, J. B., et al. *Proc. Natl. Acad. Sci. U.S.A.*, 92:7839–7843 (1995).

Seo, S., Tomita, Y., Tori, K., Yoshimura, Y. *J. Am. Chem. Soc.*, 100:3331–3339 (1978).

Service, R. F. *Sciene*, 270:724–727 (1995).
Stassi, D., Donadio, S., Staver, M. J., Katz, L. *J. Bacteriol.*, 11:182–189 (1993).
Staunton, J., Wilkinson, B., *Chem. Rev.*, 97:2611–2629 (1997).
Summers, R. G., Donadio, S., Staver, M. J., Wendt-Pienkowski, E., Hutchinson, C. R., Katz, L. *Microbiology*, 143:3251–3262 (1997).
Swan, D. G., Rodriguez, A. M., Vilches, C., Mendez, C., Salas, J. A. *Mol. Gen. Genet.*, 242:358–362 (1994).
Tuan, J. S., Weber, J. M., Staver, M. J., Leung, J. O., Donadio, S., Katz, L. *Gene*, 90:21–29 (1990).
Vilches, C., Hernandez, C., Mendez, C., Salas, J. A. *J. Bacteriol.*, 174:161–165 (1992).
von Heijne, G. *Nucleic Acids Res.*, 14:4683–4690 (1986).
von Heijne, G., Abrahmsen, L. *FEBS Lett.*, 244:439–446 (1989).
Weber, J. M., Leung, J. O., Swanson, S. J., Idler, K. B., McAlpine, J. B. *Science*, 252:114–117 (1991).

The complete disclosure of all patents, patent documents and publications cited herein are incorporated herein by reference as if individually incorporated. The foregoing detailed description and examples have been given for clarity of understanding only. No unnecessary limitations are to be understood therefrom. The invention is not limited to the exact details shown and described for variations obvious to one skilled in the art will be included within the invention defined by the claims.

What is claimed is:

1. An isolated and purified nucleic acid segment comprising a nucleic acid sequence encoding at least one desosamine biosynthetic polypeptide, wherein the nucleic acid sequence encodes DesI (SEQ ID NO:8), DesII (SEQ ID NO:10), DesIII (SEQ ID NO:12), DesIV (SEQ ID NO:14), DesV (SEQ ID NO:16), DesVI (SEQ ID NO:18), DesVII (SEQ ID NO:20), DesVIII (SEQ ID NO:22), or a fragment thereof which catalyzes a step in desosamine biosynthesis selected from the group consisting of 4-dehydrase, reductase, TDP-glucose synthase, TDP-glucose-4,6-dehydratase, aminotransferase, N-methytransferase, glycosyltransferase and tautomerase.

2. The isolated and purified nucleic acid segment of claim 1 comprising SEQ ID NO:3.

3. An isolated and purified nucleic acid segment which comprises a nucleic acid sequence encoding DesI (SEQ ID NO:8), DesII (SEQ ID NO:10), DesIII (SEQ ID NO:12), DesIV (SEQ ID NO:14), DesV (SEQ ID NO:16), DesVI (SEQ ID NO:18), DesVII (SEQ ID NO:20), DesVIII (SEQ ID NO:22) or DesR (SEQ ID NO:24), or a fragment of DesR which has glucosidase activity.

4. The isolated and purified nucleic acid segment of claim 1 which is from *Streptomyces venezuelae*.

5. An expression cassette comprising the nucleic acid segment of claim 1 or 3 operably linked to a promoter functional in a host cell.

6. A recombinant bacterial host cell in which at least a portion of a nucleotide sequence corresponding to the nucleic acid sequence of the nucleic acid segment of claim 1 or 3 is disrupted so as to result in a decrease or lack of desosamine synthesis.

7. The host cell of claim 6 wherein the nucleic acid sequence which is disrupted encodes DesI (SEQ ID NO:8), DesII (SEQ ID NO:10), DesIII (SEQ ID NO:12), DesIV (SEQ ID NO:14), DesV (SEQ ID NO:16), DesVI (SEQ ID NO:18), DesVII (SEQ ID NO:20), DesVIII (SEQ ID NO:22).

8. A host cell, the genome of which is augmented with the expression cassette of claim 5.

* * * * *